(12) United States Patent
Hagel et al.

(10) Patent No.: US 12,133,856 B2
(45) Date of Patent: Nov. 5, 2024

(54) MULTI-SUBSTITUENT PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 18/390,228

(22) Filed: Dec. 20, 2023

(65) Prior Publication Data

US 2024/0173340 A1 May 30, 2024

Related U.S. Application Data

(63) Continuation of application No. 17/956,139, filed on Sep. 29, 2022, now Pat. No. 11,918,594, which is a continuation of application No. PCT/CA2022/050206, filed on Feb. 11, 2022.

(60) Provisional application No. 63/247,881, filed on Sep. 24, 2021, provisional application No. 63/149,001, filed on Feb. 12, 2021.

(51) Int. Cl.
*A61K 31/675* (2006.01)
*A61P 25/18* (2006.01)

(52) U.S. Cl.
CPC ............ *A61K 31/675* (2013.01); *A61P 25/18* (2018.01)

(58) Field of Classification Search
CPC ............................ A61K 31/675; A61P 25/18
USPC .......................................................... 514/80
See application file for complete search history.

(56) References Cited

U.S. PATENT DOCUMENTS

| | | | |
|---|---|---|---|
| 3,182,071 A | 5/1965 | Shavel, Jr. et al. | |
| 7,157,488 B2 | 1/2007 | Chen | |
| 2023/0040398 A1 | 2/2023 | Hagel et al. | |
| 2023/0044066 A1 | 2/2023 | Hagel et al. | |

FOREIGN PATENT DOCUMENTS

| | | | |
|---|---|---|---|
| WO | 2016134145 A2 | 8/2016 | |
| WO | 2019183358 A2 | 9/2019 | |
| WO | 2020181194 A1 | 9/2020 | |
| WO | 2021226416 A1 | 11/2021 | |

OTHER PUBLICATIONS

Von Strandtmann et al Journal of Medicinal Chemistry, 1965, 8(2), 200-204 (Year: 1965).*
Palangsuntikul et al Molecules, 2013, 21, 8799-8811 (Year: 2013).*
Carillo and Lipton (SIAM J. Applied Math., 1988, 48:1073.
Fang 2012, Exp Opin Drug Discov 7:969.
Kremer, A. and Li, S-M, Appl. Microbial. 79:951-961, 2008.
Rojas and Fiedler 2016, Front Cell Neurosci 10: 272.
Rudolf, J. et al. J. Am. Chem. Soc. 135-1895-1902, 2013.
Abramovitch, R.A. et al. Chem. Soc. 4593-4602, 1956.
Devereux et al., Nucleic Acids Res., 1984, 12: 387.
Altschul et al., J. Mol. Biol., 1990:215:403.
Sokolov et al (Vesti Akademii Navuk BSSR, Seryya Khimichnykh Navuk, 1991, 2, 82-85; STN abstract (Year: 1991).
Romanos et al., 1992, Yeast 8: 423-488.
Niedz et al., 1995, Plant Cell Rep., 14: 403.
Sleight et al., 1996, Biochem Pharmacol 51:71.
Toll et al., NIDA Res. Monogr. 1998, 178: 440.
Blair et al., 2000, J Med Chem 43: 4701.
Cregg et al., Mol Biotechnol. (2000) 16(1): 23-52.
Yamada, F. et al. Chem Pharm. Bull. 50(1) 92-99, 2002.
Pimentel et al Marine Biotechnology, 2003, 5(4) 395-400 (Year: 2003).
Setola et al., Molec Pharmacol 2003, 63: 1223.
Pratuangdejkul et al Current Medicinal Chemistry, 2005, 12, 2393-2410 (Year: 2005).
Diers et al Pharmacology, Biochemistry and Behavior, 2008, 89, 46-53. (Year: 2008).
Pyrgiotakis G. et al., Cell death discrimination with Raman spectroscopy and support vector machines. 2009, Ann. Biomed. Eng. 37: 1464-1473.
S. Kawai et al., 2010, Bioeng. Bugs 1(6): 395-403.
Grob, C. et al. Pilot study of psilocybin treatment for anxiety in patients with advanced-stage cancerArch. Gen. Psychiatry, 2011, 68(1) 71-78.
Maguire et al., Radioligand binding assays and their analysis. 2012, Methods Mol Biol 897: 31.
Mattanovich et al., Methods Mol. Biol., 2012, 824:329-58.
Nunez et al., Target-drug interactions: first principles and their application to drug discovery. 2012, Drug Disc Today 17: 10.
Servillo L. et al., 2013, J. Agric. Chem. 61: 5156-5162.
Simmler et al., Br. J. Pharmacol. 2013, 168: 458.
Frese, M. et al. ChemCatChem 6:1270-1276, 2014.
Chang et al., 2015, Plant Physiol. 169: 1127-1140.
Donato et al., Culture and Functional Characterization of Human Hepatoma HepG2 Cells. 2015, Methods Mal Biol 1250: 77.
Jones et al., 2015, Sci Rep. 5: 11301.
Rickli et al., Neuropharmacology 2015, 99: 546.
Cathart-Harris, R.L. et al. Psilocybin with psychological support for treatment-resistant depression: an open-label feasibility study. Lancet Psychiatry, 2016, 3: 619-627.
Menon, B.R. et al. Org. Biol. Chem. 9354-9361, 2016.

(Continued)

*Primary Examiner* — Yevgeny Valenrod
(74) *Attorney, Agent, or Firm* — BERESKIN & PARR LLP/ S.E.N.C.R.L., s.r.l.; Michael Fenwick

(57) ABSTRACT

Disclosed are novel multi-substituent psilocybin derivative compounds and pharmaceutical and recreational drug formulations containing the same. The compounds may be produced by reacting a reactant psilocybin derivative with a substituent containing compound.

28 Claims, 82 Drawing Sheets

Specification includes a Sequence Listing.

(56) References Cited

OTHER PUBLICATIONS

Winkelblech, J. et al. Org. Biomo. Chem. 14:9883-9885, 2016.
Daniel, J. et al. Clinical potential of psilocybin as a treatment for mental health conditions. Mental Health Clin/, 2017;7 (1): 24-28.
Terrasso et al., Human neuron-astrocyte 3D co-culture-based assay for evaluation of neuroprotective compounds. 2017, J Pharmacol Toxicol Methods 83: 72.
Weaver et al., Test systems in drug discovery for hazard identification and risk assessment of human drug-induced liver injury. 2017, Expert Opin Drug Metab Toxicol 13: 767.
Chen et al., 2018, Nat. Chem Biol. 14: 738-743.
Couillaud et al., 2019, ACS, Omega, 4, 7838-7859.
Dastmalchi et al., 2019, Nat. Chem Biol. 15: 384-390.
Inserra et al., Psychedelics in Psychiatry: Neuroplastic, Immunomodulatory, and Neurotransmitter Mechanisms. 2020, Pharmacol Rev 73: 202.
Kim K. et al., Structure of a Hallucinogen-Activated Gq-Coupled 5-HT 2A Serotonin Receptor. 2020, Cell 182: 1574-1588.
Sherwood, A.M. et al. Synthesis and Biological Evaluation of Tryptamines Found in Hallucinogenic Mushrooms: Norbaeocystin, Baeocystin, Norpsilocin, and Aeruginascin. J. Nat. Prod. 2020, 83, 461-46.
Menendez-Perdomo et al., 2021, Mass Spectrom 56: 34683.
Ross et al ACS Pharmacol. Transl. Sci. 4: 553-562, 2021.
Sikorski and Hieter, 1989, Genetics 122(1): 19-27.
Romeo J Psychiatr Res 137: 273-282, 2021.
Finnin, B. and Morgan, T.M., Transdermal penetration enhancers: applications, limitations and potential. J Pharm Sci. Oct. 1999;88(10):955-8.
Liechti et al., Curr Top Behav Neurosci 2021.
Flanagan 2016, Methods Cell Biol 132: 191.
Thompson, J D, Higgines, D G and Gibson T J, 1993, Nucleic Acid Res 22(22): 4673-4680.
Henikoff S & Henikoff, J G, 1992, Proc. Natl. Acad. Sci. USA 89: 10915-10919.

\* cited by examiner

MULTI-SUBSTITUENT PSILOCYBIN DERIVATIVES AND METHODS OF USING

RELATED APPLICATIONS

This application is a continuation of U.S. patent application Ser. No. 17/956,139 filed Sep. 29, 2022, which is a continuation of PCT Application No. PCT/CA2022/050206 filed Feb. 11, 2022, which claims the benefit of U.S. Provisional Application No. 63/149,001 filed Feb. 12, 2021 and U.S. Provisional Application No. 63/247,881 filed Sep. 24, 2021; the entire contents of patent application Ser. No. 17/956,139, PCT/CA2022/050206, 63/149,001 and 63/247,881 are hereby incorporated by reference.

INCORPORATION OF SEQUENCE LISTING

A computer readable form of the Sequence Listing "29664-P63978US04_SequenceListing" (151,104 bytes), submitted via EFS-WEB and created on Dec. 18, 2023, is herein incorporated by reference.

FIELD OF THE DISCLOSURE

The compositions and methods disclosed herein relate to a chemical compound known as psilocybin. Furthermore, the compositions and methods disclosed herein relate in particular to derivatives of psilocybin comprising multiple substituent groups.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al., Mental Health Clin/, 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Harris, R. L. et al., Lancet Psychiatry, 2016, 3: 619-627).

Although the toxicity of psilocybin is low, adverse side effects, including, for example, panic attacks, paranoia, and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds thereof.

In another aspect, the present disclosure relates to psilocybin derivative compounds and methods of making and using these compounds.

In another aspect, the present disclosure relates to multiple-substituent psilocybin derivative compounds.

Accordingly, in one aspect, the present disclosure provides, in at least one embodiment, in accordance with the teachings herein, a chemical compound or a salt thereof having a formula (I):

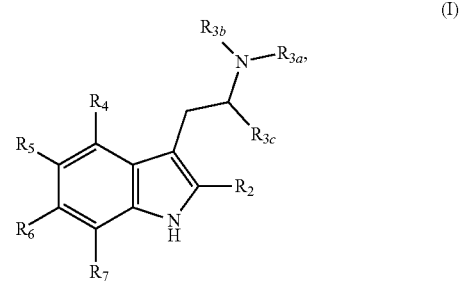

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, and wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group.

In at least one embodiment, in an aspect, at least three of $R_2$, $R_4$, $R_5$, $R_6$, or $R_7$ can be substituents selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

In at least one embodiment, in an aspect, at least three of $R_2$, $R_4$, $R_5$, $R_6$, or $R_7$ can be substituents selected from at least three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

In at least one embodiment, in an aspect, when $R_4$ is not substituted with a substituents, $R_4$ can be a hydrogen atom.

In at least one embodiment, in an aspect, $R_4$ and $R_5$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_6$ and $R_7$ can be hydrogen atoms.

In at least one embodiment, in an aspect, $R_4$ and $R_5$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_4$ and $R_5$ can be a prenyl group or a halogen atom, and $R_2$, $R_6$ and $R_7$ can be hydrogen atoms.

In at least one embodiment, in an aspect, $R_4$ and $R_6$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_4$ and $R_7$ can be hydrogen atoms.

In at least one embodiment, in an aspect, $R_4$ and $R_6$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_4$ and $R_6$ can be a prenyl group or a halogen atom, and $R_2$, $R_4$ and $R_7$ can be hydrogen atoms.

In at least one embodiment, in an aspect, $R_4$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_5$ and $R_6$ can be hydrogen atoms.

In at least one embodiment, in an aspect, $R_4$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_4$ and $R_7$ can be a prenyl group or a halogen atom, and $R_2$, $R_5$ and $R_6$ can be hydrogen atoms.

In at least one embodiment, in an aspect, $R_5$ and $R_6$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_4$ and $R_7$ can be hydrogen atoms.

In at least one embodiment, in an aspect, $R_5$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_5$ and $R_6$ can be a prenyl group or a halogen atom, and $R_2$, $R_4$ and $R_6$ can be hydrogen atoms.

In at least one embodiment, in an aspect, $R_5$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_4$ and $R_6$ can be hydrogen atoms.

In at least one embodiment, in an aspect, $R_5$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_5$ and $R_7$ can be a prenyl group or a halogen atom, and $R_2$, $R_4$ and $R_6$ can be hydrogen atoms.

In at least one embodiment, in an aspect, $R_6$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and $R_2$, $R_4$ and $R_5$ can be hydrogen atoms.

In at least one embodiment, in an aspect, $R_6$ and $R_7$ can be selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and at least one of $R_6$ and $R_7$ can be a prenyl group or a halogen atom, and $R_2$, $R_4$ and $R_5$ can be hydrogen atoms.

In at least one embodiment, in an aspect, $R_2$ can be hydrogen, and only two of $R_4$, $R_5$, $R_6$, or $R_7$, are substituted, wherein the first substituent is selected from (i) a halogen atom, (ii) a prenyl group, and (iii) a nitrile group, and the second substituent is selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein the first and second substituents are from different groups.

In at least one embodiment, in an aspect, $R_2$ can be hydrogen, and only two of $R_4$, $R_5$, $R_6$, or $R_7$, are substituted, wherein the first substituent is a halogen atom, and the second substituent is selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a nitrile group.

In at least one embodiment, in an aspect, $R_2$ can be hydrogen, and only two of $R_4$, $R_5$, $R_6$, or $R_7$, are substituted, wherein the first substituent is a prenyl group, and the second substituent is selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, and (viii) a nitrile group.

In at least one embodiment, in an aspect, $R_2$ can be hydrogen, and only two of $R_4$, $R_5$, $R_6$, or $R_7$, are substituted, wherein the first substituent is a nitrile atom, and the second substituent is selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, and (viii) a prenyl group.

In at least one embodiment, in an aspect, $R_2$ can be hydrogen, and only two of $R_4$, $R_5$, $R_6$, or $R_7$, are substituted, wherein the first substituent is selected from (i) a halogen atom, (ii) a prenyl group, and (iii) a nitrile group, and the second substituent is selected from (i) a hydroxy group, (ii) a nitro group, (iii) a glycosyloxy group, (iv) an amino group or an N-substituted amino group, (v) a carboxyl group or a carboxylic acid derivative, and (vi) an aldehyde or a ketone group.

In at least one embodiment, in an aspect, $R_2$ can be hydrogen, and only two of $R_4$, $R_5$, $R_6$, or $R_7$, are substituted, wherein the first substituent is a halogen atom, and the second substituent is selected from can be selected from (i) an amino group or N-substituted amino group, (ii) a nitrile group, (iii) a nitro group, (iv) a hydroxy group and (v) a prenyl group.

In at least one embodiment, in an aspect, $R_2$ can be hydrogen, and only two of $R_4$, $R_5$, $R_6$, or $R_7$, are substituted, wherein the first substituent is a prenyl group, and the second substituent is selected from (i) a carboxyl group or a carboxylic acid derivative, (ii) a halogen, and (iii) a hydroxy group, wherein $R_2$ can be a hydrogen atom, and two of $R_4$, $R_5$, $R_6$, or $R_7$ can be substituents.

In at least one embodiment, in an aspect, $R_2$ can be hydrogen, and only two of $R_4$, $R_5$, $R_6$, or $R_7$, are substituted, wherein the first substituent is a halogen atom, and the second substituent is a prenyl group.

In at least one embodiment, in an aspect, $R_2$ can be hydrogen, and only two of $R_4$, $R_5$, $R_6$, or $R_7$, are substituted, wherein the first substituent is a nitrile group, and the second substituent is an amino group or N-substituted amino group.

In at least one embodiment, in an aspect, $R_5$ can be a carboxyl group or an acetyl group, and $R_7$ can be an amino group, a nitrile group, a hydroxy group, or a halogen.

In at least one embodiment, in an aspect, $R_5$ can be an acetamidyl group, and $R_7$ can be an aldehyde group, a carboxyl group, or a carboxyester.

In at least one embodiment, in an aspect, $R_5$ can be an acetamidyl group, $R_6$ can be an amino group, a nitro group, or a halogen, and $R_7$ can be an aldehyde group, a carboxyl group, or a carboxyester.

In at least one embodiment, in an aspect, $R_5$ can be a carboxy-methyl group or an amide group, and $R_7$ can be a nitro group, and amino group or a halogen.

In at least one embodiment, in an aspect, $R_4$ can be a glycosyloxy group, $R_5$ can be a carboxy-methyl group or an amide group, and $R_7$ can be a nitro group, and amino group or a halogen.

In at least one embodiment, in an aspect, chemical compound (I) can be selected from a compound having a chemical formula (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX), (XXX), (XXXI), (XXXII), (XXXIII), (XXXIV), (XXXV), (XXXVI), (XXXVII), (XXXVII), (XXXIX), (XL), (XLI), (XLII), (XLIII), (XLIV), (XLV), (XLVI), (XLVII), (XLVIII), (XLIX), (L), (LI), (LII), (LIII), (LIV), (LV) or (LXXVI):

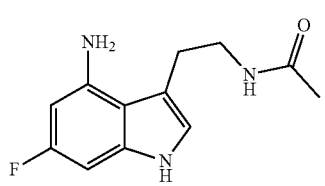

(IX)

-continued

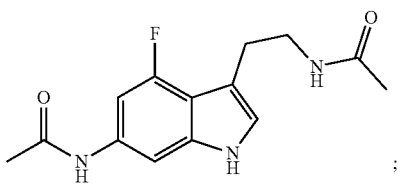

(X)

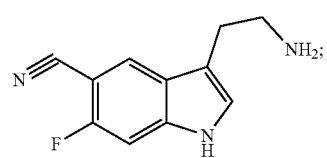

(XI)

(XII)

(XIII)

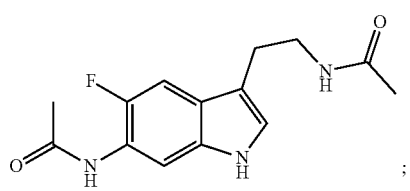

(XIV)

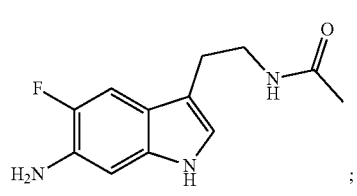

(XV)

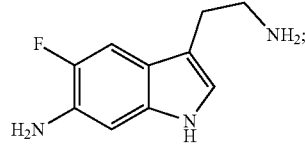

(XVI)

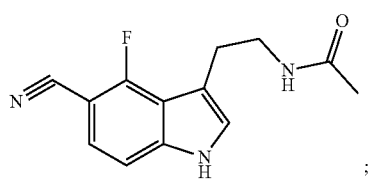

(XVII)

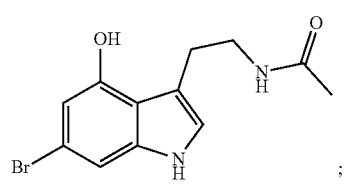 (XVIII)
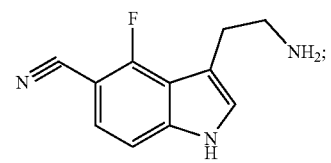 (XIX)
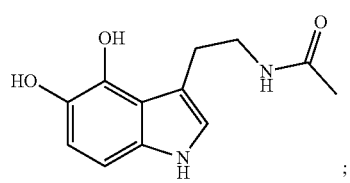 (XX)
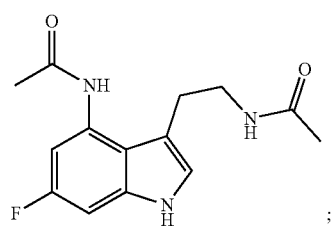 (XXI)
 (XXII)
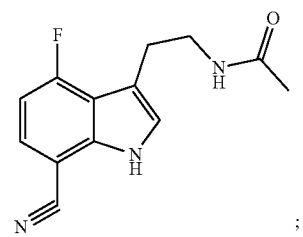 (XXIII)
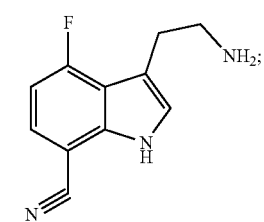 (XXIV)
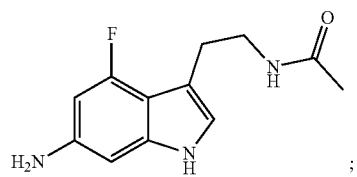 (XXV)
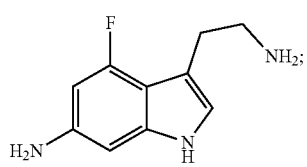 (XXVI)
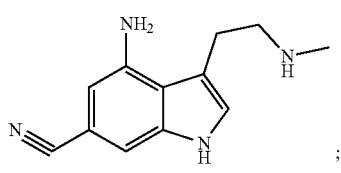 (XXVII)
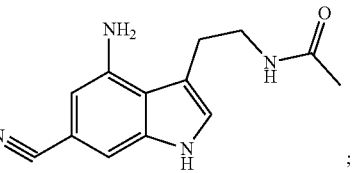 (XXVIII)
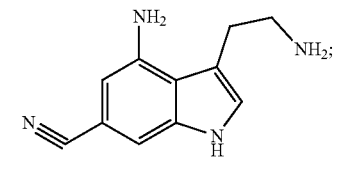 (XXIX)
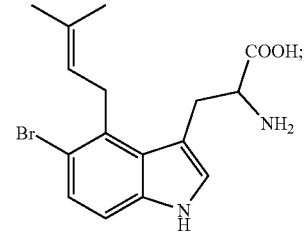 (XXX)
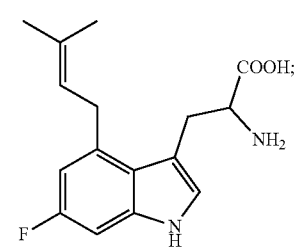 (XXXI)
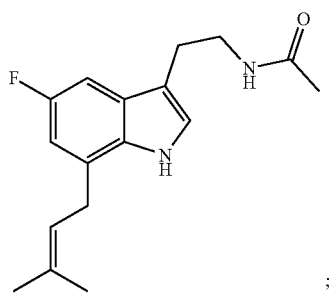 (XXXII)

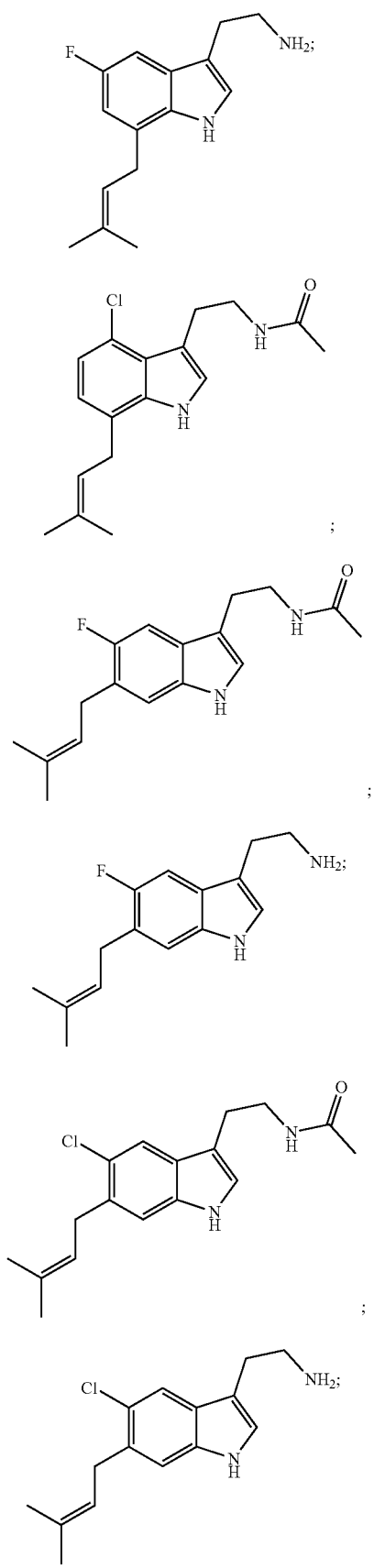

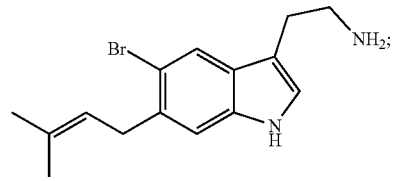
(XLVI)

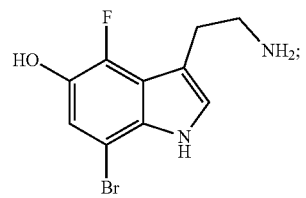
(XLVII)

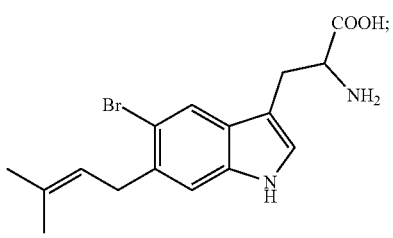
(XLVIII)

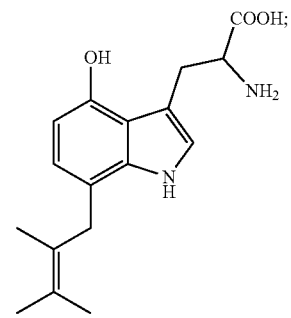
(XLIX)

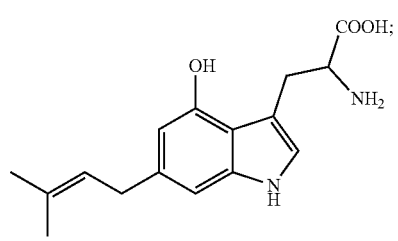
(L)

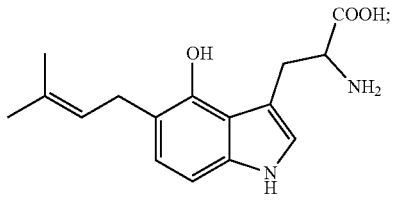
(LI)

(LII)

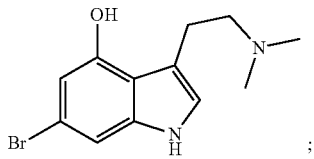
(LIII)

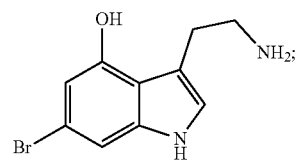
(LIV)

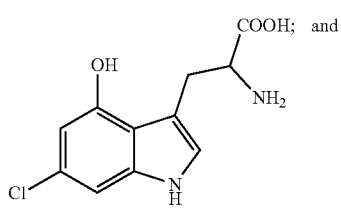
(LV)

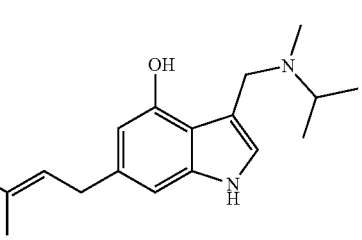
(LXXVI)

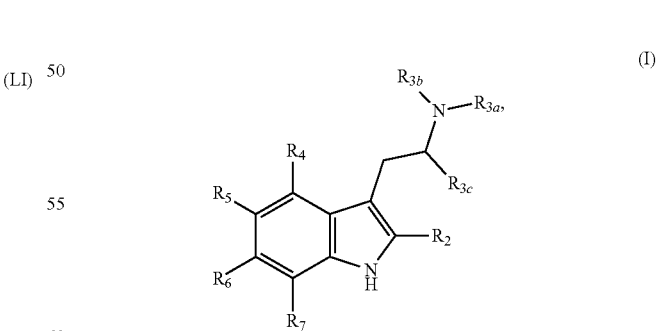

In at least one embodiment, chemical compound (I) can be any one of the compounds shown in FIG. 13A, FIG. 13B and FIG. 13C and labeled therein as 13A-3, 13A-4, 13A-5, 13A-6, 13A-7, 13A-8, 13A-9, 13A-10, 13B-3, 13B-4, 13B-5, 13B-6, 13B-7, 13B-8, 13B-8, 13C-6, 13C-7, 13C-8, 13C-9, 13C-10, or 13C-11.

In another aspect, the present disclosure relates to pharmaceutical and recreational drug formulations comprising psilocybin derivative compounds. Accordingly, in one aspect, the present disclosure provides, in at least one embodiment, a pharmaceutical or recreational drug formulation comprising an effective amount of a chemical compound or a salt thereof having a formula (I):

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, together with a pharmaceutically acceptable excipient, diluent or carrier.

In another aspect, the present disclosure relates to methods of treatment of psychiatric disorders. Accordingly, the present disclosure further provides, in one embodiment a method for treating a psychiatric disorder, the method comprising administering to a subject in need thereof a pharmaceutical formulation comprising a chemical compound or a salt thereof having a formula (I):

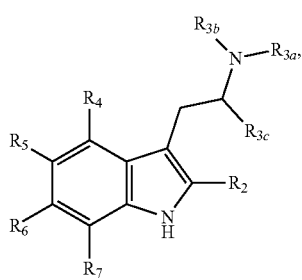

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, wherein the pharmaceutical formulation is administered in an effective amount to treat the psychiatric disorder in the subject.

In at least one embodiment, in an aspect, the disorder can be a 5-$HT_{2A}$ receptor mediated disorder, or a 5-$HT_{1A}$ receptor mediated disorder.

In at least one embodiment, in an aspect, a dose can be administered of about 0.001 mg to about 5,000 mg.

In another aspect, the present disclosure provides, in at least one embodiment, a method for modulating a 5-$HT_{2A}$ receptor or a 5-$HT_{1A}$ receptor, the method comprising contacting a 5-$HT_{2A}$ receptor or a 5-$HT_{1A}$ receptor with a chemical compound or salt thereof having a formula (I):

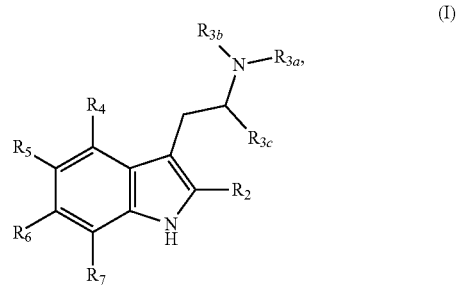

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group.

In at least one embodiment, in an aspect, the reaction conditions can be in vitro reaction conditions.

In at least one embodiment, in an aspect, the reaction conditions can be in vivo reaction conditions.

In another aspect, the present disclosure relates to methods of making multi-substituent psilocybin derivative compounds. Accordingly, in one aspect, the present disclosure provides, in at least one embodiment, a method of making a psilocybin derivative or salt thereof having a chemical formula (I):

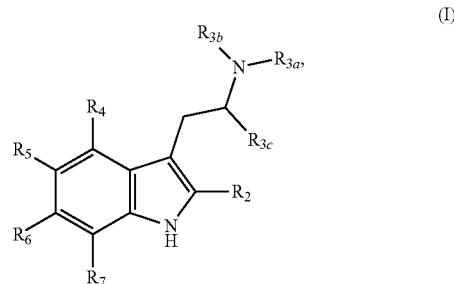

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, the method comprising:

reacting a reactant psilocybin derivative having a chemical formula (II):

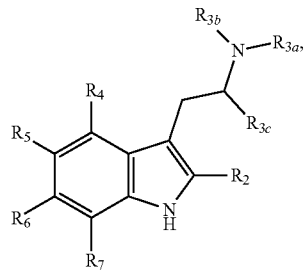

(II)

wherein, one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom or an alcohol group and when $R_4$ is not substituted with any of the foregoing substituents, $R_4$, is a hydrogen atom, a hydroxy group, an O-alkyl group, O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group with a substituent containing compound, wherein the substituent in the substituent containing compound is selected from (i) a halogen containing compound, (ii) a hydroxy group containing compound, (iii) a nitro group containing compound, (iv) a glycosyloxy group containing compound, (v) an amino group or an N-substituted amino group containing compound, (vi) a carboxyl group or a carboxylic acid derivative containing compound, (vii) an aldehyde or a ketone group containing compound, (viii) a prenyl group containing compound, and (ix) a nitrile group containing compound under reaction conditions sufficient to form the psilocybin substituent or salt thereof having chemical formula (I).

In at least one embodiment, in an aspect, the substituent in the reactant psilocybin derivative having the formula (II) can be a nitro group, the substituent containing compound can be the carboxylic acid derivative acetic anhydride ($Ac_2O$), and the reactant psilocybin derivative and the substituent containing compound can be reacted in a Friedl-Crafts acylation reaction to form a first psilocybin derivative having formula (I), wherein one of $R_2$, $R_4$, $R_5$, $R_6$, or $R_7$ is a nitro group, and at least one of $R_2$, $R_4$, $R_5$, $R_6$, or $R_7$ is an acetyl group.

In at least one embodiment, in an aspect, the formed first psilocybin derivative can be the compound shown in FIG. 13A and labeled 13A-3.

In at least one embodiment, in an aspect, the formed first psilocybin derivative having formula (I) can be reacted to oxidize the acetyl group and form a second psilocybin derivative having formula (I), wherein one of $R_2$, $R_4$, $R_5$, $R_6$, or $R_7$ can be a nitro group, and at least one of $R_2$, $R_4$, $R_5$, $R_6$, or $R_7$ can be a carboxyl group.

In at least one embodiment, in an aspect, the formed second psilocybin derivative can be the compound shown in FIG. 13A and labeled 13A-4.

In at least one embodiment, in an aspect, the formed second psilocybin derivative having formula (I) can be reacted to reduce the nitro group and form an amino group, and a third psilocybin derivative having formula (I), wherein one of $R_2$, $R_4$, $R_5$, $R_6$, or $R_7$ can be an amino group, and at least one of $R_2$, $R_4$, $R_5$, $R_6$, or $R_7$ can be a carboxyl group.

In at least one embodiment, in an aspect, the formed third psilocybin derivative can be the compound shown in FIG. 13A and labeled 13A-5.

In at least one embodiment, in an aspect, the formed third psilocybin derivative having formula (I) can be reacted with a nitrite to convert the amino group in a diazonium salt and form an intermediate psilocybin derivative having formula (I), wherein one of $R_2$, $R_4$, $R_5$, $R_6$, or $R_7$ can be a diazonium group, and at least one of $R_2$, $R_4$, $R_5$, $R_6$, or $R_7$ can be a carboxyl group.

In at least one embodiment, in an aspect, the intermediate formed psilocybin derivative can be the compound shown in FIG. 13A and labeled 13A-6.

In at least one embodiment, in an aspect, the intermediate formed psilocybin derivative having formula (I) can be reacted with a nitrile containing compound to convert the diazonium group and form a fourth psilocybin derivative having formula (I), wherein one of $R_2$, $R_4$, $R_5$, $R_6$, or $R_7$ can be a nitrile group, and at least one of $R_2$, $R_4$, $R_5$, $R_6$, or $R_7$ can be a carboxyl group.

In at least one embodiment, in an aspect, the formed fourth psilocybin derivative can be the compound shown in FIG. 13A and labeled 13A-7.

In at least one embodiment, in an aspect, the intermediate formed psilocybin derivative having formula (I) can be reacted with water to convert the diazonium group and form a fifth psilocybin derivative having formula (I), wherein one of $R_2$, $R_4$, $R_5$, $R_6$, or $R_7$ can be a hydroxy group, and at least one of $R_2$, $R_4$, $R_5$, $R_6$, or $R_7$ can be a carboxyl group.

In at least one embodiment, in an aspect, the formed fifth psilocybin derivative can be the compound shown in FIG. 13A and labeled 13A-8.

In at least one embodiment, in an aspect, the intermediate formed psilocybin derivative having formula (I) can be reacted with a halogen containing compound to convert the diazonium group and form a sixth psilocybin derivative having formula (I), wherein one of $R_2$, $R_4$, $R_5$, $R_6$, or $R_7$ can be a halogen atom, and at least one of $R_2$, $R_4$, $R_5$, $R_6$, or $R_7$ can be a carboxyl group.

In at least one embodiment, in an aspect, the formed sixth psilocybin derivative can be the compound shown in FIG. 13A and labeled 13A-9 or 13A-10.

In at least one embodiment, in an aspect, the substituent in the reactant psilocybin derivative having formula (II) can be a methoxycarbonyl group, the substituent containing compound can be the halogen containing compound N-halosuccinimide, and the reactant psilocybin derivative and the substituent containing compound can be reacted to form a first psilocybin derivative having formula (I), wherein one of $R_2$, $R_4$, $R_5$, $R_6$, or $R_7$ can be a methoxy carbonyl group, and at least one of $R_2$, $R_4$, $R_5$, $R_6$, or $R_7$ can be a halogen atom.

In at least one embodiment, in an aspect, the N-halosuccinimide can be N-chloro-succinimide, and the formed first psilocybin derivative can be the compound shown in FIG. 13B and labeled 13B-3.

In at least one embodiment, in an aspect, the substituent in the reactant psilocybin derivative having formula (II) can be a methoxycarbonyl group, the substituent containing compound can be the nitro containing compound nitronium tetrafluoroborate, and the reactant psilocybin derivative and the substituent containing compound can be reacted to form a second psilocybin derivative having formula (I), wherein one of $R_2$, $R_4$, $R_5$, $R_6$, or $R_7$ is a methoxy carbonyl group, and at least one of $R_2$, $R_4$, $R_5$, $R_6$, or $R_7$ is a nitro group.

In at least one embodiment, in an aspect, and the formed second psilocybin derivative can be the compound shown in FIG. 13B and labeled 13B-4.

In at least one embodiment, in an aspect, the formed first psilocybin derivative having formula (I) can be reacted with an acetylated glycosyl compound and form a third psilocybin derivative having formula (I), wherein one of $R_2$, $R_4$, $R_5$, $R_6$, or $R_7$ is a methoxy carbonyl group, at least one of $R_2$, $R_4$, $R_5$, $R_6$, or $R_7$ can be a glycosyloxy group, and at least one of $R_2$, $R_4$, $R_5$, $R_6$, or $R_7$ can be a halogen atom.

In at least one embodiment, in an aspect, the formed third psilocybin derivative can be the compound shown in FIG. 13B and labeled 13B-5.

In at least one embodiment, in an aspect, the formed second psilocybin derivative having formula (I) can be reacted with an acetylated glycosyl compound and form a fourth psilocybin derivative having formula (I), wherein one of $R_2$, $R_4$, $R_5$, $R_6$, or $R_7$ can be a methoxycarbonyl group, at least one of $R_2$, $R_4$, $R_5$, $R_6$, or $R_7$ can be a glycosyloxy group, and at least one of $R_2$, $R_4$, $R_5$, $R_6$, or $R_7$ is a nitro group.

In at least one embodiment, in an aspect, the formed fourth psilocybin derivative can be the compound shown in FIG. 13B and labeled 13B-6.

In at least one embodiment, in an aspect, the formed third psilocybin derivative having formula (I) can be reacted with ammonia to convert the methoxycarbonyl group in an amido group and form a fifth psilocybin derivative having formula (I), wherein one of $R_2$, $R_4$, $R_5$, $R_6$, or $R_7$ can be an amido group, at least one of $R_2$, $R_4$, $R_5$, $R_6$, or $R_7$ is a glycosyloxy group, and at least one of $R_2$, $R_4$, $R_5$, $R_6$, or $R_7$ can be a halogen atom.

In at least one embodiment, in an aspect, the formed fifth psilocybin derivative can be the compound shown in FIG. 13B and labeled 13B-7.

In at least one embodiment, in an aspect, the formed fourth psilocybin derivative having formula (I) can be reacted with ammonia to convert the methoxycarbonyl group in an amido group and form a sixth psilocybin derivative having formula (I), wherein one of $R_2$, $R_4$, $R_5$, $R_6$, or $R_7$ can be an amido group, at least one of $R_2$, $R_4$, $R_5$, $R_6$, or $R_7$ can be a glycosyloxy group, and at least one of $R_2$, $R_4$, $R_5$, $R_6$, or $R_7$ is a nitro group.

In at least one embodiment, in an aspect, the formed sixth psilocybin derivative can be the compound shown in FIG. 13B and labeled 13B-8.

In at least one embodiment, in an aspect, the formed sixth psilocybin derivative having formula (I) can be reacted to reduce the nitro group to form an amino group and a seventh psilocybin derivative having formula (I), wherein one of $R_2$, $R_4$, $R_5$, $R_6$, or $R_7$ can be an amido group, at least one of $R_2$, $R_4$, $R_5$, $R_6$, or $R_7$ is a glycosyloxy group, and at least one of $R_2$, $R_4$, $R_5$, $R_6$, or $R_7$ can be a nitro group.

In at least one embodiment, in an aspect, the formed seventh psilocybin derivative can be the compound shown in FIG. 13B and labeled 13B-9.

In at least one embodiment, in an aspect, the substituent in the reactant psilocybin derivative having formula (II) can be an acetamidyl group, the substituent containing compound can be the halogen containing compound N-halo-succinimide, and the reactant psilocybin derivative and the substituent containing compound can be reacted to form a first psilocybin derivative having formula (I), wherein one of $R_2$, $R_4$, $R_5$, $R_6$, or $R_7$ can be an acetamidyl group, and at least one of $R_2$, $R_4$, $R_5$, $R_6$, or $R_7$ can be a halogen atom.

In at least one embodiment, in an aspect, the N-halo-succinimide can be N-bromo-succinimide (NBS), and the formed first psilocybin derivative can be the compound shown in FIG. 13C and labeled 13C-6.

In at least one embodiment, in an aspect, the substituent in the reactant psilocybin derivative having formula (II) can be an acetamidyl group, the substituent containing compound can be dimethyl formamide, and the reactant psilocybin derivative and the substituent containing compound can be reacted to form an intermediate psilocybin derivative having formula (I), wherein one of $R_2$, $R_4$, $R_5$, $R_6$, or $R_7$ is an acetamidyl group, and at least one of $R_2$, $R_4$, $R_5$, $R_6$, or $R_7$ can be a methanol group, and wherein the intermediate psilocybin derivative can be reacted to oxidize the methanol group, and form a second psilocybin derivative having formula (I), wherein one of $R_2$, $R_4$, $R_5$, $R_6$, or $R_7$ can be an acetamidyl group, and at least one of $R_2$, $R_4$, $R_5$, $R_6$, or $R_7$ can be a carboxy group.

In at least one embodiment, in an aspect, the intermediate psilocybin derivative can be the compound shown in FIG. 13C and labeled 13C-5, and the formed second psilocybin derivative can be the compound shown in FIG. 13C and labeled 13C-7.

In at least one embodiment, in an aspect, the formed second psilocybin derivative having formula (I) can be reacted with an alcohol to esterify the carboxy group to form an ester and a third psilocybin derivative having formula (I), wherein one of $R_2$, $R_4$, $R_5$, $R_6$, or $R_7$ can be an acetamidyl group, at least one of $R_2$, $R_4$, $R_5$, $R_6$, or $R_7$ can be a carboxyl ester.

In at least one embodiment, in an aspect, the formed third psilocybin derivative can be the compound shown in FIG. 13C and labeled 13C-8.

In at least one embodiment, in an aspect, the formed third psilocybin derivative having formula (I) can be reacted with a nitro group containing compound and form a fourth psilocybin derivative having formula (I), wherein one of $R_2$, $R_4$, $R_5$, $R_6$, or $R_7$ can be an acetamidyl group, at least one of $R_2$, $R_4$, $R_5$, $R_6$, or $R_7$ can be a carboxyl ester, and at least one of $R_2$, $R_4$, $R_5$, $R_6$, or $R_7$ is a nitro group.

In at least one embodiment, in an aspect, the formed fourth psilocybin derivative can be the compound shown in FIG. 13C and labeled 13C-9.

In at least one embodiment, in an aspect, the formed fourth psilocybin derivative having formula (I) can be reacted to reduce the nitro group to form an amino group and a fifth psilocybin derivative having formula (I), wherein one of $R_2$, $R_4$, $R_5$, $R_6$, or $R_7$ is an acetamidyl group, at least one of $R_2$, $R_4$, $R_5$, $R_6$, or $R_7$ is a carboxyl ester, and at least one of $R_2$, $R_4$, $R_5$, $R_6$, or $R_7$ is an amino group.

In at least one embodiment, in an aspect, the formed fifth psilocybin derivative can be the compound shown in FIG. 13C and labeled 13C-10.

In at least one embodiment, in an aspect, the formed fifth psilocybin derivative having formula (I) can be reacted with ammonia to form an amido group and a sixth psilocybin derivative having formula (I), wherein one of $R_2$, $R_4$, $R_5$, $R_6$, or $R_7$ can be an acetamidyl group, at least one of $R_2$, $R_4$, $R_5$, $R_6$, or $R_7$ is a carboxyester, and at least one of $R_2$, $R_4$, $R_5$, $R_6$, or $R_7$ can be an amido group.

In at least one embodiment, in an aspect, the formed sixth psilocybin derivative can be the compound shown in FIG. 13C and labeled 13C-11.

In another aspect, the present disclosure relates to further methods of making multi-substituent psilocybin derivatives. Accordingly, in one aspect, the present disclosure provides, in at least one aspect, a method of making a multi-substituent psilocybin derivative, the method comprising contacting a psilocybin derivative precursor compound having a formula (LVII):

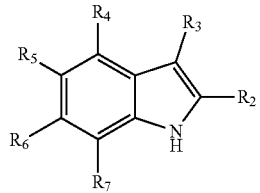

(LVII)

wherein at least one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, and wherein $R_3$ is a hydrogen atom or —CH$_2$—CHNH$_2$COOH or —CH$_2$—CH$_2$NH$_2$, with a catalytic quantity of a psilocybin biosynthetic enzyme complement under reaction conditions permitting an enzyme catalyzed conversion of the psilocybin derivative precursor compound to form a multi-substituent psilocybin derivative compound having a formula (I):

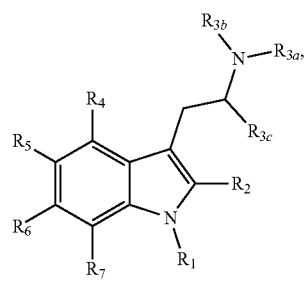

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$, is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

In at least one embodiment, in an aspect, the reaction conditions can be in vitro reaction conditions.

In at least one embodiment, in an aspect, the reaction conditions can be in vivo reaction conditions.

In at least one embodiment, in an aspect, the psilocybin derivative precursor compound and the substituent containing compound can be contacted with the psilocybin biosynthetic enzyme complement in a host cell, wherein the host cell can comprise a chimeric nucleic acid sequence comprising as operably linked components:
  (i) a nucleic acid sequence controlling expression in the host cell; and
  (ii) a nucleic acid sequence encoding psilocybin biosynthetic enzyme complement,
and the host cell can be grown to express the psilocybin biosynthetic enzyme complement and to produce the multi-substituent psilocybin derivative compound.

In at least one embodiment, in an aspect, the psilocybin biosynthetic enzyme complement can comprise at least one enzyme encoded by a nucleic acid selected from:
  (a) SEQ.ID NO: 1, SEQ.ID NO: 3, SEQ.ID NO: 5, SEQ.ID NO: 7, SEQ.ID NO: 9, SEQ.ID NO 11, SEQ.ID NO: 13, SEQ.ID NO: 15, SEQ.ID NO: 17, SEQ.ID NO: 19, SEQ.ID NO: 21, SEQ.ID NO 23, SEQ.ID NO: 25, and SEQ.ID NO: 48;
  (b) a nucleic acid sequence that is substantially identical to any one of the nucleic acid sequences of (a);
  (c) a nucleic acid sequence that is substantially identical to any one of the nucleic acid sequences of (a) but for the degeneration of the genetic code;
  (d) a nucleic acid sequence that is complementary to any one of the nucleic acid sequences of (a);
  (e) a nucleic acid sequence encoding a polypeptide having any one of the amino acid sequences set forth in SEQ.ID NO: 2, SEQ.ID NO: 4, SEQ.ID NO: 6, SEQ.ID NO: 8, SEQ.ID NO: 10, SEQ.ID NO 12, SEQ.ID NO: 14, SEQ.ID NO: 16, SEQ.ID NO: 18, SEQ.ID NO: 20, SEQ.ID NO: 22, SEQ.ID NO 24, SEQ.ID NO: 26, and SEQ.ID NO: 49;
  (f) a nucleic acid sequence that encodes a functional variant of any one of the amino acid sequences set forth in SEQ.ID NO: 2, SEQ.ID NO: 4, SEQ.ID NO: 6, SEQ.ID NO: 8, SEQ.ID NO: 10, SEQ.ID NO 12, SEQ.ID NO: 14, SEQ.ID NO: 16, SEQ.ID NO: 18, SEQ.ID NO: 20, SEQ.ID NO: 22, SEQ.ID NO 24, SEQ.ID NO: 26, and SEQ.ID NO: 49; and
  (g) a nucleic acid sequence that hybridizes under stringent conditions to any one of the nucleic acid sequences set forth in (a), (b), (c), (d), (e) or (f).

In at least one embodiment, in an aspect, the psilocybin biosynthetic enzyme complement can comprise a tryptophan synthase subunit B polypeptide, encoded by a nucleic acid selected from:
  (a) SEQ.ID NO: 1;
  (b) a nucleic acid sequence that is substantially identical to the nucleic acid sequence of (a);
  (c) a nucleic acid sequence that is substantially identical to the nucleic acid sequence of (a) but for the degeneration of the genetic code;
  (d) a nucleic acid sequence that is complementary to the nucleic acid
  (e) a nucleic acid sequence encoding a polypeptide having an amino acid sequences set forth in SEQ.ID NO: 2;
  (f) a nucleic acid sequence that encodes a functional variant of the amino acid sequence set forth in SEQ.ID NO: 2; and (g) a nucleic acid sequence that hybridizes under stringent conditions to any one of the nucleic acid sequences set forth in (a), (b), (c), (d), (e) or (f), wherein in the psilocybin derivative precursor compound having formula (LVII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group.

In at least one embodiment, in an aspect, the psilocybin derivative precursor compound can be a chemical compound having a formula (LVIII):

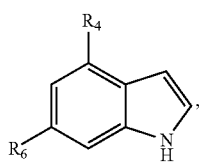
(LVIII)

wherein $R_4$ is a hydroxy group, and wherein $R_6$ is a chlorine atom, and the first formed multi-substituent psilocybin derivative compound has a formula (LV):

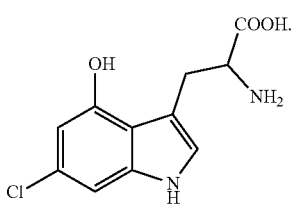
(LV)

In at least one embodiment, in an aspect, the psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein $R_{3a}$ and $R_{3b}$ each are a hydrogen atom, the tryptophan decarboxylase encoded by a nucleic acid sequence selected from:
 (a) SEQ.ID NO: 3, SEQ.ID NO: 5, and SEQ.ID NO: 7;
 (b) a nucleic acid sequence that is substantially identical to any one of the nucleic acid sequences of (a);
 (c) a nucleic acid sequence that is substantially identical to any one of the nucleic acid sequences of (a) but for the degeneration of the genetic code;
 (d) a nucleic acid sequence that is complementary to any one of the nucleic acid sequences of (a);
 (e) a nucleic acid sequence encoding a polypeptide having any one of the amino acid sequences set forth in SEQ.ID NO: 4, SEQ.ID NO: 6, and SEQ.ID NO 8;
 (f) a nucleic acid sequence that encodes a functional variant of any one of the amino acid sequences set forth in SEQ.ID NO: 4, SEQ.ID NO: 6, and SEQ.ID NO 8; and
 (g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LVIII):

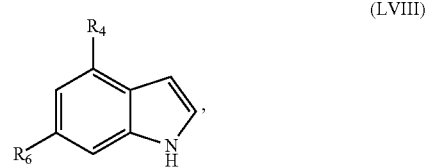
(LVIII)

wherein $R_4$ is a fluorine atom, an amino group, or a hydroxy group, wherein $R_6$ is a fluorine atom, an amino group, a nitrile, or a bromine atom, and the first formed multi-substituent psilocybin derivative compound has a formula (LIX):

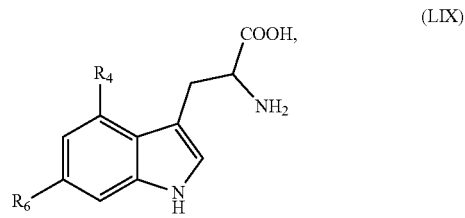
(LIX)

wherein $R_4$ is a fluorine atom, an amino group, or a hydroxy group, wherein $R_6$ is a fluorine atom, an amino group, a nitrile, or a bromine atom, and wherein the second multi-substituent psilocybin derivative has a formula (XXII), (XXVI), (XXIX), (LII), or (LIV):

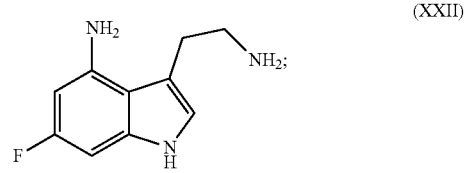
(XXII)

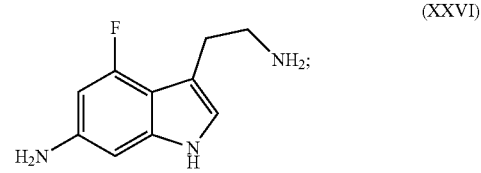
(XXVI)

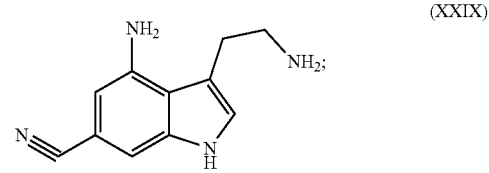
(XXIX)

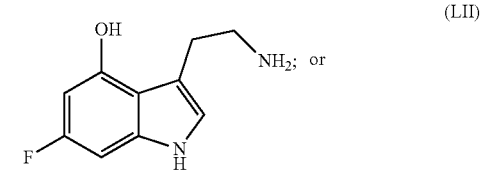
(LII)

(LIV)

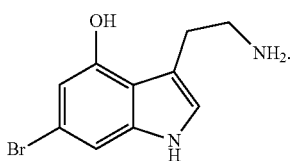

(LX)

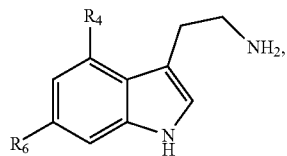

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:
(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of the amino acid sequence set forth in SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LVIII):

(LVIII)

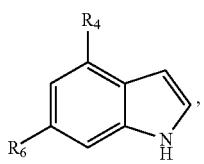

wherein $R_4$ is an acetamidyl group, a fluorine atom, an amino group, or a hydroxy group, wherein $R_6$ is a fluorine atom, an amino group, a nitrile, or a bromine atom, and the first formed multi-substituent psilocybin derivative compound has a formula (LIX):

(LIX)

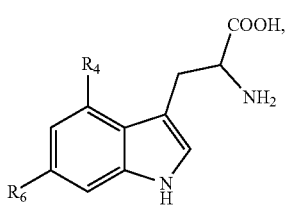

wherein $R_4$ is an acetamidyl group, a fluorine atom, an amino group, or a hydroxy group, wherein $R_6$ is a fluorine atom, an amino group, a nitrile, or a bromine atom, and wherein the second multi-substituent psilocybin derivative has a formula (LX):

and wherein the third multi-substituent psilocybin derivative has a formula (IX), (X), (XVIII), (XXI), (XXV), or (XXVIII):

(IX)

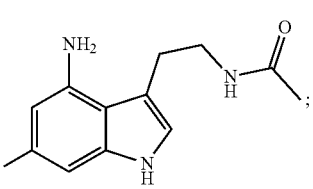

(X)

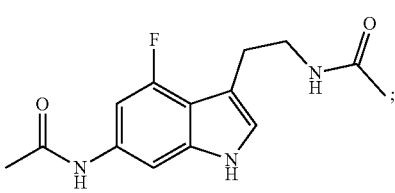

(XVIII)

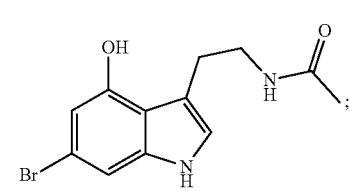

(XXI)

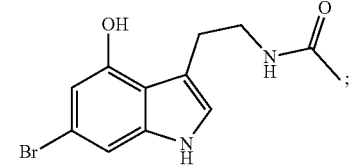

(XXV)

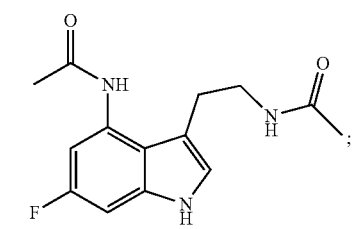

; or (XXVIII)

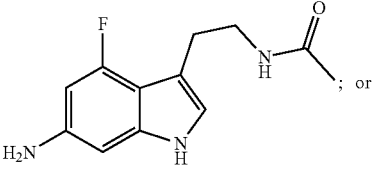

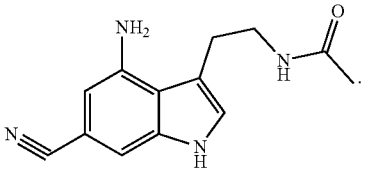

In at least one embodiment, in an aspect, the psilocybin biosynthetic enzyme complement can further comprise an N-methyl transferase to methylate the $R_3$ amino group at $R_3$ and form a fourth multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:
(a) SEQ.ID NO: 11 and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14;
(f) a nucleic acid sequence that encodes a functional variant of any one of the amino acid sequences set forth in SEQ.ID NO: 12 and SEQ.ID NO 14; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LVIII):

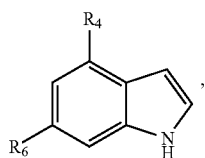

(LVIII)

wherein $R_4$ is an amino group or a hydroxy group, wherein $R_6$ is a chlorine atom, a nitrile group, or a bromine atom, and the first formed multi-substituent psilocybin derivative compound has a formula (LIX):

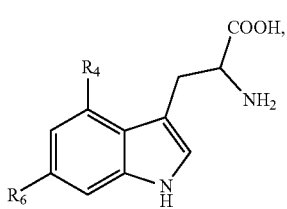

(LIX)

wherein $R_4$ is an amino group or a hydroxy group, wherein $R_6$ is a chlorine atom, a nitrile group, or a bromine atom, and wherein the second multi-substituent psilocybin derivative has a formula (LX):

(LX)

and wherein the fourth multi-substituent psilocybin derivative has a formula (XXVII), (XL), or (LIII):

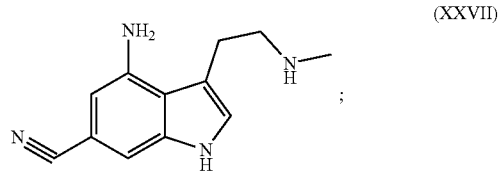

(XXVII)

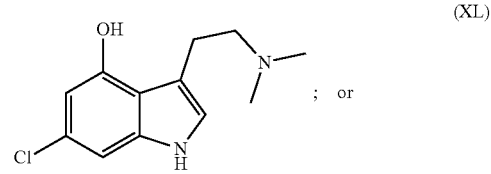

(XL) ; or

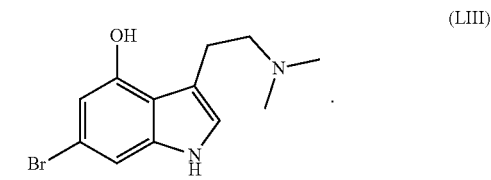

(LIII)

In at least one embodiment, in an aspect, the psilocybin biosynthetic enzyme complement can comprise a prenyl transferase, encoded by a nucleic acid selected from:
(a) SEQ.ID NO: 15, SEQ.ID NO: 17, SEQ.ID NO: 19, and SEQ.ID NO 21;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 16, SEQ.ID NO: 18, SEQ.ID NO: 20, and SEQ.ID NO 22;
(f) a nucleic acid sequence that encodes a functional variant of any one of the amino acid sequences set forth in SEQ.ID NO: 16, SEQ.ID NO: 18, SEQ.ID NO: 20, and SEQ.ID NO 22; and
(g) a nucleic acid sequence that hybridizes under stringent conditions to any one of the nucleic acid sequences set forth in (a), (b), (c), (d), (e) or (f), wherein in the psilocybin derivative precursor compound having formula (LVII), one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is —$CH_2$—$CHNH_2COOH$, and wherein a first multi-substituent psilocybin derivative compound having formula (I) is formed wherein at least one of $R_2$, $R_4$, $R_5$, $R_6$, or $R_7$, is a prenyl group, and $R_{3c}$ is a hydrogen atom.

In at least one embodiment, in an aspect, the psilocybin derivative precursor compound can be a chemical compound having a formula (LXI):

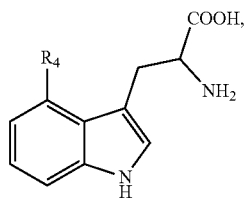

(LXI)

wherein $R_4$ is a hydroxy group, and the first formed multi-substituent psilocybin derivative compound has a formula (L):

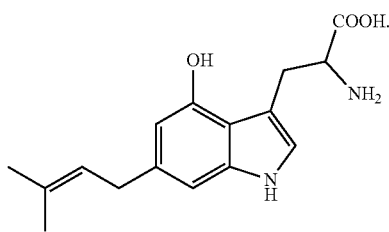

(L)

In at least one embodiment, in an aspect, the psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:

(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;
(f) a nucleic acid sequence that encodes a functional variant of any one of the amino acid sequences set forth in SEQ.ID NO: 4, SEQ.ID NO: 6 and SEQ.ID NO 8; and
(g) a nucleic acid sequence that hybridizes under stringent conditions to any one of the nucleic acid sequences set forth in (a), (b), (c), (d), (e) or (f).

In at least one embodiment, in an aspect, the psilocybin biosynthetic enzyme complement can further comprise an N-methyl transferase to methylate the $R_3$ amino group at $R_3$ and form a fourth multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:

(a) SEQ.ID NO: 11, and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14;
(f) a nucleic acid sequence that encodes a functional variant of any one of the amino acid sequences set forth in SEQ.ID NO: 12, and SEQ.ID NO 14; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXI):

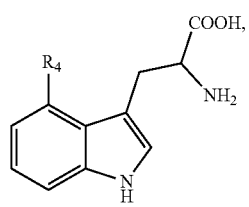

(LXI)

wherein $R_4$ is a propionyloxy or an acetoxy group, and the first formed multi-substituent psilocybin derivative compound has a formula (LIX):

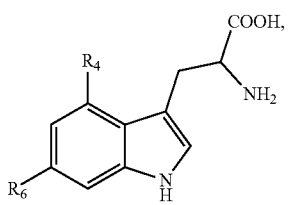

(LIX)

wherein $R_4$ is a propionyloxy or an acetoxy group, wherein $R_6$ is a prenyl group, and wherein the second multi-substituent psilocybin derivative has a formula:

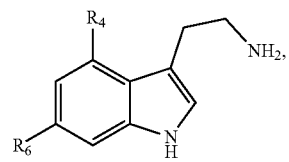

(LX)

wherein $R_4$ is a propionyloxy or an acetoxy group, wherein $R_6$ is a prenyl group, wherein the third multi-substituent psilocybin derivative has a formula (XLI) or (XLII):

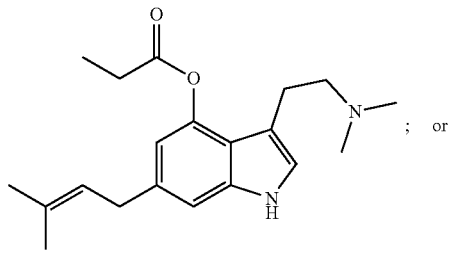

(XLI)

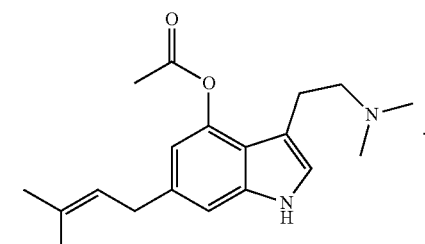

(XLII)

In at least one embodiment, in an aspect, the psilocybin derivative precursor compound can be a chemical compound having a formula (LXII):

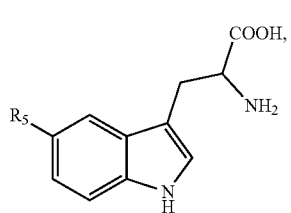

(LXII)

wherein $R_5$ is a chlorine or a fluorine atom, and the first formed multi-substituent psilocybin derivative compound has a formula (LXIII):

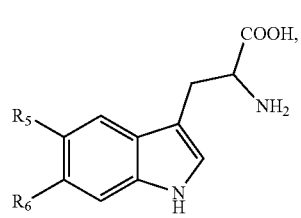

(LXIII)

wherein $R_5$ is a chlorine or a fluorine atom, and wherein $R_6$ is a prenyl group, and wherein the second formed multi-substituent psilocybin derivative compound has a formula (XXXVI) and (XXXVIII):

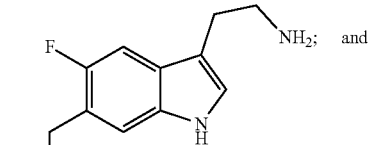

(XXXVI)

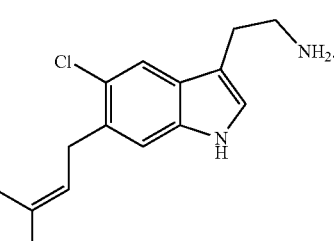

(XXXVIII)

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXI):

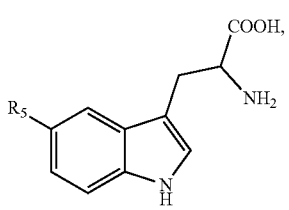

(LXI)

wherein $R_5$ is a chlorine or a fluorine atom, and the first formed multi-substituent psilocybin derivative compound has a formula (LXIII):

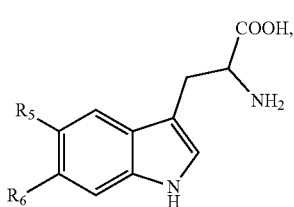

(LXIII)

wherein $R_5$ is a chlorine or a fluorine atom, and wherein $R_6$ is a prenyl group, and wherein the second formed multi-substituent psilocybin derivative compound has a formula (LXIV):

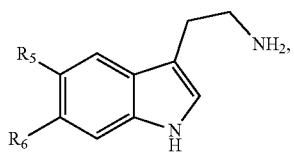

(LXIV)

wherein $R_5$ is a chlorine or a fluorine atom, and wherein $R_6$ is a prenyl group, and wherein the third multi-substituent psilocybin derivative has a formula (XXXV) or (XXXVII):

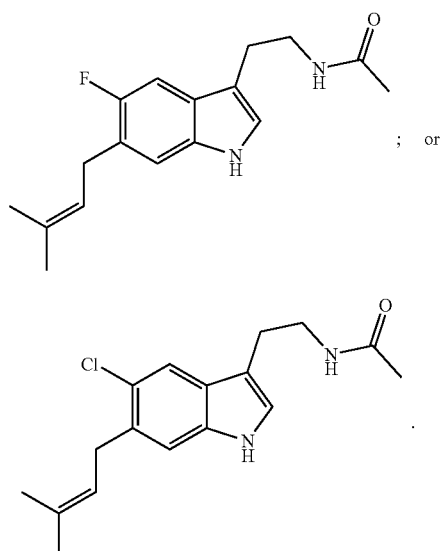

(XXXV)

; or (XXXVII)

In at least one embodiment, in an aspect, the psilocybin biosynthetic enzyme complement can comprise a tryptophan synthase subunit B polypeptide, encoded by a nucleic acid selected from:
(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f), wherein in the psilocybin derivative precursor compound having formula (LVIII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group.

In at least one embodiment, in an aspect, the psilocybin derivative precursor compound can be a chemical compound having a formula (LXV):

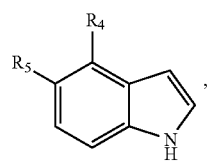

(LXV)

wherein $R_4$ is a hydroxy group, and wherein $R_5$ is a prenyl group, and the first formed multi-substituent psilocybin derivative compound has a formula (LI):

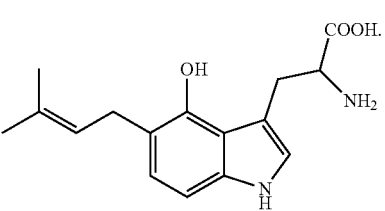

(LI)

In at least one embodiment, in an aspect, the psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:
(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;
(f) a nucleic acid sequence that encodes a functional variant of any one of the amino acid sequences set forth in SEQ.ID NO: 4, SEQ.ID NO: 6 and SEQ.ID NO 8; and (g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXV):

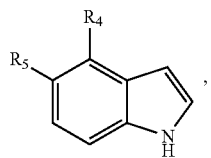
(LXV)

wherein $R_4$ is a fluorine atom and $R_5$ is nitrile group, and the first formed multi-substituent psilocybin derivative compound has a formula (LXIX):

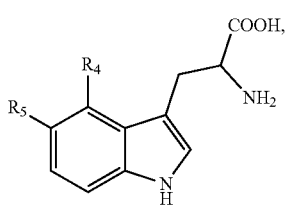
(LXIX)

wherein $R_4$ is a fluorine atom and wherein $R_5$ is a nitrile group, and wherein the second formed multi-substituent psilocybin derivative compound has a formula (XIX):

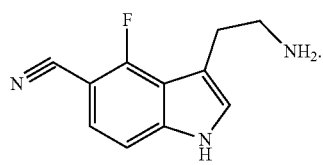
(XIX)

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:
(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXV):

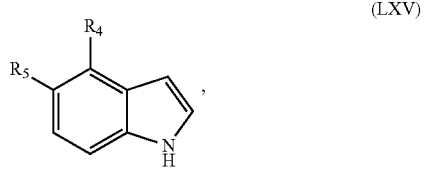
(LXV)

wherein $R_4$ is a fluorine atom and $R_5$ is a hydroxy group or a nitrile group, and the first formed multi-substituent psilocybin derivative compound has a formula (LXIX):

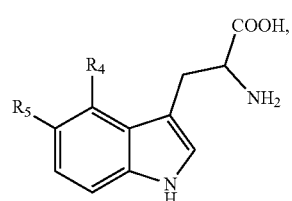
(LXIX)

wherein $R_4$ is a fluorine atom and wherein $R_5$ is a hydroxy group or a nitrile group, and wherein the second formed multi-substituent psilocybin derivative compound has a formula (LXXII):

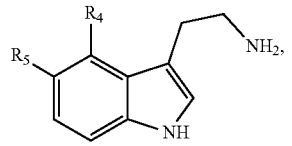
(LXXII)

wherein $R_4$ is a fluorine atom, and wherein $R_5$ is a hydroxy group or a nitrile group, and wherein the third multi-substituent psilocybin derivative has a formula (XVII) or (XX):

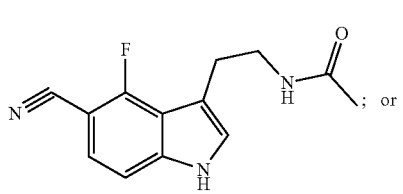
(XVII)
; or

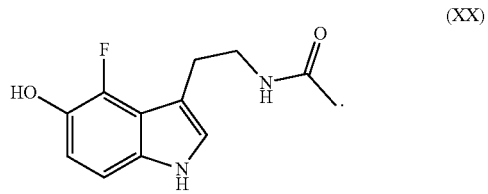
(XX)

In at least one embodiment, in an aspect, the psilocybin biosynthetic enzyme complement can comprise a tryptophan synthase subunit B polypeptide, encoded by a nucleic acid selected from:

(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f), wherein in the psilocybin derivative precursor compound having formula (LVIII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group.

In at least one embodiment, in an aspect, the psilocybin derivative precursor compound can be a chemical compound having a formula (LXVI):

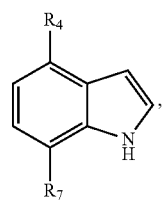

(LXVI)

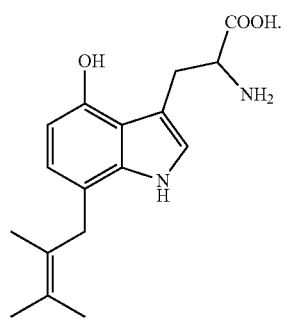

wherein $R_4$ is a hydroxy group, and wherein $R_7$ is a prenyl group, and the first formed multi-substituent psilocybin derivative compound has a formula (XLIX):

(XLIX)

In at least one embodiment, in an aspect, the psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:

(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;
(f) a nucleic acid sequence that encodes a functional variant of any one of the amino acid sequences set forth in SEQ.ID NO: 4, SEQ.ID NO: 6 and SEQ.ID NO 8; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVI):

(LXVI)

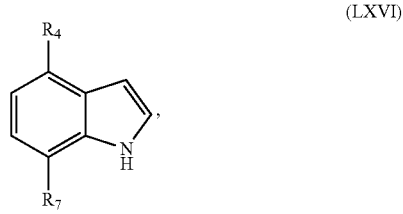

wherein $R_4$ is a fluorine atom and $R_7$ is nitrile group, and the first formed multi-substituent psilocybin derivative compound has a formula (LXX)

(LXX)

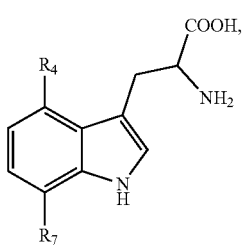

wherein $R_4$ is a fluorine atom and wherein $R_7$ is a nitrile group, and wherein the second formed multi-substituent psilocybin derivative compound has a formula (XXIV):

(XXIV)

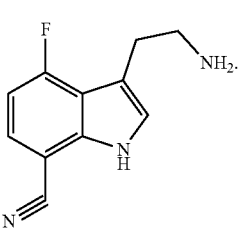

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVI):

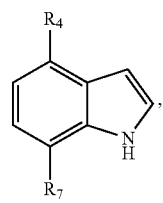

(LXVI)

wherein $R_4$ is a fluorine atom or a chlorine atom and $R_7$ is a prenyl group or a nitrile group, and the first formed multi-substituent psilocybin derivative compound has a formula (LXX):

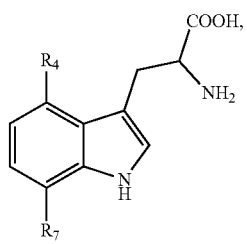

(LXX)

wherein $R_4$ is a fluorine atom or a chlorine atom and wherein $R_7$ is a prenyl group or a nitrile group, and wherein the second formed multi-substituent psilocybin derivative compound has a formula (LXXIII):

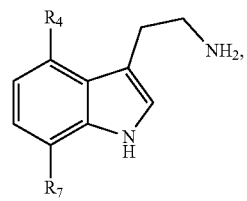

(LXXIII)

wherein $R_4$ is a fluorine atom or a chlorine atom, and wherein $R_7$ is a prenyl group or a nitrile group, and wherein the third multi-substituent psilocybin derivative has a formula (XXIII) or (XX):

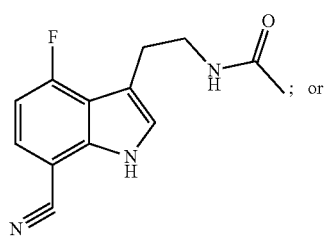

(XXIII); or

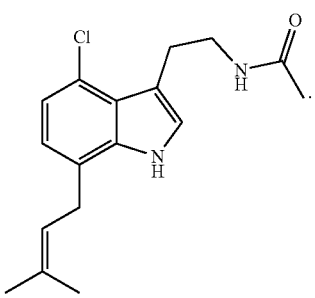

(XXXIV)

In at least one embodiment, in an aspect, the psilocybin biosynthetic enzyme complement can further comprise an N-methyl transferase to methylate the $R_3$ amino group at $R_3$ and form a further multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:

(a) SEQ.ID NO: 11, and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14;
(f) a nucleic acid sequence that encodes a functional variant of any one of the amino acid sequences set forth in SEQ.ID NO: 12, and SEQ.ID NO 14; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVI):

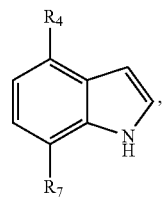

(LXVI)

wherein $R_4$ is a chlorine atom and $R_7$ is a hydroxy group, and the first formed multi-substituent psilocybin derivative compound has a formula (LXX)

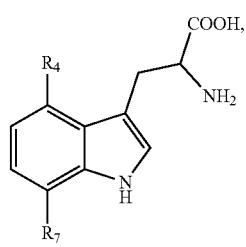

(LXX)

wherein $R_4$ is a hydroxy group and wherein $R_7$ is a chlorine atom, and wherein the second formed multi-substituent psilocybin derivative compound has a formula

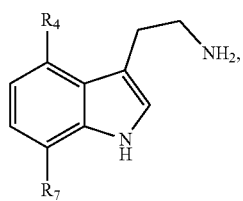

(LXXIII)

wherein $R_4$ is a hydroxy group, and wherein $R_7$ is a chlorine atom, and wherein the third multi-substituent psilocybin derivative has a formula (XXXIX):

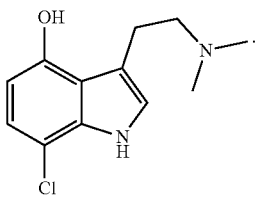

(XXXIX)

In at least one embodiment, in an aspect, the psilocybin biosynthetic enzyme complement can comprise a tryptophan synthase subunit B polypeptide, encoded by a nucleic acid selected from:
(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f), wherein in the psilocybin derivative precursor compound having formula (LVIII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group, and the psilocybin biosynthetic enzyme complement further comprises a tryptophan decarboxylase to decarboxylate a $R_3$—$CH_2$—$CHNH_2COOH$ group of the first multi-substituent psilocybin derivative compound, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:
(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;
(f) a nucleic acid sequence that encodes a functional variant of any one of the amino acid sequences set forth in SEQ.ID NO: 4, SEQ.ID NO: 6 and SEQ.ID NO 8; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVII):

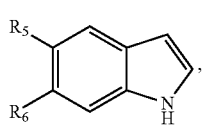

(LXVII)

wherein $R_5$ is a fluorine atom, a chlorine atom, or a nitrile group and $R_6$ is a fluorine atom, an amino group or a prenyl group, and the first formed multi-substituent psilocybin derivative compound has a formula (LXIII):

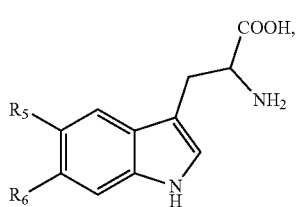

(LXIII)

wherein R₅ is a fluorine atom, a chlorine atom, or a nitrile group and wherein R₆ is a is a fluorine atom, an amino group or a prenyl group, and wherein the second formed multi-substituent psilocybin derivative compound has a formula (XI), (XVI), (XXXVI), or (XXXVIII):

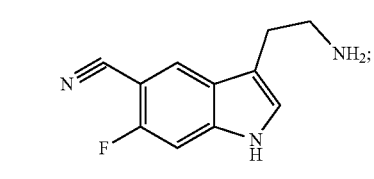

(XI)

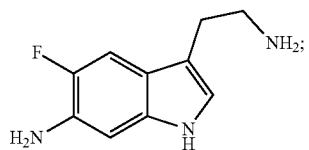

(XVI)

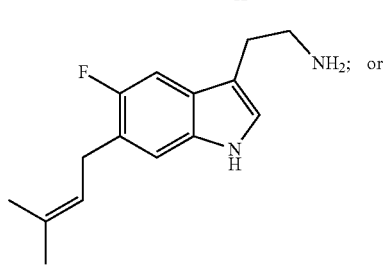

(XXXVI)

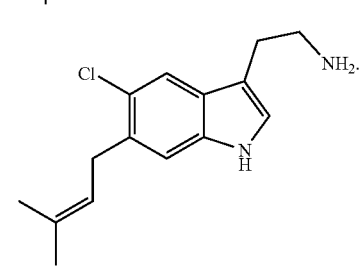

(XXXVIII)

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVII):

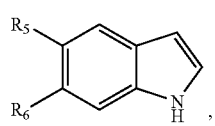

(LXVII)

wherein R₅ is a fluorine atom or a chlorine atom and R₆ is an amino group, an acetamidyl group, or a prenyl group, and the first formed multi-substituent psilocybin derivative compound has a formula (LXIII):

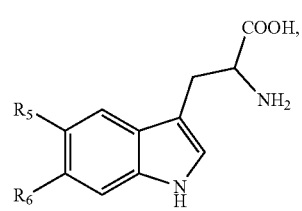

(LXIII)

wherein R₅ is a fluorine atom or a chlorine atom and wherein R₆ is an amino group, an acetamidyl group, or a prenyl group, and wherein the second formed multi-substituent psilocybin derivative compound has a formula (LXXIV):

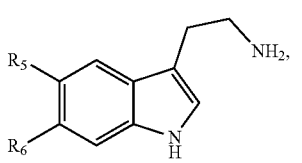

(LXXIV)

wherein R₅ is a fluorine atom or a chlorine atom, and wherein R₆ is an amino group, an acetamidyl group, or a prenyl group, and wherein the third multi-substituent psilocybin derivative has a formula (XIV), (XV), (XXXV), or (XXXVII):

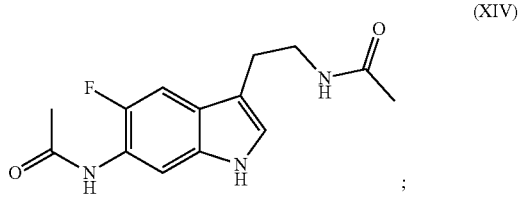

(XIV)

(XV)

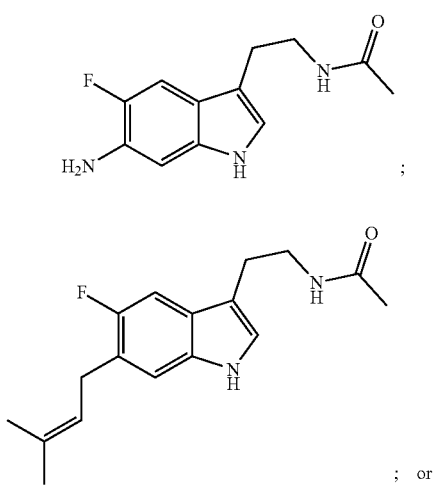

; (XXXV)

(XXXVII)

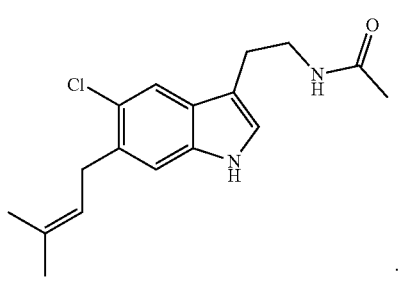

In at least one embodiment, in an aspect, the psilocybin biosynthetic enzyme complement can further comprise an N-methyl transferase to methylate the $R_3$ amino group at $R_3$ and form a fourth multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:

(a) SEQ.ID NO: 11, and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14; (f) a nucleic acid sequence that encodes a functional variant of any one of the amino acid sequences set forth in SEQ.ID NO: 12, and SEQ.ID NO 14; and
(g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVII):

(LXVII)

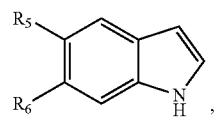

wherein $R_5$ is a chlorine atom and $R_6$ is a prenyl group, and the first formed multi-substituent psilocybin derivative compound has a formula (LXIII):

(LXIII)

wherein $R_5$ is a chlorine atom and wherein $R_6$ is a prenyl group, and wherein the second formed multi-substituent psilocybin derivative compound has a formula (LXXIV):

(LXXIV)

wherein $R_5$ is a chlorine atom, and wherein $R_6$ is a prenyl group, and wherein the third multi-substituent psilocybin derivative has a formula (XLIV):

(XLIV)

In at least one embodiment, in an aspect, the psilocybin biosynthetic enzyme complement can comprise a tryptophan synthase subunit B polypeptide, encoded by a nucleic acid selected from:

(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and (g) a nucleic acid sequence that hybridizes under stringent conditions to any one of the nucleic acid sequences set forth in (a), (b), (c), (d), (e) or (f), wherein in the psilocybin derivative precursor compound having formula (LVIII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group, and the psilocybin biosynthetic enzyme complement further comprises a tryptophan decarboxylase to decarboxylate a $R_3$—$CH_2$—$CHNH_2COOH$ group of the first multi-substituent psilocybin derivative compound, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:

(a) SEQ.ID NO: 3, SEQ.ID NO: 5, and SEQ.ID NO: 7;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 4, SEQ.ID NO: 6, SEQ.ID NO: and SEQ.ID NO 8;

(f) a nucleic acid sequence that encodes a functional variant of any one of the amino acid sequences set forth in SEQ.ID NO: 4, SEQ.ID NO: 6 and SEQ.ID NO 8; and (g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVIII):

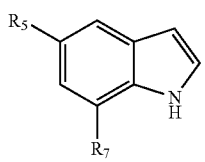

(LXVIII)

wherein $R_5$ is a fluorine atom, and $R_7$ is a nitro group or a prenyl group, and the first formed multi-substituent psilocybin derivative compound has a formula (LXXI):

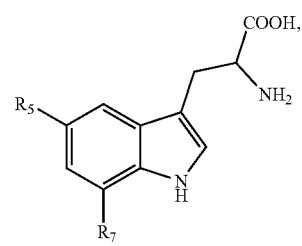

(LXXI)

wherein $R_5$ is a fluorine atom, and wherein $R_7$ is a nitro group atom or a prenyl group, and wherein the second formed multi-substituent psilocybin derivative compound has a formula (XIII) or (XXXIII):

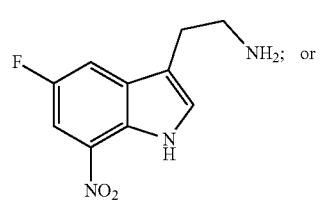

(XIII)

(XXXIII)

In at least one embodiment, in an aspect, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;

(b) a nucleic acid sequence that is substantially identical to the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having the amino acid sequence set forth in SEQ.ID NO: 10;

(f) a nucleic acid sequence that encodes a functional variant of any one of the amino acid sequences set forth in SEQ.ID NO: 10; and (g) a nucleic acid sequence that hybridizes under stringent conditions to any one of the nucleic acid sequences set forth in (a), (b), (c), (d), (e) or (f).

In at least one embodiment, in an aspect, the psilocybin derivative precursor compound can be a chemical compound having a formula (LXVIII):

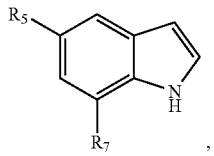

(LXVIII)

wherein $R_5$ is a fluorine atom, and $R_7$ is a nitro group or a prenyl group, and the first formed multi-substituent psilocybin derivative compound has a formula (LXXI):

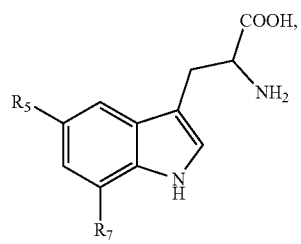

(LXXI)

wherein $R_5$ is a fluorine atom, and wherein $R_7$ is a nitro group atom or a prenyl group, and wherein the second formed multi-substituent psilocybin derivative compound has a formula (LXXV):

(LXXV)

wherein $R_5$ is a fluorine atom, and wherein $R_7$ is a nitro group or a prenyl group, and wherein the third multi-substituent psilocybin derivative has a formula (XII) or (XXXII):

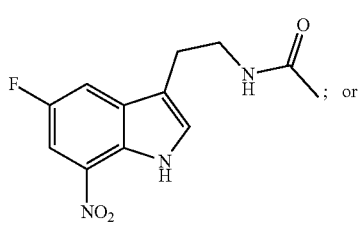

(XII)

; or

-continued

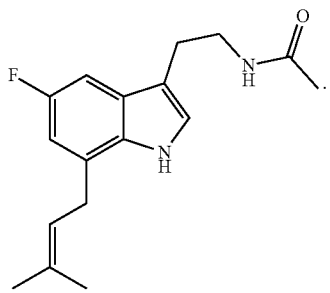

(XXXII)

In at least one embodiment, in an aspect, the psilocybin biosynthetic enzyme complement can contain a prenyl transferase encoded by a nucleic acid selected from:

(a) SEQ.ID NO: 15, SEQ.ID NO: 17, SEQ.ID NO: 19, and SEQ.ID NO 21, (b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 16, SEQ.ID NO: 18, SEQ.ID NO: 20, and SEQ.ID NO 22;

(f) a nucleic acid sequence that encodes a functional variant of any one of the amino acid sequences set forth in SEQ.ID NO: 16, SEQ.ID NO: 18, SEQ.ID NO: 20, and SEQ.ID NO 22; and (g) a nucleic acid sequence that hybridizes under stringent conditions to any one of the nucleic acid sequences set forth in (a), (b), (c), (d), (e) or (f), wherein in the psilocybin derivative precursor compound having formula (LVIII), one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group or a hydrogen atom.

In at least one embodiment, the psilocybin derivative precursor compound having formula (LXXVII):

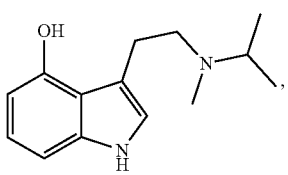

(LXXVII)

and the first multi-substituent psilocybin derivative compound has the formula (LXXVI):

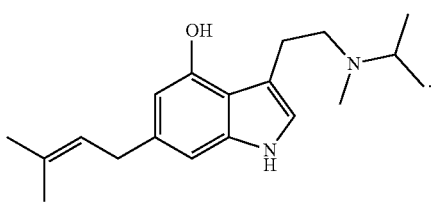

(LXXVI)

In at least one embodiment, in an aspect, the method can further include a step comprising isolating the multi-substituent psilocybin derivative compound, from the host cell and/or a host cell medium.

In at least one embodiment, in an aspect, the host cell can be a microorganism.

In at least one embodiment, in an aspect, the host cell can be a bacterial cell or a yeast cell.

In at least one embodiment, in an aspect, the host cell can be an *Escherichia coli* cell or a *Saccharomyces cerevisiae* cell.

In another aspect the present disclosure provides, in at least one embodiment, a use of a chemical compound or a salt thereof having a formula (I):

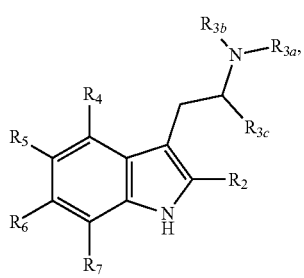

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, in the manufacture of a pharmaceutical or recreational drug formulation.

In at least one embodiment the manufacture can comprise formulating the chemical compound with an excipient, diluent, or carrier.

In another aspect the present disclosure provides, in at least one embodiment, a use of a chemical compound or a salt thereof having a formula (I):

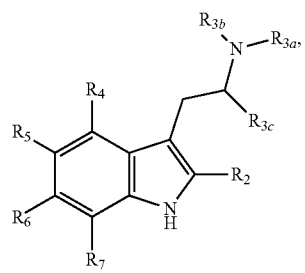

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIG. 11C depicts a possible direction amination method with $H_2O_2$ and $NH_3 \cdot H_2O$ with the help of a catalyst.

FIG. 13A depicts transformations for an initially synthesized 7-nitrated psilocybin derivative to other psilocybin derivatives containing two types of groups at the $C_5$ and $C_7$ atoms, notably the group at the $C_5$ atom is either a keto group or a carboxylic acid, and the group at the $C_7$ atom is either a nitro, amine, nitrile, hydroxyl, iodide, or fluoride. FIG. 13B depicts example chemical transformations using an initially synthesized 5-carboxy psilocybin derivative to other O-4-glycosylated psilocybin derivatives containing two types of groups at the $C_5$ atom and the $C_7$ atom, notably the group at the $C_5$ atom is either an ester or an amide, the group at the $C_7$ atom is either a nitro or amine. FIG. 13C depicts further example chemical transformations of an initially synthesized 5-nitrated psilocybin derivative to form 5,6,7-tri-substituted psilocybin derivatives containing up to three types of groups at the $C_5$, $C_6$ and $C_7$ carbon atoms. The groups attached to the $C_5$ carbon atom can be either a nitro, amino, or an N-acetamido group, while the group attached to the $C_6$ carbon atom can be either a halide, a nitro group or an amino group, and the group attached to the $C_7$ carbon atom can be either a formyl, carboxy or amide group. FIG. 13-D depicts the preparation of a hydroxy-psilocybin derivative (Compound 13-D4) which can then be prenylated, either in vitro or in vivo, using a prenyl transferase to form, for example, a $C_6$ prenylated derivative of compound 13-D4. It is noted that specific chemical compounds in FIGS. 13A-13D are labeled as 13A-1, 13A-2 etc. (FIG. 13A); 13B-1, 13B-2 etc. (FIG. 13B); 13C-1, 13C-2 etc. (FIG. 13C) and 13D-1, 13D-2 etc. (FIG. 13D).

Figure 1:
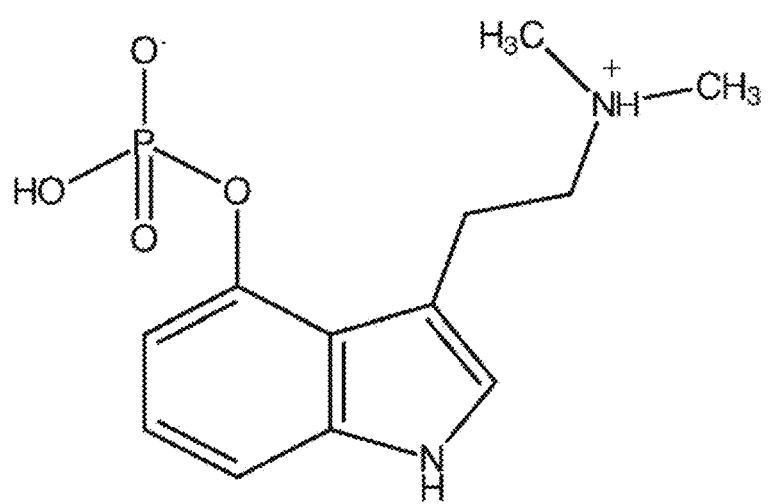
FIG. 1 depicts the chemical structure of psilocybin.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "psilocybin", refers to a chemical compound having the structure set forth in FIG. 1.

Figure 2:
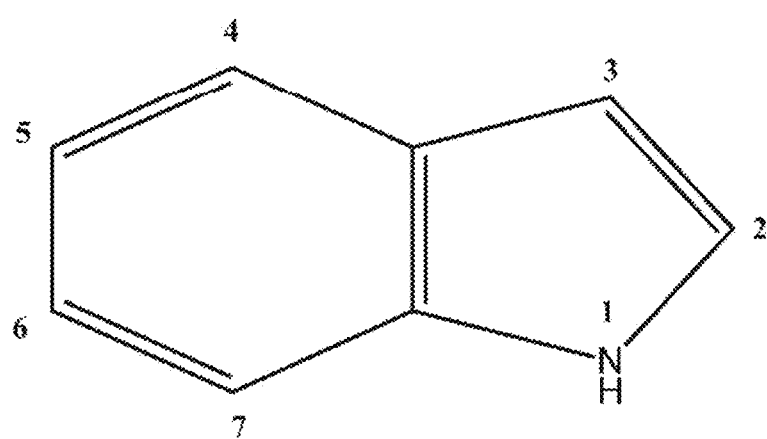
FIG. 2 depicts a certain prototype structure of psilocybin and psilocybin derivative compounds, namely an indole. Certain carbon and nitrogen atoms may be referred to herein by reference to their position within the indole structure, i.e., $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example, $R_4$ and $R_6$ reference chemical groups attached to the $C_4$ and $C_6$ atom, respectively. In addition, $R_{3A}$ and $R_{3B}$, in this respect, reference chemical groups extending from the ethyl-amino group extending in turn from the $C_3$ atom of the prototype indole structure.

The terms "psilocybin derivative", as used herein, refers to compounds that can be derivatized from psilocybin, wherein such compounds include an indole prototype structure and a $C_3$ ethylamine or ethylamine derivative group having the formula (LXXVIII):

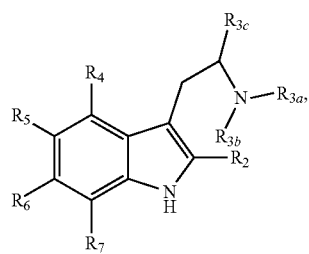

(LXXVIII)

wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group. Psilocybin derivatives include compounds containing one or more substituents at each of $C_2$, $C_4$, $C_5$, $C_6$ and $C_7$. Thus, in formula (LXXVIII), $R_2$, $R_4$, $R_5$, $R_6$ and $R_7$ can each be, for example, any of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, (x) an O-alkyl group, (xi) an (xii) O-acyl group, (xiii) a phosphate group, or (xiv) a hydrogen atom.

The term "multiple-substituent psilocybin derivative" refers to a psilocybin derivative compound wherein two or more substituent entities have been bonded to psilocybin or a psilocybin derivative. Reference may be made to specific carbon atoms which may be substituted. Furthermore the substituent entities may be referred to as S1, S2, S3 or S4, wherein each of S1, S2, S3 and S4 refer to a different substituent entity. For example, a 5,7-S1,S2-di-psilocybin derivative refers to a psilocybin derivative in which carbon atom number 5 and carbon number 7 (as identified in the indole prototype structure) each possess a different substituent entity, or, similarly, a 2,5,6-tri-S1,S2,S3-psilocybin derivative refers to a psilocybin derivative in which carbon atom number 2,5,6 (as identified in the indole prototype structure) possess a different substituent entity (or at least two of the three substituents are different). By way of another example, a 2,5,6-tri-S1,S2,S2-psilocybin derivative refers to a psilocybin derivative in which carbon atom number 2,5,6 (as identified in the indole prototype structure) each possess a substituent entity, the substituent entity possessed by carbon atom number 5 and 6 being the same. It is noted that S1, S2, S3 and S4 can herein additionally include numerical subscripts, such as $S1_5$, $S3_6$, $S4_7$ etc. Where such numerical values are included, they reference the numbered C atom of the prototype indole structure. Thus, for example, $S1_5$ is a substituent entity extending from the $C_5$ atom of the indole ring structure, $S3_7$ is a substituent entity extending the $C_7$ atom of the indole ring structure, and so forth. The term multiple-substituent psilocybin derivatives further includes chemical compounds having a chemical formula (I):

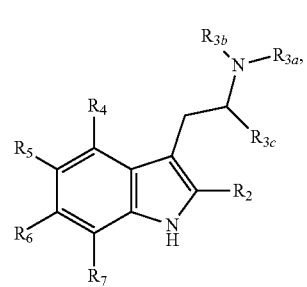

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group. The term multiple-substituent psilocybin derivatives, further also includes compounds having a formula (IV):

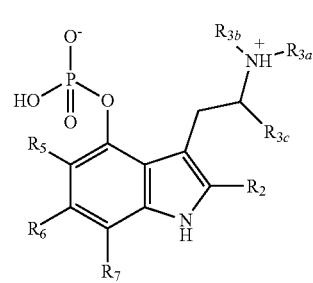

(IV)

wherein, at least two of $R_2$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group. The term further includes salts of multiple-substituent psilocybins, such as a sodium salt, a potassium salt etc.

The terms "halogen", "halogenated" and "halo-", as used herein, refer to the class of chemical elements consisting of fluorine (F), chlorine (C$_1$), bromine (Br), and iodine (I). Accordingly, halogenated compounds can refer to "fluorinated", "chlorinated", "brominated", or "iodinated" compounds.

The terms "phosphate group" or "phospho group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein refers to a molecule containing one atom of oxygen bonded to one atom of hydrogen, and having the formula —OH. A hydroxy group through its oxygen atom may be chemically bonded to another entity.

The term "nitro group" and "nitro", as used herein refers to a molecule containing one atom of nitrogen bonded to two atoms of oxygen and having the formula —NO$_2$. A nitro group through its nitrogen atom may be chemically bonded to another entity. Furthermore, it is noted that an entity attached to a nitro group may be referred to herein as a "nitrated" entity, e.g., a nitrated psilocybin derivative is a psilocybin derivative possessing a nitro group.

The term "amino group" and "amino", as used herein refers to a molecule containing one atom of nitrogen bonded to hydrogen atoms and having the formula —NH$_2$. An amino group also may be protonated and having the formula —NH$_3^+$. An amino group through its nitrogen atom may be chemically bonded to another entity. Furthermore, it is noted that an entity attached to an amino group may be referred to herein as an "aminated" entity, e.g., an aminated psilocybin derivative is a psilocybin derivative possessing either an amino group or a N-substituted amino group.

The term "N-substituted amino group", as used herein, refers to an amino group wherein at least one of the hydrogen atoms has been substituted by another atom or group, such as, for example, an alkyl group, an acyl group, an aryl group a sulfonyl group etc. An N-substituted amino group also may be protonated, and the amino group through its nitrogen atom may be chemically bonded to another entity. Thus, N-substituted amino group may be represented herein as:

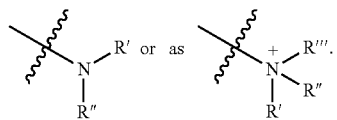

Furthermore N-substituted amino groups include:
chemical group (IV) (an alkyl group, an aryl group):

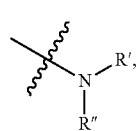

(IV)

wherein R' and R" are each independently selected from a hydrogen atom, an alkyl group, and an aryl group, provided however that at least one of R', and R" is not a hydrogen atom;

chemical group (V):

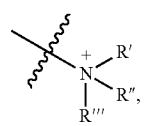

(V)

wherein R', R" and R''' are each independently selected from a hydrogen atom, an alkyl group, and an aryl group, provided however that at least one of R', R", and R''' is not a hydrogen atom;

chemical group (VI) (an acyl group):

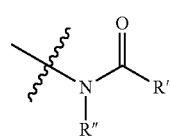

(VI)

wherein R' and R" are each independently selected from a hydrogen atom, an alkyl group and an aryl group;

chemical group (VII) (a sulfonyl group):

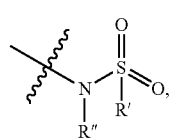

(VII)

wherein R', and R" are each independently selected from a hydrogen atom, an alkyl group and an aryl group; and chemical group (VIII) (a sulfonate group):

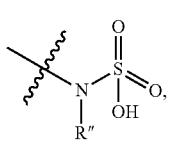

(VIII)

wherein R" is selected from a hydrogen atom, an alkyl group, and an aryl group. The nitrogen atom of chemical groups (VI), (VII) and (VIII) can also be positively charged and be further substituted with H, or R'''. It is noted that R', R" and R''' can herein additionally include numerical subscripts, such as $_{5a}$, $_{6b}$, $_{7b}$ etc., and be represented, for example, as R'$_{5a}$, R"$_{6b}$ or R'''$_{7a}$, respectively. Where such numerical values are included, they reference chemical entity extending from the amino group extending in turn from the thus numbered C atom of the prototype indole structure. Thus, for example, R'$_{5a}$ is a chemical entity extending from an aminated group attached to the C$_5$ atom of the indole ring structure, R'$_{2a}$ is a chemical entity extending from an aminated group attached to the C$_2$ atom of the indole ring structure, and so forth. Furthermore, it is noted that an entity attached to an N-substituted amino group may be referred to herein as an "aminated" entity, e.g., an aminated psilocybin derivative is a psilocybin derivative possessing either an amino group or a N-substituted amino group.

The terms "carboxyl group", "carboxyl", and "carboxy", as used herein, refer to a molecule containing one atom of carbon bonded to an oxygen atom and a hydroxy group and having the formula —COOH. A carboxyl group includes a deprotonated carboxyl group, i.e., a carboxyl ion, having the formula —COO⁻. In its deprotonated form a carboxyl group may form a carboxyl salt, for example, a sodium or potassium carboxyl salt, or an organic carboxyl salt, all of which may be represented herein as COO⁻M⁺. It is further to be understood that a carboxyl group through its carbon atom may be chemically bonded to another entity. Furthermore, it is noted that an entity attached to a carboxyl group may be referred to herein as a "carboxylated" entity, e.g., a carboxylated psilocybin derivative is a psilocybin derivative possessing either a carboxyl group or a OH-substituted carboxyl group.

The term "carboxylic acid derivative", as used herein, refers to a carboxyl group wherein the hydroxy group of the carboxyl group has been substituted by another atom or group, such as, for example, an —OR" group or an —NR'R" group. Thus a carboxylic acid derivative includes chemical group (III):

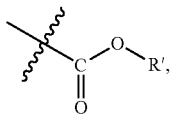

(III)

wherein, R', is an alkyl group, an aryl group and a hydrogen atom. It is noted that chemical group (III) is an ester. It is noted that R' can herein additionally include numerical subscripts, such as $_{3c, 6b, 7b}$ etc., and be represented, for example, as $R'_{3c}$, $R'_{6b}$ or $R'_{7a}$, respectively. Where such numerical values are included, they reference chemical entity extending from the carboxyl group extending in turn from the thus numbered C atom of the prototype indole structure. Thus, for example, $R'_{5a}$ is a chemical entity extending from a carboxylated group attached to the $C_5$ atom of the indole ring structure, $R'_{2a}$ is a chemical entity extending from a carboxylated group attached to the $C_2$ atom of the indole ring structure, and so forth. Furthermore, it is noted that an entity attached to a carboxylic acid derivative may be referred to herein as an "carboxylated" entity, e.g., a carboxylated psilocybin derivative is a psilocybin derivative possessing either a carboxyl group or an OH-substituted carboxyl group.

The terms "aldehyde" or "aldehyde group", as used herein, refers to a molecule containing one atom of carbon double bonded to an oxygen atom, and bonded to a hydrogen atom, and having the chemical formula:

which may, further alternatively be represented herein as —CHO. A —CHO group may also by referred to herein as a formyl group. It is to be understood that an aldehyde through its carbon atom may be chemically bonded to another entity.

The terms "ketone" or "ketone group", as used herein, refer to a molecule containing two atoms of carbon, a first carbon atom double bonded to an oxygen atom, and the first carbon further bonded to a second carbon atom, the molecule having the chemical formula:

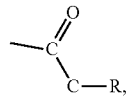

wherein R is any entity or plurality of entities which taken together allow the carbon atom bonded to R to achieve its ordinary valency. Thus, for example, R may represent 3 hydrogen atoms, or R may represent 2 hydrogen atoms and a methyl group. It is to be understood that a ketone through its first carbon atom may be chemically bonded to another entity, such as an alkylene group $(C_1$-$C_6)$-alkylene.

The term "nitrile group" and "nitrile", as used herein, refer to a molecule containing one atom of carbon bonded to a nitrogen atom and having the formula

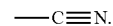

It is to be understood that a nitrile group through its carbon atom may be chemically bonded to another entity. Furthermore, it is noted that an entity attached to a nitrile group may be referred to herein as a "nitrilated" entity, e.g., a nitrilated psilocybin derivative is a psilocybin derivative possessing a nitrile group.

The terms "glycosylated" or "glycosyl", as used herein, refer to a saccharide group, such as a mono-, di-, tri- oligo- or a poly-saccharide group, which can be or has been bonded from its anomeric carbon either in the pyranose or furanose form, either in the α or the β conformation. When bonded through its anomeric carbon via an oxygen atom to another entity, the bonded saccharide group, inclusive of the oxygen atom, may be referred to herein as a "glycosyloxy" group. Example monosaccharide groups include, but are not limited to, a pentosyl, a hexosyl, or a heptosyl group. The glycosyloxy group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical isomers, anomers, and epimers of the glycosyloxy group. Thus, a hexose group, for example, can be either an aldose or a ketose group, can be of D- or L-configuration, can assume either an α or β conformation, and can be a dextro- or levo-rotatory with respect to plane-polarized light. Example glycosyloxy groups further include, without limitation, glucosyl groups, glucuronic acid groups, galactosyl groups, fucosyl groups, xylose groups, arabinose groups, and rhamnose groups.

The terms "prenyl group", and "prenyl", as used herein refers to a chemical group having the structure (LVI):

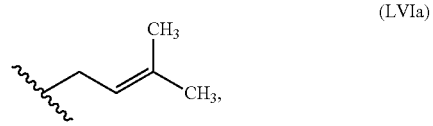 [SMILES: *CC=C(C)C]

(LVIa)

and further includes poly-prenyl compounds having the structure:

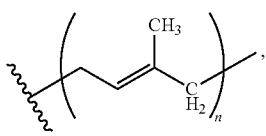

(LVIb)

Wherein n is an integer having a value of 2 or more, e.g., 2, 3, 4, 5, etc. Furthermore, the term "prenyl compound" refers to a chemical compound being, substantially being, or possessing a reactive prenyl group, i.e., a prenyl group that may be received by another entity. Prenyl compounds include, for example, geranyl pyrophosphate (GPP), dimethylallyl diphosphate (DMAPP), farnesyl pyrophosphate (FPP) and geranylgeranyl pyrophosphate (GGPP).

The term "alkyl group", as used herein, refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$), further also includes cyclic alkyl groups, including cyclo-propane, cyclo-butane, cyclo-pentane, cyclo-hexane, and cyclo-heptane.

The term "cycloalkyl" refers to cyclic alkyl groups, including ($C_3$-$C_{20}$), ($C_3$-$C_{10}$), and ($C_3$-$C_6$) cycloalkyl groups, and further including cyclo-propane, cyclo-butane, cyclo-pentane, cyclo-hexane, and cyclo-heptane.

The term "O-alkyl group", as used herein, refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "aryl group", as used herein, refers to a hydrocarbon group arranged in an aromatic ring and can, for example, be a $C_6$-$C_{14}$-aryl, a $C_6$-$C_{10}$-aryl. Aryl groups further include phenyl, naphthyl, tetrahydronaphthyl, phenanthrenyl, biphenylenyl, indanyl, tolyl, xylyl, or indenyl groups, and the like.

The term "acyl group", as used herein, refers to a carbon atom double bonded to an oxygen and single bonded to an alkyl group. The carbon atom further can be bonded to another entity. An acyl group can be described by the chemical formula: —C(═O)—$C_nH_{2n+1}$.

The term "O-acyl group", as used herein, refers to an acyl group in which the carbon atom is single bonded to an additional oxygen atom. The additional oxygen atom can be bonded to another entity. An O-acyl group can be described by the chemical formula: —O—C(═O)—$C_nH_{2n+1}$. Furthermore, depending on the carbon chain, length specific O-acyl groups may be termed an acetoxy group (n=1), a propanoyloxy group (n=2), butyryloxy group (n=3), a pentanoyloxy group (n=4) etc.

The term "alcohol group" or "hydroxylalkyl", as used herein, refers to a hydrocarbon group arranged in a chain having the chemical formula $C_nH_{n+1}OH$. Depending on the carbon chain, length specific alcohol groups may be termed a methanol group (n=1) or hydroxymethyl, an ethanol group (n=2) or hydroxyethyl, a propanol group (n=3) or hydroxypropyl, a butanol group (n=4) or hydroxybutyl etc.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner. It is further noted that the prenylated psilocybin derivatives may alter the function of a 5-$HT_{2A}$ receptor by acting as an agonist or antagonist of the 5-$HT_{1A}$ receptor, and that prenylated psilocybin derivatives according to the present disclosure may alter the function of a 5-$HT_{2A}$ receptor by directly interacting therewith or binding thereto, or by indirectly interacting therewith through one or more other molecular entities.

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-$HT_{1A}$ is generally not associated with hallucination, although many hallucinogenic compounds are known to modulate 5-$HT_{1A}$ receptors to impart complex physiological responses (Inserra et al., 2020, Pharmacol Rev 73: 202).

The term "modulating 5-$HT_{1A}$ receptors", as used herein, refers to the ability of a compound disclosed herein to alter the function of 5-$HT_{1A}$ receptors. A 5-$HT_{1A}$ receptor modulator may activate the activity of a 5-$HT_{1A}$ receptor, may activate or inhibit the activity of a 5-$HT_{1A}$ receptor depending on the concentration of the compound exposed to the 5-HT$_{1A}$ receptor, or may inhibit the activity of a 5-HT$_{1A}$ receptor. Such activation or inhibition may be contingent on the occurrence of a specific event, such as activation of a signal transduction pathway, and/or maybe manifest only in particular cell types. The term "modulating 5-HT$_{1A}$ receptors," also refers to altering the function of a 5-HT$_{1A}$ receptor by increasing or decreasing the probability that a complex forms between a 5-HT$_{1A}$ receptor and a natural binding partner to form a multimer. A 5-HT$_{1A}$ receptor modulator may increase the probability that such a complex forms between the 5-HT$_{1A}$ receptor and the natural binding partner, may increase or decrease the probability that a complex forms between the 5-HT$_{1A}$ receptor and the natural binding partner depending on the concentration of the compound exposed to the 5-HT$_{1A}$ receptor, and or may decrease the probability that a complex forms between the 5-HT$_{1A}$ receptor and the natural binding partner. It is further noted that the prenylated psilocybin derivatives may alter the function of a 5-HT$_{1A}$ receptor by acting as an agonist or antagonist of the 5-HT$_{1A}$ receptor, and that prenylated psilocybin derivatives according to the present disclosure may alter the function of a 5-HT$_{1A}$ receptor by directly interacting therewith or binding thereto, or by indirectly interacting therewith through one or more other molecular entities.

The term "5-HT$_{1A}$ receptor-mediated disorder", as used herein, refers to a disorder that is characterized by abnormal 5-HT$_{1A}$ receptor activity. A 5-HT$_{1A}$ receptor-mediated disorder may be completely or partially mediated by modulating 5-HT$_{1A}$ receptors. In particular, a 5-HT$_{1A}$ receptor-mediated disorder is one in which modulation of 5-HT$_{1A}$ receptors results in some effect on the underlying disorder e.g., administration of a 5-HT$_{1A}$ receptor modulator results in some improvement in at least some of the subjects being treated.

The term "reactant psilocybin derivative compound", as used herein, refers to a psilocybin derivative compound capable of reacting in a synthetic or biosynthetic reaction to thereby form another psilocybin derivative compound, and generally includes indole structure containing reactants. The term "reactant psilocybin derivative compound" includes the term "psilocybin derivative precursor compound".

The term "psilocybin derivative precursor compound", as used herein, refers to a chemical compound that may serve as a precursor compound in the synthesis or biosynthesis of a multi-substituent psilocybin derivative, and includes compounds comprising an indole prototype structure, including, for example, tryptophan and tryptamine, and further includes a psilocybin derivative precursor compound having a formula (LVII):

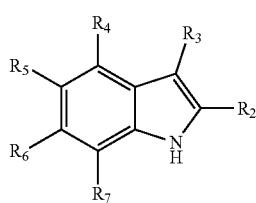
(LVII)

wherein at least one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, and wherein $R_3$ is a hydrogen atom or —CH$_2$—CHNH$_2$COOH or —CH$_2$—CH$_2$NH$_2$.

The term "psilocybin biosynthetic enzyme complement", as used herein, refers to one or more polypeptides which alone or together are capable of facilitating the chemical conversion of a psilocybin derivative precursor compound, and form a multi-substituent psilocybin derivative compound. A psilocybin biosynthetic enzyme complement can include, for example, one or more of a tryptophan synthase B polypeptide, a tryptophan decarboxylase, an N-acetyl transferase, a N-methyl transferase and a prenyl transferase.

The term "tryptophan synthase B polypeptide", as used herein, refers to any and all enzymes comprising a sequence of amino acid residues which is (i) substantially identical to the amino acid sequences constituting any tryptophan synthase B polypeptide set forth herein, including, for example, SEQ.ID NO: 2, or (ii) encoded by a nucleic acid sequence capable of hybridizing under at least moderately stringent conditions to any nucleic acid sequence encoding any tryptophan synthase B polypeptide set forth herein, but for the use of synonymous codons.

The term "tryptophan decarboxylase", as used herein, refers to any and all enzymes comprising a sequence of amino acid residues which is (i) substantially identical to the amino acid sequences constituting any tryptophan decarboxylase polypeptide set forth herein, including, for example, SEQ.ID NO: 4, SEQ.ID NO: 6 and SEQ.ID NO: 8, or (ii) encoded by a nucleic acid sequence capable of hybridizing under at least moderately stringent conditions to any nucleic acid sequence encoding any tryptophan decarboxylase set forth herein, but for the use of synonymous codons.

The term "N-acetyl transferase", as used herein, refers to any and all enzymes comprising a sequence of amino acid residues which is (i) substantially identical to the amino acid sequences constituting any acetyl transferase polypeptide set forth herein, including, for example, SEQ.ID NO: 10, or (ii) encoded by a nucleic acid sequence capable of hybridizing under at least moderately stringent conditions to any nucleic acid sequence encoding any acetyl transferase set forth herein, but for the use of synonymous codons.

The term "N-methyl transferase", as used herein, refers to any and all enzymes comprising a sequence of amino acid residues which is (i) substantially identical to the amino acid sequences constituting any N-methyl transferase polypeptide set forth herein, including, for example, SEQ.ID NO: 12 and SEQ.ID NO: 14, or (ii) encoded by a nucleic acid sequence capable of hybridizing under at least moderately stringent conditions to any nucleic acid sequence encoding any N-methyl transferase set forth herein, but for the use of synonymous codons.

The term "prenyl transferase", as used herein, refers to any and all enzymes comprising a sequence of amino acid residues which is (i) substantially identical to the amino acid sequences constituting any prenyl transferase polypeptide set forth herein, including, for example, SEQ.ID NO: 16, SEQ.ID NO: 18, SEQ.ID NO: 20, and SEQ.ID NO: 22, or (ii) encoded by a nucleic acid sequence capable of hybridizing under at least moderately stringent conditions to any nucleic acid sequence encoding any prenyl transferase set forth herein, but for the use of synonymous codons.

The term "PsiH", as used herein, refers to any and all enzymes comprising a sequence of amino acid residues which is (i) substantially identical to the amino acid sequences constituting any PsiH polypeptide set forth herein, including, for example, SEQ.ID NO: 24, or (ii) encoded by a nucleic acid sequence capable of hybridizing under at least moderately stringent conditions to any nucleic acid sequence encoding any PsiH set forth herein, but for the use of synonymous codons.

The term "CPR", as used herein, refers to any and all enzymes comprising a sequence of amino acid residues which is (i) substantially identical to the amino acid sequences constituting any CPR polypeptide set forth herein, including, for example, SEQ.ID NO: 26, or (ii) encoded by a nucleic acid sequence capable of hybridizing under at least moderately stringent conditions to any nucleic acid sequence encoding any CPR set forth herein, but for the use of synonymous codons.

The term "PsiK", as used herein, refers to any and all enzymes comprising a sequence of amino acid residues which is (i) substantially identical to the amino acid sequences constituting any PsiK set forth herein, including, for example, SEQ.ID NO: 49, or (ii) encoded by a nucleic acid sequence capable of hybridizing under at least moderately stringent conditions to any nucleic acid sequence encoding any PsiK set forth herein, but for the use of synonymous codons.

The terms "nucleic acid sequence encoding tryptophan synthase B polypeptide", and "nucleic acid sequence encoding a tryptophan synthase B polypeptide", as may be used interchangeably herein, refer to any and all nucleic acid sequences encoding a tryptophan synthase B polypeptide, including, for example, SEQ.ID NO: 1. Nucleic acid sequences encoding a tryptophan synthase B polypeptide further include any and all nucleic acid sequences which (i) encode polypeptides that are substantially identical to the tryptophan synthase B polypeptide sequences set forth herein; or (ii) hybridize to any tryptophan synthase B polypeptide nucleic acid sequences set forth herein under at least moderately stringent hybridization conditions or which would hybridize thereto under at least moderately stringent conditions but for the use of synonymous codons.

The terms "nucleic acid sequence encoding tryptophan decarboxylase", and "nucleic acid sequence encoding a tryptophan decarboxylase polypeptide", as may be used interchangeably herein, refer to any and all nucleic acid sequences encoding a tryptophan decarboxylase polypeptide, including, for example, SEQ.ID NO: 3, SEQ.ID NO: 5 and SEQ.ID NO: 7. Nucleic acid sequences encoding a tryptophan decarboxylase polypeptide further include any and all nucleic acid sequences which (i) encode polypeptides that are substantially identical to the tryptophan decarboxylase polypeptide sequences set forth herein; or (ii) hybridize to any tryptophan decarboxylase nucleic acid sequences set forth herein under at least moderately stringent hybridization conditions or which would hybridize thereto under at least moderately stringent conditions but for the use of synonymous codons.

The terms "nucleic acid sequence encoding an N-acetyl transferase", and "nucleic acid sequence encoding an N-acetyl transferase polypeptide", as may be used interchangeably herein, refer to any and all nucleic acid sequences encoding an N-acetyl transferase polypeptide, including, for example, SEQ.ID NO: 9. Nucleic acid sequences encoding an N-acetyl transferase polypeptide further include any and all nucleic acid sequences which (i) encode polypeptides that are substantially identical to the N-acetyl transferase polypeptide sequences set forth herein; or (ii) hybridize to any N-acetyl transferase nucleic acid sequences set forth herein under at least moderately stringent hybridization conditions or which would hybridize thereto under at least moderately stringent conditions but for the use of synonymous codons.

The terms "nucleic acid sequence encoding N-methyl transferase", and "nucleic acid sequence encoding a N-methyl transferase polypeptide", as may be used interchangeably herein, refer to any and all nucleic acid sequences encoding a N-methyl transferase polypeptide, including, for example, SEQ.ID NO: 11 and SEQ.ID NO: 13. Nucleic acid sequences encoding a N-methyl transferase polypeptide further include any and all nucleic acid sequences which (i) encode polypeptides that are substantially identical to the N-methyl transferase polypeptide sequences set forth herein; or (ii) hybridize to any N-methyl transferase nucleic acid sequences set forth herein under at least moderately stringent hybridization conditions or which would hybridize thereto under at least moderately stringent conditions but for the use of synonymous codons.

The terms "nucleic acid sequence encoding a prenyl transferase", and "nucleic acid sequence encoding a prenyl transferase polypeptide", as may be used interchangeably herein, refer to any and all nucleic acid sequences encoding a prenyl transferase polypeptide, including, for example, SEQ.ID NO: 15, SEQ.ID NO: 17, SEQ.ID NO: 19 and SEQ.ID NO: 21. Nucleic acid sequences encoding a prenyl transferase polypeptide further include any and all nucleic acid sequences which (i) encode polypeptides that are substantially identical to the prenyl transferase polypeptide sequences set forth herein; or (ii) hybridize to any prenyl transferase nucleic acid sequences set forth herein under at least moderately stringent hybridization conditions or which would hybridize thereto under at least moderately stringent conditions but for the use of synonymous codons.

The terms "nucleic acid sequence encoding PsiH", and "nucleic acid sequence encoding a PsiH polypeptide", as may be used interchangeably herein, refer to any and all nucleic acid sequences encoding a PsiH, including, for example, SEQ.ID NO: 23. Nucleic acid sequences encoding a PsiH polypeptide further include any and all nucleic acid sequences which (i) encode polypeptides that are substantially identical to the PsiH polypeptide sequences set forth herein; or (ii) hybridize to any PsiH nucleic acid sequences set forth herein under at least moderately stringent hybridization conditions or which would hybridize thereto under at least moderately stringent conditions but for the use of synonymous codons.

The terms "nucleic acid sequence encoding CPR", and "nucleic acid sequence encoding an CPR polypeptide", as may be used interchangeably herein, refer to any and all nucleic acid sequences encoding a CPR, including, for example, SEQ.ID NO: 25. Nucleic acid sequences encoding a CPR polypeptide further include any and all nucleic acid sequences which (i) encode polypeptides that are substantially identical to the CPR polypeptide sequences set forth herein; or (ii) hybridize to any CPR nucleic acid sequences set forth herein under at least moderately stringent hybridization conditions or which would hybridize thereto under at least moderately stringent conditions but for the use of synonymous codons.

The terms "nucleic acid sequence encoding a PsiK", and "nucleic acid sequence encoding a PsiK polypeptide", as may be used interchangeably herein, refer to any and all nucleic acid sequences encoding PsiK, including, for example, SEQ.ID NO: 48. Nucleic acid sequences encoding a PsiK further include any and all nucleic acid sequences which (i) encode polypeptides that are substantially identical to the PsiK polypeptide sequences set forth herein; or (ii) hybridize to any PsiK nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine, and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence, or a nucleoside sequence.

The term "polypeptide", as used herein in conjunction with a reference SEQ.ID NO, refers to any and all polypeptides comprising a sequence of amino acid residues which is (i) substantially identical to the amino acid sequence constituting the polypeptide having such reference SEQ.ID NO, or (ii) encoded by a nucleic acid sequence capable of hybridizing under at least moderately stringent conditions to any nucleic acid sequence encoding the polypeptide having such reference SEQ.ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ.ID NO, refers to any and all nucleic acid sequences encoding a polypeptide having such reference SEQ.ID NO. Nucleic acid sequences encoding a polypeptide, in conjunction with a reference SEQ.ID NO, further include any and all nucleic acid sequences which (i) encode polypeptides that are substantially identical to the polypeptide having such reference SEQ.ID NO; or (ii) hybridize to any nucleic acid sequences encoding polypeptides having such reference SEQ.ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/ 0.1% SDS at 60° C. Moderately stringent hybridization conditions include a washing step in 3×SSC at 42° C. It is understood however that equivalent stringencies may be achieved using alternative buffers, salts, and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ.ID NO: 2, refers to a polypeptide capable of performing the same function as the polypeptide set forth in SEQ.ID NO: 2. Functional variants include modified a polypeptide wherein, relative to a noted reference polypeptide, the modification includes a substitution, deletion, or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine, and valine, (iv) asparagine and glutamine, and (v) tryptophan, tyrosine, and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The terms "substantially pure" and "isolated", as may be used interchangeably herein describe a compound, e.g., a psilocybin derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., by chromatography, gel electrophoresis or HPLC analysis.

The term "recovered", as used herein in association with an enzyme, protein, or a chemical compound, refers to a more or less pure form of the enzyme, protein, or chemical compound.

The term "in vivo", as used herein relation to a method of making a multi-substituent psilocybin derivative compound, refers to a method involving contacting a psilocybin derivative precursor compound with an enzyme capable of converting the psilocybin derivative precursor compound within a cell, for example, a cell or a microorganism, cultivated, for example, in a growth medium, to convert the psilocybin derivative precursor compound into a multi-substituent psilocybin derivative compound. The cell generally expresses a psilocybin biosynthetic enzyme complex, including a heterologously expressed tryptophan synthase B polypeptide, a tryptophan decarboxylase, an N-acetyl transferase, a N-methyl transferase and a prenyl transferase, for example.

The term "in vitro", as used herein relation to a method of making a multi-substituent psilocybin derivative compound, refers to a method involving contacting a psilocybin derivative precursor compound with an enzyme capable of converting the psilocybin derivative precursor outside a cell, for example, in a microwell plate, a tube, a flask, a beaker, a tank, a reactor, or the like, to convert the psilocybin derivative precursor compound into a multi-substituent psilocybin derivative compound.

General Implementation

As hereinbefore mentioned, the present disclosure relates to psilocybin derivatives. In particular, the present disclosure provides novel multiple-substituent psilocybin derivatives. In general, the herein provided compositions exhibit functional properties which deviate from the functional properties of psilocybin. Thus, for example, the multiple-substituent psilocybin derivatives, can exhibit pharmacological properties which deviate from psilocybin. Furthermore, the multiple-substituent derivatives may psilocybin derivatives may exhibit physico-chemical properties which differ from psilocybin. Thus, for example, multiple-substituent psilocybin derivatives may exhibit superior solubility in a solvent, for example, an aqueous solvent. The multiple-substituent psilocybin derivatives in this respect are useful in the formulation of pharmaceutical and recreational drug formulations. In one embodiment, the multiple-substituent psilocybin derivatives of the present disclosure can conveniently be chemically and/or biosynthetically produced. The practice of this method avoids the extraction of psilocybin from mushrooms and the performance of subsequent chemical reactions to achieve multiple-substituent derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of multiple-substituent psilocybin derivatives.

Figure 3A:
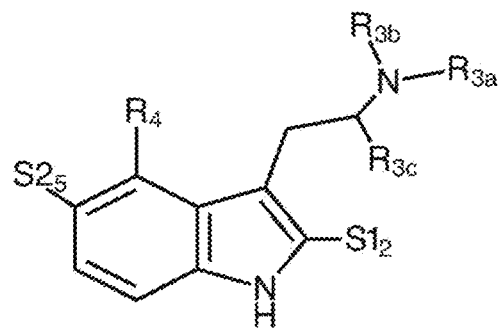
FIGS. 3A, 3B, 3C, 3D, 3E, 3F, 3G, 3H, 3I, 3J, 3K and 3L depict the chemical structures of certain example psilocybin derivatives, notably a 2,5-di-S1,S2-psilocybin derivative (FIG. 3A), a 2,5-di-S2,S1-psilocybin derivative (FIG. 3B), a 2,6-di-S1,S2-psilocybin derivative (FIG. 3C), a 2,6-di-S2,S1-psilocybin derivative (FIG. 3D), a 2,7-di-S1,S2-psilocybin derivative (FIG. 3E), a 2,7-di-S2,S1-psilocybin derivative (FIG. 3F), a 5,6-di-S1,S2-psilocybin derivative (FIG. 3G), a 5,6-di-S2,S1-psilocybin derivative (FIG. 3H), a 5,7-di-S1,S2-psilocybin derivative (FIG. 3I), a 5,7-di-S2,S1-psilocybin derivative (FIG. 3J), a 6,7-di-S1,S2-psilocybin derivative (FIG. 3K), and a 6,7-di-S2,S1-psilocybin derivative (FIG. 3L). In each of the foregoing S1 and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone, (viii) a prenyl group, and (ix) a nitrile group. It is noted that in each of FIGS. 3A-3L, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 3B:
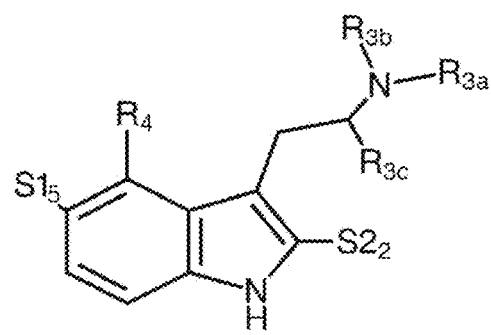
Figure 3C:
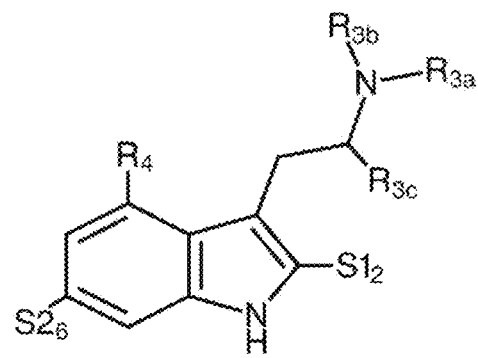
Figure 3D:
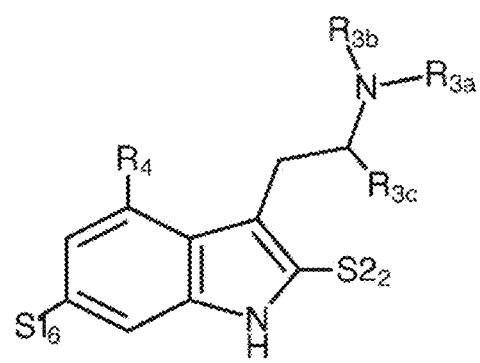
Figure 3E:
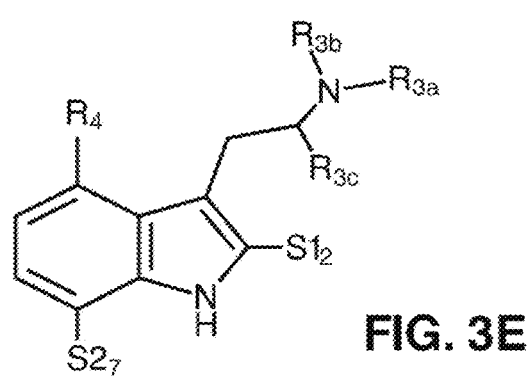
Figure 3F:
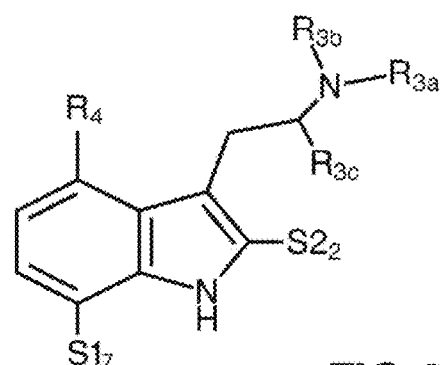
Figure 3G:
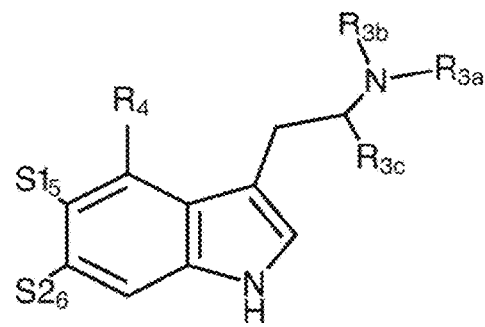
Figure 3H:
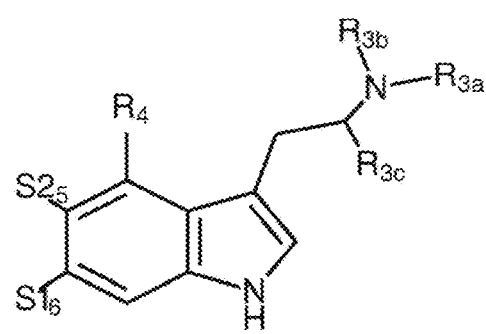
Figure 3I:
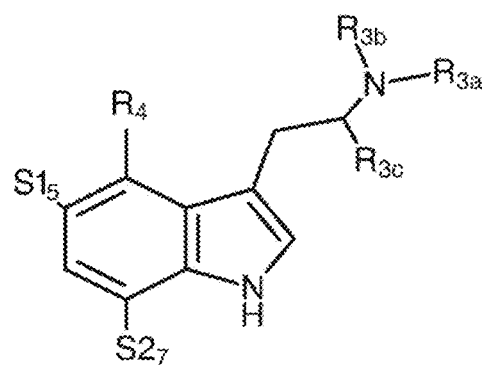
Figure 3J:
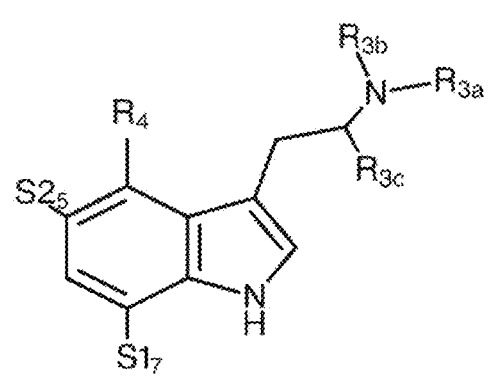
Figure 3K:
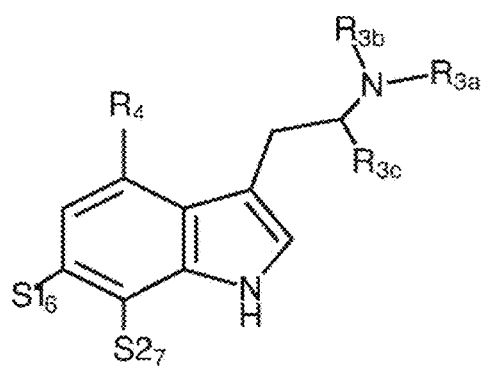
Figure 3L:
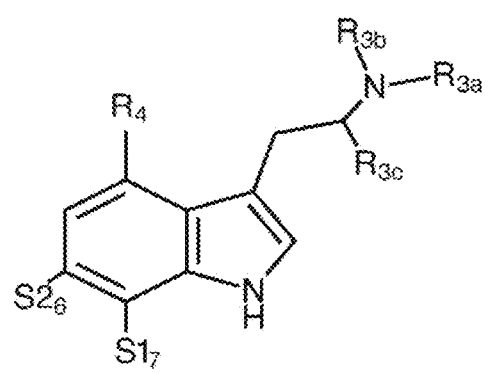

In what follows selected embodiments are described with reference to the drawings.

Initially example multiple-substituent psilocybin derivatives will be described. Thereafter example methods of using and making the multiple-substituent psilocybin derivatives will be described.

Accordingly, in one aspect the present disclosure provides derivatives of a compound known as psilocybin of which the chemical structure is shown in FIG. 1. The derivatives herein provided are, in particular, multiple-substituent derivatives including psilocybin derivatives possessing two or more substituent entities.

Thus, in one aspect, the present disclosure provides, in accordance with the teachings herein, in at least one embodiment, a chemical compound having a formula (I):

(I)

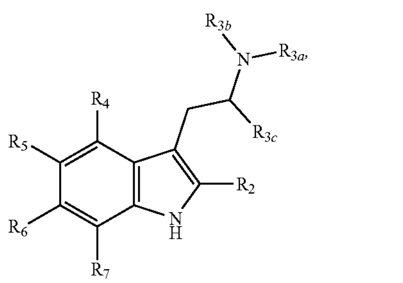

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

Thus, referring to the chemical compound having the formula (I), initially it is noted that, in an aspect hereof, at least two of $R_2$, $R_4$, $R_5$, $R_6$, or $R_7$ are substituent entities selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. Thus, it is to be understood that, in accordance with an aspect of the present disclosure, at least two of $R_2$, $R_4$, $R_5$, $R_6$, or $R_7$ are substituent entities. The substituent entities are each independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and where two (but no more than two) substituent entities are selected, they are non-identical, and where three or more substituent entities are selected, at least two of the selected substituent entities are non-identical.

In an aspect hereof, in an embodiment, at least three of $R_2$, $R_4$, $R_5$, $R_6$, or $R_7$ can be substituents selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

In an aspect hereof, in an embodiment, at least three of $R_2$, $R_4$, $R_5$, $R_6$, or $R_7$ can be substituents selected from at least three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Continuing to refer to the chemical compound having the formula (I), in a further aspect hereof, $R_4$ can be a phosphate group or a hydrogen atom.

Continuing to refer to the chemical compound having the formula (I), in a further aspect hereof, $R_{3a}$ and $R_{3b}$ can be a hydrogen atom, an alkyl group, an acyl group or an aryl group. Thus, $R_{3a}$ and $R_{3b}$ can each be a hydrogen atom, or $R_{3a}$ and $R_{3b}$ can each be an alkyl group, such as a methyl group, ethyl group, propyl group, or longer chain alkyl group, or $R_{3a}$ and $R_{3b}$ can be each be an acyl group, or $R_{3a}$ and $R_{3b}$ can each be an aryl group. Furthermore, one of $R_{3a}$ and $R_{3b}$ can be a hydrogen atom, and one of $R_{3a}$ and $R_{3b}$ can be an alkyl group. One of $R_{3a}$ and $R_{3b}$ can be a hydrogen atom, and one of $R_{3a}$ and $R_{3b}$ can be an acyl group. One of $R_{3a}$ and $R_{3b}$ can be a hydrogen atom, and one of $R_{3a}$ and $R_{3b}$ can be an aryl group. One of $R_{3a}$ and $R_{3b}$ can be an alkyl group, and one of $R_{3a}$ and $R_{3b}$ can be an aryl group. One of $R_{3a}$ and $R_{3b}$ can be an alkyl group, and one of $R_{3a}$ and $R_{3b}$ can be an acyl group. One of $R_{3a}$ and $R_{3b}$ can be an acyl group, and one of $R_{3a}$ and $R_{3b}$ can be an aryl group.

Continuing to refer to the chemical compound having the formula (I), in a further aspect hereof, each of the non-substituted groups $R_2$, $R_5$, $R_6$, or $R_7$ can be a hydrogen atom. Moreover, as hereinbefore noted, $R_4$ can also be a hydrogen atom.

In accordance herewith disclosed herein, in an aspect, multiple-substituent psilocybin derivatives including two, or three substituent groups. Examples of each of these will next be discussed, by referring to selected figures. In particular, examples including multiple-substituent psilocybin derivatives including two substituent groups are discussed by referring to FIGS. 3A-3L; and examples of multiple-substituent psilocybins including three substituent groups are discussed by referring to FIGS. 4A-4I, 5A-5I, 6A-6I and 7A-7I. For clarity, it is noted that in each of these figures, notations such as $S1_5$, $S2_5$, and $S1_7$ for example, indicate, respectively, a first substituent S1 at the 5-position ($C_5$), a second substituent S2 at the 5-position ($C_5$), and a first substituent S1 at the 7-position ($C_7$). Similarly, in certain figures, notation within the same chemical compound, such as $S2_2$ and $S2_6$, for example, denote a second substituent S2 at the 2-position ($C_2$) and that same second substituent at the 6 position ($C_6$) of the compound (see: e.g., FIG. 6I).

Thus, referring next to FIGS. 3A-3L, examples of multiple-substituent psilocybin derivatives in accordance herewith, wherein two of $R_2$, $R_5$, $R_6$, or $R_7$ are substituents, are: the 2,5-di-S1 S2-psilocybin derivative depicted in FIG. 3A, the 2,5-di-S2,S1-psilocybin derivative depicted in FIG. 3B, the 2,6-di-S1,32-psilocybin derivative depicted in FIG. 3C, the 2,6-di-S2,S1-psilocybin derivative depicted in FIG. 3D, the 2,7-di-S1,S2-psilocybin derivative depicted in FIG. 3E, the 2,7-di-S2,S1-psilocybin derivative depicted in FIG. 3F, the 5,6-di-S1,S2-psilocybin derivative depicted in FIG. 3G, the 5,6-di-S2,S1-psilocybin derivative depicted in FIG. 3H, the 5,7-di-S1,S2-psilocybin derivative depicted in FIG. 3I, the 5,7-di-S2,S1-psilocybin derivative depicted in FIG. 3J, the 6,7-di-S1,S2-psilocybin derivative depicted in FIG. 3K, and the 6,7-di-S2,S1-psilocybin derivative depicted in FIG. 3L. As will be clear from the foregoing, in each of FIGS. 3A-3L, S1 and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Thus, for example, referring to the chemical compound having the formula (I), in one example embodiment, two of $R_4$, $R_5$, $R_6$, or $R_7$ can be substituents, one of which can be selected from (i) a halogen atom, (ii) a prenyl group, and (iii) a nitrile group, and one of $R_4$, $R_5$, $R_6$, or $R_7$ can be a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, provided however the two substituents are non-identical, and $R_2$ and the non-substituted $R_4$, $R_5$, $R_6$ and $R_7$ are hydrogen atoms. Thus, in such example embodiment, referring to FIGS. 3A-3L, S1 can be selected from (i) a halogen atom, (ii) a prenyl group, and (iii) a nitrile group, and S2 can be selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, or, conversely, S2 can be selected from (i) a halogen atom, (ii) a prenyl group, and (iii) a nitrile group, and S1 can be selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Thus, for example, referring to the chemical compound having the formula (I), in a further example embodiment, two of $R_4$, $R_5$, $R_6$, or $R_7$ can be substituents, one of which is a halogen atom, and one of $R_4$, $R_5$, $R_6$, or $R_7$ can be a substituent selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a nitrile group, and $R_2$ and the non-substituted $R_4$, $R_5$, $R_6$ and $R_7$ are hydrogen atoms. Thus, in such example embodiment, referring to FIGS. 3A-3L, S1 can be a halogen atom, and S2 can be selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a nitrile group.

Thus, for example, referring to the chemical compound having the formula (I), in a further example embodiment, two of $R_4$, $R_5$, $R_6$, or $R_7$ can be substituents, one of which is a halogen atom, and one of $R_4$, $R_5$, $R_6$, or $R_7$ can be a substituent selected from (i) an amino group, (ii) a nitrile group, (iii) a nitro group, (iv) a hydroxy group, and a (vii) a prenyl group, and $R_2$ and the non-substituted $R_4$, $R_5$, $R_6$ and $R_7$ are hydrogen atoms. Thus, in such example embodiment, referring to FIGS. 3A-3L, S1 can be a halogen atom, and S2 can be selected from (i) an amino group, (ii) a nitrile group, (iii) a nitro group, (iv) a hydroxy group, and a (vii) a prenyl group, or, conversely, S2 can be a halogen atom, and S1 can be (i) an amino group, (ii) a nitrile group, (iii) a nitro group, (iv) a hydroxy group, and a (v) a prenyl group.

Thus, for example, referring to the chemical compound having the formula (I), in a further example embodiment, two of $R_4$, $R_5$, $R_6$, or $R_7$ can be substituents, one of which is a halogen atom, and one of $R_4$, $R_5$, $R_6$, or $R_7$ can be a prenyl group, and $R_2$ and the non-substituted $R_4$, $R_5$, $R_6$ and $R_7$ are hydrogen atoms. Thus, in such example embodiment, referring to FIGS. 3A-3L, S1 can be a halogen atom, and S2 can be a prenyl group, or, conversely, S2 can be a prenyl group, and S1 can be a halogen atom.

Thus, for example, referring to the chemical compound having the formula (I), in a further example embodiment, two of $R_4$, $R_5$, $R_6$, or $R_7$ can be substituents, one of which is a prenyl group, and one of $R_4$, $R_5$, $R_6$, or $R_7$ can be a substituent selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a halogen atom, and (viii) a nitrile group, and $R_2$ and the non-substituted $R_4$, $R_5$, $R_6$ and $R_7$ are hydrogen atoms. Thus, in such example embodiment, referring to FIGS. 3A-3L, S1 can be a prenyl group, and S2 can be selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a halogen atom, and (viii) a nitrile group, or, conversely, S2 can be a prenyl group, and S1 can be (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a halogen atom, and (viii) a nitrile group.

Thus, for example, referring to the chemical compound having the formula (I), in a further example embodiment, two of $R_4$, $R_5$, $R_6$, or $R_7$ can be substituents, one of which is a prenyl group, and one of $R_4$, $R_5$, $R_6$, or $R_7$ can be a substituent selected from (i) a carboxyl group or a carboxylic acid derivative, (ii) a halogen atom, and (iii) a hydroxy group, and $R_2$ and the non-substituted $R_4$, $R_5$, $R_6$ and $R_7$ are hydrogen atoms. Thus, in such example embodiment, referring to FIGS. 3A-3L, S1 can be a prenyl group, and S2 can be selected from (i) a carboxyl group or a carboxylic acid derivative, (ii) a halogen atom, and (iii) a hydroxy group, or, conversely, S2 can be a prenyl group, and S1 can be (i) a carboxyl group or a carboxylic acid derivative, (ii) a halogen atom, and (iii) a hydroxy group.

Thus, for example, referring to the chemical compound having the formula (I), in a further example embodiment, two of $R_4$, $R_5$, $R_6$, or $R_7$ can be substituents, one of which is a nitrile group, and one of $R_4$, $R_5$, $R_6$, or $R_7$ can be a substituent selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a halogen atom, and $R_2$ and the non-substituted $R_4$, $R_5$, $R_6$ and $R_7$ are hydrogen atoms. Thus, in such example embodiment, referring to FIGS. 3A-3L, S1 can be a nitril group, and S2 can be selected from (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a halogen atom, or, conversely, S2 can be a nitrile group, and S1 can be (i) a hydroxy group, (ii) a nitro group, (iii) a glycosyloxy group, (iv) an amino group or an N-substituted amino group, (v) a carboxyl group or a carboxylic acid derivative, (vi) an aldehyde or a ketone group, (vii) a prenyl group, and (viii) a halogen atom.

Thus, for example, referring to the chemical compound having the formula (I), in a further example embodiment, two of $R_4$, $R_5$, $R_6$, or $R_7$ can be substituents, one of which is a nitrile group, and one of $R_4$, $R_5$, $R_6$, or $R_7$ can be an amino group or an N-substituted amino group, and $R_2$ and the non-substituted $R_4$, $R_5$, $R_6$ and $R_7$ are hydrogen atoms. Thus, in such example embodiment, referring to FIGS. 3A-3L, S1 can be a nitrile group, and S2 can be an amino group or an N-substituted amino group, conversely, S2 can be a nitrile group, and S1 can be an amino group or an N-substituted amino group.

Figure 4A:
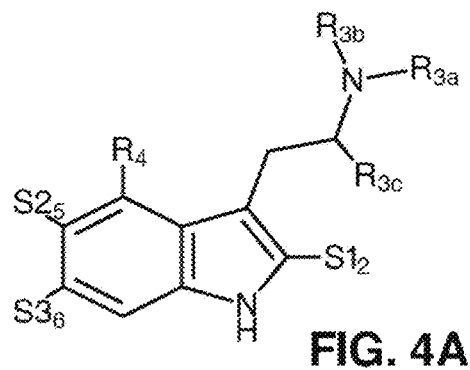
FIGS. 4A, 4B, 4C, 4D, 4E, and 4F depict the chemical structures of certain example psilocybin derivatives, notably a 2,5,6-tri-S1,S2,S3-psilocybin derivative (FIG. 4A), a 2,5,6-tri-S1,S3,S2-psilocybin derivative (FIG. 46), a 2,5,6-tri-S3,S1,S2-psilocybin derivative (FIG. 4C), a 2,5,6-tri-S2,S1,S3-psilocybin derivative (FIG. 4D), a 2,5,6-tri-S3,S2,S1-psilocybin derivative (FIG. 4E), and a 2,5,6-tri-S2,S3,S1-psilocybin derivative (FIG. 4F). In each of the foregoing S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 4A-4F, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 4B:
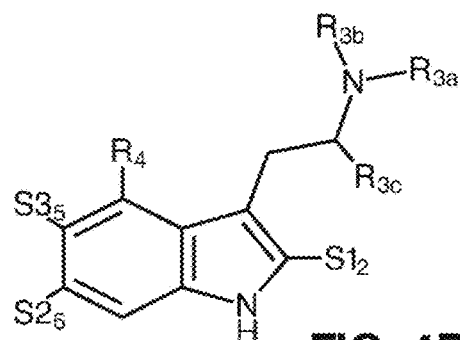
Figure 4C:
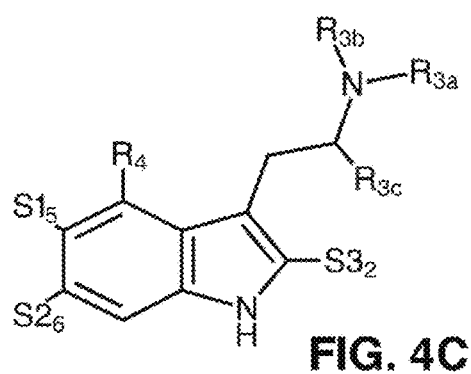
Figure 4D:
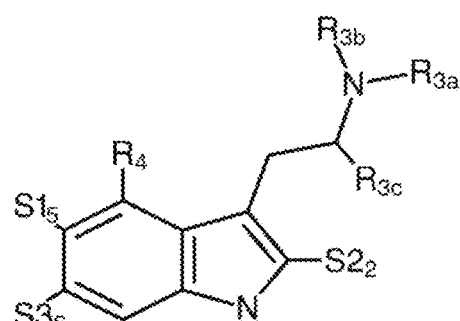
Figure 4E:
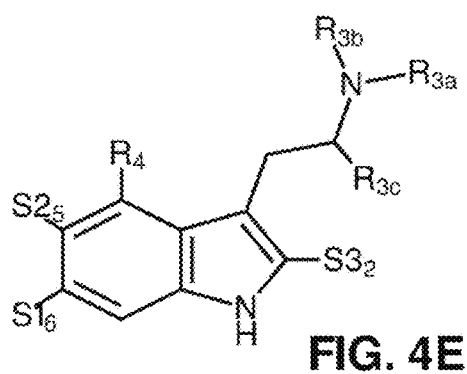
Figure 4F:
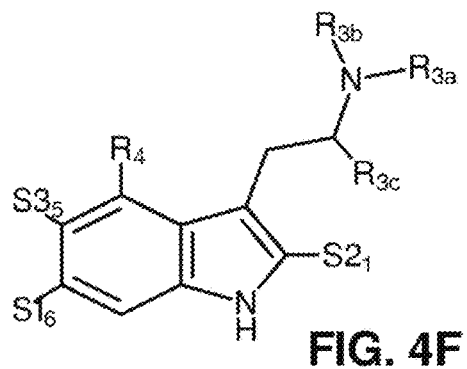

Turning now to multiple-substituent psilocybin derivatives, including three substituent groups, and referring to FIGS. 4A-4F, 4G-4I, 5A-5F, 5G-5I, 6A-6F, 6G-6I, 7A-7F, 7G-7I, shown therein are examples of multiple-substituent psilocybin derivatives in accordance herewith, wherein three of $R_2$, $R_5$, $R_6$, or $R_7$ are substituents. It is noted that in the examples shown in FIGS. 4A-4F, 5A-5F, 6A-6F, 6G-6I, and 7A-7F, the three substituents are three different substituents S1, S2, S3. In the examples shown in FIGS. 4G-4I, 5G-5I, 6G-6I, and 7G-7I, the three substituents are selected such that two of the three substituents are the same, i.e., S1, S2, S2. Examples, in this respect, are in particular: the 2,5,6-tri-S1S2,S3-psilocybin derivative shown in FIG. 4A, the 2,5,6-tri-S1,S3,S2-psilocybin derivative shown in FIG. 46, the 2,5,6-tri-S3,S1,S2-psilocybin derivative shown in FIG. 4C, the 2,5,6-tri-S2,S1,S3-psilocybin derivative shown in FIG. 4D, the 2,5,6-tri-S3,S2,S1-psilocybin derivative shown in FIG. 4E, and the 2,5,6-tri-S2,S3,S1-psilocybin derivative (FIG. 4F). As will be clear from the foregoing, in each of FIGS. 4A-4F S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 4G:
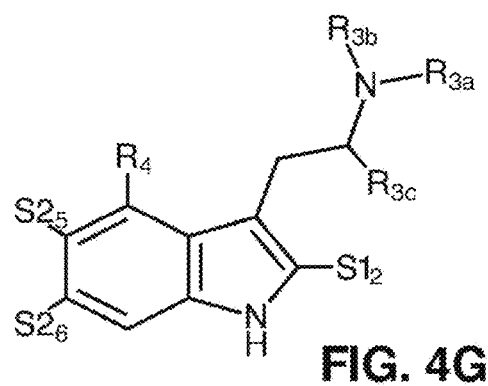
FIGS. 4G, 4H, and 4I depict the chemical structures of certain example psilocybin derivatives, notably a 2,5,6-tri-S1,S2,S2-psilocybin derivative (FIG. 4G), a 2,5,6-tri-S2,S1,S2-psilocybin derivative (FIG. 4H), and a 2,5,6-tri-S2,S2,S1-psilocybin derivative (FIG. 4I). In each of the foregoing S1 and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 4G-4I, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 4H:
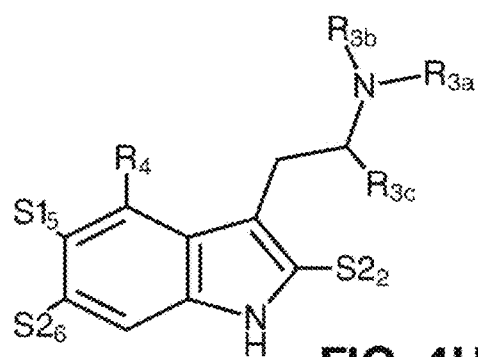
Figure 4I:
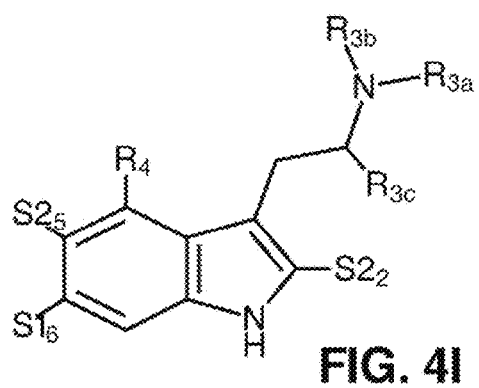

Further examples, wherein three of $R_2$, $R_5$, $R_6$, or $R_7$ are substituents are shown in FIGS. 4G, 4H, and 4I, in particular the 2,5,6-tri-S1,S2,S2-psilocybin derivative shown in FIG. 4G, the 2,5,6-tri-S2,S1,S2-psilocybin derivative shown in FIG. 4H, and the 2,5,6-tri-S2,S2,S1-psilocybin derivative shown FIG. 4I. As will be clear from the foregoing, in each of FIGS. 4G-4I S1 and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 5A:
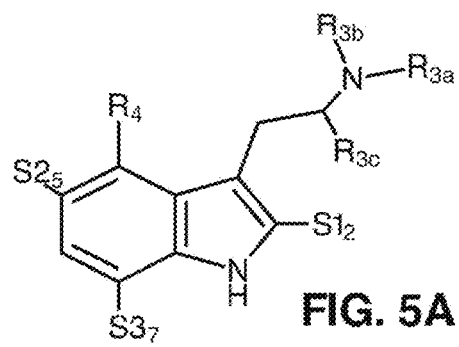
FIGS. 5A, 5B, 5C, 5D, 5E, and 5F depict the chemical structures of certain example psilocybin derivatives, notably a 2,5,7-tri-S1,S2,S3-psilocybin derivative (FIG. 5A), a 2,5,7-tri-S1,S3,S2-psilocybin derivative (FIG. 5B), a 2,5,7-tri-S3,S1,S2-psilocybin derivative (FIG. 5C), a 2,5,7-tri-S2,S1,S3-psilocybin derivative (FIG. 5D), a 2,5,7-tri-S3,S2,S1-psilocybin derivative (FIG. 5E), and a 2,5,7-tri-S2,S3,S1-psilocybin derivative (FIG. 5F). In each of the foregoing S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 5A-5F, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 5B:
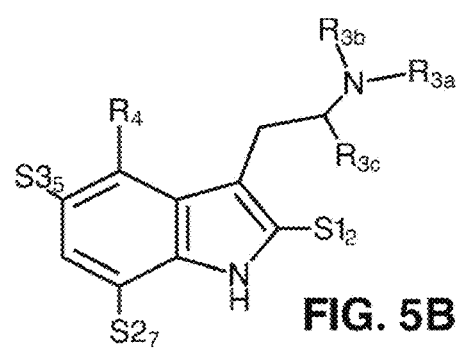
Figure 5C:
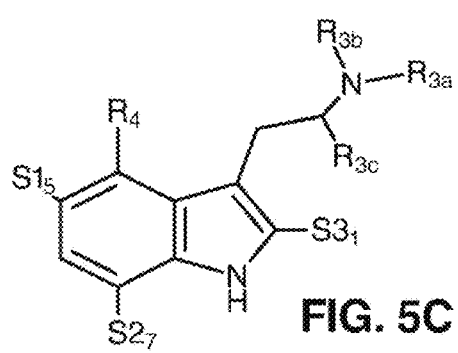
Figure 5D:
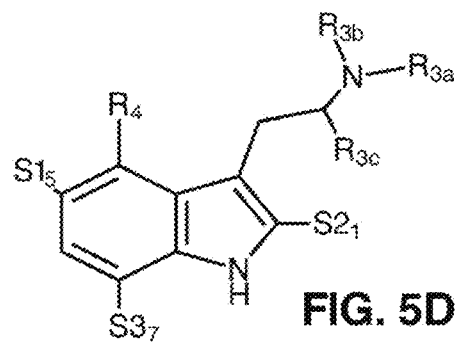
Figure 5E:
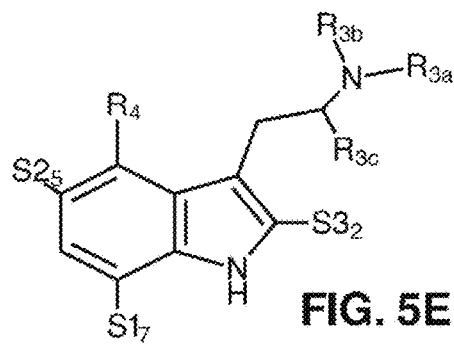
Figure 5F:
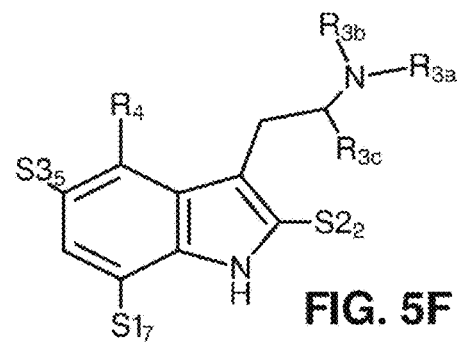

Further examples, wherein three of $R_2$, $R_5$, $R_6$, or $R_7$ are substituents are shown in FIGS. 5A, 5B, 5C, 5D, 5E, and 5F, in particular the 2,5,7-tri-S1,S2,S3-psilocybin derivative shown in FIG. 5A), the 2,5,7-tri-S1,S3,S2-psilocybin derivative shown in FIG. 5B, the 2,5,7-tri-S3,S1,S2-psilocybin derivative shown in FIG. 5C, the 2,5,7-tri-S2,S1,S3-psilocybin derivative shown in FIG. 5D, the 2,5,7-tri-S3,S2,S1-psilocybin derivative shown in FIG. 5E, and the 2,5,7-tri-S2,S3,S1-psilocybin derivative shown in FIG. 5F. As will be clear from the foregoing in each of FIGS. 5A-5I S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 5G:
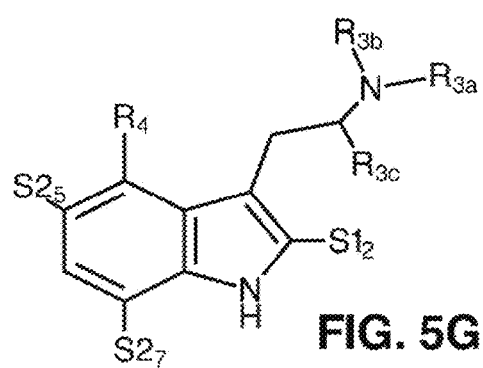
FIGS. 5G, 5H, and 5I depict the chemical structures of certain example psilocybin derivatives, notably a 2,5,7-tri-S1,S2,S2-psilocybin derivative (FIG. 5G), a 2,5,7-tri-S2,S1,S2-psilocybin derivative (FIG. 5H), and a 2,5,7-tri-S2,S2,S1-psilocybin derivative (FIG. 5I), In each of the foregoing S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 5A-5I, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 5H:
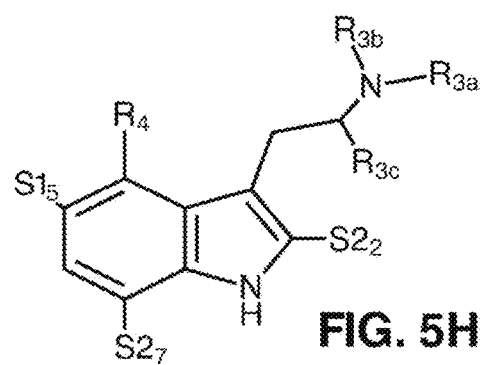
Figure 5I:
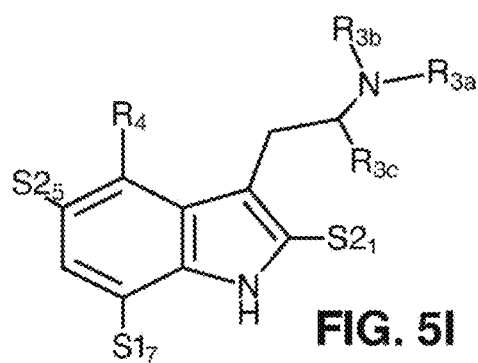

Further examples, wherein three of $R_2$, $R_5$, $R_6$, or $R_7$ are substituents are shown in FIGS. 5G, 5H, and 5I, in particular the 2,5,7-tri-S1,S2,S2-psilocybin derivative shown in FIG. 5G, the 2,5,7-tri-S2,S1,S2-psilocybin derivative shown in FIG. 5H), and the 2,5,7-tri-S2,S2,S1-psilocybin derivative shown in FIG. 5I. As will be clear from the foregoing in each of FIGS. 5G-5I, S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 6A:

FIGS. 6A, 6B, 6C, 6D, 6E, and 6F depict the chemical structures of certain example psilocybin derivatives, notably a 2,6,7-tri-S1,S2,S3-psilocybin derivative (FIG. 6A), a 2,6,7-tri-S1,S3,S2-psilocybin derivative (FIG. 6B), a 2,6,7-tri-S3,S1,S2-psilocybin derivative (FIG. 6C), a 2,6,7-tri-S2,S1,S3-psilocybin derivative (FIG. 6D), a 2,6,7-tri-S3,S2,S1-psilocybin derivative (FIG. 6E), and a 2,6,7-tri-S2,S3,S1-psilocybin derivative (FIG. 6F). In each of the foregoing S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 6A-6F, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 6B:
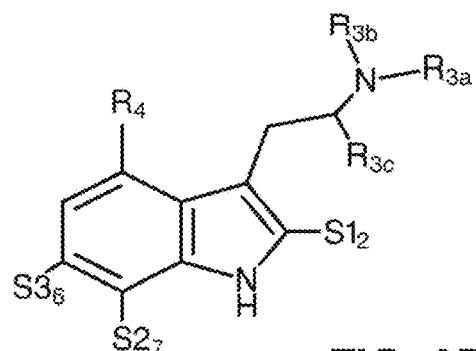
Figure 6C:
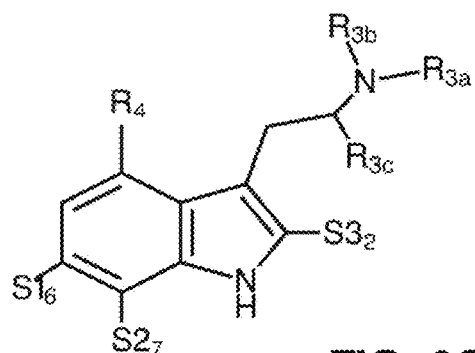
Figure 6D:
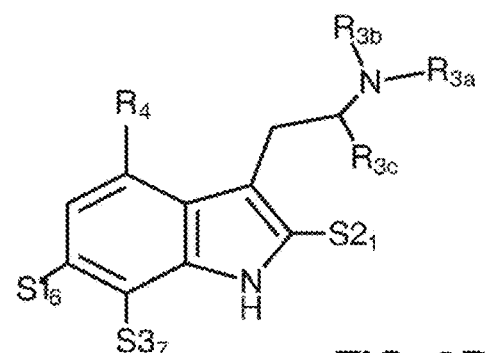
Figure 6E:
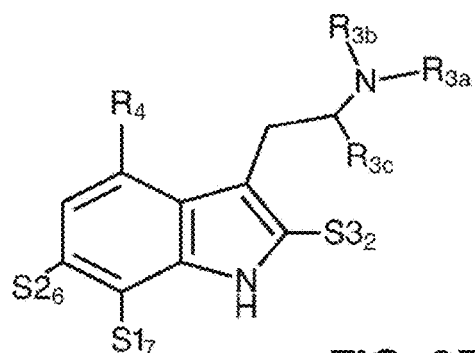
Figure 6F:
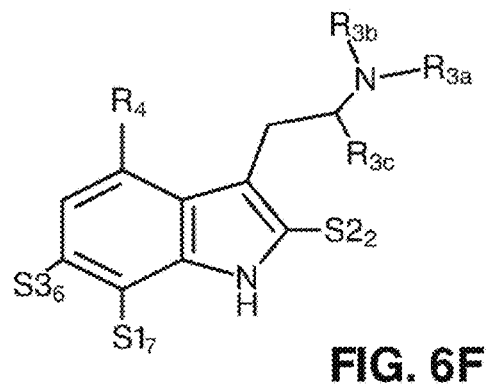

Further examples, wherein three of $R_2$, $R_5$, $R_6$, or $R_7$ are substituents are shown in FIGS. 6A, 6B, 6C, 6D, 6E, and 6F, in particular, the 2,6,7-tri-S1, S2, S3-psilocybin derivative shown in FIG. 6A, the 2,6,7-tri-S1,S3,S2-psilocybin derivative shown in FIG. 68, the 2,6,7-tri-S3,S1,S2-psilocybin derivative shown in FIG. 6C, the 2,6,7-tri-S2,S1,S3-psilocybin derivative shown in FIG. 6D, the 2,6,7-tri-S3,S2,S1-psilocybin derivative shown in FIG. 6E, and the 2,6,7-tri-S2,S3,S1-psilocybin derivative (FIG. 6F). It will be clear from the foregoing, that in FIGS. 6A-6F, S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 6G:
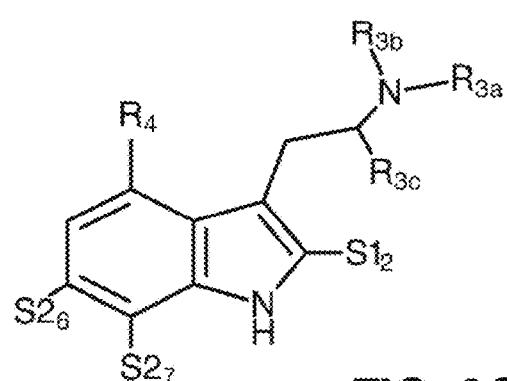
FIGS. 6G, 6H, and 6I depict the chemical structures of certain example psilocybin derivatives, notably a 2,6,7-tri-S1,S2,S2-psilocybin derivative (FIG. 6G), a 2,6,7-tri-S2,S1,S2-psilocybin derivative (FIG. 6H), and a 2,6,7-tri-S2,S2,S1-psilocybin derivative (FIG. 6I). In each of the foregoing S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 6G-6I, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 6H:
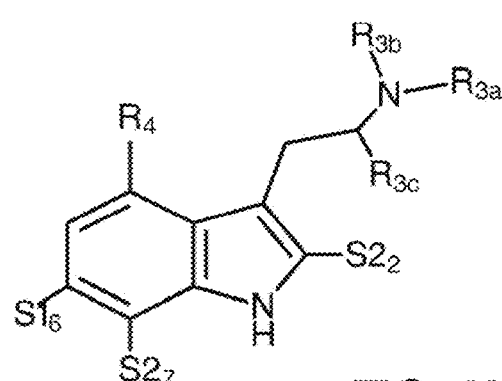
Figure 6I:
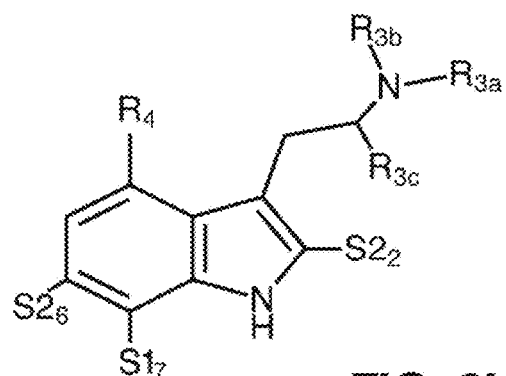

Further examples, wherein three of $R_2$, $R_5$, $R_6$, or $R_7$ are substituents are shown in FIGS. 6G, 6H, and 6I, in particular the 2,6,7-tri-S1,S2,S2-psilocybin derivative shown in FIG. 6G, the 2,6,7-tri-S2,S1,S2-psilocybin derivative shown in FIG. 6H, and the 2,6,7-tri-S2,S2,S1-psilocybin derivative shown in FIG. 6I. It will be clear from the foregoing that in FIGS. 6A-6I, S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix a nitrile group.

Figure 7A:
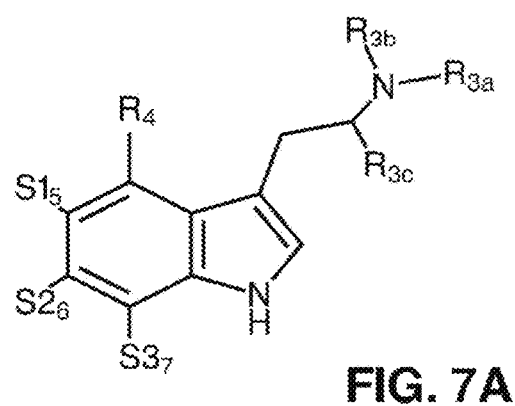
FIGS. 7A, 7B, 7C, 7D, 7E, and 7F depict the chemical structures of certain example psilocybin derivatives, notably a 5,6,7-tri-S1,S2,S3-psilocybin derivative (FIG. 7A), a 5,6,7-tri-S1,S3,S2-psilocybin derivative (FIG. 7B), a 5,6,7-tri-S3,S1,S2-psilocybin derivative (FIG. 7C), a 5,6,7-tri-S2,S1,S3-psilocybin derivative (FIG. 7D), a 5,6,7-tri-S3,S2,S1-psilocybin derivative (FIG. 7E), and a 5,6,7-tri-S2,S3,S1-psilocybin derivative (FIG. 7F). In each of the foregoing S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 7A-7F, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 7B:
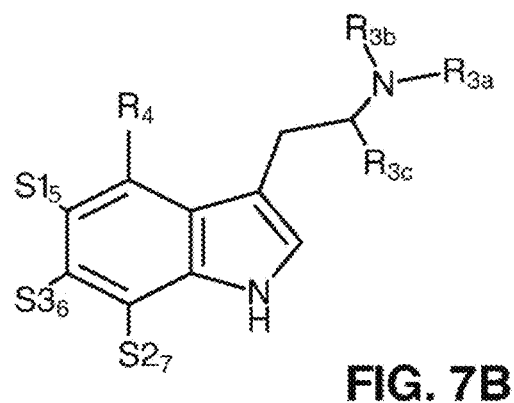
Figure 7C:
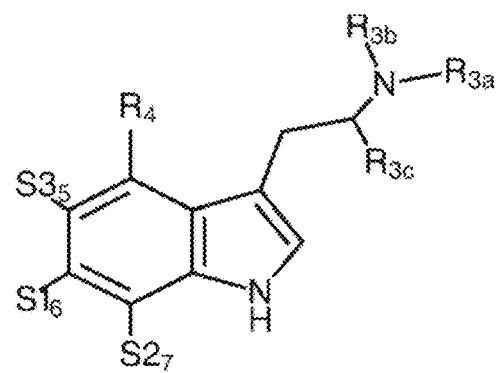
Figure 7D:
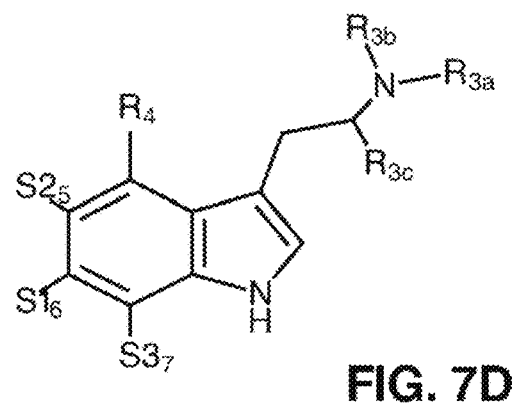
Figure 7E:
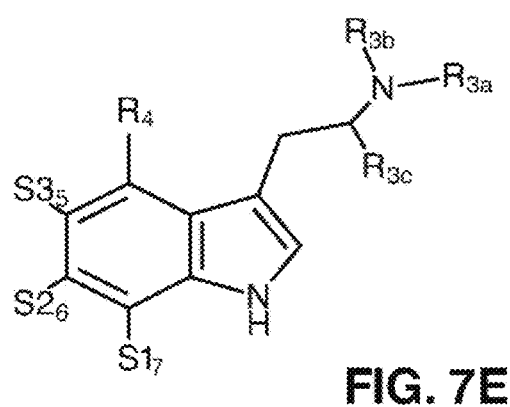
Figure 7F:
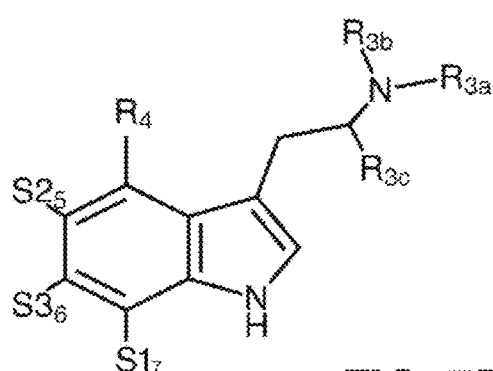

Further examples, wherein three of $R_2$, $R_5$, $R_6$, or $R_7$ are substituents are shown in FIGS. 7A, 7B, 7C, 7D, 7E, and 7F, in particular the 5,6,7-tri-S1, 2,S3-psilocybin derivative shown in FIG. 7A, the 5,6,7-tri-S1 S3,S2-psilocybin derivative shown in FIG. 7B, the 5,6,7-tri-S3,S1,S2-psilocybin derivative shown in FIG. 7C, the 5,6,7-tri-S2,S1,S3-psilocybin derivative shown in FIG. 7D, the 5,6,7-tri-S3,S2,S1-psilocybin derivative shown in FIG. 7E, and the 5,6,7-tri-S2,S3,S1-psilocybin derivative shown FIG. 7F. It will be clear from the foregoing that in FIGS. 7A-7F, S1, S2 and S3 are selected from three of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Figure 7G:
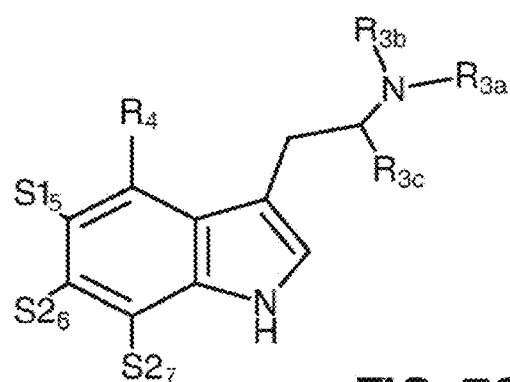
FIGS. 7G, 7H, and 7I depict the chemical structures of certain example psilocybin derivatives, notably a 5,6,7-tri-S1,S2,S2-psilocybin derivative (FIG. 7G), a 5,6,7-tri-S2,S1,S2-psilocybin derivative (FIG. 7H), and a 5,6,7-tri-S2,S2,S1-psilocybin derivative (FIG. 7I). In each of the foregoing S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group. It is noted that in each of FIGS. 7G-7I, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 7H:
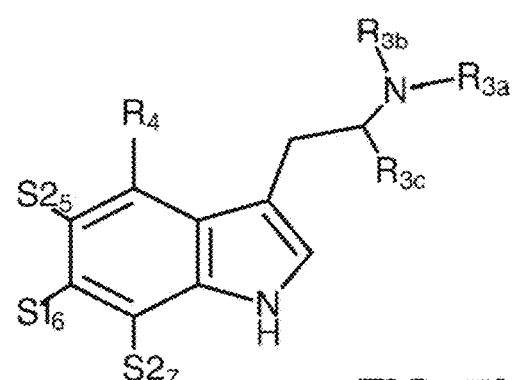
Figure 7I:
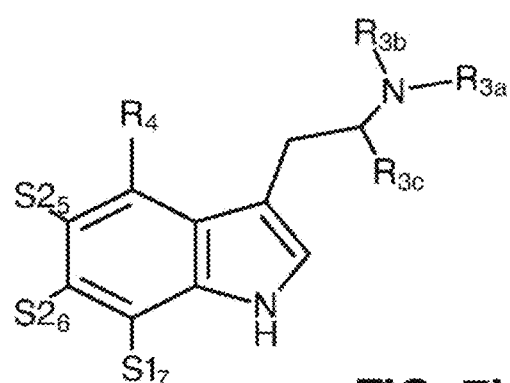

Yet further examples, wherein three of $R_2$, $R_5$, $R_6$, or $R_7$ are substituents are shown in FIGS. 7G, 7H, and 7I in particular the 5,6,7-tri-S1,S2,S2-psilocybin derivative shown in FIG. 7G, the 5,6,7-tri-S2,S1,S2-psilocybin derivative shown in FIG. 7H, and the 5,6,7-tri-S2,S2,S1-psilocybin derivative shown in FIG. 7I. It will be clear from the foregoing that in each of FIGS. 7G-7I, S1, and S2 are selected from two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group.

Furthermore, in each of the example embodiments shown in FIGS. 3A-3L, 4A-4I, 5A-5I, 6A-6I, and 7A-7I it is noted that $R_{3a}$ and $R_{3b}$ can be a hydrogen atom, an alkyl group, an acyl group, or an aryl group. Thus, $R_{3a}$ and $R_{3b}$ can each be a hydrogen atom, or $R_{3a}$ and $R_{3b}$ can each be an alkyl group, such as a methyl group, ethyl group, propyl group, or longer chain alkyl group, or $R_{3a}$ and $R_{3b}$ can be each be an acyl group, or $R_{3a}$ and $R_{3b}$ can each be an aryl group. Furthermore, one of $R_{3a}$ and $R_{3b}$ can be a hydrogen atom, and one of $R_{3a}$ and $R_{3b}$ can be an alkyl group. One of $R_{3A}$ and $R_{3B}$ can be a hydrogen atom, and one of $R_{3a}$ and $R_{3b}$ can be an acyl group. One of $R_{3a}$ and $R_{3b}$ can be a hydrogen atom, and one of $R_{3a}$ and $R_{3b}$ can be an aryl group. One of $R_{3a}$ and $R_{3b}$ can be an alkyl group, and one of $R_{3A}$ and $R_{3B}$ can be an aryl group. One of $R_{3a}$ and $R_{3b}$ can be an alkyl group, and one of $R_{3a}$ and $R_{3b}$ can be an acyl group. One of $R_{3a}$ and $R_{3b}$ can be an acyl group, and one of $R_{3a}$ and $R_{3b}$ can be an aryl group.

It is noted that in a further aspect hereof in each of the example embodiments shown in FIGS. 3A-3L, 4A-4I, 5A-5I, 6A-6I, and 7A-7I, $R_{3c}$ can be a hydrogen atom or a carboxy group.

It is noted that in a further aspect hereof in each of the example embodiments shown in FIGS. 3A-3L, 4A-4I, 5A-5I, 6A-6I, and 7A-7I, $R_4$ can be a hydrogen atom, an O-alkyl group, an O-acyl group, or a phosphate group.

Furthermore, in one example embodiment, a multi-substituent psilocybin derivative according to the present disclosure can be a chemical compound having a formula (IX):

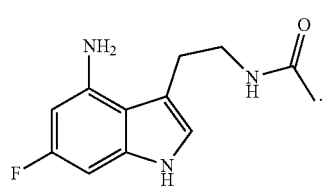

(IX)

Furthermore, in one example embodiment, a multi-substituent psilocybin derivative according to the present disclosure can be a chemical compound having a formula (X):

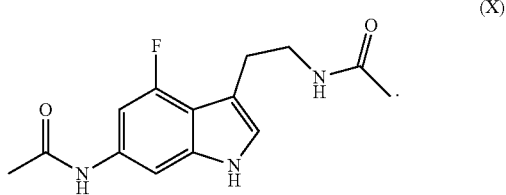 [SMILES: CC(=O)NCCc1c[nH]c2cc(NC(C)=O)cc(F)c12]

(X)

Furthermore, in one example embodiment, a multi-substituent psilocybin derivative according to the present disclosure can be a chemical compound having a formula (XI):

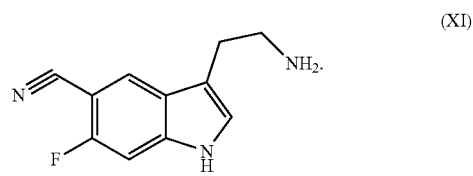 [SMILES: N#Cc1cc2c(CCN)c[nH]c2cc1F]

(XI)

Furthermore, in one example embodiment, a multi-substituent psilocybin derivative according to the present disclosure can be a chemical compound having a formula (XII):

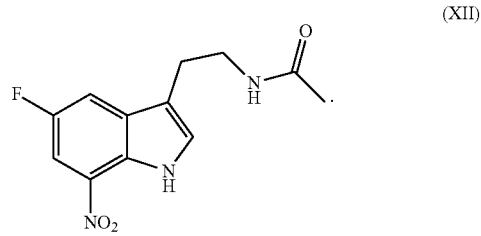 [SMILES: CC(=O)NCCc1c[nH]c2c([N+](=O)[O-])cc(F)cc12]

(XII)

Furthermore, in one example embodiment, a multi-substituent psilocybin derivative according to the present disclosure can be a chemical compound having a formula (XIII):

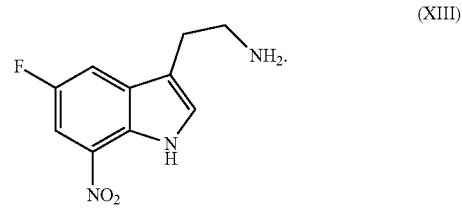

(XIII)

Furthermore, in one example embodiment, a multi-substituent psilocybin derivative according to the present disclosure can be a chemical compound having a formula (XIV):

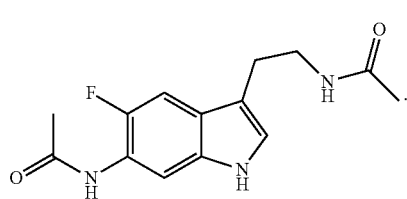

(XIV)

Furthermore, in one example embodiment, a multi-substituent psilocybin derivative according to the present disclosure can be a chemical compound having a formula (XV):

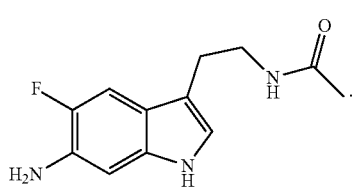

(XV)

Furthermore, in one example embodiment, a multi-substituent psilocybin derivative according to the present disclosure can be a chemical compound having a formula (XV):

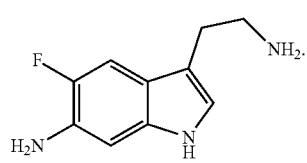

(XVI)

Furthermore, in one example embodiment, a multi-substituent psilocybin derivative according to the present disclosure can be a chemical compound having a formula (XVII):

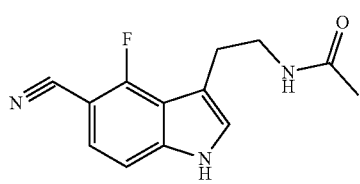

(XVII)

Furthermore, in one example embodiment, a multi-substituent psilocybin derivative according to the present disclosure can be a chemical compound having a formula (XVIII):

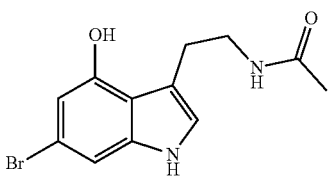

(XVIII)

Furthermore, in one example embodiment, a multi-substituent psilocybin derivative according to the present disclosure can be a chemical compound having a formula (XIX):

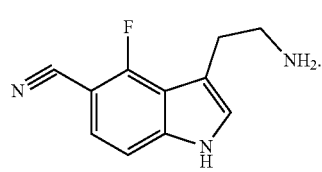

(XIX)

Furthermore, in one example embodiment, a multi-substituent psilocybin derivative according to the present disclosure can be a chemical compound having a formula (XX):

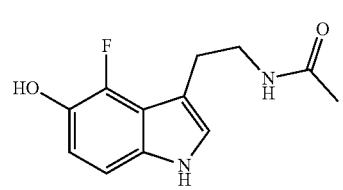

(XX)

Furthermore, in one example embodiment, a multi-substituent psilocybin derivative according to the present disclosure can be a chemical compound having a formula (XXI):

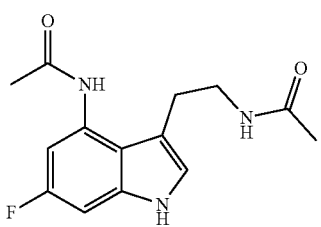

(XXI)

Furthermore, in one example embodiment, a multi-substituent psilocybin derivative according to the present disclosure can be a chemical compound having a formula (XXII):

 (XXII)

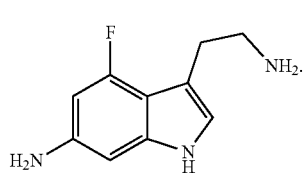 (XXVI)

Furthermore, in one example embodiment, a multi-substituent psilocybin derivative according to the present disclosure can be a chemical compound having a formula (XXIII):

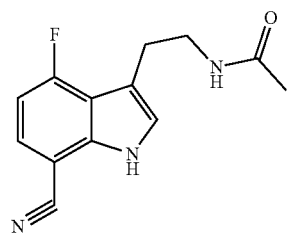 (XXIII)

Furthermore, in one example embodiment, a multi-substituent psilocybin derivative according to the present disclosure can be a chemical compound having a formula (XXIV):

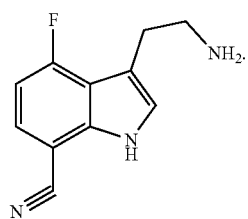 (XXIV)

Furthermore, in one example embodiment, a multi-substituent psilocybin derivative according to the present disclosure can be a chemical compound having a formula (XXV):

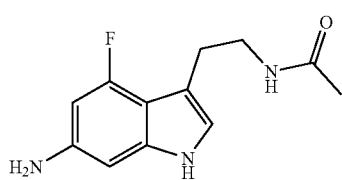 (XXV)

Furthermore, in one example embodiment, a multi-substituent psilocybin derivative according to the present disclosure can be a chemical compound having a formula (XVI):

Furthermore, in one example embodiment, a multi-substituent psilocybin derivative according to the present disclosure can be a chemical compound having a formula (XXVII):

 (XXVII)

Furthermore, in one example embodiment, a multi-substituent psilocybin derivative according to the present disclosure can be a chemical compound having a formula (XXVIII):

 (XXVIII)

Furthermore, in one example embodiment, a multi-substituent psilocybin derivative according to the present disclosure can be a chemical compound having a formula (XXIX):

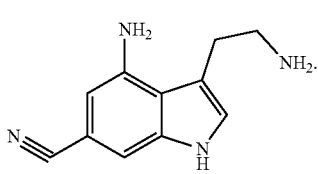 (XXIX)

Furthermore, in one example embodiment, a multi-substituent psilocybin derivative according to the present disclosure can be a chemical compound having a formula (XXX):

(XXX)

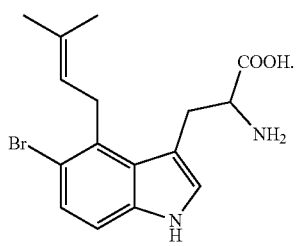

Furthermore, in one example embodiment, a multi-substituent psilocybin derivative according to the present disclosure can be a chemical compound having a formula (XXXI):

(XXXI)

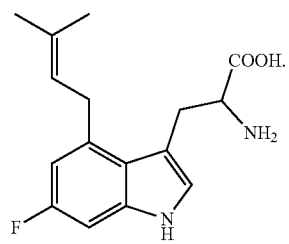

Furthermore, in one example embodiment, a multi-substituent psilocybin derivative according to the present disclosure can be a chemical compound having a formula (XXXII):

(XXXII)

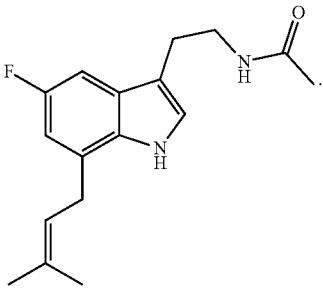

Furthermore, in one example embodiment, a multi-substituent psilocybin derivative according to the present disclosure can be a chemical compound having a formula (XXXIII):

(XXXIII)

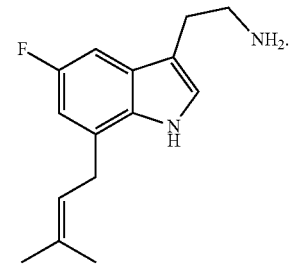

Furthermore, in one example embodiment, a multi-substituent psilocybin derivative according to the present disclosure can be a chemical compound having a formula (XXXIV):

(XXXIV)

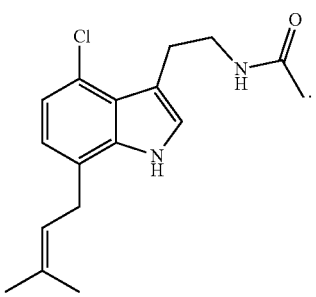

Furthermore, in one example embodiment, a multi-substituent psilocybin derivative according to the present disclosure can be a chemical compound having a formula (XXXV):

(XXXV)

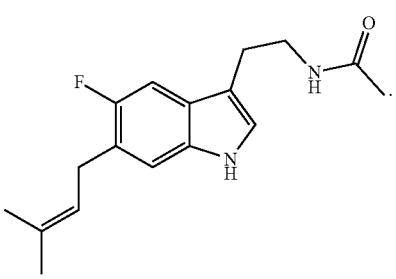

Furthermore, in one example embodiment, a multi-substituent psilocybin derivative according to the present disclosure can be a chemical compound having a formula (XXXVI):

(XXXVI)

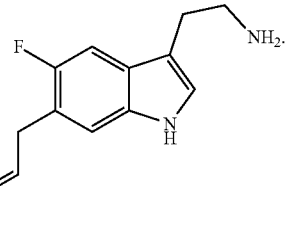

Furthermore, in one example embodiment, a multi-substituent psilocybin derivative according to the present disclosure can be a chemical compound having a formula (XXXVII):

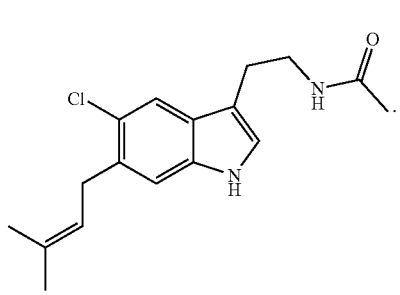
(XXXVII)

Furthermore, in one example embodiment, a multi-substituent psilocybin derivative according to the present disclosure can be a chemical compound having a formula (XXXVIII):

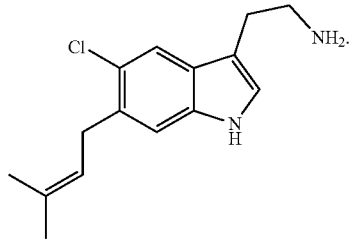
(XXXVIII)

Furthermore, in one example embodiment, a multi-substituent psilocybin derivative according to the present disclosure can be a chemical compound having a formula (XXXIX):

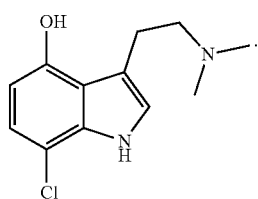
(XXXIX)

Furthermore, in one example embodiment, a multi-substituent psilocybin derivative according to the present disclosure can be a chemical compound having a formula (XL):

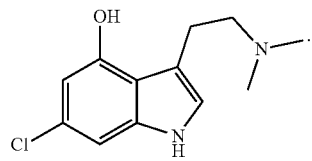
(XL)

Furthermore, in one example embodiment, a multi-substituent psilocybin derivative according to the present disclosure can be a chemical compound having a formula (XLI):

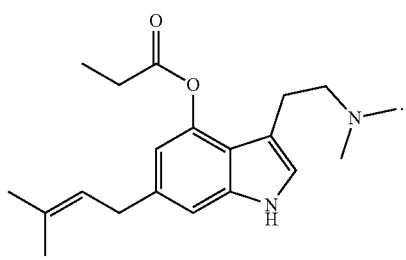
(XLI)

Furthermore, in one example embodiment, a multi-substituent psilocybin derivative according to the present disclosure can be a chemical compound having a formula (XLII):

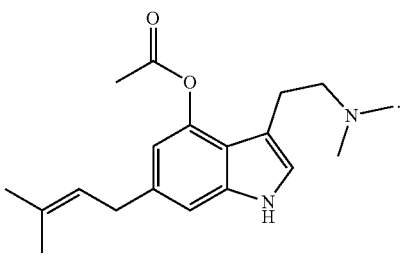
(XLII)

Furthermore, in one example embodiment, a multi-substituent psilocybin derivative according to the present disclosure can be a chemical compound having a formula (XLIII):

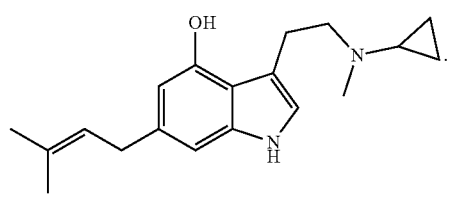
(XLIII)

Furthermore, in one example embodiment, a multi-substituent psilocybin derivative according to the present disclosure can be a chemical compound having a formula (XLIV):

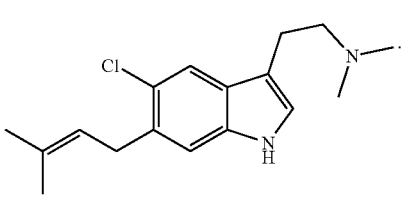
(XLIV)

Furthermore, in one example embodiment, a multi-substituent psilocybin derivative according to the present disclosure can be a chemical compound having a formula (XLV):

(XLV)

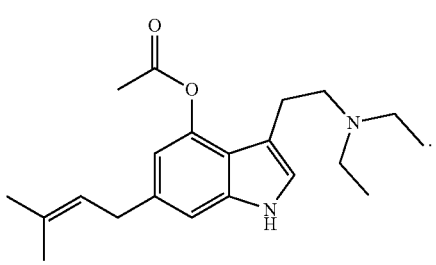

Furthermore, in one example embodiment, a multi-substituent psilocybin derivative according to the present disclosure can be a chemical compound having a formula (XLVI):

(XLVI)

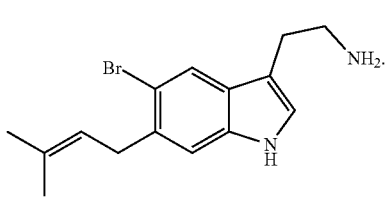

Furthermore, in one example embodiment, a multi-substituent psilocybin derivative according to the present disclosure can be a chemical compound having a formula (XLVII):

(XLVII)

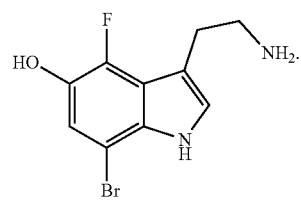

Furthermore, in one example embodiment, a multi-substituent psilocybin derivative according to the present disclosure can be a chemical compound having a formula (XLVIII):

(XLVIII)

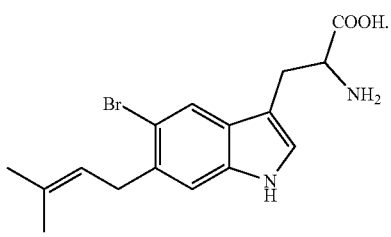

Furthermore, in one example embodiment, a multi-substituent psilocybin derivative according to the present disclosure can be a chemical compound having a formula (XLIX):

(XLIX)

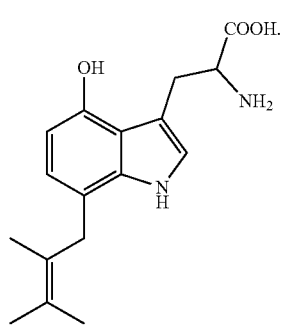

Furthermore, in one example embodiment, a multi-substituent psilocybin derivative according to the present disclosure can be a chemical compound having a formula (L):

(L)

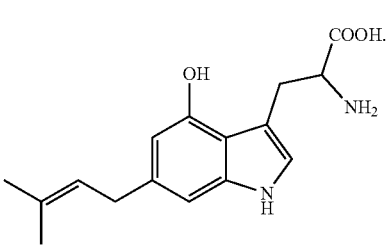

Furthermore, in one example embodiment, a multi-substituent psilocybin derivative according to the present disclosure can be a chemical compound having a formula (LI):

(LI)

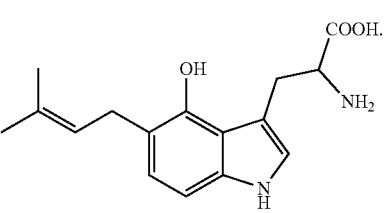

Furthermore, in one example embodiment, a multi-substituent psilocybin derivative according to the present disclosure can be a chemical compound having a formula (LII):

(LII)

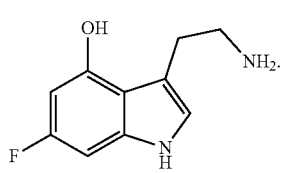

Furthermore, in one example embodiment, a multi-substituent psilocybin derivative according to the present disclosure can be a chemical compound having a formula (LIII):

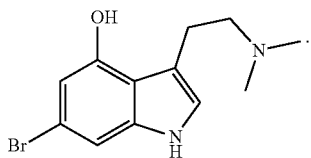
(LIII)

Furthermore, in one example embodiment, a multi-substituent psilocybin derivative according to the present disclosure can be a chemical compound having a formula (LIV):

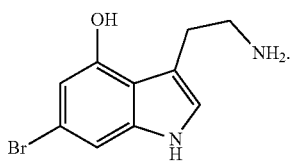
(LIV)

Furthermore, in one example embodiment, a multi-substituent psilocybin derivative according to the present disclosure can be a chemical compound having a formula (LV):

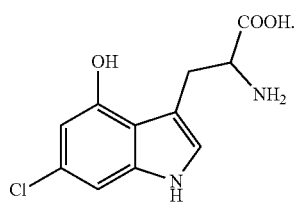
(LV)

Furthermore, in one example embodiment, a multi-substituent psilocybin derivative according to the present disclosure can be a chemical compound having a formula (LXXVI):

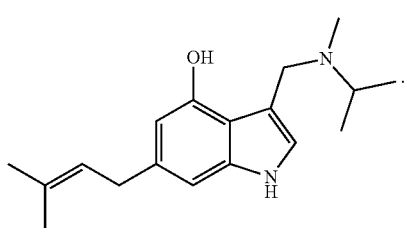
(LXXVI)

Furthermore, it is noted that the multi-substituent psilocybin derivatives of the present disclosure include salts thereof, including pharmaceutically acceptable salts. Thus, the nitrogen atom of the ethyl-amino group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term prenylated psilocybin derivative also includes compounds having a formula (IV):

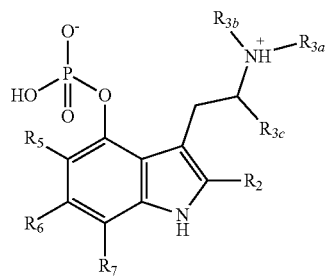
(IV)

wherein, at least two of $R_2$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group. When $R_{3c}$ is a carboxy group, further included are compounds having a formula (Iva):

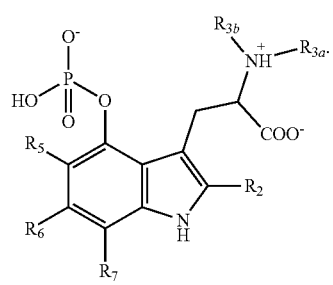
(IVa)

Further included are salts of prenylated psilocybin derivatives having a formula (IV) and (IVa), such as a sodium salt, a potassium salt, etc.

Thus, to briefly recap, the present disclosure provides multi-substituent psilocybin derivatives. The disclosure provides, in particular, a chemical compound having a formula (I):

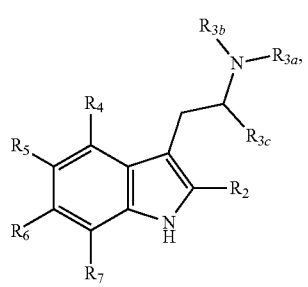
(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

In another embodiment, $R_{3a}$ and $R_{3b}$ are a hydrogen atom, a $(C_1-C_{20})$-alkyl group, a $(C_6-C_{14})$-aryl group, or a —C(=O)($C_1-C_{20}$)-alkyl group. In another embodiment, $R_{3a}$ and $R_{3b}$ are a hydrogen atom, a $(C_1-C_{10})$-alkyl group, a $(C_6-C_{10})$-aryl group, or a —C(=O)($C_1-C_{10}$)-alkyl group. In another embodiment, $R_{3a}$ and $R_{3b}$ are a hydrogen atom, a $(C_1-C_6)$-alkyl group, a phenyl group, or a —C(=O)($C_1-C_6$)-alkyl group. In another embodiment, $R_{3a}$ and $R_{3b}$ are a hydrogen atom, a methyl group, an ethyl group, a propyl group, a phenyl group, —C(=O)—$CH_3$, —C(=O)—$CH_2CH_3$, or —C(=O)—$CH_2CH_2CH_3$.

In another embodiment, $R_{3a}$ and/or $R_{3b}$ are a $(C_1-C_{20})$-cyclo-alkyl group, or a $(C_1-C_{10})$-cyclo-alkyl group, a $(C_1-C_{10})$-cyclo-alkyl group, or a $(C_1-C_{10})$-cyclo-alkyl group. In one embodiment, $R_{3a}$ and/or $R_{3b}$ are a cyclo-propane group, a cyclo-butane group, a cyclo-pentane group, or a cyclo-hexane group.

In one embodiment, the alkyl groups (including O-alkyl) in any of the definitions of the formulas of the disclosure is $C_1-C_{20}$-alkyl. In another embodiment, the alkyl group is $C_1-C_{10}$-alkyl. In another embodiment, the alkyl group is $C_1-C_6$-alkyl. In another embodiment, the alkyl group is methyl, ethyl, propyl, butyl or pentyl.

In one embodiment, the acyl groups (including O-acyl) in any of the definitions of the formulas of the disclosure is $C_1-C_{20}$-acyl (or $C_1-C_{20}$-acyl-O—). In another embodiment, the alkyl group is $C_1-C_{10}$-acyl (or $C_1-C_{10}$-acyl-O—). In another embodiment, the alkyl group is $C_1-C_6$-acyl (or $C_1-C_6$-acyl-O—). In another embodiment, the acyl group is an O-acyl group, a methanoyl, ethanoyl, propanoyl, butanoyl or pentanoyl.

In one embodiment, the aryl groups in any of the definitions of the formulas of the disclosure is optionally substituted $C_6-C_{14}$-aryl. In another embodiment, the aryl group is optionally substituted $C_6-C_{10}$-aryl, or phenyl. In another embodiment, the aryl group is phenyl, naphthyl, tetrahydronaphthyl, phenanthrenyl, biphenylenyl, indanyl, or indenyl and the like.

The multi-substituent psilocybin derivatives of the present disclosure may be used to prepare a pharmaceutical or recreational drug formulation. Thus in one embodiment, the present disclosure further provides in another aspect, pharmaceutical and recreational drug formulations comprising multi-substituent psilocybin derivatives. Accordingly, in one aspect, the present disclosure provides in a further embodiment a pharmaceutical or recreational drug formulation comprising a chemical compound having a formula (I):

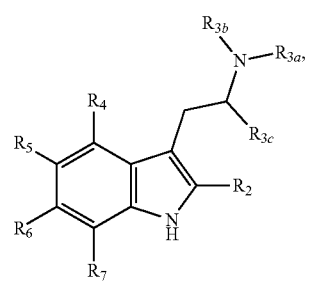

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the nitrilated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", $22^{nd}$ Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the multi-substituent psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the multi-substituent psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the multi-substituent psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the multi-substituent psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the multi-substituent psilocybin derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

Thus it will be clear the multi-substituent psilocybin derivative compounds may be used as a pharmaceutical or recreational drug. Accordingly, in another aspect the present disclosure provides, in at least one embodiment, a use of a chemical compound having a formula (I):

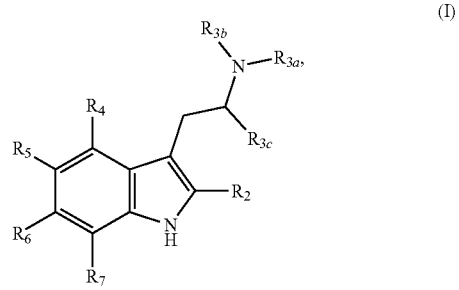

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound having a formula (I):

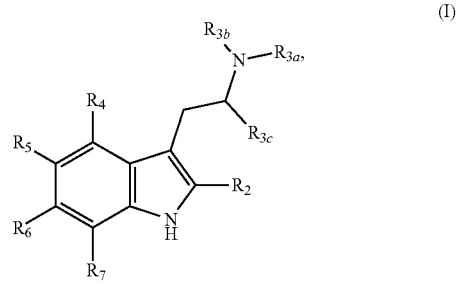

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, cannabis related disorders, inhalant-use related disorders, stimulant use disorders, and tobacco use disorders; neurocognitive disorders, such as delirium;

schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a 5-$HT_{2A}$ receptor to thereby modulate the 5-$HT_{2A}$ receptor. Such contacting includes bringing a compound of the present disclosure and 5-$HT_{2A}$ receptor together under in vitro conditions, for example, by introducing the compounds in a sample containing a 5-$HT_{2A}$ receptor, for example, a sample containing purified 5-$HT_{2A}$ receptors, or a sample containing cells comprising 5-$HT_{2A}$ receptors. In vitro conditions further include the conditions described in Example 1 hereof. Contacting further includes bringing a compound of the present disclosure and 5-$HT_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{2A}$ receptor or inhibit the 5-$HT_{2A}$ receptor.

Thus, in a further aspect, the condition that may be treated in accordance herewith can be any 5-$HT_{2A}$ receptor mediated disorder. Such disorders include, but are not limited to schizophrenia, psychotic disorder, attention deficit hyperactivity disorder, autism, and bipolar disorder.

In an aspect, the compounds of the present disclosure may be used to be contacted with a 5-$HT_{1A}$ receptor to thereby modulate the 5-$HT_{1A}$ receptor. Such contacting includes bringing a compound of the present disclosure and 5-$HT_{1A}$ receptor together under in vitro conditions, for example, by introducing the compounds in a sample containing a 5-$HT_{1A}$ receptor, for example, a sample containing purified 5-$HT_{1A}$ receptors, or a sample containing cells comprising 5-$HT_{1A}$ receptors. In vitro conditions further include the conditions described in Example 1 hereof. Contacting further includes bringing a compound of the present disclosure and 5-$HT_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{1A}$ receptor, the compound may activate the 5-$HT_{1A}$ receptor or inhibit the 5-$HT_{1A}$ receptor.

Thus, in a further aspect, the condition that may be treated in accordance herewith can be any 5-$HT_{1A}$ receptor mediated disorder. Such disorders include, but are not limited to schizophrenia, psychotic disorder, attention deficit hyperactivity disorder, autism, and bipolar disorder.

In some embodiments, upon having contacted a 5-$HT_{1A}$ receptor and a 5-$HT_{2A}$ receptor, the compound may modulate the 5-$HT_{1A}$ receptor, e.g., activate or inhibit the 5-$HT_{1A}$ receptor, however the compound may at the same time not modulate the 5-$HT_{2A}$ receptor.

In some embodiments, upon having contacted a 5-$HT_{2A}$ receptor and a 5-$HT_{1A}$ receptor, the compound may modulate the 5-$HT_{2A}$ receptor, e.g., activate or inhibit the 5-$HT_{2A}$ receptor, however the compound may at the same time not modulate the 5-$HT_{1A}$ receptor.

Turning now to methods of making the multi-substituent psilocybin derivatives of the present disclosure, it is initially noted that the multi-substituent psilocybin derivatives of the present disclosure may be prepared in any suitable manner, including by any organic chemical synthesis methods, biosynthetic methods, or a combination thereof. Next, initially example methods for chemically making the multi-substituent psilocybin derivatives of the present disclosure will be discussed. Thereafter, example biosynthetic methods for making the multi-substituent psilocybin derivatives will be discussed.

One suitable method of making the multi-substituent psilocybin derivatives of the present disclosure initially involves selecting and obtaining or preparing a reactant psilocybin derivative compound and selecting and obtaining or preparing a substituent group containing compound and, thereafter chemically or biochemically reacting the reactant psilocybin derivative compound and the substituent group containing compound to obtain a multi-substituent psilocybin derivative compound. It is noted that in embodiments hereof where the reactant psilocybin derivative compound does not already possess at least one substituent group, the non-substituent reactant psilocybin derivative compound (i.e., generally an indole structure containing reactant wherein $R_2$, $R_5$, $R_6$ and $R_7$ are each hydrogen atoms) can be reacted, generally sequentially, with at least two substituent groups containing compounds. Examples thereof are shown in FIGS. 9, 10, 11A-11C, and 12A-12D (depicting example reactions to form a first psilocybin derivative possessing a single substituent), in conjunction with FIGS. 13A-13C (depicting follow-on example reactions to form multi-substituent psilocybin derivatives possessing two or more substituents). In other embodiments, the reactant psilocybin derivative compound may possess at least one substituent group, and is reacted with at least one additional substituent group containing compound (such as depicted in FIGS. 8A-8G).

Accordingly, in one aspect, the present disclosure provides, in at least one embodiment, a method of making a psilocybin derivative or salt thereof having a formula (I):

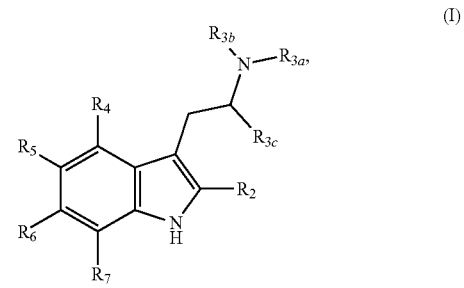

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group, the method comprising:

reacting a reactant psilocybin derivative compound having a chemical formula (II):

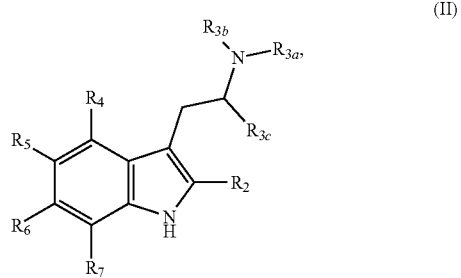

(II)

wherein, one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom or an alcohol group and when $R_4$ is not substituted with any of the foregoing substituents, $R_4$ is a hydrogen atom, a hydroxy group, an O-alkyl group, O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group with a substituent containing compound, wherein the substituent in the substituent containing compound is selected from (i) a halogen containing compound, (ii) a hydroxy group containing compound, (iii) a nitro group containing compound, (iv) a glycosyloxy group containing compound, (v) an amino group or an N-substituted amino group containing compound, (vi) a carboxyl group or a carboxylic acid derivative containing compound, (vii) an aldehyde or a ketone group containing compound, (viii) a prenyl group containing compound, and (ix) a nitrile group containing compound under reaction conditions sufficient to form the psilocybin substituent or salt thereof having chemical formula (I).

Reactant psilocybin derivative compound having formula (II) encompasses a plurality of compounds. In general, a reactant psilocybin derivative compound having formula (II) can be selected, by initially identifying a desired multi-substituent psilocybin derivative compound, and determining the substituent groups therein, and by thereafter selecting an appropriate reactant psilocybin derivative compound having formula (II). Thus, for example, if it is desirable to prepare a $S1_4$, $S2_6$ multi-substituent psilocybin derivative, a $S1_4$ reactant psilocybin derivative compound may be selected and reacted with an S2 substituent containing compound to form the desired $S1_4$, $S2_6$ multi-substituent psilocybin derivative compound, or if it is desirable to prepare a $S1_5$, $S2_6$ multi-substituent psilocybin derivative, a $S1_5$ reactant psilocybin derivative compound may be selected and reacted with an S2 substituent containing compound to form the $S1_5$, $S2_6$ multi-substituent psilocybin derivative. Thus, furthermore it can be said that the performance of chemical reactions to make the compounds of the present disclosure, in general involves a substitution at different carbon atoms, i.e. the $C_2$, $C_4$, $C_5$, $C_6$ and/or $C_7$ atom.

Figure 8A:
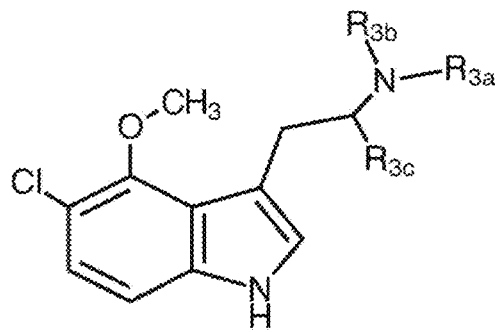
FIGS. 8A, 8B, 8C, 8D, 8E, 8F, and 8G depict the chemical structures of certain example psilocybin derivatives, notably O-alkylated psilocybin derivatives, notably a 4-O-methyl-5-chloro-psilocybin derivative (FIG. 8A), a 4-O-ethyl-5-chloro-psilocybin derivative (FIG. 8B), a 4-acetoxy-5-chloro-psilocybin derivative (FIG. 8C), a 4-propionyloxy-5-chloro-psilocybin derivative (FIG. 8D), a 4-hydroxy-5-chloro-psilocybin derivative (FIG. 8E), a 4-phospho-5-chloro-psilocybin derivative (FIG. 8F), and a 5-chloro-psilocybin derivative (FIG. 8H). It is noted that in each of FIGS. 8A-8G, $R_{3a}$ and $R_{3b}$ can each be a hydrogen atom, an alkyl group, a cycloalkyl group, an acyl group, or an aryl group, and $R_{3c}$ can be a hydrogen atom or a carboxyl group.
Figure 8B:
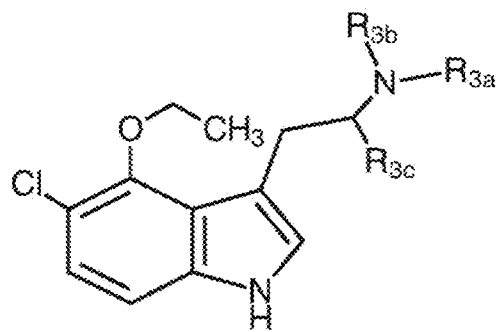

Thus, in one example embodiment, to form a multi-substituent psilocybin derivative wherein $S1_5$ is a chlorine atom, and $R_2$, $R_6$, and $R_7$ are $S2_2$, $S2_6$ or $S2_7$, the reactant psilocybin derivative can be selected to be a chemical compound wherein $R_4$ is an O-alkyl group, $R_2$, $R_6$, and $R_7$ are a hydrogen atom, $R_5$ is a chlorine atom, and $R_{3A}$ and $R_{3B}$ are a hydrogen atom, an alkyl group, an acyl group, or an aryl group, such as, for example, the reactant psilocybin derivative shown in FIGS. 8A and 8B.

Figure 8C:
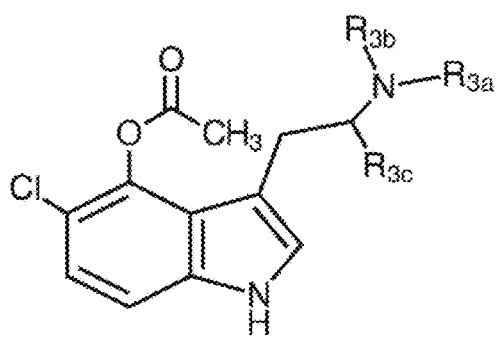
Figure 8D:
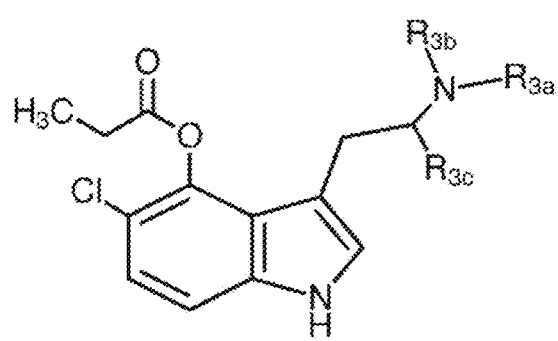

In one further example embodiment, to form a multi-substituent psilocybin derivative wherein $S1_5$ is a chlorine atom, and $R_2$, $R_6$, and $R_7$ are $S2_2$, $S2_6$ or $S2_7$, the reactant psilocybin derivative can be selected to be a chemical compound wherein $R_4$ is an O-acyl group, $R_2$, $R_6$, and $R_7$ are a hydrogen atom, $R_5$ is a chlorine atom, and $R_{3A}$ and $R_{3B}$ are a hydrogen atom, an alkyl group, an acyl group, or an aryl group, such as, for example, the reactant psilocybin derivative shown in FIGS. 8C and 8D.

Figure 8E:
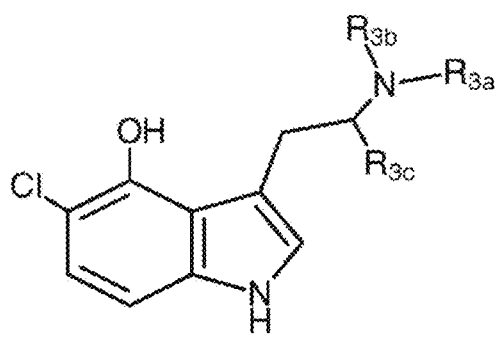

In one further example embodiment, to form a multi-substituent psilocybin derivative wherein $S1_5$ is a chlorine atom, and $R_2$, $R_6$, and $R_7$ are $S2_2$, $S2_6$ or $S2_7$, the reactant psilocybin derivative can be selected to be a chemical compound wherein $R_4$ is a hydroxyl group, $R_2$, $R_6$, and $R_7$ are a hydrogen atom, $R_5$ is a chlorine atom, and $R_{3A}$ and $R_{3B}$ are a hydrogen atom, an alkyl group, an acyl group, or an aryl group, such as, for example, the reactant psilocybin derivative shown in FIG. 8E.

Figure 8F:
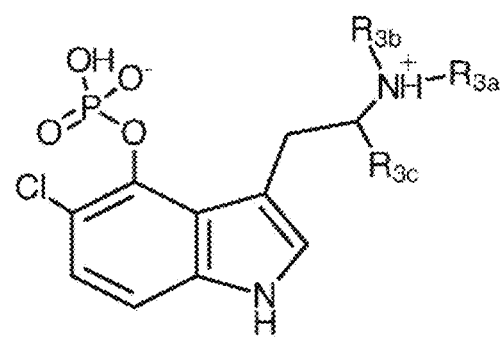

In one further example embodiment, to form a multi-substituent psilocybin derivative wherein $S1_5$ is a chlorine atom, and $R_2$, $R_6$, and $R_7$ are $S2_2$, $S2_6$ or $S2_7$, the reactant psilocybin derivative can be selected to be a chemical compound wherein $R_4$ is a phosphate group, $R_2$, $R_6$, and $R_7$ are a hydrogen atom, $R_5$ is a chlorine atom, and $R_{3A}$ and $R_{3B}$ are a hydrogen atom, an alkyl group, an acyl group, or an aryl group, such as, for example, the reactant psilocybin derivative shown in FIG. 8F.

Figure 8G:
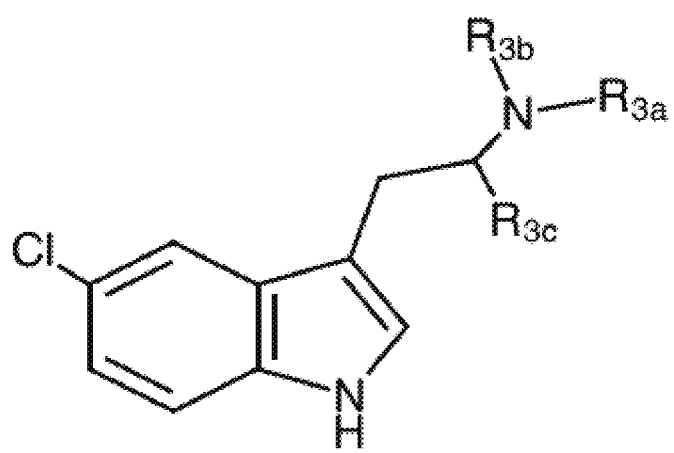
Figure 9:
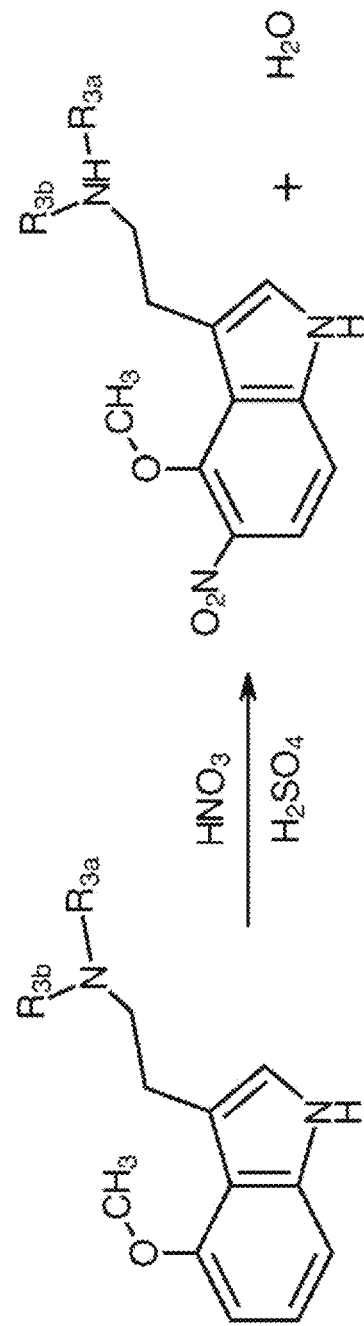
FIG. 9 depicts an example chemical reaction for synthesizing a nitrated psilocybin derivative, notably a reaction wherein a 4-O-methyl-psilocybin derivative is reacted with nitric acid in the presence of sulfuric acid to form a 4-O-methyl-5-nitro-psilocybin derivative.
Figure 10:
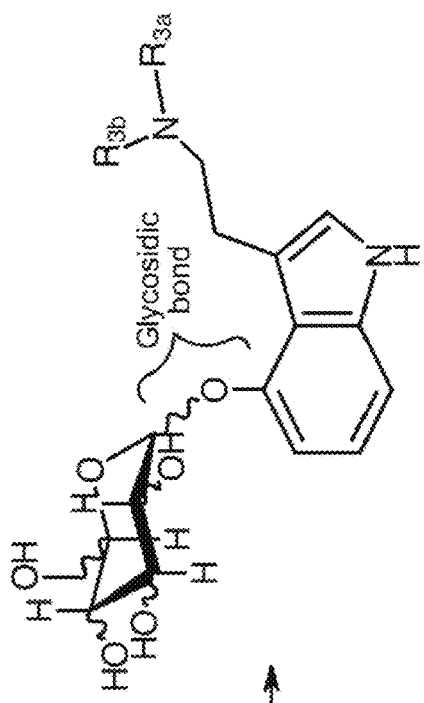
FIG. 10 depicts an example chemical reaction for synthesizing a glycosylated psilocybin derivative, notably a reaction wherein a 4-hydroxy-psilocybin derivative is reacted with a glycosyl compound to form a 4-glycosyl-psilocybin derivative.
Figure 10:
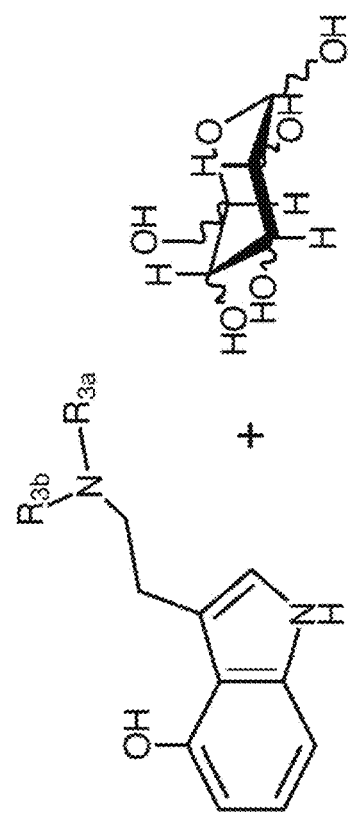
Figure 11A:
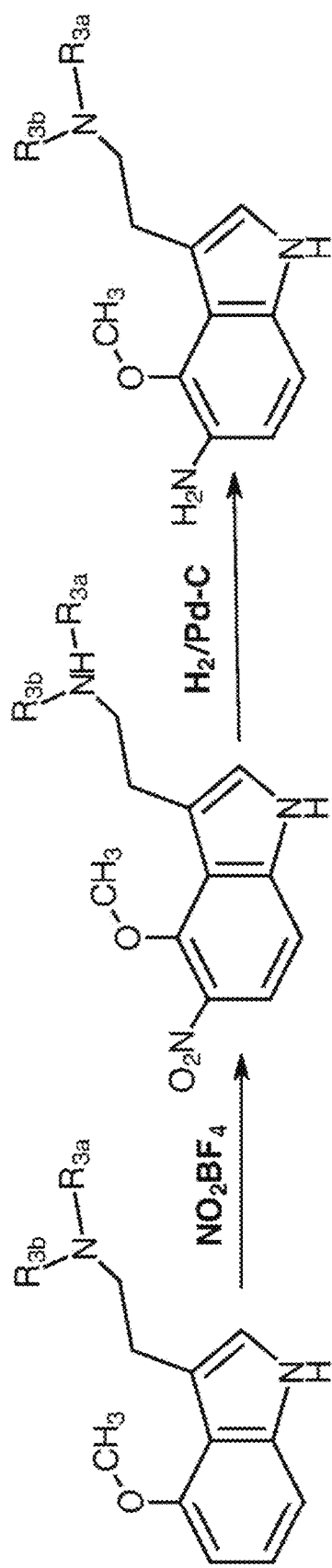
FIGS. 11A, 11B and 11C depict certain example chemical reactions for synthesizing aminated psilocybin derivatives with subsequent N-substitutions, notably a reaction wherein a 4-O-methyl-5-nitro-psilocybin derivative is reacted with hydrogen under the catalysis of palladium on charcoal to form a 4-O-methyl-5-amino-psilocybin derivative (FIG. 11A). The formed amino group at the 5-position can then be substituted with different group such as an acylation with acetic anhydride. The amino group can also be alkylated via a condensation with an aldehyde (such as acetaldehyde) followed by a reduction of the intermediate imine with borohydride (FIG. 11B).
Figure 11B:
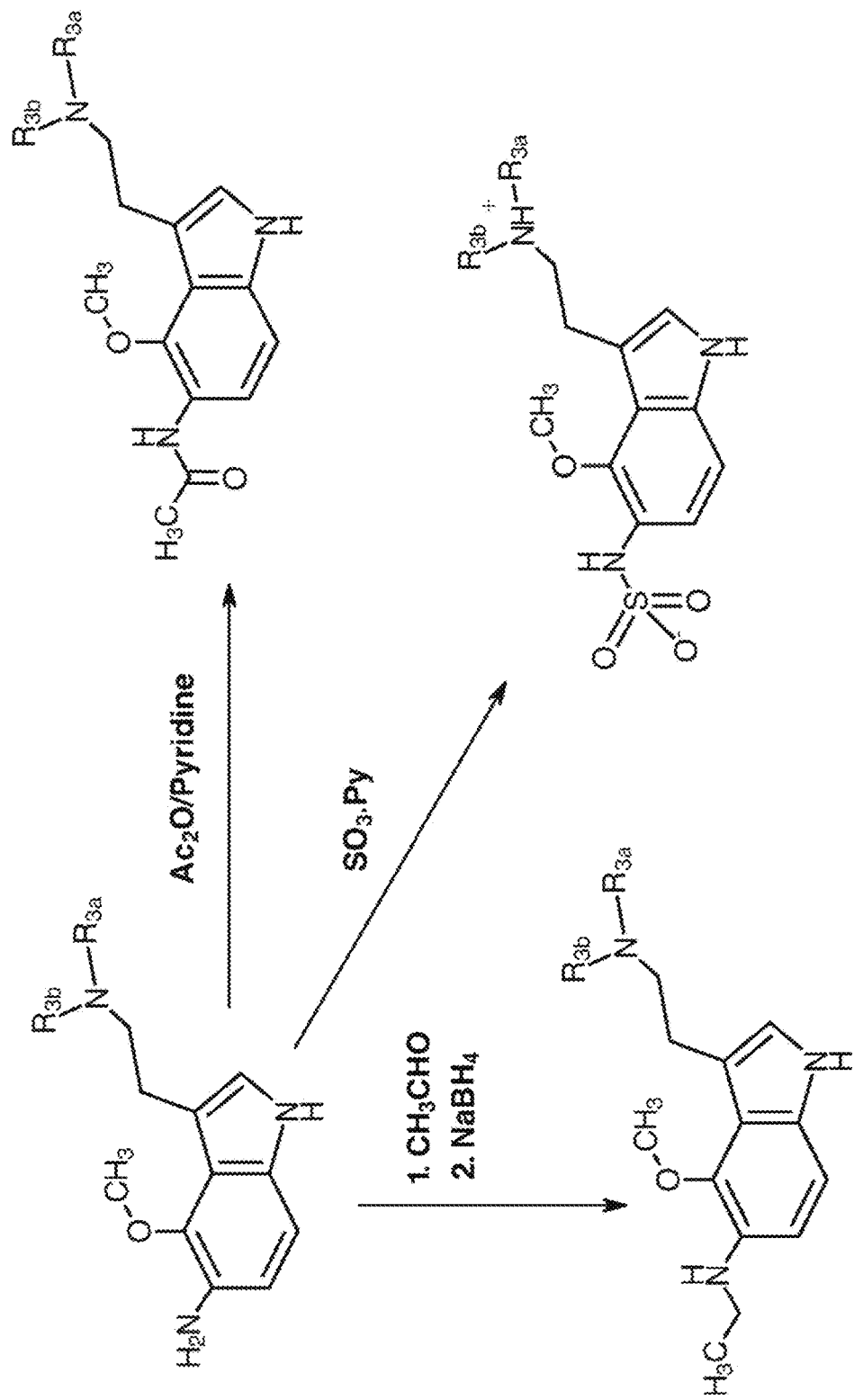
Figure 11C:
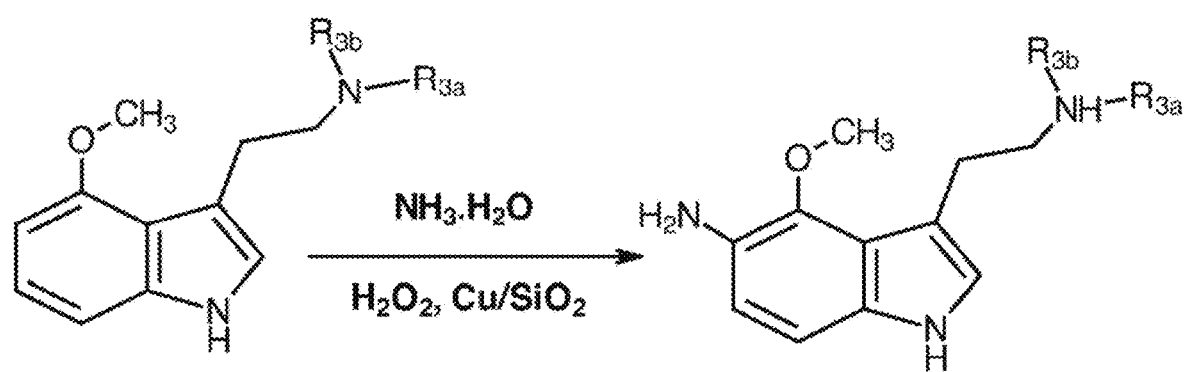
Figure 12A:
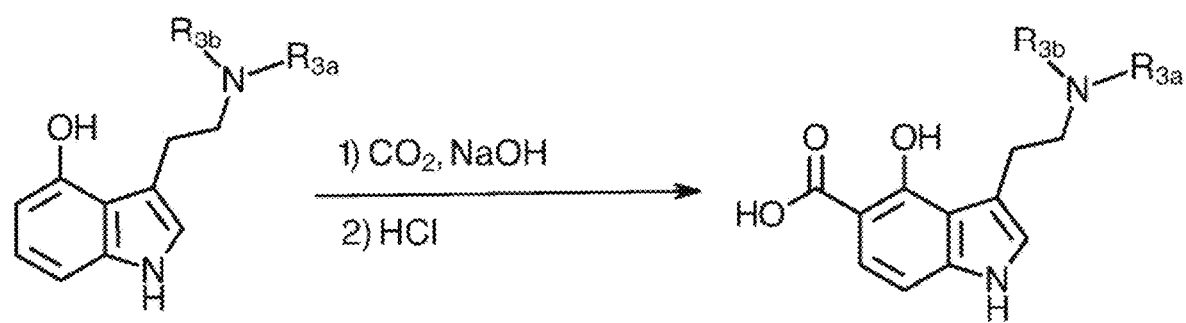
FIGS. 12A, 12B, 12C and 12D depicts depict example chemical reactions showing the formation of a 4-hydroxy-5-carboxyl psilocybin derivative using a 4-hydroxy-psilocybin derivative as a reactant (FIG. 12A); a 4-hydroxy-7-carboxyl psilocybin derivative using an arylhalide-psilocybin derivative as a reactant (FIG. 12B); a carboxylated protected psilocybin derivate using a protected psilocybin derivative as a reagent (FIG. 12C), and a sodium salt of a carboxylated psilocybin derivative (a); an OH substituted carboxyl group forming an ester; (b) or an OH substituted carboxyl group forming an amide (c), using a carboxylated psilocybin derivative as a reagent (FIG. 12D)
Figure 12B:
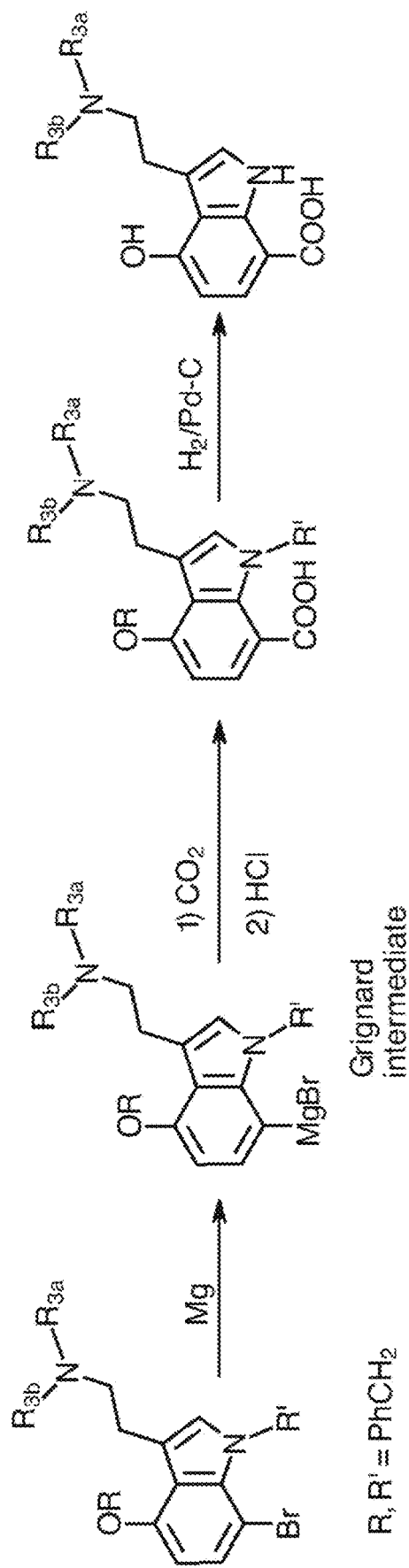
Figure 12C:
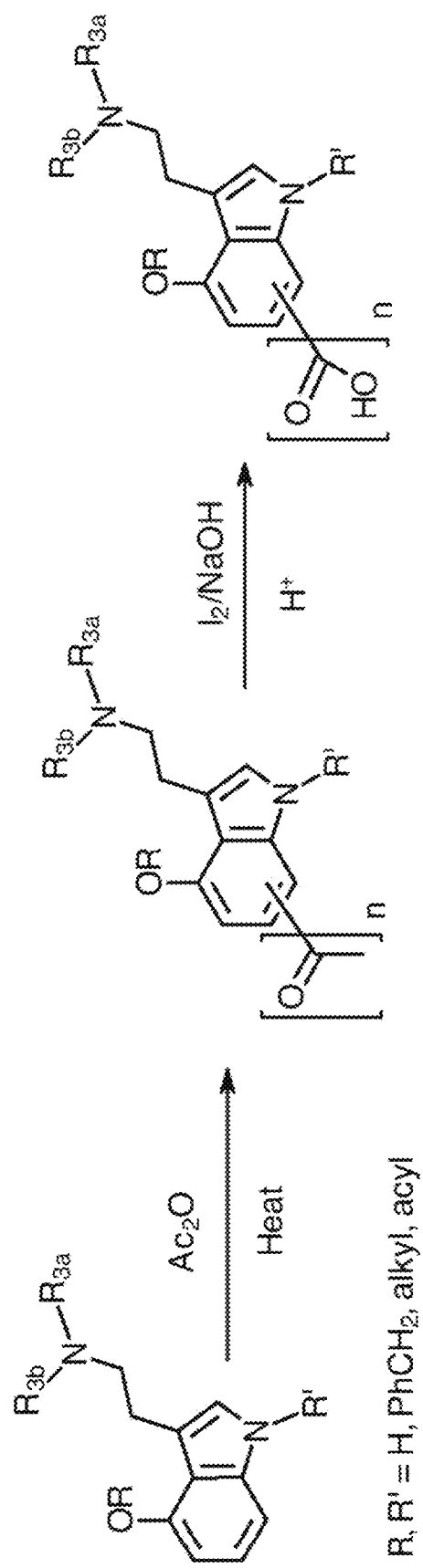
Figure 12D:
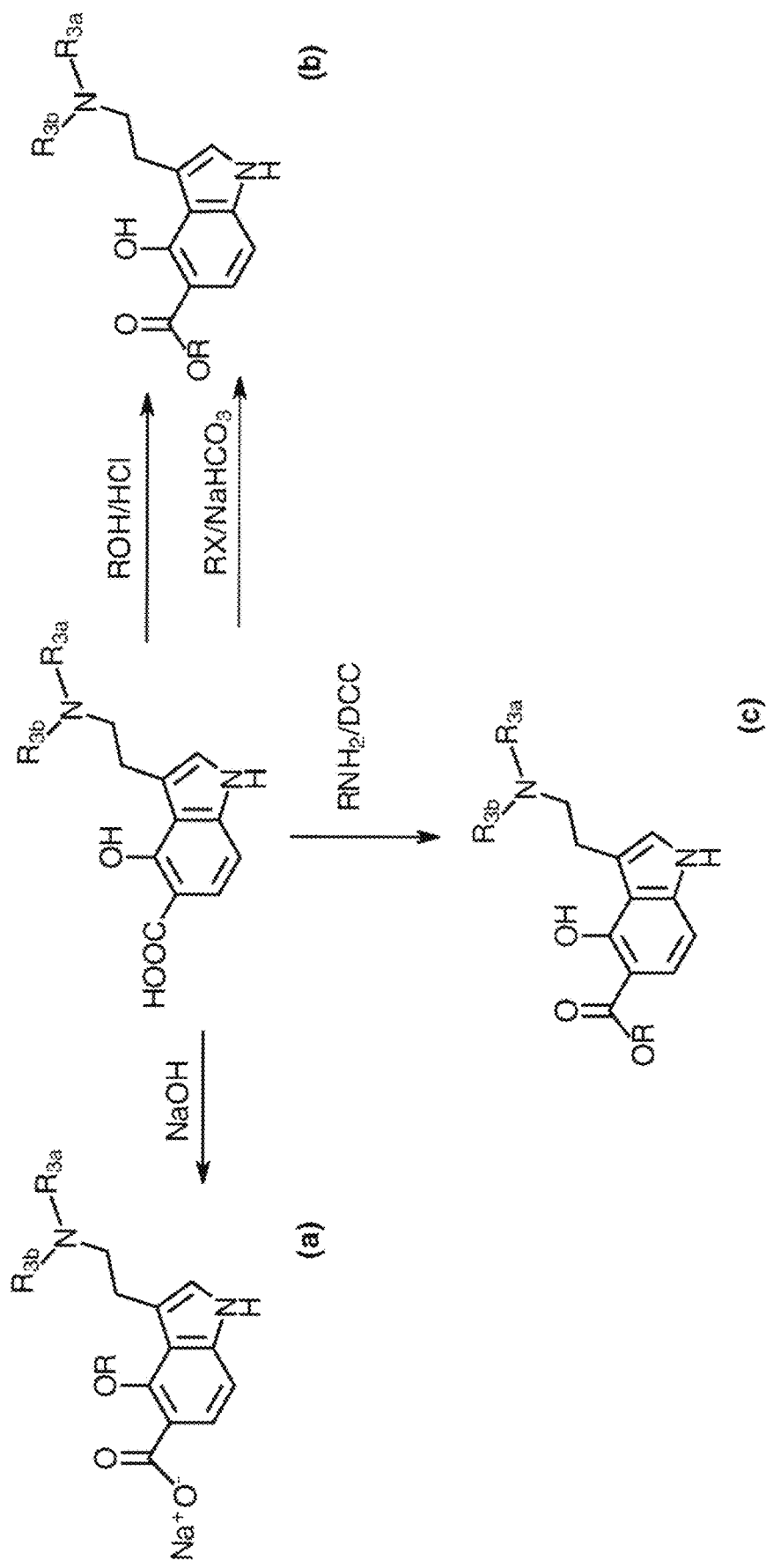

In yet one further example embodiment, to form a multi-substituent psilocybin derivative wherein $S1_5$ is a chlorine atom, and $R_2$, $R_6$, and $R_7$ are $S2_2$, $S2_6$ or $S2_7$, the reactant psilocybin derivative can be selected to be a chemical compound wherein $R_4$ is a hydrogen atom, $R_2$, $R_6$, and $R_7$ are a hydrogen atom, $R_5$ is a chlorine atom, and $R_{3A}$ and $R_{3B}$ are a hydrogen atom, an alkyl group, an acyl group, or an aryl group, such as, for example, the reactant psilocybin derivative shown in FIG. 8G.

The reactant psilocybin derivative compounds may be provided in a more or less chemically pure form, for example, in the form of a psilocybin derivative preparation having a purity of at least about 95%, at least about 96%, at least about 97%, at least about 98%, at least about 99%, or at least 99.9%. The psilocybin derivative may be chemically synthesized, or obtained from a fine chemical manufacturer, such as, for example, Sigma-Aldrich® (St. Louis, MO, USA).

The substituent group containing compound can be any compound comprising a substituent group selected from (i) a halogen atom, (ii) a hydroxy group, (iii) a nitro group, (iv)

a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group capable of reacting with the selected reactant psilocybin derivative compound.

The substituent group containing compound may be provided in a more or less chemically pure form, for example, having a purity of at least about 95%, at least about 96%, at least about 97%, at least about 98%, at least about 99%, or at least 99.9%. The nitrile containing compound may be synthesized or purified, or can be conveniently obtained from a fine chemical manufacturer, such as, for example, Sigma-Aldrich® (St. Louis, MO, USA).

By way of an example, shown in FIGS. 9, 10, 11A-11C, 12A-12D, and 13A-13C are example reactions to form an initial nitrated (FIG. 9), glycosylated (FIG. 10), aminated (FIG. 11A-11C), and carboxylated (FIG. 12A-12D) psilocybin derivatives. Each of the obtained compounds may subsequently then be reacted with an additional substituent containing compound, as shown, by way of example, in FIGS. 13A-13C.

Figure 13A:
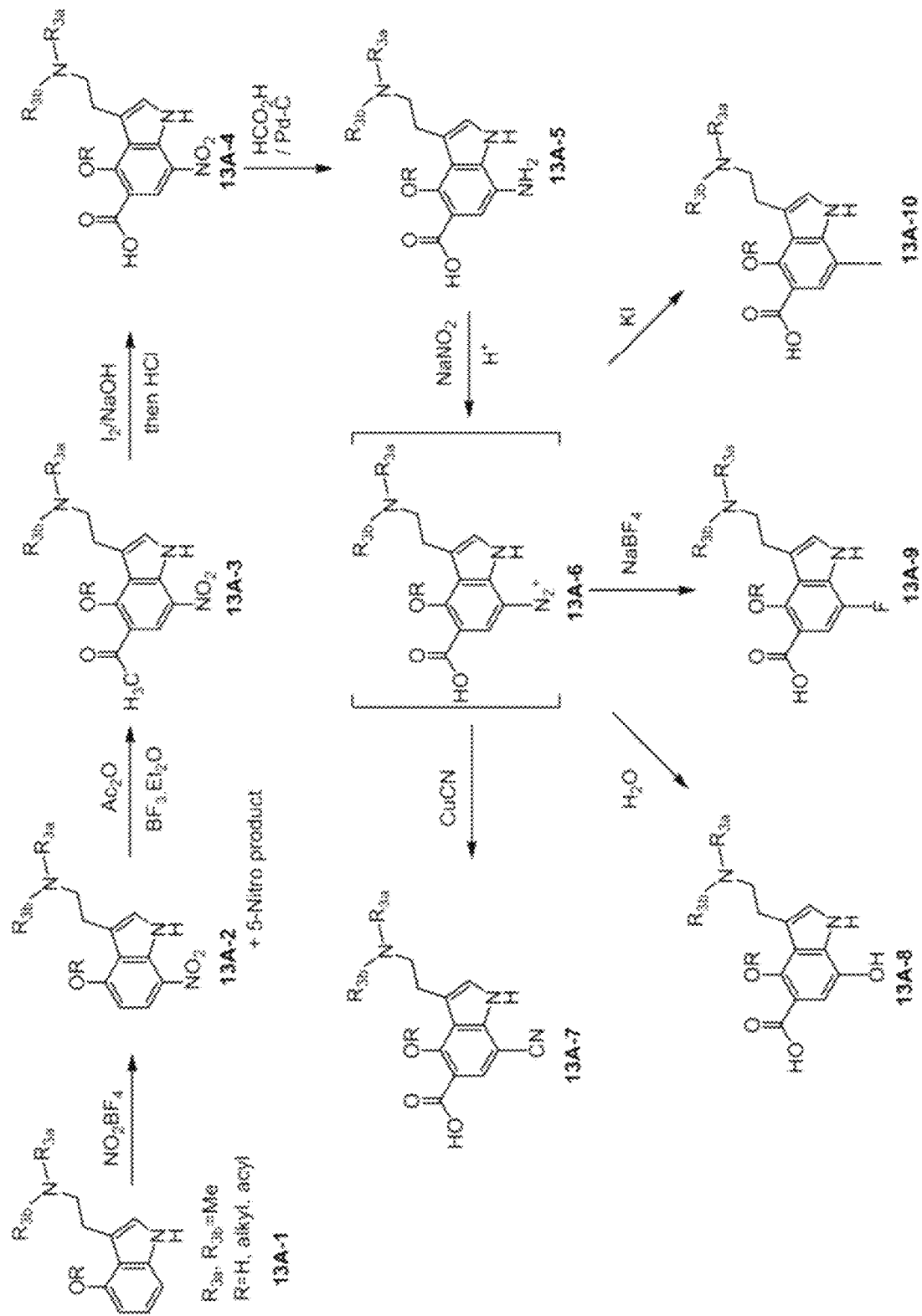
FIGS. 13A, 13B, 13C and 13D depict example chemical reactions for making psilocybin derivatives.

Thus, referring to FIG. 13A, shown therein are example chemical transformations for an initially synthesized 7-nitrated psilocybin derivative (see: compound 13A-2) to other 5,7-di-substituted psilocybin derivatives containing two types of groups at the $C_5$ and $C_7$ carbon atom. For example, a Friedel-Crafts acylation with compound 13A-2 will regioselectively install an acetyl group at the $C_5$ carbon to afford compound 13A-3, which, in turn, can be further oxidized to the corresponding 5-carboxy derivative (compound 13A-4) via an iodoform reaction. The 7-nitro group can then be reduced to the corresponding 7-amino-psilocibin derivative (compound 13A-5) through a palladium-mediated reduction using formic acid as the hydrogen source. The 7-amino group can be further converted to the reactive and versatile 7-diazonium salt (compound 13A-6) using sodium nitrite as a reagent under acidic condition. From the reactive 7-diazonium salt intermediate compound 13A-6, the corresponding 5-carboxy-psilocibin derivatives additionally containing a 7-nitrile (compound 13A-7), a 7-hydroxy group (compound 13A-8), a 7-fluoride group (compound 13A-9), or a 7-iodide group (compound 13A-10) can be obtained.

In one example embodiment, in an aspect, the formed first psilocybin derivative can be the compound possessing an acetyl group, such as, for example, the compound shown in FIG. 13A and labeled 13A-3. In other examples, $R_2$, $R_4$, or $R_6$ or $R_7$ can possess an acetyl group.

Thus, referring further to FIG. 13A, and the chemical compound having formula (I), it will be clear that a formed first multi-substituent psilocybin derivative compound can be further reacted to form additional multi-substituent psilocybin derivative compounds. Thus, for example, the formed first psilocybin derivative can be the compound shown in FIG. 13A and labeled 13A-3, or a compound wherein other combinations of $R_2$, $R_4$, $R_5$, $R_6$ and $R_7$ posses a nitro group and an acetyl group. This formed first psilocybin derivative can be reacted to oxidize the acetyl group and form a second psilocybin derivative having formula (I), wherein one or at least one of $R_2$, $R_4$, $R_5$, $R_6$, or $R_7$ is a nitro group, and wherein one or at least one of $R_2$, $R_4$, $R_5$, $R_6$, or $R_7$ is a carboxyl group, and form a second psilocybin derivative, for example, the compound shown in FIG. 13A and labeled 13A-4.

Continuing to refer to FIG. 13A, and the chemical compound having formula (I), the formed second psilocybin derivative can be reacted to reduce the nitro group and form an amino group, and a third psilocybin derivative, wherein one or at least one of $R_2$, $R_4$, $R_5$, $R_6$, or $R_7$ is an amino group, and wherein in one or at least one of $R_2$, $R_4$, $R_5$, $R_6$, or $R_7$ is a carboxyl group. The formed third psilocybin derivative can be the compound shown in FIG. 13A and labeled 13A-5.

Continuing to refer to FIG. 13A, and the chemical compound having formula (I), the formed third psilocybin derivative can be reacted with a nitrite to convert the amino group in a diazonium salt and form an intermediate psilocybin derivative, wherein one or at least one of $R_2$, $R_4$, $R_5$, $R_6$, or $R_7$ is a diazonium group, and one or at least one of $R_2$, $R_4$, $R_5$, $R_6$, or $R_7$ is a carboxyl group. The intermediate formed psilocybin derivative can, for example, be the compound shown in FIG. 13A and labeled 13A-6.

Continuing to refer to FIG. 13A, and the chemical compound having formula (I), the intermediate formed psilocybin derivative can be reacted with a nitrile containing compound to convert the diazonium group and form a fourth psilocybin derivative, wherein one or at least one of $R_2$, $R_4$, $R_5$, $R_6$, or $R_7$ is a nitrile group, and one or at least one of $R_2$, $R_4$, $R_5$, $R_6$, or $R_7$ is a carboxyl group, for example, the compound shown in FIG. 13A and labeled 13A-7.

Continuing to refer to FIG. 13A, and the chemical compound having formula (I), the intermediate formed psilocybin derivative can be reacted with water to convert the diazonium group and form a fifth psilocybin, wherein one or at least one of $R_2$, $R_4$, $R_5$, $R_6$, or $R_7$ is a hydroxy group, and one or at least one of $R_2$, $R_4$, $R_5$, $R_6$, or $R_7$ is a carboxyl group, for example, the compound shown in FIG. 13A and labeled 13A-8.

Continuing to refer to FIG. 13A, and the chemical compound having formula (I), the intermediate formed psilocybin derivative can be reacted with a halogen containing compound to convert the diazonium group and form a sixth psilocybin derivative wherein one or at least one of $R_2$, $R_4$, $R_5$, $R_6$, or $R_7$ is a halogen atom, and one or at least one of $R_2$, $R_4$, $R_5$, $R_6$, or $R_7$ is a carboxyl group, for example, the compounds shown in FIG. 13A and labeled 13A-9 and 13A-10.

Figure 13B:
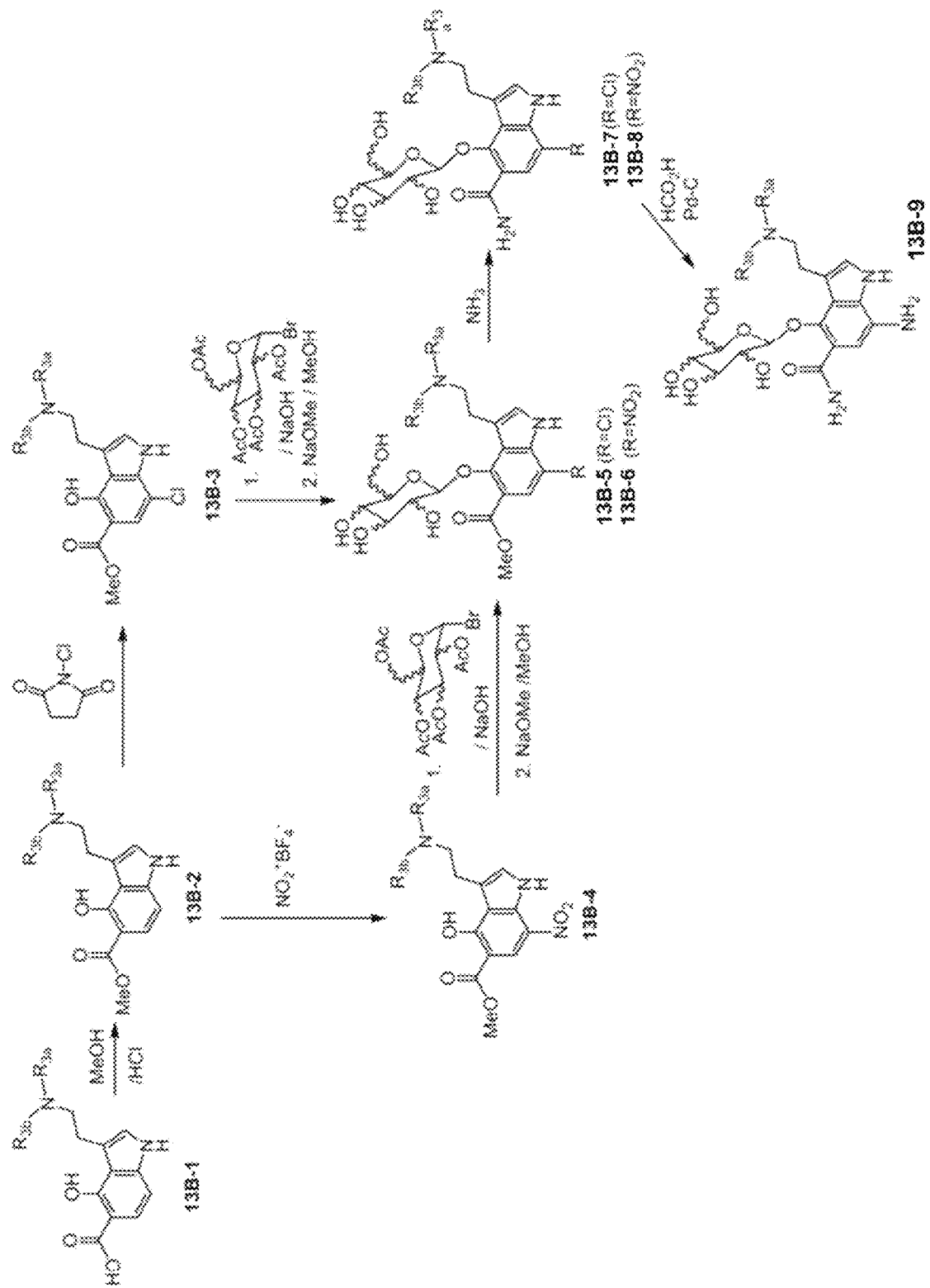

Referring next to FIG. 13B, shown therein are example chemical transformations using the initially synthesized 5-carboxy psilocybin derivative (see compound: 13B-1) to other O-4-glycosylated psilocybin derivatives containing two types of groups at carbon atoms $C_5$ and $C_7$. Thus, starting with compound 13B-1, the 5-carboxy functionality can be selectively esterified in methanol under Fisher esterification conditions to afford compound 13B-2 which can be used to synthesize the corresponding 7-chloro (compound 13B-3) and 7-nitro (compound 13B-4) derivatives, respectively. Both compounds 13B-3 and 13B-4 can be glycosylated at the O-4 position with a per-O-acetylated glycosyl bromide and after removing all the O-acetates, the corresponding 4-O-glycosylated derivative compounds 13A-5 and 13A-6 can be obtained. The 5-ester functionality of both compounds can be further converted to a 5-amido group via an aminolysis reaction to afford, respectively, 4-O-glycosylated psilocybin derivative compounds 13B-7 and 13B-8. The 7-nitro group of compound 13B-8 can be further reduced to afford compound 13B-9 through a palladium-mediated reduction using formic acid as the hydrogen source.

Referring further to FIG. 13B, and the chemical compound having formula (I), it will be clear that a reactant psilocybin derivative compound containing a substituent group can be used to react with a substituent containing compound and form an initial multi-substituent psilocybin derivative compound, which in turn can be used to form additional multi-substituent psilocybin derivative compounds. Thus, for example, the substituent in the reactant psilocybin derivative can be a methoxycarbonyl group, the substituent containing compound can be the halogen containing compound N-halo-succinimide, and the reactant psilocybin derivative and the substituent containing compound can be reacted to form a first psilocybin derivative, wherein one of $R_2$, $R_4$, $R_5$, $R_6$, or $R_7$ is a methoxy carbonyl group, and one or at least one of $R_2$, $R_4$, $R_5$, $R_6$, or $R_7$ is a halogen atom, for example, the compound shown in FIG. 13B and labeled 13B-3.

Continuing to refer to FIG. 13B, and the chemical compound having formula (I) and (II), the reactant psilocybin derivative can possess a methoxycarbonyl group, the substituent containing compound can be the nitro containing compound nitronium tetrafluoroborate, and the reactant psilocybin derivative and the substituent containing compound can be reacted to form a second psilocybin derivative wherein one or at least one of $R_2$, $R_4$, $R_5$, $R_6$, or $R_7$ is a methoxy carbonyl group, and one or at least one of $R_2$, $R_4$, $R_5$, $R_6$, or $R_7$ is a nitro group, and the formed second psilocybin derivative can be the compound shown in FIG. 13B and labeled 13B-4.

Continuing to refer to FIG. 13B, and the chemical compound having formula (I), the formed first psilocybin derivative can be reacted with an acetylated glycosyl compound and form a third psilocybin, wherein one or at least one of $R_2$, $R_4$, $R_5$, $R_6$, or $R_7$ is a methoxy carbonyl group, one or at least one of $R_2$, $R_4$, $R_5$, $R_6$, or $R_7$ is a glycosyloxy group, and one or at least one of $R_2$, $R_4$, $R_5$, $R_6$, or $R_7$ is a halogen atom, for example, the compound shown in FIG. 13B and labeled 13B-5.

Continuing to refer to FIG. 13B, and the chemical compound having formula (I), the formed second psilocybin derivative can be reacted with an acetylated glycosyl compound and form a fourth psilocybin derivative, wherein one or at least one of $R_2$, $R_4$, $R_5$, $R_6$, or $R_7$ is a methoxycarbonyl group, one or at least one of $R_2$, $R_4$, $R_5$, $R_6$, or $R_7$ is a glycosyloxy group, and one or at least one of $R_2$, $R_4$, $R_5$, $R_6$, or $R_7$ is a nitro group. For example, the formed fourth psilocybin derivative can be the compound shown in FIG. 13B and labeled 13B-6.

Continuing to refer to FIG. 13B, and the chemical compound having formula (I), the formed third psilocybin derivative can be reacted with ammonia to convert the methoxycarbonyl group in an amido group and form a fifth psilocybin derivative, wherein one or at least one of $R_2$, $R_4$, $R_5$, $R_6$, or $R_7$ is an amido group, one or at least one of $R_2$, $R_4$, $R_5$, $R_6$, or $R_7$ is a glycosyloxy group, and one or at least one of $R_2$, $R_4$, $R_5$, $R_6$, or $R_7$ is a halogen atom, for example the compound shown in FIG. 13B and labeled 13B-7.

Continuing to refer to FIG. 13B, and the chemical compound having formula (I), the formed third psilocybin derivative can be reacted with ammonia to convert the methoxycarbonyl group in an amido group and form a sixth psilocybin derivative, wherein one or at least one of $R_2$, $R_4$, $R_5$, $R_6$, or $R_7$ is an amido group, one or at least one of $R_2$, $R_4$, $R_5$, $R_6$, or $R_7$ is a glycosyloxy group, and one or at least one of $R_2$, $R_4$, $R_5$, $R_6$, or $R_7$ is a nitro group, for example, the compound shown in FIG. 13B and labeled 13B-8.

Continuing to refer to FIG. 13B, and the chemical compound having formula (I), the formed sixth psilocybin derivative can be reacted to reduce the nitro group to form an amino group and a seventh psilocybin derivative, wherein one or at least one of $R_2$, $R_4$, $R_5$, $R_6$, or $R_7$ is an amido group, one or at least one of $R_2$, $R_4$, $R_5$, $R_6$, or $R_7$ is a glycosyloxy group, and one or at least one of $R_2$, $R_4$, $R_5$, $R_6$, or $R_7$ is a nitro group, for example the compound shown in FIG. 13B and labeled 13B-9.

Figure 13C:
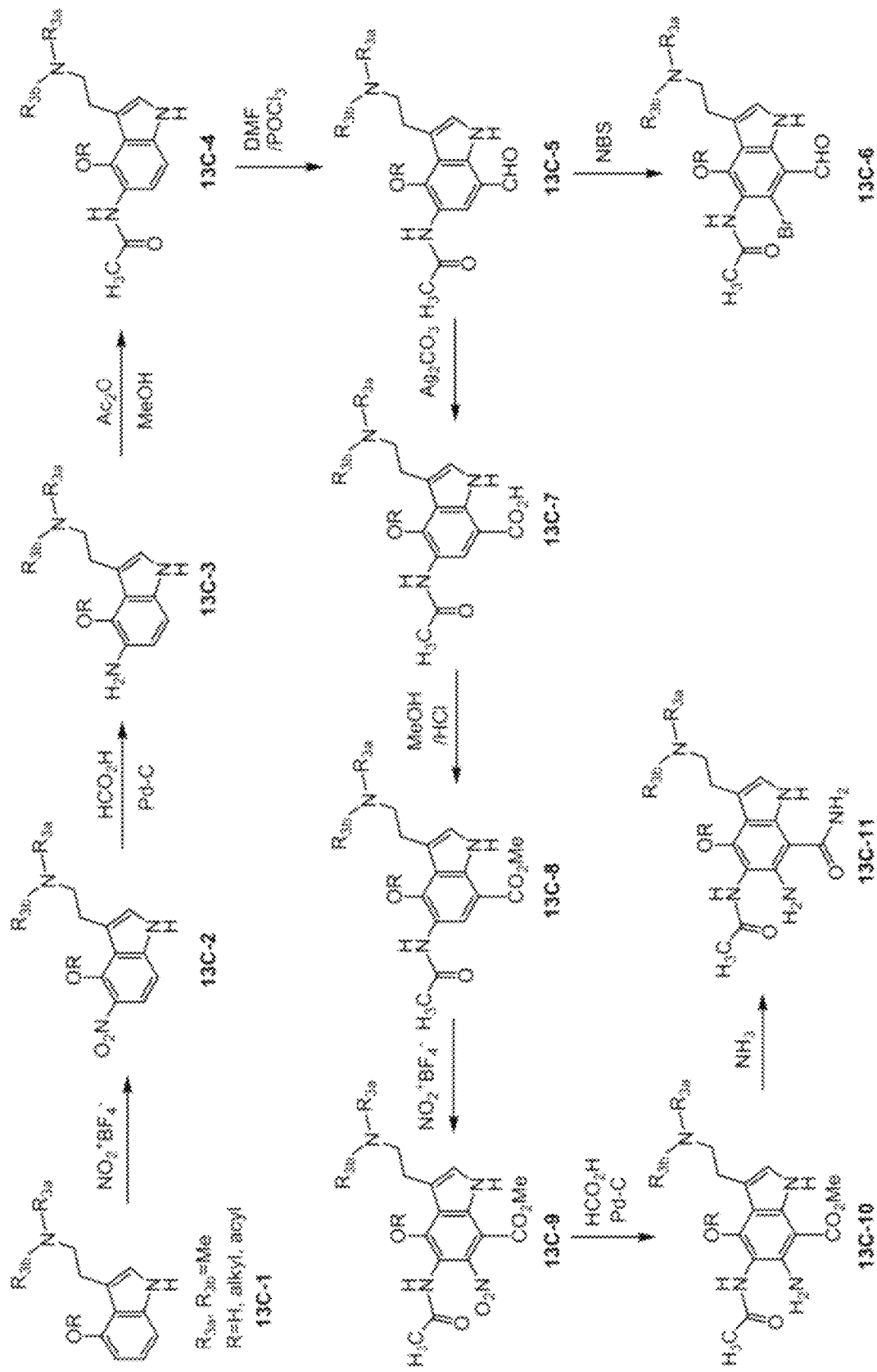

Thus, referring to FIG. 13C, shown therein are more example chemical transformations of synthesized 5-nitrated psilocybin derivatives (see: compound 13C-2) to 5,6,7-tri-substituted psilocybin derivatives containing up to three types of substituent groups. For example, the 5-nitro group can be reduced to produce 5-amino derivatives (compound: 13C-3) through a palladium-mediated reduction in the presence of formic acid as the hydrogen source. A chemoselective N-acetylation can be carried out in methanol to afford the corresponding 5-acetamino psilocybin derivative compound 13C-4, which can then be formylated at carbon atom $C_7$ to obtain 7-aldehyde compound 13C-5 using DMF-$POCl_3$ as the reagent. A further bromination using N-bromosuccinimide can provide the 5-acetamido-6-bromo-7-formyl-psilocybin derivative compound 13C-6. Alternatively, using compound 13C-5 as a substrate, the 7-formyl group can be oxidized under mild conditions using silver carbonate as a reagent to afford the 7-carboxy derivative compound 13C-7 which can be esterified using Fisher esterification conditions to obtain compound 13C-8. By reacting compound 13C-8 with nitrosonium tetrafluoroborate, a nitro group can be installed at carbon atom $C_6$ to afford a 5,6,7-trisubstituted psilocybin derivative compound 13C-9 which can have its 6-nitro group reduced to form compound 13C-10 and subsequently undergo an aminolysis reaction to convert the 7-ester group to an amide. This affords the novel 5,6,7-tri-substituted psilocybin derivative compound 13C-11.

Referring further to FIG. 13C and the chemical compounds having formula (I) and (II), it will be clear that a reactant psilocybin derivative compound containing a substituent group can be used to react with a substituent containing compound and form an initial multi-substituent psilocybin derivative compound, which in turn can be used to form additional multi-substituent psilocybin derivative compounds. Thus, for example, the substituent in the reactant psilocybin derivative can be an acetamidyl group, the substituent containing compound can be the halogen containing compound N-halo-succinimide (e.g., N-bromo-succinimide (NBS)), and the reactant psilocybin derivative and the substituent containing compound can be reacted to form a first psilocybin derivative, wherein one or at least one of $R_2$, $R_4$, $R_5$, $R_6$, or $R_7$ is an acetamidyl group, and one or at least one of $R_2$, $R_4$, $R_5$, $R_6$, or $R_7$ is a halogen atom, for example, the compound shown in FIG. 13C and labeled 13C-6.

Referring further to FIG. 13C and the chemical compound having formula (I) and (II), the reactant psilocybin derivative compound can possess an acetamidyl group, the substituent containing compound can be dimethyl formamide, and the reactant psilocybin derivative and the substituent containing compound can be reacted to form an intermediate psilocybin derivative, wherein one or at least one of $R_2$, $R_4$, $R_5$, $R_6$, or $R_7$ is an acetamidyl group, and at least one or at least one of $R_2$, $R_4$, $R_5$, $R_6$, or $R_7$ is a methanol group, and wherein the intermediate psilocybin derivative is reacted to oxidize the methanol group, and form a second psilocybin derivative, wherein one or at least one of $R_2$, $R_4$, $R_5$, $R_6$, or $R_7$ is an acetamidyl group, and one or at least one of $R_2$, $R_4$, $R_5$, $R_6$, or $R_7$ is a carboxy group. For example, the intermediate psilocybin derivative can be the compound shown in FIG. 13C and labeled 13C-5, and the formed second psilocybin derivative can be the compound shown in FIG. 13C and labeled 13C-7.

Referring further to FIG. 13C and the chemical compound having formula (I) the formed second psilocybin derivative having formula (I) can be reacted with an alcohol to esterify the carboxy group to form an ester and a third psilocybin derivative, wherein one or at least one of $R_2$, $R_4$, $R_5$, $R_6$, or $R_7$ is an acetamidyl group, one or at least one of $R_2$, $R_4$, $R_5$, $R_6$, or $R_7$ is a carboxyl ester, for example, the compound shown in FIG. 13C and labeled 13C-8.

Referring further to FIG. 13C and the chemical compound having formula (I), the formed third psilocybin derivative can be reacted with a nitro group containing compound and form a fourth psilocybin derivative, wherein one or at least one of $R_2$, $R_4$, $R_5$, $R_6$, or $R_7$ is an acetamidyl group, one or at least one of $R_2$, $R_4$, $R_5$, $R_6$, or $R_7$ is a carboxyl ester, and at least one of $R_2$, $R_4$, $R_5$, $R_6$, or $R_7$ is a nitro group, for example, the compound shown in FIG. 13C and labeled 13C-9.

Referring further to FIG. 13C and the chemical compound having formula (I), the formed fourth psilocybin derivative can be reacted to reduce the nitro group to form an amino group and a fifth psilocybin derivative, wherein one or at least one of $R_2$, $R_4$, $R_5$, $R_6$, or $R_7$ is an acetamidyl group, one or at least one of $R_2$, $R_4$, $R_5$, $R_6$, or $R_7$ is a carboxyl ester, and one at least one of $R_2$, $R_4$, $R_5$, $R_6$, or $R_7$ is an amino group, for example, the compound shown in FIG. 13C and labeled 13C-10.

Referring further to FIG. 13C and the chemical compound having formula (I), the formed fifth psilocybin derivative can be reacted with ammonia to form an amido group and a sixth psilocybin derivative having formula (I), wherein one or at least one of $R_2$, $R_4$, $R_5$, $R_6$, or $R_7$ is an acetamidyl group, one or at least one of $R_2$, $R_4$, $R_5$, $R_6$, or $R_7$ is a carboxyester, and at least one of $R_2$, $R_4$, $R_5$, $R_6$, or $R_7$ is an amido group, for example, the compound shown in FIG. 13C and labeled 13C-11.

Thus, in general, a reactant psilocybin derivative is provided, and the reactant psilocybin derivative is employed to react in a chemical reaction resulting in the formation of a multiple-substituent psilocybin derivatives.

The reactions, such as the example reaction shown in FIGS. 9, 10, 11A-11C, 12A-12D, and 13A-13C, may be conducted in any suitable reaction vessel (e.g., a tube, bottle). Suitable solvents that may be used are for example, water, alcohol (such as methanol, ethanol, tetrahydrofuran (THF), dichloromethane, acetone, N,N-dimethylformamide (DMF), dimethylsulfoxide (DMSO), or a combination of solvents. Suitable temperatures may range from, for example, e.g., from about 20° C. to about 100° C. Furthermore, reaction times may be varied. As will readily be appreciated by those of skill in the art, the reaction conditions may be optimized, for example by preparing several psilocybin derivative reactants preparations and reacting these in different reaction vessels under different reaction conditions, for example, at different temperatures, using different solvents, using different catalysts etc., evaluating the obtained multiple-substituent psilocybin derivative reaction product, adjusting reaction conditions, and selecting a desired reaction condition.

Turning next to biosynthetic methods to make the multiple-substituent compounds of the present disclosure, such methods, in general, involve the use of psilocybin biosynthetic enzyme complement to enzymatically catalyze the conversion of a psilocybin derivative precursor compound and form a multi-substituent psilocybin derivative compound. The enzymes included in the psilocybin biosynthetic enzyme complement may vary, as hereinafter will be discussed with reference to certain example enzymes and example compounds shown in FIGS. 14A, 14B, and 14C.

Thus, in one aspect, the present disclosure further provides a method of making a multi-substituent psilocybin derivative, the method comprising contacting a psilocybin derivative precursor compound having a formula (LVII):

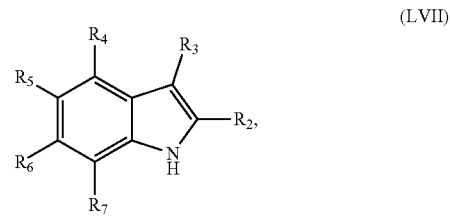

(LVII)

wherein at least one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, and wherein $R_3$ is a hydrogen atom or —$CH_2$—$CHNH_2COOH$ or —$CH_2$—$CH_2NH_2$, with a catalytic quantity of a psilocybin biosynthetic enzyme complement under reaction conditions permitting an enzyme catalyzed conversion of the psilocybin derivative precursor compound to form a multi-substituent psilocybin derivative compound having a formula (I):

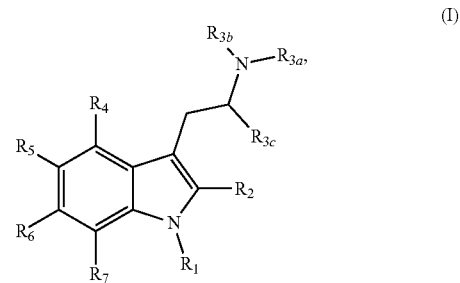

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

The reaction conditions can be in vitro reaction conditions, or in vivo reaction conditions, or a combination thereof.

In Vitro Synthesis

In vitro synthesis, in general, involves initially providing the reagents, including the precursor psilocybin derivative compound and other reactants, in a more or less pure form. Thus, the reactants may be provided as a particulate in a substantially pure form, or they may be dissolved, in a more or less pure form, in a suitable solvent or diluent, such as water or a buffer. The reagents can then be combined and contacted with one another in a suitable reaction vessel, such as a tube, beaker, flask, or the like, or, at a larger scale, in a tank or reactor, generally preferably in liquid form, which may be prepared by further including a diluent, such as water or a buffer, as necessary. The combined reagents may be mixed, by, in general, gentle stirring, using a suitable stirring or mixing device, such as a laboratory size magnetic stirrer (e.g., as manufactured by Fisher Scientific®), or a handheld or industrial mixer, for example, to form a mixture. Relative quantities and absolute quantities of reagents may be selected as desired. Absolute quantities will typically depend on the scale one wishes to perform the reaction at, such as, for example, at a laboratory scale (e.g., at a less than 1 L, a less than 100 mL, a less than 10 mL, or a less than 1 mL scale), or, for example, at a commercial production scale (e.g., at a more than 100 L, a more than 1,000 L, or a more than 10,000 L scale). Relative quantities of the reagents may vary. Thus, for example, in one embodiment, stoichiometric quantities of each of a precursor psilocybin derivative and a substituent containing compound can be mixed with catalytic quantities of enzymes. If desired, off-stoichiometric quantities of reagents, for example, a molar ratio of psilocybin precursor derivative to substituent containing compound of 1:0.95; 1:0.9; 1:0.75; or 1:1.05, 1:1.1 or 1:1.25, may be selected.

As will be understood by those of skill in the art, in molar quantity terms, small quantities of enzyme suffice to conduct the reaction, since the enzyme acts as a catalytic agent, and, unlike the precursor psilocybin derivatives and the substituent containing compound, the enzyme is not consumed in the reaction. Thus, in general terms, catalytic quantities can be thought of as the at least minimal quantity of enzyme required to convert precursor psilocybin derivatives and the substituent containing compound, and form desirable quantities of multi-substituent psilocybin derivatives. Thus, for example, from 0.1 to 1,000 enzyme units (e.g., 0.1 enzyme unit, 1 enzyme unit, 10 enzyme units, 50 enzyme units, 100 enzyme units, 250 enzyme units, 500 enzyme units, or 1,000 enzyme units) may be included in a reaction mixture, wherein, as is known to those of skill in the art, 1 enzyme unit is an amount of enzyme that catalyzes 1 μmole of substrate (i.e., psilocybin precursor compound) per minute. Furthermore, in vitro reaction conditions may vary and may include temperatures ranging from, for example, between about 18° C. and about 37° C., and a pH in the range of about pH 5.0 to about pH 8.5. Furthermore, other agents may be included to facilitate catalysis, for example, a diluent (e.g., water or a buffer), salts, and pH modifying agents. The in vitro reaction conditions may be adjusted and optimized, for example, by preparing a plurality of samples, each being reacted at a different operating condition, e.g., at a different temperature, a different pH, including a different quantity of enzyme, including different relative quantities of reagents, and so forth, and detecting the formed multi-substituent psilocybin derivative.

In Vivo Synthesis

In one embodiment, the psilocybin derivative precursor compound and the substituent containing compound can be contacted with the psilocybin biosynthetic enzyme complement in a host cell, wherein the host cell comprises a chimeric nucleic acid sequence comprising as operably linked components:

(i) a nucleic acid sequence controlling expression in the host cell, and
(ii) a nucleic acid sequence encoding psilocybin biosynthetic enzyme complement, and the host cell is grown to express the psilocybin biosynthetic enzyme complement and to produce the multi-substituent psilocybin derivative compound.

Suitable chimeric nucleic acid sequences include any nucleic acid sequence comprising a nucleic acid sequence controlling expression in the host cell operably linked to a sequence encoding psilocybin biosynthetic enzyme complement, such as, for example, one or more of tryptophan synthase subunit B polypeptide, tryptophan decarboxylase, N-acetyl transferase, N-methyl transferase, and prenyl transferase, as herein after further described.

Nucleic acid sequences capable of controlling expression of a nucleic acid sequence encoding biosynthetic enzyme complement in host cells that can be used herein include any transcriptional promoter capable of controlling expression of polypeptides in host cells. Generally, promoters obtained from bacterial cells are used when a bacterial host is selected in accordance herewith, while a fungal promoter will be used when a fungal host cell is selected, a plant promoter will be used when a plant cell is selected, and so on. Specific examples that can be used, for example for expression in yeast cells include a galactose inducible promoter, such as a Gal10/Gal 1 promoter, or for expression in *Escherichia coli* cells, a beta-galactosidase promoter. Further nucleic acid elements capable elements of controlling expression in a host cell include transcriptional terminators, enhancers, and the like, all of which may be included in the chimeric nucleic acid sequences of the present disclosure.

The chimeric nucleic acid sequences can be integrated into a recombinant expression vector which ensures good expression in the host cell, wherein the expression vector is suitable for expression in a host cell. The term "suitable for expression in a host cell" means that the recombinant expression vector comprises the chimeric nucleic acid sequence linked to genetic elements required to achieve expression in a cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example. If a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin, or an auxotrophic marker, for example, a leu marker (Sikorski and Hieter, 1989, Genetics 122(1): 19-27) or a ura marker (Rose and Winston, 1984, Mol. Gen. Genet. 193 (3): 557-560. Screenable markers that may be employed to identify transformants through visual inspection include β-glucuronidase (GUS)

(U.S. Pat. Nos. 5,268,463 and 5,599,670) and green fluorescent protein (GFP) (Niedz et al., 1995, Plant Cell Rep., 14: 403).

A variety of host cells can be used in accordance herewith. The selected host cell may be able to naturally produce psilocybin compounds, or derivatives thereof or the cell may not be able to naturally produce psilocybin compounds or derivatives thereof. Host cells, upon the introduction of the chimeric nucleic acid sequence can be said to be able to heterologously express psilocybin biosynthetic enzyme complement.

In some embodiments, the host cell can be a microbial cell, for example, bacterial cell or a yeast cell. An example bacterial cell that can be used in accordance herewith is an *Escherichia coli* cell. Example yeast cells that can be in accordance herewith are a *Saccharomyces cerevisiae* cell or a *Yarrowia lipolytica* cell.

In a further embodiment, the host cell can be a plant cell or an algal cell.

A variety of techniques and methodologies to manipulate host cells to introduce nucleic acid sequences, including expression vectors comprising the chimeric nucleic acid sequences of the current disclosure, in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include, for example, the T7 promoter, the T5 promoter, tryptophan (trp) promoter, lactose (lac) promoter, tryptophan/lactose (tac) promoter, lipoprotein (lpp) promoter, and λ phage PL promoter, Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well-known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces, Schizosaccharomyces, Pichia, Hansenula,* and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors, Yep type vectors, Yrp type vectors, Ycp type vectors, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 µm plasmids. Such vectors are known to the art and are, for example, described in Cregg et al, Mol Biotechnol (2000) 16(1): 23-52. Suitable promoter sequences for use in yeast host cells are also known and described, for example, in Mattanovich et al., Methods Mol. Biol., 2012, 824:329-58, and in Romanos et al., 1992, Yeast 8: 423-488. Examples of suitable promoters for use in yeast host cells include promoters of glycolytic enzymes, like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAL1), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S Kawai et al, 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Figure 14A:
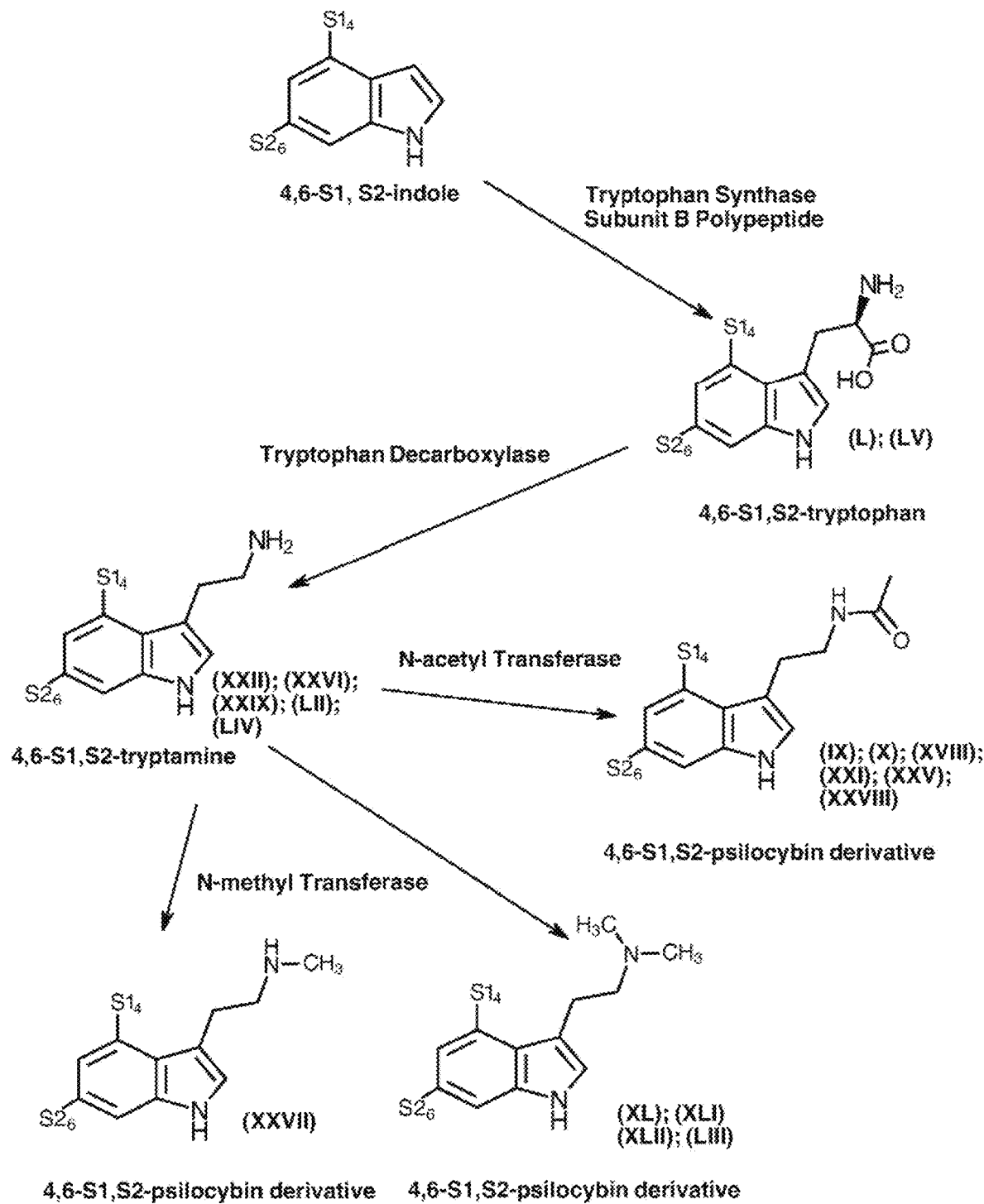
FIGS. 14A, 14B, 14C, 14D, 14E, 14F and 14G depict certain pathways to biosynthetically make example multi-substituent psilocybin derivative compounds, notably example compounds possessing a $S1_4$ and a $S2_6$ substituent (FIG. 14A), example compounds possessing a $S1_4$ and a $S2_6$ prenyl group (FIG. 14B), example compounds possessing a $S1_5$ and a $S2_6$ prenyl group (FIG. 14C), example compounds possessing a $S1_4$ and a $S2_5$ substituent (FIG. 14D), example compounds possessing a $S1_4$ and a $S2_7$ substituent (FIG. 14E), example compounds possessing a $S1_5$ and a $S2_6$ substituent (FIG. 14F), and example compounds possessing a $S1_5$ and a $S2_7$ substituent (FIG. 14G). Roman numerals adjacent to the example compounds in each of FIGS. 14A-14G refer to the example compounds thus numbered in this disclosure.
Figure 14B:
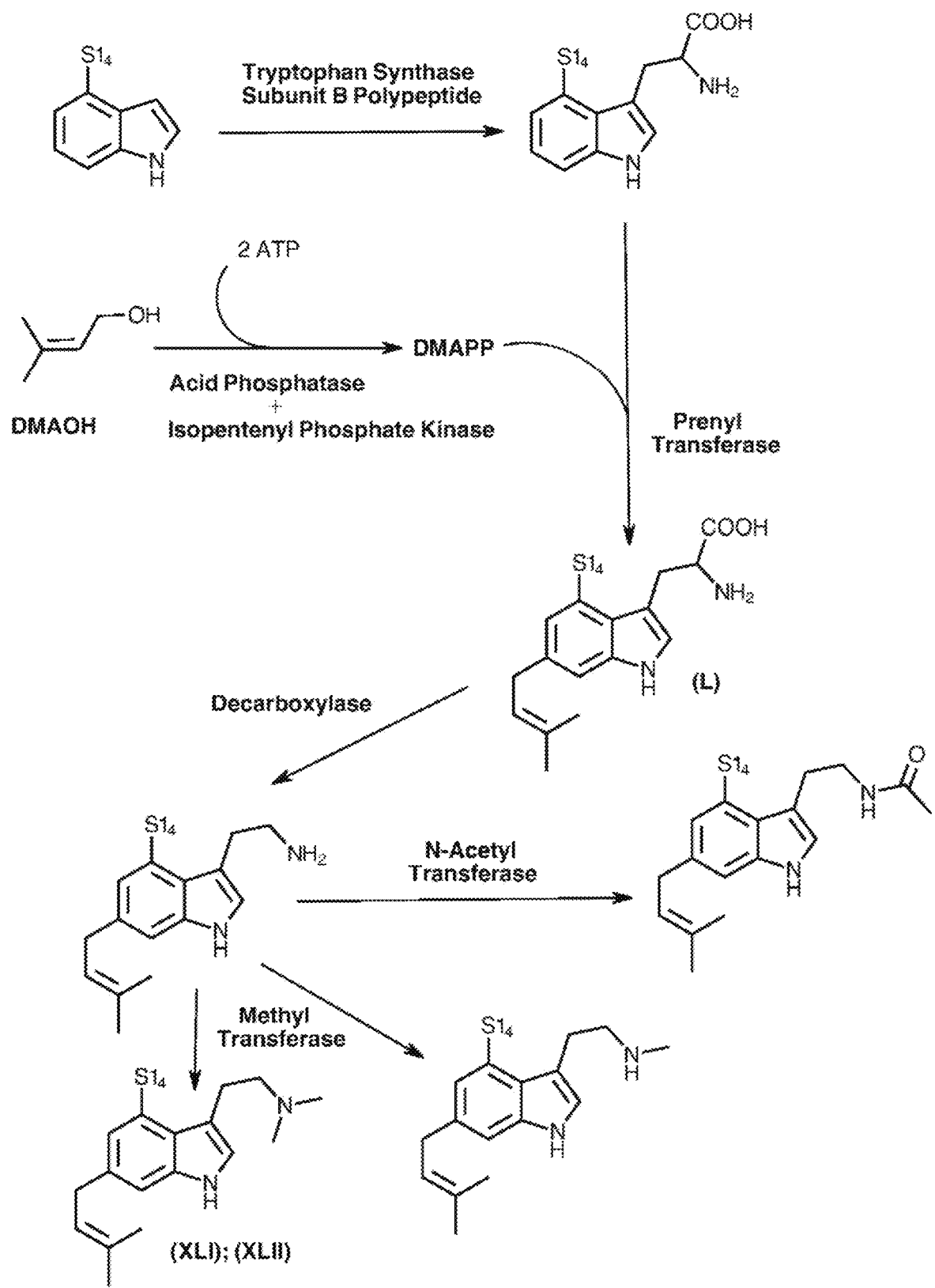
Figure 14C:
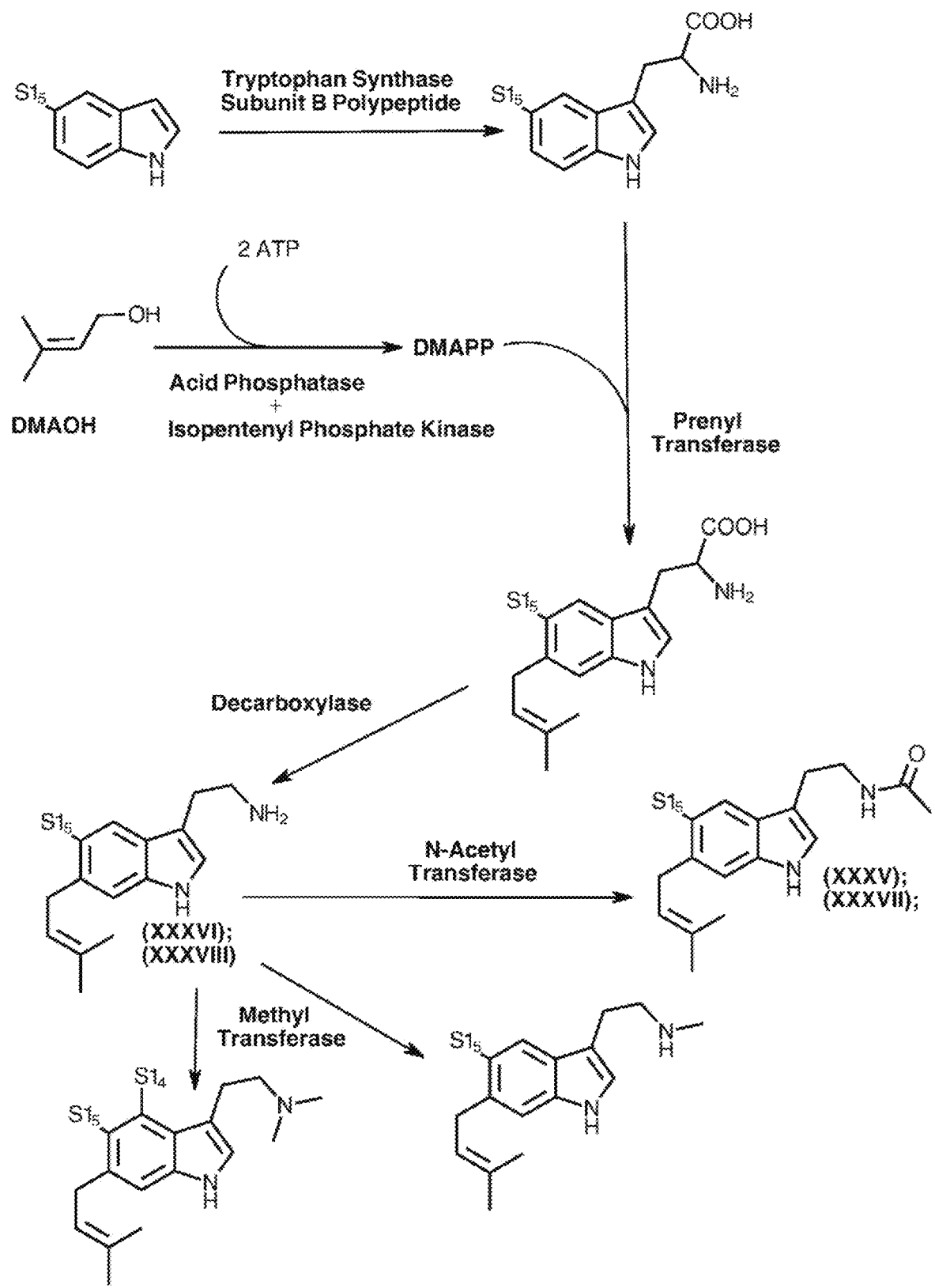
Figure 14D:
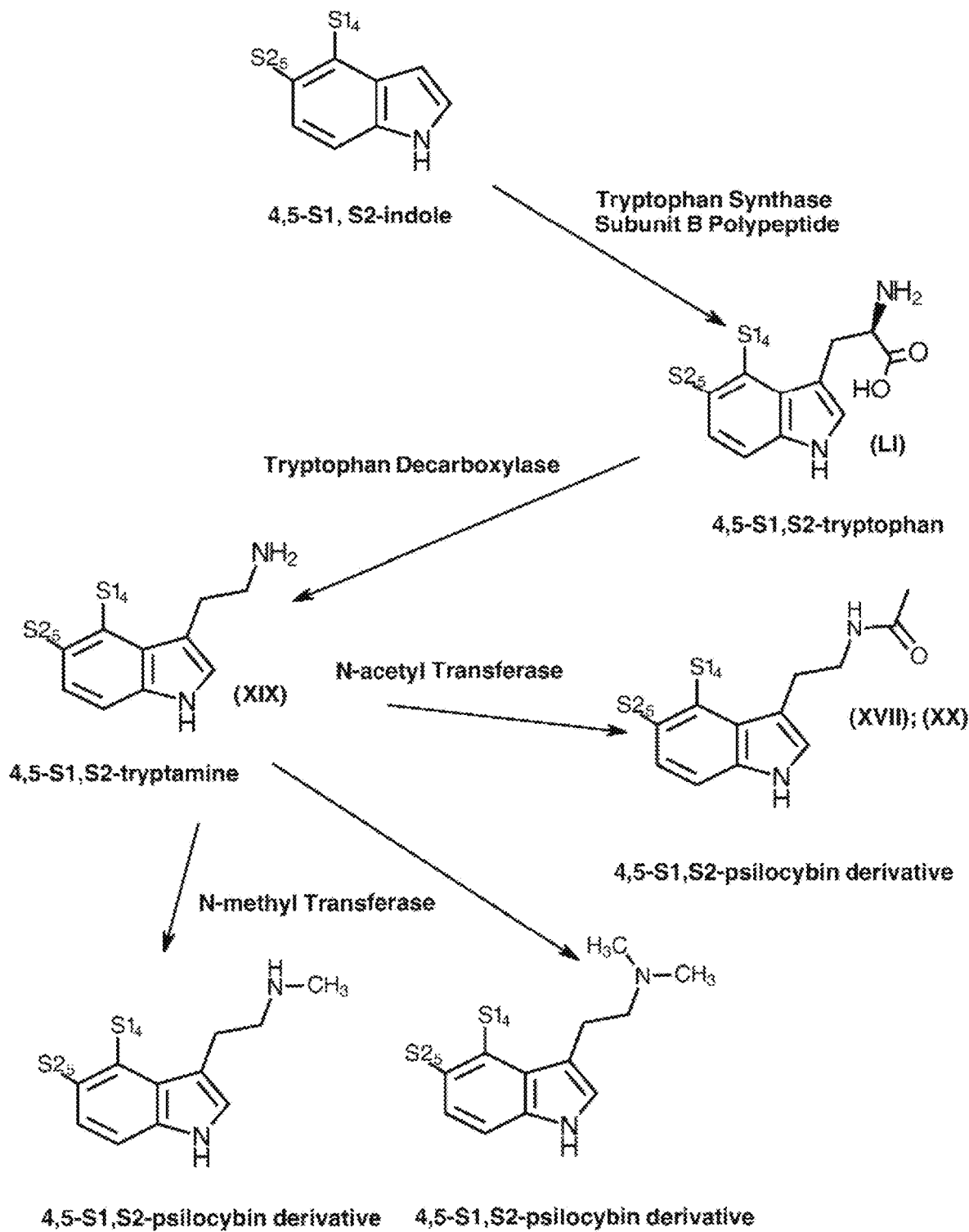
Figure 14E:
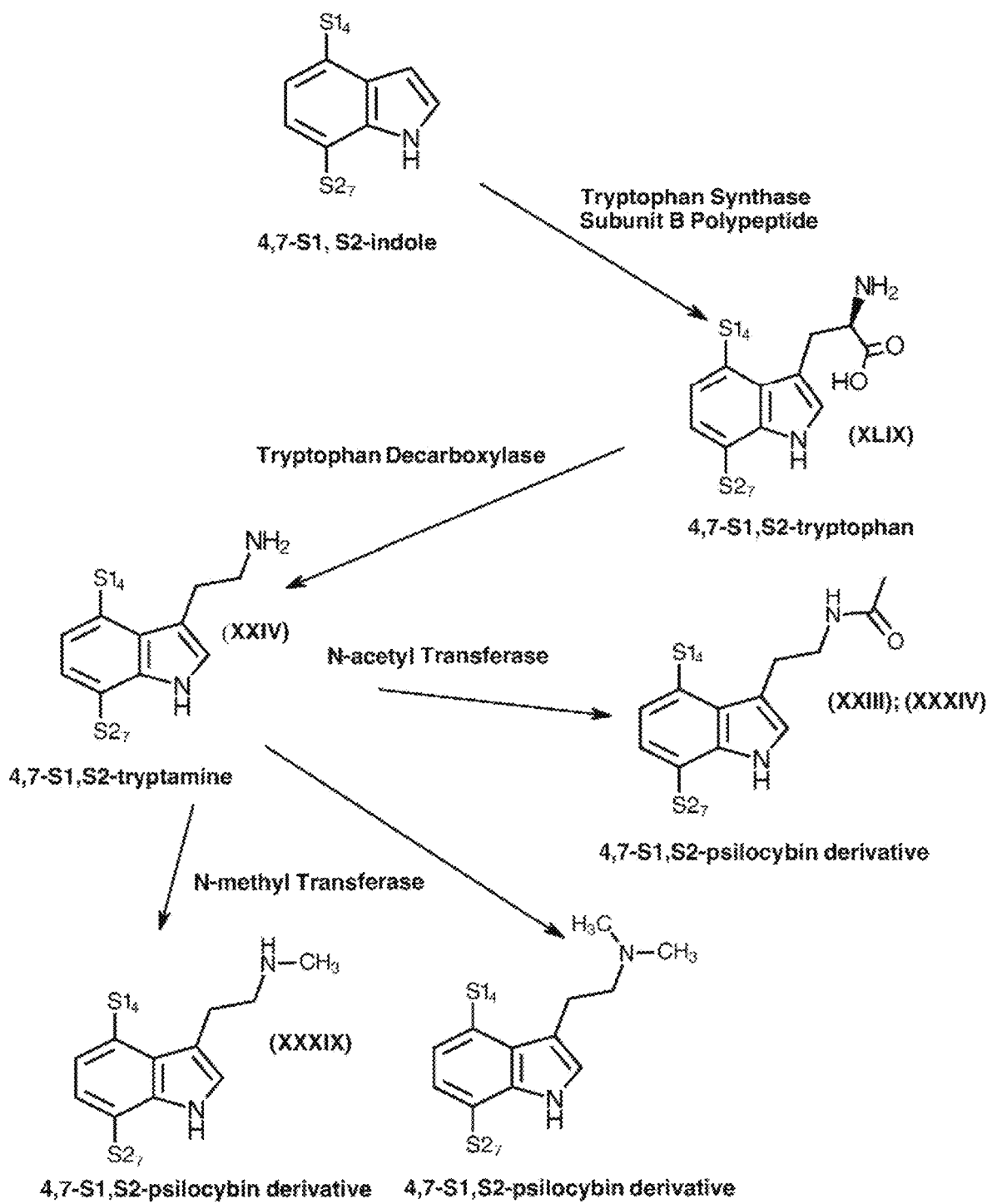
Figure 14F:
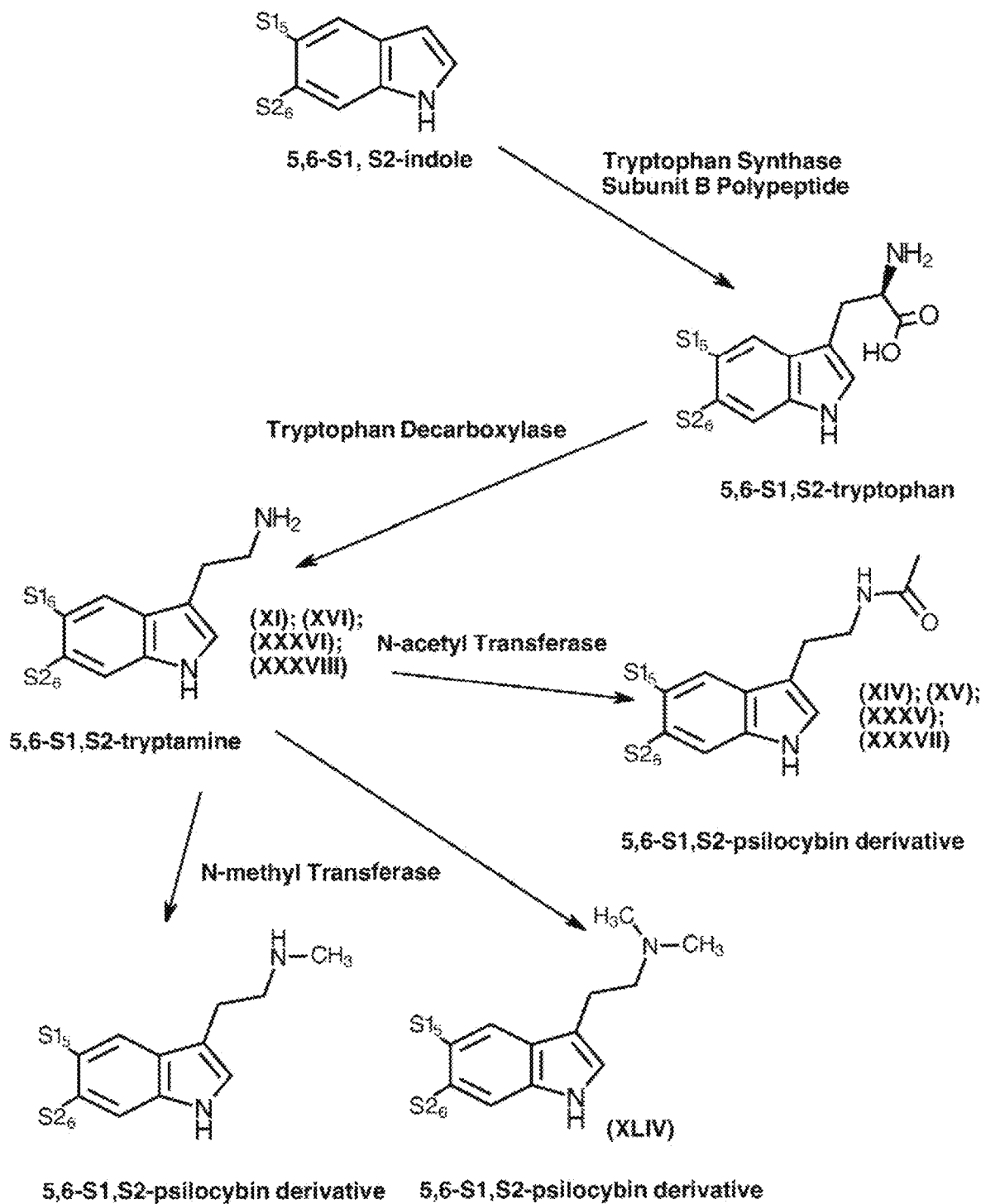
Figure 14G:
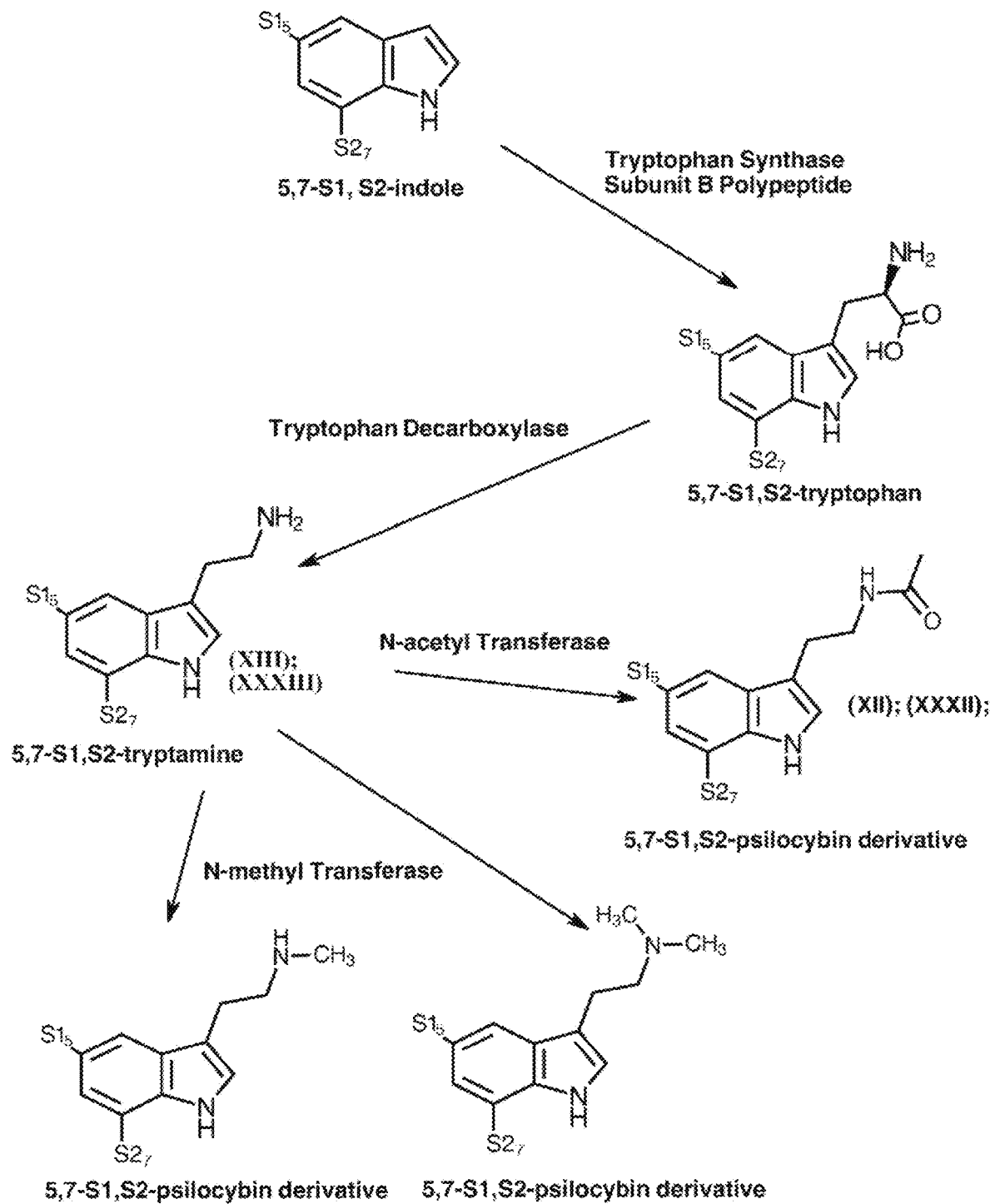

Referring next to FIGS. 14A-14G, shown therein are example biosynthetic pathways to make the multi-substituent psilocybin derivative compounds of the present disclosure, notably FIG. 14A, by way of example, illustrates how example $S1_4$, $S2_6$ multi-substituent psilocybin derivative compounds may be biosynthetically made. FIG. 14B, by way of further example, illustrates how further example $S1_4$, $S2_6$ multi-substituent psilocybin derivative compounds may be biosynthetically made. FIG. 14C by way of a further example, illustrates how further example $S1_5$, $S2_6$ multi-substituent psilocybin derivative compounds may be biosynthetically made. FIG. 14D, by way of example, illustrates how example $S1_4$, $S2_5$ multi-substituent psilocybin derivative compounds may be biosynthetically made. FIG. 14E, by way of example, illustrates how example $S1_4$, $S2_7$ multi-substituent psilocybin derivative compounds may be biosynthetically made. FIG. 14F, by way of example, illustrates how example $S1_5$, $S2_6$ multi-substituent psilocybin derivative compounds may be biosynthetically made. FIG. 14G, by way of yet a further example, illustrates how example $S1_5$, $S2_7$ multi-substituent psilocybin derivative compounds may be biosynthetically made. It is to be understood that, in addition to the pathways, enzymes and compounds shown in FIGS. 14A-14G other biosynthetic pathways may be used to make other multi-substituent psilocybin derivative compounds, comprising multiple substituents, wherein two or more of the carbon atoms $C_2$, $C_4$, $C_5$, $C_6$ and $C_7$ possess a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, including further, for example, the multi-substituent compounds shown in FIGS. 3A-3L, 4A-4I, 5A-5I, 6A-6I, and 7A-7F, and further including any multi-substituent psilocybin derivative compounds having a formula (I):

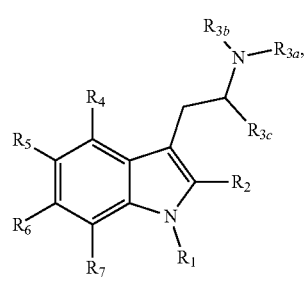

(I)

wherein, at least two of $R_2$, $R_4$, $R_5$, $R_6$, or $R_7$ are substituents independently selected from at least two of (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, and wherein each non-substituted $R_2$, $R_5$, $R_6$, or $R_7$ is a hydrogen atom and when $R_4$ is not substituted with any of the foregoing substituents, $R_4$ is a hydrogen atom, an O-alkyl group, an O-acyl group, or a phosphate group, wherein $R_{3a}$ and $R_{3b}$ are each independently a hydrogen atom, an alkyl group, a cycloalkyl group, an acyl group, or an aryl group, and wherein and $R_{3c}$ is a hydrogen atom or a carboxyl group.

Following the teachings set forth herein, including by referring to the examples shown in FIGS. 14A-14G, those of skill In the art will be able to select appropriate psilocybin precursor compounds, psilocybin biosynthetic enzyme complement enzymes to biosynthetically make the multi-substituent psilocybin derivative compounds of the present disclosure.

Thus, referring further to FIG. 14A, and a psilocybin derivative precursor compound (LVII), the psilocybin biosynthetic enzyme complement can, for example, comprise a tryptophan synthase subunit B polypeptide, encoded by a nucleic acid selected from:
(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f).

A first psilocybin derivative precursor compound having formula (I) can be used wherein two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom. A first multi-substituent psilocybin derivative compound having formula (I) can be formed wherein $R_{3c}$ is a carboxyl group. For example, a psilocybin derivative precursor compound can be a chemical compound having a formula (LVIII):

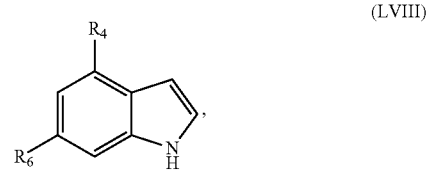

(LVIII)

wherein $R_4$ is a hydroxy group, and wherein $R_6$ is a chlorine atom, and a first multi-substituent psilocybin derivative compound has a formula (LV):

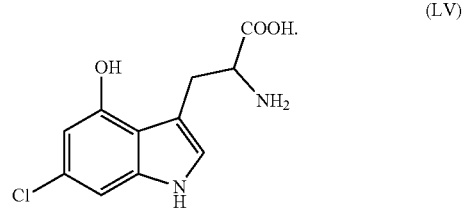 [SMILES: NC(Cc1c[nH]c2cc(Cl)cc(O)c12)C(=O)O]

(LV)

can be formed in an in vivo or in vitro reaction catalyzed by a tryptophan synthase subunit B polypeptide.

Continuing to refer to FIG. 14A, a psilocybin biosynthetic enzyme complement can further comprise a tryptophan decarboxylase to decarboxylate the $R_3$—$CH_2$—$CHNH_2COOH$ group of a first multi-substituent psilocybin derivative compound to thereby form a second multi-substituent psilocybin derivative having formula (I) wherein $R_{3a}$ and $R_{3b}$ each are a hydrogen atom, a tryptophan decarboxylase encoded by a nucleic acid sequence selected from:
(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, and SEQ.ID NO 8;

(f) a nucleic acid sequence that encodes a functional variant of any one of the amino acid sequences set forth in SEQ.ID NO: 4, SEQ.ID NO: 6, and SEQ.ID NO 8; and (g) a nucleic acid sequence that hybridizes under stringent conditions to any one of the nucleic acid sequences set forth in (a), (b), (c), (d), (e) or (f).

Continuing to refer to FIG. 14A, in an example embodiment, a psilocybin derivative precursor compound can be a chemical compound having a formula (LVIII):

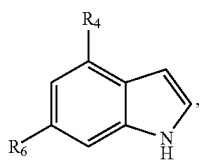

(LVIII)

wherein $R_4$ is a fluorine atom, an amino group, or a hydroxy group, wherein $R_6$ is a fluorine atom, an amino group, a nitrile, or a bromine atom, and a first multi-substituent psilocybin derivative compound has a formula (LIX):

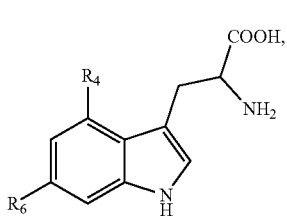

(LIX)

wherein $R_4$ is a fluorine atom, an amino group, or a hydroxy group, wherein $R_6$ is a fluorine atom, an amino group, a nitrile, or a bromine atom can be formed. The first multi-substituent psilocybin can be decarboxylated, and a second multi-substituent psilocybin can be formed, for example, a second multi-substituent psilocybin derivative having a formula (XXII), (XXVI), (XXIX), (LII), or (LIV):

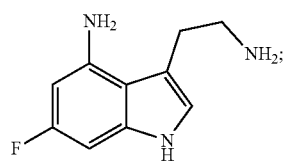

(XXII)

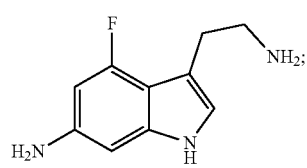

(XXVI)

(XXIX)

(LII)

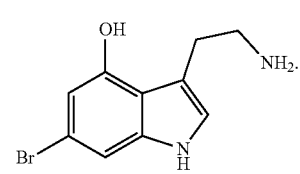

(LIV)

A psilocybin biosynthetic enzyme complement can further, for example, comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group. A N-acetyl transferase can be encoded by a nucleic acid sequence selected from:

(a) SEQ.ID NO: 9;

(b) a nucleic acid sequence that is substantially identical to the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having the amino acid sequence set forth in SEQ.ID NO: 10;

(f) a nucleic acid sequence that encodes a functional variant of the amino acid sequence set forth in SEQ.ID NO: 10; and (g) a nucleic acid sequence that hybridizes under stringent conditions to any one of the nucleic acid sequences set forth in (a), (b), (c), (d), (e) or (f).

Thus, continuing to refer to FIG. 14A, in an example embodiment, a psilocybin derivative precursor compound can be a chemical compound having a formula (LVIII):

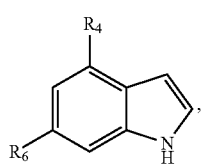

(LVIII)

wherein $R_4$ is an acetamidyl group, a fluorine atom, an amino group, or a hydroxy group, wherein $R_6$ is a fluorine atom, an amino group, a nitrile, or a bromine atom, and a first multi-substituent psilocybin derivative compound having a formula (LIX):

(LIX)

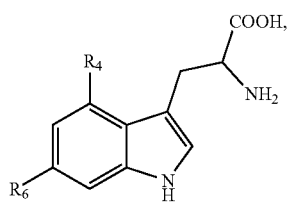

wherein R₄ is an acetamidyl group, a fluorine atom, an amino group, or a hydroxy group, wherein R₆ is a fluorine atom, an amino group, a nitrile, or a bromine atom can be formed. Then the first multi-substituent psilocybin derivative can be decarboxylated and a second multi-substituent psilocybin derivative having a formula (LX):

(LX)

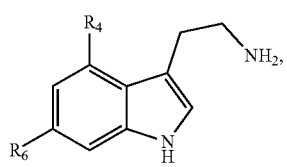

can be formed. Thereafter, the second multi-substituent psilocybin derivative can be acetylated, and a third multi-substituent psilocybin derivative can be formed, for example, a third multi-substituent psilocybin derivative having a formula (IX), (X), (XVIII), (XXI), (XXV), or (XXVIII):

(IX)

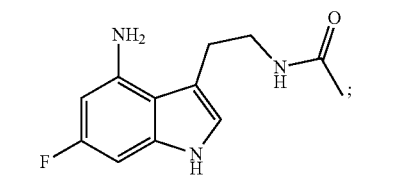

(X)

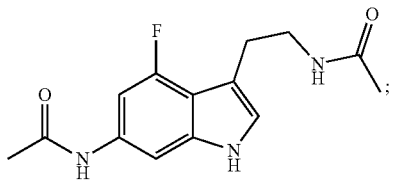

(XVIII)

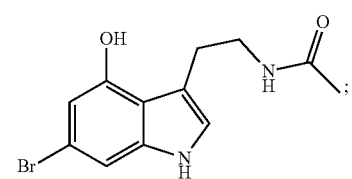

(XXI)

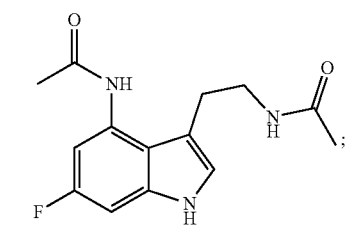

(XXV)

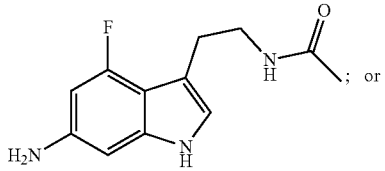

; or (XXVIII)

A psilocybin biosynthetic enzyme complement, in accordance herewith can further, for example, comprise an N-methyl transferase to methylate the R₃ amino group at R₃ and form a fourth multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group. A N-methyl transferase can be encoded by a nucleic acid sequence selected from:

(a) SEQ.ID NO: 11 and SEQ.ID NO 13;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 12 and SEQ.ID NO 14;

(f) a nucleic acid sequence that encodes a functional variant of any one of the amino acid sequences set forth in SEQ.ID NO: 12 and SEQ.ID NO 14; and (g) a nucleic acid sequence that hybridizes under stringent conditions to any one of the nucleic acid sequences set forth in (a), (b), (c), (d), (e) or (f).

Continuing to refer to FIG. 14A, in an example embodiment, a psilocybin derivative precursor compound can be a chemical compound having a formula (LVIII):

(LVIII)

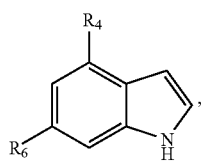

wherein R₄ is an amino group or a hydroxy group, wherein R₆ is a chlorine atom, a nitrile group, or a bromine atom, and a first multi-substituent psilocybin derivative compound having a formula (LIX):

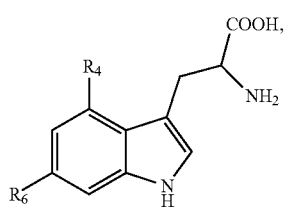

(LIX)

wherein $R_4$ is an amino group or a hydroxy group, wherein $R_6$ is a chlorine atom, a nitrile group, or a bromine atom can be formed. The first multi-substituent psilocybin derivative compound can be decarboxylated to form a second multi-substituent psilocybin derivative compound, wherein the second multi-substituent psilocybin derivative has a formula (LX):

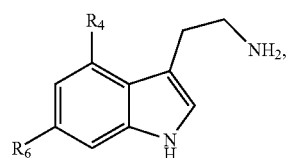

(LX)

The third multi-substituent psilocybin derivative compound can be methylated to form a fourth multi-substituent psilocybin derivative, for example, a fourth multi-substituent psilocybin derivative compound having a formula (XXVII), (XL), or (LIII):

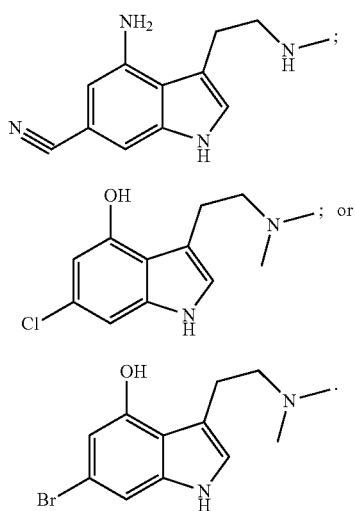

(XXVII)

(XL)

(LII)

In accordance herewith, a psilocybin biosynthetic enzyme complement can, in a further example embodiment, comprise a prenyl transferase, encoded by a nucleic acid selected from:
(a) SEQ.ID NO: 15, SEQ.ID NO: 17, SEQ.ID NO: 19, and SEQ.ID NO 21;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 16, SEQ.ID NO: 18, SEQ.ID NO: 20, and SEQ.ID NO 22;
(f) a nucleic acid sequence that encodes a functional variant of any one of the amino acid sequences set forth in SEQ.ID NO: 16, SEQ.ID NO: 18, SEQ.ID NO: 20, and SEQ.ID NO 22; and
(g) a nucleic acid sequence that hybridizes under stringent conditions to any one of the nucleic acid sequences set forth in (a), (b), (c), (d), (e) or (f).

Referring, in this respect, next to FIG. 14B, in a further example embodiment, a psilocybin derivative precursor compound can be a chemical compound having a formula (LXI):

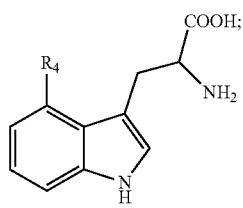

(LXI)

wherein $R_4$ is a hydroxy group, and a first multi-substituent psilocybin derivative compound can be formed, for example, a first formed multi-substituent psilocybin derivative compound having a formula (L):

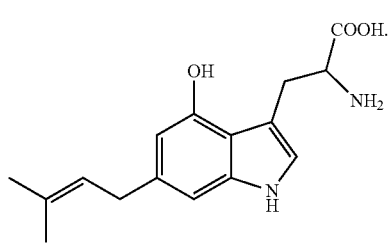

(L)

Continuing to referring FIG. 14B, a psilocybin biosynthetic enzyme complement can, in a further example embodiment, comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom. A tryptophan decarboxylase can be encoded by a nucleic acid sequence selected from:
(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;

(f) a nucleic acid sequence that encodes a functional variant of any one of the amino acid sequences set forth in SEQ.ID NO: 4, SEQ.ID NO: 6 and SEQ.ID NO 8; and (g) a nucleic acid sequence that hybridizes under stringent conditions to any one of the nucleic acid sequences set forth in (a), (b), (c), (d), (e) or (f).

A psilocybin biosynthetic enzyme complement can in a further example embodiment, comprise an N-methyl transferase to methylate the $R_3$ amino group at $R_3$ and form a fourth multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group. A N-methyl transferase encoded by a nucleic acid sequence can be selected from:

(a) SEQ.ID NO: 11, and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14;
(f) a nucleic acid sequence that encodes a functional variant of any one of the amino acid sequences set forth in SEQ.ID NO: 12, and SEQ.ID NO 14; and
(g) a nucleic acid sequence that hybridizes under stringent conditions to any one of the nucleic acid sequences set forth in (a), (b), (c), (d), (e) or (f).

Continuing to referring FIG. 14B, in an example embodiment, a psilocybin derivative precursor compound can be a chemical compound having a formula (LXI):

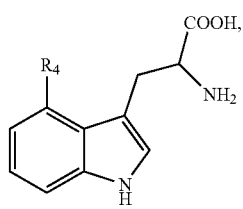

(LXI)

wherein $R_4$ is a propionyloxy or an acetoxy group, and a first formed multi-substituent psilocybin derivative compound having a formula (LIX):

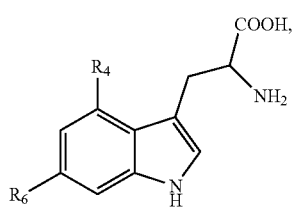

(LIX)

wherein $R_4$ is a propionyloxy or an acetoxy group, wherein $R_6$ is a prenyl group is formed. The first multi-substituent psilocybin derivative compound can be decarboxylated to form a second multi-substituent psilocybin derivative having a formula:

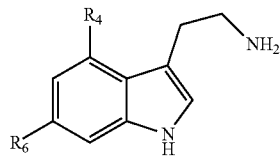

(LX)

wherein $R_4$ is a propionyloxy or an acetoxy group, wherein $R_6$ is a prenyl group. The second multi-substituent psilocybin derivative can be methylated to for a third multi-substituent psilocybin derivative having a formula (XLI) or (XLII):

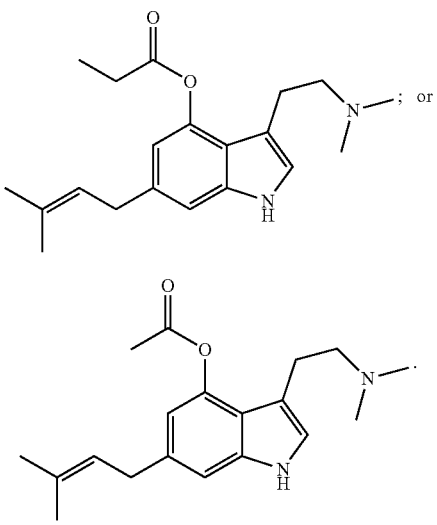

Referring further to FIG. 14B, its noted in order to prenylate the $S1_4$ psilocybin derivative precursor compound, dimethylallyl pyrophosphate (DMAPP) can be used as a substituent containing compound. Other prenyl containing compounds, such as geranyl pyrophosphate (GPP), farnesyl pyrophosphate (FPP), and geranylgeranyl pyrophosphate (GGPP) may alternatively be used as substituent containing compounds. As further shown in FIG. 14B, DMAPP itself may optionally be formed biosynthetically (in vitro or in vivo) from dimethylallyl alcohol DMAOH using acid phosphatase and isopentenyl phosphate kinase as catalyzing enzymes, as further described by Couillaud et al., 2019, ACS, Omega, 4, 7838-7859.

Referring next to FIG. 14C, in a further example embodiment, a psilocybin derivative precursor compound can be a chemical compound having a formula (LXII):

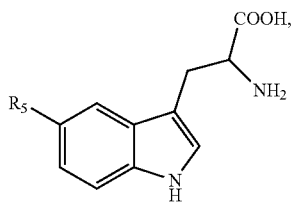

(LXII)

wherein R₅ is a chlorine or a fluorine atom, and a first multi-substituent psilocybin derivative compound having a formula (LXIII):

(LXIII)

wherein R₅ is a chlorine or a fluorine atom, and wherein R₆ is a prenyl group can be formed. The first multi-substituent psilocybin derivative can be decarboxylated to form a second multi-substituent psilocybin derivative compound having a formula (XXXVI) or (XXXVIII):

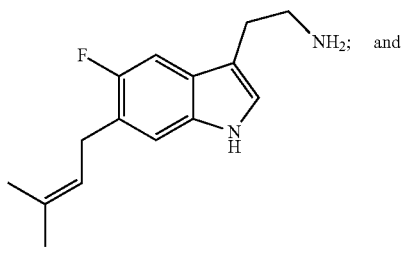

(XXXVI)

(XXXVIII)

In one further example embodiment, a psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:
(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code; (d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

Continuing to refer to FIG. 14C, a psilocybin derivative precursor compound can, in a further example embodiment, be a chemical compound having a formula (LXII):

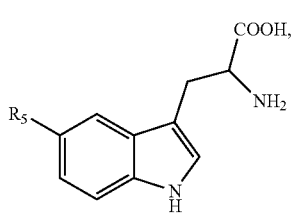

(LXI)

wherein R₅ is a chlorine or a fluorine atom, and a first multi-substituent psilocybin derivative compound having a formula (LXIII):

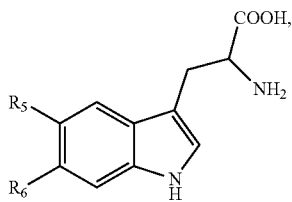

(LXIII)

wherein R₅ is a chlorine or a fluorine atom, and wherein R₆ is a prenyl group can be formed. The first multi-substituent psilocybin derivative compound can be decarboxylated to form a second formed multi-substituent psilocybin derivative compound having a formula (LXIV):

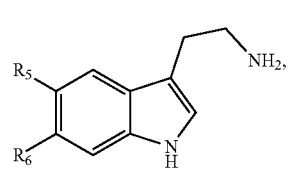

(LXIV)

wherein R₅ is a chlorine or a fluorine atom, and wherein R₆ is a prenyl group. The second multi-substituent psilocybin derivative compound can be acetylated to form a wherein third multi-substituent psilocybin derivative having a formula (XXXV) or (XXXVII):

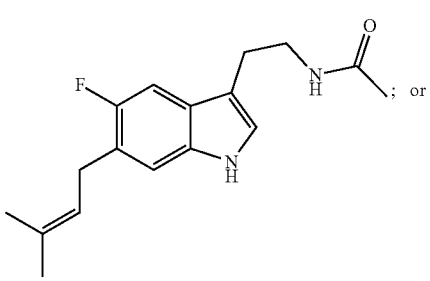

(XXXV)

; or (XXXVII)

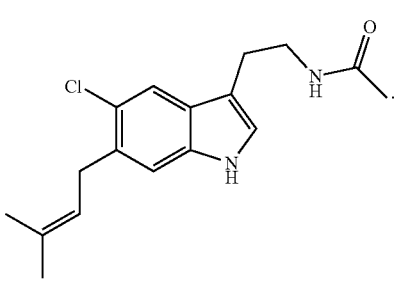

Referring further to FIG. 14C, similar to the biosynthetic pathway depicted in FIG. 14B, in order to prenylate the $S1_5$ psilocybin derivative precursor compound shown in FIG. 14C, dimethylallyl pyrophosphate (DMAPP) can be used as a substituent containing compound.

Referring next to FIG. 14D, and a psilocybin derivative precursor compound having formula (LVII), the psilocybin biosynthetic enzyme complement can, for example, comprise a tryptophan synthase subunit B polypeptide, encoded by a nucleic acid selected from:
 (a) SEQ.ID NO: 1;
 (b) a nucleic acid sequence that is substantially identical to the nucleic acid sequence of (a);
 (c) a nucleic acid sequence that is substantially identical to the nucleic acid sequence of (a) but for the degeneration of the genetic code;
 (d) a nucleic acid sequence that is complementary to the nucleic acid sequences of (a);
 (e) a nucleic acid sequence encoding a polypeptide having an amino acid sequences set forth in SEQ.ID NO: 2;
 (f) a nucleic acid sequence that encodes a functional variant of the amino acid sequence set forth in SEQ.ID NO: 2; and
 (g) a nucleic acid sequence that hybridizes under stringent conditions to any one of the nucleic acid sequences set forth in (a), (b), (c), (d), (e) or (f).

A first psilocybin derivative precursor compound having formula (I) can be used wherein two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom. A first multi-substituent psilocybin derivative compound having formula (I) can be formed wherein $R_{3c}$ is a carboxyl group. For example, a psilocybin derivative precursor compound can be a chemical compound having a formula: (LXV):

(LXV)

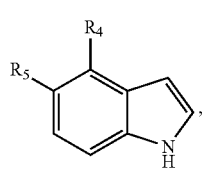

wherein $R_4$ is a hydroxy group, and wherein $R_5$ is a prenyl group, and a first formed multi-substituent psilocybin derivative compound having formula (LI):

(LI)

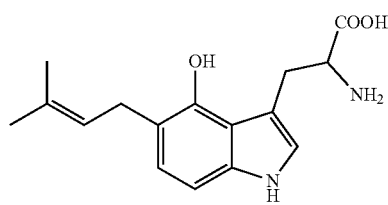

can be formed.

The psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:
 (a) SEQ.ID NO: 3, SEQ.ID NO: 5, and SEQ.ID NO: 7;
 (b) a nucleic acid sequence that is substantially identical to any one of the nucleic acid sequences of (a);
 (c) a nucleic acid sequence that is substantially identical to any one of the nucleic acid sequences of (a) but for the degeneration of the genetic code;
 (d) a nucleic acid sequence that is complementary to any one of the nucleic acid sequences of (a);
 (e) a nucleic acid sequence encoding a polypeptide having any one of the amino acid sequences set forth in SEQ.ID NO: 4, SEQ.ID NO: 6, SEQ.ID NO: and SEQ.ID NO 8;
 (f) a nucleic acid sequence that encodes a functional variant of any one of the amino acid sequences set forth in SEQ.ID NO: 4, SEQ.ID NO: 6 and SEQ.ID NO 8; and
 (g) a nucleic acid sequence that hybridizes under stringent conditions to any one of the nucleic acid sequences set forth in (a), (b), (c), (d), (e) or (f).

Continuing to refer to FIG. 14D, for example, a psilocybin derivative precursor compound can be a chemical compound having a formula (LXV):

(LXV)

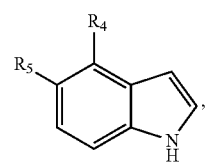

wherein $R_4$ is a fluorine atom and $R_5$ is nitrile group, a first formed multi-substituent psilocybin derivative compound having a formula (LXIX):

(LXIX)

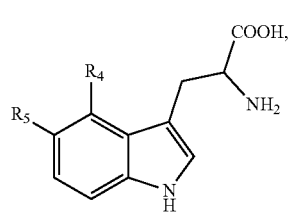

wherein R₄ is a fluorine atom and wherein R₅ is a nitrile group can be formed. A second formed multi-substituent psilocybin derivative compound can then be formed by decarboxylating the first multi-substituent derivative compound, the second multi-substituent psilocybin derivative compound having a formula (XIX):

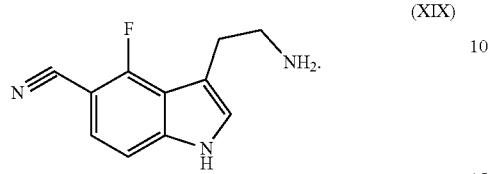

(XIX)

In a further embodiment, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:
(a) SEQ.ID NO: 9;
(b) a nucleic acid sequence that is substantially identical to the nucleic acid sequence of (a);
(c) a nucleic acid sequence that is substantially identical to the nucleic acid sequence of (a) but for the degeneration of the genetic code; (d) a nucleic acid sequence that is complementary to the nucleic acid sequence of (a);
(e) a nucleic acid sequence encoding a polypeptide having the amino acid sequence set forth in SEQ.ID NO: 10;
(f) a nucleic acid sequence that encodes a functional variant of any one of the amino acid sequences set forth in SEQ.ID NO: 10; and
(g) a nucleic acid sequence that hybridizes under stringent conditions to any one of the nucleic acid sequences set forth in (a), (b), (c), (d), (e) or (f).

Continuing to refer to FIG. 14D, for example, the psilocybin derivative precursor compound can be a chemical compound having a formula (LXV):

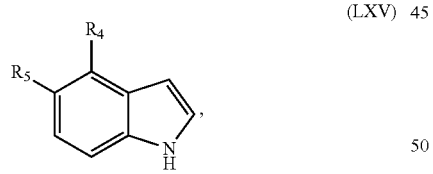

(LXV)

wherein R₄ is a fluorine atom and R₅ is a hydroxy group or a nitrile group, and a first formed multi-substituent psilocybin derivative compound having a formula (LXIX):

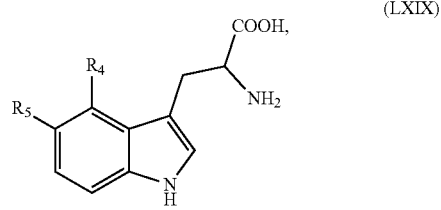

(LXIX)

wherein R₄ is a fluorine atom and wherein R₅ is a hydroxy group or a nitrile group can be formed. The first formed multi-substituent psilocybin derivative can be decarboxylated to form a second multi-substituent psilocybin derivative compound having a formula (LXXII):

(LXXII)

wherein R₄ is a fluorine atom, and wherein R₅ is a hydroxy group or a nitrile group. The second formed multi-substituent psilocybin derivative can then be acetylated to form a third multi-substituent psilocybin derivative having a formula (XVII) or (XX):

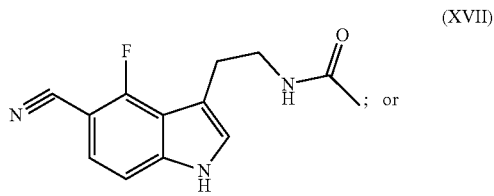

(XVII) ; or

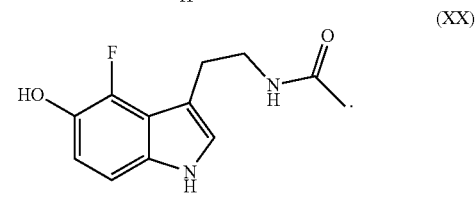

(XX)

Referring next to FIG. 14E, the psilocybin biosynthetic enzyme complement can comprise a tryptophan synthase subunit B polypeptide, encoded by a nucleic acid selected from:
(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f),
wherein in the psilocybin derivative precursor compound having formula (LVIII), two of R₂, R₄, R₅, R₆, or R₇ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein R₃ is a hydrogen atom, and wherein a first multi-substituent psilocybin derivative compound having formula (I) is formed wherein $R_{3c}$ is a carboxyl group. For example,
the psilocybin derivative precursor compound can be a chemical compound having a formula (LXVI):

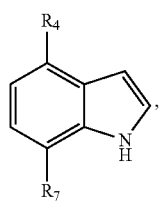
(LXVI)

wherein $R_4$ is a hydroxy group, and wherein $R_7$ is a prenyl group, and a first formed multi-substituent psilocybin derivative compound having a formula (XLIX):

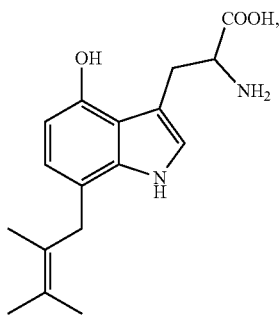
(XLIX)

can be formed.

In a further embodiment, the psilocybin biosynthetic enzyme complement can further comprise a tryptophan decarboxylase to decarboxylate the $R_3$—$CH_2$—$CHNH_2COOH$ group, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:
  (a) SEQ.ID NO: 3, SEQ.ID NO: 5, and SEQ.ID NO: 7;
  (b) a nucleic acid sequence that is substantially identical to any one of the nucleic acid sequences of (a);
  (c) a nucleic acid sequence that is substantially identical to any one of the nucleic acid sequences of (a) but for the degeneration of the genetic code;
  (d) a nucleic acid sequence that is complementary to any one of the nucleic acid sequences of (a);
  (e) a nucleic acid sequence encoding a polypeptide having any one of the amino acid sequences set forth in SEQ.ID NO: 4, SEQ.ID NO: 6, SEQ.ID NO: and SEQ.ID NO 8;
  (f) a nucleic acid sequence that encodes a functional variant of any one of the amino acid sequences set forth in SEQ.ID NO: 4, SEQ.ID NO: 6 and SEQ.ID NO 8; and
  (g) a nucleic acid sequence that hybridizes under stringent conditions to any one of the nucleic acid sequences set forth in (a), (b), (c), (d), (e) or (f).

Continuing to refer to FIG. 14E, the psilocybin derivative precursor compound can be a chemical compound having a formula (LXVI):

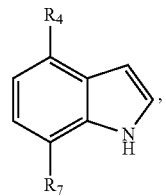
(LXVI)

wherein $R_4$ is a fluorine atom and $R_7$ is nitrile group, and a first multi-substituent psilocybin derivative compound having a formula (LXX):

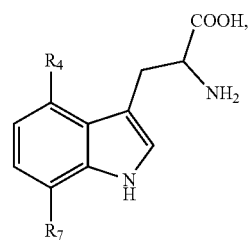
(LXX)

wherein $R_4$ is a fluorine atom and wherein $R_7$ is a nitrile group, can be formed. A second formed multi-substituent psilocybin derivative compound having a formula (XXIV):

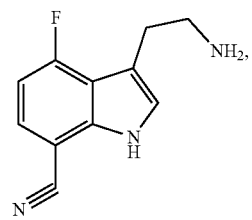
(XXIV)

can be formed by decarboxylating the first multi-substituent psilocybin derivative compound.

In a further embodiment, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:
  (a) SEQ.ID NO: 9,
  (b) a nucleic acid sequence that is substantially identical to the nucleic acid sequence of (a);
  (c) a nucleic acid sequence that is substantially identical to the nucleic acid sequence of (a) but for the degeneration of the genetic code;
  (d) a nucleic acid sequence that is complementary to the nucleic acid sequence of (a);
  (e) a nucleic acid sequence encoding a polypeptide having the amino acid sequence set forth in SEQ.ID NO: 10;
  (f) a nucleic acid sequence that encodes a functional variant of any one of the amino acid sequences set forth in SEQ.ID NO: 10; and
  (g) a nucleic acid sequence that hybridizes under stringent conditions to any one of the nucleic acid sequences set forth in (a), (b), (c), (d), (e) or (f).

135

Continuing to refer to FIG. 14E, the psilocybin derivative precursor compound can be a chemical compound having a formula (LXVI):

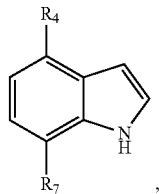

(LXVI)

wherein $R_4$ is a fluorine atom or a chlorine atom and $R_7$ is a prenyl group or a nitrile group, and a multi-substituent psilocybin derivative compound having a formula (LXX):

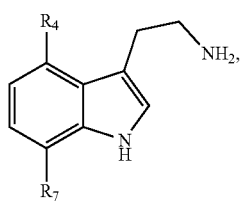

(LXX)

wherein $R_4$ is a fluorine atom or a chlorine atom and wherein $R_7$ is a prenyl group or a nitrile group can be formed. Upon decarboxylation of the first multi-substituent psilocybin derivative compound, a second multi-substituent psilocybin derivative compound having a formula (LXXIII):

(LXXIII)

wherein $R_4$ is a fluorine atom or a chlorine atom, and wherein $R_7$ is a prenyl group or a nitrile group, can be formed. Following acetylation, a third multi-substituent psilocybin derivative having a formula (XXIII) or (XX):

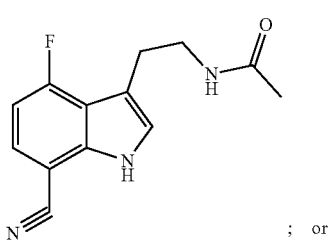

(XXIII)

; or

136

-continued

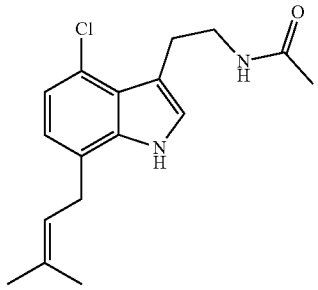

(XXXIV)

can be formed.

The psilocybin biosynthetic enzyme complement can further comprise an N-methyl transferase to methylate the $R_3$ amino group at $R_3$ and form a further multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:

(a) SEQ.ID NO: 11, and SEQ.ID NO 13;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 12 and SEQ.ID NO 14;

(f) a nucleic acid sequence that encodes a functional variant of any one of the amino acid sequences set forth in SEQ.ID NO: 12, and SEQ.ID NO 14; and (g) a nucleic acid sequence that hybridizes under stringent conditions to any one of the nucleic acid sequences set forth in (a), (b), (c), (d), (e) or (f).

In one embodiment, for example, the psilocybin derivative precursor compound can be a chemical compound having a formula (LXVI):

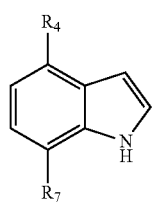

(LXVI)

wherein $R_4$ is a chlorine atom and $R_7$ is a hydroxy group, and a first formed multi-substituent psilocybin derivative compound has a formula (LXX):

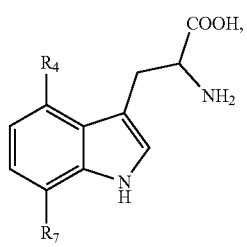

(LXX)

wherein R$_4$ is a hydroxy group and wherein R$_7$ is a chlorine atom can be formed. Following decarboxylation, a second formed multi-substituent psilocybin derivative compound having a formula (LXXIII):

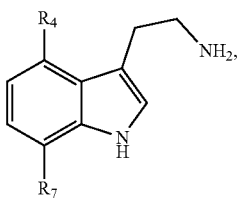

(LXXIII)

wherein R$_4$ is a hydroxy group, and wherein R$_7$ is a chlorine atom can be formed Following methylation a third multi-substituent psilocybin derivative having a formula (XXXIX):

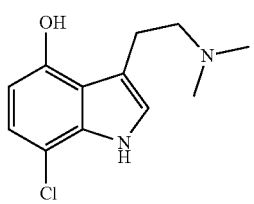

(XXXIX)

can be formed.

Referring next to FIG. 14F, in another embodiment, the psilocybin biosynthetic enzyme complement can comprise a tryptophan synthase subunit B polypeptide, encoded by a nucleic acid selected from:
(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f),
wherein in the psilocybin derivative precursor compound having formula (LVIII), two of R$_2$, R$_4$, R$_5$, R$_6$, or R$_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein R$_3$ is a hydrogen atom, and wherein a first multi-substituent psilocybin derivative compound having formula (I) is formed wherein R$_{3c}$ is a carboxyl group, and the psilocybin biosynthetic enzyme complement further comprises a tryptophan decarboxylase to decarboxylate a R$_3$—CH$_2$—CHNH$_2$COOH group of the first multi-substituent psilocybin derivative compound, and thereby form a second multi-substituent psilocybin derivative having formula (I) wherein an R$_{3a}$ and R$_{3b}$ each are a hydrogen atom, the tryptophan decarboxylase encoded by a nucleic acid sequence selected from:
(a) SEQ.ID NO: 3, SEQ.ID NO: 5, and SEQ.ID NO: 7;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 4, SEQ.ID NO: 6, SEQ.ID NO: and SEQ.ID NO 8;
(f) a nucleic acid sequence that encodes a functional variant of any one of the amino acid sequences set forth in SEQ.ID NO: 4, SEQ.ID NO: 6 and SEQ.ID NO 8; and
(g) a nucleic acid sequence that hybridizes under stringent conditions to any one of the nucleic acid sequences set forth in (a), (b), (c), (d), (e) or (f).

Continuing to refer to FIG. 14F, the psilocybin derivative precursor compound can be a chemical compound having a formula (LXVII):

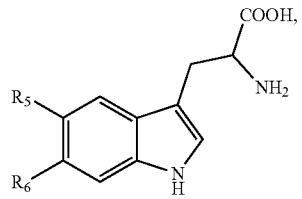

(LXVII)

wherein R$_5$ is a fluorine atom, a chlorine atom, or a nitrile group and R$_6$ is a fluorine atom, an amino group or a prenyl group, and a first formed multi-substituent psilocybin derivative compound has a formula (LXIII):

(LXIII)

wherein R$_5$ is a fluorine atom, a chlorine atom, or a nitrile group and wherein R$_6$ is a is a fluorine atom, an amino group or a prenyl group, can be formed. Following decarboxylation, a second formed multi-substituent psilocybin derivative compound having a formula (XI), (XVI), (XXXVI) or (XXXVIII):

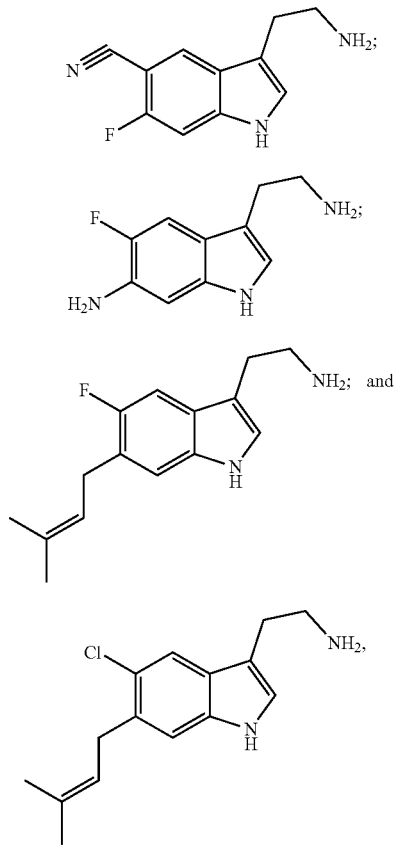

can be formed.

The psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;

(b) a nucleic acid sequence that is substantially identical to the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having the amino acid sequence set forth in SEQ.ID NO: 10;

(f) a nucleic acid sequence that encodes a functional variant of any one of the amino acid sequences set forth in SEQ.ID NO: 10; and (g) a nucleic acid sequence that hybridizes under stringent conditions to any one of the nucleic acid sequences set forth in (a), (b), (c), (d), (e) or (f).

Continuing to refer to FIG. 14F, in one embodiment, for example, the psilocybin derivative precursor compound can be a chemical compound having a formula (LXVII):

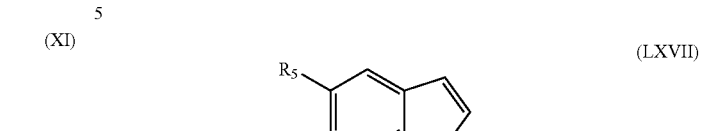

wherein $R_5$ is a fluorine atom or a chlorine atom and $R_6$ is an amino group, an acetamidyl group, or a prenyl group, and a first formed multi-substituent psilocybin derivative compound having a formula (LXIII):

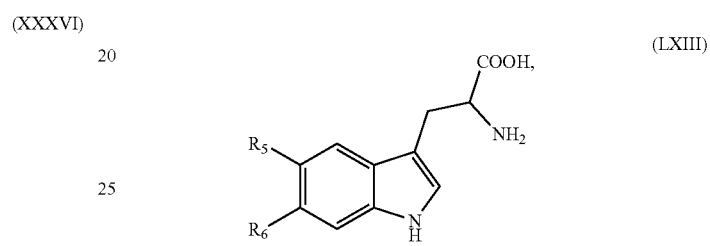

wherein $R_5$ is a fluorine atom or a chlorine atom and wherein $R_6$ is an amino group, an acetamidyl group, or a prenyl group can be formed. Following decarboxylation a second multi-substituent psilocybin derivative compound having a formula (LXXIV):

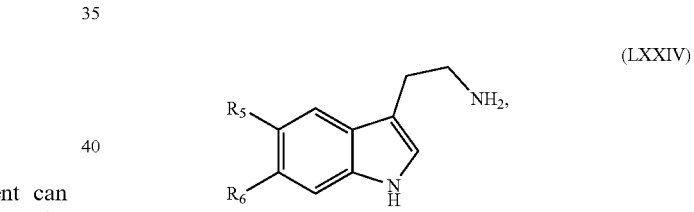

wherein $R_5$ is a fluorine atom or a chlorine atom, and wherein $R_6$ is an amino group, an acetamidyl group, or a prenyl group can be formed. Following acetylation, a third multi-substituent psilocybin derivative has a formula (XIV), (XV), (XXXV), or (XXXVII):

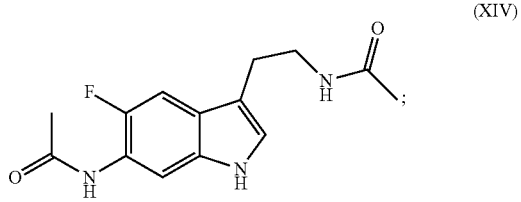

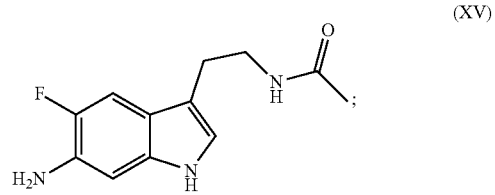

(XXXV)

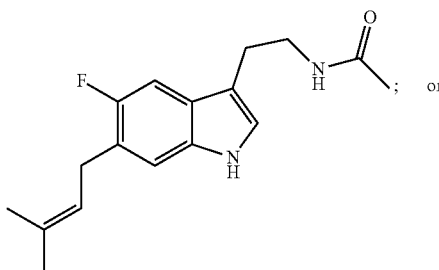

; or (XXXVII)

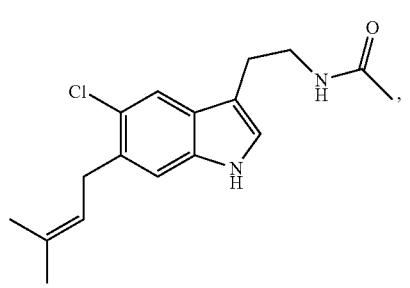

, can be formed.

The psilocybin biosynthetic enzyme complement can further comprise an N-methyl transferase to methylate the $R_3$ amino group at $R_3$ and form a further multi-substituent psilocybin derivative having a chemical formula (I), wherein $R_{3a}$ and $R_{3b}$ are each a methyl group, or wherein $R_{3a}$ is a hydrogen atom and $R_{3b}$ is a methyl group, the N-methyl transferase encoded by a nucleic acid sequence selected from:

(a) SEQ.ID NO: 11, and SEQ.ID NO 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 12 and SEQ.ID NO 14;
(f) a nucleic acid sequence that encodes a functional variant of any one of the amino acid sequences set forth in SEQ.ID NO: 12, and SEQ.ID NO 14; and
(g) a nucleic acid sequence that hybridizes under stringent conditions to any one of the nucleic acid sequences set forth in (a), (b), (c), (d), (e) or (f).

Continuing to refer to FIG. 14F, the psilocybin derivative precursor compound can be a chemical compound having a formula (LXVII):

(LXVII)

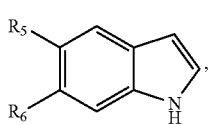

, wherein $R_5$ is a chlorine atom and $R_6$ is a prenyl group, and a first formed multi-substituent psilocybin derivative compound has a formula (LXIII):

(LXIII)

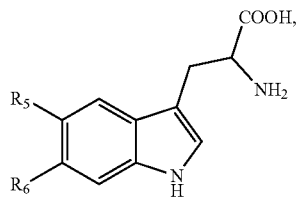

wherein $R_5$ is a chlorine atom and wherein $R_6$ is a prenyl group can be formed. Following decarboxylation, a second multi-substituent psilocybin derivative compound having a formula (LXXIV):

(LXXIV)

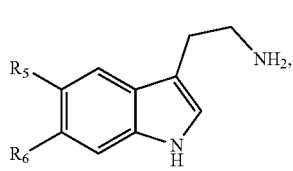

wherein $R_5$ is a chlorine atom, and wherein $R_6$ is a prenyl group can be formed. Following methylation, a third multi-substituent psilocybin derivative having a formula (XLIV):

(XLIV)

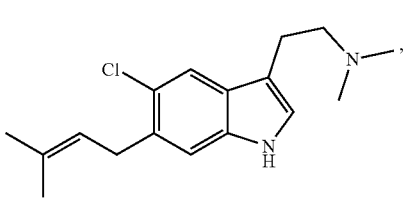

can be formed.

Referring next to FIG. 14G, in another embodiment, the psilocybin biosynthetic enzyme complement can comprise a tryptophan synthase subunit B polypeptide, encoded by a nucleic acid selected from:

(a) SEQ.ID NO: 1;
(b) a nucleic acid sequence that is substantially identical to the nucleic acid sequence of (a);
(c) a nucleic acid sequence that is substantially identical to the nucleic acid sequence of (a) but for the degeneration of the genetic code; (d) a nucleic acid sequence that is complementary to the nucleic acid sequences of (a);
(e) a nucleic acid sequence encoding a polypeptide having an amino acid sequences set forth in SEQ.ID NO: 2;
(f) a nucleic acid sequence that encodes a functional variant of the amino acid sequence set forth in SEQ.ID NO: 2; and
(g) a nucleic acid sequence that hybridizes under stringent conditions to any one of the nucleic acid sequences set forth in (a), (b), (c), (d), (e) or (f), wherein in the psilocybin derivative precursor compound having formula (LVIII), two of $R_2$, $R_4$, $R_5$, $R_6$, or $R_7$ are a substituent independently selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group, and the psilocybin biosynthetic enzyme complement further comprises a tryptophan decarboxylase to decarboxylate a $R_3$—$CH_2$—$CHNH_2COOH$ group of the first multi-substituent psilocybin derivative compound, and thereby form a second multi-substituent psilocybin derivative having formula (I) wherein an $R_{3a}$ and $R_{3b}$ each are a hydrogen atom, the tryptophan decarboxylase encoded by a nucleic acid sequence selected from:

(a) SEQ.ID NO: 3, SEQ.ID NO: 5, and SEQ.ID NO: 7;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 4, SEQ.ID NO: 6, SEQ.ID NO: and SEQ.ID NO 8;

(f) a nucleic acid sequence that encodes a functional variant of any one of the amino acid sequences set forth in SEQ.ID NO: 4, SEQ.ID NO: 6 and SEQ.ID NO 8; and (g) a nucleic acid sequence that hybridizes under stringent conditions to any one of the nucleic acid sequences set forth in (a), (b), (c), (d), (e) or (f).

Continuing to refer to FIG. 14G, the psilocybin derivative precursor compound can, for example, be a chemical compound having a formula (LXVIII):

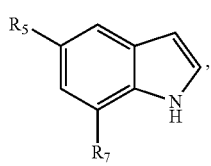
(LXVIII)

wherein $R_5$ is a fluorine atom, and $R_7$ is a nitro group or a prenyl group, a first formed multi-substituent psilocybin derivative compound having a formula (LXXI):

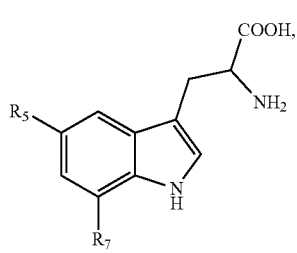
(LXXI)

wherein $R_5$ is a fluorine atom, and wherein $R_7$ is a nitro group atom or a prenyl group can be formed. Following decarboxylation, a second formed multi-substituent psilocybin derivative compound having a formula (XIII) or (XXXIII):

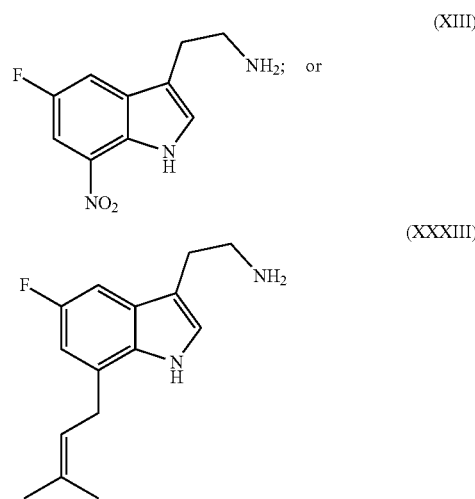
(XIII)

(XXXIII)

can be formed.

In one embodiment, the psilocybin biosynthetic enzyme complement can further comprise an N-acetyl transferase to acetylate the second psilocybin derivative having chemical formula (I) and thereby form a third multi-substituent psilocybin having chemical formula (I), wherein $R_{3a}$ is a hydrogen atom and $R_{3b}$ is an acetyl group, the N-acetyl transferase encoded by a nucleic acid sequence selected from:

(a) SEQ.ID NO: 9;

(b) a nucleic acid sequence that is substantially identical to the nucleic acid sequence of (a);

(c) a nucleic acid sequence that is substantially identical to the nucleic acid sequence of (a) but for the degeneration of the genetic code;

(d) a nucleic acid sequence that is complementary to the nucleic acid sequence of (a);

(e) a nucleic acid sequence encoding a polypeptide having the amino acid sequence set forth in SEQ.ID NO: 10;

(f) a nucleic acid sequence that encodes a functional variant of any one of the amino acid sequences set forth in SEQ.ID NO: 10; and (g) a nucleic acid sequence that hybridizes under stringent conditions to any one of the nucleic acid sequences set forth in (a), (b), (c), (d), (e) or (f).

Continuing to refer to FIG. 14G, the psilocybin derivative precursor compound can, for example, be a chemical compound having a formula (LXVIII):

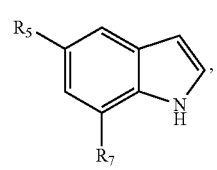
(LXVIII)

wherein $R_5$ is a fluorine atom, and $R_7$ is a nitro group or a prenyl group, a first formed multi-substituent psilocybin derivative compound having a formula (LXXI):

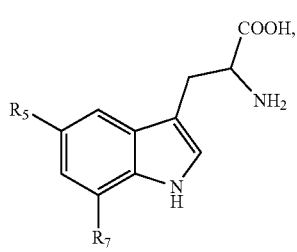

(LXXI)

wherein $R_5$ is a fluorine atom, and wherein $R_7$ is a nitro group atom or a prenyl group can be formed. Following decarboxylation thereof a second formed multi-substituent psilocybin derivative compound has a formula (LXXV):

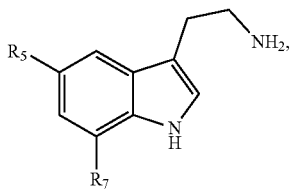

(LXXV)

wherein $R_5$ is a fluorine atom, and wherein $R_7$ is a nitro group or a prenyl group can be formed. Following acetylation thereof a third multi-substituent psilocybin derivative has a formula (XII) or (XXXII):

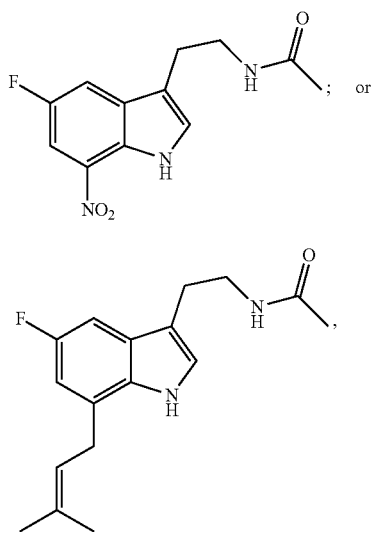

(XII)

(XXXII)

can be formed.

Figure 13D:
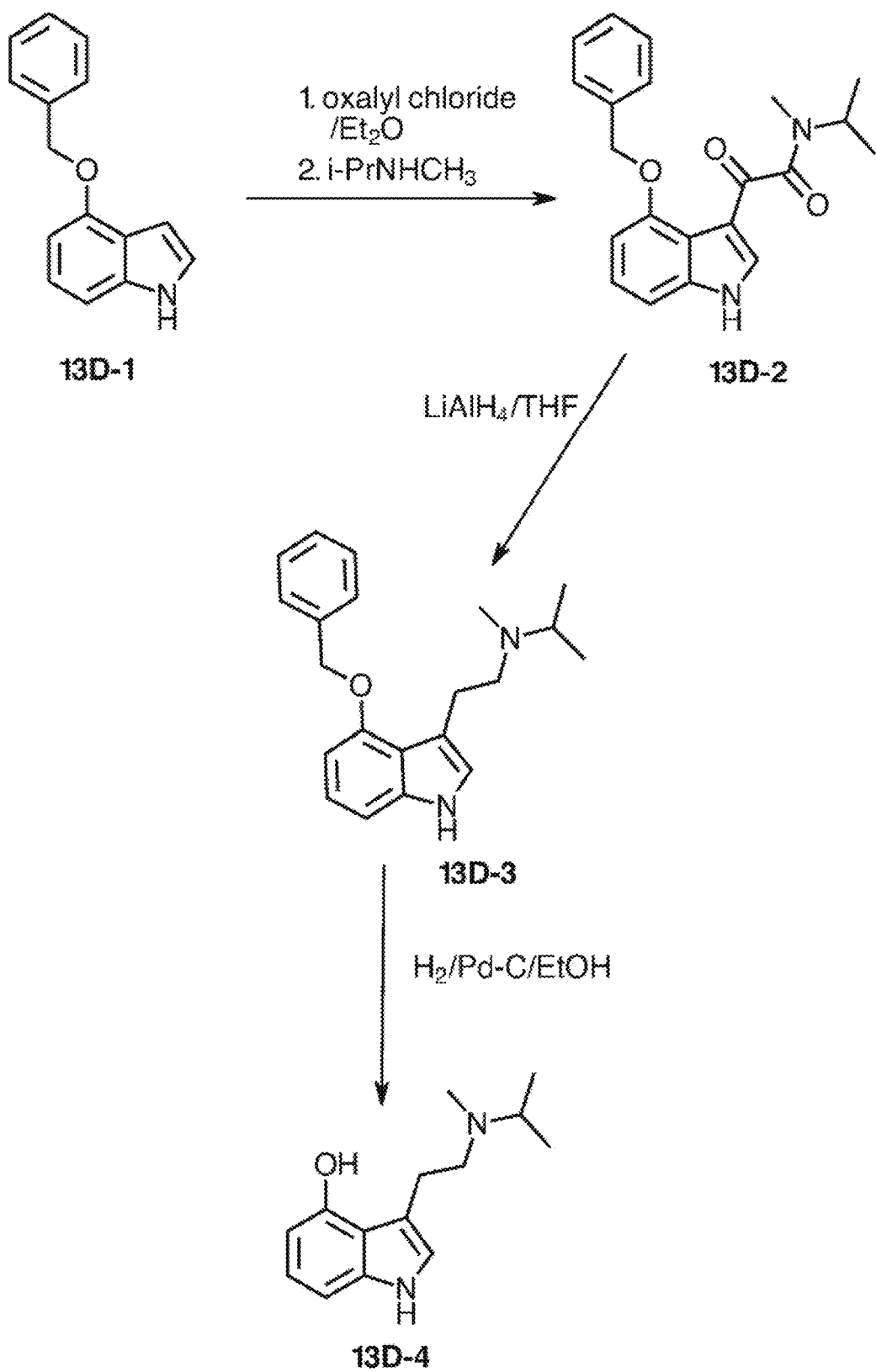

As hereinbefore noted, in some embodiments, a multi-substituent psilocybin derivative may be made by a employing a combination of synthetic and biosynthetic methods. Thus, for example, referring to FIG. 13D, compound 13-D4, may be made synthetically in accordance with the synthesis schematic shown in FIG. 13D (and as herein further described in Example 42). Compound 13-D4 then be prenylated, either in vitro or in vivo, using a prenyl transferase to form, for example, a $C_6$ prenylated derivative of compound 13-D4.

Thus, in one embodiment, a psilocybin biosynthetic enzyme complement can contain a prenyl transferase encoded by a nucleic acid selected from:
 (a) SEQ.ID NO: 15, SEQ.ID NO: 17, SEQ.ID NO: 19, and SEQ.ID NO 21;
 (b) a nucleic acid sequence that is substantially identical to any one of the nucleic acid sequences of (a);
 (c) a nucleic acid sequence that is substantially identical to any one of the nucleic acid sequences of (a) but for the degeneration of the genetic code;
 (d) a nucleic acid sequence that is complementary to any one of the nucleic acid sequences of (a);
 (e) a nucleic acid sequence encoding a polypeptide having any one of the amino acid sequences set forth in SEQ.ID NO: 16, SEQ.ID NO: 18, SEQ.ID NO: 20, and SEQ.ID NO 22;
 (f) a nucleic acid sequence that encodes a functional variant of any one of the amino acid sequences set forth in SEQ.ID NO: 16, SEQ.ID NO: 18, SEQ.ID NO: 20, and SEQ.ID NO 22; and
 (g) a nucleic acid sequence that hybridizes under stringent conditions to any one of the nucleic acid sequences set forth in (a), (b), (c), (d), (e) or (f),
wherein in the psilocybin derivative precursor compound having formula (LVIII), one of $R_2$, $R_4$, $R_5$, $R_6$, or $R_7$ is a substituent selected from (i) a halogen atom, (ii) a hydroxy group, (iii) a nitro group, (iv) a glycosyloxy group, (v) an amino group or an N-substituted amino group, (vi) a carboxyl group or a carboxylic acid derivative, (vii) an aldehyde or a ketone group, (viii) a prenyl group, and (ix) a nitrile group, wherein $R_3$ is a hydrogen atom, and wherein a first multi-substituent psilocybin derivative compound having formula (I) is formed wherein $R_{3c}$ is a carboxyl group or a hydrogen atom.

In one embodiment, the psilocybin derivative precursor compound can have a formula (LXXVII):

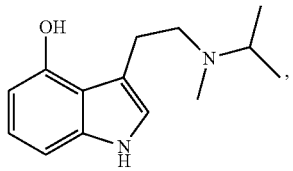

(LXXVII)

and a multi-substituent psilocybin derivative compound having the formula (LXXVI):

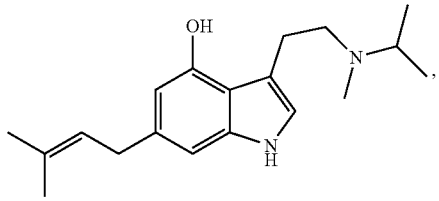

(LXXVI)

can be formed.

It will be clear to those of skill in the art that a significant variety of different psilocybin precursor compounds may be selected. FIGS. 14A and 14G in this respect provide guidance and allow a person of skill in the art to select appropriate psilocybin derivative precursor compounds and a matching a psilocybin biosynthetic enzyme complement.

Upon production by the host cells of a multi-substituent psilocybin compound in accordance with the methods of the present disclosure, the multi-substituent psilocybin derivative compounds may be extracted from the host cell suspension, and separated from other constituents within the host cell suspension, such as media constituents and cellular debris. Separation techniques will be known to those of skill in the art and include, for example, solvent extraction (e.g., butane, chloroform, ethanol), column chromatography based techniques, high-performance liquid chromatography (HPLC), for example, and/or countercurrent separation (CCS) based systems. The recovered multi-substituent psilocybin derivative compounds may be obtained in a more or less pure form, for example, a preparation of multi-substituent derivative psilocybin compounds of at least about 60% (w/w), about 70% (w/w), about 80% (w/w), about 90% (w/w), about 95% (w/w), about 96% (w/w), about 97% (w/w), about 98% (w/w) or about 99% (w/w) purity may be obtained. Thus, in this manner, multi-substituent psilocybin derivatives in more or less pure form may be prepared.

It will now be clear from the foregoing that novel multiple-substituent psilocybin derivatives are disclosed herein, as well as methods of making multiple-substituent psilocybin derivatives. The multiple-substituent psilocybin compounds may be formulated for use as a pharmaceutical drug or recreational drug.

Summary of Sequences

SEQ.ID NO: 1 sets forth a *Pyrococcus furiosus* nucleic acid sequence encoding tryptophan synthase subunit B polypeptide, named PfTrpB-B0A9.

SEQ.ID NO: 2 sets forth a deduced amino acid sequence of a *Pyrococcus furiosus* subunit B tryptophan synthase subunit B polypeptide, named PfTrpB-B0A9.

SEQ. ID NO: 3 sets forth a *Bacillus atrophaeaus* nucleic acid sequence encoding a tryptophan decarboxylase polypeptide, named BaTDC.

SEQ.ID NO: 4 sets forth a deduced amino acid sequence of *Bacillus atrophaeaus* tryptophan decarboxylase polypeptide, named BaTDC.

SEQ. ID NO: 5 sets forth a *Clostridium sporidium* nucleic acid sequence encoding a tryptophan decarboxylase polypeptide, named ClostSporTDC.

SEQ.ID NO: 6 sets forth a deduced amino acid sequence of *Clostridium sporidium* tryptophan decarboxylase polypeptide, named ClostSporTDC.

SEQ.ID NO: 7 sets forth a *Psilocybe cubensis* nucleic acid sequence encoding a PsiD polypeptide.

SEQ.ID NO: 8 sets forth a deduced amino acid sequence of a *Psilocybe cubensis* PsiD polypeptide.

SEQ. ID NO: 9 sets forth a *Streptomyces griseofuscus* nucleic acid sequence encoding an N-acetyl transferase, named PmsF.

SEQ.ID NO: 10 sets forth a deduced amino acid sequence of a *Streptomyces griseofuscus* an N-acetyl polypeptide, named PmsF.

SEQ. ID NO: 11 sets forth an Ephedra *sinica* nucleic acid sequence encoding an N-methyl transferase, named EsNMT.

SEQ.ID NO: 12 sets forth a deduced amino acid sequence of an Ephedra *sinica* an N-methyl transferase polypeptide, named EsNMT.

SEQ.ID NO: 13 sets forth a *Psilocybe cubensis* nucleic acid sequence encoding a PsiM polypeptide.

SEQ.ID NO: 14 sets forth a deduced amino acid sequence of a *Psilocybe cubensis* PsiM polypeptide.

SEQ.ID NO: 15 sets forth an *Aspergillus fumigatus* nucleic acid sequence encoding a tryptophan 7-prenyl transferase polypeptide, named 7DMATS.

SEQ.ID NO: 16 sets forth a deduced amino acid sequence of an *Aspergillus fumigatus* tryptophan 7-prenyl transferase polypeptide, named 7DMATS.

SEQ.ID NO: 17 sets forth a *Streptomyces* sp. RM-5-8 nucleic acid sequence encoding a 6-prenyl transferase polypeptide, named PriB.

SEQ.ID NO: 18 sets forth a deduced amino acid sequence of a *Streptomyces* sp. RM-5-8 6-prenyl transferase polypeptide, named PriB.

SEQ.ID NO: 19 sets forth a *Streptomyces coelicolor* nucleic acid sequence encoding a tryptophan 5-prenyl transferase polypeptide, named SCO7467.

SEQ.ID NO: 20 sets forth a deduced amino acid sequence of a *Streptomyces coelicolor* tryptophan 5-prenyl transferase polypeptide, named SCO7467.

SEQ.ID NO: 21 sets forth an *Aspergillus fumigatus* nucleic acid sequence encoding a tryptophan 4-prenyl transferase polypeptide, named FgaPT2.

SEQ.ID NO: 22 sets forth a deduced amino acid sequence of an *Aspergillus fumigatus* tryptophan 4-prenyl transferase polypeptide, named FgaPT2.

SEQ.ID NO: 23 sets forth a *Psilocybe cubensis* nucleic acid sequence encoding a PsiH polypeptide.

SEQ.ID NO: 24 sets forth a deduced amino acid sequence of a *Psilocybe cubensis* PsiH polypeptide.

SEQ.ID NO: 25 sets forth a *Psilocybe cubensis* nucleic acid sequence encoding a CPR polypeptide.

SEQ.ID NO: 26 sets forth a deduced amino acid sequence of a *Psilocybe cubensis* CPR polypeptide.

SEQ. ID NO: 27 sets forth an artificial nucleic acid useful as an integration cassette, named XII-4::TADH1-PsiH-HA-PPGK1-PTDH3-CPR-c-myc-TCYC1.

SEQ. ID NO: 28 sets forth an artificial nucleic acid useful as an integration cassette, named XII-5::TADH1-PsiK-V5-PPGK1-PTDH3-PsiM-FLAG-TCYC1.

SEQ. ID NO: 29 sets forth an artificial nucleic acid useful as an integration cassette, named pMM1-PTDH3-ClostSporTDC-His-TCYC1.

SEQ. ID NO: 30 sets forth an artificial nucleic acid useful as a promoter, named PGK1_promoter.

SEQ. ID NO: 31 sets forth an artificial nucleic acid useful as a promoter, named TDH3_promoter.

SEQ. ID NO: 32 sets forth an artificial nucleic acid useful as a promoter, named CLN1_promoter.

SEQ. ID NO: 33 sets forth an artificial nucleic acid useful as a promoter, named UGA1_promoter.

SEQ. ID NO: 34 sets forth an artificial nucleic acid useful as a vector, named pMM1.

SEQ. ID NO: 35 sets forth an artificial nucleic acid useful as a vector, named pCDM4.

SEQ. ID NO: 36 sets forth an artificial nucleic acid useful as a vector, named pET28a(+).

SEQ. ID NO: 37 sets forth an artificial nucleic acid useful as a vector, named pET23(+).

SEQ. ID NO: 38 sets forth an artificial nucleic acid encoding a polypeptide sequence useful as a tag, named HA-tag.

SEQ. ID NO: 39 sets forth an artificial polypeptide sequence useful as a tag, named HA-tag.

SEQ. ID NO: 40 sets forth an artificial nucleic acid sequence encoding a polypeptide sequence useful as a tag, named c-myc-tag.

SEQ. ID NO: 41 sets forth an artificial polypeptide sequence useful as a tag, named c-myc-tag.

SEQ. ID NO: 42 sets forth an artificial nucleic acid sequence encoding a polypeptide sequence useful as a tag, named FLAG-tag.

SEQ. ID NO: 43 sets forth an artificial polypeptide sequence useful as a tag, named FLAG-tag.

SEQ.ID NO: 44 sets forth an artificial nucleic acid sequence encoding a polypeptide sequence useful as a tag, named V5-tag.

SEQ.ID NO: 45 sets forth an artificial polypeptide sequence useful as a tag, named V5-tag.

SEQ.ID NO: 46 sets forth an artificial nucleic acid sequence encoding a polypeptide sequence useful as a tag, named His-tag.

SEQ.ID NO: 47 sets forth an artificial polypeptide sequence useful as a tag, named His-tag.

SEQ.ID NO: 48 sets forth a *Psilocybe cubensis* nucleic acid sequence encoding a PsiK polypeptide.

SEQ.ID NO: 49 sets forth a deduced amino acid sequence of a *Psilocybe cubensis* PsiK polypeptide.

SEQ.ID NO: 50 sets forth an artificial nucleic acid useful as an integration cassette, named X-3::TADH1-BaTDC-Flag-PPGK1-PTDH3-CPR-c-myc-TCYC1.

SEQ.ID NO: 51 sets forth an artificial nucleic acid useful as an integration cassette, named Xii-2::TADH1-PPGK1-PTDH3-PriB-His-TCYC1.

SEQ.ID NO: 52 sets forth an artificial nucleic acid useful as an integration cassette, named X-3::TADH1-ClostSporTDC-Flag-PPGK1-PTDH3-CPR-c-myc-TCYC1.

SEQ.ID NO: 53 sets forth an artificial nucleic acid useful as an integration cassette, named Xii-2::TADH1-PPGK1-PTDH3-Af-7DMATS-His-TCYC1.

SEQ. ID NO: 54 sets forth an artificial nucleic acid useful as a vector, named pET26b(+).

```
SEQUENCES
                                                          SEQ. ID NO: 1
ATGTGGTTCGGTGAGTTTGGTGGACAATATGTGCCAGAGACTTTAGTGGGTCCTCTTAA

GGAATTGGAAAAGGCATATAAAAGGTTCAAGGACGATGAGGAGTTCAACAGGCAACTAA

ACTATTATTTGAAGACATGGGCCGGTAGACCAACGCCCTTGTATTATGCTAAGAGGTTA

ACTGAAAAGATTGGCGGCGCGAAAGTGTATCTGAAAAGAGAAGACCTAGTTCATGGTGG

AGCACACAAGACAAATAATGCCATTGGACAAGCACTATTGGCAAAGCTAATGGGTAAAA

CTAGATTGATAGCTGAGACAGGAGCGGGTCAACATGGGGTCGCGACAGCGATGGCTGGT

GCACTACTGGGGATGAAGGTAGATATTTACATGGGTGCTGAGGACGTTGAGCGTCAGAA

ACTAAATGTCTTCAGGATGAAGCTATTAGGTGCCAATGTTATACCTGTAAATTCTGGCT

CAAGAACACTAAAGGACGCCTTCGACGAGGCTCTTAGAGACTGGGTTGCCACTTTCGAG

TATACTCATTACTTGATCGGTTCAGTGGTTGGACCACATCCATACCCAACCATCGTTAG

GGACTTTCAGAGCGTGATTGGTAGAGAGGCTAAGGCACAGATCTTAGAAGCAGAGGGAC

AGCTACCTGACGTCATAGTTGCCTGCGTCGGCGGTGGCTCTAACGCAATGGGTATATTC

TATCCATTCGTTAATGACAAGAAGGTTAAATTAGTAGGAGTCGAAGCTGGCGGAAAGGG

GTTAGAGTCGGGTAAACACTCAGCAAGCTTAAATGCAGGACAGGTAGGGGTGTCCCACG

GCATGTTGTCGTATTTCTTGCAAGACGAGGAAGGTCAGATAAAGCCAAGTCATTCAATT

GCTCCAGGCCTTGACCACCCCGGTGTTGGTCCAGAGCACGCTTACTTAAAGAAGATTCA

AAGGGCCGAGTACGTCGCTGTAACAGACGAAGAGGCATTGAAAGCTTTCCATGAGCTAT

CCAGAACTGAGGGGATTATACCCGCCCTTGAGTCTGCCCATGCTGTGGCGTACGCCATG

AAGTTAGCTAAAGAGATGTCCCGTGACGAAATCATCATTGTAAATCTATCAGGGAGAGG

AGACAAGGATTTGGACATTGTATTGAAGGCAAGCGGAAATGTTTGA

SEQ. ID NO: 2
MWFGEFGGQYVPETLVGPLKELEKAYKRFKDDEEFNRQLNYYLKTWAGRPTPLYYAKRL

TEKIGGAKVYLKREDLVHGGAHKTNNAIGQALLAKLMGKTRLIAETGAGQHGVATAMAG

ALLGMKVDIYMGAEDVERQKLNVERMKLLGANVIPVNSGSRTLKDAFDEALRDWVATFE

YTHYLIGSVVGPHPYPTIVRDFQSVIGREAKAQILEAEGQLPDVIVACVGGGSNAMGIF

YPFVNDKKVKLVGVEAGGKGLESGKHSASLNAGQVGVSHGMLSYFLQDEEGQIKPSHSI

APGLDHPGVGPEHAYLKKIQRAEYVAVTDEEALKAFHELSRTEGIIPALESAHAVAYAM

KLAKEMSRDEIIIVNLSGRGDKDLDIVLKASGNV
```

-continued

SEQ. ID NO: 3
ATGATGTCTGAAAATTTGCAATTGTCAGCTGAAGAAATGAGACAATTGGGTTACCAAGC
AGTTGATTTGATCATCGATCACATGAACCATTTGAAGTCTAAGCCAGTTTCAGAAACAA
TCGATTCTGATATCTTGAGAAATAAGTTGACTGAATCTATCCCAGAAAATGGTTCAGAT
CCAAAGGAATTGTTGCATTTCTTGAACAGAAACGTTTTTAATCAAATTACACATGTTGA
TCATCCACATTTCTTGGCTTTTGTTCCAGGTCCAAATAATTACGTTGGTGTTGTTGCAG
ATTTCTTGGCTTCTGGTTTTAATGTTTTTCCAACTGCATGGATTGCTGGTGCAGGTGCT
GAACAAATCGAATTGACTACAATTAATTGGTTGAAATCTATGTTGGGTTTTCCAGATTC
AGCTGAAGGTTTATTTGTTTCTGGTGGTTCAATGGCAAATTTGACAGCTTTGACTGTTG
CAAGACAGGCTAAGTTGAACAACGATATCGAAAATGCTGTTGTTTACTTCTCTGATCAA
ACACATTTCTCAGTTGATAGAGCATTGAAGGTTTTAGGTTTTAAACATCATCAAATCTG
TAGAATCGAAACAGATGAACATTTGAGAATCTCTGTTTCAGCTTTGAAGAAACAAATTA
AAGAAGATAGAACTAAGGGTAAAAAGCCATTCTGTGTTATTGCAAATGCTGGTACTACA
AATTGTGGTGCTGTTGATTCTTTGAACGAATTAGCAGATTTGTGTAACGATGAAGATGT
TTGGTTGCATGCTGATGGTTCTTATGGTGCTCCAGCTATCTTGTCTGAAAAGGGTTCAG
CTATGTTGCAAGGTATTCATAGAGCAGATTCTTTGACTTTAGATCCACATAAGTGGTTG
TTCCAACCATACGATGTTGGTTGTGTTTTGATCAGAAACTCTCAATATTTGTCAAAGAC
TTTTAGAATGATGCCAGAATACATCAAGGATTCAGAAACTAACGTTGAAGGTGAAATTA
ATTTCGGTGAATGTGGTATCGAATTGTCAAGAAGATTCAGAGCTTTGAAGGTTTGGTTG
TCTTTTAAAGTTTTCGGTGTTGCTGCTTTTAGACAAGCAATCGATCATGGTATCATGTT
AGCAGAACAAGTTGAAGCATTTTTGGGTAAAGCAAAAGATTGGGAAGTTGTTACACCAG
CTCAATTGGGTATCGTTACTTTTAGATACATTCCATCTGAATTGGCATCAACAGATACT
ATTAATGAAATTAATAAGAAATTGGTTAAGGAAATCACACATAGAGGTTTCGCTATGTT
ATCTACTACAGAATTGAAGGAAAAGGTTGTTATTAGATTGTGTTCAATTAATCCAAGAA
CTACAACTGAAGAAATGTTGCAAATCATGATGAAGATTAAAGCATTGGCTGAAGAAGTT
TCTATTTCATACCCATGTGTTGCTGAATAA

SEQ. ID NO: 4
MMSENLQLSAEEMRQLGYQAVDLIIDHMNHLKSKPVSETIDSDILRNKLTESIPENGSD
PKELLHFLNRNVENQITHVDHPHFLAFVPGPNNYVGVVADFLASGENVFPTAWIAGAGA
EQIELTTINWLKSMLGFPDSAEGLFVSGGSMANLTALTVARQAKLNNDIENAVVYESDQ
THFSVDRALKVLGFKHHQICRIETDEHLRISVSALKKQIKEDRTKGKKPFCVIANAGTT
NCGAVDSLNELADLCNDEDVWLHADGSYGAPAILSEKGSAMLQGIHRADSLTLDPHKWL
FQPYDVGCVLIRNSQYLSKTERMMPEYIKDSETNVEGEINFGECGIELSRRFRALKVWL
SFKVFGVAAFRQAIDHGIMLAEQVEAFLGKAKDWEVVTPAQLGIVTFRYIPSELASTDT
INEINKKLVKEITHRGFAMLSTTELKEKVVIRLCSINPRTTTEEMLQIMMKIKALAEEV
SISYPCVAE

SEQ. ID NO: 5
ATGAAGTTCTGGAGAAAGTACACACAACAAGAAATGGATGAAAAGATTACTGAATCTTT
GGAAAAGACTTTGAACTACGATAACACTAAGACAATCGGTATTCCAGGTACTAAGTTGG
ATGATACAGTTTTCTATGATGATCATTCTTTCGTTAAGCATTCACCATACTTGAGAACT
TTTATTCAAAACCCAAACCATATCGGTTGTCATACTTATGATAAGGCTGATATCTTGTT
CGGTGGTACATTCGATATCGAAAGAGAATTAATCCAATTGTTAGCAATCGATGTTTTGA

-continued

ACGGTAACGATGAAGAATTTGATGGTTACGTTACTCAAGGTGGTACAGAAGCTAACATC

CAAGCAATGTGGGTTTACAGAAACTACTTCAAGAAAGAAAGAAAGGCTAAGCATGAAGA

AATCGCTATCATCACTTCAGCAGATACACATTACTCTGCATACAAAGGTTCAGATTTGT

TGAACATCGATATTATTAAGGTTCCAGTTGATTTTTATTCAAGAAAAATTCAAGAAAAT

ACATTGGATTCAATTGTTAAAGAAGCTAAAGAAATTGGTAAAAAGTACTTCATCGTTAT

CTCTAACATGGGTACTACAATGTTTGGTTCAGTTGATGATCCAGATTTGTACGCTAACA

TCTTCGATAAGTACAATTTGGAATACAAAATTCATGTTGATGGTGCATTTGGTGGTTTT

ATATATCCAATTGATAATAAGGAATGTAAAACTGATTTCTCTAATAAGAACGTTTCTTC

AATCACATTAGATGGTCATAAGATGTTGCAAGCTCCATACGGTACTGGTATCTTCGTTT

CAAGAAAGAATTTGATCCATAACACTTTGACAAAGGAAGCAACTTACATCGAAAATTTG

GATGTTACATTGTCTGGTTCAAGATCTGGTTCAAATGCTGTTGCAATTTGGATGGTTTT

AGCTTCTTATGGTCCATACGGTTGGATGGAAAAGATTAATAAGTTGAGAAATAGAACTA

AATGGTTGTGTAAGCAATTGAACGATATGAGAATTAAATATTACAAAGAAGATTCAATG

AATATTGTTACAATTGAAGAACAATATGTTAATAAGGAAATCGCTGAAAAGTACTTTTT

AGTTCCAGAAGTTCATAACCCAACTAACAACTGGTACAAGATCGTTGTTATGGAACATG

TTGAATTGGATATCTTGAACTCTTTGGTTTACGATTTGAGAAAGTTTAATAAGGAACAT

TTGAAGGCAATGTAA

SEQ. ID NO: 6

MKFWRKYTQQEMDEKITESLEKTLNYDNTKTIGIPGTKLDDTVFYDDHSFVKHSPYLRT

FIQNPNHIGCHTYDKADILFGGTFDIERELIQLLAIDVLNGNDEEFDGYVTQGGTEANI

QAMWVYRNYFKKERKAKHEEIAIITSADTHYSAYKGSDLLNIDIIKVPVDFYSRKIQEN

TLDSIVKEAKEIGKKYFIVISNMGTTMFGSVDDPDLYANIFDKYNLEYKIHVDGAFGGF

IYPIDNKECKTDFSNKNVSSITLDGHKMLQAPYGTGIFVSRKNLIHNTLTKEATYIENL

DVTLSGSRSGSNAVAIWMVLASYGPYGWMEKINKLRNRTKWLCKQLNDMRIKYYKEDSM

NIVTIEEQYVNKEIAEKYFLVPEVHNPTNNWYKIVVMEHVELDILNSLVYDLRKENKEH

LKAM

SEQ. ID NO: 7

ATGCAGGTGATACCCGCGTGCAACTCGGCAGCAATAAGATCACTATGTCCTACTCCCGA

GTCTTTTAGAAACATGGGATGGCTCTCTGTCAGCGATGCGGTCTACAGCGAGTTCATAG

GAGAGTTGGCTACCCGCGCTTCCAATCGAAATTACTCCAACGAGTTCGGCCTCATGCAA

CCTATCCAGGAATTCAAGGCTTTCATTGAAAGCGACCCGGTGGTGCACCAAGAATTTAT

TGACATGTTCGAGGGCATTCAGGACTCTCCAAGGAATTATCAGGAACTATGTAATATGT

TCAACGATATCTTTCGCAAAGCTCCCGTCTACGGAGACCTTGGCCCTCCCGTTTATATG

ATTATGGCCAAATTAATGAACACCCGAGCGGGCTTCTCTGCATTCACGAGACAAAGGTT

GAACCTTCACTTCAAAAAACTTTTCGATACCTGGGGATTGTTCCTGTCTTCGAAAGATT

CTCGAAATGTTCTTGTGGCCGACCAGTTCGACGACAGACATTGCGGCTGGTTGAACGAG

CGGGCCTTGTCTGCTATGGTTAAACATTACAATGGACGCGCATTTGATGAAGTCTTCCT

CTGCGATAAAAATGCCCCATACTACGGCTTCAACTCTTACGACGACTTCTTTAATCGCA

GATTTCGAAACCGAGATATCGACCGACCTGTAGTCGGTGGAGTTAACAACACCACCCTC

ATTTCTGCTGCTTGCGAATCACTTTCCTACAACGTCTCTTATGACGTCCAGTCTCTCGA

CACTTTAGTTTTCAAAGGAGAGACTTATTCGCTTAAGCATTTGCTGAATAATGACCCTT

```
TCACCCCACAATTCGAGCATGGGAGTATTCTACAAGGATTCTTGAACGTCACCGCTTAC

CACCGATGGCACGCACCCGTCAATGGGACAATCGTCAAAATCATCAACGTTCCAGGTAC

CTACTTTGCGCAAGCCCCGAGCACGATTGGCGACCCTATCCCGGATAACGATTACGACC

CACCTCCTTACCTTAAGTCTCTTGTCTACTTCTCTAATATTGCCGCAAGGCAAATTATG

TTTATTGAAGCCGACAACAAGGAAATTGGCCTCATTTTCCTTGTGTTCATCGGCATGAC

CGAAATCTCGACATGTGAAGCCACGGTGTCCGAAGGTCAACACGTCAATCGTGGCGATG

ACTTGGGAATGTTCCATTTCGGTGGTTCTTCGTTCGCGCTTGGTCTGAGGAAGGATTGC

AGGGCAGAGATCGTTGAAAAGTTCACCGAACCCGGAACAGTGATCAGAATCAACGAAGT

CGTCGCTGCTCTAAAGGCTTAG
```

SEQ. ID NO: 8
```
MQVIPACNSAAIRSLCPTPESFRNMGWLSVSDAVYSEFIGELATRASNRNYSNEFGLMQ

PIQEFKAFIESDPVVHQEFIDMFEGIQDSPRNYQELCNMENDIFRKAPVYGDLGPPVYM

IMAKLMNTRAGESAFTRQRLNLHFKKLFDTWGLFLSSKDSRNVLVADQFDDRHCGWLNE

RALSAMVKHYNGRAFDEVELCDKNAPYYGENSYDDFFNRRERNRDIDRPVVGGVNNTTL

ISAACESLSYNVSYDVQSLDTLVFKGETYSLKHLLNNDPFTPQFEHGSILQGELNVTAY

HRWHAPVNGTIVKIINVPGTYFAQAPSTIGDPIPDNDYDPPPYLKSLVYFSNIAARQIM

FIEADNKEIGLIFLVFIGMTEISTCEATVSEGQHVNRGDDLGMFHFGGSSFALGLRKDC

RAEIVEKFTEPGTVIRINEVVAALKA
```

SEQ. ID NO: 9
```
ATGAACACCTTCAGAACAGCCACTGCCAGAGACATACCTGATGTAGCAGCAACTCTTAC

GGAAGCCTTCGCAACTGATCCACCCACGCAGTGGGTGTTCCCCGACGGTACTGCCGCCG

TCAGCAGGTTCTTTACACATGTTGCAGATAGGGTTCACACGGCCGGTGGTATTGTTGAG

CTACTACCAGACAGAGCCGCCATGATTGCATTGCCACCACACGTGAGGCTGCCAGGAGA

AGCTGCCGACGGAAGGCAGGCGGAAATTCAGAGAAGGCTGGCAGACAGGCACCCGCTGA

CACCTCACTACTACCTGCTGTTTTACGGAGTTAGAACGGCACACCAGGGTTCGGGATTG

GGCGGAAGAATGCTGGCCAGATTAACTAGCAGAGCTGATAGGGACAGGGTGGGTACATA

TACTGAGGCATCCACCTGGCGTGGCGCTAGACTGATGCTGAGACATGGATTCCATGCTA

CAAGGCCACTAAGATTGCCAGATGGACCCAGCATGTTTCCACTTTGGAGAGATCCAATC

CATGATCATTCTGAT
```

SEQ. ID NO: 10
```
MNTFRTATARDIPDVAATLTEAFATDPPTQWVFPDGTAAVSRFFTHVADRVHTAGGIVE

LLPDRAAMIALPPHVRLPGEAADGRQAEIQRRLADRHPLTPHYYLLFYGVRTAHQGSGL

GGRMLARLTSRADRDRVGTYTEASTWRGARLMLRHGFHATRPLRLPDGPSMFPLWRDPI

HDHSD
```

SEQ. ID NO: 11
```
ATGGGATCCATGGAAGAAGCAAAAATGGCGACCCTGGGCGGTGCGTCCTATGCGATGAT

TGTGAAAACGATGATGCGCTCTCTGGAAGCAAACCTGATTCCGGATTTTGTGCTGCGTC

GCCTGACGCGTATCCTGCTGGCTAGTCGCCTGAAACTGGGTTATAAGCAGACCGCTGAA

CTGCAACTGGCGGATCTGATGTCATTCGTTGCGTCGCTGAAAACGATGCCGATTGCCCT

GTGCACCGAAGAAGCAAAGGGTCAGCATTACGAACTGCCGACCAGCTTTTTCAAACTGG

TCCTGGGCAAACATCTGAAGTATAGCTCTGCCTACTTTTCTGAACACACCCGTACGCTG

GATGAAGCGGAAGAAGCCATGCTGGCACTGTATTGCGAACGCGCCAAAATTGAAGATGG

TCAGAAGATTCTGGACATCGGCTGTGGTTGGGGCAGTTTTTCCCTGTATGTGGCAGAAC
```

-continued

```
GTTACCCGAAATGCGAAATTACGGGCCTGTGTAACAGTTCCACCCAAAAAGCCTTCATC

GAACAGCAATGCAGCGAACGTCGCCTGTGTAATGTTACCATTTATGCAGATGACATCAG

CACCTTTGATACGGAATCTACCTACGACCGCATTATCAGCATCGAAATGTTCGAACACA

TGAAGAACTACAGTACGCTGCTGAAGAAAATTAGCAAGTGGATGAATCAGGAATGCCTG

CTGTTTGTCCATTATTTCTGTCACAAAACCTTTGCGTACCACTTCGAAGATGTGGACGA

AGATGACTGGATGGCTCGTTATTTCTTTACCGGCGGCACCATGCCGGCGTCATCGCTGC

TGCTGTACTTTCAGGATGACGTCTCAGTGGTTGATCATTGGCTGATTAACGGTAAACAC

TATGCTCAAACCTCGGAAGAATGGCTGAAGCGTATGGACCACAATCTGAGCTCTATTCT

GCCGATCTTTAACGAAACGTATGGCGAAAATGCGGCCAAAAAGTGGCTGGCATACTGGC

GCACCTTTTTCATCGCAGTTGCTGAACTGTTCAAATACAACGATGGCGAAGAATGGATG

GTGTCCCACTTCCTGTTCAAAAAGAAATAA
```

SEQ. ID NO: 12
```
MGSMEEAKMATLGGASYAMIVKTMMRSLEANLIPDFVLRRLTRILLASRLKLGYKQTAE

LQLADLMSFVASLKTMPIALCTEEAKGQHYELPTSFFKLVLGKHLKYSSAYFSEHTRTL

DEAEEAMLALYCERAKIEDGQKILDIGCGWGSFSLYVAERYPKCEITGLCNSSTQKAFI

EQQCSERRLCNVTIYADDISTEDTESTYDRIISIEMFEHMKNYSTLLKKISKWMNQECL

LFVHYFCHKTFAYHFEDVDEDDWMARYFFTGGTMPASSLLLYFQDDVSVVDHWLINGKH

YAQTSEEWLKRMDHNLSSILPIFNETYGENAAKKWLAYWRTFFIAVAELFKYNDGEEWM

VSHFLEKKK
```

SEQ. ID NO: 13
```
ATGCATATCAGAAATCCTTACCGTACACCAATTGACTATCAAGCACTTTCAGAGGCCTT

CCCTCCCCTCAAGCCATTTGTGTCTGTCAATGCAGATGGTACCAGTTCTGTTGACCTCA

CTATCCCAGAAGCCCAGAGGGCGTTCACGGCCGCTCTTCTTCATCGTGACTTCGGGCTC

ACCATGACCATACCAGAAGACCGTCTGTGCCCAACAGTCCCCAATAGGTTGAACTACGT

TCTGTGGATTGAAGATATTTTCAACTACACGAACAAAACCCTCGGCCTGTCGGATGACC

GTCCTATTAAAGGCGTTGATATTGGTACAGGAGCCTCCGCAATTTATCCTATGCTTGCC

TGTGCTCGGTTCAAGGCATGGTCTATGGTTGGAACAGAGGTCGAGAGGAAGTGCATTGA

CACGGCCCGCCTCAATGTCGTCGCGAACAATCTCCAAGACCGTCTCTCGATATTAGAGA

CATCCATTGATGGTCCTATTCTCGTCCCCATTTTCGAGGCGACTGAAGAATACGAATAC

GAGTTTACTATGTGTAACCCTCCATTCTACGACGGTGCTGCCGATATGCAGACTTCGGA

TGCTGCCAAAGGATTTGGATTTGGCGTGGGCGCTCCCCATTCTGGAACAGTCATCGAAA

TGTCGACTGAGGGAGGTGAATCGGCTTTCGTCGCTCAGATGGTCCGTGAGAGCTTGAAG

CTTCGAACACGATGCAGATGGTACACGAGTAACTTGGGAAAGCTGAAATCCTTGAAAGA

AATAGTGGGCTGCTGAAAGAACTTGAGATAAGCAACTATGCCATTAACGAATACGTTC

AGGGGTCCACACGTCGTTATGCCGTTGCGTGGTCTTTCACTGATATTCAACTGCCTGAG

GAGCTTTCTCGTCCCTCTAACCCCGAGCTCAGCTCTCTTTTCTAG
```

SEQ. ID NO: 14
```
MHIRNPYRTPIDYQALSEAFPPLKPFVSVNADGTSSVDLTIPEAQRAFTAALLHRDFGL

TMTIPEDRLCPTVPNRLNYVLWIEDIFNYTNKTLGLSDDRPIKGVDIGTGASAIYPMLA

CARFKAWSMVGTEVERKCIDTARLNVVANNLQDRLSILETSIDGPILVPIFEATEEYEY
```

-continued

EFTMCNPPFYDGAADMQTSDAAKGFGFGVGAPHSGTVIEMSTEGGESAFVAQMVRESLK
LRTRCRWYTSNLGKLKSLKEIVGLLKELEISNYAINEYVQGSTRRYAVAWSFTDIQLPE
ELSRPSNPELSSLF

SEQ. ID NO: 15
ATGTCCATCGGAGCCGAGATCGATTCGCTGGTTCCTGCTCCACCGGGCCTCAACGGCAC
CGCTGCGGGCTATCCAGCCAAGACGCAGAAGGAGTTAAGCAACGGAGACTTTGACGCGC
ACGATGGTCTTTCTCTTGCACAACTGACACCGTACGATGTCTTGACGGCTGCACTTCCG
CTGCCGGCTCCGGCTTCGAGCACAGGGTTCTGGTGGCGGGAGACGGGCCCTGTTATGAG
CAAGCTTTTGGCCAAGGCGAACTACCCTCTTTACACTCATTACAAGTACCTTATGTTAT
ACCATACCCATATTCTCCCATTGTTGGGACCTCGACCGCCGCTGAGAACTCGACGCAC
CCGTCGCCGAGTAACGCGCCGTGGAGGTCCTTCCTGACAGACGACTTCACTCCGCTCGA
GCCGAGCTGGAACGTGAACGGGAACTCGGAAGCACAGAGCACAATCCGTCTTGGTATTG
AACCTATAGGCTTTGAAGCCGGGGCTGCAGCGGACCCATTCAACCAAGCTGCCGTGACG
CAGTTCATGCACTCATACGAGGCAACCGAAGTCGGTGCCACGCTGACGCTGTTCGAGCA
CTTCCGCAACGACATGTTTGTTGGCCCAGAAACGTACGCTGCGTTAAGAGCGAAGATAC
CAGAAGGCGAGCATACCACACAGAGTTTCCTGGCGTTCGACCTGGACGCGGGTCGTGTC
ACCACAAAGGCGTACTTTTTCCCGATTCTCATGTCGTTGAAAACTGGACAGAGCACAAC
AAAGGTGGTCTCTGATTCCATTCTGCATCTAGCGCTGAAGAGTGAGGTGTGGGGTGTGC
AGACCATCGCCGCGATGTCGGTCATGGAGGCGTGGATAGGTAGCTACGGTGGCGCGGCA
AAGACGGAGATGATCAGCGTCGATTGCGTGAACGAGGCAGACTCTCGGATCAAGATATA
CGTGCGGATGCCACATACATCCTTGCGGAAGGTAAAAGAGGCGTACTGCTTAGGTGGGC
GGTTGACAGACGAGAACACAAAGGAGGGCCTGAAGCTGCTGGACGAGCTGTGGAGGACG
GTCTTCGGCATCGACGACGAGGACGCGGAGCTGCCACAGAATAGCCATCGCACCGCAGG
CACAATATTCAATTTCGAGCTGAGGCCAGGGAAATGGTTCCCCGAGCCCAAGGTATACC
TGCCCGTCCGACACTACTGTGAAAGTGATATGCAGATTGCTAGTCGGCTACAAACGTTC
TTTGGAAGGCTCGGATGGCACAACATGGAGAAAGATTATTGCAAGCATCTGGAAGATTT
GTTTCCCCATCATCCACTGTCCTCGTCAACGGGCACACACACCTTTCTCTCATTTTCGT
ATAAGAAGCAGAAGGGGGTCTATATGACCATGTATTATAATCTCCGGGTGTACAGCACC
TAA

SEQ. ID NO: 16
MSIGAEIDSLVPAPPGLNGTAAGYPAKTQKELSNGDFDAHDGLSLAQLTPYDVLTAALP
LPAPASSTGEWWRETGPVMSKLLAKANYPLYTHYKYLMLYHTHILPLLGPRPPLENSTH
PSPSNAPWRSELTDDFTPLEPSWNVGNSEAQSTIRLGIEPIGFEAGAAADPENQAAVT
QFMHSYEATEVGATLTLFEHERNDMFVGPETYAALRAKIPEGEHTTQSFLAFDLDAGRV
TTKAYFFPILMSLKTGQSTTKVVSDSILHLALKSEVWGVQTIAAMSVMEAWIGSYGGAA
KTEMISVDCVNEADSRIKIYVRMPHTSLRKVKEAYCLGGRLTDENTKEGLKLLDELWRT
VFGIDDEDAELPQNSHRTAGTIFNFELRPGKWFPEPKVYLPVRHYCESDMQIASRLQTF
FGRLGWHNMEKDYCKHLEDLFPHHPLSSTGTHTFLSFSYKKQKGVYMTMYYNLRVYST

SEQ. ID NO: 17
ATGGGAGGTCCGATGAGCGGTTTCCATTCGGGGGAGGCGCTGCTCGGTGACCTCGCCAC
CGGTCAGCTGACCAGGCTGTGCGAGGTGGCGGGGCTGACCGAGGCCGACACGGCGGCCT
ACACGGGGGTGCTGATCGAAAGTCTGGGGACGTCGGCCGGACGGCCGTTGTCCCTGCCA

-continued

CCCCCGTCGCGGACCTTTCTCTCCGACGACCACACCCCCGTGGAGTTCTCCCTGGCCTT
CCTGCCGGGACGCGCACCGCACCTGCGGGTCCTGGTGGAACCGGGCTGCTCCAGCGGCG
ACGACCTGGCGGAAAACGGCCGGGCCGGTCTGCGGGCGGTCCACACCATGGCGGACCGC
TGGGGATTCTCCACCGAGCAACTCGACCGGCTGGAGGACCTGTTCTTCCCCTCCTCCCC
CGAGGGCCCGCTGGCCCTGTGGTGCGCCCTGGAGCTCCGCTCCGGTGGGGTGCCGGGGG
TGAAGGTCTACCTCAACCCCGCGGCGAATGGCGCCGACCGGGCCGCCGAGACGGTACGC
GAGGCGCTGGCCAGGCTGGGCCACCTGCAGGCGTTCGACGCGCTGCCCCGGGCGGACGG
CTTCCCGTTCCTCGCCCTGGACCTCGGCGACTGGGACGCCCCGCGGGTGAAGATCTACC
TCAAACACCTCGGCATGTCCGCCGCCGACGCGGGCTCCCTCCCCCGGATGTCGCCCGCA
CCCAGCCGGGAGCAGCTGGAGGAGTTCTTCCGCACCGCCGGTGACCTCCCGGCCCCGGG
AGACCCGGGGCCCACCGAGGACACCGGCCGGCTCGCCGGGCGCCCCGCCCTCACCTGCC
ACTCCTTCACGGAGACGGCGACCGGGCGGCCCAGCGGCTACACCCTCCACGTGCCGGTC
CGCGACTACGTCCGGCACGACGGCGAGGCACGGGACCGGGCGGTGGCCGTGCTGCGCGA
ACATGACATGGACAGTGCGGCACTGGACCGGGCGCTGGCCGCCGTGAGCCCCCGCCCGC
TGAGTGACGGGGTGGGCCTGATCGCCTATCTGGCACTGGTCCACCAGCGCGGCCGGCCG
ACACGGGTGACCGTCTACGTCTCCTCCGAGGCGTACGAGGTGCGGCCGCCCCGCGAGAC
GGTCCCCACCCGCGACCGGGCGCGGGCACGGCTGTGA

SEQ. ID NO: 18
MGGPMSGFHSGEALLGDLATGQLTRLCEVAGLTEADTAAYTGVLIESLGTSAGRPLSLP
PPSRTFLSDDHTPVEFSLAFLPGRAPHLRVLVEPGCSSGDDLAENGRAGLRAVHTMADR
WGESTEQLDRLEDLFFPSSPEGPLALWCALELRSGGVPGVKVYLNPAANGADRAAETVR
EALARLGHLQAFDALPRADGEPFLALDLGDWDAPRVKIYLKHLGMSAADAGSLPRMSPA
PSREQLEEFFRTAGDLPAPGDPGPTEDTGRLAGRPALTCHSFTETATGRPSGYTLHVPV
RDYVRHDGEARDRAVAVLREHDMDSAALDRALAAVSPRPLSDGVGLIAYLALVHQRGRP
TRVTVYVSSEAYEVRPPRETVPTRDRARARL

SEQ. ID NO: 19
ATGAGGGCCGCGTCGACGGGCGCGGACCCGCAGGACGCATCCACGCTCGGCTCTTTCAC
CGGCGGCCAGTTGCGAAGACTCGGCTCGGTCGCCGGTCTGTCCCGCGCCGACGTCGAGA
CCTACGCACAGGTCCTGACCGACGCATTGGGCCCGGTGGCCCAGCGGCCGCTGAGCCTG
GCGCCGCCCACCCGCACCTTCCTGTCGGACGACCACACCCCCGTGGAGTTCTCCCTCTC
CTTCCGGCCCGGGGCGGCGCCCGCCATGCGGGTCCTCGTGGAACCGGGCTGCGGTGCGA
CCAGCCTGGCCGACAACGGCCGTGCCGGTCTTGAGGCGGTCCGCACGATGGCGCGGCGC
TGGCACTTCACCACCGACGCCCTCGACGAACTCCTGGACCTGTTCCTGCCGCCCGCTCC
GCAGGGCCCCCTCGCCCTGTGGTGCGCCCTGGAACTCAGGCCCGGGGGTGTACCGGGCG
TCAAGGTCTATCTGAACCCTGCGGTGGGCGGGAGGAACGTTCCGCCGCGACGGTGCGC
GAGGCCCTGCGCCGGCTCGGGCACCACCAGGCCTTCGACAGCCTCCCCAGGGCAGTGG
ATACCCGTTCCTCGCCCTGGACCTCGGGAACTGGACGGAGCCCCGGGCGAAGGTCTACC
TGCGCCACGACAACCTCACGGCCGGTCGGCCGCACGGCTGTCCCGGACGGACTCGGGC
CTCGTGCCGACCGCGGTCGAGGGTTTCTTCCGCACCGCCGCGGGTCCCGGCTCCGACGC
GGGTGGGCTCGACGGGCGGCCTGCTCAGTCCTGCCACTCCTTCACCGACCCCGGCGCGG
AGCGGCCGAGCGGCTTCACCCTGTACATCCCGGTTCGTGACTACGTCCGGCATGACGGG

-continued

```
GAGGCCCTGGCGCGGGCGTCCACCGTGCTGCACCACCACGGCATGGACGCCTCCGTGCT

CCACCGCGCCCTGGCCGCCCTCACCGAGCGGCGGCCCGAGGACGGGGTGGGCCTGATCG

CCTACCTGGCCCTCGCCGGCCAACGGGACCAGCCGCCGCGGGTGACGGCCTACCTCTCC

TCGGAGGCCTACACGGTCCGGCCGCCGGTCGTGGAGACCGTCCGCCAACCGCTGTCGGT

CGGCTGA
```

SEQ. ID NO: 20
```
MRAASTGADPQDASTLGSFTGGQLRRLGSVAGLSRADVETYAQVLTDALGPVAQRPLSL

APPTRTFLSDDHTPVEFSLSFRPGAAPAMRVLVEPGCGATSLADNGRAGLEAVRTMARR

WHFTTDALDELLDLFLPPAPQGPLALWCALELRPGGVPGVKVYLNPAVGGEERSAATVR

EALRRLGHHQAFDSLPQGSYPFLALDLGNWTEPRAKVYLRHDNLTAGRAARLSRTDSG

LVPTAVEGFFRTAAGPGSDAGGLDGRPAQSCHSFTDPGAERPSGFTLYIPVRDYVRHDG

EALARASTVLHHHGMDASVLHRALAALTERRPEDGVGLIAYLALAGQRDQPPRVTAYLS

SEAYTVRPPVVETVRQPLSVG
```

SEQ. ID NO: 21
```
ATGAAGGCAGCCAATGCCTCCAGTGCGGAGGCCTATCGAGTTCTTAGTCGCGCCTTTAG

ATTCGATAATGAAGATCAGAAGCTGTGGTGGCACAGCACTGCCCCGATGTTTGCAAAAA

TGCTGGAAACTGCCAACTACACCACACCTTGTCAGTATCAATACCTCATCACCTATAAG

GAGTGCGTAATTCCCAGTCTCGGATGCTATCCGACCAACAGCGCCCCCCGCTGGTTGAG

CATCCTCACTCGATACGGCACTCCGTTCGAATTGAGCCTAAATTGCTCTAATTCAATAG

TGAGATACACATTCGAGCCGATCAATCAACATACCGGAACAGATAAAGACCCATTCAAT

ACGCACGCCATCTGGGAGAGCCTGCAGCACCTGCTTCCACTGGAGAAGAGCATTGATCT

GGAGTGGTTCCGCCACTTCAAGCACGATCTCACCCTCAACAGTGAAGAATCTGCTTTTC

TGGCTCATAATGATCGCCTCGTGGGCGGCACTATCAGGACGCAGAACAAGCTCGCGCTC

GATCTGAAGGATGGCCGCTTTGCACTTAAGACGTACATATACCCGGCTCTCAAAGCTGT

CGTCACCGGCAAGACAATTCATGAGTTGGTCTTTGGCTCAGTCCGCCGGCTGGCAGTGA

GGGAGCCCCGAATCTTGCCCCCACTCAACATGCTGGAGGAATACATCCGATCACGCGGT

TCCAAGAGCACTGCCAGTCCCCGCCTAGTGTCCTGTGATCTGACCAGTCCTGCCAAGTC

GAGAATCAAGATCTACCTGCTGGAGCAGATGGTTTCACTAGAAGCCATGGAGGACCTGT

GGACTCTGGGCGGACGGCGCCGAGACGCTTCCACTTTAGAGGGGCTCTCTCTGGTGCGT

GAGCTTTGGGATCTGATCCAACTGTCGCCGGGATTGAAGTCCTATCCGGCGCCGTATCT

GCCTCTCGGGGTTATCCCAGACGAGAGGCTGCCGCTTATGGCCAATTTCACCCTGCACC

AGAATGACCCGGTCCCAGAGCCGCAAGTATATTTCACAACCTTCGGCATGAACGACATG

GCGGTGGCGGATGCCCTGACGACGTTCTTCGAGCGCCGGGGTTGGAGTGAAATGGCCCG

CACCTACGAAACTACTTTGAAGTCGTACTACCCCCATGCGGATCATGACAAACTTAACT

ACCTCCACGCCTACATATCCTTCTCCTACAGGGACCGTACCCCTTATCTGAGTGTCTAT

CTTCAATCCTTCGAGACAGGGGACTGGGCAGTTGCAAACTTATCCGAATCAAAGGTCAA

GTGTCAGGATGCGGCCTGTCAACCCACAGCTTTACCTCCAGATCTGTCAAAGACAGGGG

TATATTATTCCGGTCTCCACTGA
```

SEQ. ID NO: 22
```
MKAANASSAEAYRVLSRAFREDNEDQKLWWHSTAPMFAKMLETANYTTPCQYQYLITYK

ECVIPSLGCYPTNSAPRWLSILTRYGTPFELSLNCSNSIVRYTFEPINQHTGTDKDPFN

THAIWESLQHLLPLEKSIDLEWFRHFKHDLTLNSEESAFLAHNDRLVGGTIRTQNKLAL
```

-continued

DLKDGRFALKTYIYPALKAVVTGKTIHELVEGSVRRLAVREPRILPPLNMLEEYIRSRG

SKSTASPRLVSCDLTSPAKSRIKIYLLEQMVSLEAMEDLWTLGGRRRDASTLEGLSLVR

ELWDLIQLSPGLKSYPAPYLPLGVIPDERLPLMANFTLHQNDPVPEPQVYFTTFGMNDM

AVADALTTFFERRGWSEMARTYETTLKSYYPHADHDKLNYLHAYISFSYRDRTPYLSVY

LQSFETGDWAVANLSESKVKCQDAACQPTALPPDLSKTGVYYSGLH

SEQ. ID NO: 23

ATGATCGCTGTACTATTCTCCTTCGTCATTGCAGGATGCATATACTACATCGTTTCTCG

TAGAGTGAGGCGGTCGCGCTTGCCACCAGGGCCGCCTGGCATTCCTATTCCCTTCATTG

GGAACATGTTTGATATGCCTGAAGAATCTCCATGGTTAACATTTCTACAATGGGGACGG

GATTACAGTCTGTCTTGCCGCGTTGACTTCTAATATATGAACAGCTAATATATTGTCAG

ACACCGATATTCTCTACGTGGATGCTGGAGGGACAGAAATGGTTATTCTTAACACGTTG

GAGACCATTACCGATCTATTAGAAAAGCGAGGGTCCATTTATTCTGGCCGGTGAGCTGA

TGTTGAGTTTTTTGCAATTGAATTTGTGGTCACACGTTTCCAGACTTGAGAGTACAATG

GTCAACGAACTTATGGGGTGGGAGTTTGACTTAGGGTTCATCACATACGGCGACAGGTG

GCGCGAAGAAAGGCGCATGTTCGCCAAGGAGTTCAGTGAGAAGGGCATCAAGCAATTTC

GCCATGCTCAAGTGAAAGCTGCCCATCAGCTTGTCCAACAGCTTACCAAAACGCCAGAC

CGCTGGGCACAACATATTCGCCAGTAAGTACTACTTGAGGAAAATAGCGTACGCTTCGC

TGACCGGTCCGTACATCAAAGTCAGATAGCGGCAATGTCACTGGATATTGGTTATGGAA

TTGATCTTGCAGAAGACGACCCTTGGCTGGAAGCGACCCATTTGGCTAATGAAGGCCTC

GCCATAGCATCAGTGCCGGGCAAATTTTGGGTCGATTCGTTCCCTTCTCGTGAGCATCC

TTCTTCTATGTAGGAAGGGAAGGAGTCTAACAAGTGTTAGTAAAATACCTTCCTGCTTG

GTTCCCAGGTGCTGTCTTCAAGCGCAAAGCGAAGGTCTGGCGAGAAGCCGCCGACCATA

TGGTTGACATGCCTTATGAAACTATGAGGAAATTAGCAGTTAGTCAAATGCGTTCTCCC

CGTATTTTTTCAATACTCTAACTTCAGCTCACAGCCTCAAGGATTGACTCGTCCGTCGT

ATGCTTCAGCTCGTCTGCAAGCCATGGATCTCAACGGTGACCTTGAGCATCAAGAACAC

GTAATCAAGAACACAGCCGCAGAGGTTAATGTCGGTAAGTCAAAAGCGTCCGTCGGCAA

TTCAAAATTCAGGCGCTAAAGTGGGTCTTCTCACCAAGGTGGAGGCGATACTGTAAGGA

TTTCTCAATCGTTAGAGTATAAGTGTTCTAATGCAGTACATACTCCACCAACCAGACTG

TCTCTGCTATGTCTGCGTTCATCTTGGCCATGGTGAAGTACCCTGAGGTCCAGCGAAAG

GTTCAAGCGGAGCTTGATGCTCTGACCAATAACGGCCAAATTCCTGACTATGACGAAGA

AGATGACTCCTTGCCATACCTCACCGCATGTATCAAGGAGCTTTTCCGGTGGAATCAAA

TCGCACCCCTCGCTATACCGCACAAATTAATGAAGGACGACGTGTACCGCGGGTATCTG

ATTCCCAAGAACACTCTAGTCTTCGCAAACACCTGGTGAGGCTGTCCATTCATTCCTAG

TACATCCGTTGCCCCACTAATAGCATCTTGATAACAGGGCAGTATTAAACGATCCAGAA

GTCTATCCAGATCCCTCTGTGTTCCGCCCAGAAAGATATCTTGGTCCTGACGGGAAGCC

TGATAACACTGTACGCGACCCACGTAAAGCGGCATTTGGCTATGGACGACGAAATTGGT

AAGTGCGCTTTCAGAACCCCCCCTTCCGTTGACTAGTGCCATGCGCGCATACAATATCG

CTATTGATCTGATATAACTTCCCTGCGGCATTTATTTTGGCATTCCTTTAGTCCCGGAA

TTCATCTAGCGCAGTCGACGGTTTGGATTGCAGGGGCAACCCTCTTATCAGCGTTCAAT

ATCGAGCGACCTGTCGATCAGAATGGGAAGCCCATTGACATACCGGCTGATTTTACTAC

AGGATTCTTCAGGTAGCTAATTTCCGTCTTTGTGTGCATAATACCCCTAACGACGCACG

-continued

TTTACCTTTTTGTAAAGACACCCAGTGCCTTTCCAGTGCAGGTTTGTTCCTCGAACAGA

GCAAGTCTCACAGTCGGTATCCGGACCCTGA

SEQ. ID NO: 24

MIAVLFSFVIAGCIYYIVSRRVRRSRLPPGPPGIPIPFIGNMEDMPEESPWLTFLQWGR

DYNTDILYVDAGGTEMVILNTLETITDLLEKRGSIYSGRLESTMVNELMGWEFDLGFIT

YGDRWREERRMFAKEFSEKGIKQFRHAQVKAAHQLVQQLTKTPDRWAQHIRHQIAAMSL

DIGYGIDLAEDDPWLEATHLANEGLAIASVPGKFWVDSFPSLKYLPAWFPGAVEKRKAK

VWREAADHMVDMPYETMRKLAPQGLTRPSYASARLQAMDLNGDLEHQEHVIKNTAAEVN

VGGGDTTVSAMSAFILAMVKYPEVQRKVQAELDALTNNGQIPDYDEEDDSLPYLTACIK

ELFRWNQIAPLAIPHKLMKDDVYRGYLIPKNTLVFANTWAVLNDPEVYPDPSVFRPERY

LGPDGKPDNTVRDPRKAAFGYGRRNCPGIHLAQSTVWIAGATLLSAFNIERPVDQNGKP

IDIPADFTTGFFRHPVPFQCRFVPRTEQVSQSVSGP

SEQ. ID NO: 25

ATGGCTTCTAGTTCTTCCGATGTCTTCGTTTTGGGTCTAGGTGTTGTTTTGGCTGCCTT

GTATATCTTCAGAGACCAATTATTCGCTGCTTCTAAGCCAAAGGTGGCTCCAGTTTCCA

CTACGAAGCCTGCCAACGGTTCCGCTAACCCAAGAGACTTCATCGCCAAGATGAAACAA

GGTAAGAAGAGAATCGTAATCTTCTACGGTTCTCAAACTGGTACCGCTGAAGAATATGC

TATTCGTTTGGCTAAGGAAGCTAAGCAAAAGTTCGGTCTAGCCTCCTTGGTTTGTGATC

CAGAAGAATACGATTTTGAAAAGTTGGACCAATTGCCAGAAGATTCTATTGCTTTCTTC

GTCGTTGCTACCTATGGTGAAGGTGAACCTACAGACAACGCTGTCCAATTGTTGCAAAA

CTTGCAAGATGAAAGCTTCGAATTCTCCTCTGGTGAGAGAAAGTTGTCAGGTTTGAAGT

ACGTTGTTTTTGGTCTGGGTAACAAGACCTACGAACATTACAACCTCATTGGGAGAACT

GTTGACGCTCAATTGGCCAAGATGGGTGCTATCAGAATCGGTGAAAGAGGTGAAGGTGA

TGATGACAAGTCCATGGAAGAAGACTACTTGGAATGGAAGGATGGTATGTGGGAAGCGT

TTGCCACTGCTATGGGTGTTGAAGAAGGTCAAGGTGGTGACTCCGCTGATTTCGTCGTT

TCCGAATTGGAATCTCACCCACCAGAAAAGGTTTACCAAGGTGAATTTTCTGCTAGAGC

TTTAACCAAAACCAAGGGTATTCACGACGCTAAGAATCCTTTTGCTGCTCCAATTGCGG

TTGCTAGAGAATTGTTCCAATCTGTTGTCGATAGAAACTGTGTCCACGTCGAATTCAAC

ATTGAAGGCTCTGGTATCACCTATCAACACGGTGACCACGTTGGTTTGTGGCCATTGAA

TCCAGATGTTGAAGTCGAACGGTTGTTGTGTGTTTTAGGTTTAGCTGAAAAGAGAGATG

CTGTCATCTCCATTGAATCCTTAGACCCGGCTTTGGCTAAGGTTCCATTCCCAGTCCCA

ACTACTTACGGTGCTGTGTTGAGACACTACATTGACATCTCTGCTGTCGCCGGTAGACA

AATCTTGGGTACTTTGTCCAAATTCGCTCCAACCCCAGAAGCTGAAGCTTTCTTGAGAA

ACTTGAACACTAACAAGGAAGAATACCACAACGTCGTCGCTAACGGTTGTTTGAAATTG

GGTGAAATTTTGCAAATCGCTACCGGTAACGACATTACTGTCCCACCAACTACTGCCAA

CACCACCAAATGGCCAATTCCATTCGACATCATTGTTTCTGCCATCCCAAGATTGCAAC

CAAGATACTACTCTATCTCTTCTTCCCCAAAAATTCATCCAAACACCATCCACGCTACC

GTTGTTGTGCTCAAATACGAAAACGTTCCAACCGAACCAATCCCAAGAAAGTGGGTTTA

CGGTGTCGGTAGTAACTTCTTGTTGAATTTAAAGTACGCTGTTAACAAGGAACCAGTTC

CATACATCACTCAAAATGGCGAACAAAGAGTCGGTGTCCCGGAATACTTGATTGCTGGT

CCACGTGGTTCTTACAAGACTGAATCTTTCTACAAGGCTCCAATCCATGTTAGACGTTC

TACTTTCCGTTTGCCAACCAACCCAAAGTCTCCAGTCATCATGATTGGTCCAGGTACTG

-continued

```
GTGTCGCCCCATTCAGAGGCTTCGTTCAAGAAAGAGTTGCCTTGGCCAGAAGATCCATC

GAAAAGAACGGTCCTGACTCTTTGGCTGACTGGGGTCGTATTTCCTTGTTCTACGGTTG

TAGAAGATCCGACGAAGACTTCTTGTACAAGGACGAATGGCCACAATACGAAGCTGAGT

TGAAGGGTAAGTTCAAGTTGCACTGTGCTTTCTCCAGACAAAACTACAAGCCAGACGGT

TCTAAGATTTACGTCCAAGATTTGATCTGGGAAGACAGAGAACACATTGCCGATGCCAT

CTTAAACGGTAAGGGTTACGTCTACATCTGCGGTGAAGCTAAGTCCATGTCTAAACAAG

TTGAAGAAGTTCTAGCCAAGATCTTGGGCGAAGCCAAAGGTGGTTCCGGTCCAGTTGAA

GGTGTTGCTGAAGTCAAGTTACTGAAGGAACGGTCCAGATTGATGTTGGATGTCTGGTC

TAGG
```

SEQ. ID NO: 26
```
MASSSSDVFVLGLGVVLAALYIFRDQLFAASKPKVAPVSTTKPANGSANPRDFIAKMKQ

GKKRIVIFYGSQTGTAEEYAIRLAKEAKQKFGLASLVCDPEEYDFEKLDQLPEDSIAFF

VVATYGEGEPTDNAVQLLQNLQDESFEFSSGERKLSGLKYVVFGLGNKTYEHYNLIGRT

VDAQLAKMGAIRIGERGEGDDDKSMEEDYLEWKDGMWEAFATAMGVEEGQGGDSADFVV

SELESHPPEKVYQGEFSARALTKTKGIHDAKNPFAAPIAVARELFQSVVDRNCVHVEFN

IEGSGITYQHGDHVGLWPLNPDVEVERLLCVLGLAEKRDAVISIESLDPALAKVPFPVP

TTYGAVLRHYIDISAVAGRQILGTLSKFAPTPEAEAFLRNLNTNKEEYHNVVANGCLKL

GEILQIATGNDITVPPTTANTTKWPIPEDIIVSAIPRLQPRYYSISSSPKIHPNTIHAT

VVVLKYENVPTEPIPRKWVYGVGSNFLLNLKYAVNKEPVPYITQNGEQRVGVPEYLIAG

PRGSYKTESFYKAPIHVRRSTFRLPTNPKSPVIMIGPGTGVAPERGFVQERVALARRSI

EKNGPDSLADWGRISLFYGCRRSDEDFLYKDEWPQYEAELKGKFKLHCAFSRQNYKPDG

SKIYVQDLIWEDREHIADAILNGKGYVYICGEAKSMSKQVEEVLAKILGEAKGGSGPVE

GVAEVKLLKERSRLMLDVWS
```

SEQ. ID NO: 27
```
GTATCCGGCTGTTCCTTCATAGCCCTTTCAATGAACGTTGCAGCCCTTTGAAGATTGGC

CATTTTGTCAGGACTCGAGCCTGACAGTTGGACCAACGCAACTTTAATTTTTTGTGAAA

GAATCTTCGAAGCACTCATACTGGCGATCTTCACGCCCTCCTGCTATTACAAAAGCTGT

GTTTTTACAAGAATCAAATTAAGTTAGCAAGATATTATACAACATTATTGATAATTTCA

ATATCGTGTTCGTACCTGATGACGTATCTGTGCATTGATAAGGCCCGCATGGTTTCAGA

AAGCAGAGCGGAACGATTCCAAATTAGTGGCCTTGTGCTTTGCATGTCAATTGTGTTAC

CTTCAGCTCGTGGATTTGTTTTATCAATACACAGTCTACAGTCAAGAATTTTTTTTATC

AAATTTTGCGTTCGAGCGTATAAAATAGCCGCTGTAGCTACTTAAGTTCCTGTTCAGCG

ATAGTTTTTTTCCATCACACGTACTATGGCAATTAAGTCCTCAGCGAGCTCGCATGGAA

TGCGTGCGATGAGCGACCTCATGCTATACCTGAGAAAGCAACCTGACCTACAGGAAAGA

GTTACTCAAGAATAAGAATTTTCGTTTTAAAACCTAAGAGTCACTTTAAAATTTGTATA

CACTTATTTTTTTATAACTTATTTAATAATAAAAATCATAAATCATAAGAAATTCGCT

TATTTAGAAGTGTCAACAACGTATCTACCAACGGAATGCGTGCGATTCAGGCGTAGTCT

GGAACGTCGTATGGGTATGGACCAGAGACGGATTGAGAAACTTGTTCGGTTCTTGGGAC

GAATCTACATTGGAATGGAACTGGGTGCCTGAAGAAACCAGTGGTGAAATCAGCTGGGA

TGTCAATTGGCTTACCGTTTTGGTCAACTGGTCTTTCAATGTTGAAAGCAGACAACAAA

GTAGCACCGGCAATCCAAACAGTAGATTGAGCTAGGTGAATACCTGGGCAGTTTCTTCT
```

-continued

```
ACCGTAACCGAAAGCAGCCTTTCTTGGGTCTCTAACAGTGTTGTCTGGTTTACCATCAG

GACCCAAGTATCTTTCTGGACGGAAAACGGATGGATCTGGATAGACTTCTGGGTCATTC

AAAACTGCCCAGGTGTTAGCAAAAACCAATGTGTTCTTTGGAATCAAATAACCTCTGTA

AACATCATCCTTCATCAATTTATGAGGGATGGCTAATGGAGCAATTTGGTTCCATCTGA

ATAATTCCTTGATACAAGCGGTCAAATATGGGAGTGAGTCGTCTTCCTCATCGTAGTCA

GGGATTTGACCGTTGTTGGTCAAAGCATCCAATTCAGCTTGAACCTTTCTTTGCACTTC

TGGGTATTTAACCATGGCCAATATGAAAGCGGACATAGCAGAGACGGTAGTGTCGCCAC

CACCAACGTTAACTTCAGCAGCAGTGTTCTTGATAACATGTTCTTGGTGTTCTAAATCA

CCGTTCAAGTCCATAGCTTGTAATCTAGCAGAAGCGTAAGATGGTCTGGTTAGACCTTG

TGGAGCCAACTTTCTCATAGTTTCGTATGGCATGTCAACCATGTGGTCAGCGGCTTCTC

TCCAGACCTTGGCCTTACGCTTGAAGACGGCACCTGGGAACCAAGCTGGCAAGTACTTC

AAAGATGGGAAGGAGTCAACCCAGAACTTACCTGGAACACTAGCAATGGCCAAACCTTC

GTTGGCTAAGTGGGTAGCTTCTAACCATGGGTCATCTTCGGCTAGATCGATACCGTAAC

CAATGTCCAAAGACATAGCAGCGATTTGATGTCTGATGTGTTGAGCCCACCGGTCCGGA

GTCTTGGTCAATTGTTGAACCAATTGGTGAGCAGCCTTGACTTGAGCGTGTCTGAATTG

CTTGATACCCTTTTCAGAGAATTCCTTAGCAAACATTCTTCTTTCTTCTCTCCAACGGT

CACCGTAAGTGATAAAACCCAGATCAAATTCCCAACCCATCAATTCATTGACCATAGTG

GATTCCAATCTACCGGAGTAGATGGAACCACGTTTTTCCAAGAGATCCGTGATAGTTTC

CAAGGTGTTTAAAATGACCATTTCGGTACCACCAGCATCTACGTACAAGATATCAGTGT

TGTAGTCACGACCCCATTGCAAGAAAGTCAACCATGGAGATTCTTCTGGCATGTCGAAC

ATGTTACCAATAAATGGGATTGGAATTCCTGGTGGACCAGGTGGCAATCTGGATCTACG

AACTCTTCTGGAGACGATGTAGTAAATACAACCAGCAATGACGAAAGAGAACAAGACAG

CAATCATTGTTTTATATTTGTTGTAAAAAGTAGATAATTACTTCCTTGATGATCTGTAA

AAAAGAGAAAAGAAAGCATCTAAGAACTTGAAAAACTACGAATTAGAAAAGACCAAAT

ATGTATTTCTTGCATTGACCAATTTATGCAAGTTTATATATATGTAAATGTAAGTTTCA

CGAGGTTCTACTAAACTAAACCACCCCCTTGGTTAGAAGAAAAGAGTGTGTGAGAACAG

GCTGTTGTTGTCACACGATTCGGACAATTCTGTTTGAAAGAGAGAGAGTAACAGTACGA

TCGAACGAACTTTGCTCTGGAGATCACAGTGGGCATCATAGCATGTGGTACTAAACCCT

TTCCCGCCATTCCAGAACCTTCGATTGCTTGTTACAAAACCTGTGAGCCGTCGCTAGGA

CCTTGTTGTGTGACGAAATTGGAAGCTGCAATCAATAGGAAGACAGGAAGTCGAGCGTG

TCTGGGTTTTTTCAGTTTTGTTCTTTTTGCAAACAACAGTTTATTCCTGGCATCCACTA

AATATAATGGAGCCCGCTTTTTAAGCTGGCATCCAGAAAAAAAAAGAATCCCAGCACCA

AAATATTGTTTTCTTCACCAACCATCAGTTCATAGGTCCATTCTCTTAGCGCAACTACA

GAGAACAGGGGCACAAACAGGCAAAAAACGGGCACAACCTCAATGGAGTGATGCAACCT

GCCTGGAGTAAATGATGACACAAGGCAATTGACCCACGCATGTATCTATCTCATTTTCT

TACACCTTCTATTACCTTCTGCTCTCTCTGATTTGGAAAAAGCTGAAAAAAAAGGTTGA

AACCAGTTCCCTGAAATTATTCCCCTACTTGACTAATAAGTATATAAAGACGGTAGGTA

TTGATTGTAATTCTGTAAATCTATTTCTTAAACTTCTTAAATTCTACTTTTATAGTTAG

TCTTTTTTTAGTTTTAAAACACCAAGAACTTAGTTTCGAATAAACACACATAAACAAA

CAAAATGGCTTCTAGTTCTTCCGATGTCTTCGTTTTGGGTCTAGGTGTTGTTTTGGCTG

CCTTGTATATCTTCAGAGACCAATTATTCGCTGCTTCTAAGCCAAAGGTGGCTCCAGTT
```

```
TCCACTACGAAGCCTGCCAACGGTTCCGCTAACCCAAGAGACTTCATCGCCAAGATGAA

ACAAGGTAAGAAGAGAATCGTAATCTTCTACGGTTCTCAAACTGGTACCGCTGAAGAAT

ATGCTATTCGTTTGGCTAAGGAAGCTAAGCAAAAGTTCGGTCTAGCCTCCTTGGTTTGT

GATCCAGAAGAATACGATTTTGAAAAGTTGGACCAATTGCCAGAAGATTCTATTGCTTT

CTTCGTCGTTGCTACCTATGGTGAAGGTGAACCTACAGACAACGCTGTCCAATTGTTGC

AAAACTTGCAAGATGAAAGCTTCGAATTCTCCTCTGGTGAGAGAAAGTTGTCAGGTTTG

AAGTACGTTGTTTTTGGTCTGGGTAACAAGACCTACGAACATTACAACCTCATTGGGAG

AACTGTTGACGCTCAATTGGCCAAGATGGGTGCTATCAGAATCGGTGAAAGAGGTGAAG

GTGATGATGACAAGTCCATGGAAGAAGACTACTTGGAATGGAAGGATGGTATGTGGGAA

GCGTTTGCCACTGCTATGGGTGTTGAAGAAGGTCAAGGTGGTGACTCCGCTGATTTCGT

CGTTTCCGAATTGGAATCTCACCCACCAGAAAAGGTTTACCAAGGTGAATTTTCTGCTA

GAGCTTTAACCAAAACCAAGGGTATTCACGACGCTAAGAATCCTTTTGCTGCTCCAATT

GCGGTTGCTAGAGAATTGTTCCAATCTGTTGTCGATAGAAACTGTGTCCACGTCGAATT

CAACATTGAAGGCTCTGGTATCACCTATCAACACGGTGACCACGTTGGTTTGTGGCCAT

TGAATCCAGATGTTGAAGTCGAACGGTTGTTGTGTGTTTTAGGTTTAGCTGAAAAGAGA

GATGCTGTCATCTCCATTGAATCCTTAGACCCGGCTTTGGCTAAGGTTCCATTCCCAGT

CCCAACTACTTACGGTGCTGTGTTGAGACACTACATTGACATCTCTGCTGTCGCCGGTA

GACAAATCTTGGGTACTTTGTCCAAATTCGCTCCAACCCCAGAAGCTGAAGCTTTCTTG

AGAAACTTGAACACTAACAAGGAAGAATACCACAACGTCGTCGCTAACGGTTGTTTGAA

ATTGGGTGAAATTTTGCAAATCGCTACCGGTAACGACATTACTGTCCCACCAACTACTG

CCAACACCACCAAATGGCCAATTCCATTCGACATCATTGTTTCTGCCATCCCAAGATTG

CAACCAAGATACTACTCTATCTCTTCTTCCCCAAAAATTCATCCAAACACCATCCACGC

TACCGTTGTTGTGCTCAAATACGAAAACGTTCCAACCGAACCAATCCCAAGAAAGTGGG

TTTACGGTGTCGGTAGTAACTTCTTGTTGAATTTAAAGTACGCTGTTAACAAGGAACCA

GTTCCATACATCACTCAAAATGGCGAACAAAGAGTCGGTGTCCCGGAATACTTGATTGC

TGGTCCACGTGGTTCTTACAAGACTGAATCTTTCTACAAGGCTCCAATCCATGTTAGAC

GTTCTACTTTCCGTTTGCCAACCAACCCAAAGTCTCCAGTCATCATGATTGGTCCAGGT

ACTGGTGTCGCCCCATTCAGAGGCTTCGTTCAAGAAAGAGTTGCCTTGGCCAGAAGATC

CATCGAAAAGAACGGTCCTGACTCTTTGGCTGACTGGGGTCGTATTTCCTTGTTCTACG

GTTGTAGAAGATCCGACGAAGACTTCTTGTACAAGGACGAATGGCCACAATACGAAGCT

GAGTTGAAGGGTAAGTTCAAGTTGCACTGTGCTTTCTCCAGACAAAACTACAAGCCAGA

CGGTTCTAAGATTTACGTCCAAGATTTGATCTGGGAAGACAGAGAACACATTGCCGATG

CCATCTTAAACGGTAAGGGTTACGTCTACATCTGCGGTGAAGCTAAGTCCATGTCTAAA

CAAGTTGAAGAAGTTCTAGCCAAGATCTTGGGCGAAGCCAAAGGTGGTTCCGGTCCAGT

TGAAGGTGTTGCTGAAGTCAAGTTACTGAAGGAACGGTCCAGATTGATGTTGGATGTCT

GGTCTGAACAAAAGTTAATTTCTGAAGAAGATTTGGAATGAATCGCGTGCATTCATCCG

CTCTAACCGAAAAGGAAGGAGTTAGACAACCTGAAGTCTAGGTCCCTATTTATTTTTTT

ATAGTTATGTTAGTATTAAGAACGTTATTTATATTTCAAATTTTTCTTTTTTTCTGTA

CAGACGCGTGTACGCATGTAACATTATACTGAAAACCTTGCTTGAGAAGGTTTTGGGAC

GCTCGAAGATCGCGTCCCAATTCGCCCTATAGTGAGTCGTATTACGCGCGCTCACTGGC
```

```
                                               -continued
CGTCGTTTTACAACGTCGTGACTGGGAAAACCCTGGCGTTACCCCTGCAGGACTAGTGC

TGAGGCATTAATAGTTTACTCAATTCTTGAAGCCAATTTGTACAATTCCCCATTAGAGT

CAAATAAAGGATGCCTCACGGAGGTATGTTACCCGCGCTATTTCACATGGCTCATTGA

ATTAGAGGTGGAATTTGGTGTACCCTCCCCTCCTCATCTGATGAAGTAGTGATCCGACA

ATTCTTAAAAGTTGTAGACATTACTTTTACCACCAACTAAGTTGTATTTATATTGCTAC

CCTTATCCTTTTATATCTAACTAGCGCTCATAAGGTTGGGGCAATACTAAAACTGTGTT

CTTATTCAACTCATTAAATACGTGGCAGTACGTACCCTATTAGAAACAATAGGAAACAG

CAGAGTCGGAAGAAGCCAAATGCCAGATTTGAAGTCCAAAACCTTGTCAAGCCAATCTT

TGGGAGCGGCTATTCCTCCAGAAATTGTGTACCAAATACTTACATACCAGTTTAGGGAT

TTGTTAAGAAATGACCATCCAGGTACGGCAGAAA

SEQ. ID NO: 28
CAATCTGGCGGCTTGAGTTCTCAACATGTTTTATTTTTTACTTATATTGCTGGTAGGGT

AAAAAAATATAACTCCTAGGAATAGGTTGTCTATATGTTTTTGTCTTGCTTCTATAATT

GTAACAAACAAGGAAAGGGAAAATACTGGGTGTAAAAGCCATTGAGTCAAGTTAGGTCA

TCCCTTTTATACAAAATTTTTCAATTTTTTTTCCAAGATTCTTGTACGATTAATTATTT

TTTTTTTGCGTCCTACAGCGTGATGAAAATTTCGCCTGCTGCAAGATGAGCGGGAACGG

GCGAAATGTGCACGCGCACAACTTACGAAACGCGGATGAGTCACTGACAGCCACCGCAG

AGGTTCTGACTCCTACTGAGCTCTATTGGAGGTGGCAGAACCGGTACCGGAGGAGGCCG

CTATAACCGGTTTGAATTTATTGTCACAGTGTCACATCAGCATTAAGTCCTCAGCGAGC

TCGCATGGAATGCGTGCGATGAGCGACCTCATGCTATACCTGAGAAAGCAACCTGACCT

ACAGGAAAGAGTTACTCAAGAATAAGAATTTTCGTTTTAAAACCTAAGAGTCACTTTAA

AATTTGTATACACTTATTTTTTTATAACTTATTTAATAATAAAAATCATAAATCATAA

GAAATTCGCTTATTTAGAAGTGTCAACAACGTATCTACCAACGGAATGCGTGCGATTCA

GGTGGAGTCCAAACCCAACAAAGGATTTGGAATTGGCTTACCGGCAGTGGAGGATTCCT

TTAGCAACGTGGAAGTGATTTCACCGTTGTCGTTGTTACCTCTAGCATCGTGGAAAGCA

GCAACACCCTTCTTAACAAAGTTGATTCTTTCTTCTTCAGAACCCCATTGCATGAAGTC

AGTCCACATAACAATGTGAGCGGCGATACCAGCGGTAACCTTGGCGTAGTTGATGGAAT

GCTTGGAAGTACGGGCGTAAGATTGCAAGTAAGCTTGTCTCATGGTTGTACCAACTTGT

TCGTCTTGGAATCTGCTAATCAAGTAACAGTCACCCAAGAAGTAACCCAAATCCAATGA

AGCTGGACCGTACTTACACAATTCCCAGTCTAAGATGTAGATCTTTTGCAACTTAGATG

GGTTACCTTCTTCAAGTTGCAACAAGATGTTCCCAGACCACAAGTCAGCCATGACCAAA

GTTTCTTCGGAGTGCATAACATCGTCAACTAGATCCTTGACAACAGTTGGCAACAATGG

ATCATCGACGCCGTATTTAGCGGCGTTTGGGATAATAGTTTGGTACAATTGGTCAGAGG

TGGTTCTACCGACAATGTTACCAGAGAAGAACTTGAATTCTGGGTCGTCTCTTCTTTCT

CTACCTATGTTGTGCAATCTGGCGACGAAACCACCAATCTCGGTACCAACCAATCTAGC

AATATCGGTAGCCAAAGGTGGCTTAGCAGTAACGTAGTCTAATAAGGTCTTCATTTTAC

CGACATCTTGCATAATCAAAGCATTGTTTTCCAAGTCATAGTTGAGACCTTCTGGAACA

GAGACAATACCATCAACACCACCCAAAACTTCTCTGTTAGCCATCATCAACTTGATAGC

TTGGTATTCGTAGACAGAACGTTCAACACCGATTTTGAAATCTTCATCAGTAGACATGT

GTGGTTGAGCGTGCTTCAAAATGATAGAAGTGTGACCTTGGTATGGAGCGTTCAATTTA

ATACGCCAGGTGACGTTAACGAAACCACCGGATAATCTCTTGACACCAGAAGTGTCAAC
```

```
                                        -continued
ATCTAAAGACAAATGCTTGGTCAAATAGGTGATTAAACCGTCTTCAGTCTTCAAGTCAA

AGGCCATTGTTTTATATTTGTTGTAAAAAGTAGATAATTACTTCCTTGATGATCTGTAA

AAAAGAGAAAAGAAAGCATCTAAGAACTTGAAAAACTACGAATTAGAAAAGACCAAAT

ATGTATTTCTTGCATTGACCAATTTATGCAAGTTTATATATATGTAAATGTAAGTTTCA

CGAGGTTCTACTAAACTAAACCACCCCCTTGGTTAGAAGAAAAGAGTGTGTGAGAACAG

GCTGTTGTTGTCACACGATTCGGACAATTCTGTTTGAAAGAGAGAGAGTAACAGTACGA

TCGAACGAACTTTGCTCTGGAGATCACAGTGGGCATCATAGCATGTGGTACTAAACCCT

TTCCCGCCATTCCAGAACCTTCGATTGCTTGTTACAAAACCTGTGAGCCGTCGCTAGGA

CCTTGTTGTGTGACGAAATTGGAAGCTGCAATCAATAGGAAGACAGGAAGTCGAGCGTG

TCTGGGTTTTTTCAGTTTTGTTCTTTTTGCAAACAACAGTTTATTCCTGGCATCCACTA

AATATAATGGAGCCCGCTTTTTAAGCTGGCATCCAGAAAAAAAAAGAATCCCAGCACCA

AAATATTGTTTTCTTCACCAACCATCAGTTCATAGGTCCATTCTCTTAGCGCAACTACA

GAGAACAGGGGCACAAACAGGCAAAAAACGGGCACAACCTCAATGGAGTGATGCAACCT

GCCTGGAGTAAATGATGACACAAGGCAATTGACCCACGCATGTATCTATCTCATTTTCT

TACACCTTCTATTACCTTCTGCTCTCTCTGATTTGGAAAAAGCTGAAAAAAAAGGTTGA

AACCAGTTCCCTGAAATTATTCCCCTACTTGACTAATAAGTATATAAAGACGGTAGGTA

TTGATTGTAATTCTGTAAATCTATTTCTTAAACTTCTTAAATTCTACTTTTATAGTTAG

TCTTTTTTTTAGTTTTAAAACACCAAGAACTTAGTTTCGAATAAACACACATAAACAAA

CAAAATGCATATCAGAAACCCATATAGAACTCCAATTGACTACCAAGCTTTGTCTGAAG

CTTTCCCACCATTGAAGCCATTTGTTTCCGTTAACGCTGATGGTACCTCCTCAGTTGAC

TTGACCATTCCAGAAGCCCAAAGAGCTTTTACCGCTGCCCTTTTGCACAGAGACTTCGG

CTTGACTATGACTATCCCAGAAGATCGTTTGTGTCCAACCGTTCCAAACAGATTGAACT

ACGTTTTGTGGATTGAAGACATTTTCAACTACACCAACAAGACTTTGGGTTTATCTGAC

GACCGTCCAATCAAGGGTGTTGATATCGGTACCGGTGCTTCTGCCATTTACCCAATGTT

GGCTTGCGCCAGATTCAAGGCTTGGTCCATGGTTGGTACTGAAGTTGAAAGAAAGTGTA

TCGACACTGCTAGATTAAACGTTGTTGCTAACAACTTGCAAGATCGTCTATCCATCTTG

GAAACCTCTATTGACGGTCCAATTTTAGTCCCAATTTTCGAAGCTACCGAAGAATACGA

ATACGAATTCACCATGTGTAACCCACCTTTCTACGATGGTGCCGCTGACATGCAAACTA

GCGATGCTGCAAAGGGTTTTGGTTTCGGTGTCGGTGCTCCACACTCTGGTACAGTCATC

GAAATGTCTACTGAAGGTGGTGAATCCGCTTTCGTGGCTCAAATGGTTAGAGAATCTCT

TAAGTTGAGAACCAGATGTAGATGGTACACTTCTAACTTAGGTAAGTTGAAATCTTTGA

AGGAAATTGTCGGTTTGTTGAAGGAATTAGAAATCTCTAATTACGCCATCAACGAATAT

GTCCAAGGTTCCACTAGAAGATACGCTGTCGCTTGGAGTTTCACTGATATCCAATTGCC

AGAAGAATTGTCCAGACCATCTAATCCTGAATTGTCCTCTTTGTTCGACTACAAGGATG

ACGATGACAAATGAATCGCGTGCATTCATCCGCTCTAACCGAAAAGGAAGGAGTTAGAC

AACCTGAAGTCTAGGTCCCTATTTATTTTTTTATAGTTATGTTAGTATTAAGAACGTTA

TTTATATTTCAAATTTTTCTTTTTTTTCTGTACAGACGCGTGTACGCATGTAACATTAT

ACTGAAAACCTTGCTTGAGAAGGTTTTGGGACGCTCGAAGATCGCGTACCCAATTCGCC

CTATAGTGAGTCGTATTACGCGCGCTCACTGGCCGTCGTTTTACAACGTCGTGACTGGG

AAAACCCTGGCGTTACCCCTGCAGGACTAGTGCTGAGGCATTAATGCAACTCAGAAGTT

TGACAGCAAGCAAGTTCATCATTCGAACTAGCCTTATTGTTTTAGTTCAGTGACAGCGA
```

-continued

ACTGCCGTACTCGATGCTTTATTTCTCACGGTAGAGCGGAAGAACAGATAGGGGCAGCG

TGAGAAGAGTTAGAAAGTAAATTTTTATCACGTCTGAAGTATTCTTATTCATAGGAAAT

TTTGCAAGGTTTTTTAGCTCAATAACGGGCTAAGTTATATAAGGTGTTCACGCGATTTT

CTTGTTATGTATACCTCTTCTCTGAGGAATGGTACTACTGTCCTGATGTAGGCTCCTTA

AATTGGTGGGCAAGAATAACTTATCGATATTTTGTATATTGGTCTTGGAGTTCACCACG

TAATGCCTGTTTAAGACCATCAGTTAACTCTAGTATTATTTGGTCTTGGCTACTGGCCG

TTTGCTATTATTCAAGTCTTTTGTGCCTTCCCGTCGGGTAAGGGAGTTATTTAGGGATA

CAGAATCTAACGAAAACTAAATCTCAATGATTAACTCTATTTAATCCTTTTTTGAAAGG

CAAAAGAGGTCCCTTGTTCACTTACAACGTTCTTAGCCAAATTCGCTTATCACTTACTA

CTTCACGATATACAGAAGTAAAAACATATAAAAAGATGTCTGTTTGTTTAGCCATCACA

AAAGGTATCGCAG

SEQ. ID NO: 29
TGTTTTATATTTGTTGTAAAAAGTAGATAATTACTTCCTTGATGATCTGTAAAAAGAG

AAAAAGAAAGCATCTAAGAACTTGAAAAACTACGAATTAGAAAAGACCAAATATGTATT

TCTTGCATTGACCAATTTATGCAAGTTTATATATATGTAAATGTAAGTTTCACGAGGTT

CTACTAAACTAAACCACCCCCTTGGTTAGAAGAAAAGAGTGTGTGAGAACAGGCTGTTG

TTGTCACACGATTCGGACAATTCTGTTTGAAAGAGAGAGTAACAGTACGATCGAACG

AACTTTGCTCTGGAGATCACAGTGGGCATCATAGCATGTGGTACTAAACCCTTTCCCGC

CATTCCAGAACCTTCGATTGCTTGTTACAAAACCTGTGAGCCGTCGCTAGGACCTTGTT

GTGTGACGAAATTGGAAGCTGCAATCAATAGGAAGACAGGAAGTCGAGCGTGTCTGGGT

TTTTTCAGTTTTGTTCTTTTTGCAAACAACAGTTTATTCCTGGCATCCACTAAATATAA

TGGAGCCCGCTTTTTAAGCTGGCATCCAGAAAAAAAAAGAATCCCAGCACCAAATATT

GTTTTCTTCACCAACCATCAGTTCATAGGTCCATTCTCTTAGCGCAACTACAGAGAACA

GGGGCACAAACAGGCAAAAAACGGGCACAACCTCAATGGAGTGATGCAACCTGCCTGGA

GTAAATGATGACACAAGGCAATTGACCCACGCATGTATCTATCTCATTTTCTTACACCT

TCTATTACCTTCTGCTCTCTCTGATTTGGAAAAAGCTGAAAAAAAAGGTTGAAACCAGT

TCCCTGAAATTATTCCCCTACTTGACTAATAAGTATATAAAGACGGTAGGTATTGATTG

TAATTCTGTAAATCTATTTCTTAAACTTCTTAAATTCTACTTTTATAGTTAGTCTTTTT

TTTAGTTTTAAAACACCAAGAACTTAGTTTCGAATAAACACACATAAACAAACAAAGGA

TCCATGATGAAGTTCTGGAGAAAGTACACACAACAAGAAATGGATGAAAAGATTACTGA

ATCTTTGGAAAAGACTTTGAACTACGATAACACTAAGACAATCGGTATTCCAGGTACTA

AGTTGGATGATACAGTTTTCTATGATGATCATTCTTTCGTTAAGCATTCACCATACTTG

AGAACTTTTATTCAAAACCCAAACCATATCGGTTGTCATACTTATGATAAGGCTGATAT

CTTGTTCGGTGGTACATTCGATATCGAAAGAGAATTAATCCAATTGTTAGCAATCGATG

TTTTGAACGGTAACGATGAAGAATTTGATGGTTACGTTACTCAAGGTGGTACAGAAGCT

AACATCCAAGCAATGTGGGTTTACAGAAACTACTTCAAGAAAGAAAGAAAGGCTAAGCA

TGAAGAAATCGCTATCATCACTTCAGCAGATACACATTACTCTGCATACAAAGGTTCAG

ATTTGTTGAACATCGATATTATTAAGGTTCCAGTTGATTTTATTCAAGAAAAATTCAA

GAAAATACATTGGATTCAATTGTTAAAGAAGCTAAAGAAATTGGTAAAAAGTACTTCAT

CGTTATCTCTAACATGGGTACTACAATGTTTGGTTCAGTTGATGATCCAGATTTGTACG

CTAACATCTTCGATAAGTACAATTTGGAATACAAAATTCATGTTGATGGTGCATTTGGT

-continued

```
GGTTTTATATATCCAATTGATAATAAGGAATGTAAAACTGATTTCTCTAATAAGAACGT
TTCTTCAATCACATTAGATGGTCATAAGATGTTGCAAGCTCCATACGGTACTGGTATCT
TCGTTTCAAGAAAGAATTTGATCCATAACACTTTGACAAAGGAAGCAACTTACATCGAA
AATTTGGATGTTACATTGTCTGGTTCAAGATCTGGTTCAAATGCTGTTGCAATTTGGAT
GGTTTTAGCTTCTTATGGTCCATACGGTTGGATGGAAAAGATTAATAAGTTGAGAAATA
GAACTAAATGGTTGTGTAAGCAATTGAACGATATGAGAATTAAATATTACAAAGAAGAT
TCAATGAATATTGTTACAATTGAAGAACAATATGTTAATAAGGAAATCGCTGAAAAGTA
CTTTTTAGTTCCAGAAGTTCATAACCCAACTAACAACTGGTACAAGATCGTTGTTATGG
AACATGTTGAATTGGATATCTTGAACTCTTTGGTTTACGATTTGAGAAAGTTTAATAAG
GAACATTTGAAGGCAATGCATCATCATCATCATCATTAACCGCGGCTAGCTAAGATCCG
CTCTAACCGAAAAGGAAGGAGTTAGACAACCTGAAGTCTAGGTCCCTATTTATTTTTTT
ATAGTTATGTTAGTATTAAGAACGTTATTTATATTTCAAATTTTTCTTTTTTTCTGTA
CAGACGCGTGTACGCATGTAACATTATACTGAAAACCTTGCTTGAGAAGGTTTTGGGAC
GCTCGAAGATCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTC
TGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAAT
AGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTA
```

-continued

```
TGCGGCGACCGAGTTGCTCTTGCCCGGCGTCAATACGGGATAATACCGCGCCACATAGC

AGAACTTTAAAAGTGCTCATCATTGGAAAACGTTCTTCGGGGCGAAAACTCTCAAGGAT

CTTACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCGCA

AAAAAGGGAATAAGGGCGACACGGAAATGTTGAATACTCATACTCTTCCTTTTTCAATA

TTATTGAAGCATTTATCAGGGTTATTGTCTCATGAGCGGATACATATTTGAATGTATTT

AGAAAAATAAACAAATAGGGGTTCCGCGCACATTTCCCCGAAAAGTGCCACCTGAACGA

AGCATCTGTGCTTCATTTTGTAGAACAAAAATGCAACGCGAGAGCGCTAATTTTTCAAA

CAAAGAATCTGAGCTGCATTTTTACAGAACAGAAATGCAACGCGAAAGCGCTATTTTAC

CAACGAAGAATCTGTGCTTCATTTTTGTAAAACAAAAATGCAACGCGAGAGCGCTAATT

TTTCAAACAAAGAATCTGAGCTGCATTTTTACAGAACAGAAATGCAACGCGAGAGCGCT

ATTTTACCAACAAAGAATCTATACTTCTTTTTTGTTCTACAAAAATGCATCCCGAGAGC

GCTATTTTTCTAACAAAGCATCTTAGATTACTTTTTTTCTCCTTTGTGCGCTCTATAAT

GCAGTCTCTTGATAACTTTTTGCACTGTAGGTCCGTTAAGGTTAGAAGAAGGCTACTTT

GGTGTCTATTTTCTCTTCCATAAAAAAAGCCTGACTCCACTTCCCGCGTTTACTGATTA

CTAGCGAAGCTGCGGGTGCATTTTTTCAAGATAAAGGCATCCCCGATTATATTCTATAC

CGATGTGGATTGCGCATACTTTGTGAACAGAAAGTGATAGCGTTGATGATTCTTCATTG

GTCAGAAAATTATGAACGGTTTCTTCTATTTTGTCTCTATATACTACGTATAGGAAATG

TTTACATTTTCGTATTGTTTTCGATTCACTCTATGAATAGTTCTTACTACAATTTTTTT

GTCTAAAGAGTAATACTAGAGATAAACATAAAAAATGTAGAGGTCGAGTTTAGATGCAA

GTTCAAGGAGCGAAAGGTGGATGGGTAGGTTATATAGGGATATAGCACAGAGATATATA

GCAAAGAGATACTTTTGAGCAATGTTTGTGGAAGCGGTATTCGCAATATTTTAGTAGCT

CGTTACAGTCCGGTGCGTTTTTGGTTTTTTGAAAGTGCGTCTTCAGAGCGCTTTTGGTT

TTCAAAAGCGCTCTGAAGTTCCTATACTTTCTAGAGAATAGGAACTTCGGAATAGGAAC

TTCAAAGCGTTTCCGAAAACGAGCGCTTCCGAAAATGCAACGCGAGCTGCGCACATACA

GCTCACTGTTCACGTCGCACCTATATCTGCGTGTTGCCTGTATATATATATACATGAGA

AGAACGGCATAGTGCGTGTTTATGCTTAAATGCGTACTTATATGCGTCTATTTATGTAG

GATGAAAGGTAGTCTAGTACCTCCTGTGATATTATCCCATTCCATGCGGGGTATCGTAT

GCTTCCTTCAGCACTACCCTTTAGCTGTTCTATATGCTGCCACTCCTCAATTGGATTAG

TCTCATCCTTCAATGCTATCATTTCCTTTGATATTGGATCATACTAAGAAACCATTATT

ATCATGACATTAACCTATAAAAATAGGCGTATCACGAGGCCCTTTCGTCTCGCGCGTTT

CGGTGATGACGGTGAAAACCTCTGACACATGCAGCTCCCGGAGACGGTCACAGCTTGTC

TGTAAGCGGATGCCGGGAGCAGACAAGCCCGTCAGGGCGCGTCAGCGGGTGTTGGCGGG

TGTCGGGGCTGGCTTAACTATGCGGCATCAGAGCAGATTGTACTGAGAGTGCACCATAT

TTCACACCGCATAGATCCGTCGAGTTCAAGAGAAAAAAAAGAAAAAGCAAAAGAAAA

AAGGAAAGCGCGCCTCGTTCAGAATGACACGTATAGAATGATGCATTACCTTGTCATCT

TCAGTATCATACTGTTCGTATACATACTTACTGACATTCATAGGTATACATATATACAC

ATGTATATATATCGTATGCTGCAGCTTTAAATAATCGGTGTCACTACATAAGAACACCT

TTGGTGGAGGGAACATCGTTGGTACCATTGGGCGAGGTGGCTTCTCTTATGGCAACCGC

AAGAGCCTTGAACGCACTCTCACTACGGTGATGATCATTCTTGCCTCGCAGACAATCAA

CGTGGAGGGTAATTCTGCTAGCCTCTGCAAAGCTTTCAAGAAAATGCGGGATCATCTCG
```

-continued

```
CAAGAGAGATCTCCTACTTTCTCCCTTTGCAAACCAAGTTCGACAACTGCGTACGGCCT

GTTCGAAAGATCTACCACCGCTCTGGAAAGTGCCTCATCCAAAGGCGCAAATCCTGATC

CAAACCTTTTTACTCCACGCACGGCCCCTAGGGCCTCTTTAAAAGCTTGACCGAGAGCA

ATCCCGCAGTCTTCAGTGGTGTGATGGTCGTCTATGTGTAAGTCACCAATGCACTCAAC

GATTAGCGACCAGCCGGAATGCTTGGCCAGAGCATGTATCATATGGTCCAGAAACCCTA

TACCTGTGTGGACGTTAATCACTTGCGATTGTGTGGCCTGTTCTGCTACTGCTTCTGCC

TCTTTTTCTGGGAAGATCGAGTGCTCTATCGCTAGGGGACCACCCTTTAAAGAGATCGC

AATCTGAATCTTGGTTTCATTTGTAATACGCTTTACTAGGGCTTTCTGCTCTGTCATCT

TTGCCTTCGTTTATCTTGCCTGCTCATTTTTTAGTATATTCTTCGAAGAAATCACATTA

CTTTATATAATGTATAATTCATTATGTGATAATGCCAATCGCTAAGAAAAAAAAAGAGT

CATCCGCTAGGTGGAAAAAAAAAATGAAAATCATTACCGAGGCATAAAAAAATATAGA

GTGTACTAGAGGAGGCCAAGAGTAATAGAAAAAGAAAATTGCGGGAAGGACTGTGTTA

TGACTTCCCTGACTAATGCCGTGTTCAAACGATACCTGGCAGTGACTCCTAGCGCTCAC

CAAGCTCTTAAAACGGGAATTTATGGTGCACTCTCAGTACACGCGCCAGATCTGTTTAG

CTTGCCTCGTCCCCGCCGGGTCACCCGGCCAGCGACATGGAGGCCCAGAATACCCTCCT

TGACAGTCTTGACGTGCGCAGCTCAGGGCATGATGTGACTGTCGCCCGTACATTTAGC

CCATACATCCCCATGTATAATCATTTGCATCCATACATTTTGATGGCCGCACGGCGCGA

AGCAAAAATTACGGCTCCTCGCTGCAGACCTGCGAGCAGGGAAACGCTCCCCTCACAGA

CGCGTTGAATTGTCCCCACGCCGCGCCCCTGTAGAGAAATATAAAAGGTTAGGATTTGC

CACTGAGGTTCTTCTTTCATATACTTCCTTTTAAAATCTTGCTAGGATACAGTTCTCAC

ATCACATCCGAACATAAACAACCATGGGTAAGGAAAAGACTCACGTTTCGAGGCCGCGA

TTAAATTCCAACATGGATGCTGATTTATATGGGTATAAATGGGCTCGCGATAATGTCGG

GCAATCAGGTGCGACAATCTATCGATTGTATGGGAAGCCCGATGCGCCAGAGTTGTTTC

TGAAACATGGCAAAGGTAGCGTTGCCAATGATGTTACAGATGAGATGGTCAGACTAAAC

TGGCTGACGGAATTTATGCCTCTTCCGACCATCAAGCATTTTATCCGTACTCCTGATGA

TGCATGGTTACTCACCACTGCGATCCCCGGCAAAACAGCATTCCAGGTATTAGAAGAAT

ATCCTGATTCAGGTGAAAATATTGTTGATGCGCTGGCAGTGTTCCTGCGCCGGTTGCAT

TCGATTCCTGTTTGTAATTGTCCTTTTAACAGCGATCGCGTATTTCGTCTCGCTCAGGC

GCAATCACGAATGAATAACGGTTTGGTTGATGCGAGTGATTTTGATGACGAGCGTAATG

GCTGGCCTGTTGAACAAGTCTGGAAAGAAATGCATAAGCTTTTGCCATTCTCACCGGAT

TCAGTCGTCACTCATGGTGATTTCTCACTTGATAACCTTATTTTTGACGAGGGGAAATT

AATAGGTTGTATTGATGTTGGACGAGTCGGAATCGCAGACCGATACCAGGATCTTGCCA

TCCTATGGAACTGCCTCGGTGAGTTTTCTCCTTCATTACAGAAACGGCTTTTTCAAAAA

TATGGTATTGATAATCCTGATATGAATAAATTGCAGTTTCATTTGATGCTCGATGAGTT

TTTCTAATCAGTACTGACAATAAAAAGATTCTTGTTTTCAAGAACTTGTCATTTGTATA

GTTTTTTTATATTGTAGTTGTTCTATTTTAATCAAATGTTAGCGTGATTTATATTTTTT

TTCGCCTCGACATCATCTGCCCAGATGCGAAGTTAAGTGCGCAGAAAGTAATATCATGC

GTCAATCGTATGTGAATGCTGGTCGCTATACTGCTGTCGATTCGATACTAACGCCGCCA

TCCAGTGTCGAATTCGCCATTCAGGCTGCGCAACTGTTGGGAAGGGCGATCGGTGCGGG

CCTCTTCGCTATTACGCCAGCTGAATTGGAGCGACCTCATGCTATACCTGAGAAAGCAA
```

```
CCTGACCTACAGGAAAGAGTTACTCAAGAATAAGAATTTTCGTTTTAAAACCTAAGAGT

CACTTTAAAATTTGTATACACTTATTTTTTTTATAACTTATTTAATAATAAAAATCATA

AATCATAAGAAATTCGCTTATTTAGAAGTGTCAACAACGTATCTACCAACGATTTGACC

CTTTTCCATCTTTTCGTAAATTTCTGGCAAGGTAGACAAGCCGACAACCTTGATTGGAG

ACTTGACCAAACCTCTGGCGAAGAATTGTTAATTAAGAGCTCAGATCTTTTGCGGCCGC

SEQ. ID NO: 30
GTTTGCAAAAGAACAAAACTGAAAAAACCCAGACACGCTCGACTTCCTGTCTTCCTAT

TGATTGCAGCTTCCAATTTCGTCACACAACAAGGTCCTAGCGACGGCTCACAGGTTTTG

TAACAAGCAATCGAAGGTTCTGGAATGGCGGGAAAGGGTTTAGTACCACATGCTATGAT

GCCCACTGTGATCTCCAGAGCAAAGTTCGTTCGATCGTACTGTTACTCTCTCTCTTTCA

AACAGAATTGTCCGAATCGTGTGACAACAACAGCCTGTTCTCACACACTCTTTTCTTCT

AACCAAGGGGTGGTTTAGTTTAGTAGAACCTCGTGAAACTTACATTTACATATATATA

AACTTGCATAAATTGGTCAATGCAAGAAATACATATTTGGTCTTTTCTAATTCGTAGTT

TTTCAAGTTCTTAGATGCTTTCTTTTTCTCTTTTTTACAGATCATCAAGGAAGTAATTA

TCTACTTTTTACAACAAATATAAAACA

SEQ. ID NO: 31
ACAGTTTATTCCTGGCATCCACTAAATATAATGGAGCCCGCTTTTTAAGCTGGCATCCA

GAAAAAAAAGAATCCCAGCACCAAAATATTGTTTTCTTCACCAACCATCAGTTCATAG

GTCCATTCTCTTAGCGCAACTACAGAGAACAGGGGCACAAACAGGCAAAAAACGGGCAC

AACCTCAATGGAGTGATGCAACCTGCCTGGAGTAAATGATGACACAAGGCAATTGACCC

ACGCATGTATCTATCTCATTTTCTTACACCTTCTATTACCTTCTGCTCTCTCTGATTTG

GAAAAAGCTGAAAAAAAAGGTTGAAACCAGTTCCCTGAAATTATTCCCCTACTTGACTA

ATAAGTATATAAAGACGGTAGGTATTGATTGTAATTCTGTAAATCTATTTCTTAAACTT

CTTAAATTCTACTTTTATAGTTAGTCTTTTTTTTAGTTTTAAAACACCAAGAACTTAGT

TTCGAATAAACACACATAAACAAACAAA

SEQ. ID NO: 32
GCTGGATTGAGCTGAATGGTGCCAGGTCGAGGCTGGGAGGGAGACTAACTCGAAAGTGA

CGAAGACTCGAAAATTAAAAAAAAAGATACTGCAGAAGGCAAGATTGAGAATGGAGTAA

AGGCAGCGTGGGTCCCCTGTGGAAACCGCAGTTTTCCTGCGCCAAGTGGTACCGGTGCG

AGTGCAGCAATTAATCTCTCGATATTTTCTTAGTATCTCTTTTTATATAAGAATATATT

TTGGAATTGGTAATGCTTATCTTCAATAGTTTCTTAGTTGAATGCACACTTAAGAGCAA

ATTGGCCAAGGAGTTCTTCGTTCGCTTTAATTTATTTCCTGGTTATTGTCAATTTATTC

ATCCCATCTCCCCAGGATAGAAGAAATTAGTGTAATTTTGCTGACAATACATTTTAACG

ACGATAACAATAATAGCAATTAAATAAAATAGCACTACCACCACTCCACTGCTCGTTAG

CTATTTCTGTAAAATAAATAAAAAGATC

SEQ. ID NO: 33
ATTCGCGCTATCTCGATTTCTACCTATATAGTTAATCTCTGTACAAAAACAATCTTTCC

AACTATCCATTAATCATAGTATATTATCAGCGTCGGCGATTTTACCACGCTTGACAAAA

GCCGCGGGCGGGATTCCTGTGGGTAGTGGCACCGGCAGTTAATCTAATCAAAGGCGCTT

GAAGGAAGAGATAGATAATAGAACAAAGCAATCGCCGCTTTGGACGGCAAATATGTTTA

TCCATTGGTGCGGTGATTGGATATGATTTGTCTCCAGTAGTATAAGCAAGCGCCAGATC

TGTTTACTGTAAAATTAAGTGAGTAATCTCGCGGGATGTAATGATTTAAGGGAATCTGG

TTCAGGTTTTCACATATATTTGTATATAAGGCCATTTGTAATTTCAATAGTTTTAGGAT
```

-continued

TTTTCCTTCTCCCAAAATACTCACTTACTGTGTTACATTACAGAAAGAACAGACAAGAA
ACCGTCAATAAGAAATATAACTAAGAACA

SEQ. ID NO: 34
CAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATATTG
AAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAA
GATCAGTTGGGTGCACGAGTGGGTTACATCGAACTGGATCTCAACAGCGGTAAGATCCT
TGAGAGTTTTCGCCCCGAAGAACGTTTTCCAATGATGAGCACTTTTAAAGTTCTGCTAT
GTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCA
ACTTACTTCTGACAACGATCGGAGGACCGAAGGAGCTAACCGCTTTTTTGCACAACATG
GGGGATCATGTAACTCGCCTTGATCGTTGGGAACCGGAGCTGAATGAAGCCATACCAAA
CGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGAT
AAAGTTGCAGGACCACTTCTGCGCTCGGCCCTTCCGGCTGGCTGGTTTATTGCTGATAA
ATCTGGAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCA
AGTTTACTCATATATACTTTAGATTGATTTAAAACTTCATTTTTAATTTAAAAGGATCT
AGGTGAAGATCCTTTTTGATAATCTCATGACCAAAATCCCTTAACGTGAGTTTTCGTTC
CACTGAGCGTCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATA
CCAAATACTGTTCTTCTAGTGTAGCCGTAGTTAGGCCACCACTTCAAGAACTCTGTAGC
ACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCT
TTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCCAATACGCA
AACCGCCTCTCCCCGCGCGTTGGCCGATTCATTAATGCAGCTGGATCTTCGAGCGTCCC
AAAACCTTCTCAAGCAAGGTTTTCAGTATAATGTTACATGCGTACACGCGTCTGTACAG
AAAAAAAAGAAAAATTTGAAATATAAATAACGTTCTTAATACTAACATAACTATAAAAA
AATAAATAGGGACCTAGACTTCAGGTTGTCTAACTCCTTCCTTTTCGGTTAGAGCGGAT
CTTAGCTAGCCGCGGTACCAAGCTGGTGGATCCTTTGTTTGTTTATGTGTGTTTATTCG

-continued

```
AAACTAAGTTCTTGGTGTTTTAAAACTAAAAAAAAGACTAACTATAAAAGTAGAATTTA
AGAAGTTTAAGAAATAGATTTACAGAATTACAATCAATACCTACCGTCTTTATATACTT
ATTAGTCAAGTAGGGGAATAATTTCAGGGAACTGGTTTCAACCTTTTTTTTCAGCTTTT
TCCAAATCAGAGAGAGCAGAAGGTAATAGAAGGTGTAAGAAAATGAGATAGATACATGC
GTGGGTCAATTGCCTTGTGTCATCATTTACTCCAGGCAGGTTGCATCACTCCATTGAGG
TTGTGCCCGTTTTTGCCTGTTTGTGCCCCTGTTCTCTGTAGTTGCGCTAAGAGAATGG
ACCTATGAACTGATGGTTGGTGAAGAAAACAATATTTTGGTGCTGGGATTCTTTTTTTT
TCTGGATGCCAGCTTAAAAAGCGGGCTCCATTATATTTAGTGGATGCCAGGAATAAACT
GTTGTTTGCAAAAGAACAAAACTGAAAAAACCCAGACACGCTCGACTTCCTGTCTTCC
TATTGATTGCAGCTTCCAATTTCGTCACACAACAAGGTCCTAGCGACGGCTCACAGGTT
TTGTAACAAGCAATCGAAGGTTCTGGAATGGCGGGAAAGGGTTTAGTACCACATGCTAT
GATGCCCACTGTGATCTCCAGAGCAAAGTTCGTTCGATCGTACTGTTACTCTCTCTCTT
TCAAACAGAATTGTCCGAATCGTGTGACAACAACAGCCTGTTCTCACACACTCTTTTCT
TCTAACCAAGGGGGTGGTTTAGTTTAGTAGAACCTCGTGAAACTTACATTTACATATAT
ATAAACTTGCATAAATTGGTCAATGCAAGAAATACATATTTGGTCTTTTCTAATTCGTA
GTTTTTCAAGTTCTTAGATGCTTTCTTTTTCTCTTTTTTACAGATCATCAAGGAAGTAA
TTATCTACTTTTTACAACAAATATAAAACAGCGGCCGCAAAAGATCTGAGCTCTTAATT
AACAATTCTTCGCCAGAGGTTTGGTCAAGTCTCCAATCAAGGTTGTCGGCTTGTCTACC
TTGCCAGAAATTTACGAAAAGATGGAAAAGGGTCAAATCGTTGGTAGATACGTTGTTGA
CACTTCTAAATAAGCGAATTTCTTATGATTTATGATTTTTATTATTAAATAAGTTATAA
AAAAAATAAGTGTATACAAATTTTAAAGTGACTCTTAGGTTTTAAAACGAAAATTCTTA
TTCTTGAGTAACTCTTTCCTGTAGGTCAGGTTGCTTTCTCAGGTATAGCATGAGGTCGC
TCCAATTCAGCTGGCGTAATAGCGAAGAGGCCCGCACCGATCGCCCTTCCCAACAGTTG
CGCAGCCTGAATGGCGAATTCGACACTGGATGGCGGCGTTAGTATCGAATCGACAGCAG
TATAGCGACCAGCATTCACATACGATTGACGCATGATATTACTTTCTGCGCACTTAACT
TCGCATCTGGGCAGATGATGTCGAGGCGAAAAAAAATATAAATCACGCTAACATTTGAT
TAAAATAGAACAACTACAATATAAAAAAACTATACAAATGACAAGTTCTTGAAAACAAG
AATCTTTTTATTGTCAGTACTGATTAGAAAAACTCATCGAGCATCAAATGAAACTGCAA
TTTATTCATATCAGGATTATCAATACCATATTTTTGAAAAAGCCGTTTCTGTAATGAAG
GAGAAAACTCACCGAGGCAGTTCCATAGGATGGCAAGATCCTGGTATCGGTCTGCGATT
CCGACTCGTCCAACATCAATACAACCTATTAATTTCCCCTCGTCAAAAATAAGGTTATC
AAGTGAGAAATCACCATGAGTGACGACTGAATCCGGTGAGAATGGCAAAAGCTTATGCA
TTTCTTTCCAGACTTGTTCAACAGGCCAGCCATTACGCTCGTCATCAAAATCACTCGCA
TCAACCAAACCGTTATTCATTCGTGATTGCGCCTGAGCGAGACGAAATACGCGATCGCT
GTTAAAAGGACAATTACAAACAGGAATCGAATGCAACCGGCGCAGGAACACTGCCAGCG
CATCAACAATATTTTCACCTGAATCAGGATATTCTTCTAATACCTGGAATGCTGTTTTG
CCGGGGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTAACAT
CATTGGCAACGCTACCTTTGCCATGTTTCAGAAACAACTCTGGCGCATCGGGCTTCCCA
TACAATCGATAGATTGTCGCACCTGATTGCCCGACATTATCGCGAGCCCATTTATACCC
```

-continued

```
ATATAAATCAGCATCCATGTTGGAATTTAATCGCGGCCTCGAAACGTGAGTCTTTTCCT

TACCCATGGTTGTTTATGTTCGGATGTGATGTGAGAACTGTATCCTAGCAAGATTTTAA

AAGGAAGTATATGAAAGAAGAACCTCAGTGGCAAATCCTAACCTTTTATATTTCTCTAC

AGGGGCGCGGCGTGGGACAATTCAACGCGTCTGTGAGGGGAGCGTTTCCCTGCTCGCA

GGTCTGCAGCGAGGAGCCGTAATTTTTGCTTCGCGCCGTGCGGCCATCAAAATGTATGG

ATGCAAATGATTATACATGGGGATGTATGGGCTAAATGTACGGGCGACAGTCACATCAT

GCCCCTGAGCTGCGCACGTCAAGACTGTCAAGGAGGGTATTCTGGGCCTCCATGTCGCT

GGCCGGGTGACCCGGCGGGGACGAGGCAAGCTAAACAGATCTGGCGCGTGTACTGAGAG

TGCACCATAAATTCCCGTTTTAAGAGCTTGGTGAGCGCTAGGAGTCACTGCCAGGTATC

GTTTGAACACGGCATTAGTCAGGGAAGTCATAACACAGTCCTTTCCCGCAATTTTCTTT

TTCTATTACTCTTGGCCTCCTCTAGTACACTCTATATTTTTTATGCCTCGGTAATGAT

TTTCATTTTTTTTTTCCACCTAGCGGATGACTCTTTTTTTTTCTTAGCGATTGGCATT

ATCACATAATGAATTATACATTATATAAAGTAATGTGATTCTTCGAAGAATATACTAA

AAAATGAGCAGGCAAGATAAACGAAGGCAAAGATGACAGAGCAGAAAGCCCTAGTAAAG

CGTATTACAAATGAAACCAAGATTCAGATTGCGATCTCTTTAAAGGGTGGTCCCCTAGC

GATAGAGCACTCGATCTTCCCAGAAAAAGAGGCAGAAGCAGTAGCAGAACAGGCCACAC

AATCGCAAGTGATTAACGTCCACACAGGTATAGGGTTTCTGGACCATATGATACATGCT

CTGGCCAAGCATTCCGGCTGGTCGCTAATCGTTGAGTGCATTGGTGACTTACACATAGA

CGACCATCACACCACTGAAGACTGCGGGATTGCTCTCGGTCAAGCTTTTAAAGAGGCCC

TAGGGGCCGTGCGTGGAGTAAAAAGGTTTGGATCAGGATTTGCGCCTTTGGATGAGGCA

CTTTCCAGAGCGGTGGTAGATCTTTCGAACAGGCCGTACGCAGTTGTCGAACTTGGTTT

GCAAAGGGAGAAAGTAGGAGATCTCTCTTGCGAGATGATCCCGCATTTTCTTGAAAGCT

TTGCAGAGGCTAGCAGAATTACCCTCCACGTTGATTGTCTGCGAGGCAAGAATGATCAT

CACCGTAGTGAGAGTGCGTTCAAGGCTCTTGCGGTTGCCATAAGAGAAGCCACCTCGCC

CAATGGTACCAACGATGTTCCCTCCACCAAAGGTGTTCTTATGTAGTGACACCGATTAT

TTAAAGCTGCAGCATACGATATATATACATGTGTATATATGTATACCTATGAATGTCAG

TAAGTATGTATACGAACAGTATGATACTGAAGATGACAAGGTAATGCATCATTCTATAC

GTGTCATTCTGAACGAGGCGCGCTTTCCTTTTTTCTTTTTGCTTTTTCTTTTTTTTCT

CTTGAACTCGACGGATCTATGCGGTGTGAAATATGGTGCACTCTCAGTACAATCTGCTC

TGATGCCGCATAGTTAAGCCAGCCCCGACACCCGCCAACACCCGCTGACGCGCCCTGAC

GGGCTTGTCTGCTCCCGGCATCCGCTTACAGACAAGCTGTGACCGTCTCCGGGAGCTGC

ATGTGTCAGAGGTTTTCACCGTCATCACCGAAACGCGCGAGACGAAAGGGCCTCGTGAT

ACGCCTATTTTTATAGGTTAATGTCATGATAATAATGGTTTCTTAGTATGATCCAATAT

CAAAGGAAATGATAGCATTGAAGGATGAGACTAATCCAATTGAGGAGTGGCAGCATATA

GAACAGCTAAAGGGTAGTGCTGAAGGAAGCATACGATACCCCGCATGGAATGGGATAAT

ATCACAGGAGGTACTAGACTACCTTTCATCCTACATAAATAGACGCATATAAGTACGCA

TTTAAGCATAAACACGCACTATGCCGTTCTTCTCATGTATATATATATACAGGCAACAC

GCAGATATAGGTGCGACGTGAACAGTGAGCTGTATGTGCGCAGCTCGCGTTGCATTTTC

GGAAGCGCTCGTTTTCGGAAACGCTTTGAAGTTCCTATTCCGAAGTTCCTATTCTCTAG

AAAGTATAGGAACTTCAGAGCGCTTTTGAAAACCAAAAGCGCTCTGAAGACGCACTTTC

AAAAAACCAAAAACGCACCGGACTGTAACGAGCTACTAAAATATTGCGAATACCGCTTC
```

-continued

```
CACAAACATTGCTCAAAAGTATCTCTTTGCTATATATCTCTGTGCTATATCCCTATATA

ACCTACCCATCCACCTTTCGCTCCTTGAACTTGCATCTAAACTCGACCTCTACATTTTT

TATGTTTATCTCTAGTATTACTCTTTAGACAAAAAAATTGTAGTAAGAACTATTCATAG

AGTGAATCGAAAACAATACGAAAATGTAAACATTTCCTATACGTAGTATATAGAGACAA

AATAGAAGAAACCGTTCATAATTTTCTGACCAATGAAGAATCATCAACGCTATCACTTT

CTGTTCACAAAGTATGCGCAATCCACATCGGTATAGAATATAATCGGGGATGCCTTTAT

CTTGAAAAAATGCACCCGCAGCTTCGCTAGTAATCAGTAAACGCGGGAAGTGGAGTCAG

GCTTTTTTTATGGAAGAGAAAATAGACACCAAAGTAGCCTTCTTCTAACCTTAACGGAC

CTACAGTGCAAAAAGTTATCAAGAGACTGCATTATAGAGCGCACAAAGGAGAAAAAAAG

TAATCTAAGATGCTTTGTTAGAAAAATAGCGCTCTCGGGATGCATTTTTGTAGAACAAA

AAAGAAGTATAGATTCTTTGTTGGTAAAATAGCGCTCTCGCGTTGCATTTCTGTTCTGT

AAAAATGCAGCTCAGATTCTTTGTTTGAAAAATTAGCGCTCTCGCGTTGCATTTTTGTT

TTACAAAAATGAAGCACAGATTCTTCGTTGGTAAAATAGCGCTTTCGCGTTGCATTTCT

GTTCTGTAAAAATGCAGCTCAGATTCTTTGTTTGAAAAATTAGCGCTCTCGCGTTGCAT

TTTTGTTCTACAAAATGAAGCACAGATGCTTCGTT
```

SEQ. ID NO: 35

```
GCTAACAGCGCGATTTGCTGGTGACCCAATGCGACCAGATGCTCCACGCCCAGTCGCGT

ACCGTCTTCATGGGAGAAAATAATACTGTTGATGGGTGTCTGGTCAGAGACATCAAGAA

ATAACGCCGGAACATTAGTGCAGGCAGCTTCCACAGCAATGGCATCCTGGTCATCCAGC

GGATAGTTAATGATCAGCCCACTGACGCGTTGCGCGAGAAGATTGTGCACCGCCGCTTT

ACAGGCTTCGACGCCGCTTCGTTCTACCATCGACACCACCACGCTGGCACCCAGTTGAT

CGGCGCGAGATTTAATCGCCGCGACAATTTGCGACGGCGCGTGCAGGGCCAGACTGGAG

GTGGCAACGCCAATCAGCAACGACTGTTTGCCCGCCAGTTGTTGTGCCACGCGGTTGGG

AATGTAATTCAGCTCCGCCATCGCCGCTTCCACTTTTTCCCGCGTTTTCGCAGAAACGT

GGCTGGCCTGGTTCACCACGCGGGAAACGGTCTGATAAGAGACACCGGCATACTCTGCG

ACATCGTATAACGTTACTGGTTTCACATTCACCACCCTGAATTGACTCTCTTCCGGGCG

CTATCATGCCATACCGCGAAAGGTTTTGCGCCATTCGATGGTGTCCGGGATCTCGACGC

TCTCCCTTATGCGACTCCTGCATTAGGAAGCAGCCCAGTAGTAGGTTGAGGCCGTTGAG

CACCGCCGCCGCAAGGAATGGTGCATGCAAGGAGATGGCGCCCAACAGTCCCCCGGCCA

CGGGGCCTGCCACCATACCCACGCCGAAACAAGCGCTCATGAGCCCGAAGTGGCGAGCC

CGATCTTCCCCATCGGTGATGTCGGCGATATAGGCGCCAGCAACCGCACCTGTGGCGCC

GGTGATGCCGGCCACGATGCGTCCGGCGTAGCCTAGGATCGAGATCGATCTCGATCCCG

CGAAATTAATACGACTCACTATAGGGGAATTGTGAGCGGATAACAATTCCCCTCTAGAA

ATAATTTTGTTTAACTTTAAGAAGGAGATATACATATGGCAGATCTCAATTGGATATCG

GCCGGCCACGCGATCGCTGACGTCGGTACCCTCGAGTCTGGTAAAGAAACCGCTGCTGC

GAAATTTGAACGCCAGCACATGGACTCGTCTACTAGTCGCAGCTTAATTAACCTAAACT

GCTGCCACCGCTGAGCAATAACTAGCATAACCCCTTGGGGCCTCTAAACGGGTCTTGAG

GGGTTTTTTGCTAGCGAAAGGAGGAGTCGACACTGCTTCCGGTAGTCAATAAACCGGTA

AACCAGCAATAGACATAAGCGGCTATTTAACGACCCTGCCCTGAACCGACGACCGGGTC

ATCGTGGCCGGATCTTGCGGCCCCTCGGCTTGAACGAATTGTTAGACATTATTTGCCGA

CTACCTTGGTGATCTCGCCTTTCACGTAGTGGACAAATTCTTCCAACTGATCTGCGCGC
```

-continued

```
GAGGCCAAGCGATCTTCTTCTTGTCCAAGATAAGCCTGTCTAGCTTCAAGTATGACGGG
CTGATACTGGGCCGGCAGGCGCTCCATTGCCCAGTCGGCAGCGACATCCTTCGGCGCGA
TTTTGCCGGTTACTGCGCTGTACCAAATGCGGGACAACGTAAGCACTACATTTCGCTCA
TCGCCAGCCCAGTCGGGCGGCGAGTTCCATAGCGTTAAGGTTTCATTTAGCGCCTCAAA
TAGATCCTGTTCAGGAACCGGATCAAAGAGTTCCTCCGCCGCTGGACCTACCAAGGCAA
CGCTATGTTCTCTTGCTTTTGTCAGCAAGATAGCCAGATCAATGTCGATCGTGGCTGGC
TCGAAGATACCTGCAAGAATGTCATTGCGCTGCCATTCTCCAAATTGCAGTTCGCGCTT
AGCTGGATAACGCCACGGAATGATGTCGTCGTGCACAACAATGGTGACTTCTACAGCGC
GGAGAATCTCGCTCTCTCCAGGGGAAGCCGAAGTTTCCAAAAGGTCGTTGATCAAAGCT
CGCCGCGTTGTTTCATCAAGCCTTACGGTCACCGTAACCAGCAAATCAATATCACTGTG
TGGCTTCAGGCCGCCATCCACTGCGGAGCCGTACAAATGTACGGCCAGCAACGTCGGTT
CGAGATGGCGCTCGATGACGCCAACTACCTCTGATAGTTGAGTCGATACTTCGGCGATC
ACCGCTTCCCTCATACTCTTCCTTTTTCAATATTATTGAAGCATTTATCAGGGTTATTG
TCTCATGAGCGGATACATATTTGAATGTATTTAGAAAAATAAACAAATAGCCAGCTCAC
TCGGTCGCTACGCTCCGGGCGTGAGACTGCGGCGGGCGCTGCGGACACATACAAAGTTA
CCCACAGATTCCGTGGATAAGCAGGGGACTAACATGTGAGGCAAAACAGCAGGGCCGCG
CCGGTGGCGTTTTTCCATAGGCTCCGCCCTCCTGCCAGAGTTCACATAAACAGACGCTT
TTCCGGTGCATCTGTGGGAGCCGTGAGGCTCAACCATGAATCTGACAGTACGGGCGAAA
CCCGACAGGACTTAAAGATCCCCACCGTTTCCGGCGGGTCGCTCCCTCTTGCGCTCTCC
TGTTCCGACCCTGCCGTTTACCGGATACCTGTTCCGCCTTTCTCCCTTACGGGAAGTGT
GGCGCTTTCTCATAGCTCACACACTGGTATCTCGGCTCGGTGTAGGTCGTTCGCTCCAA
GCTGGGCTGTAAGCAAGAACTCCCCGTTCAGCCCGACTGCTGCGCCTTATCCGGTAACT
GTTCACTTGAGTCCAACCCGGAAAAGCACGGTAAAACGCCACTGGCAGCAGCCATTGGT
AACTGGGAGTTCGCAGAGGATTTGTTTAGCTAAACACGCGGTTGCTCTTGAAGTGTGCG
CCAAAGTCCGGCTACACTGGAAGGACAGATTTGGTTGCTGTGCTCTGCGAAAGCCAGTT
ACCACGGTTAAGCAGTTCCCCAACTGACTTAACCTTCGATCAAACCACCTCCCCAGGTG
GTTTTTTCGTTTACAGGGCAAAAGATTACGCGCAGAAAAAAAGGATCTCAAGAAGATCC
TTTGATCTTTTCTACTGAACCGCTCTAGATTTCAGTGCAATTTATCTCTTCAAATGTAG
CACCTGAAGTCAGCCCCATACGATATAAGTTGTAATTCTCATGTTAGTCATGCCCCGCG
CCCACCGGAAGGAGCTGACTGGGTTGAAGGCTCTCAAGGGCATCGGTCGAGATCCCGGT
GCCTAATGAGTGAGCTAACTTACATTAATTGCGTTGCGCTCACTGCCCGCTTTCCAGTC
GGGAAACCTGTCGTGCCAGCTGCATTAATGAATCGGCCAACGCGCGGGGAGAGGCGGTT
TGCGTATTGGGCGCCAGGGTGGTTTTTCTTTTCACCAGTGAGACGGGCAACAGCTGATT
GCCCTTCACCGCCTGGCCCTGAGAGAGTTGCAGCAAGCGGTCCACGCTGGTTTGCCCCA
GCAGGCGAAAATCCTGTTTGATGGTGGTTAACGGCGGATATAACATGAGCTGTCTTCG
GTATCGTCGTATCCCACTACCGAGATGTCCGCACCAACGCGCAGCCCGGACTCGGTAAT
GGCGCGCATTGCGCCCAGCGCCATCTGATCGTTGGCAACCAGCATCGCAGTGGGAACGA
TGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAG
ACGCAGACGCGCCGAGACAGAACTTAATGGGCCC
```

-continued
SEQ. ID NO: 36

ATCCGGATATAGTTCCTCCTTTCAGCAAAAAACCCCTCAAGACCCGTTTAGAGGCCCCA

AGGGGTTATGCTAGTTATTGCTCAGCGGTGGCAGCAGCCAACTCAGCTTCCTTTCGGGC

TTTGTTAGCAGCCGGATCTCAGTGGTGGTGGTGGTGCTCGAGTGCGGCCGCAAGCT

TGTCGACGGAGCTCGAATTCGGATCCGCGACCCATTTGCTGTCCACCAGTCATGCTAGC

CATATGGCTGCCGCGCGGCACCAGGCCGCTGCTGTGATGATGATGATGGCTGCTGC

CCATGGTATATCTCCTTCTTAAAGTTAAACAAAATTATTTCTAGAGGGGAATTGTTATC

CGCTCACAATTCCCCTATAGTGAGTCGTATTAATTTCGCGGGATCGAGATCTCGATCCT

CTACGCCGGACGCATCGTGGCCGGCATCACCGGCGCCACAGGTGCGGTTGCTGGCGCCT

ATATCGCCGACATCACCGATGGGGAAGATCGGGCTCGCCACTTCGGGCTCATGAGCGCT

TGTTTCGGCGTGGGTATGGTGGCAGGCCCCGTGGCCGGGGGACTGTTGGGCGCCATCTC

CTTGCATGCACCATTCCTTGCGGCGGCGGTGCTCAACGGCCTCAACCTACTACTGGGCT

GCTTCCTAATGCAGGAGTCGCATAAGGGAGAGCGTCGAGATCCCGGACACCATCGAATG

GCGCAAAACCTTTCGCGGTATGGCATGATAGCGCCCGGAAGAGAGTCAATTCAGGGTGG

TGAATGTGAAACCAGTAACGTTATACGATGTCGCAGAGTATGCCGGTGTCTCTTATCAG

ACCGTTTCCCGCGTGGTGAACCAGGCCAGCCACGTTTCTGCGAAAACGCGGGAAAAAGT

GGAAGCGGCGATGGCGGAGCTGAATTACATTCCCAACCGCGTGGCACAACAACTGGCGG

GCAAACAGTCGTTGCTGATTGGCGTTGCCACCTCCAGTCTGGCCCTGCACGCGCCGTCG

CAAATTGTCGCGGCGATTAAATCTCGCGCCGATCAACTGGGTGCCAGCGTGGTGGTGTC

GATGGTAGAACGAAGCGGCGTCGAAGCCTGTAAAGCGGCGGTGCACAATCTTCTCGCGC

AACGCGTCAGTGGGCTGATCATTAACTATCCGCTGGATGACCAGGATGCCATTGCTGTG

GAAGCTGCCTGCACTAATGTTCCGGCGTTATTTCTTGATGTCTCTGACCAGACACCCAT

CAACAGTATTATTTTCTCCCATGAAGACGGTACGCGACTGGGCGTGGAGCATCTGGTCG

CATTGGGTCACCAGCAAATCGCGCTGTTAGCGGGCCCATTAAGTTCTGTCTCGGCGCGT

CTGCGTCTGGCTGGCTGGCATAAATATCTCACTCGCAATCAAATTCAGCCGATAGCGGA

ACGGGAAGGCGACTGGAGTGCCATGTCCGGTTTTCAACAAACCATGCAAATGCTGAATG

AGGGCATCGTTCCCACTGCGATGCTGGTTGCCAACGATCAGATGGCGCTGGGCGCAATG

CGCGCCATTACCGAGTCCGGGCTGCGCGTTGGTGCGGATATCTCGGTAGTGGGATACGA

CGATACCGAAGACAGCTCATGTTATATCCCGCCGTTAACCACCATCAAACAGGATTTTC

GCCTGCTGGGGCAAACCAGCGTGGACCGCTTGCTGCAACTCTCTCAGGGCCAGGCGGTG

AAGGGCAATCAGCTGTTGCCCGTCTCACTGGTGAAAAGAAAAACCACCCTGGCGCCCAA

TACGCAAACCGCCTCTCCCCGCGCGTTGGCCGATTCATTAATGCAGCTGGCACGACAGG

TTTCCCGACTGGAAAGCGGGCAGTGAGCGCAACGCAATTAATGTAAGTTAGCTCACTCA

TTAGGCACCGGGATCTCGACCGATGCCCTTGAGAGCCTTCAACCCAGTCAGCTCCTTCC

GGTGGGCGCGGGGCATGACTATCGTCGCCGCACTTATGACTGTCTTCTTTATCATGCAA

CTCGTAGGACAGGTGCCGGCAGCGCTCTGGGTCATTTTCGGCGAGGACCGCTTTCGCTG

GAGCGCGACGATGATCGGCCTGTCGCTTGCGGTATTCGGAATCTTGCACGCCCTCGCTC

AAGCCTTCGTCACTGGTCCCGCCACCAAACGTTTCGGCGAGAAGCAGGCCATTATCGCC

GGCATGGCGGCCCCACGGGTGCGCATGATCGTGCTCCTGTCGTTGAGGACCCGGCTAGG

CTGGCGGGGTTGCCTTACTGGTTAGCAGAATGAATCACCGATACGCGAGCGAACGTGAA

GCGACTGCTGCTGCAAAACGTCTGCGACCTGAGCAACAACATGAATGGTCTTCGGTTTC

-continued

```
CGTGTTTCGTAAAGTCTGGAAACGCGGAAGTCAGCGCCCTGCACCATTATGTTCCGGAT

CTGCATCGCAGGATGCTGCTGGCTACCCTGTGGAACACCTACATCTGTATTAACGAAGC

GCTGGCATTGACCCTGAGTGATTTTTCTCTGGTCCCGCCGCATCCATACCGCCAGTTGT

TTACCCTCACAACGTTCCAGTAACCGGGCATGTTCATCATCAGTAACCCGTATCGTGAG

CATCCTCTCTCGTTTCATCGGTATCATTACCCCCATGAACAGAAATCCCCCTTACACGG

AGGCATCAGTGACCAAACAGGAAAAAACCGCCCTTAACATGGCCCGCTTTATCAGAAGC

CAGACATTAACGCTTCTGGAGAAACTCAACGAGCTGGACGCGGATGAACAGGCAGACAT

CTGTGAATCGCTTCACGACCACGCTGATGAGCTTTACCGCAGCTGCCTCGCGCGTTTCG

GTGATGACGGTGAAAACCTCTGACACATGCAGCTCCCGGAGACGGTCACAGCTTGTCTG

TAAGCGGATGCCGGGAGCAGACAAGCCCGTCAGGGCGCGTCAGCGGGTGTTGGCGGGTG

TCGGGCGCAGCCATGACCCAGTCACGTAGCGATAGCGGAGTGTATACTGGCTTAACTA

TGCGGCATCAGAGCAGATTGTACTGAGAGTGCACCATATATGCGGTGTGAAATACCGCA

CAGATGCGTAAGGAGAAAATACCGCATCAGGCGCTCTTCCGCTTCCTCGCTCACTGACT

CGCTGCGCTCGGTCGTTCGGCTGCGGCGAGCGGTATCAGCTCACTCAAAGGCGGTAATA

CGGTTATCCACAGAATCAGGGGATAACGCAGGAAAGAACATGTGAGCAAAAGGCCAGCA

AAAGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGACTA

TAAAGATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTAGCA

GAGCGAGGTATGTAGGCGGTGCTACAGAGTTCTTGAAGTGGTGGCCTAACTACGGCTAC

ACTAGAAGGACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTTTTCT

ACGGGGTCTGACGCTCAGTGGAACGAAAACTCACGTTAAGGGATTTTGGTCATGAACAA

TAAAACTGTCTGCTTACATAAACAGTAATACAAGGGGTGTTATGAGCCATATTCAACGG

GAAACGTCTTGCTCTAGGCCGCGATTAAATTCCAACATGGATGCTGATTTATATGGGTA

TAAATGGGCTCGCGATAATGTCGGGCAATCAGGTGCGACAATCTATCGATTGTATGGGA

AGCCCGATGCGCCAGAGTTGTTTCTGAAACATGGCAAAGGTAGCGTTGCCAATGATGTT

ACAGATGAGATGGTCAGACTAAACTGGCTGACGGAATTTATGCCTCTTCCGACCATCAA

GCATTTTATCCGTACTCCTGATGATGCATGGTTACTCACCACTGCGATCCCCGGGAAAA

CAGCATTCCAGGTATTAGAAGAATATCCTGATTCAGGTGAAAATATTGTTGATGCGCTG

GCAGTGTTCCTGCGCCGGTTGCATTCGATTCCTGTTTGTAATTGTCCTTTTAACAGCGA

TCGCGTATTTCGTCTCGCTCAGGCGCAATCACGAATGAATAACGGTTTGGTTGATGCGA

GTGATTTTGATGACGAGCGTAATGGCTGGCCTGTTGAACAAGTCTGGAAAGAAATGCAT

AAACTTTTGCCATTCTCACCGGATTCAGTCGTCACTCATGGTGATTTCTCACTTGATAA

CCTTATTTTTGACGAGGGGAAATTAATAGGTTGTATTGATGTTGGACGAGTCGGAATCG

CAGACCGATACCAGGATCTTGCCATCCTATGGAACTGCCTCGGTGAGTTTTCTCCTTCA

TTACAGAAACGGCTTTTTCAAAAATATGGTATTGATAATCCTGATATGAATAAATTGCA
```

-continued

```
GTTTCATTTGATGCTCGATGAGTTTTTCTAAGAATTAATTCATGAGCGGATACATATTT

GAATGTATTTAGAAAAATAAACAAATAGGGGTTCCGCGCACATTTCCCCGAAAAGTGCC

ACCTGAAATTGTAAACGTTAATATTTTGTTAAAATTCGCGTTAAATTTTTGTTAAATCA

GCTCATTTTTTAACCAATAGGCCGAAATCGGCAAAATCCCTTATAAATCAAAAGAATAG

ACCGAGATAGGGTTGAGTGTTGTTCCAGTTTGGAACAAGAGTCCACTATTAAAGAACGT

GGACTCCAACGTCAAAGGGCGAAAAACCGTCTATCAGGGCGATGGCCCACTACGTGAAC

CATCACCCTAATCAAGTTTTTTGGGGTCGAGGTGCCGTAAAGCACTAAATCGGAACCCT

AAAGGGAGCCCCCGATTTAGAGCTTGACGGGGAAAGCCGGCGAACGTGGCGAGAAAGGA

AGGGAAGAAAGCGAAAGGAGCGGGCGCTAGGGCGCTGGCAAGTGTAGCGGTCACGCTGC

GCGTAACCACCACACCCGCCGCGCTTAATGCGCCGCTACAGGGCGCGTCCCATTCGCCA
```

SEQ. ID NO: 37

```
ATCCGGATATAGTTCCTCCTTTCAGCAAAAAACCCCTCAAGACCCGTTTAGAGGCCCCA

AGGGGTTATGCTAGTTATTGCTCAGCGGTGGCAGCAGCCAACTCAGCTTCCTTTCGGGC

TTTGTTAGCAGCCGGATCTCAGTGGTGGTGGTGGTGCTCGAGTGCGGCCGCAAGCT

TGTCGACGGAGCTCGAATTCGGATCCTAGAGGGAAACCGTTGTGGTCTCCCTATAGTGA

GTCGTATTAATTTCGCGGGATCGAGATCTCGGGCAGCGTTGGGTCCTGGCCACGGGTGC

GCATGATCGTGCTCCTGTCGTTGAGGACCCGGCTAGGCTGGCGGGGTTGCCTTACTGGT

TAGCAGAATGAATCACCGATACGCGAGCGAACGTGAAGCGACTGCTGCTGCAAAACGTC

TGCGACCTGAGCAACAACATGAATGGTCTTCGGTTTCCGTGTTTCGTAAAGTCTGGAAA

CGCGGAAGTCAGCGCCCTGCACCATTATGTTCCGGATCTGCATCGCAGGATGCTGCTGG

CTACCCTGTGGAACACCTACATCTGTATTAACGAAGCGCTGGCATTGACCCTGAGTGAT

TTTTCTCTGGTCCCGCCGCATCCATACCGCCAGTTGTTTACCCTCACAACGTTCCAGTA

ACCGGGCATGTTCATCATCAGTAACCCGTATCGTGAGCATCCTCTCTCGTTTCATCGGT

ATCATTACCCCCATGAACAGAAATCCCCCTTACACGGAGGCATCAGTGACCAAACAGGA

AAAAACCGCCCTTAACATGGCCCGCTTTATCAGAAGCCAGACATTAACGCTTCTGGAGA

AACTCAACGAGCTGGACGCGGATGAACAGGCAGACATCTGTGAATCGCTTCACGACCAC

GCTGATGAGCTTTACCGCAGCTGCCTCGCGCGTTTCGGTGATGACGGTGAAAACCTCTG

ACACATGCAGCTCCCGGAGACGGTCACAGCTTGTCTGTAAGCGGATGCCGGGAGCAGAC

AAGCCCGTCAGGGCGCGTCAGCGGGTGTTGGCGGGTGTCGGGGCGCAGCCATGACCCAG

TCACGTAGCGATAGCGGAGTGTATACTGGCTTAACTATGCGGCATCAGAGCAGATTGTA

CTGAGAGTGCACCATATATGCGGTGTGAAATACCGCACAGATGCGTAAGGAGAAAATAC

CGCATCAGGCGCTCTTCCGCTTCCTCGCTCACTGACTCGCTGCGCTCGGTCGTTCGGCT

GCGGCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAAAAAG

GCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCTGTCC

GCCTTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAGCCCG

ACCGCTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGCGGTGC
```

-continued

```
TACAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGTCTGACGCTCAGTGGA
ACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTA
CCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTT
AATAGTTTGCGCAACGTTGTTGCCATTGCTGCAGGCATCGTGGTGTCACGCTCGTCGTT
TGGTATGGCTTCATTCAGCTCCGGTTCCCAACGATCAAGGCGAGTTACATGATCCCCCA
TGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACAT
AGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATCTT
CAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTA
TTTAGAAAAATAAACAATAGGGGTTCCGCGCACATTTCCCCGAAAAGTGCCACCTGAA
ATTGTAAACGTTAATATTTTGTTAAAATTCGCGTTAAATTTTTGTTAAATCAGCTCATT
TTTTAACCAATAGGCCGAAATCGGCAAAATCCCTTATAAATCAAAAGAATAGACCGAGA
TAGGGTTGAGTGTTGTTCCAGTTTGGAACAAGAGTCCACTATTAAAGAACGTGGACTCC
AACGTCAAAGGGCGAAAAACCGTCTATCAGGGCGATGGCCCACTACGTGAACCATCACC
CTAATCAAGTTTTTTGGGGTCGAGGTGCCGTAAAGCACTAAATCGGAACCCTAAAGGGA
GCCCCCGATTTAGAGCTTGACGGGAAAGCCGGCGAACGTGGCGAGAAAGGAAGGGAAG
AAAGCGAAAGGAGCGGGCGCTAGGGCGCTGGCAAGTGTAGCGGTCACGCTGCGCGTAAC
CACCACACCCGCCGCGCTTAATGCGCCGCTACAGGGCGCGTCCCATTCGCCA
```

|  | SEQ. ID NO: 38 |
|---|---|
| TACCCATACGACGTTCCAGACTACGCC | |
|  | SEQ. ID NO: 39 |
| YPYDVPDYA | |
|  | SEQ. ID NO: 40 |
| GAACAAAAGTTAATTTCTGAAGAAGATTTGGAA | |
|  | SEQ. ID NO: 41 |
| EQKLISEEDL | |
|  | SEQ. ID NO: 42 |
| GACTACAAGGATGACGATGACAAA | |
|  | SEQ. ID NO: 43 |
| DYKDDDDK | |

-continued

SEQ. ID NO: 44
GGTAAGCCAATTCCAAATCCTTTGTTGGGTTTGGACTCCACC

SEQ. ID NO: 45
GKPIPNPLLGLDST

SEQ. ID NO: 46
CATCATCATCATCATCAT

SEQ. ID NO: 47
HHHHHH

SEQ. ID NO: 48
ATGGCGTTCGATCTCAAGACTGAAGACGGCCTCATCACATATCTCACTAAACATCTTTC

TTTGGACGTCGACACGAGCGGAGTGAAGCGCCTTAGCGGAGGCTTTGTCAATGTAACCT

GGCGCATTAAGCTCAATGCTCCTTATCAAGGTCATACGAGCATCATCCTGAAGCATGCT

CAGCCGCACATGTCTACGGATGAGGATTTTAAGATAGGTGTAGAACGTTCGGTTTACGA

ATACCAGGCTATCAAGCTCATGATGGCCAATCGGGAGGTTCTGGGAGGCGTGGATGGCA

TAGTTTCTGTGCCAGAAGGCCTGAACTACGACTTAGAGAATAATGCATTGATCATGCAA

GATGTCGGGAAGATGAAGACCCTTTTAGATTATGTCACCGCCAAACCGCCACTTGCGAC

GGATATAGCCCGCCTTGTTGGGACAGAAATTGGGGGGTTCGTTGCCAGACTCCATAACA

TAGGCCGCGAGAGGCGAGACGATCCTGAGTTCAAATTCTTCTCTGGAAATATTGTCGGA

AGGACGACTTCAGACCAGCTGTATCAAACCATCATACCCAACGCAGCGAAATATGGCGT

CGATGACCCCTTGCTGCCTACTGTGGTTAAGGACCTTGTGGACGATGTCATGCACAGCG

AAGAGACCCTTGTCATGGCGGACCTGTGGAGTGGAAATATTCTTCTCCAGTTGGAGGAG

GGAAACCCATCGAAGCTGCAGAAGATATATATCCTGGATTGGGAACTTTGCAAGTACGG

CCCAGCGTCGTTGGACCTGGGCTATTTCTTGGGTGACTGCTATTTGATATCCCGCTTTC

AAGACGAGCAGGTCGGTACGACGATGCGGCAAGCCTACTTGCAAAGCTATGCGCGTACG

AGCAAGCATTCGATCAACTACGCCAAAGTCACTGCAGGTATTGCTGCTCATATTGTGAT

GTGGACCGACTTTATGCAGTGGGGAGCGAGGAAGAAAGGATAAATTTTGTGAAAAGG

GGGTAGCTGCCTTTCACGACGCCAGGGGCAACAACGACAATGGGGAAATTACGTCTACC

TTACTGAAGGAATCATCCACTGCGTAA

SEQ. ID NO: 49
MAFDLKTEDGLITYLTKHLSLDVDTSGVKRLSGGFVNVTWRIKLNAPYQGHTSIILKHA

QPHMSTDEDFKIGVERSVYEYQAIKLMMANREVLGGVDGIVSVPEGLNYDLENNALIMQ

DVGKMKTLLDYVTAKPPLATDIARLVGTEIGGFVARLHNIGRERRDDPEFKFFSGNIVG

RTTSDQLYQTIIPNAAKYGVDDPLLPTVVKDLVDDVMHSEETLVMADLWSGNILLQLEE

GNPSKLQKIYILDWELCKYGPASLDLGYFLGDCYLISRFQDEQVGTTMRQAYLQSYART

SKHSINYAKVTAGIAAHIVMWTDFMQWGSEEERINFVKKGVAAFHDARGNNDNGEITST

LLKESSTA

SEQ. ID NO: 50
CGAGATCTTTGTGTTCGGTTACCCGGCTCAGATCCTAACTTCTTCTTTTGGTATGTTTA

TTCGTATAAGTTACTGTTGTCCACAGGCAATACTCTGCAGAAAATTAAAACGGCATTAA

TGCTAGGACAACCAGAATTGTTACTACTGTATGTGCGATAGTTGATAACTGCAACATTA

TGCCCGGTATATTCTCAAAAAACCCTATTACTGCATACGAAGAAATCGCAAGAGAAATC

TTTCGGTTTGGAAAAGCTCACTGTGAGGTTCCTTGGAGCCAATAGTAATACAGCACAAT

CCAAGGAAAATCTGGCCTATATGCAAGGAAGGAGAGATAGTCAAAAGCATTCTTTCCC

CTAGAAGTTGGTGCATATATGGCATCGTTAAAACATATTACCCCCAAAATTTCTTCTCT

```
                                                 -continued
AAACGATGTGCTTGGCCTTTGTTTTGGTTTTTGATGTCGGTCGTTTGAGGCCCCTTGCG

GAAAATCGAGATCGCCGAATGGCACGCGAGGGAAGGGAAATAAGGTTTAAAGGCACTGA

AACAATAGGCAAGAAGTAGGCGAGAGCCGACATACGAGACTAAATTAAGTCCTCAGCGA

GCTCGCATGGAATGCGTGCGATGAGCGACCTCATGCTATACCTGAGAAAGCAACCTGAC

CTACAGGAAAGAGTTACTCAAGAATAAGAATTTTCGTTTTAAAACCTAAGAGTCACTTT

AAAATTTGTATACACTTATTTTTTTATAACTTATTTAATAATAAAAATCATAAATCAT

AAGAAATTCGCTTATTTAGAAGTGTCAACAACGTATCTACCAACGGAATGCGTGCGATT

CATTTGTCATCGTCATCCTTGTAGTCTTCAGCAACACATGGGTATGAAATAGAAACTTC

TTCAGCCAATGCTTTAATCTTCATCATGATTTGCAACATTTCTTCAGTTGTAGTTCTTG

GATTAATTGAACACAATCTAATAACAACCTTTTCCTTCAATTCTGTAGTAGATAACATA

GCGAAACCTCTATGTGTGATTTCCTTAACCAATTTCTTATTAATTTCATTAATAGTATC

TGTTGATGCCAATTCAGATGGAATGTATCTAAAAGTAACGATACCCAATTGAGCTGGTG

TAACAACTTCCCAATCTTTTGCTTTACCCAAAAATGCTTCAACTTGTTCTGCTAACATG

ATACCATGATCGATTGCTTGTCTAAAAGCAGCAACACCGAAAACTTTAAAAGACAACCA

AACCTTCAAAGCTCTGAATCTTCTTGACAATTCGATACCACATTCACCGAAATTAATTT

CACCTTCAACGTTAGTTTCTGAATCCTTGATGTATTCTGGCATCATTCTAAAAGTCTTT

GACAAATATTGAGAGTTTCTGATCAAAACACAACCAACATCGTATGGTTGGAACAACCA

CTTATGTGGATCTAAAGTCAAAGAATCTGCTCTATGAATACCTTGCAACATAGCTGAAC

CCTTTTCAGACAAGATAGCTGGAGCACCATAAGAACCATCAGCATGCAACCAAACATCT

TCATCGTTACACAAATCTGCTAATTCGTTCAAAGAATCAACAGCACCACAATTTGTAGT

ACCAGCATTTGCAATAACACAGAATGGCTTTTTACCCTTAGTTCTATCTTCTTTAATTT

GTTTCTTCAAAGCTGAAACAGAGATTCTCAAATGTTCATCTGTTTCGATTCTACAGATT

TGATGATGTTTAAAACCTAAAACCTTCAATGCTCTATCAACTGAGAAATGTGTTTGATC

AGAGAAGTAAACAACAGCATTTTCGATATCGTTGTTCAACTTAGCCTGTCTTGCAACAG

TCAAAGCTGTCAAATTTGCCATTGAACCACCAGAAACAAATAAACCTTCAGCTGAATCT

GGAAAACCCAACATAGATTTCAACCAATTAATTGTAGTCAATTCGATTTGTTCAGCACC

TGCACCAGCAATCCATGCAGTTGGAAAAACATTAAAACCAGAAGCCAAGAAATCTGCAA

CAACACCAACGTAATTATTTGGACCTGGAACAAAAGCCAAGAAATGTGGATGATCAACA

TGTGTAATTTGATTAAAAACGTTTCTGTTCAAGAAATGCAACAATTCCTTTGGATCTGA

ACCATTTTCTGGGATAGATTCAGTCAACTTATTTCTCAAGATATCAGAATCGATTGTTT

CTGAAACTGGCTTAGACTTCAAATGGTTCATGTGATCGATGATCAAATCAACTGCTTGG

TAACCCAATTGTCTCATTTCTTCAGCTGACAATTGCAAATTTTCAGACATTGTTTTATA

TTTGTTGTAAAAAGTAGATAATTACTTCCTTGATGATCTGTAAAAAAGAGAAAAAGAAA

GCATCTAAGAACTTGAAAAACTACGAATTAGAAAAGACCAAATATGTATTTCTTGCATT

GACCAATTTATGCAAGTTTATATATATGTAAATGTAAGTTTCACGAGGTTCTACTAAAC

TAAACCACCCCCTTGGTTAGAAGAAAAGAGTGTGTGAGAACAGGCTGTTGTTGTCACAC

GATTCGGACAATTCTGTTTGAAAGAGAGAGAGTAACAGTACGATCGAACGAACTTTGCT

CTGGAGATCACAGTGGGCATCATAGCATGTGGTACTAAACCCTTTCCCGCCATTCCAGA

ACCTTCGATTGCTTGTTACAAAACCTGTGAGCCGTCGCTAGGACCTTGTTGTGTGACGA

AATTGGAAGCTGCAATCAATAGGAAGACAGGAAGTCGAGCGTGTCTGGGTTTTTTCAGT

TTTGTTCTTTTTGCAAACAACAGTTTATTCCTGGCATCCACTAAATATAATGGAGCCCG
```

-continued

CTTTTTAAGCTGGCATCCAGAAAAAAAAGAATCCCAGCACCAAAATATTGTTTTCTTC

ACCAACCATCAGTTCATAGGTCCATTCTCTTAGCGCAACTACAGAGAACAGGGGCACAA

ACAGGCAAAAAACGGGCACAACCTCAATGGAGTGATGCAACCTGCCTGGAGTAAATGAT

GACACAAGGCAATTGACCCACGCATGTATCTATCTCATTTTCTTACACCTTCTATTACC

TTCTGCTCTCTCTGATTTGGAAAAAGCTGAAAAAAAAGGTTGAAACCAGTTCCCTGAAA

TTATTCCCCTACTTGACTAATAAGTATATAAAGACGGTAGGTATTGATTGTAATTCTGT

AAATCTATTTCTTAAACTTCTTAAATTCTACTTTTATAGTTAGTCTTTTTTTTAGTTTT

AAAACACCAAGAACTTAGTTTCGAATAAACACACATAAACAAACAAAATGGCTTCTAGT

TCTTCCGATGTCTTCGTTTTGGGTCTAGGTGTTGTTTTGGCTGCCTTGTATATCTTCAG

AGACCAATTATTCGCTGCTTCTAAGCCAAAGGTGGCTCCAGTTTCCACTACGAAGCCTG

CCAACGGTTCCGCTAACCCAAGAGACTTCATCGCCAAGATGAAACAAGGTAAGAAGAGA

ATCGTAATCTTCTACGGTTCTCAAACTGGTACCGCTGAAGAATATGCTATTCGTTTGGC

TAAGGAAGCTAAGCAAAAGTTCGGTCTAGCCTCCTTGGTTTGTGATCCAGAAGAATACG

ATTTTGAAAAGTTGGACCAATTGCCAGAAGATTCTATTGCTTTCTTCGTCGTTGCTACC

TATGGTGAAGGTGAACCTACAGACAACGCTGTCCAATTGTTGCAAAACTTGCAAGATGA

AAGCTTCGAATTCTCCTCTGGTGAGAGAAAGTTGTCAGGTTTGAAGTACGTTGTTTTTG

GTCTGGGTAACAAGACCTACGAACATTACAACCTCATTGGGAGAACTGTTGACGCTCAA

TTGGCCAAGATGGGTGCTATCAGAATCGGTGAAAGAGGTGAAGGTGATGATGACAAGTC

CATGGAAGAAGACTACTTGGAATGGAAGGATGGTATGTGGGAAGCGTTTGCCACTGCTA

TGGGTGTTGAAGAAGGTCAAGGTGGTGACTCCGCTGATTTCGTCGTTTCCGAATTGGAA

TCTCACCCACCAGAAAAGGTTTACCAAGGTGAATTTTCTGCTAGAGCTTTAACCAAAAC

CAAGGGTATTCACGACGCTAAGAATCCTTTTGCTGCTCCAATTGCGGTTGCTAGAGAAT

TGTTCCAATCTGTTGTCGATAGAAACTGTGTCCACGTCGAATTCAACATTGAAGGCTCT

GGTATCACCTATCAACACGGTGACCACGTTGGTTTGTGGCCATTGAATCCAGATGTTGA

AGTCGAACGGTTGTTGTGTGTTTTAGGTTTAGCTGAAAAGAGAGATGCTGTCATCTCCA

TTGAATCCTTAGACCCGGCTTTGGCTAAGGTTCCATTCCCAGTCCCAACTACTTACGGT

GCTGTGTTGAGACACTACATTGACATCTCTGCTGTCGCCGGTAGACAAATCTTGGGTAC

TTTGTCCAAATTCGCTCCAACCCCAGAAGCTGAAGCTTTCTTGAGAAACTTGAACACTA

ACAAGGAAGAATACCACAACGTCGTCGCTAACGGTTGTTTGAAATTGGGTGAAATTTTG

CAAATCGCTACCGGTAACGACATTACTGTCCCACCAACTACTGCCAACACCACCAAATG

GCCAATTCCATTCGACATCATTGTTTCTGCCATCCCAAGATTGCAACCAAGATACTACT

CTATCTCTTCTTCCCCAAAAATTCATCCAAACACCATCCACGCTACCGTTGTTGTGCTC

AAATACGAAAACGTTCCAACCGAACCAATCCCAAGAAAGTGGGTTTACGGTGTCGGTAG

TAACTTCTTGTTGAATTTAAAGTACGCTGTTAACAAGGAACCAGTTCCATACATCACTC

AAAATGGCGAACAAAGAGTCGGTGTCCCGGAATACTTGATTGCTGGTCCACGTGGTTCT

TACAAGACTGAATCTTTCTACAAGGCTCCAATCCATGTTAGACGTTCTACTTTCCGTTT

GCCAACCAACCCAAAGTCTCCAGTCATCATGATTGGTCCAGGTACTGGTGTCGCCCCAT

TCAGAGGCTTCGTTCAAGAAAGAGTTGCCTTGGCCAGAAGATCCATCGAAAAGAACGGT

CCTGACTCTTTGGCTGACTGGGGTCGTATTTCCTTGTTCTACGGTTGTAGAAGATCCGA

CGAAGACTTCTTGTACAAGGACGAATGGCCACAATACGAAGCTGAGTTGAAGGGTAAGT

-continued

TCAAGTTGCACTGTGCTTTCTCCAGACAAAACTACAAGCCAGACGGTTCTAAGATTTAC

GTCCAAGATTTGATCTGGGAAGACAGAGAACACATTGCCGATGCCATCTTAAACGGTAA

GGGTTACGTCTACATCTGCGGTGAAGCTAAGTCCATGTCTAAACAAGTTGAAGAAGTTC

TAGCCAAGATCTTGGGCGAAGCCAAAGGTGGTTCCGGTCCAGTTGAAGGTGTTGCTGAA

GTCAAGTTACTGAAGGAACGGTCCAGATTGATGTTGGATGTCTGGTCTGAACAAAAGTT

AATTTCTGAAGAAGATTTGGAATGAATCGCGTGCATTCATCCGCTCTAACCGAAAAGGA

AGGAGTTAGACAACCTGAAGTCTAGGTCCCTATTTATTTTTTATAGTTATGTTAGTAT

TAAGAACGTTATTTATATTTCAAATTTTTCTTTTTTTCTGTACAGACGCGTGTACGCA

TGTAACATTATACTGAAAACCTTGCTTGAGAAGGTTTTGGGACGCTCGAAGATCGCGTC

CCAATTCGCCCTATAGTGAGTCGTATTACGCGCGCTCACTGGCCGTCGTTTTACAACGT

CGTGACTGGGAAAACCCTGGCGTTACCCCTGCAGGACTAGTGCTGAGGCATTAATACCA

CTTTTCAATGAAACGGATATTGATATGCTAGTAAAAGGACGAGCTCAAGAGCGAAAATA

TAAGTAAAGAATTCGAGTGCACTTGTCTCCATGCAGCAAGATTTCATATGAGTCTTTTT

TATCTTTTTACTTTTTACATTACACGATATGCACTTTATGAAAATTTAACGAGGTTGGA

AGCCGGATAATCAACCAAAATCAGGCACGAAGGCACACTCGTATATGCATGTTGTTGAA

ACTCTGTTACGCTGAACTAACAATCACACATGTAGAGGTCACCGGGAAAAGTTGCGACC

CCATGGAAGGTCGATCTCTTCGTTTGGCTTTGCTTGGCTGGCGGCATTGCGCTTCTTCG

CTTATACCCGTCTCTTGACGCTCGAGCTCGTTCATTGAGATACCTTTATTCTTGCACAT

TTTCTGGCTTTTTTCGCTACTCGGGTACATGTAATCATGCACACAGAAGGTGCTGTAGG

GTGAAAGTTCCTTTGTGCTGTCGTTTGTTTTTAATGCCAAACTTTCCGGTGATCAATAA

CCACCTC

SEQ. ID NO: 51
CGGCATGCAAACATCTACACAATTAGCAAGGGCAATCCATATTTTGTCTTTTCGCGCCC

TGGAAAGGCCTAAGTAATGTCGTAAACGCATTCTATCTGTACTTCAACTCTCCTCTGTG

CATTGGTTTGTGCAAATCACATTTTACGATACTGCCAGATATATGCAAAAAGAGAAAAC

CAAGGGACCAGAACAAAGCAAAATTACGATATTCTTCGAATTCCTTCGTGCTTGACTAA

GACAAAGGGATGGACGTAGCGATTTTTAGCGGGCCAAGAACTGGTTCCGAAAAAGCACA

GGTACACCGAACCCTCAGCTAAGGAGGGACAGCACCGATGCGGAAGGACAAACTTTCTT

TTTGCCTATCACAGTATCTTATCGAGCTAACTATTTTCGACACACATGAAAAAGCAGAA

ATATTAACGAAAAAGAAAAGAAAGACCATGTCATGTACGGGCAATCAGAATCTGTAACA

AGCGCCATTTTTTTTTCTGTATCGGGCCCTCCTTACTGCTCTCCTTCCGTGTAACGCGT

TATGAAATTAAGTCCTCAGCGAGCTCGCATGGAATGCGTGCGATGAGCGACCTCATGCT

ATACCTGAGAAAGCAACCTGACCTACAGGAAAGAGTTACTCAAGAATAAGAATTTTCGT

TTTAAAACCTAAGAGTCACTTTAAAATTTGTATACACTTATTTTTTTTATAACTTATTT

AATAATAAAAATCATAAATCATAAGAAATTCGCTTATTTAGAAGTGTCAACAACGTATC

TACCAACGGAATGCGTGCGATTGTTTTATATTTGTTGTAAAAAGTAGATAATTACTTCC

TTGATGATCTGTAAAAAAGAGAAAAAGAAAGCATCTAAGAACTTGAAAAACTACGAATT

AGAAAAGACCAAATATGTATTTCTTGCATTGACCAATTTATGCAAGTTTATATATATGT

AAATGTAAGTTTCACGAGGTTCTACTAAACTAAACCACCCCCTTGGTTAGAAGAAAAGA

GTGTGTGAGAACAGGCTGTTGTTGTCACACGATTCGGACAATTCTGTTTGAAAGAGAGA

GAGTAACAGTACGATCGAACGAACTTTGCTCTGGAGATCACAGTGGGCATCATAGCATG

-continued

```
TGGTACTAAACCCTTTCCCGCCATTCCAGAACCTTCGATTGCTTGTTACAAAACCTGTG
AGCCGTCGCTAGGACCTTGTTGTGTGACGAAATTGGAAGCTGCAATCAATAGGAAGACA
GGAAGTCGAGCGTGTCTGGGTTTTTTCAGTTTTGTTCTTTTTGCAAACAACAGTTTATT
CCTGGCATCCACTAAATATAATGGAGCCCGCTTTTTAAGCTGGCATCCAGAAAAAAAAA
GAATCCCAGCACCAAAATATTGTTTTCTTCACCAACCATCAGTTCATAGGTCCATTCTC
TTAGCGCAACTACAGAGAACAGGGGCACAAACAGGCAAAAAACGGGCACAACCTCAATG
GAGTGATGCAACCTGCCTGGAGTAAATGATGACACAAGGCAATTGACCCACGCATGTAT
CTATCTCATTTTCTTACACCTTCTATTACCTTCTGCTCTCTCTGATTTGGAAAAAGCTG
AAAAAAAAGGTTGAAACCAGTTCCCTGAAATTATTCCCCTACTTGACTAATAAGTATAT
AAAGACGGTAGGTATTGATTGTAATTCTGTAAATCTATTTCTTAAACTTCTTAAATTCT
ACTTTTATAGTTAGTCTTTTTTTTAGTTTTAAAACACCAAGAACTTAGTTTCGAATAAA
CACACATAAACAAACAAAATGGGAGGTCCGATGAGCGGTTTCCATTCGGGGGAGGCGCT
GCTCGGTGACCTCGCCACCGGTCAGCTGACCAGGCTGTGCGAGGTGGCGGGGCTGACCG
AGGCCGACACGGCGGCCTACACGGGGGTGCTGATCGAAAGTCTGGGGACGTCGGCCGGA
CGGCCGTTGTCCCTGCCACCCCCGTCGCGGACCTTTCTCTCCGACGACCACACCCCCGT
GGAGTTCTCCCTGGCCTTCCTGCCGGGACGCGCACCGCACCTGCGGGTCCTGGTGGAAC
CGGGCTGCTCCAGCGGCGACGACCTGGCGGAAAACGGCCGGGCCGGTCTGCGGGCGGTC
CACACCATGGCGGACCGCTGGGGATTCTCCACCGAGCAACTCGACCGGCTGGAGGACCT
GTTCTTCCCCTCCTCCCCCGAGGGCCCGCTGGCCCTGTGGTGCGCCCTGGAGCTCCGCT
CCGGTGGGGTGCCGGGGGTGAAGGTCTACCTCAACCCCGCGGCGAATGGCGCCGACCGG
GCCGCCGAGACGGTACGCGAGGCGCTGGCCAGGCTGGGCCACCTGCAGGCGTTCGACGC
GCTGCCCCGGGCGGACGGCTTCCCGTTCCTCGCCCTGGACCTCGGCGACTGGGACGCCC
CGCGGGTGAAGATCTACCTCAAACACCTCGGCATGTCCGCCGCCGACGCGGGCTCCCTC
CCCCGGATGTCGCCCGCACCGAGCCGGGAGCAGCTGGAGGAGTTCTTCCGCACCGCCGG
TGACCTCCCGGCCCCGGGAGACCCGGGGCCCACCGAGGACACCGGCCGGCTCGCCGGGC
GCCCCGCCCTCACCTGCCACTCCTTCACGGAGACGGCGACCGGGCGGCCCAGCGGCTAC
ACCCTCCACGTGCCGGTCCGCGACTACGTCCGGCACGACGGCGAGGCACGGGACCGGGC
GGTGGCCGTGCTGCGCGAACATGACATGGACAGTGCGGCACTGGACCGGGCGCTGGCCG
CCGTGAGCCCCGCCCGCTGAGTGACGGGGTGGGCCTGATCGCCTATCTGGCACTGGTC
CACCAGCGCGGCCGGCCGACACGGGTGACCGTCTACGTCTCCTCCGAGGCGTACGAGGT
GCGGCCGCCCCGCGAGACGGTCCCCACCCGCGACCGGGCGCGGGCACGGCTGCATCATC
ATCATCATCATTGAATCGCGTGCATTCATCCGCTCTAACCGAAAAGGAAGGAGTTAGAC
AACCTGAAGTCTAGGTCCCTATTTATTTTTTTATAGTTATGTTAGTATTAAGAACGTTA
TTTATATTTCAAATTTTTCTTTTTTTTCTGTACAGACGCGTGTACGCATGTAACATTAT
ACTGAAAACCTTGCTTGAGAAGGTTTTGGGACGCTCGAAGATCGCGTCCCAATTCGCCC
TATAGTGAGTCGTATTACGCGCGCTCACTGGCCGTCGTTTTACAACGTCGTGACTGGGA
AAACCCTGGCGTTACCCCTGCAGGACTAGTGCTGAGGCATTAATACGACTCTCTCGAAA
TTTTTCTTAACGCGTCCTTGTACTGCGTCTAACGCTTTTGCCACTTGGATTTCTATTAT
AGGAAATAGTCTCACTTACTGGGCGACGAATTTTCGCGTTTTGATGAAGCACAGGAAGA
ATTTCTTTTTTTTTGGCTTCTTCTGGTTCCGTTTTTTACGCGCACAAATCTAAAAAAA
GAAATAATTATAACCTAGTCTCGAAAATTTTCATCGATCCATTCGTTCCTTTTTTTCGA
```

-continued

TTTTTTCAGATCAAAATTCTTGTTTCTTTCTTTGTCTTAGTTTTATATTAAAAGATATTT

TGATTTTACTCCTGAACTATTTATTCTTTCTAAGAAGGCCAGAACACTACAGCTGTTTT

AACCGACTACGAAGTTCTCCATTCTCGAACACTAGCCTTCATTTACCAAACAGGAACTA

GCGTATATCATTAGTCCTTATTCGAAAAGAGATTGGTAGATATTTATTGTAGTTTGTGA

GAAGGAGAAAATACTGTCATTGGACTGATAGTTAGAGGACATTAACCTCTCTTACGTTC

GCTCA

SEQ. ID NO: 52
CGAGATCTTTGTGTTCGGTTACCCGGCTCAGATCCTAACTTCTTCTTTTGGTATGTTTA

TTCGTATAAGTTACTGTTGTCCACAGGCAATACTCTGCAGAAAATTAAAACGGCATTAA

TGCTAGGACAACCAGAATTGTTACTACTGTATGTGCGATAGTTGATAACTGCAACATTA

TGCCCGGTATATTCTCAAAAAACCCTATTACTGCATACGAAGAAATCGCAAGAGAAATC

TTTCGGTTTGGAAAAGCTCACTGTGAGGTTCCTTGGAGCCAATAGTAATACAGCACAAT

CCAAGGAAAAATCTGGCCTATATGCAAGGAAGGAGAGATAGTCAAAAGCATTCTTTCCC

CTAGAAGTTGGTGCATATATGGCATCGTTAAAACATATTACCCCCAAAATTTCTTCTCT

AAACGATGTGCTTGGCCTTTGTTTTGGTTTTTGATGTCGGTCGTTTGAGGCCCCTTGCG

GAAAATCGAGATCGCCGAATGGCACGCGAGGGAAGGGAAATAAGGTTTAAAGGCACTGA

AACAATAGGCAAGAAGTAGGCGAGAGCCGACATACGAGACTAAATTAAGTCCTCAGCGA

GCTCGCATGGAATGCGTGCGATGAGCGACCTCATGCTATACCTGAGAAAGCAACCTGAC

CTACAGGAAAGAGTTACTCAAGAATAAGAATTTTCGTTTTAAAACCTAAGAGTCACTTT

AAAATTTGTATACACTTATTTTTTTATAACTTATTTAATAATAAAAATCATAAATCAT

AAGAAATTCGCTTATTTAGAAGTGTCAACAACGTATCTACCAACGGAATGCGTGCGATT

CATTTGTCATCGTCATCCTTGTAGTCCATTGCCTTCAAATGTTCCTTATTAAACTTTCT

CAAATCGTAAACCAAAGAGTTCAAGATATCCAATTCAACATGTTCCATAACAACGATCT

TGTACCAGTTGTTAGTTGGGTTATGAACTTCTGGAACTAAAAAGTACTTTTCAGCGATT

TCCTTATTAACATATTGTTCTTCAATTGTAACATATTCATTGAATCTTCTTTGTAATA

TTTAATTCTCATATCGTTCAATTGCTTACACAACCATTTAGTTCTATTTCTCAACTTAT

TAATCTTTTCCATCCAACCGTATGGACCATAAGAAGCTAAAACCATCCAAATTGCAACA

GCATTTGAACCAGATCTTGAACCAGACAATGTAACATCCAAATTTTCGATGTAAGTTGC

TTCCTTTGTCAAAGTGTTATGGATCAAATTCTTTCTTGAAACGAAGATACCAGTACCGT

ATGGAGCTTGCAACATCTTATGACCATCTAATGTGATTGAAGAAACGTTCTTATTAGAG

AAATCAGTTTTACATTCCTTATTATCAATTGGATATATAAAACCACCAAATGCACCATC

AACATGAATTTTGTATTCCAAATTGTACTTATCGAAGATGTTAGCGTACAAATCTGGAT

CATCAACTGAACCAAACATTGTAGTACCCATGTTAGAGATAACGATGAAGTACTTTTA

CCAATTTCTTTAGCTTCTTTAACAATTGAATCCAATGTATTTTCTTGAATTTTTCTTGA

ATAAAAATCAACTGGAACCTTAATAATATCGATGTTCAACAAATCTGAACCTTTGTATG

CAGAGTAATGTGTATCTGCTGAAGTGATGATAGCGATTTCTTCATGCTTAGCCTTTCTT

TCTTTCTTGAAGTAGTTTCTGTAAACCCACATTGCTTGGATGTTAGCTTCTGTACCACC

TTGAGTAACGTAACCATCAAATTCTTCATCGTTACCGTTCAAAACATCGATTGCTAACA

ATTGGATTAATTCTCTTTCGATATCGAATGTACCACCGAACAAGATATCAGCCTTATCA

TAAGTATGACAACCGATATGGTTTGGGTTTTGAATAAAAGTTCTCAAGTATGGTGAATG

CTTAACGAAAGAATGATCATCATAGAAAACTGTATCATCCAACTTAGTACCTGGAATAC

-continued

```
CGATTGTCTTAGTGTTATCGTAGTTCAAAGTCTTTTCCAAAGATTCAGTAATCTTTTCA

TCCATTTCTTGTTGTGTGTACTTTCTCCAGAACTTCATTGTTTTATATTTGTTGTAAAA

AGTAGATAATTACTTCCTTGATGATCTGTAAAAAAGAGAAAAAGAAAGCATCTAAGAAC

TTGAAAAACTACGAATTAGAAAAGACCAAATATGTATTTCTTGCATTGACCAATTTATG

CAAGTTTATATATATGTAAATGTAAGTTTCACGAGGTTCTACTAAACTAAACCACCCCC

TTGGTTAGAAGAAAAGAGTGTGTGAGAACAGGCTGTTGTTGTCACACGATTCGGACAAT

TCTGTTTGAAAGAGAGAGAGTAACAGTACGATCGAACGAACTTTGCTCTGGAGATCACA

GTGGGCATCATAGCATGTGGTACTAAACCCTTTCCCGCCATTCCAGAACCTTCGATTGC

TTGTTACAAAACCTGTGAGCCGTCGCTAGGACCTTGTTGTGTGACGAAATTGGAAGCTG

CAATCAATAGGAAGACAGGAAGTCGAGCGTGTCTGGGTTTTTTCAGTTTTGTTCTTTTT

GCAAACAACAGTTTATTCCTGGCATCCACTAAATATAATGGAGCCCGCTTTTTAAGCTG

GCATCCAGAAAAAAAAGAATCCCAGCACCAAATATTGTTTTCTTCACCAACCATCAG

TTCATAGGTCCATTCTCTTAGCGCAACTACAGAGAACAGGGGCACAAACAGGCAAAAA

CGGGCACAACCTCAATGGAGTGATGCAACCTGCCTGGAGTAAATGATGACACAAGGCAA

TTGACCCACGCATGTATCTATCTCATTTTCTTACACCTTCTATTACCTTCTGCTCTCTC

TGATTTGGAAAAAGCTGAAAAAAAAGGTTGAAACCAGTTCCCTGAAATTATTCCCCTAC

TTGACTAATAAGTATATAAAGACGGTAGGTATTGATTGTAATTCTGTAAATCTATTTCT

TAAACTTCTTAAATTCTACTTTTATAGTTAGTCTTTTTTTAGTTTTAAAACACCAAGA

ACTTAGTTTCGAATAAACACACATAAACAAACAAAATGGCTTCTAGTTCTTCCGATGTC

TTCGTTTTGGGTCTAGGTGTTGTTTTGGCTGCCTTGTATATCTTCAGAGACCAATTATT

CGCTGCTTCTAAGCCAAAGGTGGCTCCAGTTTCCACTACGAAGCCTGCCAACGGTTCCG

CTAACCCAAGAGACTTCATCGCCAAGATGAAACAAGGTAAGAAGAGAATCGTAATCTTC

TACGGTTCTCAAACTGGTACCGCTGAAGAATATGCTATTCGTTTGGCTAAGGAAGCTAA

GCAAAAGTTCGGTCTAGCCTCCTTGGTTTGTGATCCAGAAGAATACGATTTTGAAAGT

TGGACCAATTGCCAGAAGATTCTATTGCTTTCTTCGTCGTTGCTACCTATGGTGAAGGT

GAACCTACAGACAACGCTGTCCAATTGTTGCAAAACTTGCAAGATGAAAGCTTCGAATT

CTCCTCTGGTGAGAGAAAGTTGTCAGGTTTGAAGTACGTTGTTTTTGGTCTGGGTAACA

AGACCTACGAACATTACAACCTCATTGGGAGAACTGTTGACGCTCAATTGGCCAAGATG

GGTGCTATCAGAATCGGTGAAAGAGGTGAAGGTGATGATGACAAGTCCATGGAAGAAGA

CTACTTGGAATGGAAGGATGGTATGTGGGAAGCGTTTGCCACTGCTATGGGTGTTGAAG

AAGGTCAAGGTGGTGACTCCGCTGATTTCGTCGTTTCCGAATTGGAATCTCACCCACCA

GAAAAGGTTTACCAAGGTGAATTTTCTGCTAGAGCTTTAACCAAAACCAAGGGTATTCA

CGACGCTAAGAATCCTTTTGCTGCTCCAATTGCGGTTGCTAGAGAATTGTTCCAATCTG

TTGTCGATAGAAACTGTGTCCACGTCGAATTCAACATTGAAGGCTCTGGTATCACCTAT

CAACACGGTGACCACGTTGGTTTGTGGCCATTGAATCCAGATGTTGAAGTCGAACGGTT

GTTGTGTGTTTTAGGTTTAGCTGAAAAGAGAGATGCTGTCATCTCCATTGAATCCTTAG

ACCCGGCTTTGGCTAAGGTTCCATTCCCAGTCCCAACTACTTACGGTGCTGTGTTGAGA

CACTACATTGACATCTCTGCTGTCGCCGGTAGACAAATCTTGGGTACTTTGTCCAAATT

CGCTCCAACCCCAGAAGCTGAAGCTTTCTTGAGAAACTTGAACACTAACAAGGAAGAAT

ACCACAACGTCGTCGCTAACGGTTGTTTGAAATTGGGTGAAATTTTGCAAATCGCTACC
```

-continued

GGTAACGACATTACTGTCCCACCAACTACTGCCAACACCACCAAATGGCCAATTCCATT

CGACATCATTGTTTCTGCCATCCCAAGATTGCAACCAAGATACTACTCTATCTCTTCTT

CCCCAAAAATTCATCCAAACACCATCCACGCTACCGTTGTTGTGCTCAAATACGAAAAC

GTTCCAACCGAACCAATCCCAAGAAAGTGGGTTTACGGTGTCGGTAGTAACTTCTTGTT

GAATTTAAAGTACGCTGTTAACAAGGAACCAGTTCCATACATCACTCAAAATGGCGAAC

AAAGAGTCGGTGTCCCGGAATACTTGATTGCTGGTCCACGTGGTTCTTACAAGACTGAA

TCTTTCTACAAGGCTCCAATCCATGTTAGACGTTCTACTTTCCGTTTGCCAACCAACCC

AAAGTCTCCAGTCATCATGATTGGTCCAGGTACTGGTGTCGCCCCATTCAGAGGCTTCG

TTCAAGAAAGAGTTGCCTTGGCCAGAAGATCCATCGAAAAGAACGGTCCTGACTCTTTG

GCTGACTGGGGTCGTATTTCCTTGTTCTACGGTTGTAGAAGATCCGACGAAGACTTCTT

GTACAAGGACGAATGGCCACAATACGAAGCTGAGTTGAAGGGTAAGTTCAAGTTGCACT

GTGCTTTCTCCAGACAAAACTACAAGCCAGACGGTTCTAAGATTTACGTCCAAGATTTG

ATCTGGGAAGACAGAGAACACATTGCCGATGCCATCTTAAACGGTAAGGGTTACGTCTA

CATCTGCGGTGAAGCTAAGTCCATGTCTAAACAAGTTGAAGAAGTTCTAGCCAAGATCT

TGGGCGAAGCCAAAGGTGGTTCCGGTCCAGTTGAAGGTGTTGCTGAAGTCAAGTTACTG

AAGGAACGGTCCAGATTGATGTTGGATGTCTGGTCTGAACAAAAGTTAATTTCTGAAGA

AGATTTGGAATGAATCGCGTGCATTCATCCGCTCTAACCGAAAAGGAAGGAGTTAGACA

ACCTGAAGTCTAGGTCCCTATTTATTTTTTATAGTTATGTTAGTATTAAGAACGTTAT

TTATATTTCAAATTTTTCTTTTTTTCTGTACAGACGCGTGTACGCATGTAACATTATA

CTGAAAACCTTGCTTGAGAAGGTTTTGGGACGCTCGAAGATCGCGTCCCAATTCGCCCT

ATAGTGAGTCGTATTACGCGCGCTCACTGGCCGTCGTTTTACAACGTCGTGACTGGGAA

AACCCTGGCGTTACCCCTGCAGGACTAGTGCTGAGGCATTAATACCACTTTTCAATGAA

ACGGATATTGATATGCTAGTAAAAGGACGAGCTCAAGAGCGAAAATATAAGTAAAGAAT

TCGAGTGCACTTGTCTCCATGCAGCAAGATTTCATATGAGTCTTTTTATCTTTTTACT

TTTTACATTACACGATATGCACTTTATGAAAATTTAACGAGGTTGGAAGCCGGATAATC

AACCAAAATCAGGCACGAAGGCACACTCGTATATGCATGTTGTTGAAACTCTGTTACGC

TGAACTAACAATCACACATGTAGAGGTCACCGGGAAAAGTTGCGACCCCATGGAAGGTC

GATCTCTTCGTTTGGCTTTGCTTGGCTGGCGGCATTGCGCTTCTTCGCTTATACCCGTC

TCTTGACGCTCGAGCTCGTTCATTGAGATACCTTTATTCTTGCACATTTTCTGGCTTTT

TTCGCTACTCGGGTACATGTAATCATGCACACAGAAGGTGCTGTAGGGTGAAAGTTCCT

TTGTGCTGTCGTTTGTTTTAATGCCAAACTTTCCGGTGATCAATAACCACCTC

SEQ. ID NO: 53
CGGCATGCAAACATCTACACAATTAGCAAGGGCAATCCATATTTTGTCTTTTCGCGCCC

TGGAAAGGCCTAAGTAATGTCGTAAACGCATTCTATCTGTACTTCAACTCTCCTCTGTG

CATTGGTTTGTGCAAATCACATTTTACGATACTGCCAGATATATGCAAAAAGAGAAAAC

CAAGGGACCAGAACAAAGCAAAATTACGATATTCTTCGAATTCCTTCGTGCTTGACTAA

GACAAAGGGATGGACGTAGCGATTTTTAGCGGGCCAAGAACTGGTTCCGAAAAAGCACA

GGTACACCGAACCCTCAGCTAAGGAGGGACAGCACCGATGCGGAAGGACAAACTTTCTT

TTTGCCTATCACAGTATCTTATCGAGCTAACTATTTTCGACACACATGAAAAAGCAGAA

ATATTAACGAAAAGAAAAGAAAGACCATGTCATGTACGGGCAATCAGAATCTGTAACA

AGCGCCATTTTTTTTCTGTATCGGGCCCTCCTTACTGCTCTCCTTCCGTGTAACGCGT

```
TATGAAATTAAGTCCTCAGCGAGCTCGCATGGAATGCGTGCGATGAGCGACCTCATGCT

ATACCTGAGAAAGCAACCTGACCTACAGGAAAGAGTTACTCAAGAATAAGAATTTTCGT

TTTAAAACCTAAGAGTCACTTTAAAATTTGTATACACTTATTTTTTTTATAACTTATTT

AATAATAAAAATCATAAATCATAAGAAATTCGCTTATTTAGAAGTGTCAACAACGTATC

TACCAACGGAATGCGTGCGATTGTTTTATATTTGTTGTAAAAAGTAGATAATTACTTCC

TTGATGATCTGTAAAAAAGAGAAAAAGAAAGCATCTAAGAACTTGAAAAACTACGAATT

AGAAAAGACCAAATATGTATTTCTTGCATTGACCAATTTATGCAAGTTTATATATATGT

AAATGTAAGTTTCACGAGGTTCTACTAAACTAAACCACCCCCTTGGTTAGAAGAAAAGA

GTGTGTGAGAACAGGCTGTTGTTGTCACACGATTCGGACAATTCTGTTTGAAAGAGAGA

GAGTAACAGTACGATCGAACGAACTTTGCTCTGGAGATCACAGTGGGCATCATAGCATG

TGGTACTAAACCCTTTCCCGCCATTCCAGAACCTTCGATTGCTTGTTACAAAACCTGTG

AGCCGTCGCTAGGACCTTGTTGTGTGACGAAATTGGAAGCTGCAATCAATAGGAAGACA

GGAAGTCGAGCGTGTCTGGGTTTTTTCAGTTTTGTTCTTTTTGCAAACAACAGTTTATT

CCTGGCATCCACTAAATATAATGGAGCCCGCTTTTTAAGCTGGCATCCAGAAAAAAAAA

GAATCCCAGCACCAAAATATTGTTTTCTTCACCAACCATCAGTTCATAGGTCCATTCTC

TTAGCGCAACTACAGAGAACAGGGGCACAAACAGGCAAAAACGGGCACAACCTCAATG

GAGTGATGCAACCTGCCTGGAGTAAATGATGACACAAGGCAATTGACCCACGCATGTAT

CTATCTCATTTTCTTACACCTTCTATTACCTTCTGCTCTCTCTGATTTGGAAAAAGCTG

AAAAAAAGGTTGAAACCAGTTCCCTGAAATTATTCCCCTACTTGACTAATAAGTATAT

AAAGACGGTAGGTATTGATTGTAATTCTGTAAATCTATTTCTTAAACTTCTTAAATTCT

ACTTTTATAGTTAGTCTTTTTTTTAGTTTTAAAACACCAAGAACTTAGTTTCGAATAAA

CACACATAAACAAACAAAATGTCCATCGGTGCTGAAATTGACTCTTTGGTTCCAGCTCC

ACCAGGTTTGAACGGTACCGCTGCTGGTTACCCAGCCAAGACTCAAAAGGAATTGTCTA

ACGGCGATTTCGATGCTCACGATGGTCTGTCCTTGGCTCAATTGACTCCATACGATGTT

TTAACCGCTGCTTTGCCATTGCCAGCGCCAGCTTCTAGTACTGGTTTCTGGTGGAGAGA

AACTGGTCCAGTTATGTCTAAGCTCTTGGCTAAAGCCAACTACCCATTGTACACCCATT

ACAAGTATTTAATGTTGTACCACACTCACATTTTACCTTTGTTAGGTCCAAGACCACCT

TTGGAAAATTCTACCCACCCATCTCCATCAAATGCTCCTTGGAGATCCTTCTTGACCGA

TGACTTCACCCCATTAGAACCATCTTGGAACGTTAACGGTAACTCCGAAGCACAATCCA

CTATCAGATTGGGTATTGAACCAATTGGTTTCGAAGCCGGTGCTGCTGCCGACCCATTC

AACCAAGCTGCCGTCACCCAATTCATGCACTCCTACGAAGCTACGAAGTTGGTGCCAC

TCTAACTTTGTTCGAACACTTCAGAAACGACATGTTCGTCGGTCCAGAGACTTACGCTG

CCTTGAGAGCTAAGATTCCTGAAGGTGAGCACACCACTCAATCTTTCTTGGCTTTCGAC

TTGGACGCCGGTCGTGTCACTACCAAGGCTTACTTCTTCCCAATCTTGATGTCTTTGAA

GACCGGTCAATCTACGACCAAAGTIGTTTCCGATTCTATCTTGCACCTAGCTTTGAAGT

CTGAAGTTTGGGGTGTCCAAACCATTGCCGCTATGTCGGTCATGGAAGCTTGGATCGGT

TCTTACGGTGGTGCTGCTAAGACCGAAATGATCTCCGTTGACTGTGTCAACGAAGCTGA

CTCCAGAATCAAGATCTACGTTAGAATGCCACACACTAGCTTGAGAAAGGTCAAAGAAG

CTTATTGTTTGGGTGGCCGTTTGACTGACGAAAACACCAAGGAAGGTTTGAAATTGTTG

GATGAATTGTGGAGAACTGTTTTCGGTATCGATGACGAAGATGCTGAATTACCACAAAA

CTCTCACAGAACTGCTGGTACTATTTTTAACTTTGAACTAAGACCAGGTAAGTGGTTCC
```

-continued

CAGAACCAAAGGTCTACTTGCCAGTCAGACACTACTGTGAATCCGACATGCAAATTGCC

TCCAGATTACAAACTTTCTTTGGTCGTTTGGGTTGGCACAACATGGAAAAGGACTACTG

CAAGCATTTGGAAGACTTATTCCCTCACCACCCATTGTCCTCCTCTACCGGTACCCACA

CTTTCTTGTCTTTTTCTTACAAGAAGCAAAAGGGTGTTTACATGACCATGTACTACAAC

TTGAGAGTTTATTCTACACACCACCATCATCATCATTGAATCGCGTGCATTCATCCGCT

CTAACCGAAAAGGAAGGAGTTAGACAACCTGAAGTCTAGGTCCCTATTTATTTTTTAT

AGTTATGTTAGTATTAAGAACGTTATTTATATTTCAAATTTTTCTTTTTTTTCTGTACA

GACGCGTGTACGCATGTAACATTATACTGAAAACCTTGCTTGAGAAGGTTTTGGGACGC

TCGAAGATCGCGTCCCAATTCGCCCTATAGTGAGTCGTATTACGCGCGCTCACTGGCCG

TCGTTTTACAACGTCGTGACTGGGAAAACCCTGGCGTTACCCCTGCAGGACTAGTGCTG

AGGCATTAATACGACTCTCTCGAAATTTTTCTTAACGCGTCCTTGTACTGCGTCTAACG

CTTTTGCCACTTGGATTTCTATTATAGGAAATAGTCTCACTTACTGGGCGACGAATTTT

CGCGTTTTGATGAAGCACAGGAAGAATTTCTTTTTTTTTGGCTTCTTCTGGTTCCGTT

TTTTACGCGCACAAATCTAAAAAAAGAAATAATTATAACCTAGTCTCGAAAATTTTCAT

CGATCCATTCGTTCCTTTTTTCGATTTTTTCAGATCAAAATTCTTGTTTCTTTCTTTG

TCTTAGTTTATATTAAAAGATATTTTGATTTTACTCCTGAACTATTTATTCTTTCTAAG

AAGGCCAGAACACTACAGCTGTTTTAACCGACTACGAAGTTCTCCATTCTCGAACACTA

GCCTTCATTTACCAAACAGGAACTAGCGTATATCATTAGTCCTTATTCGAAAAGAGATT

GGTAGATATTTATTGTAGTTTGTGAGAAGGAGAAAATACTGTCATTGGACTGATAGTTA

GAGGACATTAACCTCTCTTACGTTCGCTCA

SEQ. ID NO: 54
ATCCGGATATAGTTCCTCCTTTCAGCAAAAAACCCCTCAAGACCCGTTTAGAGGCCCCA

AGGGGTTATGCTAGTTATTGCTCAGCGGTGGCAGCAGCCAACTCAGCTTCCTTTCGGGC

TTTGTTAGCAGCCGGATCTCAGTGGTGGTGGTGGTGCTCGAGTGCGGCCGCAAGCT

TGTCGACGGAGCTCGAATTCGGATCCGAATTAATTCCGATATCCATGGCCATCGCCGGC

TGGGCAGCGAGGAGCAGCAGACCAGCAGCAGCGGTCGGCAGCAGGTATTTCATATGTAT

ATCTCCTTCTTAAAGTTAAACAAAATTATTTCTAGAGGGGAATTGTTATCCGCTCACAA

TTCCCCTATAGTGAGTCGTATTAATTTCGCGGGATCGAGATCTCGATCCTCTACGCCGG

ACGCATCGTGGCCGGCATCACCGGCGCCACAGGTGCGGTTGCTGGCGCCTATATCGCCG

ACATCACCGATGGGGAAGATCGGGCTCGCCACTTCGGGCTCATGAGCGCTTGTTTCGGC

GTGGGTATGGTGGCAGGCCCCGTGGCCGGGGACTGTTGGGCGCCATCTCCTTGCATGC

ACCATTCCTTGCGGCGGCGGTGCTCAACGGCCTCAACCTACTACTGGGCTGCTTCCTAA

TGCAGGAGTCGCATAAGGGAGAGCGTCGAGATCCCGGACACCATCGAATGGCGCAAAAC

CTTTCGCGGTATGGCATGATAGCGCCCGGAAGAGAGTCAATTCAGGGTGGTGAATGTGA

AACCAGTAACGTTATACGATGTCGCAGAGTATGCCGGTGTCTCTTATCAGACCGTTTCC

CGCGTGGTGAACCAGGCCAGCCACGTTTCTGCGAAAACGCGGGAAAAAGTGGAAGCGGC

GATGGCGGAGCTGAATTACATTCCCAACCGCGTGGCACAACAACTGGCGGGCAAACAGT

CGTTGCTGATTGGCGTTGCCACCTCCAGTCTGGCCCTGCACGCGCCGTCGCAAATTGTC

GCGGCGATTAAATCTCGCGCCGATCAACTGGGTGCCAGCGTGGTGGTGTCGATGGTAGA

ACGAAGCGGCGTCGAAGCCTGTAAAGCGGCGGTGCACAATCTTCTCGCGCAACGCGTCA

GTGGGCTGATCATTAACTATCCGCTGGATGACCAGGATGCCATTGCTGTGGAAGCTGCC

-continued

```
TGCACTAATGTTCCGGCGTTATTTCTTGATGTCTCTGACCAGACACCCATCAACAGTAT
TATTTTCTCCCATGAAGACGGTACGCGACTGGGCGTGGAGCATCTGGTCGCATTGGGTC
ACCAGCAAATCGCGCTGTTAGCGGGCCCATTAAGTTCTGTCTCGGCGCGTCTGCGTCTG
GCTGGCTGGCATAAATATCTCACTCGCAATCAAATTCAGCCGATAGCGGAACGGGAAGG
CGACTGGAGTGCCATGTCCGGTTTTCAACAAACCATGCAAATGCTGAATGAGGGCATCG
TTCCCACTGCGATGCTGGTTGCCAACGATCAGATGGCGCTGGGCGCAATGCGCGCCATT
ACCGAGTCCGGGCTGCGCGTTGGTGCGGATATCTCGGTAGTGGGATACGACGATACCGA
AGACAGCTCATGTTATATCCCGCCGTTAACCACCATCAAACAGGATTTTCGCCTGCTGG
GGCAAACCAGCGTGGACCGCTTGCTGCAACTCTCTCAGGGCCAGGCGGTGAAGGGCAAT
CAGCTGTTGCCCGTCTCACTGGTGAAAAGAAAAACCACCCTGGCGCCCAATACGCAAAC
CGCCTCTCCCCGCGCGTTGGCCGATTCATTAATGCAGCTGGCACGACAGGTTTCCCGAC
TGGAAAGCGGGCAGTGAGCGCAACGCAATTAATGTAAGTTAGCTCACTCATTAGGCACC
GGGATCTCGACCGATGCCCTTGAGAGCCTTCAACCCAGTCAGCTCCTTCCGGTGGGCGC
GGGGCATGACTATCGTCGCCGCACTTATGACTGTCTTCTTTATCATGCAACTCGTAGGA
CAGGTGCCGGCAGCGCTCTGGGTCATTTTCGGCGAGGACCGCTTTCGCTGGAGCGCGAC
GATGATCGGCCTGTCGCTTGCGGTATTCGGAATCTTGCACGCCCTCGCTCAAGCCTTCG
TCACTGGTCCCGCCACCAAACGTTTCGGCGAGAAGCAGGCCATTATCGCCGGCATGGCG
GCCCCACGGGTGCGCATGATCGTGCTCCTGTCGTTGAGGACCCGGCTAGGCTGGCGGGG
TTGCCTTACTGGTTAGCAGAATGAATCACCGATACGCGAGCGAACGTGAAGCGACTGCT
GCTGCAAAACGTCTGCGACCTGAGCAACAACATGAATGGTCTTCGGTTTCCGTGTTTCG
TAAAGTCTGGAAACGCGGAAGTCAGCGCCCTGCACCATTATGTTCCGGATCTGCATCGC
AGGATGCTGCTGGCTACCCTGTGGAACACCTACATCTGTATTAACGAAGCGCTGGCATT
GACCCTGAGTGATTTTCTCTGGTCCCGCCGCATCCATACCGCCAGTTGTTTACCCTCA
CAACGTTCCAGTAACCGGGCATGTTCATCATCAGTAACCCGTATCGTGAGCATCCTCTC
TCGTTTCATCGGTATCATTACCCCCATGAACAGAAATCCCCCTTACACGGAGGCATCAG
TGACCAAACAGGAAAAAACCGCCCTTAACATGGCCCGCTTTATCAGAAGCCAGACATTA
ACGCTTCTGGAGAAACTCAACGAGCTGGACGCGGATGAACAGGCAGACATCTGTGAATC
GCTTCACGACCACGCTGATGAGCTTTACCGCAGCTGCCTCGCGCGTTTCGGTGATGACG
GTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGCGC
AGCCATGACCCAGTCACGTAGCGATAGCGGAGTGTATACTGGCTTAACTATGCGGCATC
AGAGCAGATTGTACTGAGAGTGCACCATATATGCGGTGTGAAATACCGCACAGATGCGT
AAGGAGAAAATACCGCATCAGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCC
```

-continued

```
CCCGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTACACTAGAAGG

ACAGTATTTGGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTTGCAAGCAGC

AGATTACGCGCAGAAAAAAGGATCTCAAGAAGATCCTTTGATCTTTTCTACGGGGTCT

GACGCTCAGTGGAACGAAAACTCACGTTAAGGGATTTTGGTCATGAACAATAAAACTGT

CTGCTTACATAAACAGTAATACAAGGGGTGTTATGAGCCATATTCAACGGGAAACGTCT

TGCTCTAGGCCGCGATTAAATTCCAACATGGATGCTGATTTATATGGGTATAAATGGGC

TCGCGATAATGTCGGGCAATCAGGTGCGACAATCTATCGATTGTATGGGAAGCCCGATG

CGCCAGAGTTGTTTCTGAAACATGGCAAAGGTAGCGTTGCCAATGATGTTACAGATGAG

ATGGTCAGACTAAACTGGCTGACGGAATTTATGCCTCTTCCGACCATCAAGCATTTTAT

CCGTACTCCTGATGATGCATGGTTACTCACCACTGCGATCCCCGGGAAAACAGCATTCC

AGGTATTAGAAGAATATCCTGATTCAGGTGAAAATATTGTTGATGCGCTGGCAGTGTTC

CTGCGCCGGTTGCATTCGATTCCTGTTTGTAATTGTCCTTTTAACAGCGATCGCGTATT

TCGTCTCGCTCAGGCGCAATCACGAATGAATAACGGTTTGGTTGATGCGAGTGATTTTG

ATGACGAGCGTAATGGCTGGCCTGTTGAACAAGTCTGGAAAGAAATGCATAAACTTTTG

CCATTCTCACCGGATTCAGTCGTCACTCATGGTGATTTCTCACTTGATAACCTTATTTT

TGACGAGGGGAAATTAATAGGTTGTATTGATGTTGGACGAGTCGGAATCGCAGACCGAT

ACCAGGATCTTGCCATCCTATGGAACTGCCTCGGTGAGTTTTCTCCTTCATTACAGAAA

CGGCTTTTTCAAAAATATGGTATTGATAATCCTGATATGAATAAATTGCAGTTTCATTT

GATGCTCGATGAGTTTTTCTAAGAATTAATTCATGAGCGGATACATATTTGAATGTATT

TAGAAAAATAAACAAATAGGGGTTCCGCGCACATTTCCCCGAAAAGTGCCACCTGAAAT

TGTAAACGTTAATATTTTGTTAAAATTCGCGTTAAATTTTTGTTAAATCAGCTCATTTT

TTAACCAATAGGCCGAAATCGGCAAAATCCCTTATAAATCAAAAGAATAGACCGAGATA

GGGTTGAGTGTTGTTCCAGTTTGGAACAAGAGTCCACTATTAAAGAACGTGGACTCCAA

CGTCAAAGGGCGAAAAACCGTCTATCAGGGCGATGGCCCACTACGTGAACCATCACCCT

AATCAAGTTTTTTGGGGTCGAGGTGCCGTAAAGCACTAAATCGGAACCCTAAAGGGAGC

CCCCGATTTAGAGCTTGACGGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCA

CCACACCCGCCGCGCTTAATGCGCCGCTACAGGGCGCGTCCCATTCGCCA
```

EXAMPLES

Example 1—Biosynthesis of a First Multi-Substituent Psilocybin Derivative

E. coli strain E1 was constructed as follows. For plasmid cloning, Top10 or XL1-blue strains were used depending on antibiotic markers. Standard LB media was used for culturing. For gene expression and feeding experiments, the parent host strain employed was BL21 (DE3). First, the plasmid pET28a(+)-PfTrpB-B0A9-HIS was created by inserting an in-frame, HIS tagged (SEQ.ID NO: 46) PfTrpB-B0A9 gene (SEQ.ID NO: 1) into the NdeI/XhoI site of pET28a(+) (SEQ.ID NO: 36). As a second step, from plasmid pCDM4 (SEQ.ID NO: 35), the plasmid pCDM4-BaTDC-HIS was created by inserting an in-frame, HIS-tagged (SEQ.ID NO: 46) BaTDC gene (SEQ.ID NO: 3) into the NdeI/XhoI site of pCDM4. Finally, from plasmid pET23a(+) (SEQ.ID NO: 37), the plasmid pET23a(+)-PsmF-HIS was created by inserting an in-frame, HIS-tagged (SEQ.ID NO: 46) PsmF gene (SEQ.ID NO: 9) into the Nde1/Xho1 site of pET23a (+). The target plasmids pET28a(+)-PfTrpB-B0A9-HIS, pCDM4-BaTDC-HIS and pET23a(+)-PsmF-HIS were transformed into BL21 (DE3) cells as follows: pCDM4-BaTDC-HIS was transformed into BL21 (DE3) first, and transformants selected using streptomycin were transformed with pET28a(+)-PfTrpB-B0A9-HIS and pET23a(+)-PsmF-HIS together. The final E. coli strain (Ec-1) was selected with streptomycin, ampicillin, and kanamycin. Scaled-up culturing of engineered E. coli was conducted as follows:

seed cultures were inoculated in AMM (Jones et al., 2015, Sci Rep. 5: 11301) medium overnight. The overnight culture was then divided into two flasks containing 500 mL each of AMM medium additionally containing 0.5% (w/v) serine, 1M IPTG, 50 ug/L streptomycin, ampicillin, and kanamycin, and 100 mg/L indole feedstock (6-fluoro-1H-indol-4-ylamine; www.bldpharm.com) for conversion by Ec-1. Cultures were grown for 24 h. Cultures were then centrifuged (10,000 g×5 minutes) to remove cellular content, and culture broth containing secreted derivative was combined and stored at −80° C. until further processing. To 1.0 L of broth, 10M NaOH solution was added until the pH reached ~7. The culture was then extracted by ethyl acetate (4×600 ml). The organic layer was combined and dried over $Na_2SO_4$, followed by concentration under reduced pressure. The residue was purified by flash chromatography on silica gel (1→2% metanol in dichloromethane), to give the compound as a light yellow solid (7 mg). Following purification, high-resolution MS (HRMS), $^1$H NMR, and selective $^{13}$C NMR were performed to assess purity, estimate total quantity, and confirm molecular structure. $^1$H NMR (400 MHz, $CD_3OD$): δ=1.94 (s, 3H), 3.00 (m, 2H), 3.38 (m, 2H), 6.10 (dd, J=11.7, 2.2 Hz, 1H), 6.38 (dd, J=9.7, 2.2 Hz, 1H), 6.84 (s, 1H). $^{13}$C NMR (100 MHz, $CD_3OD$): δ=21.0, 29.2, 41.9, 87.1 (d, $J_{C,F}$=26.1 Hz), 92.6 (d, $J_{C,F}$=27.8 Hz), 111.6, 112.4, 120.7, 138.0 (d, $J_{C,F}$=15.0 Hz), 141.7 (d, $J_{C,F}$=13.2 Hz), 160.7 (d, $J_{C,F}$=232.5 Hz), 172.1. HRMS (ESI) m/z: calcd. for $C_{12}H_{14}FN_3O$ $[M+H]^+$ 236.1194, found 236.1189. Purity was determined as 95% w/w. It is noted that these data confirm a chemical structure corresponding with that of example compound (IX):

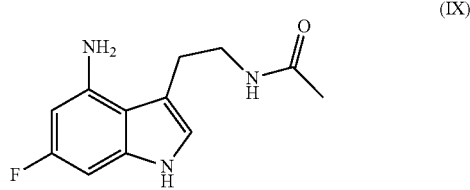 [SMILES: CC(=O)NCCc1c[nH]c2cc(F)cc(N)c12]

(IX)

set forth herein.

Assessment of Cell Viability Upon Treatment of a Psilocybin Derivative

Figure 15A:
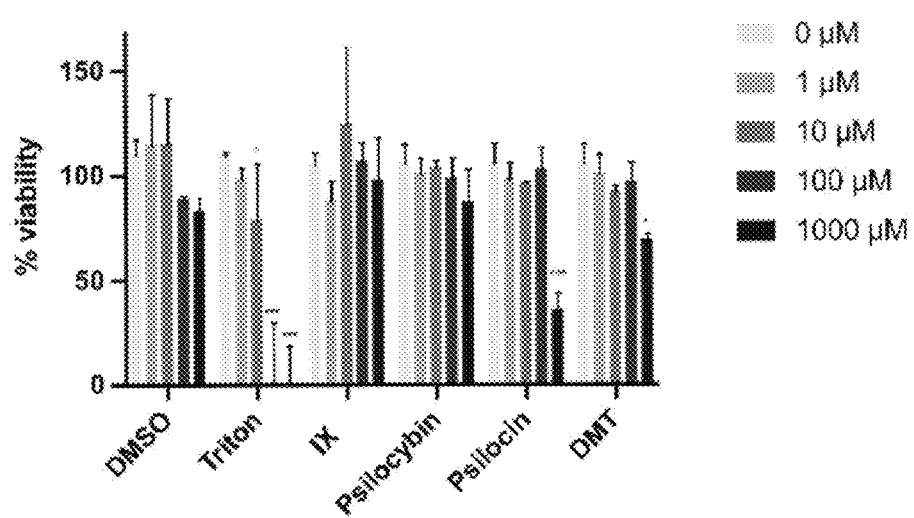
FIGS. 15A, 15B, 15C, 15D, 15E, 15F, 15G and 15H depict various graphs, obtained in the performance of experimental assays to evaluate the efficacy of an example prenylated psilocybin derivative having the chemical formula (IX) set forth herein, notably a cell viability assay for a multi-substituent psilocybin derivative having the chemical formulae (IX) (FIG. 15A); a saturation binding assay for [$^3$H]ketanserin at the 5-HT$_{2A}$ receptor (FIG. 15B); a competition assay for psilocin as a positive control (binding) (Panel A); and a competition assay for tryptophan as a negative control (no binding) (Panel B) (FIG. 15C); a competition assay for a multi-substituent psilocybin derivative compound with formula (IX), designated "IX" (FIG. 15D, plotted with two different Y-axes, panel A and panel B, for clarity); a cAMP assay in the presence of constant (4 μM) forskolin and with increasing concentration of psilocin in +5HT$_{1A}$ cells and −5HT$_{1A}$ cells (FIG. 15E); a cAMP assay in the presence of constant (4 μM) forskolin and 10 μM serotonin, and with increasing concentrations of serotonin +5HT$_{1A}$ cells and −5HT$_{1A}$ cells (FIG. 15F); a cAMP assay in the presence of constant (4 μM) forskolin and, and with increasing concentrations of tryptophan in +5HT$_{1A}$ cells and −5HT$_{1A}$ cells a cAMP assay (FIG. 14G); and a cAMP assay in the of constant (4 μM) forskolin, and with increasing concentration of multi-substituent psilocybin derivative compound having formula (IX), designated "IX" in +5HT$_{1A}$ cells and −5HT$_{1A}$ cells (FIG. 15H).

To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivative, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 μM, 10 μM, 100 μM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+/−SD, n=3. Significance was determined by 2-way ANOVA followed by Dunnett's multiple comparison test and is indicated by *(P<0.0001), (P<0.001), *(P<0.005). Data acquired for the derivative having chemical formula (IX) is displayed as "IX" on the x-axis of FIG. 15A.

Radioligand Receptor Binding Assays.

Figure 15B:
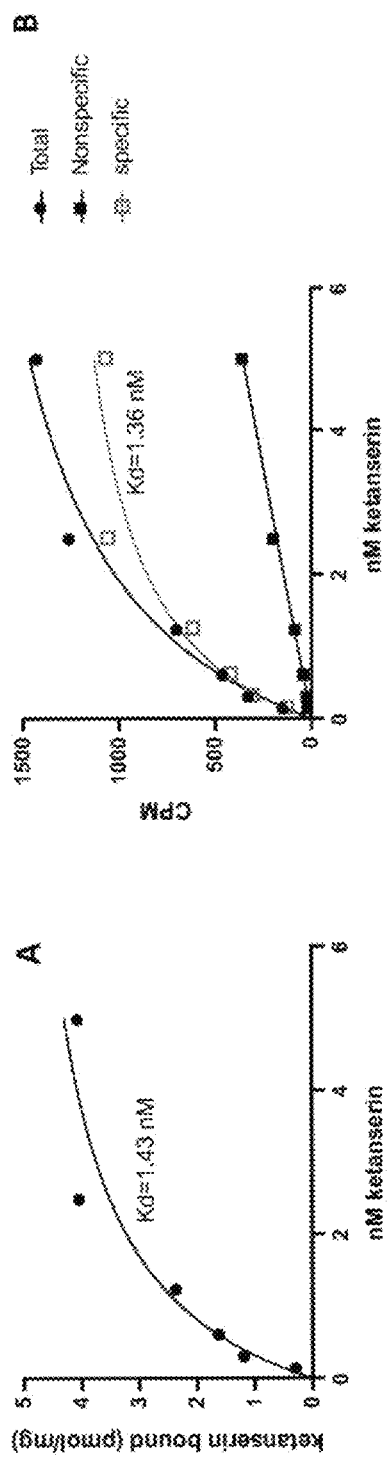
Figure 15C:
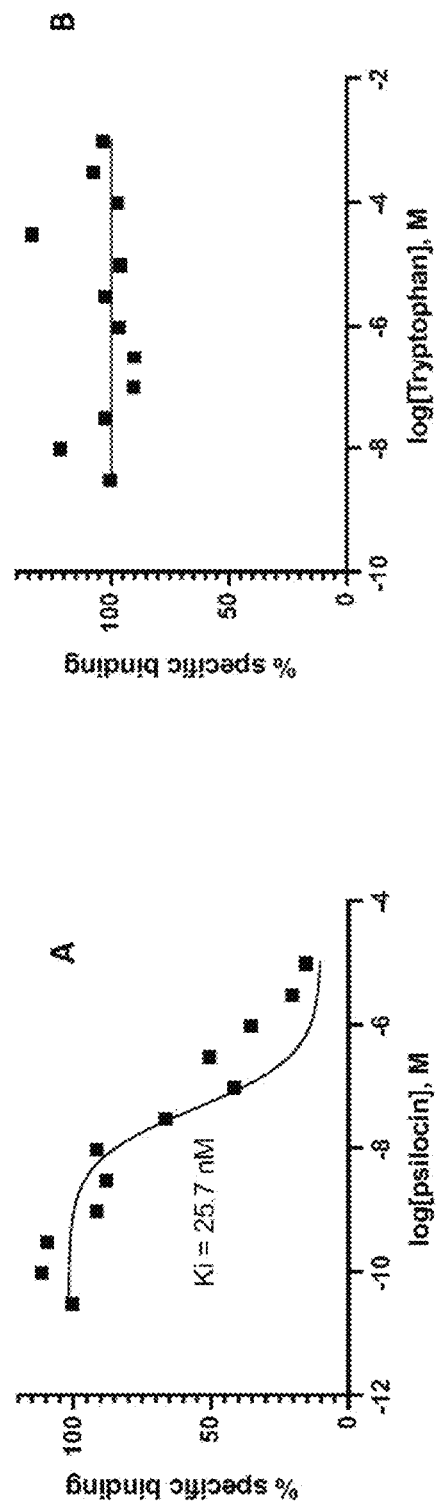
Figure 15D:
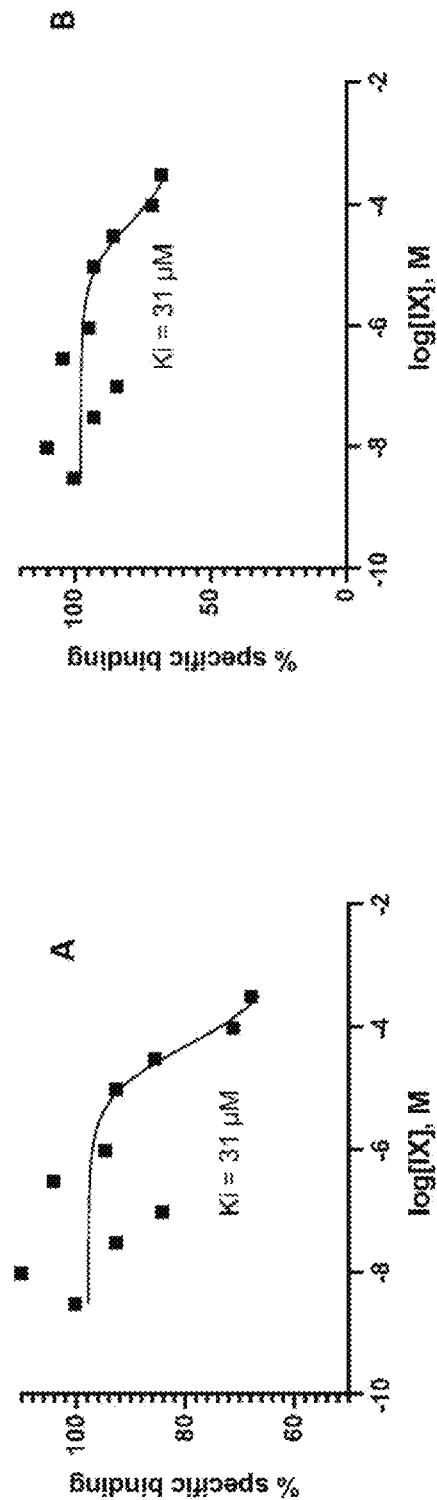

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (Núñez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-$HT_{2A}$, [$^3$H]ketanserin is a well-established antagonist used routinely in competition assays to evaluate competitive activity of novel drug candidates at the 5-$HT_{2A}$ receptor (Maguire et al., 2012, Methods Mol Biol 897: 31). Thus, to evaluate activity of novel psilocybin derivatives at the 5-$HT_{2A}$ receptor, competition assays using [$^3$H]ketanserin were employed as follows. SPA beads (RPNQ0010), [$^3$H] ketanserin (NET1233025UC), membranes containing 5-$HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-$HT_{2A}$ receptor was pre-coupled to 1 mg of SPA beads at room temperature in a tube rotator for 1 hour in binding buffer (50 mM Tris-HCl pH7.4, 4 mM $CaCl_2$, 1 mM ascorbic acid, 10 mM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 mM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H]ketanserin and different concentrations of tryptophan (3 nM to 1 mM), psilocin (30 μM to 10 mM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the $5\text{-HT}_{2A}$ receptor. In contrast, psilocin was used as a positive control since it has established binding activity at the $5\text{-HT}_{2A}$ receptor (Kim et al., 2020, Cell 182: 1574). FIG. 15B depicts the saturation binding curves for [$^3$H]ketanserin at the $5\text{-HT}_{2A}$ receptor. Panel A shows the specific saturation ligand binding of [$^3$H]ketanserin (from 0.1525 nM to 5 nM) to membranes containing $5\text{-HT}_{2A}$ receptor, which was obtained after subtracting non-specific binding values (shown in Panel B). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 15C (Panel A) shows the competition binding curve for psilocin as a positive control (binding). (Panel B) shows the competition binding curve for tryptophan as a negative control (no binding). FIG. 15D shows competition binding curves for compound with formula (IX), designated "IX" in the figure. Notably, competition of compound (IX) for $5\text{-HT}_{2A}$ sites occupied by [$^3$H]ketanserin does not appear complete, as suggested by only ~50% specific binding (refer to Panel B, which replots data of Panel A with a reformatted y-axis for clarity). It is known that ketanserin binds both primary sites normally occupied by agonist (e.g., serotonin) in addition to other sites of $5\text{-HT}_{2A}$ (Sleight et al., 1996, Biochem Pharmacol 51: 71); thus, incomplete competition by compound (IX) implies this derivative competes for a particular subset (i.e., fraction) of the total sites bound by ketanserin.

Cell Lines and Control Ligands Used to Assess Activity at $5\text{-HT}_{1A}$.

CHO-K1/$G_{\alpha15}$ (GenScript, M00257) ($-5\text{-HT}_{1A}$) and CHO-K1/$5\text{-HT}_{1A}$/$G_{\alpha15}$ (GenScript, M00330) ($+5\text{-HT}_{1A}$) cells lines were used. Briefly, CHO-K1/$G_{\alpha15}$ is a control cell line that constitutively expresses $G_{\alpha15}$ which is a promiscuous $G_q$ protein. This control cell line lacks any transgene encoding $5\text{-HT}_{1A}$ receptors, but still responds to forskolin; thus, cAMP response to forskolin should be the same regardless of whether or not $5\text{-HT}_{1A}$ agonists are present. Conversely, CHO-K1/$5\text{-HT}_{1A}$/$G_{\alpha15}$ cells stably express $5\text{-HT}_{1A}$ receptor in the CHO-K1 host background. Notably, $G_{\alpha15}$ is a promiscuous G protein known to induce calcium flux response, present in both control and $5\text{-HT}_{1A}$ cell lines. In $+5\text{-HT}_{1A}$ cells, $G_{\alpha15}$ may be recruited in place of $G_{\alpha i/o}$, which could theoretically dampen cAMP response (Rojas and Fiedler 2016, Front Cell Neurosci 10: 272). Thus, we included two known $5\text{-HT}_{1A}$ agonists, psilocin (Blair et al., 2000, J Med Chem 43: 4701) and serotonin (Rojas and Fiedler 2016, Front Cell Neurosci 10: 272) as positive controls to ensure sufficient cAMP response was observed, thereby indicating measurable recruitment of $G_{\alpha i/o}$ protein to activated $5\text{-HT}_{1A}$ receptors. In contrast, tryptophan is not known to activate, or modulate in any way, $5\text{-HT}_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 μg/ml zeocin (Thermo Scientific #R25005) and/or 100 μg/ml hygromycin (Thermo Scientific #10687010). The cells were cultured in a humidified incubator with 37° C. and 5% $CO_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of $5\text{-HT}_{1A}$ Receptor Modulation

Figure 15E:
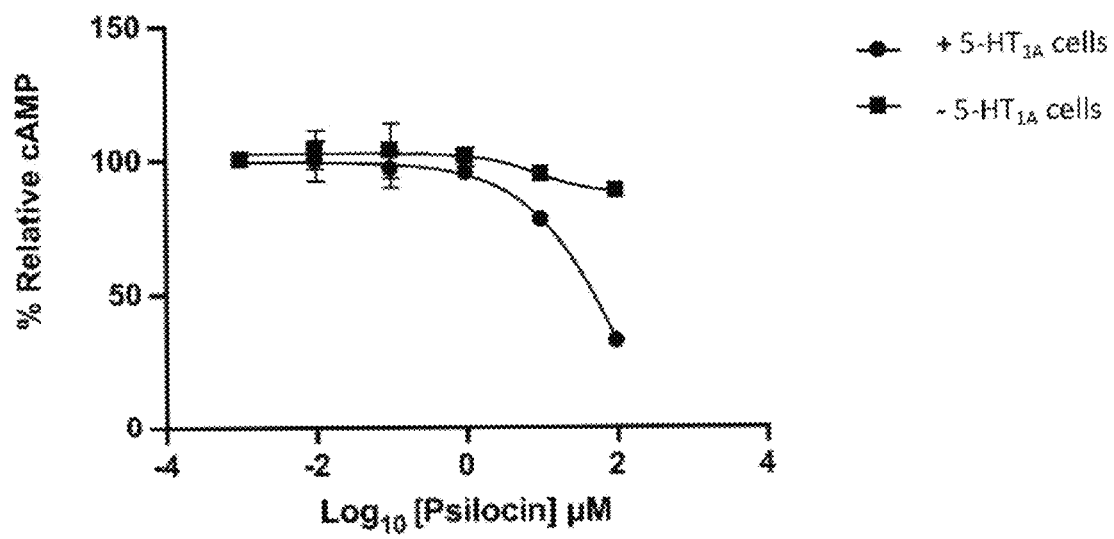
Figure 15F:
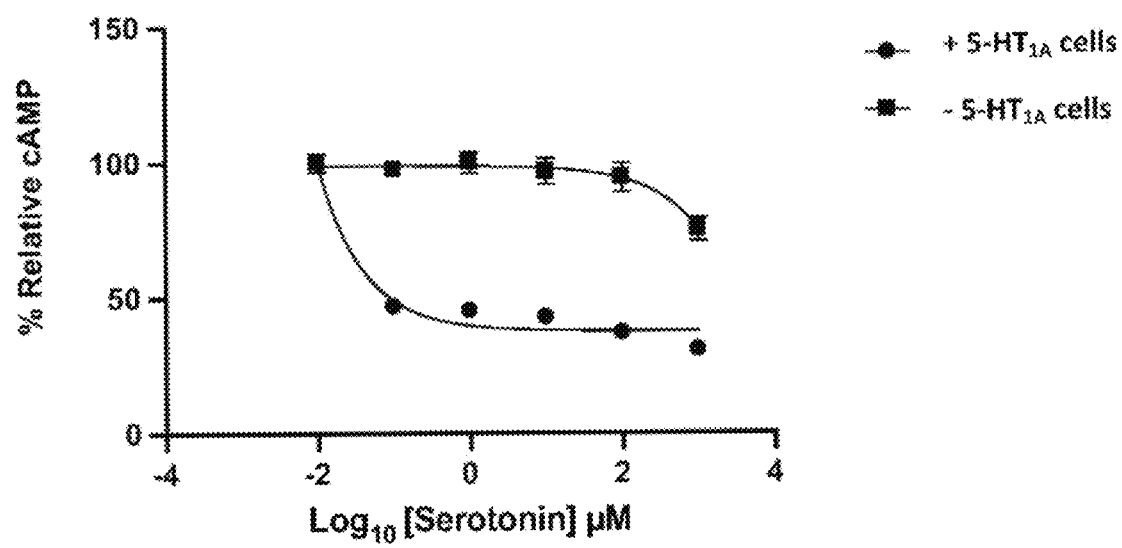
Figure 15G:
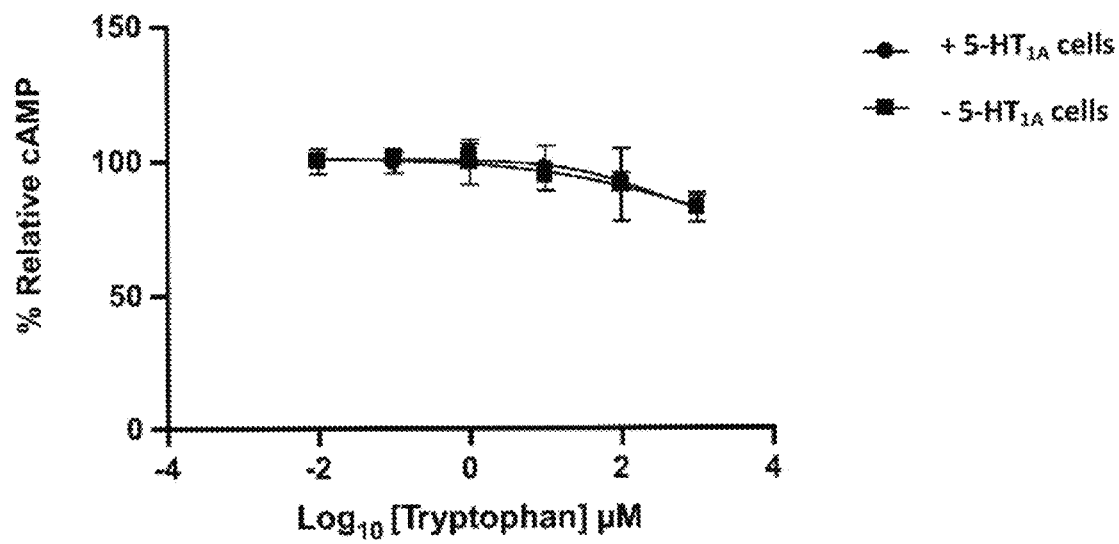
Figure 15H:
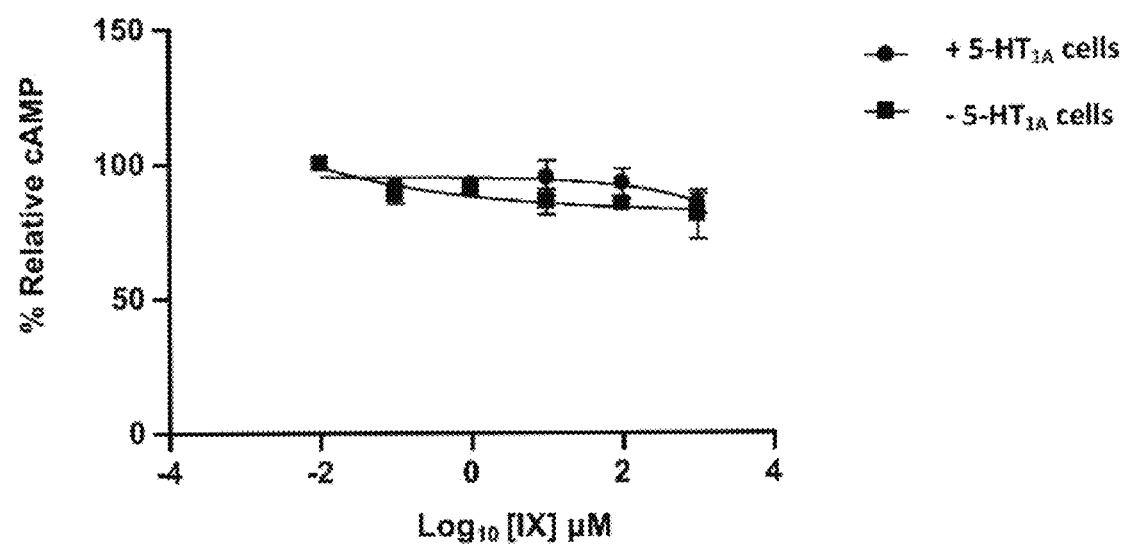

As $5\text{-HT}_{1A}$ activation inhibits cAMP formation, the ability of test molecules to modulate $5\text{-HT}_{1A}$ response was measured via changes in the levels of cAMP produced due to application of 4 μM forskolin. Changes (should any significant change occur) in intracellular cAMP levels due to the treatment of novel molecule was evaluated using cAMP-Glo Assay kit (Promega #V1501). Briefly, $+5\text{-HT}_{1A}$ cells were seeded on 1-6 columns and base $-5\text{-HT}_{1A}$ cells were seeded on columns 7-12 of the white walled clear bottom 96-well plate (Corning, #3903). Both cells were seeded at the density of 30,000 cells/well in 100 μl complete growth media and cultured 24 hrs in humidified incubator at 37° C. and 5% $CO_2$. On the experiment day, the media of cells was replaced with serum/antibiotic free culture media. Then the cells were treated for 20 minutes with test molecules dissolved in induction medium (serum/antibiotic free culture media containing 4 μM forskolin, 500 mM IBMX (isobutyl-1-methylxanthine, Sigma-Aldrich, Cat. #17018) and 100 mM (RO 20-1724, Sigma-Aldrich, Cat. #B8279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result $5\text{-HT}_{1A}$ activation. In summary: this signal cascade permits $5\text{-HT}_{1A}$ activation (positive modulation) by a test molecule to be measured in terms of decreasing % cAMP formation. Conversely, enhanced % cAMP is expected when $5\text{-HT}_{1A}$ receptor is negatively modulated by a test molecule. Finally, no significant change in % cAMP—beyond that observed for negative control experiments (e.g., with tryptophan)—indicates that a test molecule does not bind $5\text{-HT}_{1A}$ or that binding imparts a silent response. FIG. 15E shows decreased % cAMP in $+5\text{HT}_{1A}$ compared to $-5\text{HT}_{1A}$ cultures, in the presence of fixed (4 μM) forskolin, as dosages of psilocin increase, revealing $5\text{-HT}_{1A}$ activity of psilocin. FIG. 15F shows decreased % cAMP in $+5\text{HT}_{1A}$ compared to $-5\text{HT}_{1A}$ cultures, in the presence of fixed (4 μM) forskolin, as dosages of serotonin increase, revealing $5\text{-HT}_{1A}$ activity of serotonin. FIG. 15G shows no significant difference in % cAMP for $+5\text{HT}_{1A}$ compared to $-5\text{HT}_{1A}$ cultures, in the presence of fixed (4 μM) forskolin, as dosages of tryptophan increase, revealing no modulation of $5\text{-HT}_{1A}$ activity for tryptophan. FIG. 15H shows no significant difference in % cAMP for $+5\text{HT}_{1A}$ compared to $-5\text{HT}_{1A}$ cultures, in the presence of fixed (4 μM) forskolin, as dosages of compound (X) increase, revealing no modulation of $5\text{-HT}_{1A}$ activity for compound (X). Note that compound (X) is shown simply as "X" along the x-axis. FIG. 15H shows no significant difference in % cAMP for $+5\text{HT}_{1A}$ compared to $-5\text{HT}_{1A}$ cultures, in the presence of fixed (4 μM) forskolin, as dosages of compound (IX) increase, revealing no modulation of $5\text{-HT}_{1A}$ activity for compound (IX). Note that compound (IX) is shown simply as "IX" along the x-axis. For FIGS. 15E-15H, cAMP levels are reported relative (%) to values observed in ligand-free (0 mM) samples; the value "0" along the x-axis refers to a ligand concentration of 0.0001 mM; and when present, error bars represent results of three experiments (n=3).

Example 2—Biosynthesis of a Second Multi-Substituent Psilocybin Derivative

*Escherichia coli* strain Ec-1 was used to biosynthesize psilocybin derivative with formula (X) from derivatized indole feedstock. The construction of Ec-1 is described in Example 1. Scaled-up culturing and material storage of engineered *E. coli* was conducted as described in Example 1, except that 4-fluoro-1H-indol-6-ylamine (Combi-Blocks, www.combi-blocks.com) was used in place of 6-fluoro-1H-indol-4-ylamine. Scaled-up culturing and processing of engineered *E. coli* was conducted as described in Example 1, except that a total of 2.0 L was cultured. Two litres of *E. coli* culture broth was extracted by ethyl acetate (4×1.2 L). The organic layer was combined and dried over $Na_2SO_4$, followed by concentration under reduced pressure. The residue was purified by flash chromatography on silica gel (1->3% metanol in dichloromethane), to give the compound as a yellow solid (5 mg). Following purification, high-resolution MS (HRMS), $^1$H NMR, and selective $^{13}$C NMR were performed to assess purity, estimate total quantity, and confirm molecular structure. $^1$H NMR (400 MHz, $CD_3OD$): δ=1.92 (s, 3H), 2.14 (s, 3H), 2.98 (t, J=7.2, 2H), 3.47 (t, J=7.2, 2H), 6.82 (dd, J=12.9, 1.6 Hz, 1H), 7.00 (s, 1H), 7.56 (d, J=1.6 Hz, 1H). $^{13}$C NMR (100 MHz, $CD_3OD$): δ=21.1, 22.4, 25.9, 40.5 (d, $J_{C,F}$=2.0 Hz), 97.5 (d, $J_{C,F}$=24.0 Hz), 98.9 (d, $J_{C,F}$=3.4 Hz), 110.5 (d, $J_{C,F}$=2.8 Hz), 112.6 (d, $J_{C,F}$=20.0 Hz), 122.6, 133.1 (d, $J_{C,F}$=10.5 Hz), 139.2 (d, $J_{C,F}$=13.6 Hz), 156.2 (d, $J_{C,F}$=242.5 Hz), 170.0, 171.8. HRMS (ESI) m/z: calcd. for $C_{12}H_{16}FN_3O_2$ $[M+H]^+$ 278.1299, found 278.1298. Purity was determined as 95% w/w. It is noted that these data confirm a chemical structure corresponding with that of example compound (X):

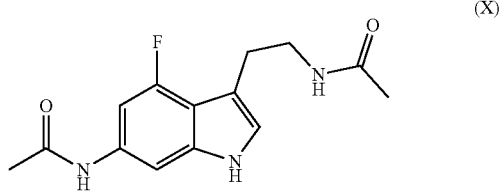 [SMILES: CC(=O)NCCc1c[nH]c2cc(NC(C)=O)cc(F)c12]

(X)

set forth herein.

Assessment of Cell Viability Upon Treatment of Psilocybin Derivative

Figure 16A:
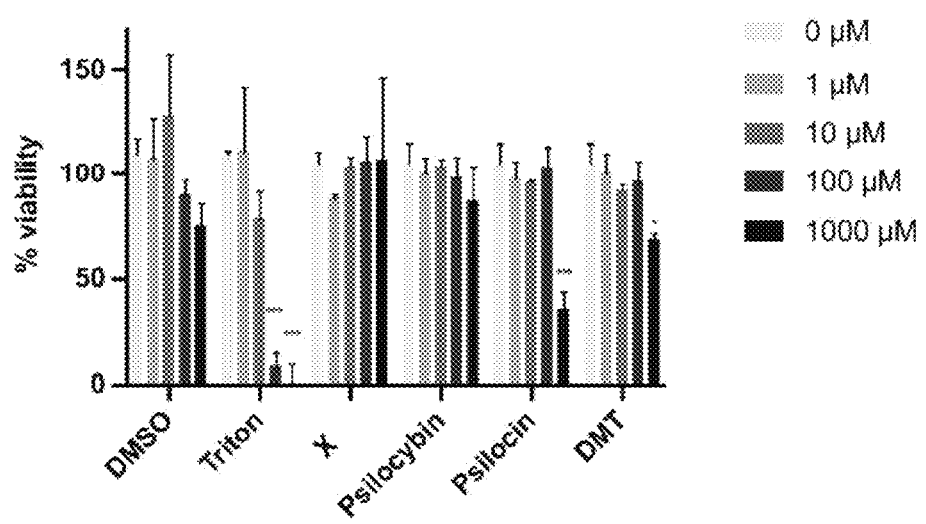
FIGS. 16A, 16B, and 16C depict various graphs, obtained in the performance of experimental assays to evaluate the efficacy of an example prenylated psilocybin derivative having the chemical formula (X) set forth herein, notably a cell viability assay for a multi-substituent psilocybin derivative having the chemical formulae (IX) (FIG. 16A); a competition assay for a multi-substituent psilocybin derivative compound with formula (IX), designated "IX" (FIG. 16B); and a cAMP assay in the of constant (4 μM) forskolin, and with increasing concentration of multi-substituent psilocybin derivative compound having formula (X), designated "X" in +5HT$_{1A}$ cells and −5HT$_{1A}$ cells (FIG. 15H).

Cell viability was assessed as described for Example 1, except the compound with formula (X) was evaluated in place of the compound with formula (IX). FIG. 16A shows PrestoBlue assay results for compound with formula (X), depicted on the x-axis as "X".

Radioligand Receptor Binding Assays.

Figure 16B:
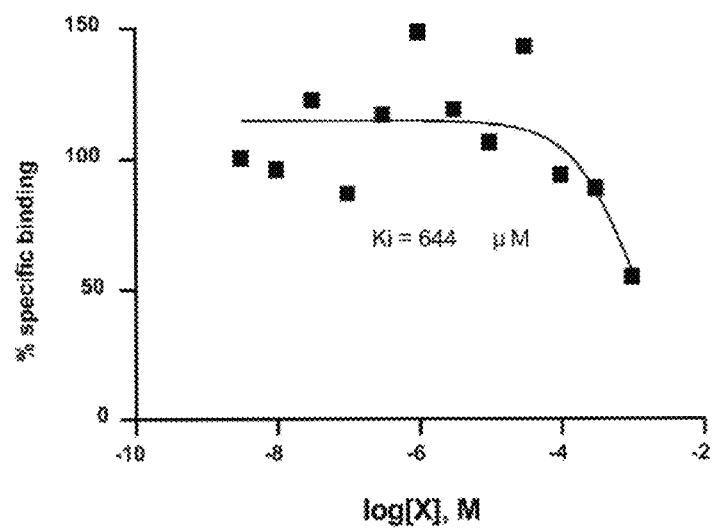

Activity at 5-$HT_{2A}$ receptor was assessed as described for Example 1, except the compound with formula (X) was evaluated in place of the compound with formula (IX). FIG. 16B shows radioligand competition assay results for compound with formula (X), depicted on the x-axis simply as "X". The relatively high $K_i$ value for the compound (X) compared with that of psilocin indicates comparatively 'loose' binding, or a mild degree of competition by compound (X) with ketanserin for 5-$HT_{2A}$ interaction. Similarly high $K_i$ values for 5-$HT_{2A}$ (e.g., micromolar range) signifying mild or 'loose' binding profiles are noted for drugs such as selegiline (Toll et al., NIDA Res. Monogr. 1998, 178: 440), an important treatment for major depressive disorder, MDMA (Simmler et al., Br. J. Pharmacol. 2013, 168: 458; Setola et al., Molec Pharmacol 2003, 63: 1223) and mescaline (Rickli et al., Neuropharmacology 2015, 99: 546) which are high-profile, potential depression treatments (Liechti et al., Curr Top Behav Neurosci 2021, doi: 10.1007/7854_2021_270).

Cell Lines, Control Ligands, and Evaluation of 5-$HT_{1A}$ Receptor Modulation

Figure 16C:
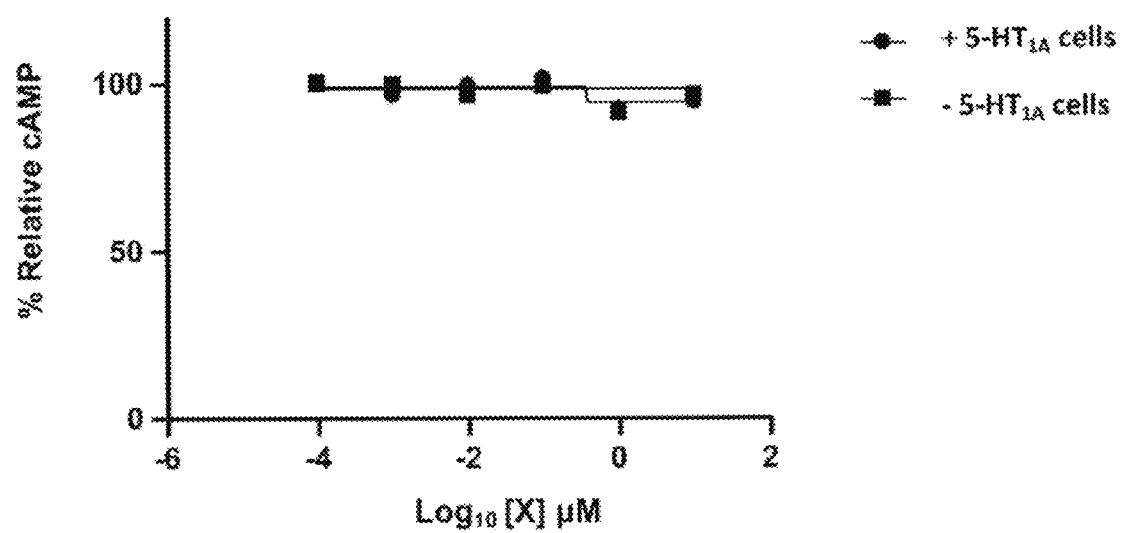

Cell lines and control ligands were as described in Example 1. Activity at 5-$HT_{1A}$ receptor was assessed as described for Example 1, except the compound with formula (X) was evaluated in place of the compound with formula (IX). FIG. 16C shows 5-$HT_{1A}$ assay results as measured in units of % relative cAMP, where compound with formula (X) is depicted on the x-axis simply as "X". FIG. 16C shows no significant difference in % cAMP for +5$HT_{1A}$ compared to −5$HT_{1A}$ cultures, in the presence of fixed (4 μM) forskolin, as dosages of compound (X) increase, revealing no modulation of 5-$HT_{1A}$ activity for compound (X).

Example 3—Biosynthesis of a Third Multi-Substituent Psilocybin Derivative

*Escherichia coli* strain Ec-1 was used to biosynthesize psilocybin derivative with formula (XII) from derivatized indole feedstock. The construction of Ec-1 is described in Example 1. Scaled-up culturing and material storage of engineered *E. coli* was conducted as described in Example 1, except that 5-fluoro-7-nitro-1H-indole (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an Ulti-Mate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 100 microliters of culture media were dried and resuspended in 100 microliters of DMSO. One tenth (10 microliters) of this suspension was injected at a flow rate of 0.5 mL/min and a gradient of solvent A (water with 0.1% of formic acid) and solvent B (ACN with 0.1% formic acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C.; source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact m/z and expected elemental formula matching the singly protonated form of N-[2-(5-fluoro-7-nitro-1H-indol-3-yl)ethyl]acetamide, having chemical formula (XII):

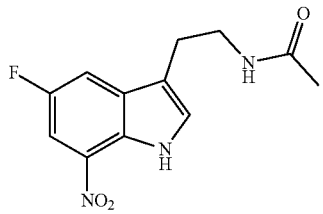

Figure 17A:
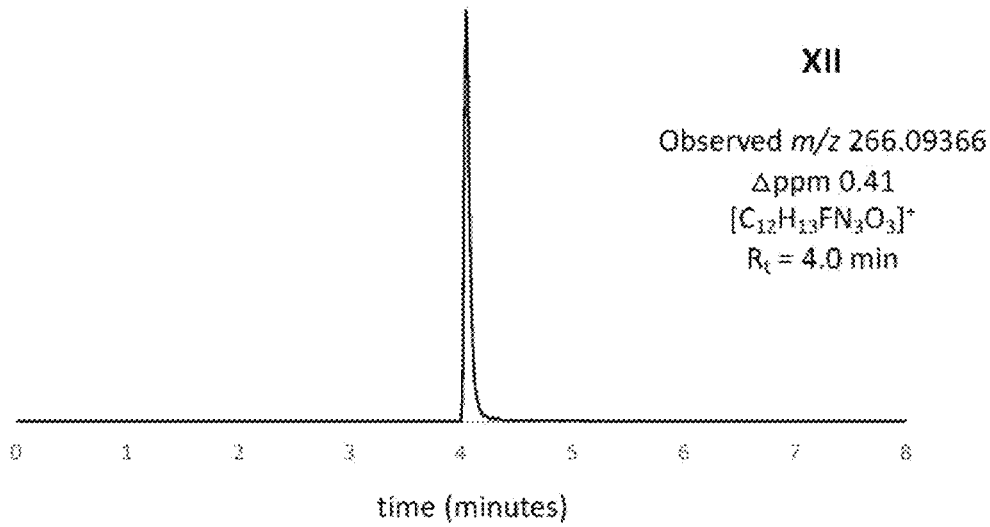
FIGS. 17 and 17B depict a representation of mass spectrometry data in the form of a chromatogram, notably a chromatogram obtained in the performance of an experiment to synthesize an example multi-substituent psilocybin derivative compound having the chemical formula (XII) set forth herein (FIG. 17A); and a representation of mass spectrometry data in the form of a further mass spectrometry spectrum obtained in the performance of an experiment to identify a multi-substituent psilocybin derivative compound having the chemical formula (XII) set forth herein (FIG. 17B).
Figure 17B:
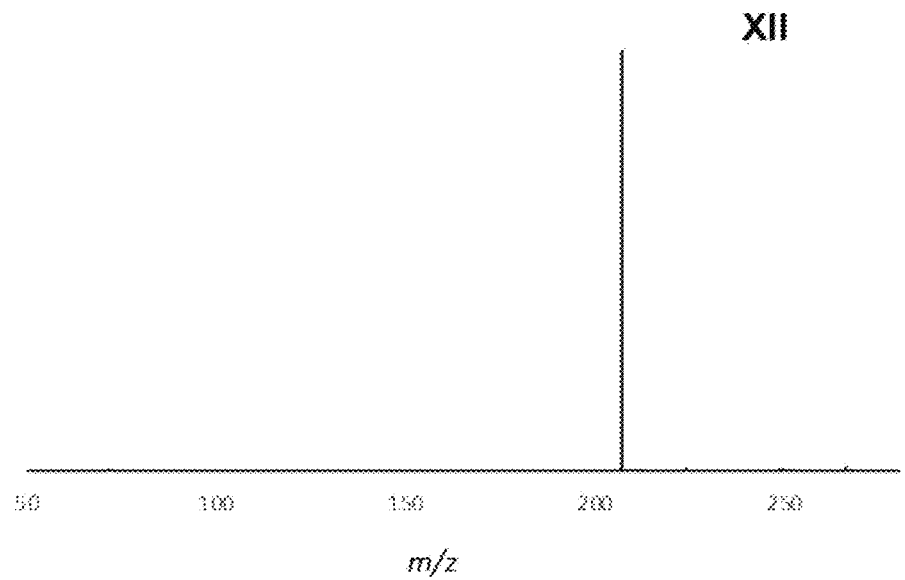

(XII)

eluted at 4.0 minutes (EIC, see: FIG. 17A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XII) as follows (FIG. 17B, Table 1) (Servillo L. et al., 2013, J. Agric. Chem. 61: 5156-5162).

TABLE 1

| m/z | % Relative abundance | Ionic species | Δ ppm |
|---|---|---|---|
| 207.05636 | 100 | $[M + H - C_2H_5NO]^+$ | 0.34 |
| 266.09362 | 1.1 | $[M + H]^+$ | 0.26 |
| 224.08303 | 0.8 | | |
| 249.06697 | 0.7 | | |
| 71.70087 | 0.5 | | |
| 66.12294 | 0.4 | | |
| 161.06346 | 0.3 | | |
| 127.24116 | 0.2 | | |
| 98.30615 | 0.2 | | |
| 192.96957 | 0.2 | | |

Example 4—Biosynthesis of a Fourth Multi-Substituent Psilocybin Derivative

*Escherichia coli* strain Ec-1 was used to biosynthesize psilocybin derivative with formula (XIV) from derivatized indole feedstock. The construction of Ec-1 is described in Example 1. Scaled-up culturing and material storage of engineered *E. coli* was conducted as described in Example 1, except that 5-fluoro-1H-indol-6-ylamine (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(6-acetylamino-5-fluoro-1H-indol-3-yl)ethyl]acetamide, having chemical formula (XIV):

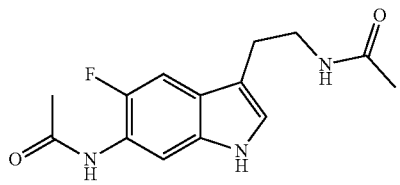

Figure 18A:
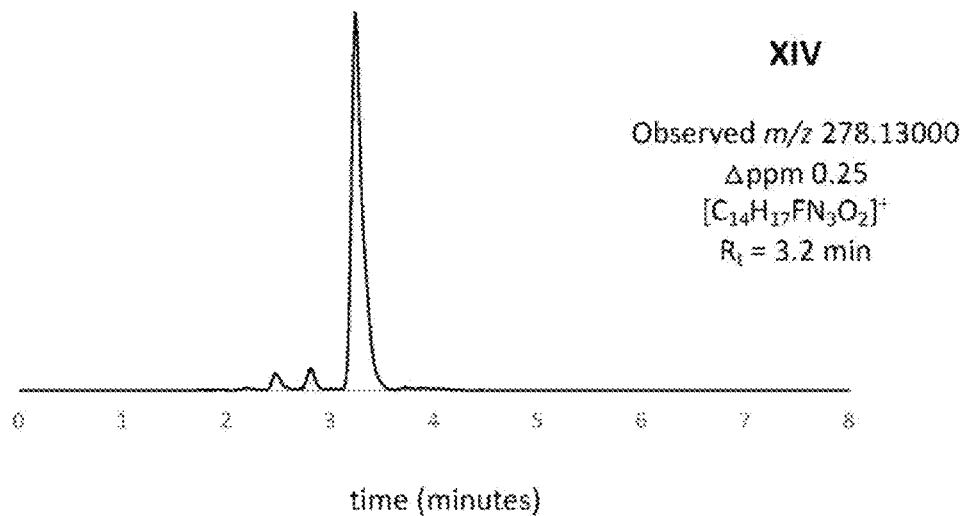
FIGS. 18A and 18B depict a representation of further mass spectrometry data in the form of a chromatogram, notably a chromatogram obtained in the performance of an experiment to synthesize an example multi-substituent psilocybin derivative compound having the chemical formula (XIV) set forth herein (FIG. 18A); and a representation of mass spectrometry data in the form of a further mass spectrometry spectrum obtained in the performance of an experiment to identify a multi-substituent psilocybin derivative compound having the chemical formula (XII) set forth herein (FIG. 18B).
Figure 18B:
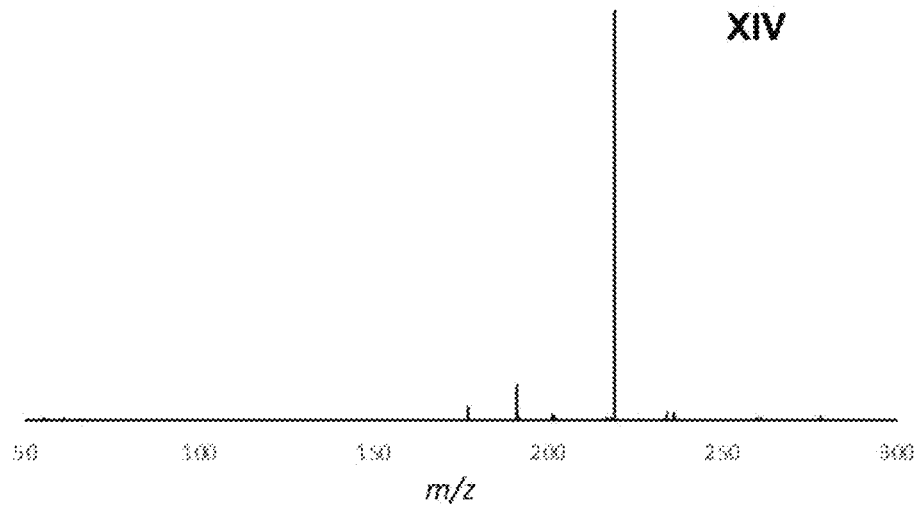

(XIV)

eluted at 3.2 minutes (EIC, see: FIG. 18A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XIV) as follows (FIG. 18B, Table 2) (Servillo L. et al., 2013, J. Agric. Chem. 61: 5156-5162).

TABLE 2

| m/z | % Relative abundance | Ionic species | Δ ppm |
|---|---|---|---|
| 219.09292 | 100 | $[M + H - C_2H_5NO]^+$ | 0.46 |
| 191.09787 | 9.0 | | |
| 177.08215 | 4.2 | | |
| 236.11933 | 2.4 | | |
| 234.10378 | 2.0 | | |
| 261.10332 | 1.4 | | |
| 278.12980 | 1.2 | $[M + H]^+$ | 0.47 |
| 226.11267 | 0.8 | | |
| 218.10916 | 0.8 | | |
| 260.11925 | 0.6 | | |

Example 5—Biosynthesis of a Fourth Multi-Substituent Psilocybin Derivative

*Escherichia coli* strain Ec-1 was used to biosynthesize psilocybin derivative with formula (XV) from derivatized indole feedstock. The construction of Ec-1 is described in Example 1. Scaled-up culturing and material storage of engineered *E. coli* was conducted as described in Example 1, except that culturing was performed for 14 hours instead of 24 hours, and 5-fluoro-1H-indol-6-ylamine (www.bldpharm.com) was used in place of 6-fluoro-1H-indol-4-ylamine. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(6-acetylamino-5-fluoro-1H-indol-3-yl)ethyl]acetamide, having chemical formula (XV):

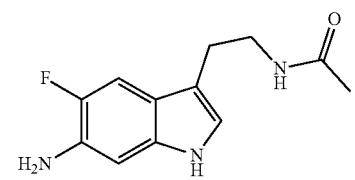

Figure 19A:
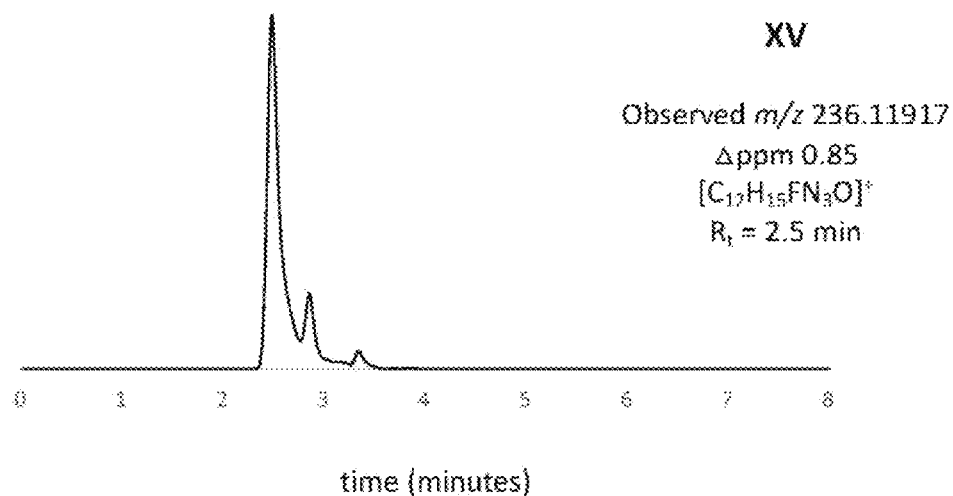
FIGS. 19A and 19B depict a representation of further mass spectrometry data in the form of a chromatogram, notably a chromatogram obtained in the performance of an experiment to synthesize an example multi-substituent psilocybin derivative compound having the chemical formula (XV) set forth herein (FIG. 19A); and a representation of mass spectrometry data in the form of a further mass spectrometry spectrum obtained in the performance of an experiment to identify a multi-substituent psilocybin derivative compound having the chemical formula (XV) set forth herein (FIG. 19B).
Figure 19B:
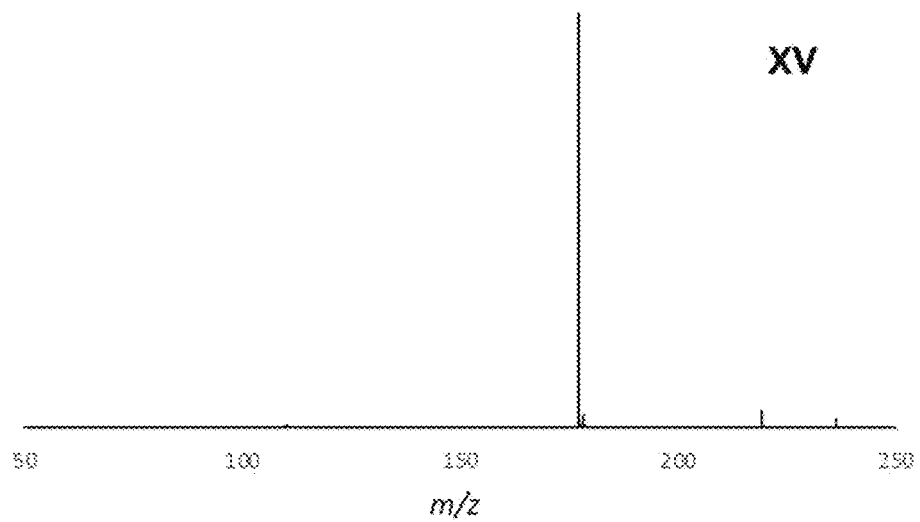

(XV)

eluted at 2.5 minutes (EIC, see: FIG. 19A). As per standard procedures (Menéndez-Perdomo et al, 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XV) as follows (FIG. 19B, Table 3) (Servillo L. et al., 2013, J. Agric. Chem. 61: 5156-5162).

TABLE 3

| m/z | % Relative abundance | Ionic species | Δ ppm |
|---|---|---|---|
| 177.08158 | 100 | $[M + H - C_2H_5NO]^+$ | 3.78 |
| 219.09224 | 4.1 | | |
| 236.11880 | 3.0 | $[M + H]^+$ | 2.41 |
| 109.66972 | 0.6 | | |
| 157.07565 | 0.4 | | |
| 181.73305 | 0.2 | | |
| 199.48006 | 0.1 | | |
| 194.10827 | 0.1 | | |
| 220.09515 | 0.1 | | |
| 207.09179 | 0.1 | | |

Example 6—Biosynthesis of a Sixth Multi-Substituent Psilocybin Derivative

*Escherichia coli* strain Ec-1 was used to biosynthesize psilocybin derivative with formula (XVII) from derivatized indole feedstock. The construction of Ec-1 is described in Example 1. Scaled-up culturing and material storage of engineered *E. coli* was conducted as described in Example 1, except that 4-fluoro-1H-indole-5-carbonitrile (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(5-cyano-4-fluoro-1H-indol-3-yl)ethyl]acetamide, having chemical formula (XVII):

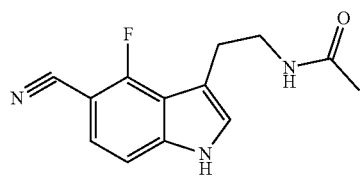

Figure 20:
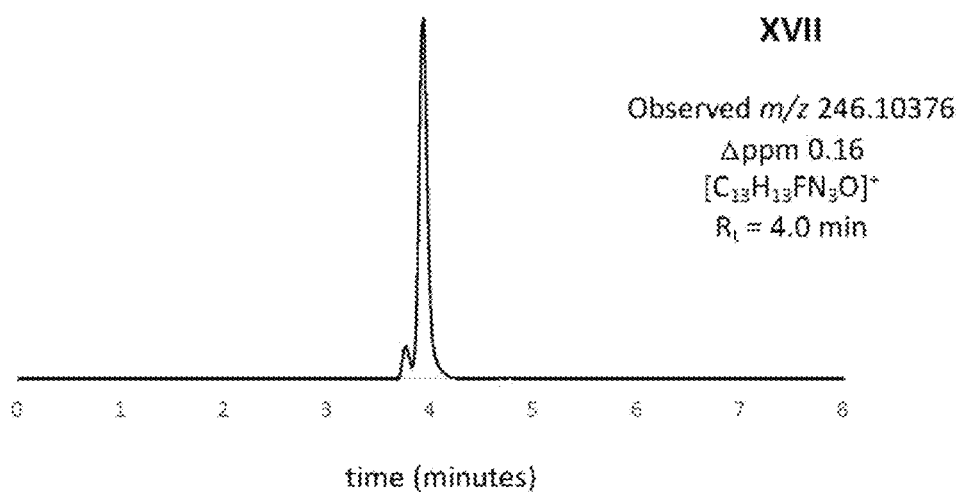
FIG. 20 depicts a representation of further mass spectrometry data in the form of a chromatogram, notably a chromatogram obtained in the performance of an experiment to synthesize an example multi-substituent psilocybin derivative compound having the chemical formula (XVII) set forth herein.

(XVII)

eluted at 4.0 minutes (EIC, see: FIG. 20).

Example 7—Biosynthesis of a Seventh Multi-Substituent Psilocybin Derivative

*Escherichia coli* strain Ec-1 was used to biosynthesize psilocybin derivative with formula (XVIII) from derivatized indole feedstock. The construction of Ec-1 is described in Example 1. Scaled-up culturing and material storage of engineered *E. coli* was conducted as described in Example 1, except that 6-bromo-1H-indol-4-ol (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(6-bromo-4-hydroxy-1H-indol-3-yl)ethyl]acetamide, having chemical formula (XVIII):

Figure 21A:
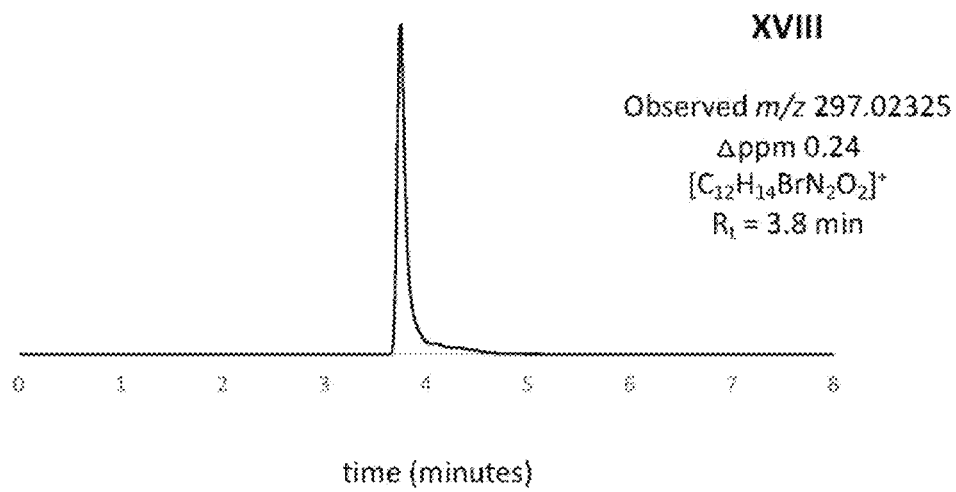
FIGS. 21A and 21B depict a representation of further mass spectrometry data in the form of a chromatogram, notably a chromatogram obtained in the performance of an experiment to synthesize an example multi-substituent psilocybin derivative compound having the chemical formula (XVIII) set forth herein (FIG. 21A); and a representation of mass spectrometry data in the form of a further mass spectrometry spectrum obtained in the performance of an experiment to identify a multi-substituent psilocybin derivative compound having the chemical formula (XVIII) set forth herein (FIG. 21B).
Figure 21B:
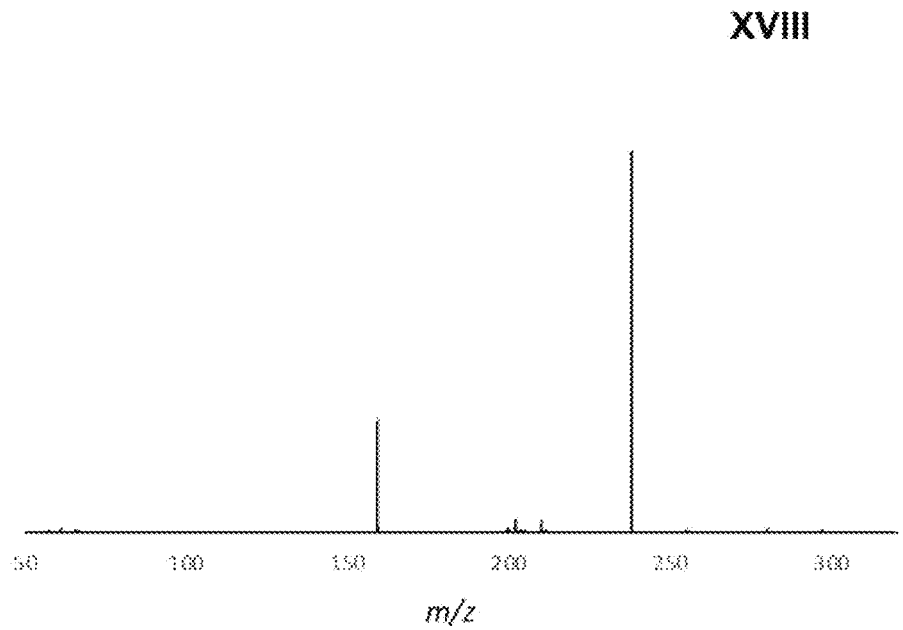

(XVIII)

eluted at 3.8 minutes (EIC, see: FIG. 21A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XVIII) as follows (FIG. 21B, Table 4) (Servillo L. et al., 2013, J. Agric. Chem. 61: 5156-5162).

TABLE 4

| m/z | % Relative abundance | Ionic species | Δ ppm |
|---|---|---|---|
| 237.98574 | 100 | $[M + H - C_2H_6NO]^+$ | 1.93 |
| 159.06737 | 29.5 | | |
| 209.99081 | 3.3 | | |
| 255.01230 | 1.2 | | |
| 279.99649 | 1.0 | | |
| 199.51968 | 1.0 | | |
| 61.09401 | 0.9 | | |
| 297.02267 | 0.7 | $[M + H]^+$ | 2.19 |
| 203.89784 | 0.6 | | |
| 177.16207 | 0.6 | | |

Example 8—Biosynthesis of an Eighth Multi-Substituent Psilocybin Derivative

*Escherichia coli* strain Ec-1 was used to biosynthesize psilocybin derivative with formula (XXI) from derivatized indole feedstock. The construction of Ec-1 is described in Example 1. Scaled-up culturing and material storage of engineered *E. coli* was conducted as described in Example 1. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(4-acetylamino-6-fluoro-1H-indol-3-yl)ethyl]acetamide, having chemical formula (XXI):

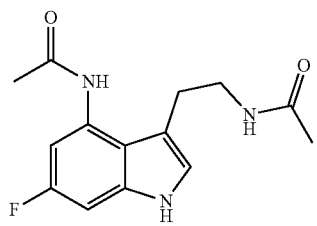

(XXI)

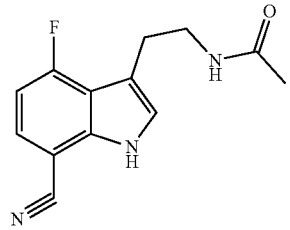

Figure 22A:
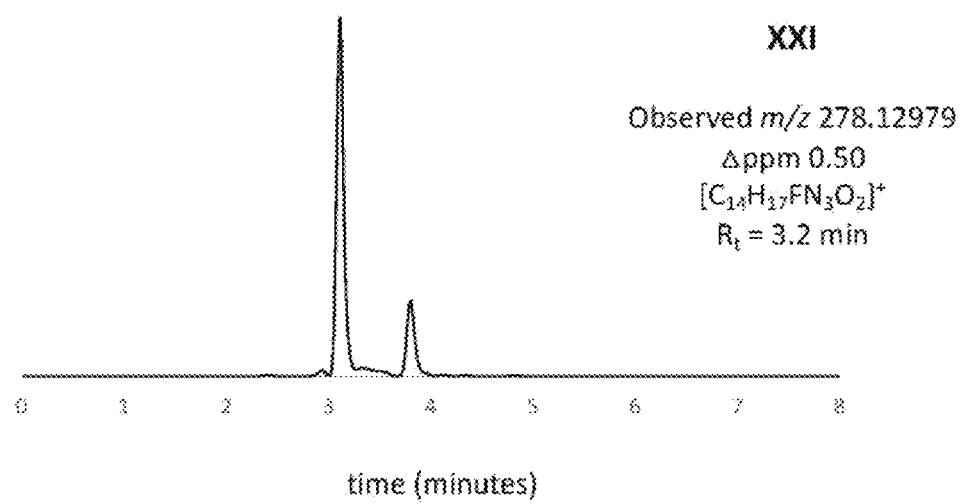
FIGS. 22A and 22B depict a representation of further mass spectrometry data in the form of a chromatogram, notably a chromatogram obtained in the performance of an experiment to synthesize an example multi-substituent psilocybin derivative compound having the chemical formula (XXI) set forth herein (FIG. 22A); and a representation of mass spectrometry data in the form of a further mass spectrometry spectrum obtained in the performance of an experiment to identify a multi-substituent psilocybin derivative compound having the chemical formula (XXI) set forth herein (FIG. 22B).
Figure 22B:
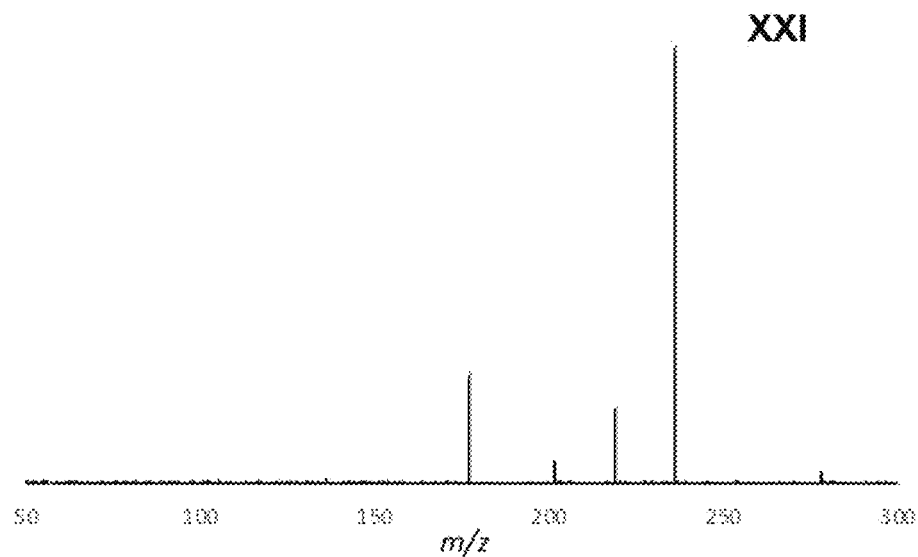

(XXIII)

eluted at 3.2 minutes (EIC, see: FIG. 22A). Notably, while the same indole feedstock was provided in this example compared to the feedstock used Example 1, the product (XXI) is not the same as product (IX). In fact, both products (XXI) and (IX) are achieved by feeding 6-fluoro-1H-indol-4-ylamine to Ec-1. However, in Example 1, only product (IX) was purified. Conversely, in this Example, only product (XXI) was analyzed. As per standard procedures (Menéndez-Perdomo et al., 2021, Mass Spectrum 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXI) as follows (FIG. 22B, Table 5) (Servillo L. et al, 2013, J. Agric. Chem. 61: 5156-5162).

TABLE 5

| m/z | % Relative abundance | Ionic species | Δ ppm |
|---|---|---|---|
| 236.11928 | 100 | $[M + H - C_2H_2O]^+$ | 0.38 |
| 177.08202 | 26.0 | $[M + H - C_2H_6NO - C_2H_2O]^+$ | 1.30 |
| 219.09267 | 17.9 | $[M + H - C_2H_6NO]^+$ | 0.68 |
| 278.12986 | 3.0 | $[M + H]^+$ | 0.25 |
| 136.07571 | 1.1 | | |
| 56.17127 | 0.9 | | |
| 199.20892 | 0.8 | | |
| 88.82042 | 0.8 | | |
| 232.86285 | 0.8 | | |
| 158.02567 | 0.8 | | |

Example 9—Biosynthesis of a Ninth Multi-Substituent Psilocybin Derivative

Figure 23A:
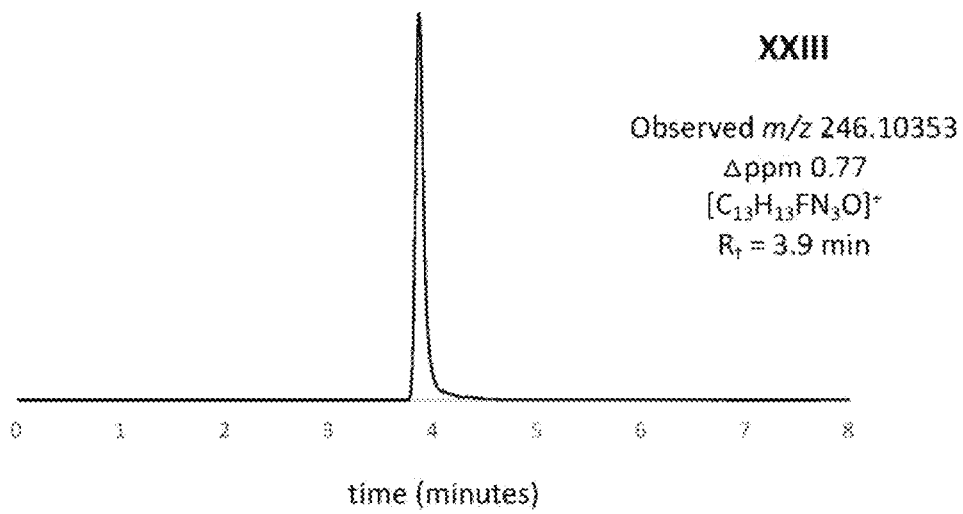
FIGS. 23A and 23B depict a representation of further mass spectrometry data in the form of a chromatogram, notably a chromatogram obtained in the performance of an experiment to synthesize an example multi-substituent psilocybin derivative compound having the chemical formula (XXIII) set forth herein (FIG. 23A); and a representation of mass spectrometry data in the form of a further mass spectrometry spectrum obtained in the performance of an experiment to identify a multi-substituent psilocybin derivative compound having the chemical formula (XXIII) set forth herein (FIG. 23B).
Figure 23B:
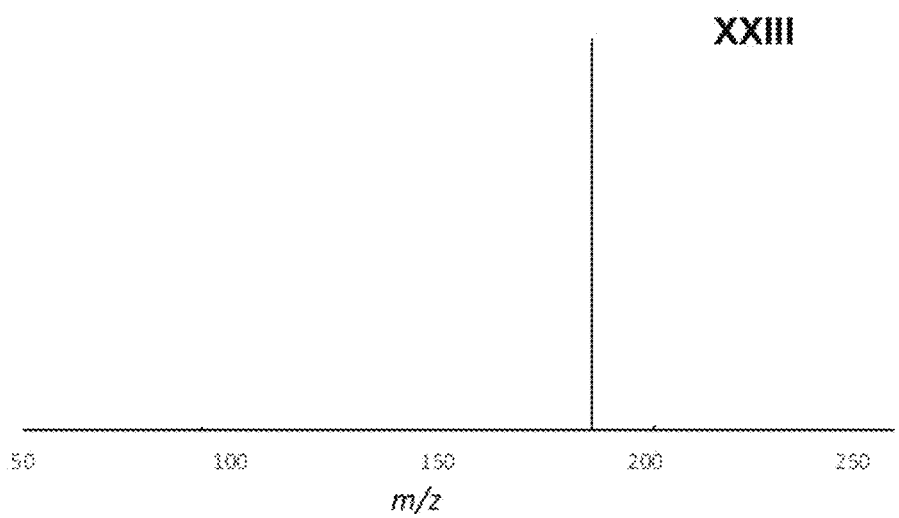

*Escherichia coli* strain Ec-1 was used to biosynthesize psilocybin derivative with formula (XXIII) from derivatized indole feedstock. The construction of Ec-1 is described in Example 1. Scaled-up culturing and material storage of engineered *E. coli* was conducted as described in Example 1, except that 4-fluoro-1H-indole-7-carbonitrile (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(7-cyano-4-fluoro-1H-indol-3-yl)ethyl]acetamide, having chemical formula (XXIII):

eluted at 3.9 minutes (EIC, see: FIG. 23A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXIII) as follows (FIG. 23B, Table 6) (Servillo L. et al., 2013, J. Agric. Chem. 61: 5156-5162).

TABLE 6

| m/z | % Relative abundance | Ionic species | Δ ppm |
|---|---|---|---|
| 187.06606 | 100 | $[M + H - C_2H_3NO]^+$ | 2.89 |
| 93.13169 | 1.0 | | |
| 204.09270 | 0.6 | | |
| 229.07666 | 0.2 | | |
| 246.10356 | 0.2 | $[M + H]^+$ | 0.61 |
| 199.66049 | 0.2 | | |
| 59.34151 | 0.1 | | |

Example 10—Biosynthesis of a Tenth Multi-Substituent Psilocybin Derivative

*Escherichia coli* strain Ec-1 was used to biosynthesize psilocybin derivative with formula (XXV) from derivatized indole feedstock. The construction of Ec-1 is described in Example 1. Scaled-up culturing and material storage of engineered *E. coli* was conducted as described in Example 1, except that 4-fluoro-1H-indol-6-ylamine was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(6-amino-4-fluoro-1H-indol-3-yl)ethyl]acetamide, having chemical formula (XXV):

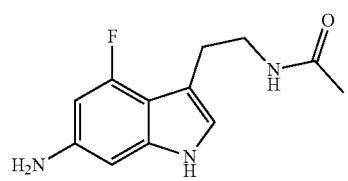

Figure 24:
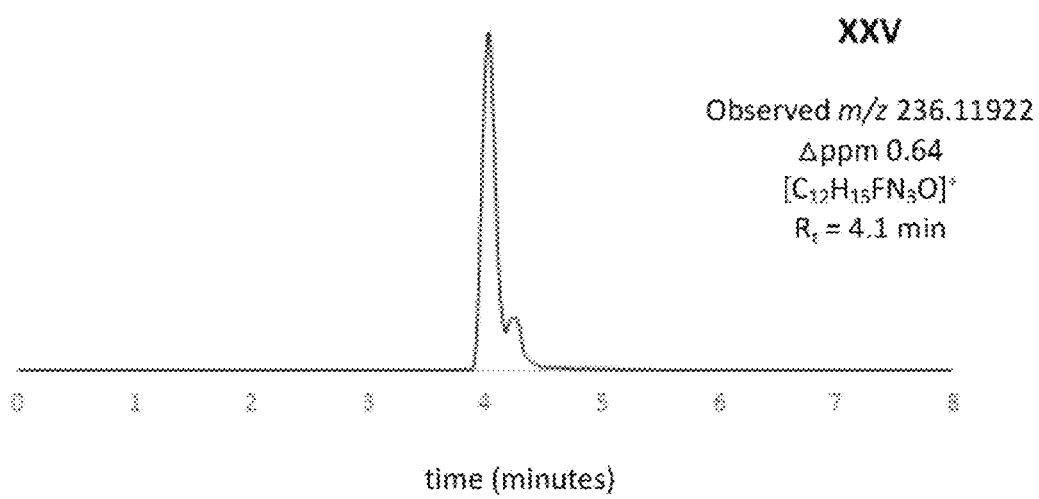
FIG. 24 depicts a representation of further mass spectrometry data in the form of a chromatogram, notably a chromatogram obtained in the performance of an experiment to synthesize an example multi-substituent psilocybin derivative compound having the chemical formula (XXV) set forth herein.

(XXV)

eluted at 4.1 minutes (EIC, see: FIG. 24). Notably, while the same indole feedstock was provided in this example compared to the feedstock used Example 2, the product (XXV)

is not the same as product (X). In fact, both products (XXV) and (X) are achieved by feeding 4-fluoro-1H-indol-6-ylamine to Ec-1. However, in Example 2, only product (X) was purified. Conversely, in this Example, only product (XXV) was analyzed.

Example 11—Biosynthesis of an Eleventh Multi-Substituent Psilocybin Derivative

*Escherichia coli* strain Ec-1 was used to biosynthesize psilocybin derivative with formula (XXVIII) from derivatized indole feedstock. The construction of Ec-1 is described in Example 1. Scaled-up culturing and material storage of engineered *E. coli* was conducted as described in Example 1, except that 4-amino-1H-indole-6-carbonitrile (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(4-amino-6-cyano-1H-indol-3-yl)ethyl]acetamide, having chemical formula (XXVIII):

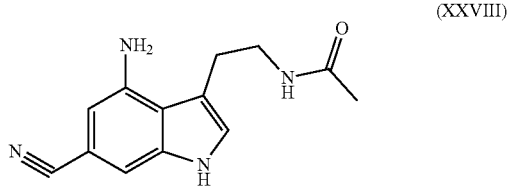 [SMILES: CC(=O)NCCc1c[nH]c2cc(C#N)cc(N)c12]

Figure 25A:
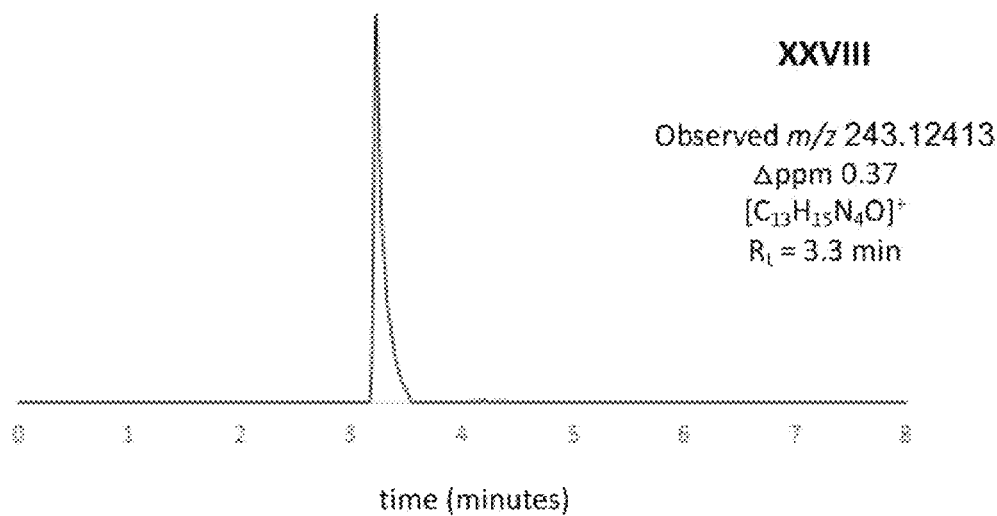
FIGS. 25A and 25B depict a representation of further mass spectrometry data in the form of a chromatogram, notably a chromatogram obtained in the performance of an experiment to synthesize an example multi-substituent psilocybin derivative compound having the chemical formula (XXVIII) set forth herein (FIG. 25A); and a representation of mass spectrometry data in the form of a further mass spectrometry spectrum obtained in the performance of an experiment to identify a multi-substituent psilocybin derivative compound having the chemical formula (XXVIII) set forth herein (FIG. 25B).
Figure 25B:
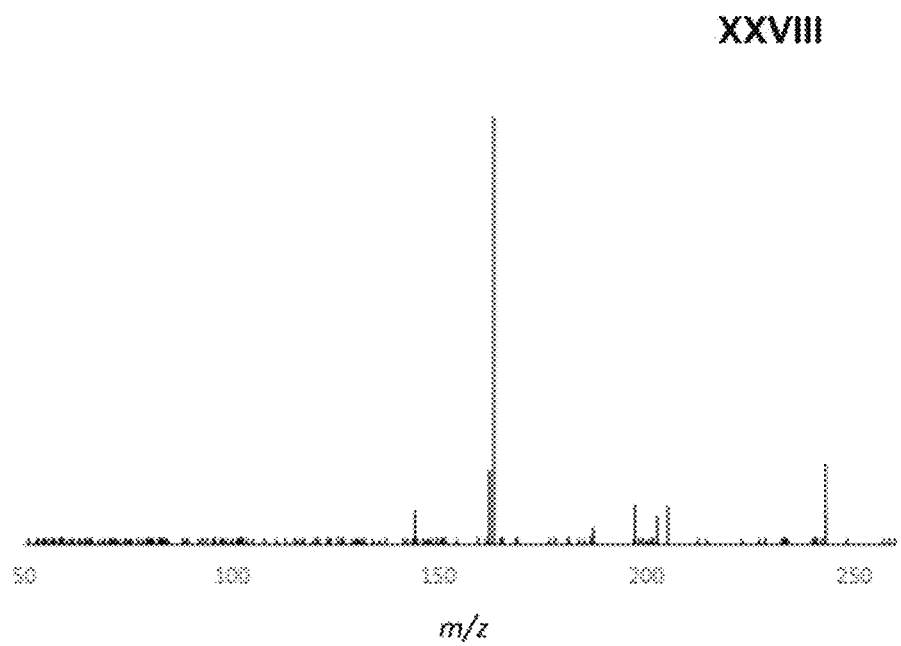

(XXVIII)

eluted at 3.3 minutes (EIC, see: FIG. 25A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXVIII) as follows (FIG. 25B, Table 7) (Servillo L. et al., 2013, J. Agric. Chem. 61: 5156-5162).

TABLE 7

| m/z | % Relative abundance | Ionic species | Empirical Formula |
|---|---|---|---|
| 163.1076 | 100 | | |
| 243.1340 | 19.2 | [M + H]⁺ | $C_{14}H_{15}N_4O$ |
| 162.0760 | 17.3 | | |
| 197.1284 | 9.2 | | |
| 205.1182 | 9.1 | | |
| 144.0653 | 7.8 | | |
| 202.4956 | 6.9 | | |
| 187.1077 | 4.2 | | |
| 115.0388 | 2.0 | | |
| 186.4933 | 1.9 | | |

Example 12—Biosynthesis of a Twelfth Multi-Substituent Psilocybin Derivative

*Escherichia coli* strain Ec-1 was used to biosynthesize psilocybin derivative with formula (XX) from derivatized indole feedstock. The construction of Ec-1 is described in Example 1. Scaled-up culturing and material storage of engineered *E. coli* was conducted as described in Example 1, except that 4-fluoro-1H-indol-5-ol (www.bldpharm.com) was used in place of 6-fluoro-1H-indol-4-ylamine. Scaled-up culturing and processing of engineered *E. coli* was conducted as described in Example 1. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-[2-(4-fluoro-5-hydroxy-1H-indol-3-yl)ethyl]acetamide, having chemical formula (XX):

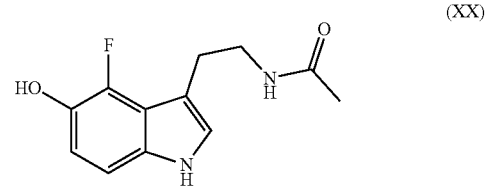 [SMILES: CC(=O)NCCc1c[nH]c2ccc(O)c(F)c12]

Figure 26:
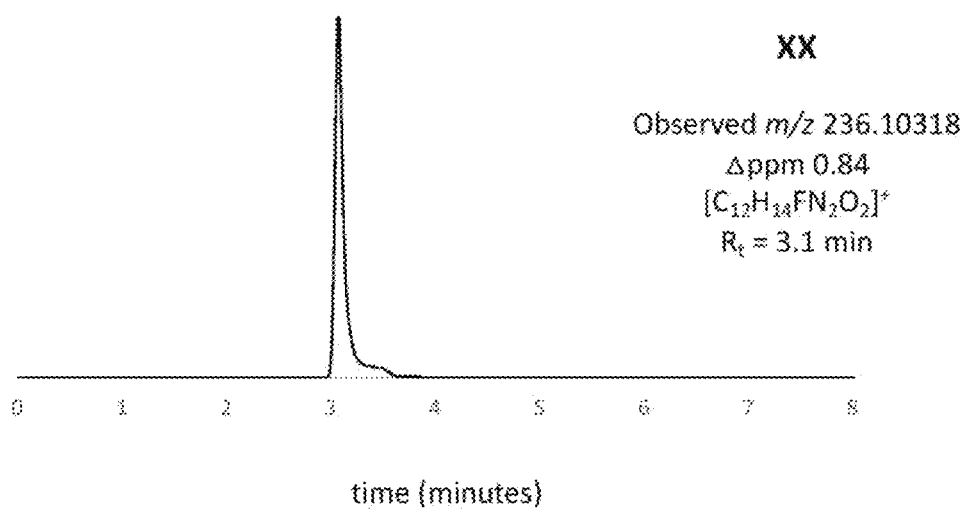
FIG. 26 depicts a representation of further mass spectrometry data in the form of a chromatogram, notably a chromatogram obtained in the performance of an experiment to synthesize an example multi-substituent psilocybin derivative compound having the chemical formula (XX) set forth herein.

(XX)

eluted at 3.1 minutes (EIC, see: FIG. 26).

Example 13—Biosynthesis of a Thirteenth Multi-Substituent Psilocybin Derivative

*Escherichia coli* strain Ec-2 was used to biosynthesize psilocybin derivative with formula (XIII) from derivatized indole feedstock. *E. coli* strain Ec-2 was constructed as follows. For plasmid cloning, Top10 or XL1-blue strains were used depending on antibiotic markers. Standard LB media was used for culturing. For gene expression and feeding experiments, the parent host strain employed was BL21 (DE3). Plasmids pET28a(+)-PfTrpB-B0A9-HIS and pCDM4-BaTDC-HIS were created as described in Example 1. The target plasmids pET28a(+)-PfTrpB-B0A9-HIS and pCDM4-BaTDC-HIS were sequentially transformed into BL21 (DE3) cells as follows: pCDM4-BaTDC-HIS was transformed into BL21 (DE3) first. Transformants selected using streptomycin were next transformed with pET28a(+)-PfTrpB-B0A9-HIS and selected with both streptomycin and kanamycin. Scaled-up culturing and material storage of engineered *E. coli* was conducted as described in Example 1, except that (1) only streptomycin and kanamycin were used for selection purposes; and (2) 5-fluoro-7-nitro-1H-indole (www.bldpharm.com) was used in place of 6-fluoro-1H-indol-4-ylamine. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-(5-fluoro-7-nitro-1H-indol-3-yl)ethylamine, having chemical formula (XIII):

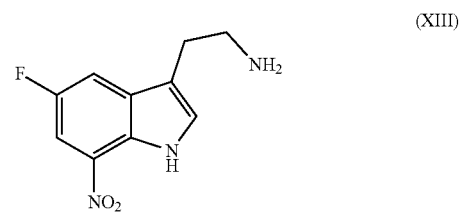 [SMILES: NCCc1c[nH]c2c([N+](=O)[O-])cc(F)cc12]

Figure 27:
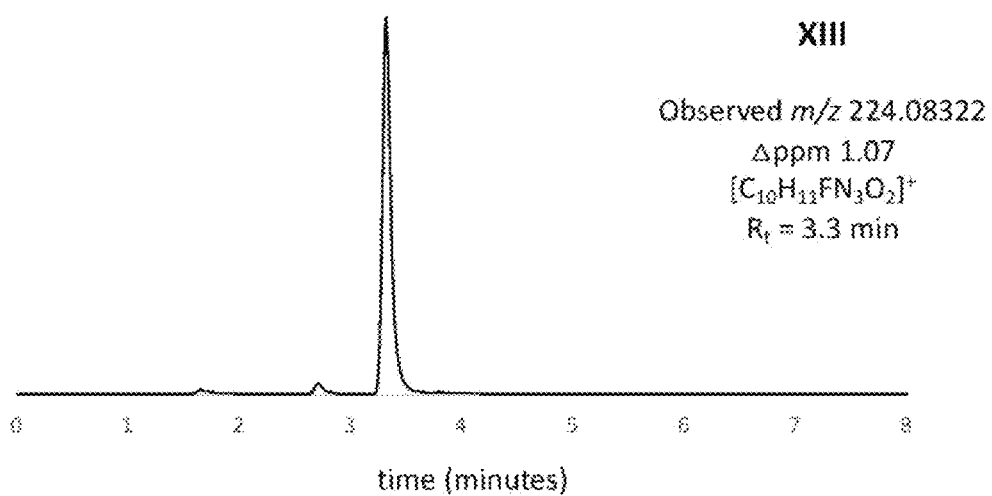
FIG. 27 depicts a representation of further mass spectrometry data in the form of a chromatogram, notably a chromatogram obtained in the performance of an experiment to synthesize an example multi-substituent psilocybin derivative compound having the chemical formula (XIII) set forth herein.

(XIII)

eluted at 3.3 minutes (EIC, see: FIG. 27).

Example 14—Biosynthesis of a Fourteenth Multi-Substituent Psilocybin Derivative

*Escherichia coli* strain Ec-2 was used to biosynthesize psilocybin derivative with formula (XVI) from derivatized indole feedstock. The construction of Ec-2 is described in Example 13. Scaled-up culturing and material storage of engineered *E. coli* was conducted as described in Example 13, except that 5-fluoro-1H-indol-6-ylamine (www.bldpharm.com) was used in place of 5-fluoro-7-nitro-1H-indole. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-5-fluoro-1H-indol-6-amine, having chemical formula (XVI):

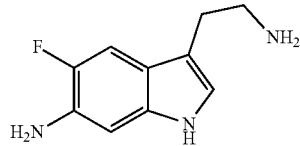

Figure 28:
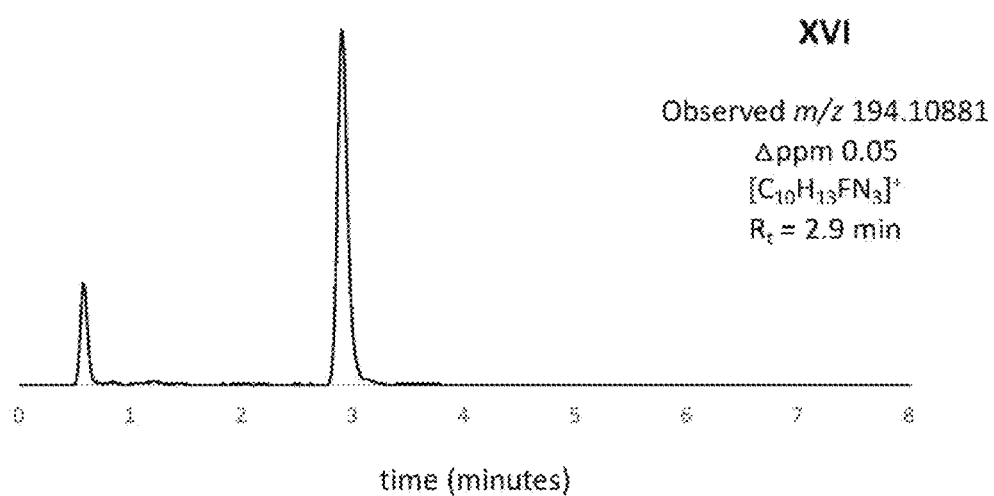
FIG. 28 depicts a representation of further mass spectrometry data in the form of a chromatogram, notably a chromatogram obtained in the performance of an experiment to synthesize an example multi-substituent psilocybin derivative compound having the chemical formula (XVI) set forth herein.

(XVI)

eluted at 2.9 minutes (EIC, see: FIG. 28).

Example 15—Biosynthesis of a Fifteenth Multi-Substituent Psilocybin Derivative

*Escherichia coli* strain Ec-2 was used to biosynthesize psilocybin derivative with formula (XIX) from derivatized indole feedstock. The construction of Ec-2 is described in Example 13. Scaled-up culturing and material storage of engineered *E. coli* was conducted as described in Example 13, except that 4-fluoro-1H-indole-5-carbonitrile (www.bldpharm.com) was used in place of 5-fluoro-7-nitro-1H-indole. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-4-fluoro-1H-indole-5-carbonitrile, having chemical formula (XIX):

Figure 29:
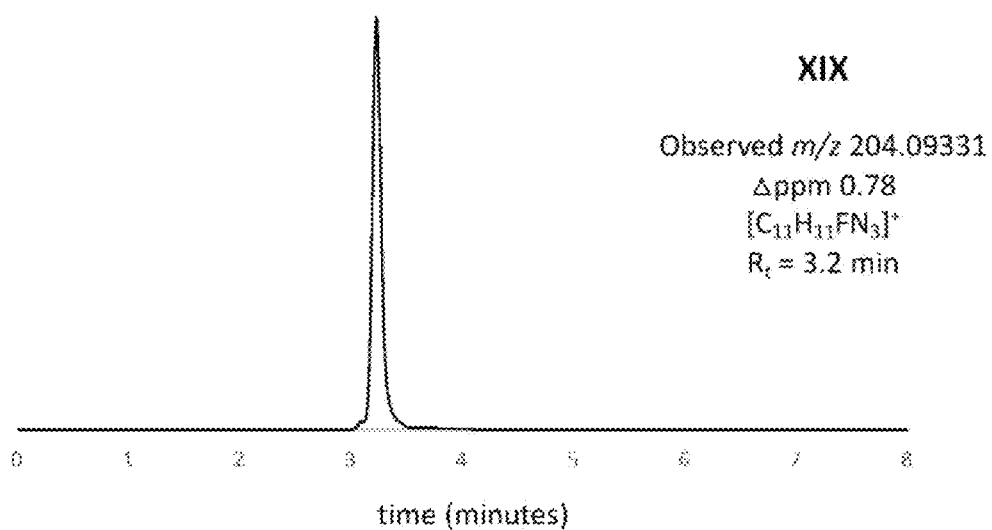
FIG. 29 depicts a representation of further mass spectrometry data in the form of a chromatogram, notably a chromatogram obtained in the performance of an experiment to synthesize an example multi-substituent psilocybin derivative compound having the chemical formula (XIX) set forth herein.

(XIX)

eluted at 3.2 minutes (EIC, see: FIG. 29).

Example 16—Biosynthesis of a Sixteenth Multi-Substituent Psilocybin Derivative

*Escherichia coli* strain Ec-2 was used to biosynthesize psilocybin derivative with formula (XXII) from derivatized indole feedstock. The construction of Ec-2 is described in Example 13. Scaled-up culturing and material storage of engineered *E. coli* was conducted as described in Example 13, except that 6-fluoro-1H-indol-4-ylamine (www.bldpharm.com) was used in place of 5-fluoro-7-nitro-1H-indole. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-6-fluoro-1H-indol-4-amine, having chemical formula (XXII):

Figure 30:
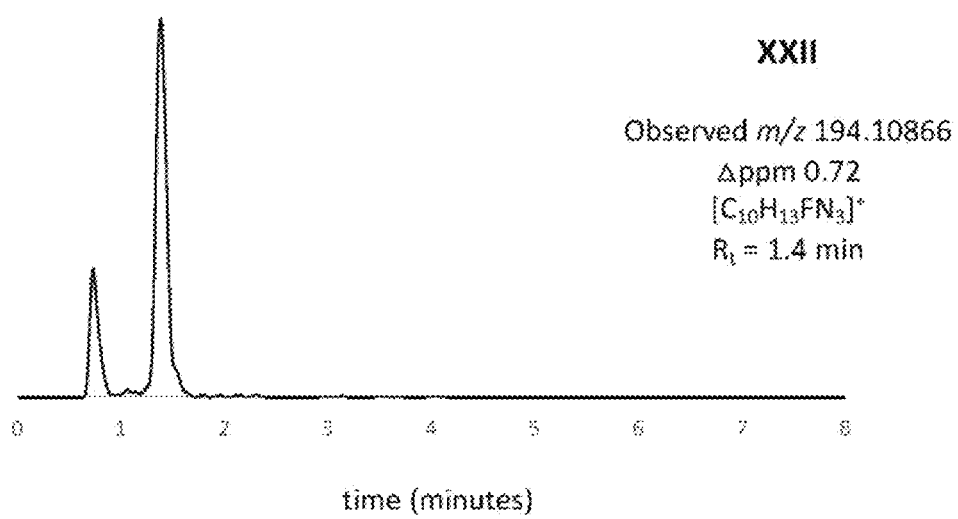
FIG. 30 depicts a representation of further mass spectrometry data in the form of a chromatogram, notably a chromatogram obtained in the performance of an experiment to synthesize an example multi-substituent psilocybin derivative compound having the chemical formula (XXII) set forth herein.

(XXII)

eluted at 1.4 minutes (EIC, see: FIG. 30).

Example 17—Biosynthesis of a Seventeenth Multi-Substituent Psilocybin Derivative

*Escherichia coli* strain Ec-2 was used to biosynthesize psilocybin derivative with formula (XXVI) from derivatized indole feedstock. The construction of Ec-2 is described in Example 13. Scaled-up culturing and material storage of engineered *E. coli* was conducted as described in Example 13, except that 3-(2-aminoethyl)-4-fluoro-1H-indol-6-amine (www.bldpharm.com) was used in place of 5-fluoro-7-nitro-1H-indole. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-4-fluoro-1H-indol-6-amine, having chemical formula (XXVI):

Figure 31:
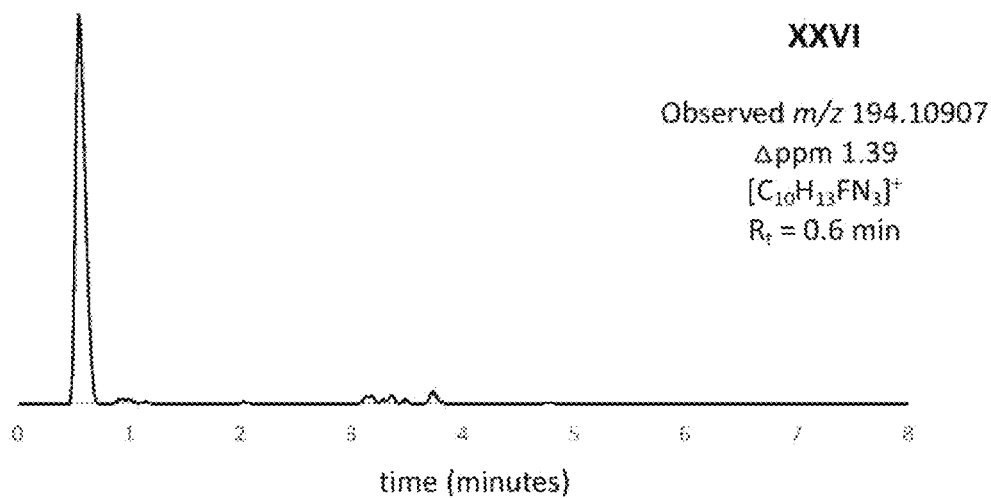
FIG. 31 depicts a representation of further mass spectrometry data in the form of a chromatogram, notably a chromatogram obtained in the performance of an experiment to synthesize an example multi-substituent psilocybin derivative compound having the chemical formula (XXVI) set forth herein.

(XXVI)

eluted at 0.6 minutes (EIC, see: FIG. 31).

Example 18—Biosynthesis of an Eighteenth Multi-Substituent Psilocybin Derivative

*Escherichia coli* strain Ec-2 was used to biosynthesize psilocybin derivative with formula (XXIX) from derivatized indole feedstock. The construction of Ec-2 is described in Example 13. Scaled-up culturing and material storage of engineered *E. coli* was conducted as described in Example 13, except that 4-amino-1H-indole-6-carbonitrile (www.bldpharm.com) was used in place of 5-fluoro-7-nitro-1H-indole. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 4-amino-3-(2-aminoethyl)-1H-indole-6-carbonitrile, having chemical formula (XXIX):

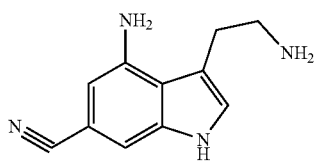

Figure 32A:
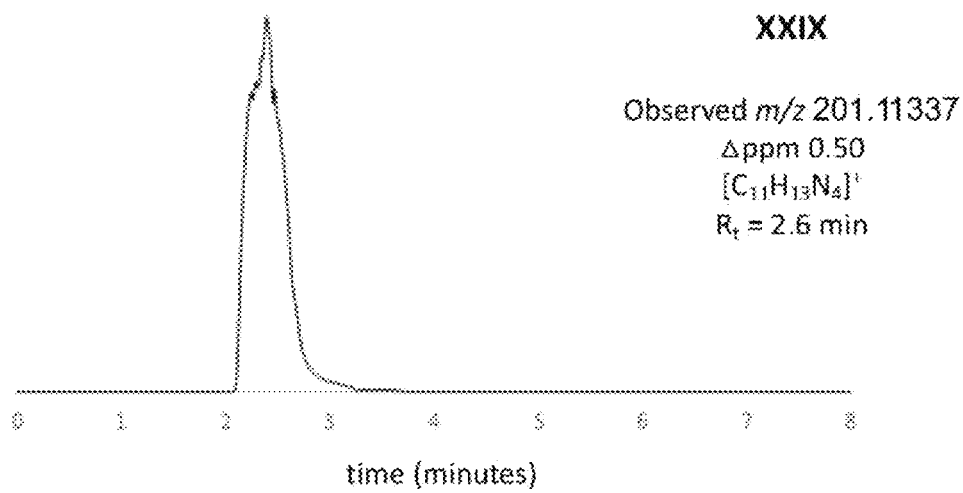
FIGS. 32A and 32B depict a representation of further mass spectrometry data in the form of a chromatogram, notably a chromatogram obtained in the performance of an experiment to synthesize an example multi-substituent psilocybin derivative compound having the chemical formula (XXIX) set forth herein (FIG. 32A); and a representation of mass spectrometry data in the form of a further mass spectrometry spectrum obtained in the performance of an experiment to identify a multi-substituent psilocybin derivative compound having the chemical formula (XXIX) set forth herein (FIG. 32B).
Figure 32B:
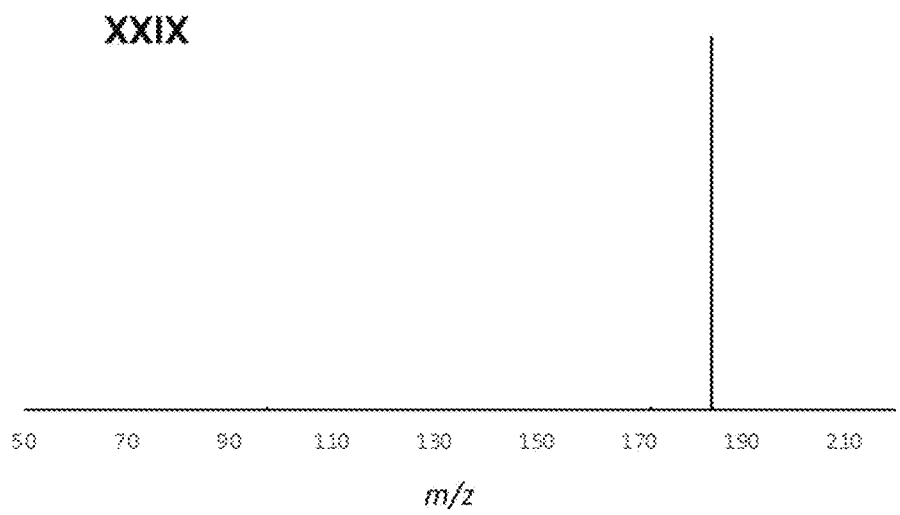

(XXIX)

eluted at 2.6 minutes (EIC, see: FIG. 32A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXIX) as follows (FIG. 32B, Table 8) (Servillo L. et al., 2013, J. Agric. Chem. 61: 5156-5162).

TABLE 8

| m/z | % Relative abundance | Ionic species | Δ ppm |
| --- | --- | --- | --- |
| 184.08655 | 100 | [M + H − NH₃]⁺ | 2.01 |
| 97.51806 | 1.0 | | |
| 172.08669 | 0.7 | | |
| 201.11313 | 0.6 | [M + H]⁺ | 1.69 |
| 199.55735 | 0.1 | | |
| 61.09273 | 0.1 | | |
| 143.08142 | 0.1 | | |
| 60.25552 | 0.1 | | |
| 209.32732 | 0.1 | | |
| 202.04140 | 0.1 | | |

Example 19—Biosynthesis of a Nineteenth Multi-Substituent Psilocybin Derivative

*Escherichia coli* strain Ec-3 was used to biosynthesize psilocybin derivative with formula (XXVII) from derivatized indole feedstock. *E. coli* strain Ec-2 was constructed as follows. For plasmid cloning, Top10 or XL1-blue strains were used depending on antibiotic markers. Standard LB media was used for culturing. For gene expression and feeding experiments, the parent host strain employed was BL21 (DE3). First, the plasmid pET28a(+)-EsNMT-HIS was created by inserting an in-frame, HIS tagged (SEQ.ID NO: 46) EsNMT gene (SEQ.ID NO: 11) into the NdeI/XhoI site of pET28a(+) (SEQ.ID NO: 36). As a second step, from plasmid pCDM4 (SEQ.ID NO: 35), the plasmid pCDM4-PsiD-HIS was created by inserting an in-frame, HIS-tagged (SEQ.ID NO: 46) PsiD gene (SEQ.ID NO: 7) into the NdeI/XhoI site of pCDM4. These target plasmids were sequentially transformed into BL21 (DE3) cells as follows: pCDM4-PsiD-HIS was transformed into BL21 (DE3) first. Transformants selected using streptomycin were next transformed with pET28a(+)-EsNMT-HIS and selected with both streptomycin and kanamycin. Scaled-up culturing and material storage of engineered *E. coli* was conducted as described in Example 1, except that (1) only streptomycin and kanamycin were used for selection purposes; and (2) 4-amino-1H-indole-6-carbonitrile (www.bldpharm.com) was used in place of 6-fluoro-1H-indol-4-ylamine. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 4-amino-3-[2-(methylamino)ethyl]-1H-indole-6-carbonitrile, having chemical formula (XXVII):

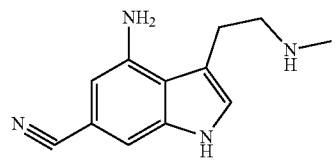

Figure 33:
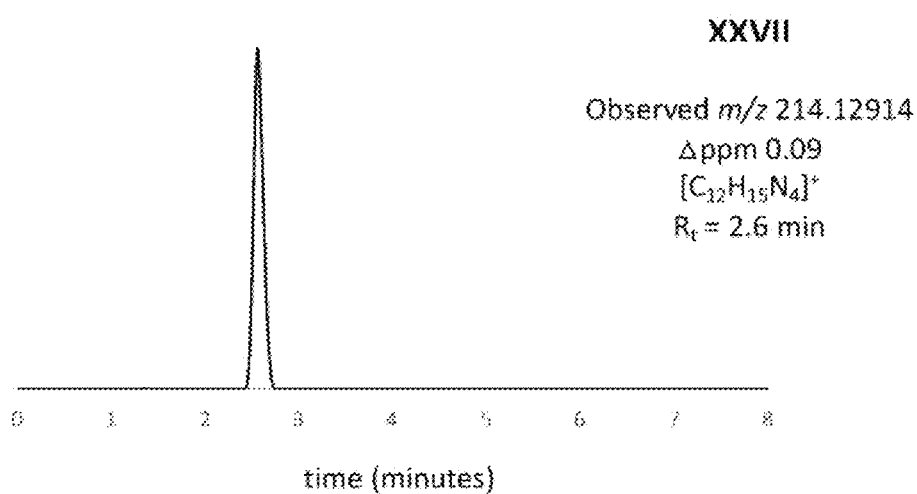
FIG. 33 depicts a representation of further mass spectrometry data in the form of a chromatogram, notably a chromatogram obtained in the performance of an experiment to synthesize an example multi-substituent psilocybin derivative compound having the chemical formula (XXVII) set forth herein.

(XXVII)

eluted at 2.6 minutes (EIC, see: FIG. 33).

Example 20—Biosynthesis of a Twentieth Multi-Substituent Psilocybin Derivative

Figure 34A:
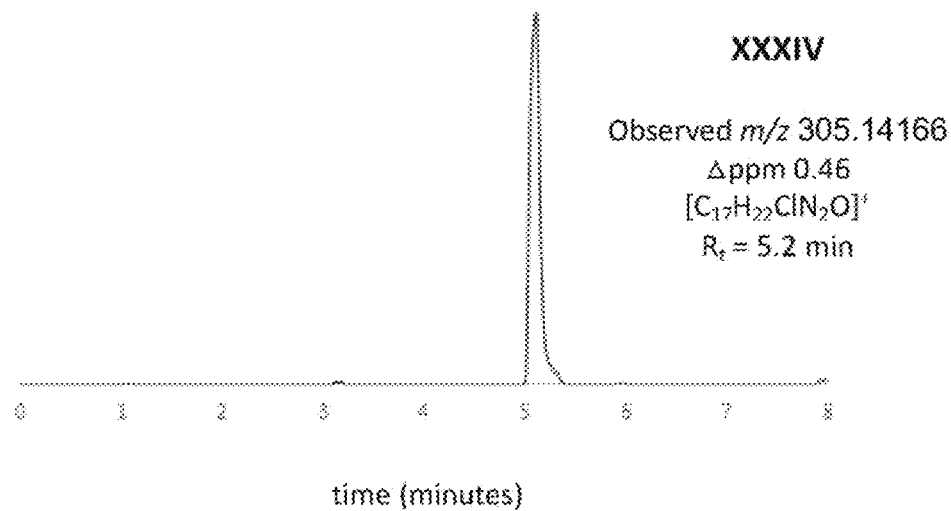
FIGS. 34A and 34B depict a representation of further mass spectrometry data in the form of a chromatogram, notably a chromatogram obtained in the performance of an experiment to synthesize an example multi-substituent psilocybin derivative compound having the chemical formula (XXXIV) set forth herein (FIG. 34A); and a representation of mass spectrometry data in the form of a further mass spectrometry spectrum obtained in the performance of an experiment to identify a multi-substituent psilocybin derivative compound having the chemical formula (XXXIV) set forth herein (FIG. 34B).
Figure 34B:
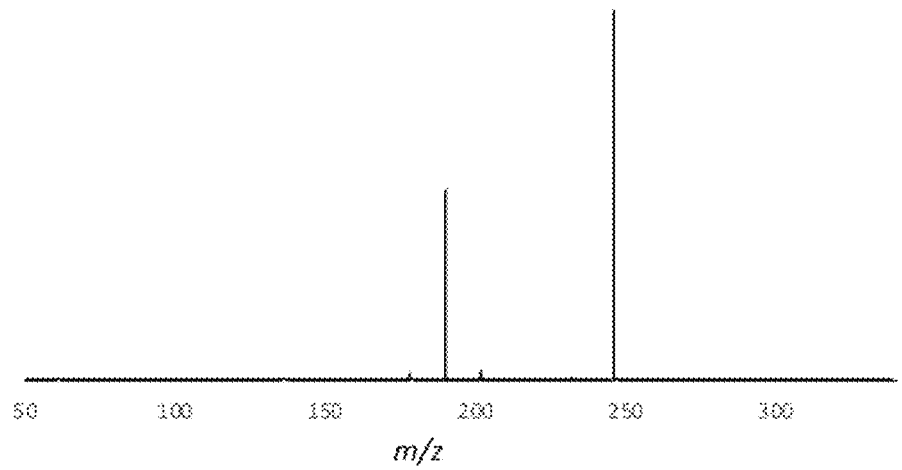

Yeast (*Saccharomyces cerevisiae*) strain Sc-1 was created through genetic engineering of a parent yeast strain, to enable bioconversion of commercially obtained, derivatized indole, tryptophan, or tryptamine feedstock to generate final product. The parent yeast (*Saccharomyces cerevisiae*) strain was CEN.PK with genotype Matα; ura3-52; trp1-289; leu2-3,112; his3Δ1; MAL2-8C; SUC2. The parent strain was engineered to include 7DMATS (SEQ.ID NO: 16), ClostSporTDC (SEQ.ID NO: 6), and PsmF (SEQ.ID NO: 10) which catalyzed three enzymatic steps. Engineering also included CPR (SEQ.ID NO: 26) although this enzyme was not used in the bioconversion process. 7DMATS, ClostSporTDC, and CPR were included in the strain through chromosomal homologous recombination of integration cassettes as described previously (Dastmalchi et al., 2019, Nat. Chem Biol. 15: 384-390; Chen et al., 2018, Nat. Chem Biol. 14: 738-743). Conversely, PsmF was built into a protein expression plasmid and transformed to the genomically integrated strain already harboring 7DMATS, ClostSporTDC, and CPR. 7DMATS, ClostSporTDC, and CPR were encoded by SEQ.ID NO: 15, SEQ.ID NO: 5 and SEQ.ID NO: 25, respectively, with addition of in-frame, C-terminal HIS (SEQ.ID NO: 46, SEQ.ID NO: 47), FLAG (SEQ.ID NO: 42, SEQ.ID NO: 43), and c-MYC (SEQ.ID NO: 40, SEQ.ID NO: 41) epitope tags, respectively. Integration cassettes were built using yeast promoter sequences amplified from *S. cerevisiae* genomic DNA as described (Dastmalchi et al., 2019; Chen et al., 2018) enabling constitutive gene expression. Amplified promoters included PGK1 (SEQ.ID NO: 30), TDH3 (SEQ.ID NO: 31), CLN1 (SEQ.ID NO: 32), and UGA1 (SEQ.ID NO: 33). Two integration cassettes were assembled: the first, (X-3)::TADH1-ClostSporTDC-Flag-PPGK1-PTDH3-CPR-c-myc-TCYC1 (SEQ.ID NO: 52), harboured tagged ClostSporTDC and CPR. The second (Xii-2)::PTDH3-7DMATS-His-TCYC1 (SEQ.ID NO: 53), harboured only tagged 7DMATS. Successive genomic integration of these cassettes was performed as described previously (Chen et al., 2018). Following stable integration of these two cassettes, the strain was further manipulated by transformation with a yeast episomal vector encoding a promiscuous N-acetyltransferase, PsmF (pMM1-pTDH3-PsmF-His-tCYC1). For construction of pMM1-pTDH3-PsmF-His-tCYC1, the gene PsmF (SEQ.ID NO: 9) fused in-frame with a HIS epitope tag (SEQ.ID NO: 46) was ligated to empty plasmid pMM1 (SEQ.ID NO: 34) using BamHI/SacII restriction sites. For this Example, heterologous expression of a non-native or engineered TrpB gene was not necessary, as endogenous tryptophan synthase activity proved sufficient. The final engineered strain was called Sc-1. For scaled-up production of derivative product, culturing was performed as follows. Seed cultures were inoculated in SD-drop-out medium overnight. The overnight culture was then divided into two flasks containing 500 ml each of SD-drop-out medium containing 2% (w/v) glucose, 0.3% (w/v) $KH_2PO_4$, 0.05% (w/v) $MgSO_4 \cdot 7H_2O$, 0.5% (w/v) $(NH_4)_2SO_4$ plus 500 µM 4-chloro-1H-indole (www.combi-blocks.com) for conversion by Sc-1. Yeast cultures were grown for 48 h. Cultures were then centrifuged (10,000 g×5 minutes) to remove cellular content, and culture broth containing secreted derivative product was stored at −80° C. until further processing. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-(2-[4-chloro-7-(3-methyl-2-butenyl)-1H-indol-3-yl]ethyl)acetamide, having chemical formula (XXXIV):

(XXXIV)

eluted at 5.2 minutes (EIC, see: FIG. 34A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXXIV) as follows (FIG. 34B, Table 9) (Servillo L. et al., 2013, J. Agric. Chem. 61: 5156-5162).

TABLE 9

| m/z | % Relative abundance | Ionic species | Δ ppm |
| --- | --- | --- | --- |
| 246.10397 | 100 | [M + H − $NH_3$]$^+$ | 1.74 |
| 190.04136 | 53.1 | | |
| 178.04141 | 2.5 | | |
| 232.05183 | 0.8 | | |
| 135.46806 | 0.7 | | |
| 61.09248 | 0.6 | | |
| 151.39211 | 0.6 | | |
| 134.24040 | 0.6 | | |
| 199.43795 | 0.6 | | |
| 118.45281 | 0.5 | | |

Example 21—Biosynthesis of a Twenty-First Multi-Substituent Psilocybin Derivative The same yeast strain (Sc-1) and procedures described in Example 20 were used to biosynthesize a psilocybin derivative with chemical formula (XXXIII), with the following exception: in place of 4-chloro-1H-indole, 500 µM 5-fluoro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-[5-fluoro-7-(3-methyl-2-butenyl)-1H-indol-3-yl]ethylamine having chemical formula (XXXII):

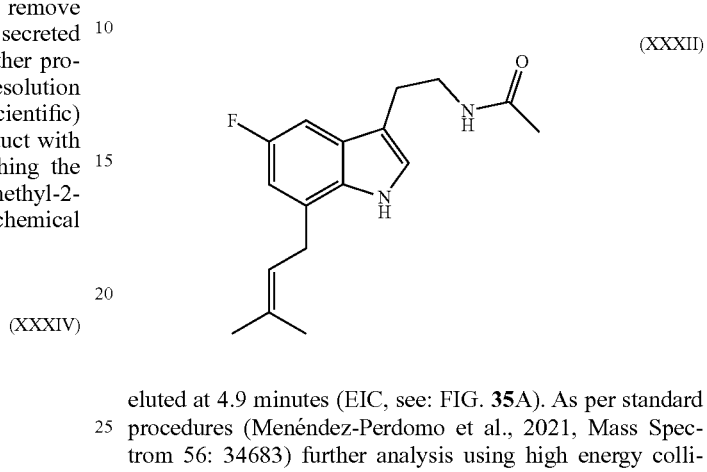

Figure 35A:
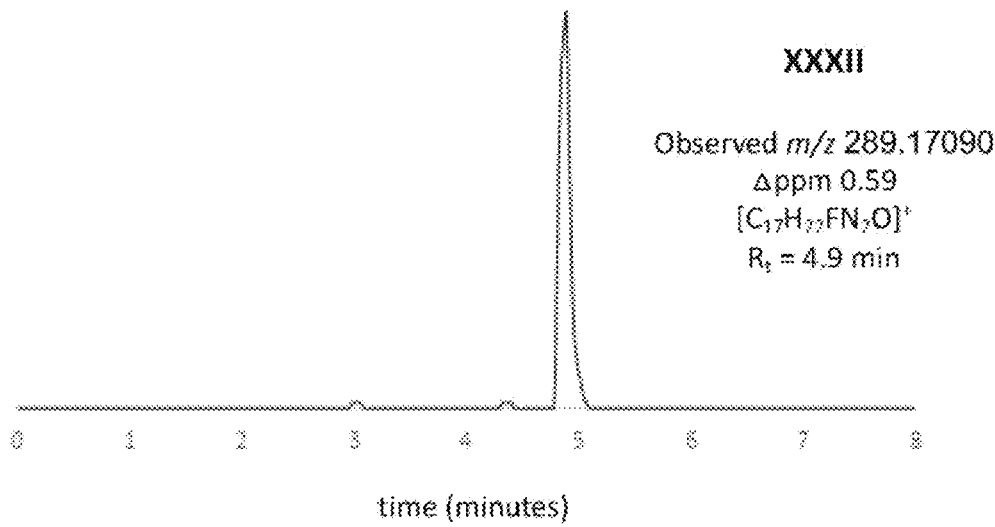
FIGS. 35A and 35B depict a representation of further mass spectrometry data in the form of a chromatogram, notably a chromatogram obtained in the performance of an experiment to synthesize an example multi-substituent psilocybin derivative compound having the chemical formula (XXXII) set forth herein (FIG. 35A); and a representation of mass spectrometry data in the form of a further mass spectrometry spectrum obtained in the performance of an experiment to identify a multi-substituent psilocybin derivative compound having the chemical formula (XXXII) set forth herein (FIG. 35B).
Figure 35B:
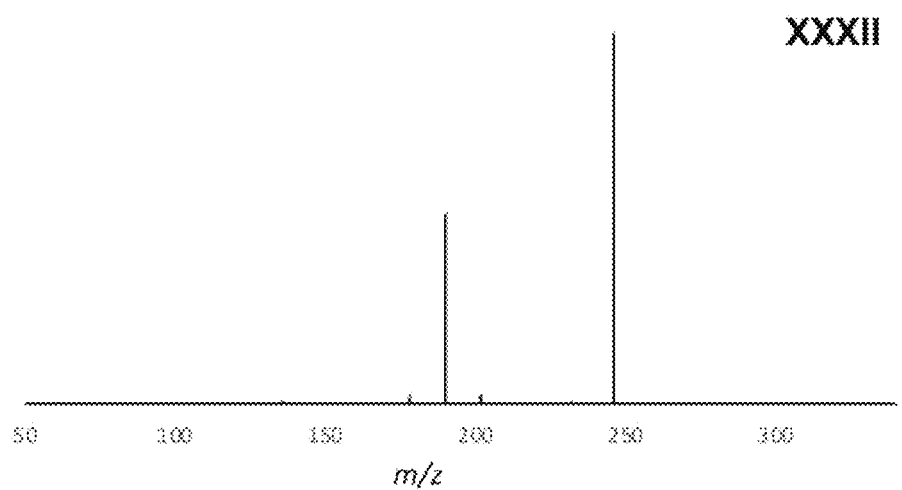

(XXXII)

eluted at 4.9 minutes (EIC, see: FIG. 35A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXXII) as follows (FIG. 35B, Table 10) (Servillo L. et al., 2013, J. Agric. Chem. 61: 5156-5162).

TABLE 10

| m/z | % Relative abundance | Ionic species | Δ ppm |
| --- | --- | --- | --- |
| 230.13354 | 100 | [M + H − $C_2H_6NO$]$^+$ | 1.78 |
| 174.07090 | 11.0 | | |
| 272.14384 | 1.9 | | |
| 233.10802 | 1.6 | | |
| 199.41144 | 0.8 | | |
| 151.39218 | 0.8 | | |
| 162.07105 | 0.8 | | |
| 216.08147 | 0.7 | | |
| 289.17040 | 0.7 | [M + H]$^+$ | 2.32 |
| 143.09824 | 0.7 | | |

Example 22—Biosynthesis of a Twenty-Second Multi-Substituent Psilocybin Derivative The same yeast strain (Sc-1) and procedures described in Example 20 were used to biosynthesize a psilocybin derivative with chemical formula (XXXIII), with the following exception: in place of 4-chloro-1H-indole, 500 µM 5-fluoro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-(2-[5-fluoro-7-(3-methyl-2-butenyl)-1H-indol-3-yl]ethyl)acetamide having chemical formula (XXXIII):

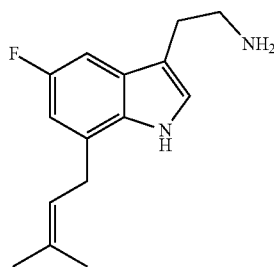

Figure 36:
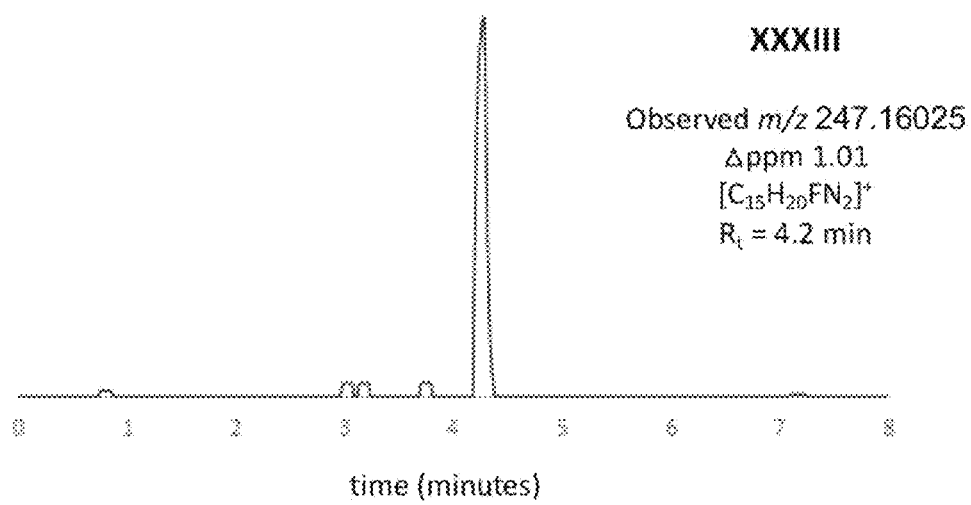
FIG. 36 depicts a representation of further mass spectrometry data in the form of a chromatogram, notably a chromatogram obtained in the performance of an experiment to synthesize an example multi-substituent psilocybin derivative compound having the chemical formula (XXXVI) set forth herein.

(XXXIII)

eluted at 4.2 minutes (EIC, see: FIG. 36). Notably, while the same indole feedstock was provided in this example compared to the feedstock used Example 21, the product (XXXII) is not the same as product (XXXIII). In fact, both products (XXXII) and (XXXIII) are achieved by feeding 5-fluoro-1H-indole to Sc-1. However, in Example 21, only product (XXXII) was analyzed. Conversely, in this Example, only product (XXXIII) was analyzed.

Example 23—Biosynthesis of a Twenty-Third Multi-Substituent Psilocybin Derivative The same yeast strain (Sc-1) and procedures described in Example 20 were used to biosynthesize a psilocybin derivative with chemical formula (XLIX), with the following exception: in place of 4-chloro-1H-indole, 500 µM 1H-indol-4-ol (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[4-hydroxy-7-(3-methyl-2-butenyl)-1H-indol-3-yl]propionic acid having chemical formula (XLIX):

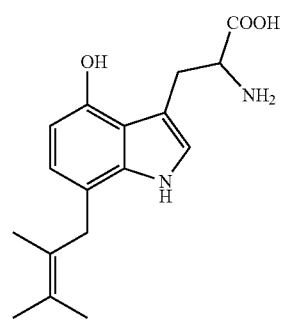

Figure 37:
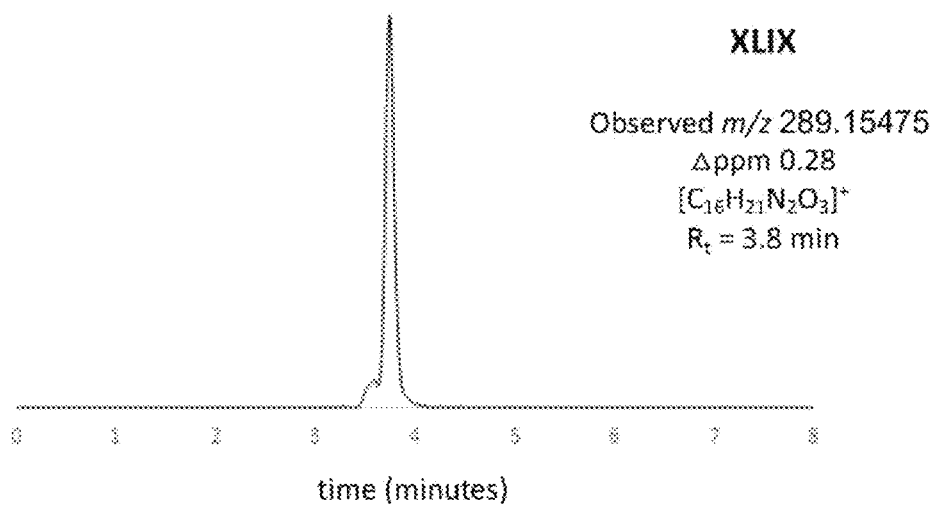
FIG. 37 depicts a representation of further mass spectrometry data in the form of a chromatogram, notably a chromatogram obtained in the performance of an experiment to synthesize an example multi-substituent psilocybin derivative compound having the chemical formula (XLIX) set forth herein.

(XLIX)

eluted at 3.8 minutes (EIC, see: FIG. 37). Notably, compound (XLIX) retains a carboxylic acid group despite the presence of ClostSporTDC enzyme in Sc-1. The decarboxylated version of compound (XLIX) was not detectable in the culture media, possibly owing to an inherent inability of ClostSporTDC enzyme to accept hydroxylated substrates.

Example 24—Biosynthesis of a Twenty-Fourth Multi-Substituent Psilocybin Derivative Yeast (*Saccharomyces cerevisiae*) strain Sc-2 was created through plasmid transformation of a parent yeast strain, to enable bioconversion of commercially obtained, derivatized indole, tryptophan, or tryptamine feedstock to generate final product. The parent yeast (*Saccharomyces cerevisiae*) strain was CEN.PK with genotype Mata; ura3-52; trp1-289; leu2-3,112; his3Δ1; MAL2-8C; SUC2. The parent strain was transformed with a yeast episomal vector (pMM1-pTDH3-PriB-His-tCYC1) encoding a HIS-tagged (SEQ.ID NO: 46, SEQ.ID NO: 47), promiscuous 6-prenyltransferase enzyme, PriB (SEQ.ID NO: 18). For construction of pMM1-pTDH3-PriB-His-tCYC1, the gene PriB (SEQ.ID NO: 17) fused in-frame with a HIS epitope tag (SEQ.ID NO: 46) was ligated to empty plasmid pMM1 (SEQ.ID NO: 34) using BamHI/SacII restriction sites. For this Example, heterologous expression of a non-native or engineered TrpB gene was not necessary, as endogenous tryptophan synthase activity proved sufficient. The final engineered strain was called Sc-2. For scaled-up production of derivative product, culturing was performed as described in Example 20, with the following exception: in place of 4-chloro-1H-indole, 500 µM 1H-indol-4-ol (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[4-hydroxy-6-(3-methyl-2-butenyl)-1H-indol-3-yl]propionic acid having chemical formula (L):

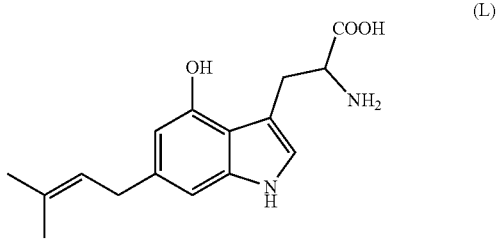 [SMILES: CC(C)=CCc1cc(O)c2c(CC(N)C(=O)O)c[nH]c2c1]

Figure 38:
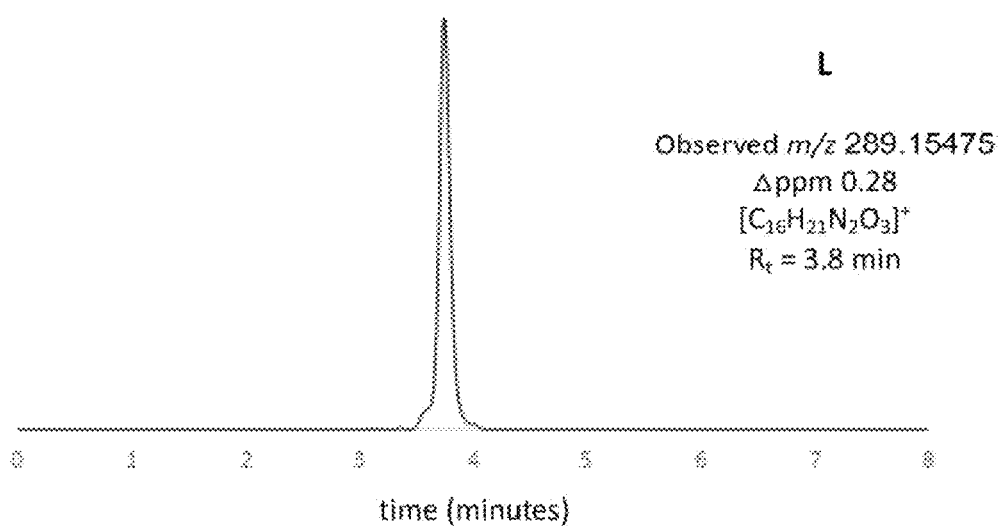
FIG. 38 depicts a representation of further mass spectrometry data in the form of a chromatogram, notably a chromatogram obtained in the performance of an experiment to synthesize an example multi-substituent psilocybin derivative compound having the chemical formula (L) set forth herein.

(L)

eluted at 3.8 minutes (EIC, see: FIG. 38).

Example 25—Biosynthesis of a Twenty-Fifth Multi-Substituent Psilocybin Derivative The same yeast strain (Sc-2) and procedures described in Example 24 were used to biosynthesize a psilocybin derivative with chemical formula (XLVIII), with the following exception: in place of 1H-indol-4-ol, 5-bromo-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[5-bromo-6-(3-methyl-2-butenyl)-1H-indol-3-yl]propionic acid having chemical formula (XLVIII):

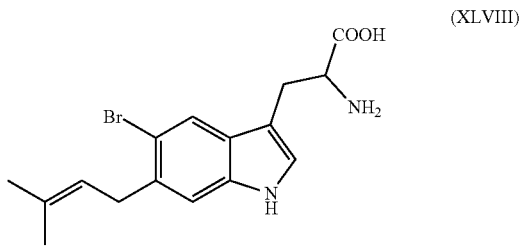 [SMILES: CC(C)=CCc1cc2[nH]cc(CC(N)C(=O)O)c2cc1Br]

Figure 39:
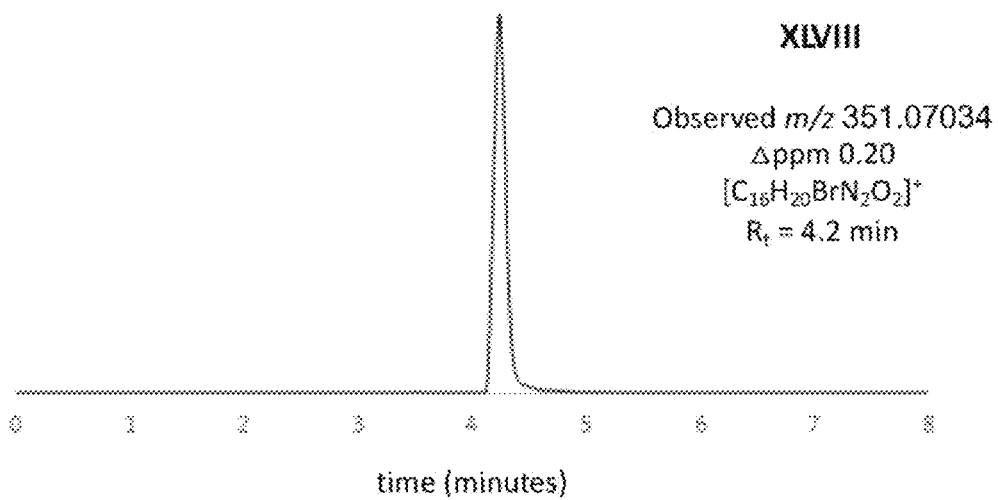
FIG. 39 depicts a representation of further mass spectrometry data in the form of a chromatogram, notably a chromatogram obtained in the performance of an experiment to synthesize an example multi-substituent psilocybin derivative compound having the chemical formula (XLVII) set forth herein.

(XLVIII)

eluted at 4.2 minutes (EIC, see: FIG. 39).

Figure 40:
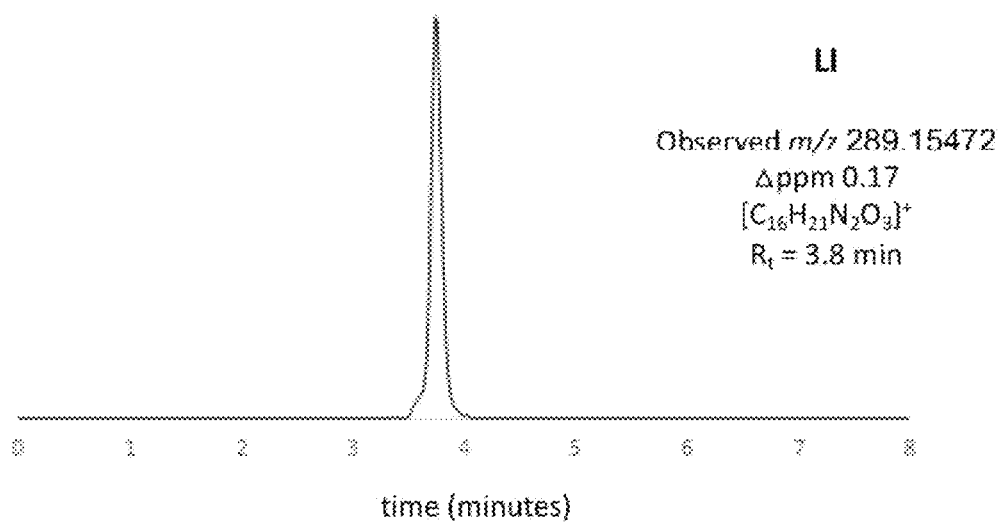
FIG. 40 depicts a representation of further mass spectrometry data in the form of a chromatogram, notably a chromatogram obtained in the performance of an experiment to synthesize an example multi-substituent psilocybin derivative compound having the chemical formula (LI) set forth herein.

Example 26—Biosynthesis of a Twenty-Sixth Multi-Substituent Psilocybin Derivative Yeast (*Saccharomyces cerevisiae*) strain Sc-3 was created through plasmid transformation of a parent yeast strain, to enable bioconversion of commercially obtained, derivatized indole, tryptophan, or tryptamine feedstock to generate final product. The parent yeast (*Saccharomyces cerevisiae*) strain was CEN.PK with genotype Mata; ura3-52; trp1-289; leu2-3,112; his3Δ1; MAL2-8C; SUC2. The parent strain was transformed with a yeast episomal vector (pMM1-pTDH3-SCO7467-tCYC1) encoding a 5-prenyltransferase enzyme, SCO7467 (SEQ.ID NO: 20). For construction of pMM1-pTDH3-SCO7467-tCYC1, the gene SCO7467 (SEQ.ID NO: 19) was ligated to empty plasmid pMM1 (SEQ.ID NO: 34) using BamHI/SacII restriction sites. For this Example, heterologous expression of a non-native or engineered TrpB gene was not necessary, as endogenous tryptophan synthase activity proved sufficient. The final engineered strain was called Sc-3. For scaled-up production of derivative product, culturing was performed as described in Example 20, with the following exception: in place of 4-chloro-1H-indole, 500 µM 1H-Indol-4-ol (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[4-hydroxy-5-(3-methyl-2-butenyl)-1H-indol-3-yl]propionic acid, having chemical formula (LI):

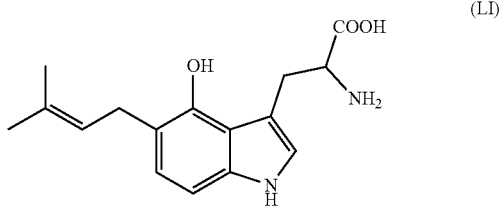 [SMILES: CC(C)=CCc1ccc2[nH]cc(CC(N)C(=O)O)c2c1O]

eluted at 3.8 minutes (EIC, see: FIG. 40).

Figure 41:
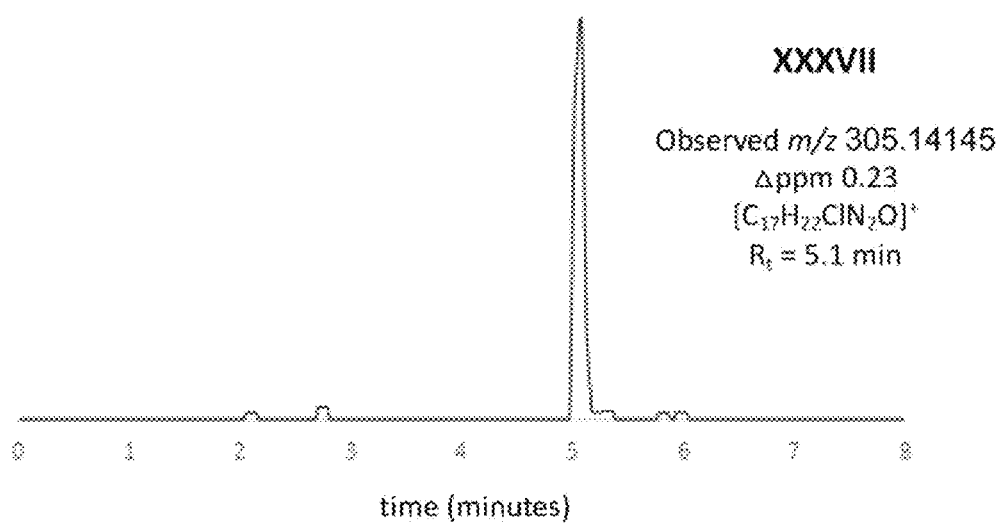
FIG. 41 depicts a representation of further mass spectrometry data in the form of a chromatogram, notably a chromatogram obtained in the performance of an experiment to synthesize an example multi-substituent psilocybin derivative compound having the chemical formula (XXXVI) set forth herein.

Example 27—Biosynthesis of a Twenty-Seventh Multi-Substituent Psilocybin Derivative Yeast (*Saccharomyces cerevisiae*) strain Sc-4 was created through genetic engineering of a parent yeast strain, to enable bioconversion of commercially obtained, derivatized indole, tryptophan, or tryptamine feedstock to generate final product. The parent yeast (*Saccharomyces cerevisiae*) strain was CEN.PK with genotype Mata; ura3-52; trp1-289; leu2-3,112; his3Δ1; MAL2-8C; SUC2. The parent strain was engineered to include PriB (SEQ.ID NO: 18), BaTDC (SEQ.ID NO: 4), and PsmF (SEQ.ID NO: 10) which catalyzed three enzymatic steps. Engineering also included CPR (SEQ.ID NO: 26) although this enzyme was not used in the bioconversion process. PriB, BaTDC, and CPR were included in the strain through chromosomal homologous recombination of integration cassettes as described previously (Dastmalchi et al., 2019, Nat. Chem Biol. 15: 384-390; Chen et al., 2018, Nat. Chem Biol. 14: 738-743). Conversely, PsmF was built into a protein expression plasmid and transformed to the genomically integrated strain already harboring PriB, BaTDC, and CPR. PriB, BaTDC, and CPR were encoded by SEQ.ID NO: 17, SEQ.ID NO: 3 and SEQ.ID NO: 25, respectively, with addition of in-frame, C-terminal HIS (SEQ.ID NO: 46, SEQ.ID NO: 47), FLAG (SEQ.ID NO: 42, SEQ.ID NO: 43), and c-MYC (SEQ.ID NO: 40, SEQ.ID NO: 41) epitope tags, respectively. Integration cassettes were built using yeast promoter sequences amplified from *S. cerevisiae* genomic DNA as described (Dastmalchi et al., 2019; Chen et al., 2018) enabling constitutive gene expression. Amplified promoters included PGK1 (SEQ.ID NO: 30), TDH3 (SEQ.ID NO: 31), CLN1 (SEQ.ID NO: 32), and UGA1 (SEQ.ID NO: 33). Two integration cassettes were assembled: the first, (X-3)::TADH1-BaTDC-Flag-PPGK1-PTDH3-CPR-c-myc-TCYC1 (SEQ.ID NO: 50), harboured tagged BaTDC and CPR, The second (Xii-2)::PTDH3-PriB-His-TCYC1 (SEQ.ID NO: 51), harboured only tagged PriB. Successive genomic integration of these cassettes was performed as described previously (Chen et al., 2018). Following stable integration of these two cassettes, the strain was further manipulated by transformation with a yeast episomal vector encoding a promiscuous N-acetyltransferase, PsmF (pMM1-pTDH3-PsmF-His-tCYC1). For construction of pMM1-pTDH3-PsmF-His-tCYC1, the gene PsmF (SEQ.ID NO: 9) fused in-frame with a HIS epitope tag (SEQ.ID NO: 46) was ligated to empty plasmid pMM1 (SEQ.ID NO: 34) using BamHI/SacII restriction sites. For this Example, heterologous expression of a non-native or engineered TrpB gene was not necessary, as endogenous tryptophan synthase activity proved sufficient. The final engineered strain was called Sc-4. For scaled-up production of derivative product, culturing was performed as described in Example 20, with the following exception: in place of 4-chloro-1H-indole, 500 µM 5-chloro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-(2-[5-chloro-6-(3-methyl-2-butenyl)-1H-indol-3-yl]ethyl)acetamide, having chemical formula (XXXVII):

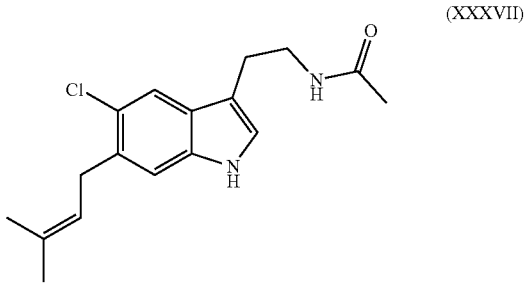 [SMILES: CC(=O)NCCc1c[nH]c2cc(CC=C(C)C)c(Cl)cc12]

eluted at 5.1 minutes (EIC, see: FIG. 41).

Example 28—Biosynthesis of a Twenty-Eighth Multi-Substituent Psilocybin Derivative The same yeast strain (Sc-4) and procedures described in Example 27 were used to biosynthesize a psilocybin derivative with chemical formula (XXXV), with the following exception: in place of 5-chloro-1H-indole, 500 µM 5-fluoro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N-(2-[5-fluoro-6-(3-methyl-2-butenyl)-1H-indol-3-yl]ethyl)acetamide, having chemical formula (XXXV):

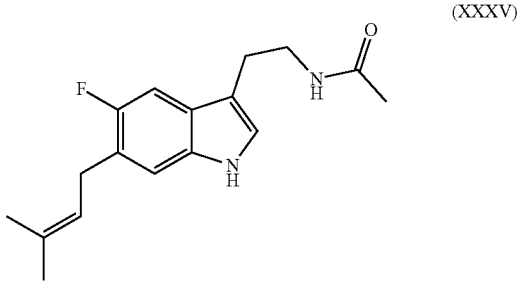 [SMILES: CC(=O)NCCc1c[nH]c2cc(CC=C(C)C)c(F)cc12]

Figure 42:
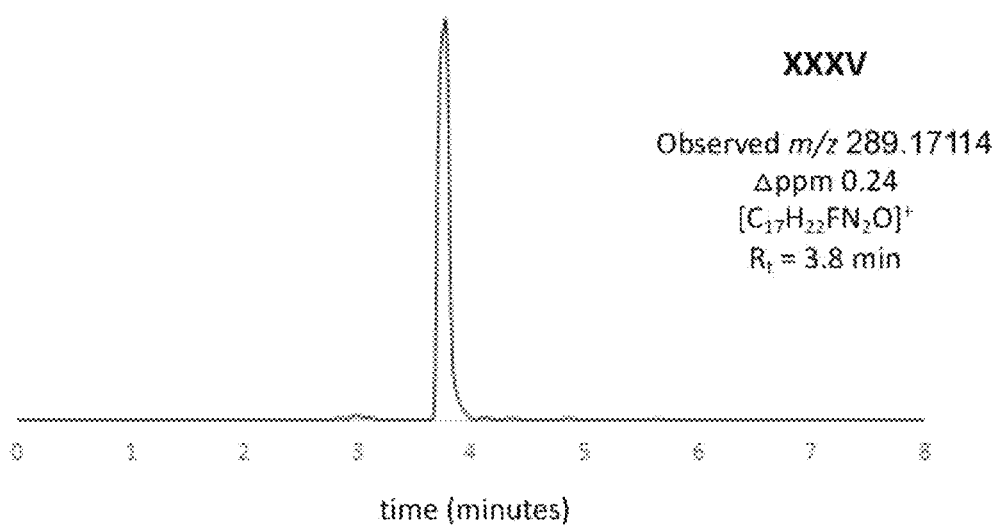
FIG. 42 depicts a representation of further mass spectrometry data in the form of a chromatogram, notably a chromatogram obtained in the performance of an experiment to synthesize an example multi-substituent psilocybin derivative compound having the chemical formula (XXXV) set forth herein.

(XXXV)

eluted at 3.8 minutes (EIC, see: FIG. 42).

Example 29—Biosynthesis of a Twenty-Ninth Multi-Substituent Psilocybin Derivative Yeast (*Saccharomyces cerevisiae*) strain Sc-5 was obtained as an intermediate in the process of assembling Sc-4. The strain Sc-5 is essentially identical to Sc-4, with the exception that Sc-5 does not harbour an additional episomal vector (pMM1-pTDH3-PsmF-His-tCYC1) encoding the promiscuous N-acetyltransferase, PsmF (SEQ.ID NO: 10). Thus, Sc-5 hosts only two enzymes through chromosomal integration—BaTDC (SEQ. ID NO: 4) and PriB (SEQ. ID NO: 18)—which participate in derivative formation. A third enzyme, CPR (SEQ.ID NO: 26) is similarly integrated but does not contribute to derivative production. Heterologous expression of a non-native or engineered TrpB gene was not necessary, as endogenous tryptophan synthase activity proved sufficient. For scaled-up production of derivative product, culturing was performed as described in Example 20, with the following exception: in place of 4-chloro-1H-indole, 500 µM 5-fluoro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-[5-fluoro-6-(3-methyl-2-butenyl)-1H-indol-3-yl]ethylamine, having chemical formula (XXXVI):

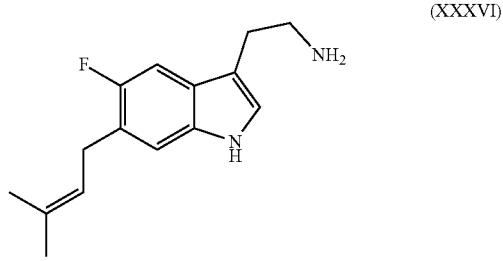 [SMILES: CC(C)=CCc1cc2[nH]cc(CCN)c2cc1F]

Figure 43A:
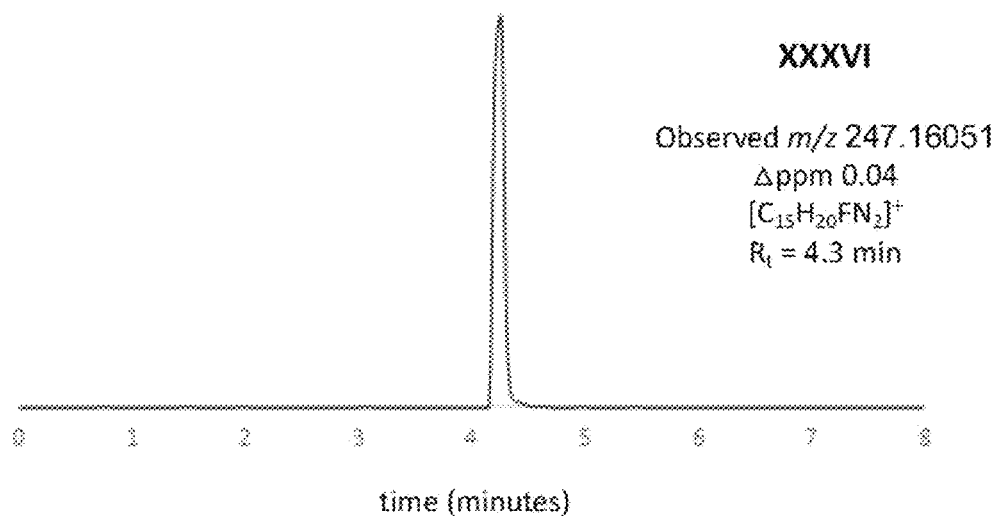
FIGS. 43A and 43B depict a representation of further mass spectrometry data in the form of a chromatogram, notably a chromatogram obtained in the performance of an experiment to synthesize an example multi-substituent psilocybin derivative compound having the chemical formula (XXXVI) set forth herein (FIG. 43A); and a representation of mass spectrometry data in the form of a further mass spectrometry spectrum obtained in the performance of an experiment to identify a multi-substituent psilocybin derivative compound having the chemical formula (XXXVI) set forth herein (FIG. 43B).
Figure 43B:
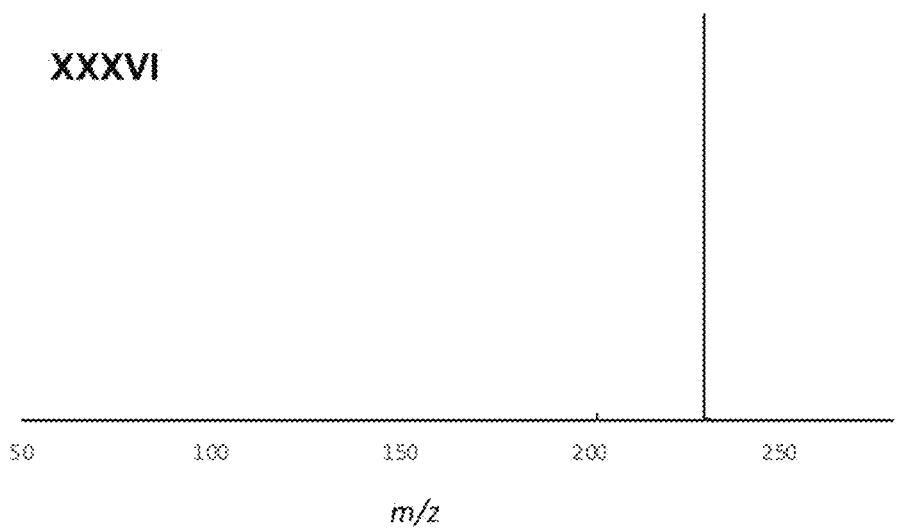

(XXXVI)

eluted at 4.3 minutes (EIC, see: FIG. 43). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XXXVI) as follows (FIG. 43B, Table 11) (Servillo L. et al, 2013, J. Agric. Chem. 61: 5156-5162).

TABLE 11

| m/z | % Relative abundance | Ionic species | Δ ppm |
|---|---|---|---|
| 230.13358 | 100 | $[M + H - NH_3]^+$ | 1.61 |
| 198.47229 | 0.6 | | |
| 89.48803 | 0.5 | | |
| 233.50280 | 0.5 | | |
| 154.92723 | 0.5 | | |
| 115.92102 | 0.5 | | |
| 132.59683 | 0.5 | | |
| 92.18462 | 0.5 | | |
| 199.41139 | 0.4 | | |
| 102.89690 | 0.4 | | |

Example 30—Biosynthesis of a Thirtieth Multi-Substituent Psilocybin Derivative The same yeast strain (Sc-5) and procedures described in Example 29 were used to biosynthesize a psilocybin derivative with chemical formula (XXXVIII), with the following exception: in place of 5-fluoro-1H-indole, 500 µM 5-chloro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-[5-chloro-6-(3-methyl-2-butenyl)-1H-indol-3-yl]ethylamine, having chemical formula (XXXVIII):

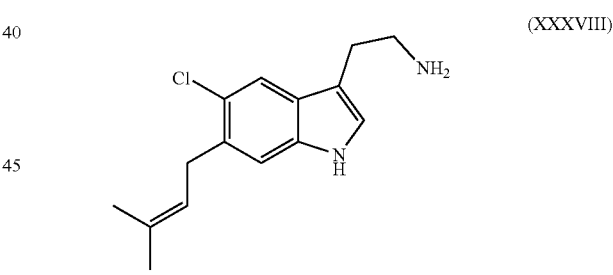

Figure 44:
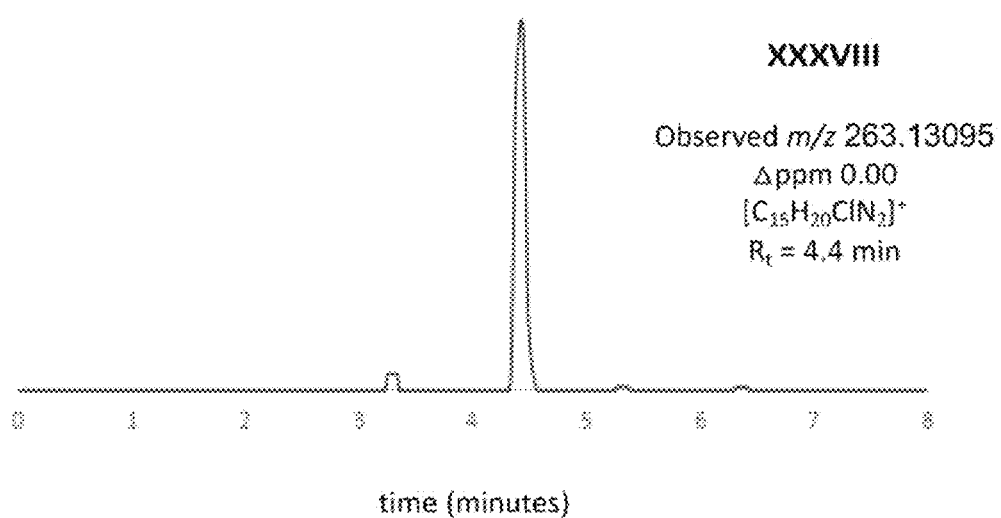
FIG. 44 depicts a representation of further mass spectrometry data in the form of a chromatogram, notably a chromatogram obtained in the performance of an experiment to synthesize an example multi-substituent psilocybin derivative compound having the chemical formula (XXXVIII) set forth herein.

(XXXVIII)

eluted at 4.4 minutes (EIC, see: FIG. 44).

Example 31—Biosynthesis of a Thirty-First Multi-Substituent Psilocybin Derivative Yeast (*Saccharomyces cerevisiae*) strain Sc-6 was created through genetic engineering of a parent yeast strain, to enable bioconversion of commercially obtained, derivatized indole, tryptophan, or tryptamine feedstock to generate final product. The parent yeast (*Saccharomyces cerevisiae*) strain was CEN PK with genotype Matα; ura3-52; trp1-289; leu2-3,112; his3Δ1; MAL2-8C; SUC2. The parent strain was engineered to include PsiH (SEQ.ID NO: 24), CPR (SEQ.ID NO: 26), ClostSporTDC (SEQ.ID NO: 6) and PsiM (SEQ.ID NO: 14) which catalyzed or supported several enzymatic steps. Engineering also included PsiK (SEQ.ID NO: 49) although this enzyme did not appear capable of contributing to the bioconversion process. PsiH, CPR, PsiM and PsiK were included in the strain through chromosomal homologous recombination of integration cassettes as described previously (Dastmalchi et al., 2019, Nat. Chem Biol. 15: 384-390; Chen et al., 2018, Nat. Chem Biol. 14: 738-743). Conversely, ClostSporTDC was built into a protein expression plasmid and transformed to the genomically integrated strain already harboring PsiH, CPR, PsiM and PsiK. PsiH, CPR, ClostSporTDC and PsiM were encoded by SEQ.ID NO: 23, SEQ.ID NO: 25, SEQ.ID NO: 5, and SEQ.ID NO: 13, respectively, with addition of in-frame, C-terminal HA (SEQ.ID NO: 38, SEQ.ID NO: 39), c-MYC (SEQ.ID NO: 40, SEQ.ID NO: 41), HIS (SEQ.ID NO: 46, SEQ.ID NO: 47) and FLAG (SEQ.ID NO: 42, SEQ.ID NO: 43) epitope tags, respectively. Integration cassettes were built using yeast promoter sequences amplified from *S. cerevisiae* genomic DNA as described (Dastmalchi et al., 2019; Chen et al., 2018) enabling constitutive gene expression. Amplified promoters included PGK1 (SEQ.ID NO: 30), TDH3 (SEQ.ID NO: 31), CLN1 (SEQ.ID NO: 32), and UGA1 (SEQ.ID NO: 33). Two integration cassettes were assembled: the first, XII-4::TADH1-PsiH-HA-PPGK1-PTDH3-CPR-c-myc-TCYC1 (SEQ.ID NO: 27), harboured tagged PsiH and CPR. The second, XII-5::TADH1-PsiK-V5-PPGK1-PTDH3-PsiM-FLAG-TCYC1 (SEQ.ID NO: 28), harboured tagged PsiK and PsiM. Successive genomic integration of these cassettes was performed as described previously (Chen et al., 2018). Following stable integration of these two cassettes, the strain was further manipulated by transformation with a yeast episomal vector encoding ClostSporTDC (pMM1-pTDH3-ClostSpor-His-tCYC1). For construction of pMM1-pTDH3-ClostSpor-His-tCYC1, the gene ClostSporTDC (SEQ.ID NO: 5) fused in-frame with a HIS epitope tag (SEQ.ID NO: 46) was ligated to empty plasmid pMM1 (SEQ.ID NO: 34) using BamHI/SacII restriction sites. For this Example, heterologous expression of a non-native or engineered TrpB gene was not necessary, as endogenous tryptophan synthase activity proved sufficient. The final engineered strain was called Sc-6. Employing Sc-6, the same procedures described in Example 20 were used to biosynthesize a psilocybin derivative with chemical formula (XL), with the following exception: in place of 4-chloro-1H-indole, 500 μM 6-chloro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 6-chloro-3-[2-(dimethylamino)ethyl]-1H-indol-4-ol, having chemical formula (XL):

Figure 45:
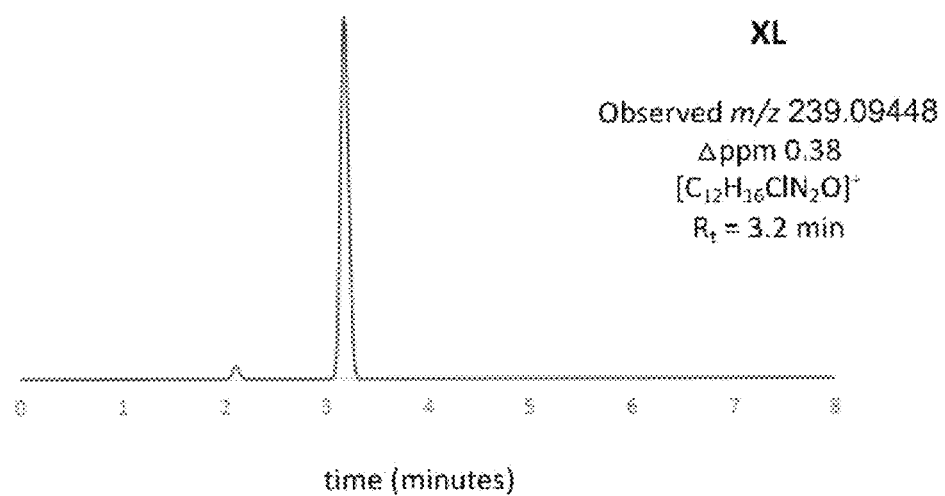
FIG. 45 depicts a representation of further mass spectrometry data in the form of a chromatogram, notably a chromatogram obtained in the performance of an experiment to synthesize an example multi-substituent psilocybin derivative compound having the chemical formula (XL) set forth herein.

(XL)

eluted at 0.38 minutes (EIC, see: FIG. 45).

Example 32—Biosynthesis of a Thirty-Second Multi-Substituent Psilocybin Derivative The same yeast strain (Sc-6) and procedures described in Example 31 were used to biosynthesize a psilocybin derivative with chemical formula (XXXIX), with the following exception: in place of 4-chloro-1H-indole, 500 μM 7-chloro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 7-chloro-3-[2-(dimethylamino)ethyl]-1H-indol-4-ol, having chemical formula (XXXIX):

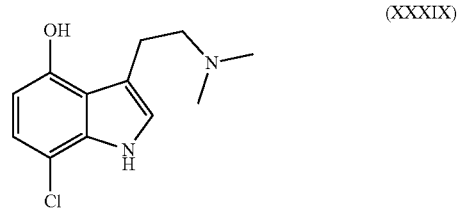 [SMILES: CN(C)CCc1c[nH]c2c(Cl)ccc(O)c12]

Figure 46:
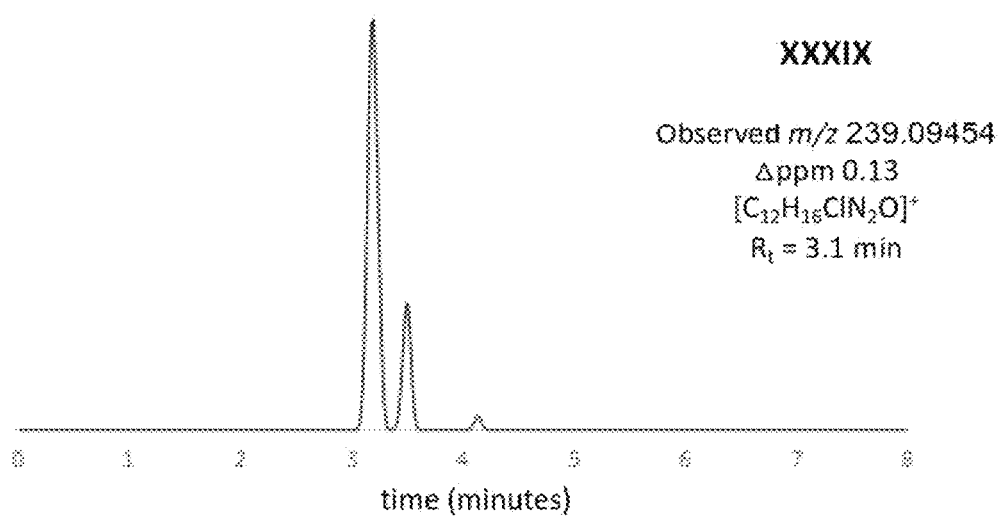
FIG. 46 depicts a representation of further mass spectrometry data in the form of a chromatogram, notably a chromatogram obtained in the performance of an experiment to synthesize an example multi-substituent psilocybin derivative compound having the chemical formula (XXXIX) set forth herein.

(XXXIX)

eluted at 3.1 minutes (EIC, see: FIG. 46).

Example 33—Biosynthesis of a Thirty-Third Multi-Substituent Psilocybin Derivative The same yeast strain (Sc-6) and procedures described in Example 31 were used to biosynthesize a psilocybin derivative with chemical formula (LII), with the following exception: in place of 4-chloro-1H-indole, 500 μM 6-fluoro-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-6-fluoro-1H-indol-4-ol, having chemical formula (LII):

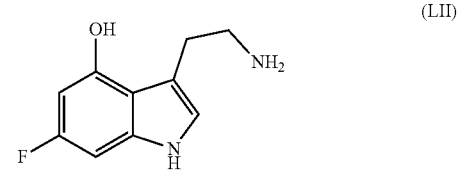 [SMILES: NCCc1c[nH]c2cc(F)cc(O)c12]

Figure 47:
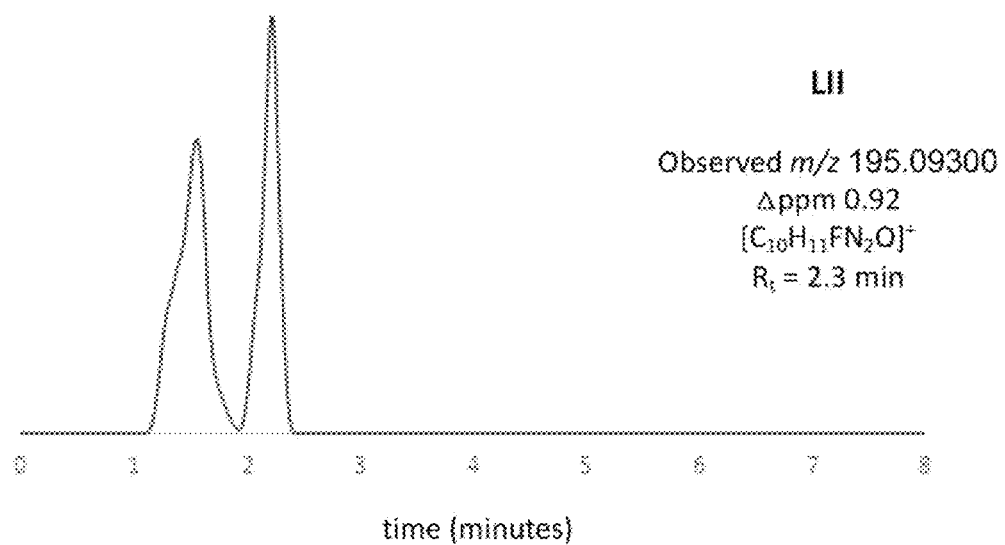
FIG. 47 depicts a representation of further mass spectrometry data in the form of a chromatogram, notably a chromatogram obtained in the performance of an experiment to synthesize an example multi-substituent psilocybin derivative compound having the chemical formula (LII) set forth herein.

(LII)

eluted at 2.3 minutes (EIC, see: FIG. 47). Notably, the product (LII) did not bear an N,N-dimethyl function despite the presence of methyltransferase enzyme PsiM, implying that PsiM was incapable of accepting this product (LII) as a substrate.

Figure 48:
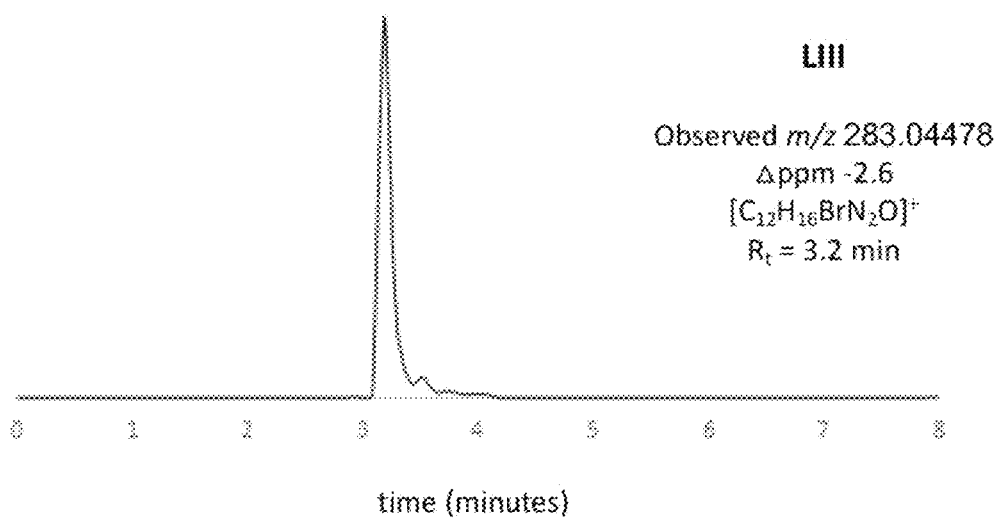
FIG. 48 depicts a representation of further mass spectrometry data in the form of a chromatogram, notably a chromatogram obtained in the performance of an experiment to synthesize an example multi-substituent psilocybin derivative compound having the chemical formula (LIII) set forth herein.

Example 34—Biosynthesis of a Thirty-Fourth Multi-Substituent Psilocybin Derivative The same yeast strain (Sc-6) and procedures described in Example 31 were used to biosynthesize a psilocybin derivative with chemical formula (LIII), with the following exception: in place of 4-chloro-1H-indole, 500 μM 6-bromo-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 6-bromo-3-[2-(dimethylamino)ethyl]-1H-indol-4-ol, having chemical formula (LIII):

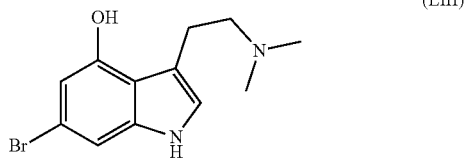
(LIII)

eluted at 3.2 minutes (EIC, see: FIG. 48).

Figure 49:
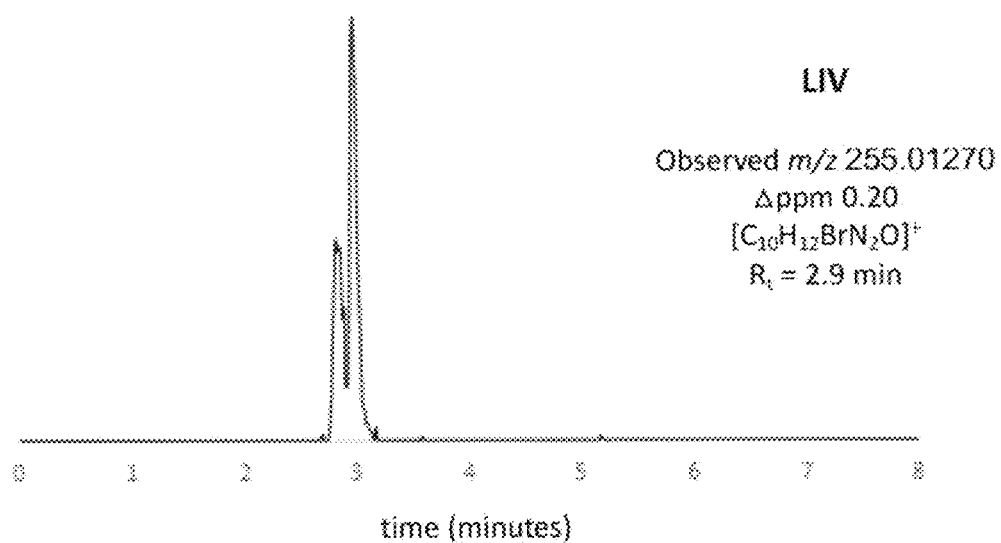
FIG. 49 depicts a representation of further mass spectrometry data in the form of a chromatogram, notably a chromatogram obtained in the performance of an experiment to synthesize an example multi-substituent psilocybin derivative compound having the chemical formula (LIV) set forth herein.

Example 35—Biosynthesis of a Thirty-Fifth Multi-Substituent Psilocybin Derivative The same yeast strain (Sc-6) and procedures described in Example 31 were used to biosynthesize a psilocybin derivative with chemical formula (LIV), with the following exception: in place of 4-chloro-1H-indole, 500 µM 6-bromo-1H-indole (Combi-Blocks, www.combi-blocks.com) was supplied as feedstock for bioconversion. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-aminoethyl)-6-bromo-1H-indol-4-ol, having chemical formula (LIV):

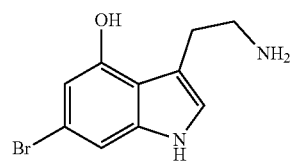
(LIV)

eluted at 2.9 minutes (EIC, see: FIG. 49). Notably, while the same indole feedstock was provided in this example compared to the feedstock used in Example 34, the product (LIII) is not the same as product (LIV). In fact, both products (LIII) and (LIV) are achieved by feeding 6-bromo-1H-indole to Sc-6. However, in Example 34, only product (LIII) was analyzed. Conversely, in this Example, only product (LIV) was analyzed.

Figure 50:
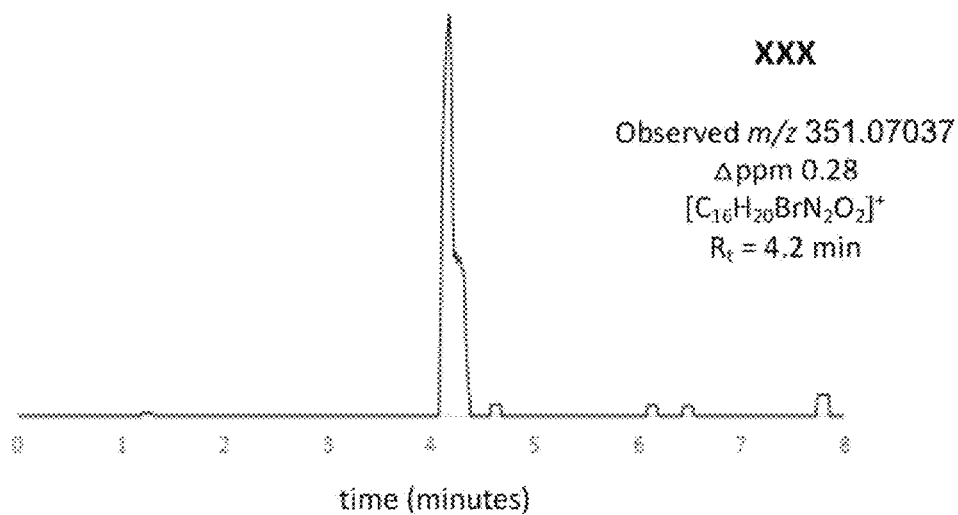
FIG. 50 depicts a representation of further mass spectrometry data in the form of a chromatogram, notably a chromatogram obtained in the performance of an experiment to synthesize an example multi-substituent psilocybin derivative compound having the chemical formula (XXX) set forth herein.

Example 36—Biosynthesis of a Thirty-Sixth Multi-Substituent Psilocybin Derivative Synthesis of a psilocybin derivative was accomplished using FgaPT2 enzyme and an in vitro procedure. cDNA encoding FgaPT2 (SEQ.ID NO: 21) was synthesized and subcloned at GenScript (www.genscript.com) using Nde1 and Xho1 sites to pET26b(+) plasmid (SEQ.ID NO: 54). The final plasmid pET26b(+)-FgaPT2 encoded an in-frame, C-terminal HIS tag fusion of FgaPT2. Purified, recombinant FgaPT2 enzyme (SEQ.ID NO: 22) was raised in E. coli and isolated as follows. The plasmid pET26b(+)-FgaPT2 was transformed into Rosetta (DE3) competent E. coli cells. Transformed Rosetta (DE3) E. coli cells were grown in LB media at 30° C. for overnight and then transferred into TB (terrific broth) media to grow at 37° C. until optical density ($OD_{600}$) reached 0.6-1.5. The cell culture was then transferred to a 16° C. incubator with the addition of IPTG at 0.2 mM to initiate recombinant protein expression. After 20 hours the cells were harvested by centrifugation at 5,000×g for 6 minutes and the cell pellet was stored in −80° C. before protein extraction. For extraction and purification of FgaPT2 recombinant protein, E. coli cells were resuspended in a buffer containing 50 mM sodium phosphate (pH 7.0) and 300 mM NaCl and then sonicated for 5-10 minutes to break the cells. The cell lysate was centrifuged at 12,000 g for 30 minutes to collect the supernatant containing soluble crude protein. The supernatant was applied to cobalt resin (TALON Superflow™, Cytiva) to isolate HIS-tagged target protein. Purified protein was stored at −80° C. in a buffer containing 50 mM Tris-HCl (pH 7.0), 100 mM NaCl, and 10% glycerol. The tryptophan derivative 2-amino-3-(5-bromo-1H-indol-3-yl)propionic acid (www.sigmaaldrich.com) and DMAPP (www.sigmaaldrich.com) were used as co-substrates in the reaction. Briefly, reactions were set up as follows: 50 mM Tris-HCl (pH 8.0), 180 µM DMAPP, 0.5 mM tryptophan derivative, and 300 µg/mL of FgaPT2 were added together and the reaction proceeded at 37° C. for 2 hours. Equal volume of MeOH was added to quench the reaction and precipitate the protein. The sample was then centrifuged at 13,000 g for 20 minutes, allowing removal of the supernatant which contained the desired product. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[5-bromo-4-(3-methyl-2-butenyl)-1H-indol-3-yl]propionic acid, having chemical formula (XXX):

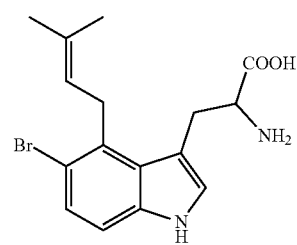
(XXX)

eluted at 4.2 minutes (EIC, see: FIG. 50).

Example 37—Biosynthesis of a Thirty-Seventh Multi-Substituent Psilocybin Derivative Synthesis of a psilocybin derivative was accomplished using FgaPT2 enzyme and the in vitro procedure described in Example 36, with the exception that 2-amino-3-(6-fluoro-1H-indol-3-yl)propionic acid (www.sigmaaldrich.com) was used in place of 2-amino-3-(5-bromo-1H-indol-3-yl)propionic acid substrate. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 2-amino-3-[6-fluoro-4-(3-methyl-2-butenyl)-1H-indol-3-yl]propionic acid, having chemical formula (XXXI):

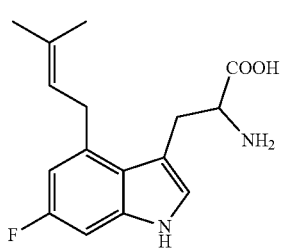

Figure 51:
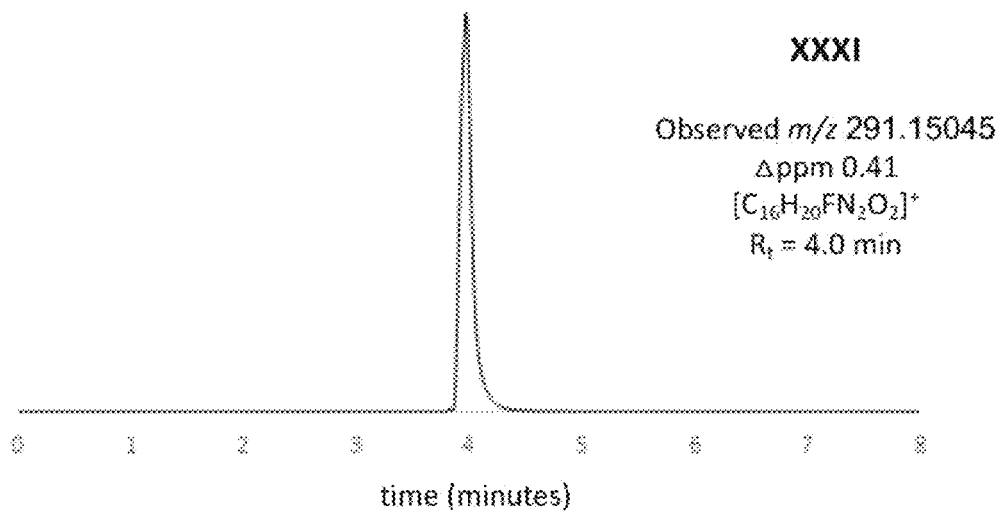
FIG. 51 depicts a representation of further mass spectrometry data in the form of a chromatogram, notably a chromatogram obtained in the performance of an experiment to synthesize an example multi-substituent psilocybin derivative compound having the chemical formula (XXXI) set forth herein.

(XXXI)

eluted at 4.0 minutes (EIC, see: FIG. 51).

Example 38—Biosynthesis of a Thirty-Eighth Multi-Substituent Psilocybin Derivative Synthesis of a psilocybin derivative was accomplished using PriB enzyme and an in vitro procedure. cDNA encoding PriB (SEQ.ID NO: 17) was synthesized and subcloned at GenScript (www.genscript.com) using Nde1 and Xho1 sites to pET26b(+) plasmid (SEQ.ID NO: 54). The final plasmid pET26b(+)-PriB encoded an in-frame, C-terminal HIS tag fusion of PriB. Purified, recombinant PriB enzyme (SEQ.ID NO: 18) was raised in *E. coli* and isolated as follows. The plasmid pET26b(+)-PriB was transformed into Rosetta (DE3) competent *E. coli* cells. Transformed Rosetta (DE3) *E. coli* cells were grown in LB media at 30° C. for overnight and then transferred into TB (terrific broth) media to grow at 37° C. until optical density ($OD_{600}$) reached 0.6-1.5. The cell culture was then transferred to a 16° C. incubator with the addition of IPTG at 0.5 mM to initiate recombinant protein expression. After 20 hours the cells were harvested by centrifugation at 5,000×g for 6 minutes and the cell pellet was stored in −80° C. before protein extraction. For extraction and purification of PriB recombinant protein, *E. coli* cells were resuspended in a buffer containing 50 mM sodium phosphate (pH 7.0) and 300 mM NaCl and then sonicated for 5-10 minutes to break the cells. The cell lysate was centrifuged at 12,000 g for 30 minutes to collect the supernatant containing soluble crude protein. The supernatant was applied to cobalt resin (TALON Superflow™, Cytiva) to isolate HIS-tagged target protein. Purified protein was stored at −80° C. in a buffer containing 50 mM Tris-HCl (pH 7.0), 100 mM NaCl, and 10% glycerol. The co-substrates 3-[2-(dimethylamino)ethyl]-1H-indol-4-yl propionate (Indole Shop; www.theindoleshop.com) and DMAPP (www.sigmaaldrich.com) were used in the reaction. Briefly, reactions were set up as follows: 50 mM Tris-HCl (pH 8.0), 180 μM DMAPP, 0.5 mM 3-[2-(dimethylamino)ethyl]-1H-indol-4-yl propionate and 392 μg/mL of PriB were added together and the reaction proceeded at 37° C. for 2 hours. Equal volume of MeOH was added to quench the protein and precipitate the protein. The sample was then centrifuged at 13,000 g for 20 minutes, allowing removal of the supernatant which contained the desired product. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-[2-(dimethylamino)ethyl]-6-(3-methyl-2-butenyl)-1H-indol-4-yl propionate, having chemical formula (XLI):

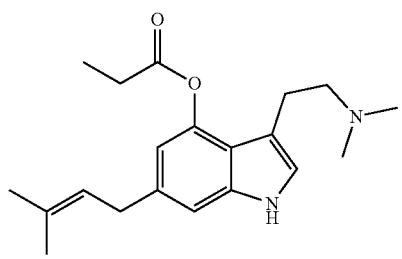

Figure 52:
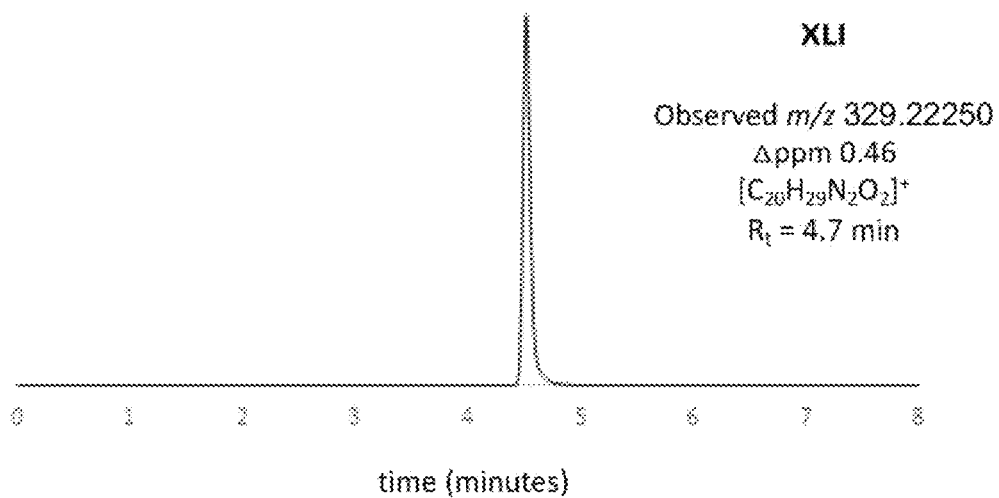
FIG. 52 depicts a representation of further mass spectrometry data in the form of a chromatogram, notably a chromatogram obtained in the performance of an experiment to synthesize an example multi-substituent psilocybin derivative compound having the chemical formula (XLI) set forth herein.

(XLI)

eluted at 4.7 minutes (EIC, see: FIG. 52).

Example 39—Biosynthesis of a Thirty-Ninth Multi-Substituent Psilocybin Derivative Synthesis of a psilocybin derivative was accomplished using PriB enzyme and the in vitro procedure described in Example 38, with the exception that 3-[2-(dimethylamino)ethyl]-1H-indol-4-yl acetate (Indole Shop; www.theindoleshop.com) was used in place of 3-[2-(dimethylamino)ethyl]-1H-indol-4-yl propionate substrate. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-[2-(dimethylamino)ethyl]-6-(3-methyl-2-butenyl)-1H-indol-4-yl acetate, having chemical formula (XLII):

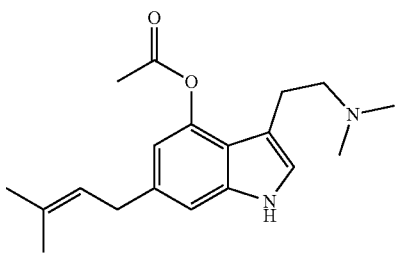

Figure 53:
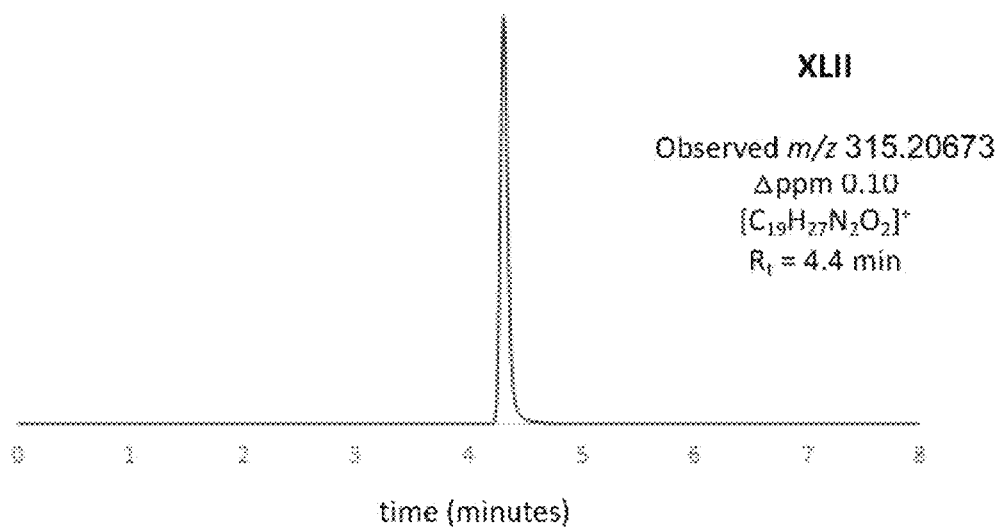
FIG. 53 depicts a representation of further mass spectrometry data in the form of a chromatogram, notably a chromatogram obtained in the performance of an experiment to synthesize an example multi-substituent psilocybin derivative compound having the chemical formula (XLII) set forth herein.

(XLII)

eluted at 4.4 minutes (EIC, see: FIG. 53).

Example 40—Biosynthesis of a Fortieth Multi-Substituent Psilocybin Derivative

Synthesis of a psilocybin derivative was accomplished using PriB enzyme and the in vitro procedure described in Example 38, with the exception that 3-[2-(diethylamino)ethyl]-1H-indol-4-yl acetate (Indole Shop; www.theindoleshop.com) was used in place of 3-[2-(dimethylamino)ethyl]-1H-indol-4-yl propionate substrate. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-[2-(diethylamino)ethyl]-6-(3-methyl-2-butenyl)-1H-indol-4-yl acetate, having chemical formula (XLV):

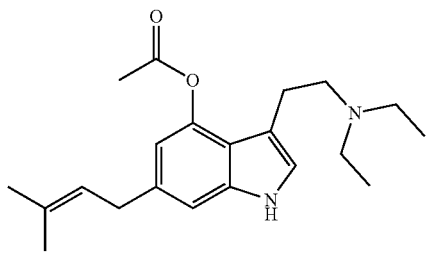

Figure 54:
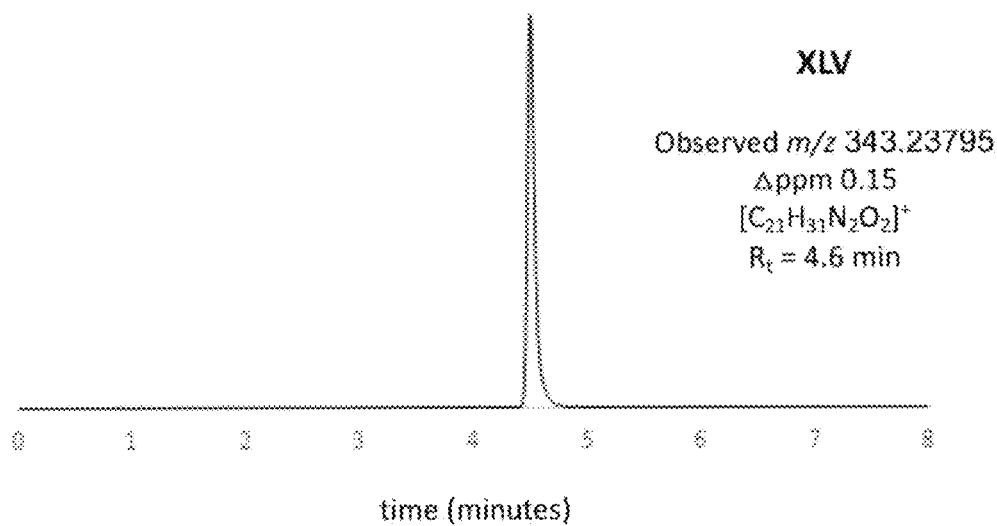
FIG. 54 depicts a representation of further mass spectrometry data in the form of a chromatogram, notably a chromatogram obtained in the performance of an experiment to synthesize an example multi-substituent psilocybin derivative compound having the chemical formula (XLV) set forth herein.

(XLV)

eluted at 4.6 minutes (EIC, see: FIG. 54).

Example 41—Synthesis of a Forty-First Multi-Substituent Psilocybin Derivative

Synthesis of a psilocybin derivative was accomplished using PriB enzyme and the in vitro procedure described in Example 38, with the exception that N,N-dimethyl[2-(5-chloro-1H-indol-3-yl)ethyl]amine (Indole Shop; www.theindoleshop.com) was used in place of 3-[2-(dimethylamino)ethyl]-1H-indol-4-yl propionate substrate. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of N,N-dimethyl(2-[5-chloro-6-(3-methyl-2-butenyl)-1H-indol-3-yl]ethyl)amine, having chemical formula (XLIV):

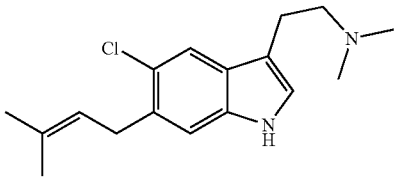

Figure 55A:
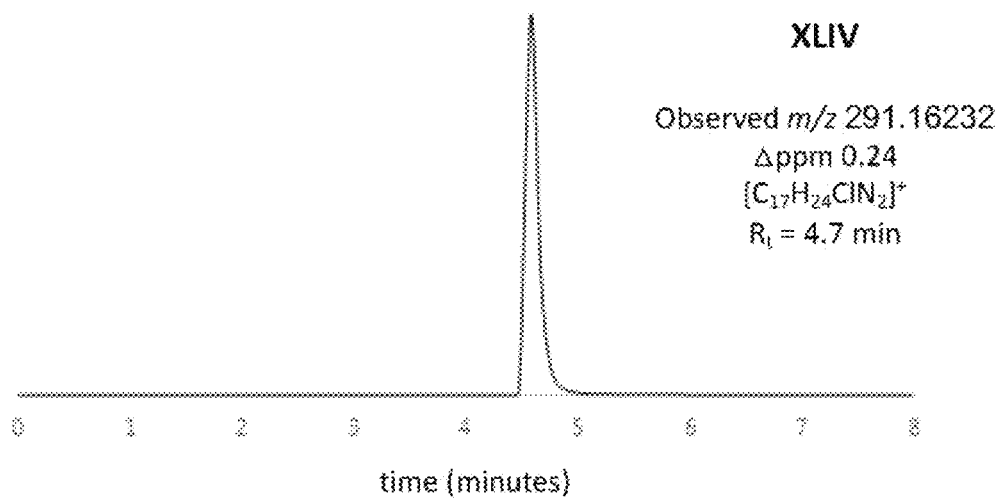
FIGS. 55A and 55B depict a representation of further mass spectrometry data in the form of a chromatogram, notably a chromatogram obtained in the performance of an experiment to synthesize an example multi-substituent psilocybin derivative compound having the chemical formula (XLIV) set forth herein (FIG. 55A); and a representation of mass spectrometry data in the form of a further mass spectrometry spectrum obtained in the performance of an experiment to identify a multi-substituent psilocybin derivative compound having the chemical formula (XLIV) set forth herein (FIG. 55B).
Figure 55B:
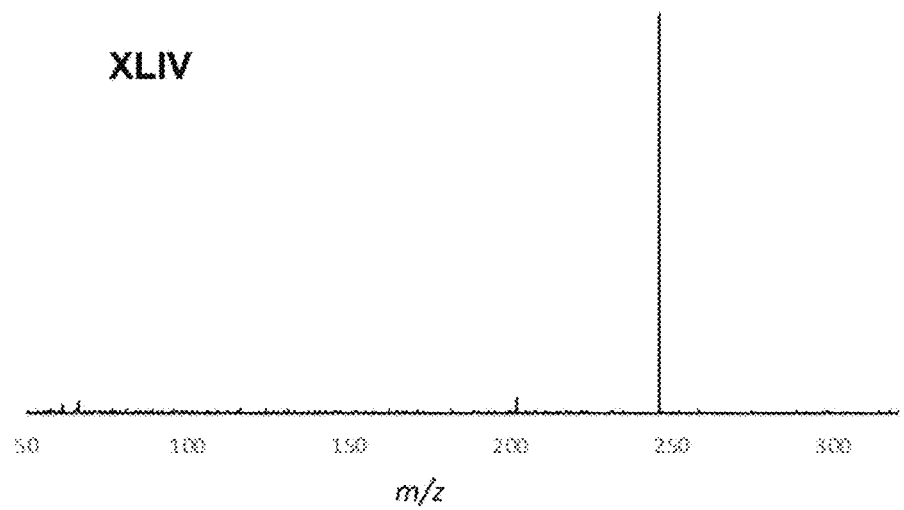

(XLIV)

eluted at 4.7 minutes (EIC, see: FIG. 55A). As per standard procedures (Menéndez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted psilocybin derivative with formula (XLIV) as follows (FIG. 55B, Table 12) (Servillo L. et al., 2013, J. Agric. Chem. 61: 5156-5162).

TABLE 12

| m/z | % Relative abundance | Ionic species | Δ ppm |
|---|---|---|---|
| 246.10398 | 100 | $[M + H - C_6H_9N]^+$ | 1.71 |
| 61.09263 | 2.0 | | |
| 199.41002 | 1.5 | | |
| 181.73308 | 1.4 | | |
| 65.66295 | 1.2 | | |
| 116.30919 | 1.2 | | |
| 56.98338 | 1.1 | | |
| 80.77037 | 1.1 | | |
| 164.10424 | 0.9 | | |
| 151.38086 | 0.9 | | |

Example 42—Biosynthesis of a Forty-Second Multi-Substituent Psilocybin Derivative Synthesis of a psilocybin derivative was accomplished using (1) chemical synthesis, followed by (2) an in vitro enzymatic conversion by PriB enzyme. Chemical synthesis was conducted using the synthesis procedure shown in FIG. 13D.

To a solution of 4-Benzyloxyindole 13D-1 (1.00 mmol, 1.00 eq) in anhydrous diethyl ether (10 mL) under argon sparging at 0° C., was added oxalyl chloride (2.05 mmol, 2.05 eq) dropwise over the course of 30 minutes, and the reaction was continued at 0-5° C. for 3 hours. A solution of N-methylisopropylamine (5.00 mmol, 5.00 eq) in anhydrous diethyl ether (5 mL) was added dropwise over the course of 1 hour. The solution was concentrated in vacuo, and the residue was redissolved in dichloromethane (30 mL). The organic solution was washed with water (4×10 mL) and brine (1×10 mL), then dried over anhydrous $Na_2SO_4$ and concentrated under reduced pressure to yield compound 13D-2, which was used in the following step without further purification. A solution of lithium aluminum hydride in a mixture of anhydrous THF (1 M, 5.20 eq) and 1,4-dioxane (2.0 mL) was brought to 60° C. under argon. A solution of compound 13D-2 in a mixture of anhydrous THF (2.0 mL) and 1,4-dioxane (3.5 mL) was added dropwise over 30 minutes, and the reaction was brought to 70° C. for 2 hours. The reaction was further refluxed at 95° C. for 20 hours. After cooling to 0° C., excess lithium aluminum hydride was quenched through a dropwise addition of a mixture of water (0.4 mL)-THF (2.0 mL). Diethyl ether (10 mL) was added, and the reaction mixture was allowed to stir at room temperature for 30 minutes. The precipitate was removed via vacuum filtration, the filtrate was dried over anhydrous $Na_2SO_4$, and concentrated under vacuo to yield compound 3 which was used without further purification. The crude compound 13D-3 was dissolved in 95% EtOH (10 mL), and 10% palladium on activated charcoal (0.110 eq) was added. The reaction flask was evacuated then backfilled with hydrogen. After stirring at room temperature for 2 hours, the catalyst was removed by a filtration and solvent was removed under reduced pressure to yield compound 13D-4, which was purified by a reverse-phase column chromatography on C18 silica gel using a water-acetonitrile+0.1% formic acid as the eluent. Compound 13D-4 was then used as a substrate for bioconversion by PriB enzyme, the latter which was generated and purified using the procedure described in Example 38. The in vitro conversion by PriB was conducted using the same procedure described in Example 38, with the exception that compound 13D-4 was used in place of 3-[2-(dimethylamino)ethyl]-1H-indol-4-yl propionate substrate. Analysis was carried out using high-resolution LC-HESI-LTQ-Orbitrap-XL MS (Thermo Fisher Scientific) as described in Example 3. Singly protonated product with exact m/z and expected elemental formula matching the singly protonated form of 3-(2-[(isopropyl)-N-methylamino]ethyl)-6-(3-methyl-2-butenyl)-1H-indol-4-ol, having chemical formula (LXXVI):

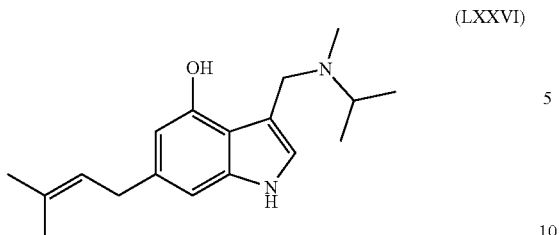

Figure 56:
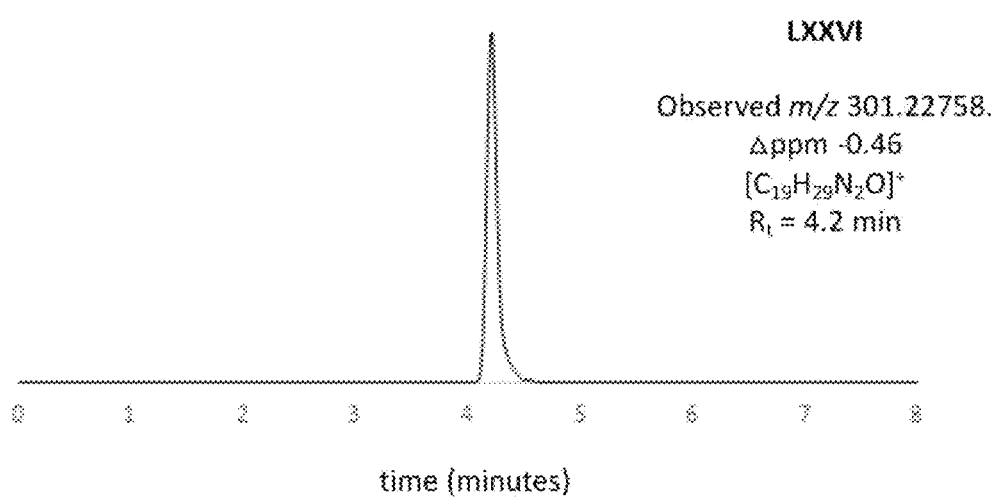
FIG. 56 depicts a representation of further mass spectrometry data in the form of a chromatogram, notably a chromatogram obtained in the performance of an experiment to synthesize an example multi-substituent psilocybin derivative compound having the chemical formula (LXVVI) set forth herein.

(LXXVI)

eluted at 4.2 minutes (EIC, see: FIG. 56).

---

The invention claimed is:

1. A chemical compound or a salt thereof having a formula (I):

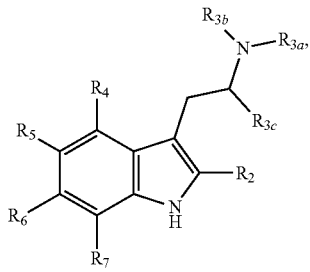

(I)

wherein, at least one of $R_2$, $R_4$, $R_5$, or $R_6$, is a halogen atom, and at least one of $R_2$, $R_4$, $R_5$, or $R_6$ is an aldehyde or a ketone group, wherein each of $R_2$, $R_5$, or $R_6$, which is not a halogen atom, or an aldehyde or ketone group, is a hydrogen atom, wherein $R_7$ is a hydrogen atom, wherein when $R_4$ is not a halogen atom, or an aldehyde or ketone group, $R_4$ is a hydrogen atom, an O-alkyl group, an O-acyl group, or a phosphate group, and wherein $R_{3a}$ and $R_{3b}$ are each independently a hydrogen atom, an alkyl group, a cycloalkyl group, an acyl group, or an aryl group, and $R_{3c}$ is a hydrogen atom or a carboxyl group.

2. A chemical compound according to claim 1, wherein one of $R_2$, $R_4$, $R_5$, or $R_6$, is a halogen atom, and one of $R_2$, $R_4$, $R_5$, or $R_6$, is an aldehyde or ketone group.

3. A chemical compound according to claim 1, wherein at least one of $R_4$, $R_5$, or $R_6$, is a halogen atom, and at least one of $R_4$, $R_5$, or $R_6$, is an aldehyde or ketone group, and wherein $R_2$ is a hydrogen atom.

4. A chemical compound according to claim 1, wherein one of $R_4$, $R_5$, or $R_6$, is a halogen atom, and one of $R_4$, $R_5$, or $R_6$ is an aldehyde or ketone group, and wherein $R_2$ is a hydrogen atom.

5. A chemical compound according to claim 1, wherein $R_4$ is (i) a halogen atom or (ii) an aldehyde or ketone group, and $R_6$ is an aldehyde or ketone group when $R_4$ is a halogen atom, or a $R_6$ is a halogen atom when $R_4$ is an aldehyde or ketone group, and wherein $R_2$ and $R_5$ are hydrogen atoms.

6. A chemical compound according to claim 5, wherein $R_4$ is a halogen atom, and $R_6$ is an aldehyde or ketone group.

7. A chemical compound according to claim 1, wherein the at least one of $R_2$, $R_4$, $R_5$, or $R_6$, is a halogen atom, and the at least one of $R_2$, $R_4$, $R_5$, or $R_6$ is a ketone group.

8. A chemical compound according to claim 7, wherein the ketone group has the formula:

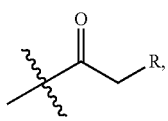

wherein R is a $(C_1-C_3)$-alkyl, $—CH_2CH_3$, or wherein the ketone group has the formula:

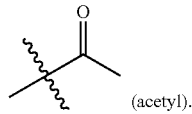 [SMILES: *C(C)=O]

(acetyl).

9. A chemical compound according to claim 7, wherein the ketone group has the formula:

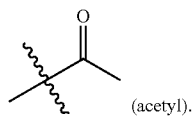 [SMILES: *C(C)=O]

(acetyl).

10. A chemical compound according to claim 1, wherein one of $R_4$, $R_5$, or $R_6$ is a halogen atom, and one of $R_4$, $R_5$, or $R_6$ is an aldehyde or ketone group, and wherein $R_2$ is a hydrogen atom, and wherein the ketone group has the formula:

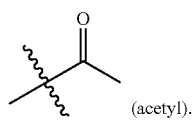 [SMILES: *C(C)=O]

(acetyl).

11. A chemical compound according to claim 1, wherein $R_4$ is (i) a halogen atom or (ii) a ketone group, and $R_6$ is a ketone group when $R_4$ is a halogen atom, or a $R_6$ is a halogen atom when $R_4$ is a ketone group, and wherein $R_2$ and $R_5$ are hydrogen atoms, and wherein the ketone group has the formula:

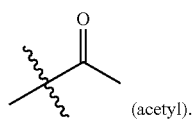 [SMILES: *C(C)=O]

(acetyl).

12. A chemical compound according to claim 1, wherein $R_4$ is a halogen atom and $R_6$ is a ketone group and wherein $R_2$ and $R_5$ are hydrogen atoms, and wherein the ketone group has the formula:

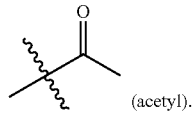 [SMILES: *C(C)=O]

(acetyl).

13. A chemical compound according to claim 10, wherein the halogen atom is fluorine.

14. A chemical compound according to claim 11, wherein the halogen atom is fluorine.

15. A chemical compound according to claim 12, wherein the halogen atom is fluorine.

16. A chemical compound according to claim 12, wherein $R_{3a}$ is a hydrogen atom and $R_{3b}$ is a $(C_1-C_3)$-alkyl group.

17. A chemical compound according to claim 12, wherein $R_{3a}$ is a hydrogen atom and $R_{3b}$ is a methyl group ($—CH_3$).

18. A chemical compound according to claim 12, wherein $R_{3a}$ and $R_{3b}$ are a ($C_1$-$C_3$)-alkyl group.

19. A chemical compound according to claim 12, wherein $R_{3a}$ and $R_{3b}$ are a methyl group (—$CH_3$).

20. A chemical compound according to claim 12, wherein $R_{3a}$ and $R_{3b}$ are a hydrogen atom.

21. A chemical compound according to claim 15, wherein $R_{3a}$ is a hydrogen atom and $R_{3b}$ is a ($C_1$-$C_3$)-alkyl group.

22. A chemical compound according to claim 15, wherein $R_{3a}$ is a hydrogen atom and $R_{3b}$ is a methyl group (—$CH_3$).

23. A chemical compound according to claim 15, wherein $R_{3a}$ and $R_{3b}$ are a ($C_1$-$C_3$)-alkyl group.

24. A chemical compound according to claim 14, wherein $R_{3a}$ and $R_{3b}$ are a methyl group (—$CH_3$).

25. A chemical compound according to claim 15, wherein $R_{3a}$ and $R_{3b}$ are a hydrogen atom.

26. A chemical compound according to claim 1, wherein chemical compound (I) is a compound having a chemical formula (A):

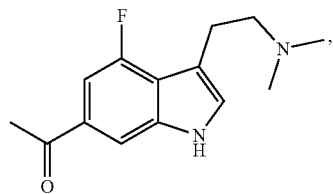

(A)

or a salt thereof.

27. A pharmaceutical or recreational drug formulation comprising an effective amount of a chemical compound according to claim 1, together with a pharmaceutically acceptable excipient, diluent, or carrier.

28. A pharmaceutical or recreational drug formulation comprising an effective amount of a chemical compound according to claim 26, together with a pharmaceutically acceptable excipient, diluent, or carrier.

* * * * *

SEQUENCE LISTING

```
Sequence total quantity: 54
SEQ ID NO: 1             moltype = DNA  length = 1167
FEATURE                  Location/Qualifiers
source                   1..1167
                         mol_type = genomic DNA
                         organism = Pyrococcus furiosus
SEQUENCE: 1
atgtggttcg gtgagtttgg tggacaatat gtgccagaga ctttagtggg tcctcttaag   60
gaattggaaa aggcatataa aaggttcaag gacgatgagg agttcaacag gcaactaaac  120
tattatttga agacatgggc cggtagacca acgcccttgt attatgctaa gaggttaact  180
gaaaagattg gcggcgcgaa agtgtatctg aaaagagaag acctagttca tggtggagca  240
cacaagacaa ataatgccat tggacaagca ctattggcaa agctaatggg taaaactaga  300
ttgatagctg agacaggagc gggtcaacat ggggtcgcga cagcgatggc tggtgcacta  360
ctggggatga aggtagatat ttacatgggt gctgaggacg ttgagcgtca gaaactaaat  420
gtcttcagga tgaagctatt aggtgccaat gttatacctg taaattctgg ctcaagaaca  480
ctaaaggacg ccttcgacga ggctcttaga gactgggttg ccactttcga gtatactcat  540
tacttgatcg gttcagtggt tggaccacat ccatacccaa ccatcgttag ggactttcag  600
agcgtgattg gtagagaggc taaggcacag atcttagaag cagagggaca gctacctgac  660
gtcatagttg cctgcgtcgg cggtggctct aacgcaatgg gtatattcta tccattcgtt  720
aatgacaaga aggttaaatt agtaggagtc gaagctggcg gaaaggggtt agagtcgggt  780
aaacactcag caagcttaaa tgcaggacag gtaggggtgt cccacggcat gttgtcgtat  840
ttcttgcaag acgaggaagg tcagataaag ccaagtcatt caattgctcc aggccttgac  900
cacccggtg ttggtccaga gcacgcttac ttaaagaaga ttcaaggggc cgagtacgtc  960
gctgtaacag acgaagaggc attgaaagct ttccatgagc tatccagaac tgaggggatt 1020
atacccgccc ttgagtctgc ccatgctgtg gcgtacgcca tgaagttagc taaagagatg 1080
tcccgtgacg aaatcatcat tgtaaatcta tcagggagag gagacaagga tttggacatt 1140
gtattgaagg caagcggaaa tgtttga                                     1167

SEQ ID NO: 2             moltype = AA   length = 388
FEATURE                  Location/Qualifiers
source                   1..388
                         mol_type = protein
                         organism = Pyrococcus furiosus
SEQUENCE: 2
MWFGEFGGQY VPETLVGPLK ELEKAYKRFK DDEEFNRQLN YYLKTWAGRP TPLYYAKRLT    60
EKIGGAKVYL KREDLVHGGA HKTNNAIGQA LLAKLMGKTR LIAETGAGQH GVATAMAGAL   120
LGMKVDIYMG AEDVERQKLN VFRMKLLGAN VIPVNSGSRT LKDAFDEALR DWVATFEYTH   180
YLIGSVVGPH PYPTIVRDFQ SVIGREAKAQ ILEAEGQLPD VIVACVGGGS NAMGIFYPFV   240
NDKKVKLVGV EAGGKGLESG KHSASLNAGQ VGVSHGMLSY FLQDEEGQIK PSHSIAPGLD   300
HPGVGPEHAY LKKIQRAEYV AVTDEEALKA FHELSRTEGI IPALESAHAV AYAMKLAKEM   360
SRDEIIIVNL SGRGDKDLDI VLKASGNV                                     388

SEQ ID NO: 3             moltype = DNA  length = 1446
FEATURE                  Location/Qualifiers
source                   1..1446
                         mol_type = genomic DNA
                         organism = Bacillus atrophaeus
SEQUENCE: 3
atgatgtctg aaaatttgca attgtcagct gaagaaatga acaattggg ttaccaagca    60
gtttgatttga tcatcgatca catgaaccat ttgaagtcta agccagtttc agaaacaatc   120
gattctgata tcttgagaaa taagttgact gaatctatcc cagaaaatgg ttcagatcca   180
aaggaattgt tgcatttctt gaacagaaac gtttttaatc aaattacaca tgttgatcat   240
ccacatttct tggcttttgt tccaggtcca ataattacg ttggtgttgt tgcagatttc    300
ttggcttctg gttttaatgt ttttccaact gcatggattg ctggtgcagg tgctgaacaa   360
atcgaattga ctacaattaa ttggttgaaa tctatgttgg ttttccaga ttcagctgaa    420
ggtttatttg tttctgttgg ttcaatggca aatttgacag ctttgactgt tgcaagacag   480
gctaagttaa caacgatat cgaaaatgct gttgtttact ctctgatca aacacatttc     540
tcagttgata gagcattgaa ggttttaggt tttaaacatc atcaaatctg tagaatcgaa   600
acagatgaac atttgagaat ctctgtttca gctttgaaga acaaattaa agaagataga   660
actaagggta aaaagccatt ctgtgttatt gcaaatgctg gtactacaaa ttgtggtgct   720
gttgattctt tgaacgaatt agcagatttg tgtaacgatg aagatgtttg gttgcatgct   780
```

```
gatggttctt atggtgctcc agctatcttg tctgaaaagg gttcagctat gttgcaaggt    840
attcatagag cagattcttt gactttagat ccacataagt ggttgttcca accatacgat    900
gttggttgtg ttttgatcag aaactctcaa tatttgtcaa agactttag aatgatgcca     960
gaatacatca aggattcaga aactaacgtt gaaggtgaaa ttaatttcgg tgaatgtggt   1020
atcgaattgt caagaagatt cagagctttg aaggtttgt tgtcttttaa agttttcggt   1080
gttgctgctt ttagacaagc aatcgatcat ggtatcatgt tagcagaaca agttgaagca   1140
ttttttggta aagcaaaaga ttgggaagtt gttacaccag ctcaattggg tatcgttact   1200
tttagataca ttccatctga attggcatca acagatacta ttaatgaaat taataagaaa   1260
ttggttaagg aaatcacaca tagaggtttc gctatgttat ctactacaga attgaaggaa   1320
aaggttgtta ttagattgtg ttcaattaat ccaagaacta caactggtga aatgttgcaa   1380
atcatgatga agattaaagc attggctgaa gaagtttcta tttcataccc atgtgttgct   1440
gaataa                                                              1446

SEQ ID NO: 4             moltype = AA  length = 481
FEATURE                  Location/Qualifiers
source                   1..481
                         mol_type = protein
                         organism = Bacillus atrophaeaus
SEQUENCE: 4
MMSENLQLSA EEMRQLGYQA VDLIIDHMNH LKSKPVSETI DSDILRNKLT ESIPENGSDP    60
KELLHFLNRN VFNQITHVDH PHFLAFVPGP NNYGVVADF LASGFNVFPT AWIAGAGAEQ    120
IELTTINWLK SMLGFPDSAE GLFVSGGSMA NLTALTVARQ AKLNNDIENA VVYFSDQTHF   180
SVDRALKVLG FKHHQICRIE TDEHLRISVS ALKKQIKEDR TKGKKPFCVI ANAGTTNCGA   240
VDSLNELADL CNDEDVWLHA DGSYGAPAIL SEKGSAMLQG IHRADSLTLD PHKWLFQPYD   300
VGCVLIRNSQ YLSKTFRMMP EYIKDSETNV EGEINFGECG IELSRRFRAL KVWLSFKVFG   360
VAAFRQAIDH GIMLAEQVEA FLGKAKDWEV VTPAQLGIVT FRYIPSELAS TDTINEINKK   420
LVKEITHRGF AMLSTTELKE KVVIRLCSIN PRTTTEEMLQ IMMKIKALAE EVSISYPCVA   480
E                                                                  481

SEQ ID NO: 5             moltype = DNA  length = 1254
FEATURE                  Location/Qualifiers
source                   1..1254
                         mol_type = genomic DNA
                         organism = Clostridium sporidium
SEQUENCE: 5
atgaagttct ggagaaagta cacacaacaa gaaatggatg aaaagattac tgaatctttg     60
gaaaagactt tgaactacga taacactaag acaatcggta ttccaggtac taagttggat    120
gatacagttt tctatgatga tcattctttc gttaagcatt caccatactt gagaactttt    180
attcaaaacc caaccatat cggttgtcat acttatgata aggctgatat cttgttcggt     240
ggtacattcg atatcgaaag agaattaatc caattgttag caatcgatgt tttgaacggt    300
aacgatgaag aatttgatgg ttacgttact caaggtggta cagaagctaa catccaagca    360
atgtgggttt acagaaacta cttcaagaaa gaagaaaagg ctaagcatga agaaatcgct    420
atcatcactt cagcagatac acattactct gcataccaag gttcagattt gttgaacatc    480
gatattatta aggttccagt tgattttat tcaagaaaaa ttcaagaaaa tacattggat    540
tcaattgtta agaagctaa agaaattggt aaaaagtact tcatcgttat ctctaacatg    600
ggtactacaa tgtttggttc agttgatgat ccagatttgt acgctaacat cttcgataag    660
tacaatttgg aatacaaaat tcatgttgat ggtgcatttg gtggttttat atatccaatt    720
gataataagg aatgtaaaac tgatttctct aataagaacg tttcttcaat cacattagat    780
ggtcataaga tgttgcaagc tccatacggt actggtatct tcgtttcaag aaagaatttg    840
atccataaca ctttgacaaa ggaagcaact tacatcgaaa atttggatgt tacattgtct    900
ggttcaagat ctggttcaaa tgctgttgca atttggatgg ttttagcttc ttatggtcca    960
tacggttgga tggaaaagat taataagttg agaaatagaa ctaaatggtt gtgtaagcaa   1020
ttgaacgata tgagaattaa atattacaaa gaagattcaa tgaatattgt tacaattgaa   1080
gaacaatatg ttaataagga aatcgctgaa aagtactttt tagttccaga agttcataac   1140
ccaactaaca actggtacaa gatcgttgtt atggaacatg ttgaattgga tatcttgaac   1200
tctttggttt acgatttgag aaagtttaat aaggaacatt tgaaggcaat gtaa         1254

SEQ ID NO: 6             moltype = AA  length = 417
FEATURE                  Location/Qualifiers
source                   1..417
                         mol_type = protein
                         organism = Clostridium sporidium
SEQUENCE: 6
MKFWRKYTQQ EMDEKITESL EKTLNYDNTK TIGIPGTKLD DTVFYDDHSF VKHSPYLRTF     60
IQNPNHIGCH TYDKADILFG GTFDIERELI QLLAIDVLNG NDEEFDGYVT QGGTEANIQA    120
MWVYRNYFKK ERKAKHEEIA IITSADTHYS AYKGSDLLNI DIIKVPVDFY SRKIQENTLD    180
SIVKEAKEIG KKYFIVISNM GTTMFGSVDD PDLYANIFDK YNLEYKIHVD GAFGGFIYPI    240
DNKECKTDFS NKNVSSITLD GHKMLQAPYG TGIFVSRKNL IHNTLTKEAT YIENLDVTLS    300
GSRSGSNAVA IWMVLASYGP YGWMEKINKL RNRTKWLCKQ LNDMRIKYYK EDSMNIVTIE    360
EQYVNKEIAE KYFLVPEVHN PTNNWYKIVV MEHVELDILN SLVYDLRKFN KEHLKAM       417

SEQ ID NO: 7             moltype = DNA  length = 1320
FEATURE                  Location/Qualifiers
source                   1..1320
                         mol_type = genomic DNA
                         organism = Psilocybe cubensis
SEQUENCE: 7
atgcaggtga taccgcgtg caactcggca gcaataagat cactatgtcc tactcccgag     60
tcttttagaa acatgggatg gctctctgtc agcgatgcgg tctacagcga gttcatagga    120
```

-continued

```
gagttggcta cccgcgcttc caatcgaaat tactccaacg agttcggcct catgcaacct   180
atccaggaat tcaaggcttt cattgaaagc gacccggtgg tgcaccaaga atttattgac   240
atgttcgagg gcattcagga ctctccaagg aattatcagg aactatgtaa tatgttcaac   300
gatatcttcc gcaaagctcc cgtctacgga gaccttggcc ctcccgttta tatgattatg   360
gccaaattaa tgaacacccg agcgggcttc tctgcattca cgagacaaag gttgaacctt   420
cacttcaaaa aacttttcga tacctgggga ttgttcctgt cttcgaaaga ttctcgaaat   480
gttcttgtgg ccgaccagtt cgacgacaga cattgcggct ggttgaacga gcgggccttg   540
tctgctatgt ttaaacatta caatggacgc gcatttgatg aagtcttcct ctgcgataaa   600
aatgccccat actacggctt caactcttac gacgacttct ttaatcgcag atttcgaaac   660
cgagatatcg accgacctgt agtcggtgga gttaacaaca ccaccctcat ttctgctgct   720
tgcgaatcac tttcctacaa cgtctcttat gactcccagt ctctcgacac tttagttttc   780
aaaggagaga cttattcgct taagcatttg ctgaataatg accctttcac cccacaattc   840
gagcatggga gtattctaca aggattcttg aacgtcaccg cttaccaccg atggcacgca   900
cccgtcaatg gacaatcgt caaaatcatc aacgttccag gtacctactt tgcgcaagcc   960
ccgagcacga ttggcgaccc tatcccggat aacgattacg acccacctcc ttaccttaag  1020
tctcttgtct acttctctaa tattgccgca aggcaaatta tgtttattga agccgacaac  1080
aaggaaattg gcctcatttt ccttgtgttc atcggcatga ccgaaatctc gacatgtgaa  1140
gccacggtgt ccgaaggtca acacgtcaat cgtggcagtg acttgggaat gttccattc   1200
ggtggttctt cgttcgcgct tggtctgagg aaggattgca gggcagagat cgttgaaaag  1260
ttcaccgaac ccggaacagt gatcagaatc aacgaagtcg tcgctgctct aaaggcttag  1320

SEQ ID NO: 8          moltype = AA   length = 439
FEATURE               Location/Qualifiers
source                1..439
                      mol_type = protein
                      organism = Psilocybe cubensis
SEQUENCE: 8
MQVIPACNSA AIRSLCPTPE SFRNMGWLSV SDAVYSEFIG ELATRASNRN YSNEFGLMQP    60
IQEFKAFIES DPVVHQEFID MFEGIQDSPR NYQELCNMFN DIFRKAPVYG DLGPPVYMIM   120
AKLMNTRAGF SAFTRQRLNL HFKKLFDTWG LFLSSKDSRN VLVADQFDDR HCGWLNERAL   180
SAMVKHYNGR AFDEVFLCDK NAPYYGFNSY DDFFNRRFRN RDIDRPVVGG VNNTTLISAA   240
CESLSYNVSY DVQSLDTLVF KGETYSLKHL LNNDPFTPQF EHGSILQGFL NVTAYHRWHA   300
PVNGTIVKII NVPGTYFAQA PSTIGDPIPD NDYDPPPYLK SLVYFSNIAA RQIMFIEADN   360
KEIGLIFLVF IGMTEISTCE ATVSEGQHVN RGDDLGMFHF GGSSFALGLR KDCRAEIVEK   420
FTEPGTVIRI NEVVAALKA                                               439

SEQ ID NO: 9          moltype = DNA   length = 546
FEATURE               Location/Qualifiers
source                1..546
                      mol_type = genomic DNA
                      organism = Streptomyces griseofuscus
SEQUENCE: 9
atgaacacct tcagaacagc cactgccaga gacatacctg atgtagcagc aactcttacg    60
gaagccttcg caactgatcc acccacgcag tgggtgttcc ccgacggtac tgccgccgtc   120
agcaggttct ttacacatgt tgcagatagg gttcacacgg ccggtggtat tgttgagcta   180
ctaccagaca gagccgccat gattgcattg ccaccacacg tgaggctgcc aggagaagct   240
gccgacggaa ggcaggcgga aattcagaga aggctggcacc ccgctgacacct   300
cactactacc tgctgttta cggagttaga acggcacacc agggttcggg attgggcgga   360
agaatgctgg ccagattaac tagcagagct gataggaca gggtgggtac atatactgag   420
gcatccacct ggcgtggcgc tagactgatg ctgagacatg gattccatgc tacaaggcca   480
ctaagattgc cagatggacc cagcatgttt ccactttgga gagatccaat ccatgatcat   540
tctgat                                                              546

SEQ ID NO: 10         moltype = AA   length = 182
FEATURE               Location/Qualifiers
source                1..182
                      mol_type = protein
                      organism = Streptomyces griseofuscus
SEQUENCE: 10
MNTFRTATAR DIPDVAATLT EAFATDPPTQ WVFPDGTAAV SRFFTHVADR VHTAGGIVEL    60
LPDRAAMIAL PPHVRLPGEA ADGRQAEIQR RLADRHPLTP HYYLLFYGVR TAHQGSGLGG   120
RMLARLTSRA DRDRVGTYTE ASTWRGARLM LRHGFHATRP LRLPDGPSMF PLWRDPIHDH   180
SD                                                                  182

SEQ ID NO: 11         moltype = DNA   length = 1092
FEATURE               Location/Qualifiers
source                1..1092
                      mol_type = genomic DNA
                      organism = Ephedra sinica
SEQUENCE: 11
atgggatcca tggaagaagc aaaaatggcg accctgggcg gtgcgtccta tgcgatgatt    60
gtgaaaacga tgatgcgctc tctggaagca aacctgattc cggattttgt gctgcgtcgc   120
ctgacgcgta tcctgctggc tagtcgcctg aaactgggtt ataagcagac cgctgaactg   180
caactggcgg atctgatgtc attcgttgcg tcgctgaacga gtgccgat cgccctgtgc   240
accgaagaag caagggtca gcattacgaa ctgccgacca gctttttcaa actggtcctg   300
ggcaaacatc tgaagtatag ctctgcctac ttttctgaac acaccgtac gctggatgaa   360
gcggaagaag ccatgctggc actgtatgc gaacgcgcca aaattgaaga tggtcagaag   420
attctggaca tcggctgtgg ttggggcagt ttttccctgt atgtggcaga acgttaccg   480
aaatgcgaaa ttacgggcct gtgtaacagt tccacccaaa aagcccttca tcgaacagcaa   540
```

```
tgcagcgaac gtcgcctgtg taatgttacc atttatgcag atgacatcag cacctttgat    600
acggaatcta cctacgaccg cattatcagc atcgaaatgt tcgaacacat gaagaactac    660
agtacgctgc tgaagaaaat tagcaagtgg atgaatcagg aatgcctgct gtttgtccat    720
tatttctgtc acaaaacctt tgcgtaccac ttcgaagatg tggacgaaga tgactggatg    780
gctcgttatt tctttaccgg cggcaccatg ccggcgtact cgctgctgct gtactttcag    840
gatgacgtct cagtggttga tcattggctg attaacggta aacactatgc tcaaacctcg    900
gaagaatggc tgaagcgtat ggaccacaat ctgagctcta ttctgccgat ctttaacgaa    960
acgtatggcg aaaatgcggc caaaaagtgg ctggcatact ggcgcacctt tttcatcgca   1020
gttgctgaac tgttcaaata caacgatggc gaagaatgga tggtgtccca cttcctgttc   1080
aaaaagaaat aa                                                        1092

SEQ ID NO: 12              moltype = AA  length = 363
FEATURE                    Location/Qualifiers
source                     1..363
                           mol_type = protein
                           organism = Ephedra sinica
SEQUENCE: 12
MGSMEEAKMA TLGGASYAMI VKTMMRSLEA NLIPDFVLRR LTRILLASRL KLGYKQTAEL     60
QLADLMSFVA SLKTMPIALC TEEAKGQHYE LPTSFFKLVL GKHLKYSSAY FSEHTRTLDE    120
AEEEAMLALYC ERAKIEDGQK ILDIGCGWGS FSLYVAERYP KCEITGLCNS STQKAFIEQQ   180
CSERRLCNVT IYADDISTFD TESTYDRIIS IEMFEHMKNY STLLKKISKW MNQECLLFVH    240
YFCHKTFAYH FEDVDEDDWM ARYFFTGGTM PASSLLLYFQ DDVSVVDHWL INGKHYAQTS    300
EEWLKRMDHN LSSILPIFNE TYGENAAKKW LAYWRTFFIA VAELFKYNDG EEWMVSHFLF    360
KKK                                                                  363

SEQ ID NO: 13              moltype = DNA  length = 930
FEATURE                    Location/Qualifiers
source                     1..930
                           mol_type = genomic DNA
                           organism = Psilocybe cubensis
SEQUENCE: 13
atgcatatca gaaatcctta ccgtacacca attgactatc aagcactttc agaggccttc     60
cctcccctca agccatttgt gtctgtcaat gcagatggta ccagttctgt tgacctcact    120
atcccagaag cccgagggc gttcacggcc gctcttcttc gtgatgactt cgggctcacc    180
atgaccatac cagaagaccg tctgtgccca acagtcccca ataggttgaa ctacgttctg    240
tggattgaag atatttttca actacacgaa caaaaccctcg gcctgtcgga tgaccgtcct    300
attaaaggcg ttgatattgg tacaggagcc tccgcaattt atcctatgct tgcctgtgct    360
cggttcaagg catggtctat ggttggaaca gaggtcgaga ggaagtgcat tgacacggcc    420
cgcctcaatg tcgtcgcgaa caatctccaa gaccgtctct cgatattaga gacatccatt    480
gatggtccta ttctcgtccc catttttgag gcgactgaag aatacgaata cgagtttact    540
atgtgtaacc ctccattcta cgacggtgct gccgatatgc agacttcgga tgctgccaaa    600
ggatttggat tggcgtggg cgctcccat tctggaacag tcatcgaaat gtcgactgag    660
ggaggtgaat cggctttcgt cgctcagatg gtccgtgaga gcttgaagct tcgaacacga    720
tgcagatggt acacgagtaa cttgggaaag ctgaaatcct tgaaagaaat agtgggctg    780
ctgaaagaac ttgagataag caactatgcc attaacgaat acgttcaggg gtccacacgt    840
cgttatgccg ttgcgtggtc tttcactgat attcaactgc ctgaggagct ttctcgtccc    900
tctaaccccg agctcagctc tcttttctag                                     930

SEQ ID NO: 14              moltype = AA  length = 309
FEATURE                    Location/Qualifiers
source                     1..309
                           mol_type = protein
                           organism = Psilocybe cubensis
SEQUENCE: 14
MHIRNPYRTP IDYQALSEAF PPLKPFVSVN ADGTSSVDLT IPEAQRAFTA ALLHRDFGLT     60
MTIPEDRLCP TVPNRLNYVL WIEDIFNYTN KTLGLSDDRP IKGVDIGTGA SAIYPMLACA    120
RFKAWSMVGT EVERKCIDTA RLNVVANNLQ DRLSILETSI DGPILVPIFE ATEEYEYEFT    180
MCNPPFYDGA ADMQTSDAAK GFGFGVGAPH SGTVIEMSTE GGESAFVAQM VRESLKLRTR    240
CRWYTSNLGK LKSLKEIVGL LKELEISNYA INEYVQGSTR RYAVAWSFTD IQLPEELSRP    300
SNPELSSLF                                                            309

SEQ ID NO: 15              moltype = DNA  length = 1419
FEATURE                    Location/Qualifiers
source                     1..1419
                           mol_type = genomic DNA
                           organism = Aspergillus fumigatus
SEQUENCE: 15
atgtccatcg gagccgagat cgattcgctg gttcctgctc caccgggcct caacggcacc     60
gctgcgggct atccagccaa gacgcagaag gagttaagca acggagactt tgacgcgcac    120
gatggtcttt ctcttgcaca actgacaccg tacgatgtct tgacggctgc acttccgctg    180
ccggctccgg cttcgagcac agggttctgg tggcgggaga cgggccctgt tatgagcaag    240
cttttggcca aggcgaacta ccctctttac actcattaca agtaccttat gttataccat    300
acccatattc tcccattgtt gggacctcga ccgccgctcg agaactcgac gcaccgtcg    360
ccgagtgacg cgcgtggag gtccttcctg acagacgact tcactccgct cgacccgagc    420
tggaacgtga acgggaactc ggaagcacag agcacaatcc gtcttggtat tgaacctata    480
ggctttgaag ccggggctgc agcggaccca ttcaaccaag ctgccgtgac gcagttcatg    540
cactcatacg aggcaaccga agtcggtgcc acgctgacgc tgttcgagca cttccgcaac    600
gacatgtttt tggcccagaa acgtacgct gcgttaagag cgaagatacc agaaggcgag    660
cataccacac agagtttcct ggcgttcgac ctggacgcgg tcgtgtcac cacaaaggcg    720
```

```
tactttttcc cgattctcat gtcgttgaaa actggacaga gcacaacaaa ggtggtctct   780
gattccattc tgcatctagc gctgaagagt gaggtgtggg gtgtgcagac catcgccgcg   840
atgtcggtca tggaggcgtg gataggtagc tacggtggcg cggcaaagac ggagatgatc   900
agcgtcgatt gcgtgaacga ggcagactct cggatcaaga tatacgtgcg gatgccacat   960
acatccttgc ggaaggtaaa agaggcgtac tgcttaggtg ggcggttgac agacgagaac  1020
acaaaggagg gcctgaagct gctggacgag ctgtggagga cggtcttcgg catcgacgac  1080
gaggacgcgg agctgccaca gaatagccat cgcaccgcag gcacaatatt caatttcgag  1140
ctgaggccag ggaaatggtt ccccgagccc aaggtatacc tgcccgtccg acactactgt  1200
gaaagtgata tgcagattgc tagtcggcta caaacgttct ttggaaggct cggatggcac  1260
aacatggaga aagattattg caagcatctg gaagatttgt ttccccatca tccactgtcc  1320
tcgtcaacgg gcacacacac ctttctctca ttttcgtata agaagcagaa ggggggtctat  1380
atgaccatgt attataatct ccgggtgtac agcacctaa                          1419

SEQ ID NO: 16            moltype = AA   length = 472
FEATURE                  Location/Qualifiers
source                   1..472
                         mol_type = protein
                         organism = Aspergillus fumigatus
SEQUENCE: 16
MSIGAEIDSL VPAPPGLNGT AAGYPAKTQK ELSNGDFDAH DGLSLAQLTP YDVLTAALPL    60
PAPASSTGFW WRETGPVMSK LLAKANYPLY THYKYLMLYH THILPLLGPR PPLENSTHPS   120
PSNAPWRSFL TDDFTPLEPS WNVNGNSEAQ STIRLGIEPI GFEAGAAADP FNQAAVTQFM   180
HSYEATEVGA TLTLFEHFRN DMFVGPETYA ALRAKIPEGE HTTQSFLAPD LDAGRVTTKA   240
YFFPILMSLK TGQSTTKVVS DSILHLALKS EVWGVQTIAA MSVMEAWIGS YGGAAKTEMI   300
SVDCVNEADS RIKIYVRMPH TSLRKVKEAY CLGGRLTDEN TKEGLKLLDE LWRTVFGIDD   360
EDAELPQNSH RTAGTIFNFE LRPGKWFPEP KVYLPVRHYC ESDMQIASRL QTFFGRLGWH   420
NMEKDYCKHL EDLFPHHPLS SSTGTHTFLS FSYKKQKGVY MTMYYNLRVY ST           472

SEQ ID NO: 17            moltype = DNA   length = 1158
FEATURE                  Location/Qualifiers
source                   1..1158
                         mol_type = other DNA
                         note = Streptomyces sp. RM-5-8
                         organism = unidentified
SEQUENCE: 17
atgggaggtc cgatgagcgg tttccattcg ggggaggcgc tgctcggtga cctcgccacc    60
ggtcagctga ccaggctgtg cgaggtggcg gggctgaccg aggccgacac ggcggcctac   120
acgggggtgc tgatcgaaag tctggggacg tcggccggac ggccgttgtc cctgccaccc   180
ccgtccgcga ccttttctctc cgacgaccac accccggtga agttctccct ggccttcctg   240
ccgggacgcg caccgcacct gcgggtcctg gtgaaccgg gctgctccag ggccgacgac   300
ctggcggaaa acgccgggc cggtctgcgg gcgtccaca ccatggcgga ccgctgggga   360
ttctccaccg agcaactcga ccggctggag gacctgttct cccctcctc ccccgagggc   420
ccgctggccc tgtggtcgc cctggagctc cgctccggtg ggtgccgg ggtgaaggtc   480
tacctcaacc ccgcgcgaa tggcgccgac cgggccgccg agacggtacg cgaggcgctg   540
gccaggctgg gccacctgca ggcgttcgac gcgctgcccc gggcggacgg cttcccgttc   600
ctcgccctgg acctcggcga ctgggacgcc cgcgggtga gatctacct caaacacctc   660
ggcatgtccg ccgcgacgc gggctccctc cccgacatgt cgcccgcgc gagccgggag   720
cagctggagg agttcttccg caccgccggt gacctcccgg ccccgggaga cccggggccc   780
accgaggaca ccggccggct cgccgggcgc ccgccctca cctgccactc cttcacggag   840
acggcgaccg ggcggcccag cggctacacc tccacgtgc cggtccgcga ctacgtccgg   900
cacgacgggg aggcacggga ccggcggtg gccgtgctgc gcgaacatga catggacagt   960
gcggcactgg accgggcgct ggccgccgtg agccccgcc cgctgagtga cggggtgggc  1020
ctgatcgcct atctggcact ggtccaccag cgcggccggc cgacacgggt gaccgtctac  1080
gtctcctccg aggcgtacga ggtgcggccc cccgcgaga cggtcccac ccgcgaccgg  1140
gcgcgggcac ggctgtga                                                1158

SEQ ID NO: 18            moltype = AA   length = 385
FEATURE                  Location/Qualifiers
source                   1..385
                         mol_type = protein
                         note = Streptomyces sp. RM-5-8
                         organism = unidentified
SEQUENCE: 18
MGGPMSGFHS GEALLGDLAT GQLTRLCEVA GLTEADTAAY TGVLIESLGT SAGRPLSLPP    60
PSRTFLSDDH TPVEFSLAFL PGRAPHLRVL VEPGCSSGDD LAENGRAGLR AVHTMADRWG   120
FSTEQLDRLE DLFFPSSPEG PLALWCALEL RSGGVPGVKV YLNPAANGAD RAAETVREAL   180
ARLGHLQAFD ALPRADGFPF LALDLGDWDA PRVKIYLKHL GMSAADAGSL PRMSPAPSRE   240
QLEEFFRTAG DLPAPGDPGP TEDTGRLAGR PALTCHSFTE TATGRPSGYT LHVPVRDYVR   300
HDGEARDRAV AVLREHDMDS AALDRALAAV SPRPLSDGVG LIAYLALVHQ RGRPTRVTVY   360
VSSEAYEVRP PRETVPTRDR ARARL                                        385

SEQ ID NO: 19            moltype = DNA   length = 1128
FEATURE                  Location/Qualifiers
source                   1..1128
                         mol_type = genomic DNA
                         organism = Streptomyces coelicolor
SEQUENCE: 19
atgagggccg cgtcgacggg cgcgaccccg caggacgcat ccacgctcgg ctctttcacc    60
ggcggccagt tgcgaagact cggctcggtc gccggtctgt cccgcgccga cgtcgagacc   120
```

-continued

```
tacgcacagg tcctgaccga cgcattgggc ccggtggccc agcggccgct gagcctggcg    180
ccgcccaccc gcaccttcct gtcggacgac cacaccccg tggagttctc cctctccttc    240
cggcccgggg cggcgccgc catgcgggtc tcgtggaac cggcgctgcgg tgcgaccagc    300
ctggccgaca acgccgtgc cggtcttgag gcggtccgca cgatggcgcg cgctggcac    360
ttcaccaccg acgccctgga cgaactcctg gacctgttcc tgccgcccgc tccgcagggc    420
ccctcgccc tgtggtgcgc cctggaactc aggcccgggg gtgtaccggg cgtcaaggtc    480
tatctgaacc ctgcggtggg cggggaggaa cgttccgccg cgacggtgcg cgaggccctg    540
cgccggctcg ggcaccacca ggccttcgac agcctccccc agggcagtgg ataccccgttc   600
ctcgccctgg acctcgggaa ctggacggag ccccggggcga aggtctacct gcgccacgac    660
aaccctcacgg ccggtcgggc cgcacggctg tcccggaacg actcgggcct cgtgccgacc    720
gcggtcgagg gtttcttccg caccgccgcg ggtcccggct ccgacgcggg tgggctcgac    780
gggcggcctg ctcagtcctg ccactccttc accgaccccg cgcggagcg gccgagcggc    840
ttcacccctgt acatcccggt tcgtgactac gtccggcatg acggggaggc cctggcgcgg    900
gcgtccacca tgctgcacca ccacggcatg gacgcctccg tgctccaccg cgccctgggc    960
gccctcaccg agcggcggcc cgaggacggg gtgggcctga tcgcctacct ggccctcgcc   1020
ggccaacggg accagccgcc gcgggtgacg gcctacctct cctcggaggc ctacacggtc   1080
cggccgccgg tcgtggagac cgtccgccaa ccgctgtcgg tcggctga                 1128
```

SEQ ID NO: 20        moltype = AA   length = 375
FEATURE              Location/Qualifiers
source               1..375
                     mol_type = protein
                     organism = Streptomyces coelicolor
SEQUENCE: 20
```
MRAASTGADP QDASTLGSFT GGQLRRLGSV AGLSRADVET YAQVLTDALG PVAQRPLSLA     60
PPTRTFLSDD HTPVEFSLSF RPGAAPAMRV LVEPGCGATS LADNGRAGLE AVRTMARRWH   120
FTTDALDELL DLFLPPAPQG PLALWCALEL RPGGVPGVKV YLNPAVGGEE RSAATVREAL   180
RRLGHHQAFD SLPQGSGYPF LALDLGNWTE PRAKVYLRHD NLTAGRAARL SRTDSGLVPT   240
AVEGFFRTAA GPGSDAGGLD GRPAQSCHSF TDPGAERPSG FTLYIPVRDY VRHDGEALAR   300
ASTVLHHHGM DASVLHRALA ALTERRPEDG VGLIAYLALA GQRDQPPRVT AYLSSEAYTV   360
RPPVVETVRQ PLSVG                                                   375
```

SEQ ID NO: 21        moltype = DNA   length = 1380
FEATURE              Location/Qualifiers
source               1..1380
                     mol_type = genomic DNA
                     organism = Aspergillus fumigatus
SEQUENCE: 21
```
atgaaggcag ccaatgcctc cagtgcggag gcctatcgag ttcttagtcg cgcctttaga     60
ttcgataatg aagatcagaa gctgtggtgg cacagcactg cccgatgtt tgcaaaaatg   120
ctggaaactg ccaactacac cacaccttgt cagtatcaat acctcatcac ctataaggag   180
tgcgtaattc ccagtctcgg atgctatccg accaacagcg ccccccgctg gttgagcatc   240
ctcactcgat acggcactcc gttcgaattg agcctaaatt gctctaattc aatagtgaga   300
tacacattcg agccgatcaa tcaacatacc ggaacagata agacccatt caatacgcac   360
gccatctggg agagcctgca gcacctgctt ccactggaga gagcattga tctggagtgg   420
ttccgccact tcaagcacga tctcacccct caacagtgaag aatctgcttt tctggctcat   480
aatgatgccc tcgtgggcgg cactatcagg acgcagaaca gcctgcaaga tctctgaag   540
gatggccgct ttgcactaa gacgtacata taccccggctc tcaaagctgt cgtcaccggc   600
aagacaattc atgagttggt ctttggctca gtccgccggc tggcagtgag ggagccccga   660
atcttgcccc cactcaacat gctggaggaa tacatccgat cacgcggttc caagagcact   720
gccagtcccc gcctagtgtc ctgtgatctg accagtccgc ccaagtcgag aatcaagatc   780
taccctgctgg agcagatggt ttcactagaa gccatggagg acctgtggac tctgggcgga   840
cggcgccgag acgcttccac tttagagggg ctctctctgg tcgtgagct tgggatctg    900
atccaactgt cgccgggatt gaagtcctat ccggcgccgt atctgcctct cggggttatc   960
ccagacgaga ggctgccgct tatggccaat ttcacccttgc accagaatga cccggtccca  1020
gagccgcaag tatatttcac aacccttcggc atgaacgaca tggcggtggc ggatgccctg  1080
acgacgttct tcgagcgcg ggggttggagt gaaatggccc gcaactacga aactactttg  1140
aagtcgtact accccccatgc ggatcatgac aaacttaact acctccacgc ctacatatcc  1200
ttctcctaca gggaccgtac cccttatctg agtgtctatc ttcaatcctt cgagacaggg  1260
gactgggcag ttgcaaactt atccgaatca aaggtcaagt gtcaggatgc ggcctgtcaa  1320
cccacagctt tacctccaga tctgtcaaag acagggtat attattccgg tctccactga  1380
```

SEQ ID NO: 22        moltype = AA   length = 459
FEATURE              Location/Qualifiers
source               1..459
                     mol_type = protein
                     organism = Aspergillus fumigatus
SEQUENCE: 22
```
MKAANASSAE AYRVLSRAFR FDNEDQKLWW HSTAPMFAKM LETANYTTPC QYQYLITYKE    60
CVIPSLGCYP TNSAPRWLSI LTRYGTPFEL SLNCSNSIVR YTFEPINQHT GTDKDPFNTH  120
AIWESLQHLL PLEKSIDLEW FRHFKHDLTL NSEESAFLAH NDRLVGGTIR TQNKLALDLK  180
DGRFALKTYI YPALKAVVTG KTIHELVFGS VRRLAVREPR ILPPLNMLEE YIRSRGSKST  240
ASPRLVSCDL TSPAKSRIKI YLLEQMVSLE AMEDLWTLGG RRRDASTLEG LSLVRELWDL  300
IQLSPGLKSY PAPYLPLGVI PDERLPLMAN FTLHQNDPVP EPQVYFTTFG MNDMAVADAL  360
TTFFERRGWS EMARTYETTL KSYYPHADHD KLNYLHAYIS FSYRDRTPYL SVYLQSFETG  420
DWAVANLSES KVKCQDAACQ PTALPPDLSK TGVYYSGLH                         459
```

SEQ ID NO: 23        moltype = DNA   length = 2155
FEATURE              Location/Qualifiers

|  |  |  |
|---|---|---|
| source | 1..2155 | |
| | mol_type = genomic DNA | |
| | organism = Psilocybe cubensis | |

SEQUENCE: 23

```
atgatcgctg tactattctc cttcgtcatt gcaggatgca tatactacat cgtttctcgt    60
agagtgaggc ggtcgcgctt gccaccaggg ccgcctggca ttcctattcc cttcattggg   120
aacatgtttg atatgcctga agaatctcca tggttaacat ttctacaatg gggacgggat   180
tacagtctgt cttgccgcgt tgacttctaa tatatgaaca gctaatatat tgtcagacac   240
cgatattctc tacgtggatg ctggagggac agaaatggtt attcttaaca cgttggagac   300
cattaccgat ctattagaaa agcgagggtc catttattct ggccggtgag ctgatgttga   360
gtttttgca attgaatttg tggtcacacg tttccagact tgagagtaca atggtcaacg   420
aacttatggg gtgggagttt gacttagggt tcatcacata cggcgacagg tggcgcgaag   480
aaaggcgcat gttcgccaag gagttcagtg agaagggcat caagcaattt cgccatgctc   540
aagtgaaagc tgcccatcag cttgtccaac agcttaccaa aacgccagac cgctgggcac   600
aacatattcg ccagtaagta ctacttgagg aaaatagcgt acgcttcgct gaccggtccg   660
tacatcaaag tcagatagcg gcaatgtcac tggatattgg ttatggaatt gatcttgcag   720
aagacgaccc ttggctggaa cgacccattt ggctaatga aggcctcgcc atagcatcag   780
tgccgggcaa attttgggtc gattcgttcc cttctcgtga gcatccttct tctatgtagg   840
aagggaagga gtctaacaag tgttagtaaa ataccttcct gcttggttcc caggtgctgt   900
cttcaagcgc aaagcgaagg tctggcgaga agccgccgac catatggttg acatgcctta   960
tgaaactatg aggaaattag cagttagtca aatgcgttct ccccgtattt tttcaatact  1020
ctaacttcag ctcacagcct caaggattga ctcgtccgtc gtatgcttca gctcgtcctga 1080
aagccatgga tctcaacggt gaccttgagc atcaagaaca cgtaatcaag aacacagccg  1140
cagaggttaa tgtcggtaag tcaaaagcgt ccgtcggcaa ttcaaaattc aggcgctaaa  1200
gtgggtcttc tcaccaaggt ggaggcgata ctgtaaggat ttctcaatcg ttagagtata  1260
agtgttcaa tgcagtacat actccaccaa ccagactgtc tctgctatgt ctgcgttcat  1320
cttggccatg gtgaagtacc ctgaggtcca gcgaaaggtt caagcggagc ttgatgctct  1380
gaccaataac ggccaaattc ctgactatga cgaagaagat gactccttgc catacctcac  1440
cgcatgtatc aaggagcttt tccggtgaa tcaaatcgca cccctcgcta taccgcacaa  1500
attaatgaag gacgacgtgt accgcgggta tctgattccc aagaacactc tagtcttcgc  1560
aaacacctgg tgaggctgtc cattcattcc tagtacatcc gttgcccac taatagcatc  1620
ttgataacag ggcagtatta aacgatccag aagtctatcc agatccctct gtgttccgcc  1680
cagaaagata tcttggtcct gacgggaagc ctgataacac tgtacgcgac ccacgtaaag  1740
cggcatttgg ctatgacga cgaaattggt aagtgcgctt tcagaacccc cccttccgtc  1800
gactagtgcc atgcgcgcat acaatatcgc tattgatctg atataacttc cctgcgcat   1860
ttattttggc attcctttag tcccggaatt catctagcgc agtcgacggt ttggattgca  1920
ggggcaaccc tcttatcagc gttcaatatc gagcgacctg tcgatcagaa tgggaagccc  1980
attgacatac cggctgattt tactacagga ttcttcaggt agctaatttc cgtcttgtg  2040
tgcataatac ccctaacgac gcacgtttac ctttttgtaa agacacccag tgcctttcca  2100
gtgcaggttt gttcctcgaa cagagcaagt ctcacagtcg gtatccggac cctga       2155
```

|  |  |  |
|---|---|---|
| SEQ ID NO: 24 | moltype = AA  length = 508 | |
| FEATURE | Location/Qualifiers | |
| source | 1..508 | |
| | mol_type = protein | |
| | organism = Psilocybe cubensis | |

SEQUENCE: 24

```
MIAVLFSFVI AGCIYYIVSR RVRRSRLPPG PPGIPIPFIG NMFDMPEESP WLTFLQWGRD    60
YNTDILYVDA GGTEMVILNT LETITDLLEK RGSIYSGRLE STMVNELMGW EFDLGFITYG   120
DRWREERRMF AKEFSEKGIK QFRHAQVKAA HQLVQQLTKT PDRWAQHIRH QIAAMSLDIG   180
YGIDLAEDDP WLEATHLANE GLAIASVPGK FWVDSFPSLK YLPAWFPGAV FKRKAKVWRE   240
AADHMVDMPY ETMRKLAPQG LTRPSYASAR LQAMDLNGDL EHQEHVIKNT AAEVNVGGGD   300
TTVSAMSAFI LAMVKYPEVQ RKVQAELDAL TNNGQIPDYD EEDDSLPYLT ACIKELFRWN   360
QIAPLAIPHK LMKDDVYRGY LIPKNTLVFA NTWAVLNDPE VYPDPSVFRP ERYLGPDGKP   420
DNTVRDPRKA AFGYGRRNCP GIHLAQSTVW IAGATLLSAF NIERPVDQNG KPIDIPADFT   480
TGFFRHPVPF QCRFVPRTEQ VSQSVSGP                                      508
```

|  |  |  |
|---|---|---|
| SEQ ID NO: 25 | moltype = DNA  length = 2187 | |
| FEATURE | Location/Qualifiers | |
| source | 1..2187 | |
| | mol_type = genomic DNA | |
| | organism = Psilocybe cubensis | |

SEQUENCE: 25

```
atggcttcta gttcttccga tgtcttcgtt ttgggtctag gtgttgtttt ggctgccttg    60
tatatcttca gagaccaatt attcgctgct tctaagccaa aggtggctcc agttccact   120
acgaagcctg ccaacggttc cgctaaccca agagacttca tcgccaagat gaaacaaggt   180
aagaagagaa tcgtaatctt ctacggttct caaactggta ccgctgaaga atatgctatt   240
cgtttggcta aggaagctaa gcaaaagttc ggtctagcct ccttggttg tgatccagaa   300
gaatacgatt ttgaaaagtt ggaccaattg ccagaagatt ctattgcttt ctccgttgga   360
gctacctatg gtgaaggtga acctacgac aacgctgtcc aattgttgca aaacttgcaa   420
gatgaaagct tcgaattctc ctctggtgag agaaagttgt caggtttgaa gtacgttgtt   480
tttggtctgg gtaacaagac ctacgaacat acaacctca tgggagaac tgttgacgct   540
caattggcca agatgggtgc tatcagaatc ggtgaaagag tgaaggtga tgatgacaag   600
tccatgggaag aagactactt ggaatggaag agtggtatgt gagagcgtt tgccactgct   660
atgggtgtta agaaggtca aggtggtgac tccgctgatt cgtcgtttc gaattggaa   720
tctcacccac cagaaaaggt ttaccaaggt gaatttctg ctagagcttt aaccaaaacc   780
aagggtattc acgacgctaa gaatccttt gctgctccaa ttgcggttgc tagagaattg   840
ttccaatctg ttgtcgatag aaactgtgtc cacgtcgaat tcaacattga aggctctggt   900
atcacctatc aacacggtga ccacgttggt ttgtggccat tgaatccaga tgttgaagtc   960
```

```
gaacggttgt tgtgtgtttt aggtttagct gaaaagagag atgctgtcat ctccattgaa  1020
tccttagacc cggctttggc taaggttcca ttcccagtcc caactactta cggtgctgtg  1080
ttgagacact acattgacat ctctgctgtc gccggtagac aaatcttggg tactttgtcc  1140
aaaattcgctc caaccccaga agctgaagct ttcttgagaa acttgaacac taacaaggaa  1200
gaataccaca acgtcgtcgc taacggttgt ttgaaattgg gtgaaatttt gcaaatcgct  1260
accggtaacg acattactgc cccaccaact actgccaaca ccaccaaatg gccaattcca  1320
ttcgacatca ttgtttctgc catcccaaga ttgcaaccaa gatactactc tatctcttct  1380
tccccaaaaa ttcatccaaa caccatccac gctaccgttg ttgtgctcaa atacgaaaac  1440
gttccaaccg aaccaatccc aagaaagtgg gtttacggtg tcggtagtaa cttcttgttg  1500
aatttaaagt acgctgttaa caaggaacca gttccataca tcactcaaaa tggcgaacaa  1560
agagtcggtg tcccggaata cttgattgct ggtccacgtg gttcttacaa gactgaatct  1620
ttctacaagg ctccaatcca tgttagacgt tctactttcc gtttgccaac caacccaaag  1680
tctccagtca tcatgattgg tccaggtact ggtgtcgcc cattcagagg cttcgttcaa  1740
gaaagagttg ccttggccag aagatccatc gaaaagaacg gtcctgactc tttggctgac  1800
tggggtcgta tttccttgtt ctacggttgt agaagatccg acgaagactt cttgtacaag  1860
gacgaatggc cacaatacga agctgagttg aagggtaagt tcaagttgca ctgtgctttc  1920
tccagacaaa actacaagcc agacggttct aagatttacg tccaagattt gatctgggaa  1980
gacagagaac acattgccga tgccatctta aacggtaagg gttacgtcta catctgcggt  2040
gaagctaagt ccatgtctaa acaagttgaa gaagttctag ccaagatctt gggcgaagcc  2100
aaaggtggtt ccggtccagt tgaaggtgtt gctgaagtca agttactgaa ggaacggtcc  2160
agattgatgt tggatgtctg gtctagg                                      2187
```

SEQ ID NO: 26        moltype = AA  length = 728
FEATURE                Location/Qualifiers
source                 1..728
                        mol_type = protein
                        organism = Psilocybe cubensis

```
SEQUENCE: 26
MASSSSDVFV LGLGVVLAAL YIFRDQLFAA SKPKVAPVST TKPANGSANP RDFIAKMKQG   60
KKRIVIFYGS QTGTAEEYAI RLAKEAKQKF GLASLVCDPE EYDFEKLDQL PEDSIAFFVV  120
ATYGEGEPTD NAVQLLQNLQ DESFEFSSGE RKLSGLKYVV FGLGNKTYEH YNLIGRTVDA  180
QLAKMGAIRI GERGEGDDDK SMEEDYLEWK DGMWEAFATA MGVEEGQGGD SADFVVSELE  240
SHPPEKVYQG EFSARALTKT KGIHDAKNPF AAPIAVAREL FQSVVDRNCV HVEFNIEGSG  300
ITYQHGDHVG LWPLNPDVEV ERLLCVLGLA EKRDAVISIE SLDPALAKVP FPVPTTYGAV  360
LRHYIDISAV AGRQILGTLS KFAPTPEAEA FLRNLNTNKE EYHNVVANGC LKLGEILQIA  420
TGNDITVPPT TANTTKWPIP FDIIVSAIPR LQPRYYSISS SPKIHPNTIH ATVVVLKYEN  480
VPTEPIPRKW VYGVGSNFLL NLKYAVNKEP VPYITQNGEQ RVGVPEYLIA GPRGSYKTES  540
FYKAPIHVRR STFRLPTNPK SPVIMIGPGT GVAPFRGFVQ ERVLARRSI  EKNGPDSLAD  600
WGRISLFYGC RRSDEDFLYK DEWPQYEAEL KGKFKLHCAF SRQNYKPDGS KIYVQDLIWE  660
DREHIADAIL NGKGYVYICG EAKSMSKQVE EVLAKILGEA KGGSGPVEGV AEVKLLKERS  720
RLMLDVWS                                                          728
```

SEQ ID NO: 27        moltype = DNA  length = 6347
FEATURE                Location/Qualifiers
misc_feature       1..6347
                        note = Synthetic construct
source                 1..6347
                        mol_type = other DNA
                        organism = synthetic construct

```
SEQUENCE: 27
gtatccggct gttccttcat agccctttca atgaacgttg cagcccttg aagattggcc    60
attttgtcag gactcgagcc tgacagttgg accaacgcaa cttaattt  ttgtgaaaga   120
atcttcgaag cactcatact ggcgatcttc acgcccctcct gctattacaa aagctgtgtt   180
tttacaagaa tcaaattaag ttagcaagat attatacaac attattgata atttcaatat   240
cgtgttcgta cctgatgacg tatctgtgca ttgataagcc ccgcatggtt tcagaaagca   300
gagcggaacg attccaaatt agtgggcctg tgctttgcat gtcaattgtg ttaccttcag   360
ctcgtggatt tgtttatca atacacagtc tacagtcaag aatttttttt atcaaatttt   420
gcgttcgagc gtataaaata gccgctgtag ctacttaagt tcctgttcag cgatagtttt   480
tttccatcac acgtactatg gcaattaagt cctcagcgag ctcgcatgga atgcgtgcga   540
tgagcgacct catgctatac ctgagaaagc aacctgacct acaggaagag gttactcaag   600
aataagaatt ttcgttttaa aacctaagag tcactttaaa atttgtatac acttattttt   660
tttataactt atttaataat aaaaatcata aatcataaga aattcgctta tttagaagtg   720
tcaacaacgt atctaccaac ggaatgcgtg cgattcaggc gtagtctgga acgtcgtatg   780
ggtatgacc agagacggat tgagaaactt gttcggttct gtggacgaat ctacattgga   840
atggaactgg gtgcctgaag aaaccagtgg tgaaatcagc tgggatgtca attggcttac   900
cgttttggtc aactggtctt tcaatgttga aagcagacaa caaagtagca ccggcaatcc   960
aaacagtaga ttgagctagg tgaatacctg gcagttttct ctaccgtaa ccgaaagcag   1020
cctttcttgg gtctctaaca gtgttgtctg gtttaccatc aggacccaag tatctttctg  1080
gacggaaaac ggatggatct ggatagactt ctggggtcatt caaaactgcc caggtgttag  1140
caaaaaccaa tgtgttcttt ggaatcaaat aacctctgta aacatcatcc ttcatcaatt  1200
tatgagggat ggctaatgga gcatttggt tccatctgaa taattccttg atacaagcgg   1260
tcaaatatgg gagtgagtcg tcttcctcat cgtagtcagg gatttgaccg ttgttggtca   1320
aagcatccaa ttcagcttga accttctttt gcacttctgt gtatttaacc atggccaata   1380
tgaaacggga catagcacag acggtagtgt cgccaccacc agcgttaact tcagcagcaa  1440
tgttcttgat aacatgttct tggtgttcta aatcaccgtt caagtccata gcttgtaatc   1500
tagcagaagc gtaagatggt ctggttagac cttgtggagc caactttctc atagtttcgt   1560
atggcatgtc aaccatgtgg tcagcggctt ctctccagac cttggcctta cgcttgaaga   1620
cggcacctgg gaaccaagct ggcaagtact tcaaagatgg gaaggagtca acccagaact  1680
tacctggaac actagcaatg gccaaacctt cgttggctaa gtgggtagct tctaaccatg  1740
```

```
ggtcatcttc ggctagatcg ataccgtaac caatgtccaa agacatagca gcgatttgat 1800
gtctgatgtg ttgagcccac cggtccggag tcttggtcaa ttgttgaacc aattggtgag 1860
cagccttgac ttgagcgtgt ctgaattgct tgataccctt ttcagagaat tccttagcaa 1920
acattcttct ttcttctctc caacggtcac cgtaagtgat aaaacccaga tcaaattccc 1980
aacccatcaa ttcattgacc atagtggatt ccaatctacc ggagtagatg gaaccacgtt 2040
tttccaagag atccgtgata gtttccaagg tgtttaaaat gaccatttcg gtaccaccag 2100
catctacgta caagatatca gtgttgtagt cacgaccccca ttgcaagaaa gtcaaccatg 2160
gagattcttc tggcatgtcg aacatgttac caataaatgg gattggaatt cctggtggac 2220
caggtggcaa tctggatcta cgaactcttc tgggacgat gtagtaaata caaccagcaa 2280
tgacgaaaga gaacaagaca gcaatcattg ttttatattt gttgtaaaaa gtagataatt 2340
acttccttga tgatctgtaa aaaagagaaa aagaaagcat ctaagaactt gaaaaactac 2400
gaattagaaa agaccaaata tgtatttctt gcattgacca atttatgcaa gtttatatat 2460
atgtaaatgt aagtttcacg aggttctact aaactaaacc accccccttgg ttagaagaaa 2520
agagtgtgtg agaacaggct gttgttgtca cacgattcgg acaattctgt ttgaaagaga 2580
gagagtaaca gtacgatcga acgaactttg ctctggagat cacagtgggc atcatagcat 2640
gtggtactaa accctttccc gccattccag aaccttcgat tgcttgttac aaaacctgtg 2700
agccgtcgct aggaccttgt tgtgtgacga aattggaagc tgcaatcaat aggaagacag 2760
gaagtcgagc gtgtctgggt ttttcagtt ttgttcttt tgcaaacaac agtttattcc 2820
tggcatccac taaatataat ggagcccgct ttttaagctg gcatccagaa aaaaaaagaa 2880
tcccagcacc aaaatattgt tttcttcacc aaccatcagt tcataggtcc attctcttag 2940
cgcaactaca gagaacaggg gcacaaacag gcaaaaaacg ggcacaacct caatggagtg 3000
atgcaacctg cctggagtaa atgatgacac aaggcaattg acccacgcat gtatctatct 3060
cattttctta caccttctat tccctttcgc tctctctgat ttggaaaaag ctgaaaaaaa 3120
aggttgaaac cagttccctg aaattattcc cctacttgac taataagtat ataaagacgg 3180
taggtattga ttgtaattct gtaaatctat ttcttaaact tcttaaattc tacttttata 3240
gttagtcttt tttttagttt taaaacacca agaacttgat ttcgaataaa cacacataaa 3300
caaacaaaat ggcttctagt tcttccgatg tcttcgttt gggtctaggt gttgttttga 3360
ctgccttgta tatcttcaga gaccaattat tcgctgcttc taagccaaag gtggctccag 3420
tttccactac gaagcctgcc aacggttccg ctaacccaag agacttcatc gccaagatga 3480
aacaaggtaa gaagagaatc gtaatcttct acggttctca aactggtacc gctgaagaat 3540
atgctattcg tttggctaag gaagctaagc aaaagttcgg tctagcctcc ttggtttgtg 3600
atccagaaga atacgatttt gaaaagttgg accaattgcc agaagattct attgctttct 3660
tcgtcgttgc tacctatggt gaaggtgaac ctacagacaa cgctgtccaa ttgttgcaaa 3720
acttgcaaga tgaaagcttc gaattctcct ctggtgagag aaagttgtca ggtttgaagt 3780
acgttgtttt tggtctgggt aacaagacct acgaacatta caacctcatt gggagaactg 3840
ttgacgctca attggccaag atgggtgcta tcagaatcgg tgaaagaggt gaaggtgatg 3900
atgacaagtc catggaagaa gactacttgg aatggaagga tggtatgtgg gaagcgtttg 3960
ccactgctat gggtgttgaa gaaggtcaag gtggtgactc cgctgatttc gtcgtttccg 4020
aattggaatc tcacccacca gaaaaggttt accaaggtga atttttctgct agagctttaa 4080
ccaaaaccaa gggtattcac gacgctaaga atcctttgc tgctccaatt gcggttgcta 4140
gagaattgtt ccaatctgtt gtcgatagaa actgtgtcca cgtcgaattc aacattgaag 4200
gctctggtat cacctatcaa cacggtgacc acgttgtttt gtggcattg aatccagatg 4260
ttgaagtcga acggttgttg tgtgttttag gtttagctga aaagagagat gctgtcatct 4320
ccattgaatc cttagacccg gctttggcta aggttccatt cccagtccca actacttacg 4380
gtgctgtgtt gagacactac attgacatct ctgctgtcgc cggtagacaa atcttgggta 4440
cttttgtccaa attcgctcca accccagaag ctgaagcttt cttgagaaac ttgaacacta 4500
acaaggaaga ataccacac gtcgtcgcta acggttgttt gaaattgggt gaaatttgc 4560
aaatcgctac cggtaacgac attactgtcc caccaactac tgccaacacc accaaatggc 4620
caattccatt cgacatcatt gttttctgcca tccaagatt gcaaccaaga tactactcta 4680
tctcttcttc cccaaaaatt catccaaaca ccatccacgc taccgttgtt gtgctcaaat 4740
acgaaaacgt tccaaccgaa ccaatcccaa gaaagtgcgt ttacggtgtc ggtagtaact 4800
tcttgttgaa tttaaagtac gctgttaaca aggaaccagt tccatacatc actcaaaatg 4860
gcgaacaaag agtcggtgtc ccggaatact tgattgctgg tccacgtggt tcttacaaga 4920
ctgaatcttt ctacaaggct ccaatccatg ttagacgttc tactttccgt ttgccaacca 4980
acccaaagtc tccagtcatc atgattggtc caggtactgg tgtcgcccca ttcagaggct 5040
tcgttcaaga aagagttgcc ttggccagaa gatccatcga aaagaacggt cctgactctt 5100
tggctgactg ggtgtcgtat tcccttgttct acgttgtag aagatccgac gaagacttct 5160
tgtacaagga cgaatggcca caatacgaag ctgagttgaa gggtaagttc aagttgcact 5220
gtgctttctc cagacaaaac tacaagccag acggttctaa gatttacgtc caagatttga 5280
tctgggaaga cagagaacac attgccgatg ccatcttaaa cggtaagggt tacgtctaca 5340
tctgcgtga agctaagtcc atgtctaaac aagttgaaga agttctagcc aagatcttgg 5400
gcgaagccaa aggtggttcc ggtccagttg aaggtgttgc tgaagtcaag ttactgaagg 5460
aacggtccag attgatgttg gatgtctggt ctgaacaaaa gttaatttct gaagaagatt 5520
tggaatgaat cgcgtgcatt catccgctct aaccgaaaag gaaggagtta gacaacctga 5580
agtctaggtc cctatttatt tttttatagt tatgttagta ttaagaacgt tatttatatt 5640
tcaaatttt cttttttttc tgtacagacg cgtgtacgca tgtaacatta tactgaaaac 5700
cttgcttgag aaggttttgg gacgctcgaa gatcgcgtcc caattcgccc tatagtgagt 5760
cgtattacgc gcgctcactg gccgtcgttt tacaacgtcg tgactgggaa aaccctggcg 5820
ttacccctgc aggactagtg ctgaggcatt aataagttttac tcaattcttg aagccaattt 5880
gtacaattcc ccattagagt caaataaaag gatgcctcac ggaggtatgt tacccgcgct 5940
atttcacatg gctcattgaa ttagaggtgg aatttggtgt accctcccct cctcatctga 6000
tgaagtagtg atccgacaat tcttaaaagt tgtagacatt acttttacca ccaactaagt 6060
tgtatttata ttgctaccct tatccttta tatctaacta gcgctcataa ggttgggggca 6120
atactaaaac tgtgttctta ttcaactcat taaatacgta gcagtacgta ccctattaga 6180
aacaatagga aacagcagag tcggaagaag ccaaatgcca gatttgaagt ccaaaacctt 6240
gtcaagccaa tctttgggag cggctattcc tccagaaatt gtgtaccaaa tacttacata 6300
ccagtttagg gatttgttaa gaaatgacca tccaggtacg gcagaaa     6347

SEQ ID NO: 28    moltype = DNA  length = 4792
```

| FEATURE | Location/Qualifiers |
|---|---|
| misc_feature | 1..4792 |
| | note = Synthetic construct |
| source | 1..4792 |
| | mol_type = other DNA |
| | organism = synthetic construct |

SEQUENCE: 28

```
caatctggcg gcttgagttc tcaacatgtt ttatttttta cttatattgc tggtagggta   60
aaaaaatata actcctagga ataggttgtc tatatgtttt tgtcttgctt ctataattgt  120
aacaaacaag gaaagggaaa atactgggtg taaaagccat tgagtcaagt taggtcatcc  180
cttttataca aaattttca  attttttttc caagattctt gtacgattaa ttatttttt  240
tttgcgtcct acagcgtgat gaaaatttcg cctgctgcaa gatgagcggg aacgggcgaa  300
atgtgcacgc gcacaactta cgaaacgcgg atgagtcact gacagcgcac gcagaggttc  360
tgactcctac tgagctctat tggaggtggc agaaccggta ccggaggagg gcgctataac  420
cggtttgaat ttattgtcac agtgtcacat cagcattaag tcctcagcga gctcgcatgg  480
aatgcgtgcg atgagcgacc tcatgctata cctgagaaag caacctgacc tacaggaaag  540
agttactcaa gaataagaat tttcgtttta aaacctaaga gtcactttaa aatttgtata  600
cacttatttt ttttataact tatttaataa taaaaatcat aaatcataag aaattcgctt  660
atttagaagt gtcaacaacg tatctaccaa cggaatgcgt gcgattcagg tggagtccaa  720
acccaacaaa ggatttggaa ttggcttacc ggcagtggag gattccttta gcaacgtgga  780
agtgatttca ccgttgtcgt tgttacctct agcatcgtgg aaagcagcaa caccccttctt  840
aacaaagttg attcttttctt cttcagaacc ccattgcagtc agtcc acataacaat  900
gtgagcggcg ataccagcgg taaccttggc gtagttgatg gaatgcttgg aagtacgggc  960
gtaagattgc aagtaagctt gtctcatggt tgtaccaact tgttcgtctt ggaatctgct 1020
aatcaagtaa cagtcaccca agaagtaacc caaatccaat gaagctggac cgtacttaca 1080
caattcccag tctaagatgt agatcttttg caacttagat gggttaccttt cttcaagttg 1140
caacaagatg ttcccagacc acaagtcagc catgaccaga gtttcttcgg agtgcataac 1200
atcgtcaact agatccttga caacagttgg caacaatgga tcatcgacgc cgtatttagc 1260
ggcgtttggg ataatagttt ggtacaattg gtcagaggtg gttctaccga caatgttacc 1320
agagaagaac ttgaattctg ggtcgtctct tctttctcta cctatgttgt gcaatctggc 1380
gacgaaacca ccaatctcgg taccaaccaa tctagcaata tcggtagcca aaggtggctt 1440
agcagtaacg tagtctaata aggtcttcat tttaccgaca tcttgcataa tcaaagcatt 1500
gtttttccaag tcatagttga gaccttctgg aacagagaca ataccatcaa caccacccaa 1560
aacttctctg ttagccatca tcaacttgat agcttgtcat tcgtagacag aacgttcaaa 1620
accgattttg aaatcttcat cagtagacat gtgtggttga gcgtgcttca aaatgataga 1680
agtgtgacct tggtatggag cgttcaattt aatacgccag gtgacgttaa cgaaaccacc 1740
ggataatctc ttgacaccag aagtgtcaac atctaaagac aaatgcttgg tcaaataggt 1800
gattaaaccg tcttcagtct tcaagtcaaa ggccattgtt ttatatttgt tgtaaaaagt 1860
agataattac ttccttgatg atctgtaaaa aagagaaaaa gaaagcatct aagaacttga 1920
aaaactacga attagaaaag accaaatatg tatttcttgc attgaccaat ttatgcaagt 1980
ttatatatat gtaaatgtaa gtttcacgag gttctactaa actaaccac ccccttggtt 2040
agaagaaaag agtgtgtgag aacaggctgt tgttgtcaca cgattcggac aattctgttt 2100
gaaagagaga gagtaacagt acgatcgaac gaacttctgct ctggagatca cagtgggcat 2160
catagcatgt ggtactaaac ccttttcccgc cattccagaa ccttcgattg cttgttacaa 2220
aacctgtgag ccgtcgctag gaccttgttg tgtgacgaaa ttggaagctg caatcaatag 2280
gaagacagga agtcgagcgt gtctgggttt tttcagttttt gttcttttttg caaacaacag 2340
tttattcctg gcatccacta aatataatgg agcccgcttt ttaagctggc atccagaaaa 2400
aaaaagaatc ccagcaccaa aatattgttt tcttccaccca ccatcagttc ataggtccat 2460
tctcttagcg caactacaga gaacaggggc acaaacaggc aaaaacggg cacaacctca 2520
atggagtgat gcaacctgcc tggagtaaat gatgacacaa ggcaattgac ccacgcatgt 2580
atctatctca ttttcttaca cctcctatta ccttctgctc tctctgattt ggaaaaagct 2640
gaaaaaaaag gttgaaacca gttccctgaa attattcccc tacttgacta ataagtatat 2700
aaagacggta ggtattgatt gtaattctgt aaatctattt cttaaacttc ttaaattcta 2760
cttttatagt tagtctttttt tttagttttta aaacaccaag aacttagttt cgaataaaca 2820
cacataaaca aacaaatgc atatcagaaa cccatataga actccaattg actaccaagc 2880
tttgtctgaa gctttcccac cattgaagcc atttgtttcc gttaacgctg atggtacctc 2940
ctcagttgac ttgaccattc cagaagccca aagagctttt accgctgccc ttttgcacag 3000
agacttcggc ttgactatga ctatcccaga agatcgtttg tgtccaaccg ttccaaacag 3060
attgaactac gttttgtgga ttgaagacat tttcaactac accaacaaga ctttgggttt 3120
atctgacgac cgtccaatca agggtgttga tatcggtacc ggtgcttctg ccatttaccc 3180
aatgttggct tgcgccagat tcaaggcttg gtccatggtt ggtactgaag ttgaaagaaa 3240
gtgtatcgac actgctagat taacgttgt tgctaacaac ttgcaagatc gtctatccat 3300
cttggaaacc tctattgacg gtccaatttt agtcccaatt ttcgaagcta ccgaagaata 3360
cgaatacgaa ttcaccatgt gtaacccacc tttctacgat ggtgccgctc acatgcaaag 3420
tagcgatgct gcaaagggtt ttggtttcgg tgtcggtgct ccacactctg gtacagtcat 3480
cgaaatgtct actgaaggtg gtgaatccgc tttcgtggct caaatggtta gaaatctct 3540
taagttgaga accagatgta gatggtacac ttctaactta ggtaagttga aatctttgaa 3600
ggaaattgtc ggtttgttga aggaattaga aatctctaat tacgccatca acgaatatgt 3660
ccaaggttcc actacaagat acgctgtcgc ttggagtttc actgatatcc aattgccaga 3720
agaattgtcc agaccatcta atcctgaatt gtcctctttg ttcgactaca aggatgacga 3780
tgacaaatga atcgcgtgca ttcatccgct ctaaccgaaa aggaaggagt tagacaacct 3840
gaagtctagg tccctatttta tttttttat gttatgttag tattaagaac gttatttata 3900
ttttcaaatttt tctttttttt tctgtacaga cgcgtgtac ccatgtaacat tatactgaaa 3960
accttgcttg agaaggtttt gggacgctcg aagatcgcgt acccaattcg ccctatagtg 4020
agtcgtatta cgcgcgctca ctggccgtcg tttacaacg tcgtgactgg gaaaaccctg 4080
gcgttacccc tgcaggacta gtgctgaggc attaatgcaa ctcagaagtt tgacagcaag 4140
caagttcatc attcgaacta gccttattgt tttagttcag tgacagcgaa ctgccgtact 4200
cgatgcttta tttctcacgg tagagcggaa aacagatag gggcagcgtg agaagagtta 4260
gaaagtaaat ttttatcacg tctgaagtat tcttattcat aggaaattt gcaaggtttt 4320
```

```
ttagctcaat aacgggctaa gttatataag gtgttcacgc gattttcttg ttatgtatac   4380
ctcttctctg aggaatggta ctactgtcct gatgtaggct ccttaaattg gtgggcaaga   4440
ataacttatc gatattttgt atattggtct tggagttcac cacgtaatgc ctgtttaaga   4500
ccatcagtta actctagtat tatttggtct tggctactgg ccgtttgcta ttattcaagt   4560
cttttgtgcc ttcccgtcgg gtaagggagt tatttaggga tacagaatct aacgaaaact   4620
aaatctcaat gattaactct atttaatcct tttttgaaag gcaaaagagg tcccttgttc   4680
acttacaacg ttcttagcca aattcgctta tcacttacta cttcacgata tacagaagta   4740
aaaacatata aaaagatgtc tgtttgttta gccatcacaa aaggtatcgc ag           4792

SEQ ID NO: 29          moltype = DNA   length = 9145
FEATURE                Location/Qualifiers
misc_feature           1..9145
                       note = Synthetic construct
source                 1..9145
                       mol_type = other DNA
                       organism = synthetic construct
SEQUENCE: 29
tgttttatat ttgttgtaaa aagtagataa ttacttcctt gatgatcgt aaaaaagaga    60
aaaagaaagc atcaagaac ttgaaaaact acgaattaga aaagaccaaa tatgtatttc    120
ttgcattgac caatttatgc aagtttatat atatgtaaat gtaagtttca cgaggttcta   180
ctaaactaaa ccacccctt ggttagaaga aaagagtgtg tgagaacagg ctgttgttgt    240
cacacgattc ggacaattct gtttgaaaga gagagataa cagtacgatc gaacgaactt    300
tgctctggag atcacagtgg gcatcatagc atgtggtact aaaccctttc ccgccattcc   360
agaaccttcg attgcttgtt acaaaacctg tgagccgtcg ctaggacctt gttgtgtgac   420
gaaattggaa gctgcaatca ataggaagac aggaagtcga gcgtgtctgg gttttttcag   480
ttttgttctt tttgcaaaca acagtttatt cctggcatcc actaaatata atggagcccg   540
ctttttaagc tggcatccag aaaaaaaaag aatcccagca ccaaaatatt gttttcttca   600
ccaaccatca gttcataggt ccattctctt agcgcaacta cagagaacag ggcacaaac    660
aggcaaaaaa cgggcacaac ctcaatggag tgatgcaacc tgcctggagt aaatgatgac   720
acaaggcaat tgacccacgc atgtatctat ctcattttct tacaccttct attaccttct   780
gctctctctg atttggaaaa agctgaaaaa aaaggttgaa accagttccc tgaaattatt   840
cccctacttg actaataagt atataaagac ggtaggtatt gattgtaatt ctgtaaatct   900
atttcttaaa cttcttaaat tctacttta tagttagtct tttttttagt tttaaaacac    960
caagaactta gtttcgaata aacacacata aacaaacaaa ggatccatga tgaagttctg  1020
gagaaagtac acacaacaag aaatggatga aaagattact gaatctttgg aaaagacttt  1080
gaactacgat aacactaaga caatcggtat tccaggtact aagttggatg atacagtttt  1140
ctatgatgat cattctttcg ttaagcattc accatacttg agaacttta ttcaaaaccc    1200
aaaccatatc ggttgtcata cttatgataa ggctgatatc ttgttcggtg gtacattcga  1260
tatcgaaaga gaattaatcc aattgttagc aatcgatatt ttgaacggta acgatgaaga  1320
atttgatggt tacgttactc aaggtggtac agaagctaac atccaagcaa tgtgggttta  1380
cagaaactac ttcaagaaag aaagaaaggc taagcatgaa gaaatcgcta tcatcacttc  1440
agcagataca cattactctg catacaaagg ttcagatttg ttgaacatcg atattattaa  1500
ggttccagtt gatttttatt caagaaaaat tcaagaaaat caattgttaa                1560
agaagctaaa gaaattggta aaagtactt catcgttatc tctaacatgg gtactacaat  1620
gtttggttca gttgatgatc cagatttgta cgctaacatc ttcgataagt acaatttgga  1680
atacaaaatt catgttgatg gtgcatttgg tggttttata tatccaattg ataataagga  1740
atgtaaaact gatttctcta ataagaacgt ttcttcaatc aattagatg gtcataagat  1800
gttgcaagct ccatacggta ctggtatctt cgttttcaaga aagaatttga tccataacac  1860
tttgacaaag gaagcaactt acatcgaaaa tttggatgtt acattgtctg gttcaagatc  1920
tggttcaaat gctgttgcaa tttggatggt tttagcttct tatggtccat acggttggat  1980
ggaaaagatt aataagttga gaaatagaac taaatgtgtt tgtaagcaat tgaacgatat  2040
gagaattaaa tattcaaag aagattcaat gaatattgt acaattgaag aacaatatgt    2100
taataaggaa atcgctgaaa agtactttt agttccagaa gttcataacc caactaacaa  2160
ctggtacaag atcgttgtta tggaacatgt tgaattggat atcttgaact ctttggttta  2220
cgatttgaga aagtttaata aggaacattt gaaggcaatg ggtcatcatc atcatcatta  2280
accgcggcta gctaagatcc gctctaaccg aaaaggaagg agttagcaa cctgaagtct   2340
aggtccctat ttatttttt atagttatgt tagtattaag aacgttattt atatttcaaa  2400
ttttttcttt ttttctgtac agacgcgtgt acgcatgtaa cattatactg aaaaccttgc  2460
ttgagaaggt tttgggacgc tcgaagatcc agctgcatta atgaatcggc caacgcgcgg  2520
ggagaggcgg tttgcgtatt gggcgctctt ccgcttcctc gctcactgac tcgctgcgct  2580
cggtcgttcg gctgcggcga gcggtatcag ctcactcaaa ggcggtaata cggttatcca  2640
cagaatcagg ggataacgca ggaaagaaca tgtgagcaaa aggccagcaa aaggccagga  2700
accgtaaaaa ggccgcgttg ctggcgtttt tccataggct ccgcccccct gacgagcatc  2760
acaaaaatcg acgctcaagt cagaggtggc gaaacccgac aggactataa agataccagg  2820
cgtttcccc tggaagctcc ctcgtgcgct ctcctgttcc gaccctgccg cttaccggat    2880
acctgtccgc ctttctccct tcgggaagcg tggcgctttc tcatagctca cgctgtaggt  2940
atctcagttc ggtgtaggtc gttcgctcca agctgggctg tgtgcacgaa ccccccgttc  3000
agcccgaccg ctgcgcctta tccggtaact atcgtcttga gtccaacccg gtaagacacg  3060
acttatcgcc actggcagca gccactggta acaggattag cagagcgagg tatgtaggcg  3120
gtgctacaga gttcttgaag tggtggccta actacggcta cactagaaga acagtatttg  3180
gtatctgcgc tctgctgaag ccagttacct tcggaaaaag agttggtagc tcttgatccg  3240
gcaaacaaac caccgctggt agcggtggtt ttttgtttg caagcagcag attacgcgca   3300
gaaaaaaagg atctcaagaa gatcctttga tcttttctac ggggtctgac gctcagtgga  3360
acgaaaactc acgttaaggg attttggtcat gagattatc aaaaaggatc ttcacctaga  3420
tccttttaaa ttaaaaatga agttttaaat caatctaaag tatatatgag taaacttggt  3480
ctgacagtta ccaatgctta atcagtgagg cacctatctc agcgatctgt ctatttcgtt  3540
catccatagt tgcctgactc cccgtcgtgt agataactac gatacgggag gcttaccat    3600
ctggccccag tgctgcaatg ataccgcgag acccacgctc accggctcca gatttatcag  3660
caataaacca gccagccgga agggccgagc gcagaagtgg tcctgcaact ttatccgcct  3720
```

```
ccatccagtc tattaattgt tgccgggaag ctagagtaag tagttcgcca gttaatagtt    3780
tgcgcaacgt tgttgccatt gctacaggca tcgtggtgtc acgctcgtcg tttggtatgg    3840
cttcattcag ctccggttcc caacgatcaa ggcgagttac atgatccccc atgttgtgca    3900
aaaaagcggt tagctccttc ggtcctccga tcgttgtcag aagtaagttg gccgcagtgt    3960
tatcactcat ggttatggca gcactgcata attctcttac tgtcatgcca tccgtaagat    4020
gcttttctgt gactggtgag tactcaacca agtcattctg agaatagtgt atgcggcgac    4080
cgagttgctc ttgcccggcg tcaatacggg ataataccgc gccacatagc agaactttaa    4140
aagtgctcat cattggaaaa cgttcttcgg ggcgaaaact ctcaaggatc ttaccgctgt    4200
tgagatccag ttcgatgtaa cccactcgtg cacccaactg atcttcagca tcttttactt    4260
tcaccagcgt ttctgggtga gcaaaaacag gaaggcaaaa tgccgcaaaa aagggaataa    4320
gggcgacacg gaaatgttga atactcatac tcttcctttt tcaatattat tgaagcattt    4380
atcagggtta ttgtctcatg agcggataca tatttgaatg tatttagaaa aataaacaaa    4440
taggggttcc gcgcacattt ccccgaaaag tgccacctga acgaagcatc tgtgcttcat    4500
tttgtagaac aaaaatgcaa cgcgagagcg ctaattttc aaacaaagaa tctgagctgc     4560
attttacag aacagaaatg caacgcgaaa gcgctatttt accaacgaag aatctgtgct     4620
tcattttgt aaaacaaaaa tgcaacgcga gagcgctaat ttttcaaaca aagaatctga     4680
gctgcatttt tacagaacag aaatgcaacg cgagagcgct atttaccaa caaagaatct     4740
atacttcttt tttgttctac aaaaatgcat cccgagagcg ctatttttct aacaaagcat    4800
cttagattac ttttttttctc ctttgtgcgc tctataatgc agtctcttga taacttttg     4860
cactgtaggt ccgttaaggt tagaagaagg ctactttggt gtctattttc tcttccataa    4920
aaaaagcctg actccacttc ccgcgtttac tgattactag cgaagctgcg ggtgcatttt    4980
ttcaagataa aggcatcccc gattatattc tataccgatg tggattgcgc atactttgtg    5040
aacagaaagt gatagcgttg atgattcttc attggtcaga aaattatgaa cggtttcttc    5100
tattttgtct ctatatacta cgtataggaa atgtttacat tttcgtattg ttttcgattc    5160
actctatgaa tagttcttac tacaattttt ttgtctaaag agtaatacta gagataaaca    5220
taaaaaatgt agaggtcgag tttagatgca agttcaagga gcgaaaggtg gatgggtagg    5280
ttatataggg atatagcaca gagatatata gcaaagagat acttttgagc aatgtttgtg    5340
gaagcggtat tcgcaatatt ttagtagctc gttacagtcc ggtgcgtttt tggttttttg    5400
aaagtgcgtc ttcagagcgc ttttggtttt caaaagcgct ctgaagttcc tatactttct    5460
agagaatagt aacttcggaa taggaacttc aaagcgtttc cgaaaacgag cgcttccgaa    5520
aatgcaacgc gagctgcgca catacagctc actgttcacg tcgcacctat atctgcgtgt    5580
tgcctgtata tatatataca tgagaagaac ggcatagtgc gtgtttatgc ttaaatgcgt    5640
acttatatgc gtctatttat gtaggatgaa aggtagtcta gtacctcctg tgatattatc    5700
ccattccatg cggggtatcg tatgcttcct tcagcactac ccttagctg ttctatatgc     5760
tgccactcct caattggatt agtctcatcc ttcaatgcta tcatttcctt tgatattgga    5820
tcatactaag aaaccattat tatcatgaca ttaacctata aaaataggcg tatcacgagg    5880
cccttttcgtc tcgcgcgttt cggtgatgac ggtgaaaacc tctgacacat gcagctcccg   5940
gagacggtca cagcttgtct gtaagcggat gccgggagca gacaagcccg tcagggcgcg    6000
tcagcgggtg ttggcgggtg tcggggctgg cttaactatg cggcatcaga cgcagattgta   6060
ctgagagtgc accatatttc acaccgcata gatccgtcga gttcaagaga aaaaaaagga   6120
aaaagcaaaa agaaaaaagg aaagcgcgcc tcgttcagaa tgacacgtat agaatgatgc    6180
attaccttgt catcttcagt atcatactgt tcgtatacat acttactgac attcataggt    6240
atacatatat acacatgtat taaatatcgta tgctgcagct ttaaataatc ggtgtcacta   6300
cataagaaca cctttggtgg agggaacatc gttggtacca ttgggcgagg tggcttctct    6360
tatggcaacc gcaagagcct tgaacgcact ctcactacgg tgatgatcat tcttgcctcg    6420
cagacaatca acgtggaggg taattctgct agcctctgca aagctttcaa gaaaatgcgg    6480
gatcatctcg caagagagat ctcctacttt ctcccttttgc aaaccaagtt cgacaactgc   6540
gtacggcctg ttcgaaagat ctaccaccgc tctggaaagt gcctcatcca aaggcgcaaa    6600
tcctgatcca aaccttttta ctccacgcac ggccctaggg gccctcttaa aagcttgacc    6660
gagagcaatc ccgcagtctt cagtggtgtg atggtcgtct atgtgtaagt caccaatgca    6720
ctcaacgatt agcgaccagc cggaatgctt ggccagaaca tgtatcatat ggtccagaaa    6780
ccctataccct gtgtggacgt taatcacttg cgattgtgtg gcctgttctg ctactgcttc    6840
tgcctctttt tctgggaaga tcgagtgctc tatcgctagg ggaccaccct ttaaagagat    6900
cgcaatctga atcttggttt catttgtaat acgctttact agggctttct gctctgtcat    6960
ctttgccttc gtttatcttg cctgctcatt ttttagtata ttcttcgaag aaatcacatt    7020
actttatata atgtataatt cattatgtga taatgccaat cgctaagaaa aaaaagagt     7080
catccgctag gtgaaaaaaa aaaatgaaa atcattaccg aggcataaaa aatatagag      7140
tgtactagag gaggccaaga gtaatagaaa aagaaaattg cgggaaagga ctgtgttatg    7200
acttccctga ctaatgccgt gttcaaacga tacctggcag tgactcctga cgctcaccaa    7260
gctcttaaaa cgggaattta tggtgcactc tcagtacacg cgccagatct gtttagcttg    7320
cctcgtcccc gccgggtcac ccggccagcg acatggaggc ccagaatacc ctccttgaca    7380
gtcttgacgt gcgcagctca ggggcatgat gtgactgtcg cccgtacatt tagcccatac    7440
atccccatgt ataatcattt gcatccatac atttttgatgg ccgcacggcg cgaagcaaaa    7500
attacggctc ctcgctgcag acctgcgagc agggaaacgc tcccctcaca gacgcgttga    7560
attgtcccca cgccgcgccc ctgtagagaa atataaaagg ttaggatttg ccactgaggt    7620
tcttctttca tacttcct tttaaaatct tgctaggata cagttctcac atcacatccg      7680
aacataaaca accatgggta aggaaagac tcacgtttcg aggccgcgat taaattccaa     7740
catggatgct gatttatatg ggtataaatg gctcgcgat aatgtcgggc aatcaggtgc     7800
gacaatctat cgattgtatg ggaagcccga tgcgccaaga ttgtttctga aacatggcaa    7860
aggtagcgtt gccaatgatg ttacagatga gatggtcaga ctaaactggc tgacggaatt    7920
tatgcctctt ccgaccatca agcatttat ccgtactcct gatgatgcat ggttactcac     7980
cactgcgatc cccggcaaaa cagcattcca ggtattagaa gaatatcctg attcaggtga    8040
aaatattgtt gatgcgctgg cagtgttcct gcgccggttg cattcgattc ctgtttgtaa    8100
ttgtcctttt aacagcgatc gcgtatttcg tctcgctcag gcgcaatcac gaatgaataa    8160
cggtttggtt gatgcgagtg attttgatga cgagcgtaat ggctggcctg ttgaacaagt    8220
ctggaaagaa atgcataagc ttttgccatt ctcaccggat tcagtcgtca ctcatggtga    8280
tttctcactt gataacctta ttttgacga ggggaaatta ataggttgta ttgatgttgg      8340
acgagtcgga atcgcagacc gataccagga tcttgccatc ctatggaact gcctcggtga    8400
gttttctcct tcattacaga aacggctttt tcaaaaatat ggtattgata atcctgatat    8460
```

```
gaataaattg cagtttcatt tgatgctcga tgagttttc taatcagtac tgacaataaa    8520
aagattcttg ttttcaagaa cttgtcattt gtatagtttt tttatattgt agttgttcta    8580
ttttaatcaa atgttagcgt gatttatatt ttttttcgcc tcgacatcat ctgcccagat    8640
gcgaagttaa gtgcgcagaa agtaatatca tgcgtcaatc gtatgtgaat gctggtcgct    8700
atactgctgt cgattcgata ctaacgccgc catccagtgt cgaattcgcc attcaggctg    8760
cgcaactgtt gggaagggcg atcggtgcgg gcctcttcgc tattacgcca gctgaattgg    8820
agcgacctca tgctatacct gagaaagcaa cctgacctac aggaaagagt tactcaagaa    8880
taagaatttt cgttttaaaa cctaagagtc actttaaaat ttgtatacac ttattttttt    8940
tataacttat ttaataataa aaatcataaa tcataagaaa ttcgcttatt tagaagtgtc    9000
aacaacgtat ctaccaacga tttgacccct ttccatcttt tcgtaaattt ctggcaaggt    9060
agacaagccg acaaccttga ttggagactt gaccaaacct ctggcgaaga attgttaatt    9120
aagagctcag atcttttgcg gccgc                                          9145

SEQ ID NO: 30          moltype = DNA   length = 499
FEATURE                Location/Qualifiers
misc_feature           1..499
                       note = Synthetic construct
source                 1..499
                       mol_type = other DNA
                       organism = synthetic construct
SEQUENCE: 30
gtttgcaaaa agaacaaaac tgaaaaaacc cagacacgct cgacttcctg tcttcctatt    60
gattgcagct tccaatttcg tcacacaaca aggtcctagc gacggctcac aggttttgta    120
acaagcaatc gaaggttctg gaatggcggg aaagggttta gtaccacatg ctatgatgcc    180
cactgtgatc tccagagcaa agttcgttcg atcgtactgt tactctctct ctttcaaaca    240
gaattgtccg aatcgtgtga caacaacagc ctgttctcac acactctttt cttctaacca    300
agggggtggt ttagtttagt agaacctcgt gaaacttaca tttacatata tataaacttg    360
cataaattgg tcaatgcaag aaatacatat ttggtctttt ctaattcgta gttttttcaag   420
ttcttagatg ctttctttttt ctctttttta cagatcatca aggaagtaat tatctacttt    480
ttacaacaaa tataaaaca                                                  499

SEQ ID NO: 31          moltype = DNA   length = 500
FEATURE                Location/Qualifiers
misc_feature           1..500
                       note = Synthetic construct
source                 1..500
                       mol_type = other DNA
                       organism = synthetic construct
SEQUENCE: 31
acagtttatt cctggcatcc actaaatata atggagcccg cttttaagc tggcatccag     60
aaaaaaaaag aatcccagca ccaaaatatt gttttcttca ccaaccatca gttcataggt    120
ccattctctt agcgcaacta cagagaacag gggcacaaac aggcaaaaaa cgggcacaac    180
ctcaatggag tgatgcaacc tgcctggagt aaatgatgac acaaggcaat tgacccacgc    240
atgtatctat ctcatttctt tacaccttcg attaccttct gctctctctg atttggaaaa    300
agctgaaaaa aaaggttgaa accagttccc tgaaattatt ccctacttg actaataagt     360
atataaagac ggtaggtatt gattgtaatt ctgtaaatct atttcttaaa cttcttaaat    420
tctactttta tagttagtct ttttttttagt tttaaaacac caagaactta gtttcgaata    480
aacacacata aacaaacaaa                                                500

SEQ ID NO: 32          moltype = DNA   length = 500
FEATURE                Location/Qualifiers
misc_feature           1..500
                       note = Synthetic construct
source                 1..500
                       mol_type = other DNA
                       organism = synthetic construct
SEQUENCE: 32
gctggattga gctgaatggt gccaggtcga ggctgggagg gagactaact cgaaagtgac    60
gaagactcga aaattaaaaa aaaagatact gcagaaggca agattgagaa tggagtaaag    120
gcagcgtggg tccctgtggg aaaccgcagt tttcctgcgc caagtggtac cggtgcgagt    180
gcagcaatta atctctcgat atttttcttag tatctctttt tatataagaa tatatttggg    240
aattggtaat gcttatcttc aatagtttct tagttgaatg cacacttaag agcaaattgg    300
ccaaggagtt cttcgttcgc tttaattttat ttcctggtta ttgtcaattt attcatccca    360
tctccccagg atagaagaaa ttagtgtaat tttgctgaca atacattta acgacgataa     420
caataatagc aattaaataa aatagcacta ccaccactcc actgctcgtt agctatttct    480
gtaaaataaa taaaaagatc                                                500

SEQ ID NO: 33          moltype = DNA   length = 501
FEATURE                Location/Qualifiers
misc_feature           1..501
                       note = Synthetic construct
source                 1..501
                       mol_type = other DNA
                       organism = synthetic construct
SEQUENCE: 33
attcgcgcta tctcgatttc tacctatata gttaatctct gtacaaaaac aatctttcca    60
actatccatt aatcatagta tattatcagc gtcggcgatt ttaccacgct tgacaaaagc    120
cgcgggcggg attcctgtgg gtagtggcac cggcagttaa tctaatcaaa ggcgcttgaa    180
ggaagagata gataatagaa caaagcaatc gccgctttgg acggcaaata tgtttatcca    240
```

```
ttggtgcggt gattggatat gatttgtctc cagtagtata agcaagcgcc agatctgttt  300
actgtaaaat taagtgagta atctcgcggg atgtaatgat ttaagggaat ctggttcagg  360
ttttcacata tatttgtata taaggccatt tgtaatttca atagttttag gattttcct   420
tctcccaaaa tactcactta ctgtgttaca ttacagaaag aacagacaag aaaccgtcaa  480
taagaaatat aactaagaac a                                            501
```

| | | |
|---|---|---|
| SEQ ID NO: 34 | moltype = DNA length = 7882 | |
| FEATURE | Location/Qualifiers | |
| misc_feature | 1..7882 | |
| | note = Synthetic construct | |
| source | 1..7882 | |
| | mol_type = other DNA | |
| | organism = synthetic construct | |

SEQUENCE: 34
```
caggtggcac ttttcgggga aatgtgcgcg gaacccctat ttgtttattt ttctaaatac  60
attcaaatat gtatccgctc atgagacaat aaccctgata aatgcttcaa taatattgaa  120
aaaggaagag tatgagtatt caacatttcc gtgtcgccct tattccctt tttgcggcat   180
tttgccttcc tgtttttgct cacccagaaa cgctggtgaa agtaaaagat gctgaagatc  240
agttgggtgc acgagtgggt tacatcgaac tggatctcaa cagcggtaag atccttgaga  300
gttttcgccc cgaagaacgt tttccaatga tgagcacttt taaagttctg ctatgtggcg  360
cggtattatc ccgtattgac gccgggcaag agcaactcgg tcgccgcata cactattctc  420
agaatgactt ggttgagtac tcaccagtca cagaaaagca tcttacggat ggcatgacag  480
taagagaatt atgcagtgct gccataacca tgagtgataa cactgcggcc aacttacttc  540
tgacaacgat cggaggaccg aaggagctaa ccgcttttt gcacaacatg ggggatcatg   600
taactcgcct tgatcgttgg gaaccggagc tgaatgaagc cataccaaac gacgagcgtg  660
acaccacgat gcctgtagca atggcaacaa cgttgcgcaa actattaact ggcgaactac  720
ttactctagc ttcccggcaa caattaatag actggatgga ggcggataaa gttgcaggac  780
cacttctgcg ctcggccctt ccggctggct ggtttattgc tgataaatct ggagccggtg  840
agcgtgggtc tcgcggtatc attgcagcac tggggccaga tggtaagccc tcccgtatcg  900
tagttatcta cacgacgggg agtcaggcaa ctatggatga acgaaataga cagatcgctg  960
agataggtgc ctcactgatt aagcattggt aactgtcaga ccaagtttac tcatatatac  1020
tttagattga ttttaaaactt cattttaat ttaaaaggat ctaggtgaag atcctttttg  1080
ataatctcat gaccaaaatc ccttaacgtg agttttcgtt ccactgagcg tcagaccccg  1140
tagaaaagat caaaggatct cttgagatc ctttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtt cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620
gaacaggaga gcgcacgagg gagcttccag ggggaaacgc ctggtatctt tatagtcctg  1680
tcgggtttcg ccacctctga cttgagcgtc gatttttgtg atgctcgtca ggggggcgga  1740
gcctatggaa aaacgccagc aacgcggcct ttttacggtt cctggccttt tgctggcctt  1800
ttgctcacat gttctttcct gcgttatccc ctgattctgt ggataaccgt attaccgcct  1860
ttgagtgagc tgataccgct cgccgcagcc gaacgaccga gcgcagcgag tcagtgagcg  1920
aggaagcgga agagcgccca atacgcaaac cgcctctccc cgcgcgttgg ccgattcatt  1980
aatgcagctg gatcttcgag cgtcccaaaa ccttctcaag caaggttttc agtataatgt  2040
tacatgcgta cacgcgtctg tacagaaaaa aagaaaaat ttgaaatata ataacgttc    2100
ttaatactaa cataactata aaaaaataaa tagggaccta gacttcaggt tgtctaactc  2160
cttccttttc ggttagagcg gatcttagct agccgcgtga ccaagctggt ggatccttg   2220
tttgtttatg tgtgtttatt cgaaactaag ttcttggtgt tttaaaacta aaaaaaagac  2280
taactataaa agtagaattt aagaagttta agaaatagat ttacagaatt acaatcaata  2340
cctaccgtct ttatatactt attagtcaag taggggaata atttcaggga actggtttca  2400
accttttttt tcagcttttt ccaaatcaga gagcgaaa ggtaatagaa ggtgtaagaa    2460
aatgagatag atacatgcgt gggtcaattg ccttgtgtca tcatttactc caggcaggtt  2520
gcatcactcc attgaggttg tgcccgtttt ttgcctgttt gtgcccctgt tctctgtagt  2580
tgcgctaaga gaatggacct atgaactgat ggttggtgaa gaaaacaata ttttggtgct  2640
gggattcttt ttttttctgg atgccagctt aaaaagcggg ctccattata tttagtgat   2700
gccaggaata aactgttgtt tgcaaaagaa acaaaactga aaaaacccag acacgctcga  2760
cttcctgtct tcctattgat tgcagcttcc aatttcgtca cacaacaagg tcctagcgac  2820
ggctcacagg ttttgtaaca agcaatcgaa ggttctggaa tggcgggaaa gggtttagta  2880
ccacatgcta tgatgcccac tgtgatctcc agagcaaagt tcgttcgatc gtactgttac  2940
tctctctctt tcaaacagaa ttgtccgaat cgtgtgacaa caacagcctg ttctcacaca  3000
ctcttttctt ctaaccaagg gggtggttta gttagtagaa acctcgtgaa acttacatt   3060
acatatatat aaacttgcat aaattggtca atgcaagaaa tacatatttg gtctttctta  3120
attcgtagtt tttcaagttc ttagatgctt tcttttctc ttttttacag atcatcaagg   3180
aagtaattat ctacttttta caacaaatat aaaacagcgg ccgcaaaaga tctgagctct  3240
taattaacaa ttcttcgcca gaggtttggt caagtctcca atcaaggttg tcggcttgtc  3300
taccttgcca gaaatttacg aaaagatgga aaagggtcaa atcgttggta gatacgttgt  3360
tgacacttct aaataagcga atttcttatg atttatgatt ttattatta aataagttat  3420
aaaaaaata agtgtataca aattttaaag tgactcttag gttttaaaac gaaaattctt  3480
attcttgagt aactcttttcc tgtaggtcag gttgctttct caggtatagc atgaggtcgc  3540
tccaattcag ctggcgtaat agcgaagagg cccgcaccga tcgcccttcc caacagttgc  3600
gcagcctgaa tggcgaattc gacactggat ggcggcgtta gtatcgaatc gacagcagta  3660
tagcgaccag cattcacata cgattgacgc atgatattac tttctgcgca cttaacttcg  3720
catctgggca gatgatgtcg aggcgaaaaa aaatataaat cacgctaaca tttgattaaa  3780
atagaacaac tacaatataa aaaaactata caaatgacaa gttcttgaaa acaagaatct  3840
ttttattgtc agtactgatt agaaaaactc atcgagcatc aaatgaaact gcaatttatt  3900
```

```
catatcagga ttatcaatac catattttg aaaaagccgt ttctgtaatg aaggagaaaa   3960
ctcaccgagg cagttccata ggatggcaag atcctggtat cggtctgcga ttccgactcg   4020
tccaacatca atacaaccta ttaatttccc ctcgtcaaaa ataaggttat caagtgagaa   4080
atcaccatga gtgacgactg aatccggtga gaatggcaaa agcttatgca tttctttcca   4140
gacttgttca acaggccagc cattacgctc gtcatcaaaa tcactcgcat caaccaaacc   4200
gttattcatt cgtgattgcg cctgagcgag acgaaatacg cgatcgctgt taaaaggaca   4260
attacaaaca ggaatcgaat gcaaccggcg caggaacact gccagcgcat caacaatatt   4320
ttcacctgaa tcaggatatt cttctaatac ctggaatgct gttttgccgg ggatcgcagt   4380
ggtgagtaac catgcatcat caggagtacg gataaaatgc ttgatggtcg gaagaggcat   4440
aaattccgtc agccagttta gtctgaccat ctcatctgta acatcattgg caacgctacc   4500
tttgccatgt ttcagaaaca actctggcgc atcgggcttc ccatacaatc gatagattgt   4560
cgcacctgat tgcccgacat tatcgcgagc ccatttatac ccatataaat cagcatccat   4620
gttggaattt aatcgcggcc tcgaaacgtg agtctttcc ttacccatgg ttgtttatgt   4680
tcggatgtga tgtgagaact gtatcctagc aagattttaa aaggaagtat atgaaagaag   4740
aacctcagtg gcaaatccta accttttata tttctctaca ggggcgcggc gtggggacaa   4800
ttcaacgcgt ctgtgagggg agcgtttccc tgctcgcagg tctgcagcga ggagccgtaa   4860
tttttgcttc gcgccgtgcg gccatcaaaa tgtatggatg caaatgatta tacatgggga   4920
tgtatgggct aaatgtacgg gcgacagtca catcatgccc ctgagctgcg cacgtcaaga   4980
ctgtcaagga gggtattctg ggcctccatg tcgctggccg ggtgaccggg cggggacgag   5040
gcaagctaaa cagatctggc gcgtgtactg agagtgcacc ataaattccc gttttaagag   5100
cttggtgagc gctaggagtc actgccaggt atcgtttgaa cacggcatta gtcagggaag   5160
tcataacaca gtccttttcc gcaatttct ttttctatta ctcttggcct cctctagtac   5220
actctatatt tttttatgcc tcggtaatga ttttcatttt ttttttttcca cctagcggat   5280
gactcttttt ttttcttagc gattggcatt atcacataat gaattataca ttatataaag   5340
taatgtgatt tcttcgaaga atatactaaa aaatgagcag gcaagataaa cgaaggcaaa   5400
gatgacagag cagaaagccc tagtaaagcg tattacaaat gaaaccaaga ttcagattgc   5460
gatctcttta aagggtggtc ccctagcgat agagcactcg atcttcccag aaaaagaggc   5520
agaagcagta gcagaacagg ccacacaatc gcaagtgatt aacgtccaca caggtatagg   5580
gtttctggac catatgatac atgctctggc caagcattcc ggctggtcgc taatcgttga   5640
gtgcattggt gacttacaca tagacgacca tcacaccact gaagactgcg ggattgctct   5700
cggtcaagct tttaaagagg ccctaggggc cgtgcgtgga gtaaaaaggt ttggatcagg   5760
atttgcgcct ttggatgagg cactttccag agcggtggta gatctttcga acaggccgta   5820
cgcagttgtc gaacttggtt tgcaaaggga gaaagtagga gatctctctt gcgagatgat   5880
cccgcatttt cttgaaagct ttgcagaggc tagcagaatt accctccacg ttgattgtct   5940
gcgaggcaag aatgatcatc accgtagtga gagtgcgttc aaggctcttg cggttgccat   6000
aagagaagcc acctcgccca atggtaccaa cgatgttccc tccaccaaag gtgttcttat   6060
gtagtgacac cgattattta aagctgcagc atacgtata tatacatgtg tatatatgta   6120
tacctatgaa tgtcagtaag tatgtatacg aacagtatga tactgaagat gacaaggtaa   6180
tgcatcattc tatacgtgtc attctgaacg aggcgcgctt tccttttttc tttttgcttt   6240
ttcttttttt ttctcttgaa ctcgacggat ctatgcggtg tgaaatatgg tgcactctca   6300
gtacaatctg ctctgatgcc gcatagttaa gccagcccg acaccgcca acacccgctg   6360
acgcgccctg acgggcttgt ctgctcccgg catccgctta cagacaagct gtgaccgtct   6420
ccgggagctg catgtgtcag aggttttcac cgtcatcacc gaaacgcgcg agacgaaagg   6480
gcctcgtgat acgcctattt ttataggtta atgtcatgat aataatggtt tcttagtatg   6540
atccaatatc aaaggaaatg atagcattga aggatgagac taatcaatt gaggagtggc   6600
agcatatag acagctaaag ggtagtgctg aaggaagcat acgataccc gcatggaatg   6660
ggataaatc acaggaggta ctagactacc tttcatccta cataaataga cgcataag   6720
tacgcatta agcataaaca cgcactatgc cgttcttctc atgtatatat atatacaggc   6780
aacacgcaga tataggtgcg acgtaacag tgagctgtat gtgcgcagct cgcgttgcat   6840
tttcggaagc gctcgttttc ggaaacgctt tgaagttcct attccgaagt tcctattctc   6900
tagaaagtat aggaacttca gagcgcttttt gaaaaccaaa agcgctctga agacgcactt   6960
tcaaaaaacc aaaacgcac cggactgtaa cgagctacta aaatattgcg aataccgctt   7020
ccacaaacat tgctcaaaag tatctctttg ctatatatct ctgtgctata tcctatata   7080
acctacccat ccacctttcg ctccttgaac ttgcatctaa actcgacctc tacattttt   7140
atgtttatct ctagtattac tctttagaca aaaaaattgt agtaagaact attcatagag   7200
tgaatcgaaa acaatacgaa aatgtaaaca tttcctatac gtagtatata gagacaaaat   7260
agaagaaacc gttcataatt ttctgaccaa tgaagaatca tcaacgctat cacttttctgt   7320
tcacaaagta tgcgcaatcc acatcggtat agaatataat cggggatgcc tttatcttga   7380
aaaaatgcac ccgcagcttc gctagtaatc agtaaacgcg ggaagtggag tcaggctttt   7440
tttatggaag agaaaataga caccaaagta gccttcttct aaccttaacg gacctacagt   7500
gcaaaaagtt atcaagagac tgcattatag agcgcacaaa ggagaaaaaa agtaatctaa   7560
gatgctttgt tagaaaaata gcgctctcgg gatgcatttt tgtagaacaa aaagaagta   7620
tagattcttt gttggtaaaa tagcgctctc gcgttgcatt tctgttctgt aaaaatgcag   7680
ctcagattct ttgtttgaaa aattagcgct ctcgcgttgc attttcacaa aatg          7740
aagcacagat tcttcgttgg taaaatagcg cttcgcgtt gcatttctgt tctgtaaaaa   7800
tgcagctcag attctttgtt tgaaaaatta gcgctctcgc gttgcatttt tgttctacaa   7860
aatgaagcac agatgcttcg tt                                               7882

SEQ ID NO: 35        moltype = DNA   length = 3810
FEATURE              Location/Qualifiers
misc_feature         1..3810
                     note = Synthetic contruct
source               1..3810
                     mol_type = other DNA
                     organism = synthetic construct
SEQUENCE: 35
gctaacagcg cgatttgctg gtgacccaat gcgaccagat gctccacgcc cagtcgcgta     60
ccgtcttcat gggagaaaat aatactgttg atgggtgtct ggtcagagac atcaagaaat    120
aacgccggaa cattagtgca ggcagcttcc acagcaatgg catcctggtc atccagcgga    180
```

```
tagttaatga tcagcccact gacgcgttgc gcgagaagat tgtgcaccgc cgctttacag   240
gcttcgacgc cgcttcgttc taccatcgac accaccacgc tggcacccag ttgatcggcg   300
cgagatttaa tcgccgcgac aatttgcgac ggcgcgtgca gggccagact ggaggtggca   360
acgccaatca gcaacgactg tttgcccgcc agttgttgtg ccacgcggtt gggaatgtaa   420
ttcagctccg ccatcgccgc ttccacttt tcccgcgttt tcgcagaaac gtggctggcc    480
tggttcacca cgcggaaac ggtctgataa gagacaccgg catactctgc gacatcgtat     540
aacgttactg gtttcacatt caccaccctg aattgactct cttccgggcg ctatcatgcc   600
ataccgcgaa aggttttgcg ccattcgatg gtgtccggga tctcgacgct ctcccttatg   660
cgactcctgc attaggaagc agcccagtag taggttgagg ccgttgagca ccgccgccgc   720
aaggaatggt gcatgcaagg agatggcgcc caacagtccc ccggccacgg ggcctgccac   780
catacccacg ccgaaacaag cgctcatgag cccgaagtgg cgagcccgat cttccccatc   840
ggtgatgtcg gcgatatagg cgccagcaac cgcacctgtg gcgccggtga tgccggccac   900
gatgcgtccg gcgtagccta ggatcgagat cgatctcgat cccgcgaaat taatacgact   960
cactataggg gaattgtgag cggataacaa ttcccctcta gaaataattt tgtttaactt  1020
taagaaggag atatacatat ggcagatctc aattggatat cggccggcca cgcgatcgct  1080
gacgtcggta ccctcgagtc tggtaaagaa accgctgctg cgaaatttga acgccagcac  1140
atggactcgt ctactagtcg cagcttaatt aacctaaact gctgccaccg ctgagcaata  1200
actagcataa ccccttgggg cctctaaacg ggtcttgagg ggtttttgc tagcgaaagg   1260
aggagtcgac actgcttccg gtagtcaata aaccggtaaa ccagcaatag acataagcgg  1320
ctatttaacg accctgccct gaaccgacga ccgggtcatc gtggccggat cttgcggccc  1380
ctcggcttga acgaattgtt agacattatt tgccgactac cttggtgatc tcgcctttca  1440
cgtagtggac aaattcttcc aactgatctg cgcgcgaggc caagcgattc tcttcttgtc  1500
caagataagc ctgtctagct tcaagtatga cgggctgata ctgggccggc aggcgctcca  1560
ttgcccagtc ggcagcgaca tccttcggcg cgattttgcc ggttactgcg ctgtaccaaa  1620
tgcgggacaa cgtaagcact acatttcgct catcgccagc ccagtcgggc ggcgagttcc  1680
atagcgttaa ggtttcattt agcgcctcaa atagatcctg ttcaggaacc ggatcaaaga  1740
gttcctccgc cgctgaccct accaaggcaa cgctatgttc tcttgctttt gtcagcaaga  1800
tagccagatc aatgtcgatc gtggctggct cgaagatacc tgcaagaatg tcattgcgct  1860
gccattctcc aaattgcagt tcgcgcttag ctggataacg ccacggaatg atgtcgtcgt  1920
gcacaacaat ggtgacttct acagcgcgga gaatctgctc tctccaggg gaagccgaag   1980
tttccaaaag gtcgttgatc aaagctcgcc gcgttgtttc atcaagcctt acggtcaccg  2040
taaccagcaa atcaatatca ctgtgtggct tcaggccgcc atccactgcg gagccgtaca  2100
aatgtacggc cagcaacgtc ggttcgagat ggcgctcgat gacgccaact acctctgata  2160
gttgagtcga tacttcggcg atcaccgctt ccctctatct cttccttttt caatattatt  2220
gaagcattta tcagggttat tgtctcatga gcggatacat atttgaatgt atttagaaaa  2280
ataaacaaat agccagctca ctcggtcgct acgctccggg cgtgagactg cggcgggcgc  2340
tgcggacaca tacaaagtta cccacagatt ccgtggataa gcaggggact aacatgtgag  2400
gcaaaacagc agggccgcgc cggtggcgtt tttccatagg ctccgcccctc ctgccagagt   2460
tcacataaac agacgctttt ccggtgcatc tgtgggagcc gtgaggctca accatgaatc  2520
tgacagtacg ggcgaaaccc gacaggactt aaagatcccc accgtttccg gcgggtcgct  2580
ccctcttgcg ctctcctgtt ccgacccctgc cgtttaccgg atacctgttc cgcctttctc   2640
ccttacggga agtgtggcgc tttctcatag ctcacacact ggtatctcgg ctcggtgtag  2700
gtcgttcgct ccaagctggg ctgtaagcaa gaactcccgt ttcagcccga ctgctgcgcc  2760
ttatccggta actgttcact tgagtccaac ccggaaaagc acgtaaaac gccactggca   2820
gcagccattg gtaactggga gttcgcgagg gatttgttta gctaaacacg cggttgctct  2880
tgaagtgtgc gccaaagtcc ggctacactg gaaggacaga tttggttgct gtgctctgcg  2940
aaagccagtt accacggtta agcagttccc caactgcatt aaccttcgat caaaccacct  3000
ccccaggtgg tttttttcgtt tacagggcaa aagattacgc gcagaaaaaa aggatctcaa  3060
gaagatcctt tgatcttttc tactgaaccg ctctagattt cagtgcaatt tatctcttca  3120
aatgtagcac ctgaagtcag ccccatacga tataagttgt aattctcatg ttagtcatgc  3180
cccgcgccca ccggaaggag ctgactgggt tgaaggctct caagggcatc ggtcgagatc  3240
ccggtgccta atgagtgagc taacttacat taattgcgtt gcgctcactg cccgctttcc  3300
agtcgggaaa cctgtcgtgc cagctgcatt aatgaatcgg ccaacgcgcg gggagaggcg  3360
gtttgcgtat tgggcgccag ggtggttttt cttttcacca gtgagacggg caacagctga  3420
ttgcccttca ccgcctggcc ctgagagagt tgcagcaagc ggtccacgct ggtttgcccc  3480
agcaggcgaa aatcctgttt gatggtggtt aacggcggga tataacatga gctgtcttcg  3540
gtatcgtcgt atcccactac cgagatgtcc gcaccaacgc gcagcccgga ctcggtaatg  3600
gcgcgcattg cgcccagcgc catctgatcg ttggcaacca gcatcgcagt gggaacgatg  3660
ccctcattca gcatttgcat ggtttgttga aaaccggaca tggcactcca gtcgccttcc  3720
cgttccgcta tcggctgaat ttgattgcga gtgagatatt tatgccagcc agccagacgc  3780
agacgcgccg agacagaact taatgggccc                                   3810

SEQ ID NO: 36           moltype = DNA  length = 5369
FEATURE                 Location/Qualifiers
misc_feature            1..5369
                        note = Synthetic construct
source                  1..5369
                        mol_type = other DNA
                        organism = synthetic construct
SEQUENCE: 36
atccggatat agttcctcct ttcagcaaaa aaccctcaa gacccgttta gaggccccaa    60
gggttatgc tagttattgc tcagcggtgg cagcagccaa ctcagcttcc tttcgggctt   120
tgttagcagc cggatctcag tggtggtggt ggtggtgctc gagtgcggcc gcaagcttgt  180
cgacgagct cgaattcgga tccgcgaccc atttgctgtc caccagtcat gctagccata  240
tggctgccgc gcggcaccag gccgctgctg tgatgatgat gatgatggct gctgcccatg  300
gtatatctcc ttcttaaagt taaacaaaat tatttctaga gggaattgt tatccgctca  360
caattcccct atagtgagtc gtattaattt cgcgggatcg agatctcgat cctctacgcc  420
ggacgcatcg tggccggcat caccggcgcc acaggtgcgg ttgctggcgc ctatatcgcc  480
gacatcaccg atggggaaga tcgggctcgc cacttcgggc tcatgagcgc ttgtttcggc  540
```

```
gtgggtatgg tggcaggccc cgtggccggg ggactgttgg gcgccatctc cttgcatgca  600
ccattccttg cggcggcggt gctcaacggc ctcaacctac tactgggctg cttcctaatg  660
caggagtcgc ataagggaga gcgtcgagat cccggacacc atcgaatggc gcaaaacctt  720
tcgcggtatg gcatgatagc gcccggaaga gagtcaattc agggtggtga atgtgaaacc  780
agtaacgtta tacgatgtcg cagagtatgc cggtgtctct tatcgagaccg tttcccgcgt  840
ggtgaaccag gccagccacg tttctgcgaa aacgcgggaa aaagtggaag cggccgatggc  900
ggagctgaat tacattccca accgcgtggc acaacaactg gcgggcaaac agtcgttgct  960
gattggcgtt gccacctcca gtctggccct gcacgcgccg tcgcaaattg tcgcggcgat  1020
taaatctcgc gccgatcaac tgggtgccag cgtggtggtg tcgatggtag aacgaagcgg  1080
cgtcgaagcc tgtaaagcgg cggtgcacaa tcttctcgcg caacgcgtca gtgggctgat  1140
cattaactat ccgctggatg accaggatgc cattgctgtg gaagctgcct gcactaatgt  1200
tccggcgtta tttcttgatg tctctgacca gacacccatc aacagtatta ttttctccca  1260
tgaagacggt acgcgactgg gcgtggagca tctggtcgca ttgggtcacc agcaaatcgc  1320
gctgttagcg ggcccattaa gttctgtctc ggcgcgtcca cgtctggctg gctggcataa  1380
atatctcact cgcaatcaaa ttcagccgat agcggaacgg gaaggcgact ggagtgccat  1440
gtccggtttt caacaaacca tgcaaatgct gaatgagggc atcgttccca ctgcgatgct  1500
ggttgccaac gatcagatgg cgctgggcgc aatgcgcgcc attaccgagt ccgggctgcg  1560
cgttggtgcg gatatctcgg tagtgggata cgacgatacc gaagacagct catgttatat  1620
cccgccgtta accaccatca aacaggattt tcgcctgctg gggcaaacca gcgtggaccg  1680
cttgctgcaa ctctctcagg gccaggcggt gaagggcaat cagctgttgc ccgtctcact  1740
ggtgaaaaga aaaaccaccc tggcgcccaa tacgcaaacc gcctctcccc gcgcgttggc  1800
cgattcatta atgcagctgg cacgacaggt tccccgactg gaaagcgggc agtgagcgca  1860
acgcaattaa tgtaagttag ctcactcatt aggcaccggg atctcgaccg atgcccttga  1920
gagccttcaa cccagtcagc tccttccggt ggggcgcgggg catgactatc gtcgccgcac  1980
ttatgactgt cttctttatc atgcaactcg taggacaggt gccggcagcg ctctgggtca  2040
ttttcggcga ggaccgcttt cgctggagcg cgacgatgat cggcctgtcg cttgcggtat  2100
tcggaatctt gcacgccctc gctcaagcct tcgtcactgg tcccgccacc aaacgtttcg  2160
gcgagaagca ggccattatc gccggcatgg cggcccacg ggtgcgcatg atcgtgctcc  2220
tgtcgttgag gaccccggcta ggctggcggg gttgccttac tggttagcag aatgaatcac  2280
cgatacgcga gcgaacgtga agcgactgct gctgcaaaac gtctgcgacc tgagcaacaa  2340
catgaatggt cttcggtttc cgtgtttcgt aaagtctgga aacgcggaag tcagcgccct  2400
gcaccattat gttccggatc tgcatcgcag gatgctgctg gctaccctgt ggaacaccta  2460
catctgtatt aacgaagcgc tggcattgac cctgagtgat ttttctctgg tcccgccgca  2520
tccataccgc cagttgttta ccctcacaac gttccagtaa ccgggcatgt tcatcatcag  2580
taacccgtat cgtgagcatc ctctctcgtt tcatcggtat cattaccccc atgaacagaa  2640
atccccctta cacggaggca tcagtgacca aacaggaaaa aaccgccctt aacatggccc  2700
gctttatcag aagccagaca ttaacgcttc tggagaaact caacgagctg gacgcggatg  2760
aacaggcaga catctgtgaa tcgcttcacg accacgctga tgagctttac cgcagctgcc  2820
tcgcgcgttt cggtgatgac ggtgaaaacc tctgacacat gcagctcccg gagacggtca  2880
cagcttgtct gtaagcggat gccgggagca gacaagcccg tcagggcgcg tcagcgggtg  2940
ttggcgggtg tcggggcgca gccatgaccc agtcacgtag cgatagcgga gtgtatactg  3000
gcttaactat gcggcatcag agcagattgt actgagagtg caccatatat gcggtgtgaa  3060
ataccgcaca gatgcgtaag gagaaaatac cgcatcaggc gctcttccgc ttcctcgctc  3120
actgactcgc tgcgctcggt cgttcggctg cggcgagcgg tatcagctca ctcaaaggcg  3180
gtaatacggt tatccacaga atcaggggat aacgcaggaa agaacatgtg agcaaaaggc  3240
cagcaaaagg ccaggaaccg taaaaaggcc gcgttgctgg cgttttttcca taggctccgc  3300
cccccctgacg agcatcacaa aaatcgacgc tcaagtcaga ggtggcgaaa cccgacagga  3360
ctataaagat accaggcgtt tccccctgga agctccctcg tgcgctctcc tgttccgacc  3420
ctgccgctta ccggatacct gtccgccttt ctcccttcgg gaagcgtggc gctttctcat  3480
agctcacgct gtaggtatct cagttcggtg taggtcgttc gctccaagct gggctgtgtg  3540
cacgaacccc ccgttcagcc cgaccgctgc gccttatccg gtaactatcg tcttgagtcc  3600
aacccggtaa gacacgactt atcgccactg gcagcagcca ctggtaacag gattagcaga  3660
gcgaggtatg taggcggtgc tacagagttc ttgaagtggt ggcctaacta cggctacact  3720
agaaggacag tatttggtat ctgcgctctg ctgaagccag ttaccttcgg aaaaagagtt  3780
ggtagctctt gatccggcaa acaaaccacc gctggtagcg gtggtttttt tgtttgcaag  3840
cagcagatta cgcgcagaaa aaaaggatct caagaagatc ctttgatctt ttctacgggg  3900
tctgacgctc agtggaacga aaactcacgt taagggattt tggtcatgaa caataaaact  3960
gtctgcttac ataaacagta atacaagggg tgttatgagc catattcaac gggaaacgtc  4020
ttgctctagg ccgcgattaa attccaacat ggatgctgat ttatatgggt ataaatggct  4080
tcgcgataat gtcgggcaat caggtgcgac aatctatcga ttgtatggga agcccgatgc  4140
gccagagttg tttctgaaac atggcaaagg tagcgttgcc aatgatgtta cagatgagat  4200
ggtcagacta aactggctga cggaatttat gcctcttccg accatcaagc atttttatccg  4260
tactcctgat gatgcatggt tactcaccac tgcgatcccc gggaaaacag cattccaggt  4320
attagaagaa tatcctgatt caggtgaaaa tattgttgat gcgctggcag tgttcctgcg  4380
ccggttgcat tcgattcctg tttgtaattg tccttttaac agcgatcgcg tatttcgtct  4440
cgctcaggcg caatcacgaa tgaataacgg tttggttgat gcgagtgatt ttgatgacga  4500
gcgtaatggc tggcctgttg aacaagtctg aaagaaatg cataaactt tgccattctc  4560
accggattca gtcgtcactc atggtgattt ctcacttgat aaccttattt ttgacgaggg  4620
gaaattaata ggttgtattg atgttggacg agtcggaatc gcagaccgat accaggatct  4680
tgccatccta tggaactgcc tcggtgagtt ttctccttca ttacagaaac ggcttttttca  4740
aaaatatggt attgataatc ctgatatgaa taaattgcag tttcatttga tgctcgatga  4800
gttttttctaa gaattaattc atgagcggat acatatttga atgtatttag aaaaataaac  4860
aaataggggt tccgcgcaca tttccccgaa aagtgccacc tgaaattgta aacgttaata  4920
ttttgttaaa attcgcgtta aatttttgtt aaatcagctc attttttaac caataggccg  4980
aaatcggcaa aatcccttat aaatcaaaag aatagaccga gatagggttg agtgttgttc  5040
cagtttggaa caagagtcca ctattaaaga acgtggactc caacgtcaaa gggcgaaaaa  5100
ccgtctatca gggcgatggc ccactacgtg aaccatcacc ctaatcaagt ttttttgggt  5160
cgaggtgccg taaagcacta aatcggaacc ctaaagggag cccccgattt agagcttgac  5220
ggggaaagcc ggcgaacgtg gcgagaaagg aaggaagaa agcgaaagga gcgggcgcta  5280
```

```
gggcgctggc aagtgtagcg gtcacgctgc gcgtaaccac cacacccgcc gcgcttaatg    5340
cgccgctaca gggcgcgtcc cattcgcca                                     5369

SEQ ID NO: 37           moltype = DNA  length = 3592
FEATURE                 Location/Qualifiers
misc_feature            1..3592
                        note = Synthetic construct
source                  1..3592
                        mol_type = other DNA
                        organism = synthetic construct
SEQUENCE: 37
atccggatat agttcctcct ttcagcaaaa aacccctcaa gacccgttta gaggccccaa    60
gggggttatgc tagttattgc tcagcggtgg cagcagccaa ctcagcttcc tttcgggctt   120
tgttagcagc cggatctcag tggtggtggt ggtggtgctc gagtgcggcc gcaagcttgt    180
cgacggagct cgaattcgga tcctagaggg aaaccgttgt ggtctcccta tagtgagtcg    240
tattaatttc gcgggatcga gatctcgggc agcgttgggt cctggccacg ggtgcgcatg    300
atcgtgctcc tgtcgttgag gacccggcta ggctggcggg gttgccttac tggttagcag    360
aatgaatcac cgatacgcga gcgaacgtga agcgactgct gctgcaaaac gtctgcgacc    420
tgagcaacaa catgaatggt cttcggtttc cgtgtttcgt aaagtctgga aacgcggaag    480
tcagcgccct gcaccattat gttccggatc tgcatcgcag gatgctgctg gctaccctgt    540
ggaacaccta catctgtatt aacgaagcgc tggcattgac cctgagtgat ttttctctgg    600
tcccgccgca tccataccgc cagttgttta ccctcacaac gttccagtaa ggcaggcatgt   660
tcatcatcag taacccgtat cgtgagcatc ctctctcgtt tcatcggtat cattacccc    720
atgaacagaa atcccccctta cacggaggca tcagtgacca aacaggaaaa aaccgccctt   780
aacatggccc gctttatcag aagccagaca ttaacgcttc tggagaaact caacgagctg   840
gacgcggatg aacaggcaga catctgtgaa tcgcttcacg accacgctga tgagctttac    900
cgcagctgcc tcgcgcgttt cggtgatgac ggtgaaaacc tctgacacat gcagctcccg    960
gagacggtca cagcttgtct gtaagcggat gccgggagca gacaagcccg tcagggcgcg   1020
tcagcggggtg ttggcgggtg tcggggcgca gccatgaccc agtcacgtag cgatagcgga   1080
gtgtatactg gcttaactat gcggcatcag agcagattgt actgagagtg caccatatat   1140
gcggtgtgaa ataccgcaca gatgcgtaag gagaaaatac cgcatcaggc gctcttccgc    1200
ttcctcgctc actgactcgc tgcgctcggt cgttcggctg cggcgagcgg tatcagctca    1260
ctcaaaggcg gtaatacggt tatccacaga atcaggggat aacgcaggaa agaacatgtg    1320
agcaaaaggc cagcaaaagg ccaggaaccg taaaaaggcc gcgttgctgg cgtttttcca    1380
taggctccgc cccccctgacg agcatcacaa aaatcgacgc tcaagtcaga ggtggcgaaa    1440
cccgacagga ctataaagat accaggcgtt tccccctgga agctccctcg tgcgctctcc    1500
tgttccgacc ctgccgctta ccggatacct gtccgccttt ctcccttcgg gaagcgtggc    1560
gctttctcat agctcacgct gtaggtatct cagttcggtg taggtcgttc gctccaagct    1620
gggctgtgtg cacgaacccc ccgttcagcc cgaccgctga gcttatccg gtaactatcg    1680
tcttgagtcc aacccggtaa gacacgactt atcgccactg gcagcagcca ctggtaacag   1740
gattagcaga gcgaggtatg taggcggtgc tacagagttc ttgaagtggt ggcctaacta    1800
cggctacact agaaggacag tatttggtat ctgcgctctg ctgaagccag ttaccttcgg    1860
aaaaagagtt ggtagctctt gatccggcaa acaaaccacc gctggtagcg gtggtttttt    1920
tgtttgcaag cagcagatta cgcgcagaaa aaaaggatct caagaagatc ctttgatctt    1980
ttctacgggg tctgacgctc agtggaacga aaactcacgt taagggattt tggtcatgag    2040
attatcaaaa aggatcttca cctagatcct ttttaaatta aaatgaagtt ttaaatcaat    2100
ctaaagtata tatgagtaaa cttggtctga cagttaccaa tgcttaatca gtgaggcacc    2160
tatctcagcg atctgtctat ttcgttcatc catagttgcc tgactccccg tcgtgtagat    2220
aactacgata cgggagggct taccatctgg ccccagtgct gcaatgatac cgcgagaccc    2280
acgctcaccg gctccagatt tatcagcaat aaaccagcca gccggaaggg ccgagcgcag    2340
aagtggtcct gcaactttat ccgcctccat ccagtctatt aattgttgcc gggaagctag    2400
agtaagtagt tcgccagtta atagtttgcg caacgttgtt gccattgctg caggcatcgt    2460
ggtgtcacgc tcgtcgtttg gtatggcttc attcagctcc ggttcccaac gatcaaggcg    2520
agttacatga tcccccatgt tgtgcaaaaa agcggttagc tccttcggtc ctccgatcgt    2580
tgtcagaagt aagttggccg cagtgttatc actcatggtt atggcagcac tgcataattc    2640
tcttactgtc atgccatccg taagatgctt ttctgtgact ggtgagtact caaccaagtc    2700
attctgagaa tagtgtatgc ggcgaccgag ttgctcttgc ccggcgtcaa tacgggataa    2760
taccgcgcca catagcagaa ctttaaaagt gctcatcatt ggaaaacgtt cttcggggcg    2820
aaaactctca aggatcttac cgctgttgag atccagttcg atgtaaccca tcgtgcacc    2880
caactgatct tcagcatctt ttactttcac cagcgtttct gggtgagcaa aaacaggaag    2940
gcaaaatgcc gcaaaaaagg gaataagggc gacacggaaa tgttgaatac tcatactctt    3000
ccttttcaa tattattgaa gcatttatca gggttattgt ctcatgagcg gatacatatt    3060
tgaatgtatt tagaaaaata aacaaatagg ggttccgcgc acatttcccc gaaaagtgcc    3120
acctgaaatt gtaaacgtta atattttgtt aaaattcgcg ttaaattttt gttaaatcag    3180
ctcattttt aaccaatagg ccgaaatcgg caaaatccct tataaatcaa aagaatagac    3240
cgagataggg ttgagtgttg ttccagtttt gaacaagagt ccactattaa agaacgtgga    3300
ctccaacgtc aaagggcgaa aaaccgtcta tcagggcgat ggcccactac gtgaaccatc    3360
accctaatca agtttttttgg ggtcgaggtg ccgtaaagca ctaaatcgga acctaaaagg    3420
gagccccga tttagagctt gacggggaaa gccggcgaac gtggcgagaa aggaagggaa    3480
gaaagcgaaa ggagcgggcg ctagggcgct ggcaagtgta gcggtcacgc tgcgcgtaac    3540
caccacaccc gccgcgctta atgcgccgct acagggcgcg tcccattcgc ca             3592

SEQ ID NO: 38           moltype = DNA  length = 27
FEATURE                 Location/Qualifiers
misc_feature            1..27
                        note = Synthetic construct
source                  1..27
                        mol_type = other DNA
                        organism = synthetic construct
```

```
SEQUENCE: 38
tacccatacg acgttccaga ctacgcc                                              27

SEQ ID NO: 39           moltype = AA  length = 9
FEATURE                 Location/Qualifiers
REGION                  1..9
                        note = Synthetic construct
source                  1..9
                        mol_type = protein
                        organism = synthetic construct
SEQUENCE: 39
YPYDVPDYA                                                                   9

SEQ ID NO: 40           moltype = DNA  length = 33
FEATURE                 Location/Qualifiers
misc_feature            1..33
                        note = Synthetic construct
source                  1..33
                        mol_type = other DNA
                        organism = synthetic construct
SEQUENCE: 40
gaacaaaagt taatttctga agaagatttg gaa                                       33

SEQ ID NO: 41           moltype = AA  length = 10
FEATURE                 Location/Qualifiers
REGION                  1..10
                        note = Synthetic construct
source                  1..10
                        mol_type = protein
                        organism = synthetic construct
SEQUENCE: 41
EQKLISEEDL                                                                 10

SEQ ID NO: 42           moltype = DNA  length = 24
FEATURE                 Location/Qualifiers
misc_feature            1..24
                        note = Synthetic construct
source                  1..24
                        mol_type = other DNA
                        organism = synthetic construct
SEQUENCE: 42
gactacaagg atgacgatga caaa                                                 24

SEQ ID NO: 43           moltype = AA  length = 8
FEATURE                 Location/Qualifiers
REGION                  1..8
                        note = Synthetic construct
source                  1..8
                        mol_type = protein
                        organism = synthetic construct
SEQUENCE: 43
DYKDDDDK                                                                    8

SEQ ID NO: 44           moltype = DNA  length = 42
FEATURE                 Location/Qualifiers
misc_feature            1..42
                        note = Synthetic construct
source                  1..42
                        mol_type = other DNA
                        organism = synthetic construct
SEQUENCE: 44
ggtaagccaa ttccaaatcc tttgttgggt ttggactcca cc                             42

SEQ ID NO: 45           moltype = AA  length = 14
FEATURE                 Location/Qualifiers
REGION                  1..14
                        note = Synthetic construct
source                  1..14
                        mol_type = protein
                        organism = synthetic construct
SEQUENCE: 45
GKPIPNPLLG LDST                                                            14

SEQ ID NO: 46           moltype = DNA  length = 18
FEATURE                 Location/Qualifiers
misc_feature            1..18
                        note = Synthetic construct
source                  1..18
                        mol_type = other DNA
```

-continued

```
                      organism = synthetic construct
SEQUENCE: 46
catcatcatc atcatcat                                                 18

SEQ ID NO: 47          moltype = AA  length = 6
FEATURE                Location/Qualifiers
REGION                 1..6
                       note = Synthetic construct
source                 1..6
                       mol_type = protein
                       organism = synthetic construct
SEQUENCE: 47
HHHHHH                                                               6

SEQ ID NO: 48          moltype = DNA  length = 1089
FEATURE                Location/Qualifiers
source                 1..1089
                       mol_type = genomic DNA
                       organism = Psilocybe cubensis
SEQUENCE: 48
atggcgttcg atctcaagac tgaagacggc ctcatcacat atctcactaa acatctttct   60
ttggacgtcg acacgagcgg agtgaagcgc cttagcggag gctttgtcaa tgtaacctgg  120
cgcattaagc tcaatgctcc ttatcaaggt catacgagca tcatcctgaa gcatgctcag  180
ccgcacatgt ctacggatga ggattttaag ataggtgtag aacgttcggt ttacgaatac  240
caggctatca agctcatgat ggccaatcgg gaggttctgg gaggcgtgga tggcatagtt  300
tctgtgccag aaggcctgaa ctacgactta gagaataatg cattgatcat gcaagatgtc  360
gggaagatga agacccttt agattatgtc accgccaaac cgccacttgc gacggatata  420
gcccgccttg ttgggacaga aattgggggg ttcgttgcca gactccataa cataggccgc  480
gagaggcgac gatcctga gttcaaattc ttctctggaa atattgtcgg aaggacgact   540
tcagaccagc tgtatcaaac catcataccc aacgcagcga aatatggtgt cgatgacccc  600
ttgctgccta ctgtggttaa ggaccttgtg gacgatgtca tgcacagcga agagaccctt  660
gtcatggcgg acctgtggag tgaaatatt cttctccagt tggaggaggg aaacccatcg   720
aagctgcaga agatatatat cctggattgg aactttgca agtacggccc agcgtcgttg   780
gacctgggct atttcttggg tgactgctat ttgatatccc gctttcaaga cgacgaggtc   840
ggtacgacga tgcggcaagc ctacttgcaa agctatgcgc gtacgagcaa gcattcgatc   900
aactacgcca agtcactgc aggtattgct gctcatattg tgatgtggac cgactttatg    960
cagtggggga gcgaggaaga aaggataaat tttgtgaaaa agggggtagc tgcctttcac  1020
gacgccaggg gcaacaacga caatgggaa attacgtcta ccttactgaa ggaatcatcc   1080
actgcgtaa                                                         1089

SEQ ID NO: 49          moltype = AA  length = 362
FEATURE                Location/Qualifiers
source                 1..362
                       mol_type = protein
                       organism = Psilocybe cubensis
SEQUENCE: 49
MAFDLKTEDG LITYLTKHLS LDVDTSGVKR LSGGFVNVTW RIKLNAPYQG HTSIILKHAQ   60
PHMSTDEDFK IGVERSVYEY QAIKLMMANR EVLGGVDGIV SVPEGLNYDL ENNALIMQDV  120
GKMKTLLDYV TAKPPLATDI ARLVGTEIGG FVARLHNIGR ERRDDPEFKF FSGNIVGRTT  180
SDQLYQTIIP NAAKYGVDDP LLPTVVKDLV DDVMHSEETL VMADLWSGNI LLQLEEGNPS  240
KLQKIYILDW ELCKYGPASL DLGYFLGDCY LISRFQDEQV GTTMRQAYLQ SYARTSKHSI  300
NYAKVTAGIA AHIVMWTDFM QWGSEEERIN FVKKGVAAFH DARGNNDNGE ITSTLLKESS  360
TA                                                                362

SEQ ID NO: 50          moltype = DNA  length = 6379
FEATURE                Location/Qualifiers
misc_feature           1..6379
                       note = Synthetic construct
source                 1..6379
                       mol_type = other DNA
                       organism = synthetic construct
SEQUENCE: 50
cgagatcttt gtgttcggtt acccggctca gatcctaact tcttcttttg gtatgtttat   60
tcgtataagt tactgttgtc cacaggcaat actctgcaga aaattaaaac ggcattaatg  120
ctaggacaac cagaattgtt actactgtat gtgcgatagt tgataactgc aacattatgc  180
ccggtatatt ctcaaaaaac cctattactg catacgaaga aatcgcaaga gaaatctttc  240
ggtttggaaa agctcactgt gaggttcctt ggagccaata gtaatacagc acaatccaag  300
gaaaaatctg gcctatatgc aaggaaggag agatagtcaa aagcattctt tcccctagaa  360
gttggtgcat atatggcatc gttaaaacat attacccca aaatttcttc tctaaacgat   420
gtgcttggcc tttgttttgg tttttgatgt cggtcgtttg aggcccctttg cggaaaatcg  480
agatcgccga atggcacgcg agggaaggga aataaggttt aaaggcactg aaacaatagg  540
caagaagtag gcgagagccg acatacgaga ctaaattaag tcctcagcga gctcgcatgg  600
aatgcgtgcg atgagcgacc tcatgctata cctgagaaag caacctgacc tacaggaaag  660
agttactgca gaataagaat tttcgtttta aaacctaaga gtcactttaa aatttgtata  720
cacttatttt ttttataact tatttaataa taaaaatcat aaatcataag aaattcgctt  780
atttagaagt gtcaacaacg tatctaccaa cggaatgcgt gcgattcatt tgtcatcgtc  840
atccttgtag tcttcagcaa cacatgggta tgaaatagaa acttcttcag ccaatgcttt  900
aatcttcatc atgatttgca acatttcttc agttgtagtt cttggattaa ttgaacacaa  960
tctaataaca accttttcct tcaattctgt agtagataac atagcgaaac ctctatgtgt  1020
```

```
gatttcctta accaatttct tattaatttc attaatagta tctgttgatg ccaattcaga  1080
tggaatgtat ctaaaagtaa cgatacccaa ttgagctggt gtaacaactt cccaatcttt  1140
tgctttaccc aaaaatgctt caacttgttc tgctaacatg ataccatgat cgattgcttg  1200
tctaaaagca gcaacaccga aaactttaaa agacaaccaa accttcaaag ctctgaatct  1260
tcttgacaat tcgataccac cttcaccgaa attaatttca ccttcaacgt tagtttctga  1320
atccttgatg tattctggca tcattctaaa agtctttgac aaatattgag agtttctgat  1380
caaaacacaa ccaacatcgt atggttggaa caaccactta tgtggatcta aagtcaaaga  1440
atctgctcta tgaataccttt gcaacatagc tgaaccctt tcagacaaga tagctggagc  1500
accataagaa ccatcagcat gcaaccaaac atcttcatcg ttacacaaat ctgctaattc  1560
gttcaaagaa tcaacagcac cacaatttgt agtaccagca tttgcaataa cacagaatgg  1620
cttttttaccc ttagttctat cttctttaat ttgtttcttc aaagctgaaa cagagattct  1680
caaatgttca tctgtttcga ttctacagat ttgatgatgt ttaaaaccta aaaccttcaa  1740
tgctctatca actgagaaat gtgtttgatc agagaagtaa acaacagcat tttcgatatc  1800
gttgttcaac ttagcctgtc ttgcaacagt caaagctgtc aaatttgcca ttgaaccacc  1860
agaaacaaat aaaccttcag ctgaatctgg aaaaacccaac atagatttca accaattaat  1920
tgtagtcaat tcgatttgtt cagcacctgc accagcaatc catgcagttg gaaaaacatt  1980
aaaaccagaa gccaagaaat ctgcaacaac accaacgtaa ttatttggac ctggaacaaa  2040
agccaagaaa tgtggatgat caacatgtgt aatttgatta aaacgtttc tgttcaagaa  2100
atgcaacaat tcctttggat ctgaaccatt ttctgggata gattcagtca acttatttct  2160
caagatatca gaatcgattg tttctgaaac tggcttagac ttcaaatggt tcatgtgatc  2220
gatgatcaaa tcaactgctt ggtaacccaa ttgtctcatt tcttcagctg acaattgcaa  2280
attttcagac attgttttat attttgttgta aaaagtagat aattacttcc ttgatgatct  2340
gtaaaaaaga gaaaagaaa gcatctaaga acttgaaaaa ctacgaatta gaaaagacca  2400
aatatgtatt tcttgcattg accaatttat gcaagtttat atatatgtaa atgtaagttt  2460
cacgaggttc tactaaacta aaccacccccc ttggttagaa gaaaagagtg tgtgagaaca  2520
ggctgttgtt gtcacacgat tcggacaatt ctgtttgaaa gagagagaag aacagtacga  2580
tcgaacgaac tttgctctgg agatcacagt gggcatcata gcatgtggta ctaaaccctt  2640
tcccgccatt ccagaacctt cgattgcttg ttacaaaacc tgtgagccgt cgctaggacc  2700
ttgttgtgtg acgaaattgg aagctgcaat caataggaag acaggaagtc gagcgtgtct  2760
gggtttttc agttttgttc ttttttgcaaa caacagttta ttcctggcat ccactaaata  2820
taatggagcc cgcttttaa gctggcatcc agaaaaaaaa agaatcccag caccaaaata  2880
ttgtttctt caccaaccat cagttcatag gtccattctc ttagcgcaac tacagagaac  2940
aggggcacaa acaggcaaaa aacgggcaca acctcaatgg agtgatgcaa cctgcctgga  3000
gtaaatgatg acacaaggca attgacccac gcatgtatct atctcatttt cttacacctt  3060
ctattacctt ctgctctctc tgatttggaa aaagctgaaa aaaaaggttg aaaccagttc  3120
cctgaaatta ttcccctact tgactaataa gtatataaag acggtaggta ttgattgtaa  3180
ttctgtaaat ctatttctta aacttcttaa attctacttt tatagttagt ctttttttta  3240
gttttaaaac accaagaact tagtttcgaa taaacacaca taaacaaaca aaatggcttc  3300
tagttcttcc gatgtcttcg ttttgggtct aggtgttgtt ttggctgcct tgtatatctt  3360
cagagaccaa ttattcgctg cttctaagcc aaaggtggct ccagtttcca ctacgaagcc  3420
tgccaacggt tccgctaacc caagagactt catcgccaag atgaaacaag gtaagaaagag  3480
aatcgtaatc ttctacggtt ctcaaactgg taccgctgaa gaatatgcta ttcgtttggc  3540
taaggaagct aagcaaaagt tcggtctagc ctcccttggt tgtgatccag agaatacga  3600
ttttgaaaag ttggaccaat tgccagaaga ttctattgct ttcttcgtcg ttgctaccta  3660
tggtgaaggt gaacctacag acaacgctgt ccaattgttg caaaacttgc aagatgaaag  3720
cttcgaattc tcctctggtg agagaaagtt gtcaggtttg aagtacgttg ttttttggtct  3780
gggtaacaag acctacgaac attacaacct cattgggaag actgttgacg tcaattggc  3840
caagatgggt gctatcagaa tcggtgaaag aggtgaaggt gatgatgaca agtccatga  3900
agaagactac ttggaatgga aggatggtat gtgggaagcg tttgccactg ctatgggtgt  3960
tgaagaaggt caaggtggtg actccgctga tttcgtcgtt tccgaattgg aatctcaccc  4020
accagaagga gtttaccaag gtgaatttc tgctagagct ttaaccaaaa ccaagggtat  4080
tcacgacgct aagaatcctt ttgctgctcc aattgcggtt gctagagaat gttccaatc  4140
tgttgtcgat agaaactgtg tccacgtcga attcaacatt gaaggctctg gtatcaccta  4200
tcaacacggt gaccacgttg gtttgtggcc attgaatcca gatgttgaag tcgaacggtt  4260
gttgtgtgtt ttaggtttag ctgaaaagag agatgctgtc atctccattg aatccttaga  4320
cccgggcttt g gctaaggttc cattcccagt cccaactact tacggtgctg tgttgagaca  4380
ctacattgac atctctgctg tcgccggtag acaaatcttg ggtactttgt ccaaattcgc  4440
tccaaccccca gaagctgaag cttttcttgag aaacttgaac actaacaagg aagaatacca  4500
caagctcgtc gctaacggtt gtttgaaatt gggtgaaatt ttgcaaatcg ctaccggtaa  4560
cgacattact gtcccaccaa ctactgccaa caccaccaaa tggccaattc cattcgacat  4620
cattgtttct gccatcccaa gattgcaacc aagatactac tctatctctt cttccccaaa  4680
aattcatcca aacaccatcc acgctaccgt tgttgtgctc aaatacgaaa acgttccaac  4740
cgaaccaatc ccaagaaagt gggtttacgg tgtcggtagt aacttcttgt tgaatttaaa  4800
gtacgctgtt aacaaggaac cagttccata catcactcaa aatggcgaac aaagagtcgg  4860
tgtcccggaa tacttgattg ctggtccacg tggttcttac aagactgaat cttctacaa  4920
ggctccaatc catgttagac gttctacttt ccgtttgcca accaacccaa gtctccagt  4980
catcatgatt ggtccaggta ctggtgtcgc cccattcaga ggcttcgttc aagaaagagt  5040
tgccttggcc agaagatcca tcgaaaagaa cggtcctgac tctttggctg actggggtcg  5100
tatttccttg ttctacggtt gtagaagatc cgacgaagac ttcttgtaca aggacgaatg  5160
gccacaatac gaagctgagt tgaagggtaa gttcaagttg cactgtgctt tctccagaca  5220
aaactacaag ccagacggtt ctaagattta cgtccaagat ttgatctggg aagacagaga  5280
acacattgcc gatgccatct aaacggtaa gggttacgtc tacatctgcg gtgaagctaa  5340
gtccatgtct aaacaagttg aagaagttct agccaagatc ttgggcgaag ccaaaggtgg  5400
ttccgtcca gttgaaggtg ttgctgaagt caagttactg aaggaacggt ccagattgca  5460
gttggatgtc tggtctgaac aaaagttaat ttctgaagaa gatttggaat gaatcgcgtg  5520
cattcatccg ctctaaccga aaaggaagga gttagacaac ctgaagtcta ggtccctatt  5580
tattttttta tagttatgtt agtattaaga acgttattta tatttcaaat tttctttttt  5640
tttctgtaca gacgcgtgta cgcatgtaac attatactga aaaccttgct tgagaaggtt  5700
ttgggacgct cgaagatcgc gtcccaattc gccctatagt gagtcgtatt acgcgcgctc  5760
```

```
actggccgtc gttttacaac gtcgtgactg ggaaaaccct ggcgttaccc ctgcaggact   5820
agtgctgagg cattaatacc acttttcaat gaaacggata ttgatatgct agtaaaagga   5880
cgagctcaag agcgaaaata taagtaaaga attcgagtgc acttgtctcc atgcagcaag   5940
atttcatatg agtctttttt atctttttac tttttacatt acacgatatg cactttatga   6000
aaatttaacg aggttggaag ccggataatc aaccaaaatc aggcacgaag gcacactcgt   6060
atatgcatgt tgttgaaact cgtttacgct gaactaacaa tcacacatgt agaggtcacc   6120
gggaaaagtt gcgaccccat ggaaggtcga tctcttcgtt tggctttgct tggctggcgg   6180
cattgcgctt cttcgcttat acccgtctct tgacgctcga gctcgttcat tgagatacct   6240
ttattcttgc acattttctg gctttttttcg ctactcgggt acatgtaatc atgcacacag   6300
aaggtgctgt agggtgaaag ttcctttgtg ctgtcgtttg tttttaatgc caaactttcc   6360
ggtgatcaat aaccacctc                                               6379

SEQ ID NO: 51          moltype = DNA   length = 3840
FEATURE                Location/Qualifiers
misc_feature           1..3840
                       note = Synthetic construct
source                 1..3840
                       mol_type = other DNA
                       organism = synthetic construct
SEQUENCE: 51
cggcatgcaa acatctacac aattagcaag ggcaatccat attttgtctt ttcgcgccct   60
ggaaaggcct aagtaatgtc gtaaacgcat tctatctgta cttcaactct cctctgtgca   120
ttggtttgtg caaatcacat tttacgatac tgccagatat atgcaaaaag agaaaaccaa   180
gggaccagaa caaagcaaaa ttcgatatt cttcgaattc cttcgtgctt gactaagaca   240
aagggatgga cgtagcgatt tttagcgggc caagaactgg ttccgaaaaa gcacaggtac   300
accgaaccct cagctaagga gggacagcac cgatgcgaca ggacaaactt tcttttttgcc   360
tatcacagta tcttatcgag ctaactattt tcgacacaca tgaaaaagca gaaatattaa   420
cgaaaaagaa aagaaagacc atgtcatgta cgggcaatca gaatctgtaa caagcgccat   480
ttttttttct gtatcgggcc ctccttactg ctctccttcc gtgtaacgcg ttatgaaatt   540
aagtcctcag cgagctcgca tggaatgcgt gcgatgacgg acctcatgct ataccgtgaga   600
aagcaacctg acctacagga aagagttact caagaataag aattttcgtt ttaaaaccta   660
agagtcactt taaaatttgt atacacttat tttttttata acttatttaa taataaaaat   720
cataaatcat aagaaattcg ctttatttaga agtgtcaaca acgtatctac caacggaatg   780
cgtgcgattg ttttatattt gttgtaaaaa gtagataatt acttccttga tgatctgtaa   840
aaaagagaaa aagaaagcat ctaagaactt gaaaaactac gaattagaaa agaccaaata   900
tgtatttctt gcattgacca atttatgcaa gtttatatat atgtaaatgt aagtttcacg   960
aggttctact aaactaaacc accccccttgg ttagaagaaa agagtgtgtg agaacaggct   1020
gttgttgtca cacgattcgg acaattctgt ttgaaagaga gagagtaaca gtacgatcga   1080
acgaacttg ctctggagat cacagtgggc atcatgcat gtggtactaa accctttccc   1140
gccattccag aaccttcgat tgcttgttac aaaacctgtg agccgtcgct aggaccttgt   1200
tgtgtgacga aattggaagc tgcaatcaat aggaagacag gaagtcgagc gtgtctgggt   1260
ttttttcagtt ttgttctttt tgcaaacaac agtttattcc tggcatccac taaatataat   1320
ggagcccgct ttttaagctg gcatccagaa aaaaaagaa ccagcacc aaaatattgt   1380
tttcttcacc aaccatcagt tcataggtcc attctcttag cgcaactaca gagaacaggg   1440
gcacaaacag gcaaaaaacg ggcacaacct caatggagtg atgcaacctg cctggagtaa   1500
atgatgacac aaggcaattg acccacgcat gtatctatct cattttctta caccttctat   1560
taccttctgc tctctctgat ttggaaaaag ctgaaaaaaa aggttgaaac cagttccctg   1620
aaattattcc cctacttgac taataagtat ataagacgg taggtattga ttgtaattct   1680
gtaaatctat ttcttaaact tcttaaattc tactttata gttagtcttt tttttagttt   1740
taaaacacca agaacttagt ttcgaataaa cacacataaa caaacaaaat gggaggtccg   1800
atgagcggtt tccattcggg ggaggcgctg ctcggtgacc tcgccaccgg tcagctgacc   1860
aggctgtgcg aggtggcggg gctgaccgag gccgacacgg cggcctcac gggggtgctg   1920
atcgaaagtc tggggacgtc ggccggacgg ccgttgtccc tgccaccccc gtcgcggacc   1980
tttctctccg acgaccacac ccccgtggag ttctccctgg ccttcctgcc gggacgcgca   2040
ccgcaccctgc gggtcctggt ggaacccggc tgctccagcg gcgacgacct ggcggaaaac   2100
ggccgggccg gtctgcgggc ggtccacacc atgcgcgacc gctgggggatt ctccaccgag   2160
caactcgacc ggctggagga cctgttcttc ccctcctccc ccgagggccc gctgccctg   2220
tggtgcgccc tggagctccg ctccggtggg gtgccggggg tgaaggtcta cctcaacccc   2280
gcggcgaatg gcgccgaccg ggccgccgag acggtacgcg aggcgctggc caggctgggc   2340
cacctgcagg cgttcgacgc cgtgccccgg cggacgggct tccgttcct cgccctggac   2400
ctcggcgact gggacgcccc gcgggtgaag atctacctca aacacctcgg catgtccgcc   2460
gccgacgcgg gctccctccc ccggatgtcg cccgcaccga gccgggagca gctggaggag   2520
ttcttccgca ccgccggtga cctccccgcc cgggagacc cggggcccac cgaggacacc   2580
ggccggctcg ccgggcgccc cgccctcacc tgccactcct tcacggagac ggttccctg   2640
cggcccagcg gctacaccct ccacgtgccg gtccgcgact acgtccggca cgacggcgag   2700
gcacgggacc gggcggtggc cgtgctgcgc gaacatgaca tggacagtgc ggcactggac   2760
cgggcgctgg ccgccgtgag cccccgcccg ctgagtgacg gggtgggcct gatcgcctat   2820
ctggcactgg tccaccagcg cggccggccg acacgggtga ccgtctacgt ctcctccgag   2880
gcgtacgagg tgcggccgcc ccgcgagacg gtccccacgc cgcacgtagg gcgggccgag   2940
ctgcatcatc atcatcatca ttgaatcgcg tgcattcatc cgctctaacc gaaaaggaag   3000
gagttagaca acctgaagtc taggtcccta tttatttttt tatagttatg ttagtattaa   3060
gaacgttatt tatatttcaa attttctttt tttttctgta cagacgcgtg tacgcatgta   3120
acattatact gaaaaccttg cttgagaagg ttttgggacg ctcgaagatc gcgtcccaat   3180
tcgccctata gtgagtcgta ttacgcgcgc tcactggccg tcgttttaca acgtcgtgat   3240
tgggaaaacc ctggcgttac ccctgcagga ctagtgctga ggcattaata cgactctctc   3300
gaaatttttc ttaacgcgtc cttgtactgc gtctaacgct tttgccactt ggatttctat   3360
tataggaaat agtctcactt actgggcgac gaatttcgc gttttgatga agcacaggaa   3420
gaatttcttt tttttttggc ttcttctggt tccgttttt acgcgcacaa atctaaaaaa   3480
agaaataatt ataacctagt ctcgaaaatt ttcatcgatc cattcgttcc ttttttttcga   3540
```

```
ttttttcaga tcaaaattct tgtttctttc tttgtcttag tttatattaa aagatatttt   3600
gattttactc ctgaactatt tattcttct aagaaggcca gaacactaca gctgttttaa    3660
ccgactacga agttctccat tctcgaacac tagccttcat ttaccaaaca ggaactagcg   3720
tatatcatta gtccttattc gaaaagagat tggtagatat ttattgtagt ttgtgagaag   3780
gagaaaatac tgtcattgga ctgatagtta gaggacatta acctctctta cgttcgctca   3840
```

SEQ ID NO: 52            moltype = DNA   length = 6190
FEATURE                  Location/Qualifiers
misc_feature             1..6190
                         note = Synthetic construct
source                   1..6190
                         mol_type = other DNA
                         organism = synthetic construct
SEQUENCE: 52

```
cgagatcttt gtgttcggtt acccggctca gatcctaact tcttcttttg gtatgtttat   60
tcgtataagt tactgttgtc cacaggcaat actctgcaga aaattaaaac ggcattaatg   120
ctaggacaac cagaattgtt actactgtat gtgcgatagt tgataactgc aacattatgc   180
ccggtatatt ctcaaaaaac cctattactg catacgaaga aatcgcaaga gaaatctttc   240
ggtttggaaa agctcactgt gaggttcctt ggagccaata gtaatacagc acaatccaag   300
gaaaaatctg gcctatatgc aaggaaggag agatagtcaa aagcattctt tcccctagaa   360
gttggtgcat atatggcatc gttaaaacat attacccccca aaatttcttc tctaaacgat   420
gtgcttggcc tttgttttgg ttttgatgt cggtcgtttg aggccccttg cggaaaatcg   480
agatcgccga atgcacgcg agggaaggga aataaggttt aaaggcactg aaacaatagg   540
caagaagtag gcgagagccg acatacgaga ctaaattaag tcctcagcga gctcgcatgg   600
aatgcgtgcg atgagcgacc tcatgctata cctgagaaag caacctgacc tacaggaaag   660
agttactcaa gaataagaat tttcgttta aaacctaagt gtcactttaa aatttgtata   720
cacttatttt ttttataact tatttaataa taaaaatcat aaatcataag aaattcgctt   780
atttagaagt gtcaacaacg tatctaccaa cggaatgcgt gcgattcatt tgtcatcgtc   840
atccttgtag tccattgcct tcaaatgttc cttattaaac tttctcaaat cgtaaaccaa   900
agagttcaag atatccaatt caacatgttc cataacaatc atcttgtacc agttgttagt   960
tgggttatga acttctggaa ctaaaaagta cttttcagcg atttcctat taacatattg   1020
ttcttcaatt gtaacaatat tcattgaatc ttctttgtaa tatttaattc tcatatcgtt   1080
caattgctta cacaaccatt tagttctatt tctcaactta ttaatcttt ccatccaacc   1140
gtatggacca taagaagcta aaaccatcca aattgcaaca gcatttgaac cagatcttga   1200
accagacaat gtaacatcca aattttcgat gtaagttgct tcctttgtca aagtgttatg   1260
gatcaaaattc tttcttgaaa cgaagatacc agtaccgtat ggagcttgca acatcttatg   1320
accatctaat gtgattgaag aaacgttctt attagagaaa tcagtttttac attccttatt   1380
atcaattgga tatataaaac caccaaatgc accatcaaca tgaattttgt attccaaatt   1440
gtacttatcg aagtagttag cgtacaaatc tggatcatca actgaaccaa acattgtagt   1500
acccatgtta gagataacga tgaagtactc tttaccaatt tctttagctt ctttaacaat   1560
tgaatccaat gtattttctt gaattttct tgaataaaaa tcaactggaa ccttaataat   1620
atcgatgttc aacaaatctg aacctttgta tgcagagtaa tgtgtatctg ctgaagtgat   1680
gatagcgatt tcttcatgct tagcctttct ttcttctttg aagtagtttc tgtaaaccca   1740
cattgcttgg atgttagctt ctgtaccacc ttgagtaacg taaccatcaa attcttcatc   1800
gttaccgttc aaaacatcga ttgctaacaa ttggattaat tctctttcga tatcgaatgt   1860
accaccgaac aagatatcag ccttatcata agtatgacaa ccgatatggt ttgggttttg   1920
aataaaagtt ctcaagtatg gtgaatgctt aacgaaagaa tgatcatcat agaaaactgt   1980
atcatccaac ttagtacctg gaataccgat tgtcttagtg ttatcgtagt tcaaagtctt   2040
ttccaaagat tcagtaatct tttcatccat ttcttgttgt gtgtactttc tccagaactt   2100
cattgtttta tatttgttgt aaaaagtaga taattacttc cttgatgatc tgtaaaaaag   2160
agaaaaagaa agcatctaag aacttgaaaa actacgaatt agaaaagacc aaatatgtat   2220
ttcttgcatt gaccaattta tgcaagttta tatatgta aatgtaagtt tcacgaggtt   2280
ctactaaact aaaccacccc cttggttaga agaaaagagt gtgtgagaac aggctgttgt   2340
tgtcacacga ttcggacaat tctgtttgaa agagagagag taacagtacg atcgaacgaa   2400
ctttgctctg gagatcacag tgggcatcat agcatgtggt actaaaccct ttcccgccat   2460
tccagaacct tcgattgctt gttacaaaac ctgtgagccg tcgctaggac cttgttgtgt   2520
gacgaaattg gaagctgcaa tcaataggaa gacaggaagt cgagcgtgtc tgggtttttt   2580
cagtttgtt cttttgcaa acaacagttt attcctggca tccactaaat ataatggagc   2640
ccgcttttta agctggcatc cagaaaaaaa aagaatccca gcaccaaaat attgtttct   2700
tcaccaacca tcagttcata ggtccattct cttagcgcaa ctacagaaaa caggggcaca   2760
aacaggcaaa aaacgggcac aacctcaatg gagtgatgca acctgcctgg agtaaatgat   2820
gacacaaggc aattgaccca cgcatgtatc tatctcattt tcttacacct tctattacct   2880
tctgctctct ctgatttgga aaaagctgaa aaaaaggtt gaaaccagtt ccctgaaatt   2940
attccctac ttgactaata agtatataaa gacggtaggt attgattgta attctgtaaa   3000
tctatttctt aaacttctta aattctactt ttatagttag tcttttttttt agttttaaaa   3060
caccaagaac ttagtttcga ataaacacac ataaacaaac aaaatggctt ctagttcttc   3120
cgatgtcttc gttttgggtc taggtgttgt tttggctgcc ttgtatatct tcagagacca   3180
attattcgct gcttctaagc caaggtggc tccagtttcc actacgaagc ctgccaacgg   3240
ttccgctaac ccaagagact tcatcgcaa gatgaaacaa ggtaagaaga gaatcgtaat   3300
cttctacggt tctcaaactg gtaccgctga agaatatgct attcgtttgg ctaaggaagc   3360
taagcaaaag ttcggtctag cctccttggt tgtgatcca gaagaatacg attttgaaaa   3420
gttggaccaa ttgccagaag attctattgc tttcttcgtc gttgctacct atggtgaagg   3480
tgaacctaca gacaacgctg tccaattgtt gcaaacttg caagatgaaa gcttcgaatt   3540
ctcctctggt gagagaaagt tgtcaggttt gaagtacgtt gtttttggtc tgggtaacaa   3600
gacctacgaa cattcaaacc tcattgggag aactgttgac gctcaattgg ccaagatggg   3660
tgctatcaga atcggtgaaa gaggtgaagg tgatgatgac aagtccatgg aagaagacta   3720
cttgaatgg aaggatggta tgtgggaagc gtttgccact gctatgggtg ttgaagaagg   3780
tcaaggtggt gactccgctg atttcgtcgt ttccgaattg gaatctcacc caccagaaaa   3840
ggtttaccaa ggtgaatttt ctgctagagc tttaaccaaa accaagggta ttcacgacgc   3900
```

```
taagaatcct tttgctgctc caattgcggt tgctagagaa ttgttccaat ctgttgtcga  3960
tagaaactgt gtccacgtcg aattcaacat tgaaggctct ggtatcacct atcaacacgg  4020
tgaccacgtt ggtttgtggc cattgaatcc agatgttgaa gtcgaacggt tgttgtgtgt  4080
tttaggttta gctgaaaaga gagatgctgt catctccatt gaatccttag acccggcttt  4140
ggctaaggtt ccattcccag tcccaactac ttacggtgct gtgttgagac actacattga  4200
catctctgct gtcgccggta gacaaatctt gggtactttg tccaaattcg ctccaacccc  4260
agaagctgaa gctttcttga gaacttgaa cactaacaag gaagaatacc acaacgtcgt  4320
cgctaacggt gtttgaaat tgggtgaaat tttgcaaatc gctaccggta acgacattac  4380
tgtcccacca actactgcca acaccaccaa atggccaatt ccattcgaca tcattgtttc  4440
tgccatccca agattgcaac caagatacta ctctatctct tcttcccaa aaattcatcc  4500
aaacaccatc cacgctaccg ttgttgtgct caaatacgaa aacgttccaa ccgaaccaat  4560
cccaagaaag tgggtttacg gtgtcggtag taacttcttg ttgaatttaa agtacgctgt  4620
taacaaggaa ccagttccat acatcactca aaatggcgaa caaagagtcg gtgtcccgga  4680
atacttgatt gctggtccac gtggttctta caagactgaa tctttctaca aggctccaat  4740
ccatgttaga cgttctactt tccgtttgcc aaccaaccca aagtctccag tcatcatgat  4800
tggtccaggt actggtgtcg ccccattcag aggcttcgtt caagaaagag ttgccttggc  4860
cagaagatcc atcgaaaaga acggtcctga ctctttggct gactggggtc gtatttcctt  4920
gttctacggt tgtagaagat ccgacgaaga cttcttgta aaggacgaat ggccacaata  4980
cgaagctgag ttgaagggta agttcaagtt gcactgtgct ttctccagac aaaactacaa  5040
gccagacggt tctaagattt acgtccaaga tttgatctgg gaagacagag aacacattgc  5100
cgatgccatc ttaaacggta agggttacgt ctacatctgc ggtgaagcta agtccatgtc  5160
taaacaagtt gaagaagttc tagccaagat cttgggcgaa gccaaaggtg gttccggtcc  5220
agttgaaggt gttgctgaag tcaagttact gaaggaacgg tccagattga tgttggatgt  5280
ctggtctgaa caaaagttaa ttctgaaga agatttggaa tgaatcgcgt gcattcatcc  5340
gctctaaccg aaaaggaagg agttagacaa cctgaagtct aggtccctat ttatttttt  5400
atagtttatgt tagtattaag aacgttattt atatttcttt ttttctttt ttttctgtac  5460
agacgcgtgt acgcatgtaa cattatactg aaaaccttgc ttgagaaggt tttgggacgc  5520
tcgaagatcg cgtcccaatt cgccctatag tgagtcgtat tacgcgcgct cactggccgt  5580
cgttttacaa cgtcgtgact gggaaaaccc tggcgttacc cctgcaggac tagtgctgag  5640
gcattaatac cacttttcaa tgaaacggat attgatatgc tagtaaaagg acgagctcaa  5700
gagcgaaaat ataagtaaag aattcgagtg cacttgtctc catgcagcaa gatttcatat  5760
gagtcttttt tatctttta cttttacat tacacgatat gcactttatg aaaatttaac  5820
gaggttggaa gccggataat caaccaaaat caggcacgaa ggcacactcg tatatgcatg  5880
ttgttgaaac tctgttacgc tgaactaaca atcacacatg tagaggtcac cgggaaaagt  5940
tgcgaccccca tggaaggtcg atctcttcgt ttggctttgc ttggctggcg gcattgcgct  6000
tcttcgctta tacccgtctc ttgacgctcg agctcgttca ttgagatacc tttattcttg  6060
cacattttct ggctttttc gctactcggg tacatgtaat catgcacaca gaaggtgctg  6120
tagggtgaaa gttcctttgt gctgtcgttt gttttttaatg ccaaactttc cggtgatcaa  6180
taaccacctc                                                          6190
```

| SEQ ID NO: 53 | moltype = DNA length = 4101 |
|---|---|
| FEATURE | Location/Qualifiers |
| misc_feature | 1..4101 |
| | note = Synthetic construct |
| source | 1..4101 |
| | mol_type = other DNA |
| | organism = synthetic construct |

SEQUENCE: 53
```
cggcatgcaa acatctacac aattagcaag ggcaatccat attttgtctt ttcgcgccct    60
ggaaaggcct aagtaatgtc gtaaacgcat tctatctgta cttcaactct cctctgtgca   120
ttggtttgtg caaatcacat tttacgatac tgccagatat atgcaaaaag agaaaactaa   180
gggaccagaa caaagcaaaa ttacgatatt cttcgaattc cttcgtgctt gactaagaca   240
aagggatgga cgtagcgatt tttagcgggc caagaactgg ttccgaaaaa gcacaggtac   300
accgaaccct cagctaagga gggacagcac cgatgcggaa ggacaaactt tcttttttgcc   360
tatcacagta tcttatcgag ctaactattt tcgacacaca tgaaaaagca gaaatattaa   420
cgaaaaagaa aagaaagacc atgtcatgta cgggcaatca gaatctgtaa caagcgccat   480
tttttttttct gtatcgggcc ctccttactg ctctccttcc gtgtaacgcg ttatgaaatt   540
aagtcctcag cgagctcgca tggaatgcgt gcgatgagcg acctcatgct atacctgaga   600
aagcaacctg acctacagga aagagttact caagaataag aattttcgtt ttaaaaccta   660
agagtcactt taaaatttgt atacacttat tttttttata acttatttaa taataaaaat   720
cataaatcat aagaaattcg cttatttaga agtgtcaaca acgtatctac caacggaatg   780
cgtgcgattg ttttatattt gttgtaaaaa gtagataatt acttccttga tgatctgtaa   840
aaaagagaaa aagaaagcat ctaagaactt gaaaaactac gaattagaaa agaccaaata   900
tgtatttctt gcattgacca atttatgcaa gtttatatat aagttcacg   960
aggttctact aaactaaacc accccctggg ttagaagaaa agagtgtgtg agaacaggct  1020
gttgttgtca cacgattcgg acaattcgt ttgaaagaga gagtaaca gtacgatcga  1080
acgaactttg ctctggagat cacagtgggc atcatagcat gtggtactaa acccttccc  1140
gccattccag aaccttcgat tgcttgttac aaaacctgtg agccgtcgct aggacctgt  1200
tgtgtgacga attggaagc tgcaatcaat aggaagacga gaagtcgagc gtgtctgggt  1260
ttttttcagtt ttgttctttt tgcaaacaac agtttattcc tggcatccac taaatataat  1320
ggagcccgct ttttaagctg gcatccagaa aaaaaagaa tcccagcacc aaaatattgt  1380
tttcttcacc aaccatcagt tcataggtcc attctcttag cgcaactaca gagaacaggg  1440
gcacaaacag gcaaaaaacg ggcacaacct caatggagtg atgcaacctg cctgagtaa  1500
atgatgacaa aaggcaattg acccacgcat gtatctatct catttttctta caccttctat  1560
taccttctgc tctctctgat ttggaaaaag ctgaaaaaaa aggttgaaac cagttccctg  1620
aaattattcc cctactgac taataagtat ataaagacgg taggtattga ttgtaattct  1680
gtaaatctat ttcttaaaact tcttaaattc tactttata gttagtctt tttttagttt  1740
taaaacacca agaacttagt tcgaataaa cacacataaa caaacaaaat gtccatcggt  1800
gctgaaattg actctttggt tccagctcca ccaggtttga acggtaccgc tgctggttac  1860
```

-continued

```
ccagccaaga ctcaaaagga attgtctaac ggcgatttcg atgctcacga tggtctgtcc 1920
ttggctcaat tgactccata cgatgtttta accgctgctt tgccattgcc agcgccagct 1980
tctagtactg gtttctggtg gagagaaact ggtccagtta tgtctaagct cttggctaaa 2040
gccaactacc cattgtacac ccattacaag tatttaatgt tgtaccacac tcacatttta 2100
cctttgttag gtccaagacc acctttggaa aattctaacc acccatctcc atcaaatgct 2160
ccttggagat ccttcttgac cgatgacttc accccattag aaccatcttg gaacgttaac 2220
ggtaactccg aagcacaatc cactatcaga ttgggtattg aaccaattgg tttcgaagcc 2280
ggtgctgctg ccgacccatt caaccaagct gccgtcaccc aattcatgca ctcctacgaa 2340
gctactgaag ttggtgccac tctaactttg ttcgaacact tcagaaacga catgttcgtc 2400
ggtccagaga cttacgctgc cttgagagct aagattcctg aaggtgagca caccactcaa 2460
tcttctcttg ctttcgactt ggacgccggt cgtgtcacta ccaaggctta cttcttccca 2520
atcttgatgt ctttgaagac cggtcaatct acgaccaaag ttgtttccga ttctatcttg 2580
cacctagctt tgaagtctga agtttggggt gtccaaacca ttgccgctat gtcggtcatg 2640
gaagcttgga tcggttctta cggtggtgct gctaagaccg aaatgatctc cgttgactgt 2700
gtcaacgaag ctgactccag aatcaagatc tacgttagaa tgccacacac tagcttgaga 2760
aaggtcaaag aagcttattg tttgggtggc cgtttgactg acgaaaacac caaggaaggt 2820
ttgaaattgt tggatgaatt gtggagaact gttttcggta tcgatgacga agatgctgaa 2880
ttaccacaaa actctcacag aactgctggt actatttta actttgaact aagaccaggt 2940
aagtggttcc cagaaccaaa ggtctacttg ccagtcagac actactgtga atccgacatg 3000
caaattgcct ccagattaca aactttcttt ggtcgtttgg gttggcacaa catggaaaag 3060
gactactgca agcatttgga agacttattc cctcaccacc cattgtcctc ctctaccggt 3120
acccacactt tcttgtcttt ttcttacaag aagcaaaagg tgtttacat gaccatgtac 3180
tacaacttga gagtttattc tacacaccac catcatcatc attgaatcgc gtgcattcat 3240
ccgctctaac cgaaaaggaa ggagttagac aacctgaagt ctaggtccct atttatttt 3300
ttatagttat gttagtatta agaacgttat ttatatttca aattttttct tttttctgt 3360
acagacgcgt gtacgcatgt aacattatac tgaaaaccct gcttgagaag gttttgggac 3420
gctcgaagat cgcgtcccaa ttcgccctat agtgagtcgt attacgcgcg ctcactggcg 3480
gtcgttttac aacgtcgtga ctgggaaaac cctggcgtta ccctgcagg actagtgctg 3540
aggcattaat acgactctct cgaaatttt cttaacgcgt ccttgtactg cgtctaacgc 3600
tttgccact tggatttcta ttataggaaa tagtctcact tactgggcga cgaatttcg 3660
cgttttgatg aagcacagga agaatttctt tttttttgg cttcttctgg ttccgttttt 3720
tacgcgcaca aatctaaaaa aagaaataat tataacctag tctcgaaat tttcatcgat 3780
ccattcgttc ctttttttcg atttttcag atcaaattc ttgtttcttt ctttgtctta 3840
gtttatatta aaagatattt tgattttact cctgaactat tattctttc taagaaggcc 3900
agaacactac agctgtttta accgactacg aagttctcca ttctcgaaca ctagccttca 3960
tttaccaaac aggaactagc gtatatcatt agtcctatt cgaaagaga ttggtagata 4020
tttattgtag tttgtgagaa ggagaaaata ctgtcattgg actgatagtt agaggacatt 4080
aacctctctt acgttcgctc a                                          4101
```

```
SEQ ID NO: 54           moltype = DNA   length = 5360
FEATURE                 Location/Qualifiers
misc_feature            1..5360
                        note = Synthetic construct
source                  1..5360
                        mol_type = other DNA
                        organism = synthetic construct
SEQUENCE: 54
atccggatat agttcctcct ttcagcaaaa aaccccctcaa gacccgttta gaggccccaa 60
ggggttatgc tagttattgc tcagcggtgg cagcagccaa ctcagcttcc tttcgggctt 120
tgttagcagc cggatctcag tggtggtggt ggtggtgctc gagtgcggcc gcaagcttgt 180
cgacggagct cgaattcgga tccgaattaa ttccgatatc catggccatc gccggctgga 240
cagcgaggag cagcagacca gcagcagcgg tcggcagcag gtatttcata tgtatatctc 300
cttcttaaag ttaaacaaaa ttatttctag aggggaattg ttatccgctc acaattcccc 360
tatagtgagt cgtattaatt tcgcgggatc gagatctcga tcctctacgc cggacgcatc 420
gtggccggca tcaccggcgc cacaggtgcg gttgctggcg cctatatcgc cgacatcacc 480
gatggggaag atcgggctcg ccacttcggg ctcatgagcg cttgtttcgg cgtgggtatg 540
gtggcaggcc ccgtggccgg gggactgttg ggcgccatct ccttgcatgc accattcctt 600
gcggcggcgg tgctcaacgg cctcaaccta ctactgggct gcttcctaat gcaggagtcg 660
cataagggag agcgtcgaga tcccggacac catcgaatgg cgcaaaacct ttcgcggtat 720
ggcatgatag cgcccggaag agagtcaatt cagggtggtg aatgtgaaac cagtaacgtt 780
atacgatgtc gcagagtatg ccggtgtctc ttatcagacc gtttcccgcg tggtgaacca 840
ggccagccac gtttctgcga aaacgcggga aaagtggaa gcggcgatgg cggagctgaa 900
ttacattccc aaccgcgtgg cacaacaact ggcgggcaaa cagtcgttgc tgattggcgt 960
tgccacctcc agtctggccc tgcacgcgcc gtcgcaaatt gtcgcggcga ttaaatctcg 1020
cgccgatcaa ctgggtgcca gcgtggtggt gtcgatggta gaacgaagcg gcgtcgaagc 1080
ctgtaaagcg gcggtgcaca atcttctcgc gcaacgcgtc agtgggctga tcattaacta 1140
tccgctggat gaccaggatg ccattgctgt ggaagctgcc tgcactaatg ttccggcgtt 1200
atttcttgat gtctctgacc agacacccat caacagtatt attttctccc atgaagacgg 1260
tacgcgactg ggcgtggagc atctggtcgc attgggtcac cagcaaatcg cgctgttagc 1320
gggcccatta agttctgtct cggcgcgtct gcgtctggct ggctggcata atatatctcac 1380
tcgcaatcaa attcagccga tagcggaacg ggaaggcgac tggagtgcca tgtccggttt 1440
tcaacaaacc atgcaaatgc tgaatgaggg catcgttccc actgcgatgc tggttgccaa 1500
cgatcagatg gcgctgggcg caatgcgcgc cattaccgag tccgggctgc gcgttggtgc 1560
ggatatctcg gtagtgggat acgacgatac cgaagacacg tcatgttata tcccgccgtt 1620
aaccaccatc aaacaggatt tcgcctgctg ggggcaaacc agcgtggacc gcttgctgca 1680
actctctcag ggccaggcgg tgaagggcaa tcagctgttg cccgtctcac tggtgaaaag 1740
aaaaaccacc ctggcgccca atacgcaaac cgcctctccc cgcgcgttgg ccgattcatt 1800
aatgcagctg gcacgacagg tttcccgact ggaaagcggg cagtgagcgc aacgcaatta 1860
atgtaagtta gctcactcat taggcaccgg gatctcgacc gatgcccttg agagccttca 1920
```

```
acccagtcag ctccttccgg tgggcgcggg gcatgactat cgtcgccgca cttatgactg   1980
tcttctttat catgcaactc gtaggacagg tgccggcagc gctctgggtc attttcggcg   2040
aggaccgctt tcgctggagc gcgacgatga tcggcctgtc gcttgcgcta ttcggaatct   2100
tgcacgccct cgctcaagcc ttcgtcactg gtcccgccac caaacgtttc ggcgagaagc   2160
aggccattat cgccggcatg gcggcccac gggtgcgcat gatcgtgctc ctgtcgttga    2220
ggacccggct aggctggcgg ggttgcctta ctggttagca gaatgaatca ccgatacgcg   2280
agcgaacgtg aagcgactgc tgctgcaaaa cgtctgcgac ctgagcaaca acatgaatgg   2340
tcttcggttt ccgtgtttcg taaagtctgg aaacgcggaa gtcagcgccc tgcaccatta   2400
tgttccggat ctgcatcgca ggatgctgct ggctaccctg tggaacacct acatctgtat   2460
taacgaagcg ctggcattga ccctgagtga ttttctctg gtcccgccgc atccataccg    2520
ccagttgttt accctcacaa cgttccagta accgggcatg ttcatcatca gtaacccgta   2580
tcgtgagcat cctctctcgt ttcatcggta tcattccccc catgaacaga aatccccctt   2640
acacggaggc atcagtgacc aaacaggaaa aaaccgccct taacatggcc cgctttatca   2700
gaagccagac attaacgctt ctggagaaac tcaacgagct ggacgcggat gaacaggcag   2760
acatctgtga atcgcttcac gaccacgctg atgagcttta ccgcagctgc ctcgcgcgtt   2820
tcggtgatga cggtgaaaac ctctgacaca tgcagctccc ggagacggtc acagcttgtc   2880
tgtaagcgga tgccgggagc agacaagccc gtcagggcgc gtcagcgggt gttggcgggt   2940
gtcggggcgc agccatgacc cagtcacgta gcgatagcgg agtgtatact ggcttaacta   3000
tgcggcatca gagcagattg tactgagagt gcaccatata tgcggtgtga aataccgcac   3060
agatgcgtaa ggagaaaata ccgcatcagg cgctcttccg cttcctcgct cactgactcg   3120
ctgcgctcgg tcgttcggct gcggcgagcg gtatcagctc actcaaaggc ggtaatacgg   3180
ttatccacag aatcagggga taacgcagga agaacatgt gagcaaaagg ccagcaaaag    3240
gccaggaacc gtaaaaaggc cgcgttgctg gcgtttttcc ataggctccg cccccctgac   3300
gagcatcaca aaaatcgacg ctcaagtcag aggtggcgaa acccgacagg actataaaga   3360
taccaggcgt ttcccctgg aagctccctc gtgcgctctc ctgttccgac cctgccgctt    3420
accggatacc tgtccgcctt tctcccttcg ggaagcgtgg cgctttctca tagctcacgc   3480
tgtaggtatc tcagttcggt gtaggtcgtt cgctccaagc tgggctgtgt gcacgaaccc   3540
cccgttcagc ccgaccgctg cgccttatcc ggtaactatc gtcttgagtc aacccggta    3600
agacacgact tatcgccact ggcagcagcc actggtaaca ggattagcag agcgaggtat   3660
gtaggcggtg ctacagagtt cttgaagtgg tggcctaact acggctacac tagaaggaca   3720
gtatttggta tctgcgctct gctgaagcca gttaccttcg gaaaaagagt tggtagctct   3780
tgatccggca aacaaaccac cgctggtagc ggtggttttt ttgtttgcaa gcagcagatt   3840
acgcgcagaa aaaaggatc tcaagaagat cctttgatct tttctacggg gtctgacgct    3900
cagtggaacg aaaactcacg ttaagggatt ttggtcatga caataaaac tgtctgctta    3960
cataaacagt aatacaaggg gtgttatgag ccatattcaa cgggaaacgt cttgctctag   4020
gccgcgatta aattccaaca tggatgctga tttatatggg tataaatggg ctcgcgataa   4080
tgtcgggcaa tcaggtgcga caatctatcg attgtatggg aagcccgatg cgccagagtt   4140
gtttctgaaa catggcaaag gtagcgttgc caatgatgtt acagatgaga tggtcagact   4200
aaactggctg acggaattta tgcctcttcc gaccatcaag catttatcc gtactcctga    4260
tgatgcatgg ttactcacca ctgcgatccc cgggaaaaca gcattccagg tattagaaga   4320
atatcctgat tcaggtgaaa atattgttga tgcgctggca gtgttcctgc gccggttgca   4380
ttcgattcct gtttgtaatt gtccttttaa cagcgatcgc gtatttcgtc tcgctcaggc   4440
gcaatcacga tgaataacg gtttggttga tgcgagtgat tttgatgacg agcgtaatgg   4500
ctggcctgtt gaacaagtct ggaaagaaat gcataaactt ttgccattct caccggattc   4560
agtcgtcact catggtgatt tctcacttga taaccttatt tttgacgagg ggaaattaat   4620
aggttgtatt gatgttggac gagtcggaat cgcagaccga taccaggatc ttgccatcct   4680
atggaactgc ctcggtgagt tttctccttc attacagaaa cggcttttc aaaaatatgg    4740
tattgataat cctgatatga ataaattgca gtttcatttg atgctcgatg agttttctcta   4800
agaattaatt catgagcgga tacatatttg aatgtattta gaaaaataaa caaatagggg   4860
ttccgcgcac atttccccga aaagtgccac ctgaaattgt aaacgttaat atttttgttaa   4920
aattcgcgtt aaattttttgt taaatcagct catttttttaa ccataggcc gaaatcggca   4980
aaatccctta taaatcaaaa gaatagaccg agatagggtt gagtgttgtt ccagtttgga   5040
acaagagtcc actattaaag aacgtggact ccaacgtcaa agggcgaaaa accgtctatc   5100
agggcgatgg cccactacgt gaaccatcac cctaatcaag ttttttgggg tcgaggtgcc   5160
gtaaagcact aaatcggaac cctaaaggga gcccccgatt tagagcttga cggggaaagc   5220
cggcgaacgt ggcgagaaag gaagggaaga agcgaaagg agcgggcgct agggcgctgg   5280
caagtgtagc ggtcacgctg cgcgtaacca ccacacccgc cgcgcttaat gcgccgctac   5340
agggcgcgtc ccattcgcca                                              5360
```